US012590101B2

(12) United States Patent
Lee et al.

(10) Patent No.: US 12,590,101 B2
(45) Date of Patent: Mar. 31, 2026

(54) COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

(71) Applicant: SAMSUNG SDI CO., LTD., Yongin-si (KR)

(72) Inventors: Seungjae Lee, Suwon-si (KR); Chang Ju Shin, Suwon-si (KR); Eunhye An, Suwon-si (KR); Jongwoo Won, Suwon-si (KR); Wooseok Jeong, Suwon-si (KR); Hyung Sun Kim, Suwon-si (KR); Seungin Park, Suwon-si (KR); Sung-Hyun Jung, Suwon-si (KR); Youngkyoung Jo, Suwon-si (KR)

(73) Assignee: SAMSUNG SDI CO., LTD., Yongin-si (KR)

( * ) Notice: Subject to any disclaimer, the term of this patent is extended or adjusted under 35 U.S.C. 154(b) by 1015 days.

(21) Appl. No.: 17/725,882

(22) Filed: Apr. 21, 2022

(65) Prior Publication Data

US 2022/0267344 A1 Aug. 25, 2022

Related U.S. Application Data

(63) Continuation of application No. PCT/KR2020/014674, filed on Oct. 26, 2020.

(30) Foreign Application Priority Data

Oct. 29, 2019 (KR) ........................ 10-2019-0135769

(51) Int. Cl.
*C07D 491/048* (2006.01)
*C07D 495/04* (2006.01)
(Continued)

(52) U.S. Cl.
CPC ....... *C07D 491/048* (2013.01); *C07D 495/04* (2013.01); *H10K 85/654* (2023.02);
(Continued)

(58) Field of Classification Search
None
See application file for complete search history.

(56) References Cited

U.S. PATENT DOCUMENTS 5,061,569 A 10/1991 Vanslyke et al.
9,876,181 B2 1/2018 Parham et al.
2015/0171340 A1 6/2015 Lee et al.

FOREIGN PATENT DOCUMENTS

CN 106537633 A 3/2017
CN 108864054 A 11/2018
(Continued)

OTHER PUBLICATIONS

Chinese Office Action (including a search report) dated May 30, 2023, of the corresponding Chinese Patent Application No. 202080075836.1.
(Continued)

*Primary Examiner* — Jay Yang
(74) *Attorney, Agent, or Firm* — Lee IP Law, P.C.

(57) ABSTRACT

A compound for an organic optoelectronic element, a composition for an organic optoelectronic element, the composition including the compound, an organic optoelectronic device including the compound or the composition for an organic optoelectronic device, and a display device including the organic optoelectronic device, the compound being represented by a combination of Chemical Formula 1, Chemical Formula 2, and Chemical Formula 3.
(Continued)

100

[Chemical Formula 1]

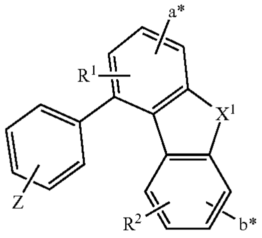

[Chemical Formula 2]

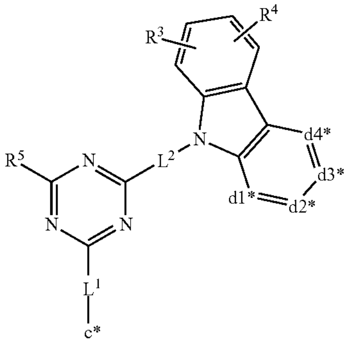

[Chemical Formula 3]

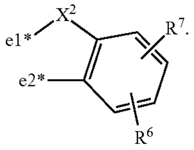

18 Claims, 1 Drawing Sheet

(51) Int. Cl.

| | |
|---|---|
| ***H01L 51/00*** | (2006.01) |
| ***H10K 85/60*** | (2023.01) |
| *H10K 50/11* | (2023.01) |
| *H10K 101/10* | (2023.01) |
| *H10K 101/30* | (2023.01) |
| *H10K 101/40* | (2023.01) |

(52) U.S. Cl.

CPC ..... *H10K 85/6574* (2023.02); *H10K 85/6576* (2023.02); *C07B 2200/05* (2013.01); *H10K 50/11* (2023.02); *H10K 2101/10* (2023.02); *H10K 2101/30* (2023.02); *H10K 2101/40* (2023.02)

(56) References Cited

FOREIGN PATENT DOCUMENTS

| | | | |
|---|---|---|---|
| CN | 108997314 | A | 12/2018 |
| EP | 2827397 | A1 | 1/2015 |
| JP | 1993-009471 | A | 1/1993 |
| JP | 1995-126615 | A | 5/1995 |
| JP | 1998-095972 | A | 4/1998 |
| JP | 5795896 | B2 | 10/2015 |
| KR | 10-2013-0094903 | A | 8/2013 |
| KR | 10-2014-0143397 | A | 12/2014 |
| KR | 10-2015-0070860 | A | 6/2015 |
| KR | 10-2016-0011582 | A | 2/2016 |
| KR | 10-2017-0041886 | A | 4/2017 |
| KR | 10-1754715 | B1 | 7/2017 |
| KR | 10-2018-0002351 | A | 1/2018 |
| KR | 10-2018-0002353 | A | 1/2018 |
| KR | 10-2018-0003478 | A | 1/2018 |
| KR | 10-2018-0007243 | A | 1/2018 |
| KR | 10-2019-0000185 | A | 1/2019 |
| KR | 10-2019-0001357 | A | 1/2019 |
| KR | 10-1959821 | B1 | 3/2019 |
| KR | 10-2044943 | B1 | 11/2019 |
| WO | WO 1995/009147 | A1 | 4/1995 |
| WO | WO 2016/023608 | A1 | 2/2016 |
| WO | WO 2018/034340 | A1 | 2/2018 |
| WO | WO 2019/190223 | A1 | 3/2019 |

OTHER PUBLICATIONS

International Search Report dated Jan. 29, 2021 for PCT/KR2020/014674.

【Figure 1】
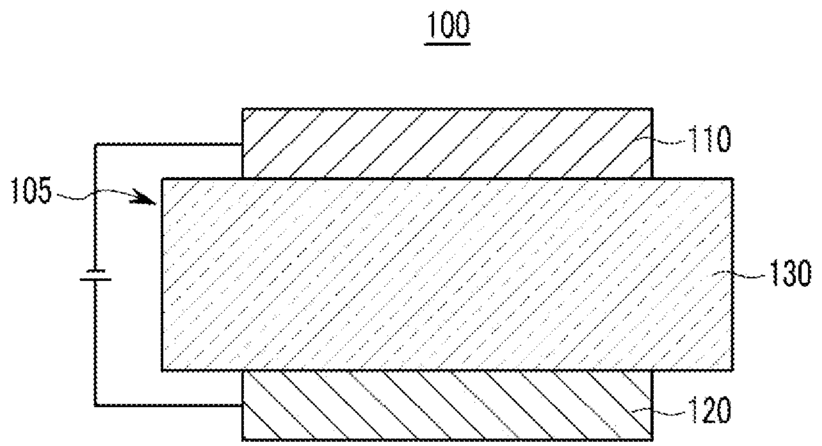
【Figure 2】
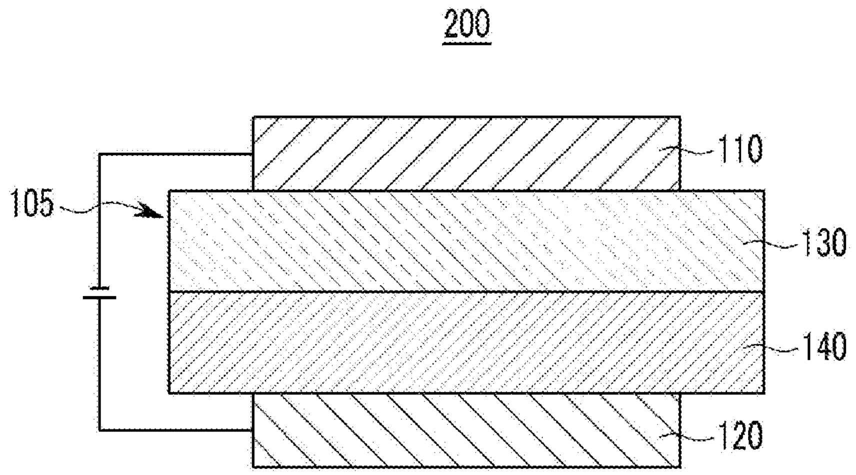

COMPOUND FOR ORGANIC OPTOELECTRONIC DEVICE, COMPOSITION FOR ORGANIC OPTOELECTRONIC DEVICE AND ORGANIC OPTOELECTRONIC DEVICE AND DISPLAY DEVICE

CROSS-REFERENCE TO RELATED APPLICATIONS

This application is a continuation of pending International Application No. PCT/KR2020/014674, entitled "Compound for Organic Optoelectronic Element, Composition for Organic Optoelectronic Element, Organic Optoelectronic Element, and Display Device," which was filed on Oct. 26, 2020, and is incorporated by reference herein in its entirety for all purposes.

Korean Patent Application No. 10-2019-0135769, filed on Oct. 29, 2019, in the Korean Intellectual Property Office, and entitled: "Compound for Organic Optoelectronic Element, Composition for Organic Optoelectronic Element, Organic Optoelectronic Element, and Display Device," is incorporated by reference herein in its entirety for all purposes.

BACKGROUND

1. Field

A compound for an organic optoelectronic element, a composition for an organic optoelectronic element, an organic optoelectronic element, and a display device are disclosed.

2. Description of the Related Art

An organic optoelectronic element (organic optoelectronic diode) is a device capable of converting electrical energy and optical energy to each other.

An organic optoelectronic element may be classified as follows in accordance with its driving principles. One is a photoelectric element that generates electrical energy by separating excitons formed by light energy into electrons and holes, and transferring the electrons and holes to different electrodes, respectively and the other is light emitting element that generates light energy from electrical energy by supplying voltage or current to the electrodes.

Examples of the organic optoelectronic element include an organic photoelectric element, an organic light emitting diode, an organic solar cell, and an organic photo conductor drum.

Among them, organic light emitting diodes (OLEDs) are attracting much attention in recent years due to increasing demands for flat panel display devices. The organic light emitting diode is a device that converts electrical energy into light, and the performance of the organic light emitting diode is greatly influenced by an organic material between electrodes.

SUMMARY

An embodiment provides a compound for an organic optoelectronic element capable of implementing a high efficiency and long life-span organic optoelectronic element.

Another embodiment provides a composition for an organic optoelectronic element including the compound.

Another embodiment provides an organic optoelectronic element including the compound or composition.

Another embodiment provides a display device including the organic optoelectronic element.

Technical Solution

According to an embodiment, a compound for an organic optoelectronic element represented by a combination of Chemical Formula 1 to Chemical Formula 3 is provided.

[Chemical Formula 1]

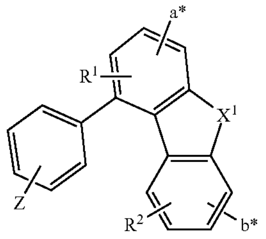

[Chemical Formula 2]

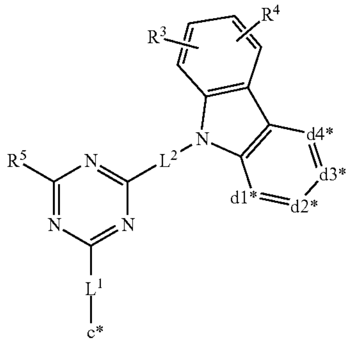

[Chemical Formula 3]

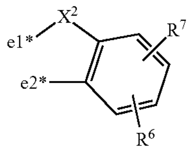

In Chemical Formula 1 to Chemical Formula 3, $X^1$ and $X^2$ are each independently O or S, Z is hydrogen, deuterium, a substituted or unsubstituted C1 to C10 alkyl group, or a substituted or unsubstituted phenyl group, $L^1$ and $L^2$ are each independently a single bond, or a substituted or unsubstituted C6 to C20 arylene group, a* or b* of Chemical Formula 1 is linked to c* of Chemical Formula 2, two adjacent ones of $d_1$* to $d_4$* of Chemical Formula 2 are linked to $e_1$* and $e_2$* of Chemical Formula 3, respectively, a* or b* not linked to c* of Chemical Formula 2 is each independently $R^a$, the remaining ones not connected to $e_1$* and $e_2$* of Chemical Formula 3 of $d_1$* to $d_4$* of Chemical Formula 2 are each independently $CR^b$, and $R^a$, $R^b$, and $R^1$ to $R^7$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

According to another embodiment, a composition for an organic optoelectronic element including a first compound for an organic optoelectronic element, and a second compound for an organic optoelectronic element is provided.

The first compound for the organic optoelectronic element includes the aforementioned compound for the organic optoelectronic element and the second compound for the organic optoelectronic element includes a compound for an organic optoelectronic element represented by Chemical Formula 4.

[Chemical Formula 4]

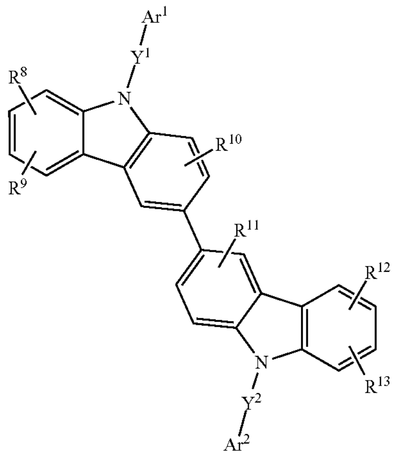

In Chemical Formula 4, $Y^1$ and $Y^2$ are each independently a single bond or a substituted or unsubstituted C6 to C20 arylene group, $Ar^1$ and $Ar^2$ are each independently a substituted or unsubstituted C6 to C20 aryl group, or a substituted or unsubstituted C2 to C30 heterocyclic group, and $R^8$ to $R^{13}$ are each independently hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof.

According to another embodiment, an organic optoelectronic element includes an anode and a cathode facing each other, and at least one organic layer between the anode and the cathode, and the organic layer includes the compound for the organic optoelectronic element or the composition for the organic optoelectronic element.

According to another embodiment, a display device including the organic optoelectronic element is provided.

Advantageous Effects

An organic optoelectronic element having high efficiency and a long life-span may be realized.

DESCRIPTION OF THE DRAWINGS

Features will become apparent to those of skill in the art by describing in detail exemplary embodiments with reference to the attached drawings in which:

FIGS. 1 and 2 are cross-sectional views each illustrating an organic light emitting diode according to embodiments.

DESCRIPTION OF SYMBOLS

100, 200: organic light emitting diode
105: organic layer
110: cathode
120: anode
130: light emitting layer
140: hole auxiliary layer

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. It will also be understood that when a layer or element is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals refer to like elements throughout.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, or a cyano group. In addition, in specific examples of the present invention, "substituted" refers to replacement of at least one hydrogen of a substituent or a compound by deuterium, a C1 to C20 alkyl group, a C6 to C30 aryl group, or a cyano group. In addition, in specific examples of the present invention, "substituted" refers to replacement of at least one hydrogen of a substituent or a compound by deuterium, a C1 to C5 alkyl group, a C6 to C18 aryl group, or a cyano group. In addition, in specific examples of the present invention, "substituted" refers to replacement of at least one hydrogen of a substituent or a compound by deuterium, a cyano group, a methyl group, an ethyl group, a propyl group, a butyl group, a phenyl group, a biphenyl group, a terphenyl group, or a naphthyl group.

As used herein, "hydrogen substitution (—H)" may include "deuterium substitution (-D)" or "tritium substitution (-T)".

In the present specification, when a definition is not otherwise provided, "hetero" refers to one including one to three heteroatoms selected from N, O, S, P, and Si, and remaining carbons in one functional group.

In the present specification, "aryl group" refers to a group including at least one hydrocarbon aromatic moiety, and may include a group in which all elements of the hydrocarbon aromatic moiety have p-orbitals which form conjugation, for example a phenyl group, a naphthyl group, and the like, a group in which two or more hydrocarbon aromatic moieties may be linked by a sigma bond, for example a biphenyl group, a terphenyl group, a quarterphenyl group, and the like, and a group in which two or more hydrocarbon aromatic moieties are fused directly or indirectly to provide a non-aromatic fused ring, for example, a fluorenyl group, and the like.

The aryl group may include a monocyclic, polycyclic or fused ring polycyclic (i.e., rings sharing adjacent pairs of carbon atoms) functional group.

In the present specification, "heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "heteroaryl group" refers to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

More specifically, the substituted or unsubstituted C6 to C30 aryl group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, or a combination thereof, but is not limited thereto.

More specifically, the substituted or unsubstituted C2 to C30 heterocyclic group may be a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted carbazolyl group, a substituted or unsubstituted dibenzofuranyl group, a substituted or unsubstituted dibenzothiophenyl group, or a combination thereof, but is not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to the highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to the lowest unoccupied molecular orbital (LUMO) level.

Hereinafter, a compound for an organic optoelectronic element according to an embodiment is described.

The compound for the organic optoelectronic element according to an embodiment is represented by a combination of Chemical Formula 1 to Chemical Formula 3.

[Chemical Formula 1]

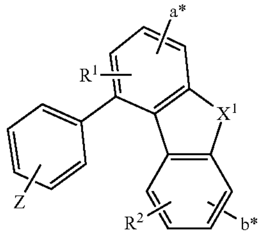

[Chemical Formula 2]

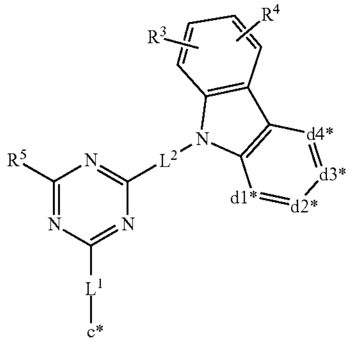

[Chemical Formula 3]

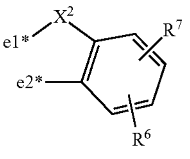

In Chemical Formula 1 to Chemical Formula 3, $X^1$ and $X^2$ are each independently O or S, Z is hydrogen, deuterium, a substituted or unsubstituted C1 to C10 alkyl group, or a substituted or unsubstituted phenyl group, $L^1$ and $L^2$ are each independently a single bond, or a substituted or unsubstituted C6 to C20 arylene group, a* or b* of Chemical Formula 1 is linked to c* of Chemical Formula 2, two adjacent ones of $d_1*$ to $d_4*$ of Chemical Formula 2 are linked to $e_1*$ and $e_2*$ of Chemical Formula 3, respectively, a* or b* not linked to c* of Chemical Formula 2 is each independently $R^a$, the remaining ones not connected to $e_1*$ and $e_2*$ of Chemical Formula 3 of $d_1*$ to $d_4*$ of Chemical Formula 2 are each independently $CR^b$, and $R^a$, $R^b$, and $R^1$ to $R^7$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

The compound represented by the combination of Chemical Formula 1 to Chemical Formula 3 has increased stability of the material by introducing a triazine moiety linked to dibenzofuran (or dibenzothiophene), and simultaneously has additional stability through bipolar characteristics by introducing a fused carbazole moiety. Since the introduction of the fused carbazole moiety has an effect of improving a glass transition temperature relative to the molecular weight, heat resistance may be secured.

In particular, a phenyl group is present at the $1^{st}$ position of dibenzofuran (or dibenzothiophene), so that device characteristics of low driving efficiency and long life-span may be realized due to the effect of improving the deposition film according to the improvement of electron mobility.

In the compound represented by the combination of Chemical Formula 1 to Chemical Formula 3, the combination of Chemical Formula 1 and Chemical Formula 2 may be, for example, represented by Chemical Formula 1A or Chemical Formula 1B depending on the specific linking point of Chemical Formulas 1 and 2.

[Chemical Formula 1A]

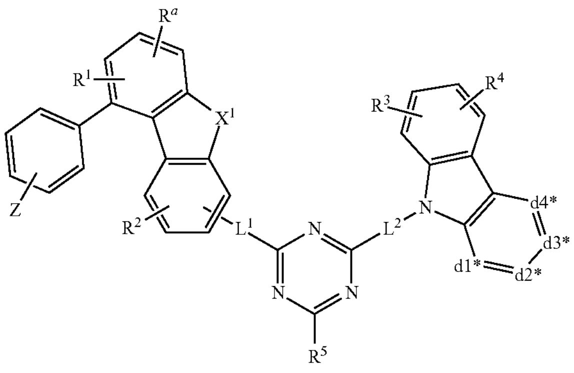

[Chemical Formula 1B]

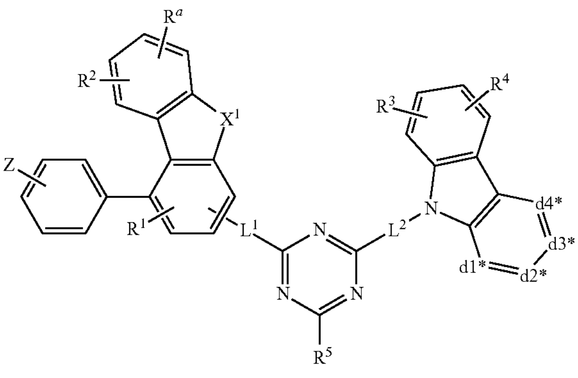

In Chemical Formula 1A and Chemical Formula 1B, $X^1$, Z, $L^1$ and $L^2$, $R^a$, $R^1$ to $R^5$, and $d_1*$ to $d_4*$ are the same as described above.

The combination of Chemical Formulas 1 and 2 may be, for example, represented by Chemical Formula 1A-1 to Chemical Formula 1A-4 and Chemical Formula 1B-1 to Chemical Formula 1B-3, depending on the specific position where dibenzofuran (or dibenzothiophene) is linked to triazine via $L^1$.

[Chemical Formula 1A-1]

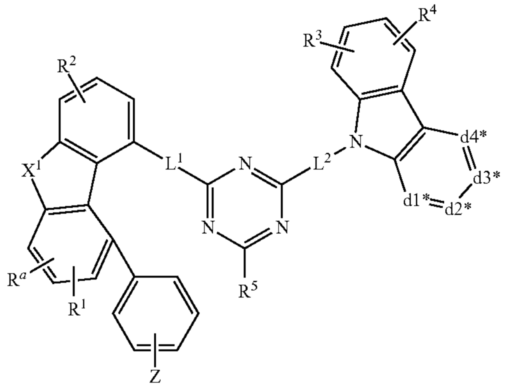

[Chemical Formula 1A-2]

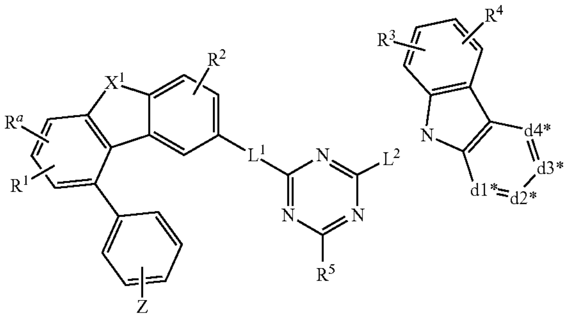

[Chemical Formula 1A-3]

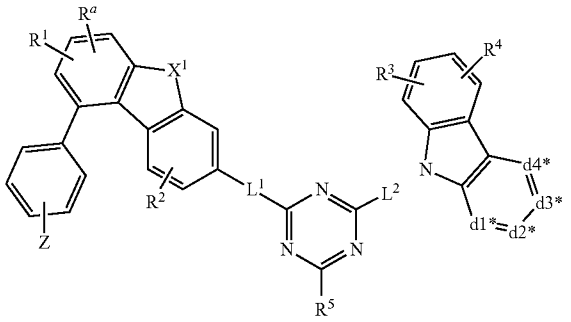

-continued

[Chemical Formula 1A-4]

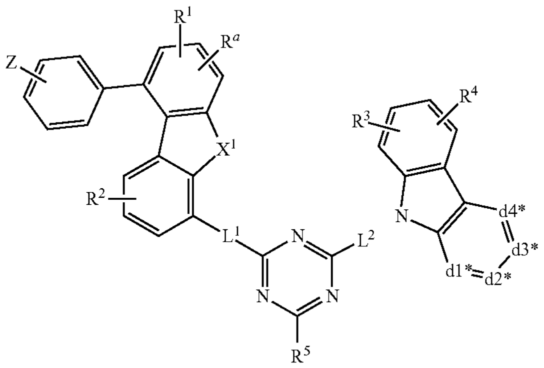

[Chemical Formula 1B-1]

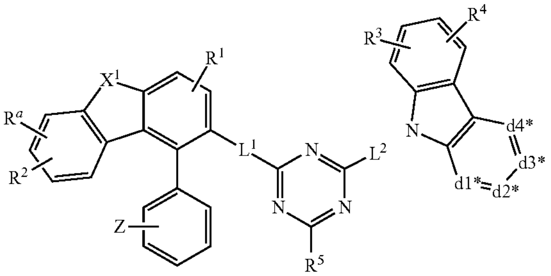

[Chemical Formula 1B-2]

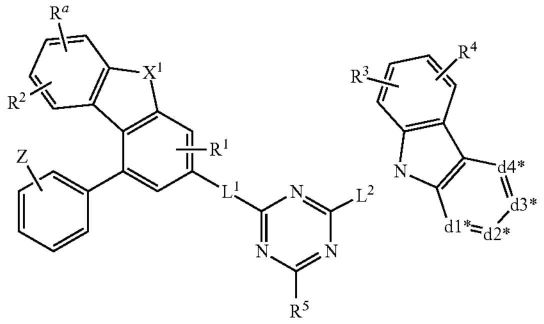

[Chemical Formula 1B-3]

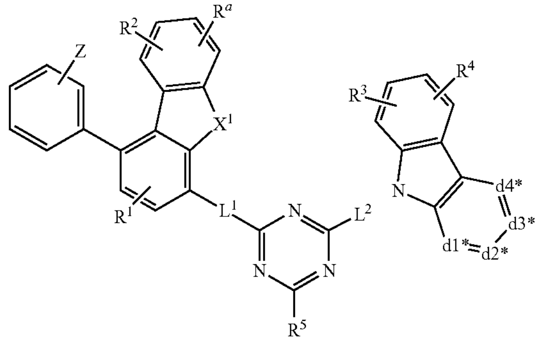

In Chemical Formula 1A-1 to Chemical Formula 1A-4 and Chemical Formula 1B-1 to Chemical Formula 1B-3, $X^1$, Z, $L^1$, $L^2$, $R^a$, $R^1$ to $R^5$, and $d_1$* to $d_4$* are the same as described above.

In an embodiment of the present invention, the combination of Chemical Formulas 1 and 2 may be represented by Chemical Formula 1A-3 or Chemical Formula 1B-2.

In a specific embodiment of the present invention, the combination of Chemical Formulas 1 and 2 may be represented by Chemical Formula 1A-3.

In the compound represented by the combination of Chemical Formula 1 to Chemical Formula 3, the combination of Chemical Formula 2 and Chemical Formula 3 may be, for example, represented by any one of Chemical Formula 2A to Chemical Formula 2F according to the specific connection position of Chemical Formulas 2 and 3.

[Chemical Formula 2A]

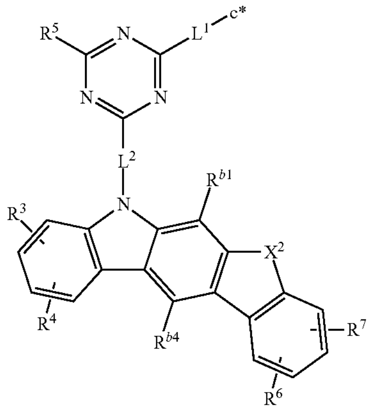

[Chemical Formula 2B]

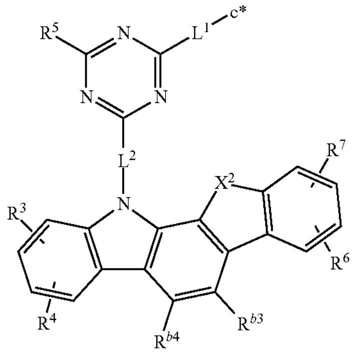

[Chemical Formula 2C]

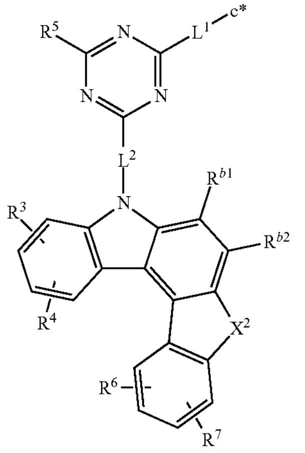

-continued

[Chemical Formula 2D]

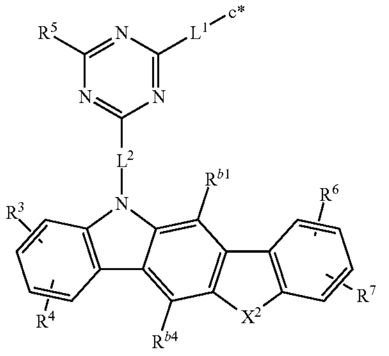

[Chemical Formula 2E]

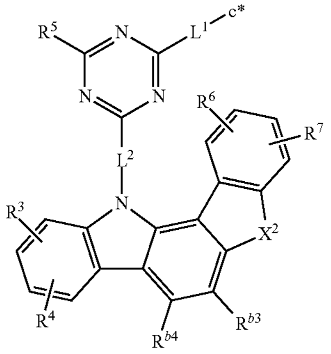

[Chemical Formula 2F]

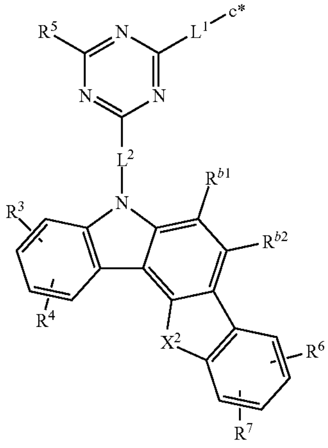

In Chemical Formula 2A to Chemical Formula 2F, $X^2$, $L^1$, $L^2$, c*, and $R^3$ to $R^7$ are the same as described above, and $R^{b1}$ to $R^{b4}$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

In a specific embodiment, the combination of Chemical Formulas 2 and 3 may be represented by any one of Chemical Formula 2A, Chemical Formula 2B, Chemical Formula 2D, and Chemical Formula 2F.

In a more specific embodiment, the combination of Chemical Formulas 1 to 3 may be represented by any one of Chemical Formula 1A-3-2A, Chemical Formula 1A-3-2B, Chemical Formula 1A-3-2D, and Chemical Formula 1A-3-2F.

[Chemical Formula 1A-3-2A]

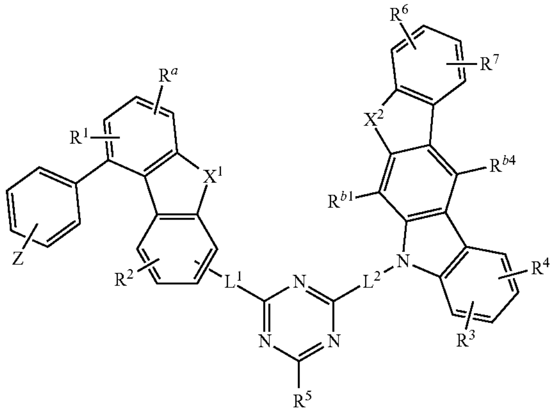

[Chemical Formula 1A-3-2B]

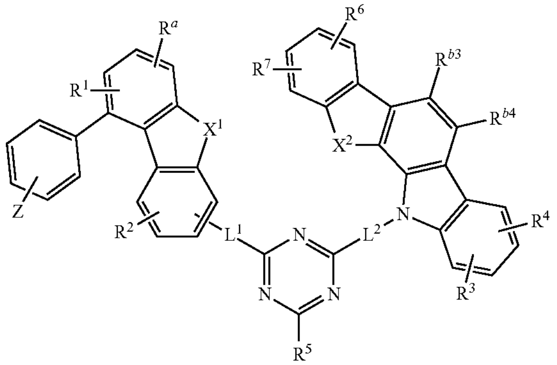

[Chemical Formula 1A-3-2D]

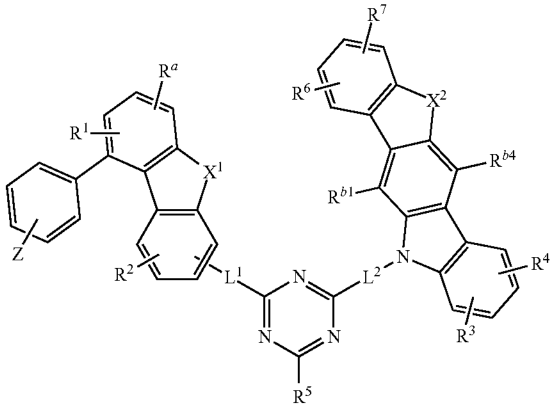

-continued

[Chemical Formula 1A-3-2F]

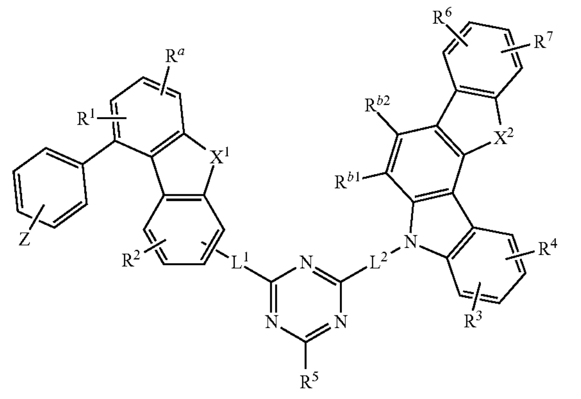

In Chemical Formula 1A-3-2A, Chemical Formula 1A-3-2B, Chemical Formula 1A-3-2D, and Chemical Formula 1A-3-2F, $X^1$, $X^2$, Z, $L^1$, $L^2$, $R^a$, $R^{b1}$ to $R^{b4}$, and $R^1$ to $R^7$ are the same as described above.

In a most specific embodiment, the combination of Chemical Formulas 1 to 3 may be represented by any one of Chemical Formula 1A-3-2A, Chemical Formula 1A-3-2D, and Chemical Formula 1A-3-2F.

For example, $X^1$ and $X^2$ may each be "O."

For example, $X^1$ may be "O" and $X^2$ may be "S."

For example, $X^1$ may be "S" and $X^2$ may be "O."

For example, Z may be hydrogen or a phenyl group.

For example, $L^1$ and $L^2$ may each independently be a single bond or a substituted or unsubstituted phenylene group and specifically, $L^1$ may be a single bond, $L^2$ may be a phenylene group, or $L^1$ may be a phenylene group, and $L^2$ may be a single bond. More specifically, both $L^1$ and $L^2$ may be a single bond.

For example, $R^a$, $R^b$, $R^{b1}$ to $R^{b4}$, and $R^1$ to $R^4$, $R^6$, and $R^7$ may each independently represent hydrogen or a substituted or unsubstituted phenyl group.

For example, $R^5$ may be a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, a substituted or unsubstituted dibenzothiophenyl group, or a substituted or unsubstituted carbazolyl group, and in an embodiment, $R^5$ may be any one selected from the substituents of Group I.

[Group I]

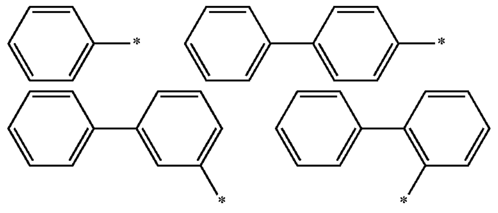

-continued

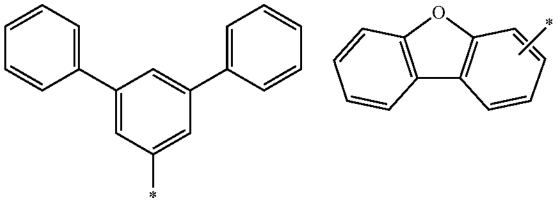

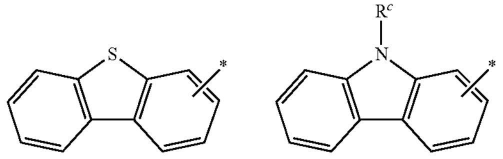

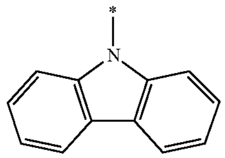

In Group I, $R^c$ is a C1 to C10 alkyl group or a C6 to C12 aryl group, and * is a linking point.

In a more specific embodiment, $R^5$ may be a phenyl group.

For example, the compound for the organic optoelectronic element represented by the combination of Chemical Formula 1 to Chemical Formula 3 may be one selected from the compounds of Group 1, but is not limited thereto.

[Group 1]

[A-1]

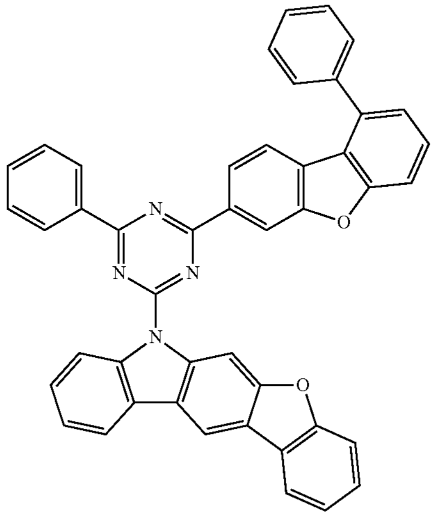

-continued
[A-2]
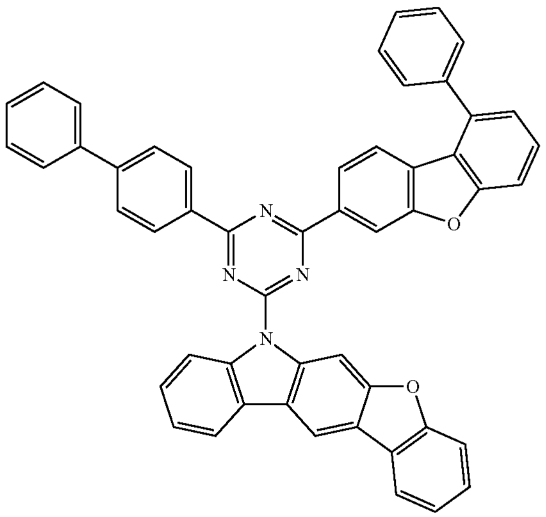
[A-3]
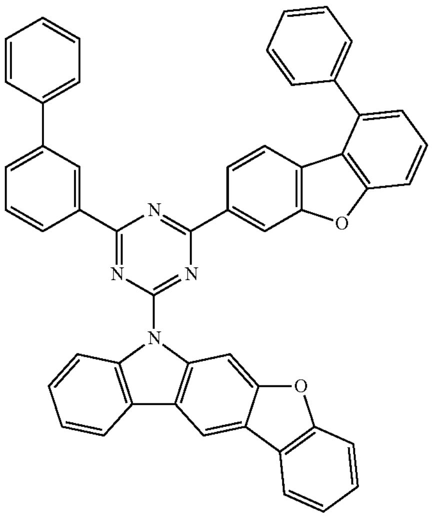
[A-4]
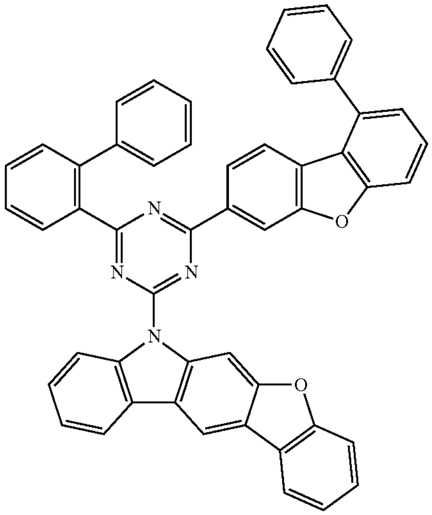
-continued
[A-5]
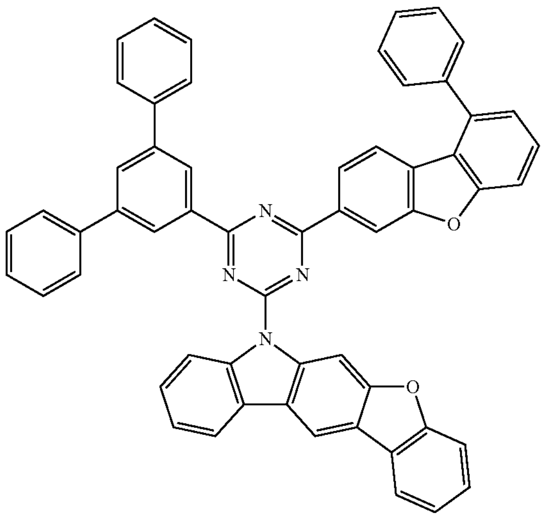
[A-6]
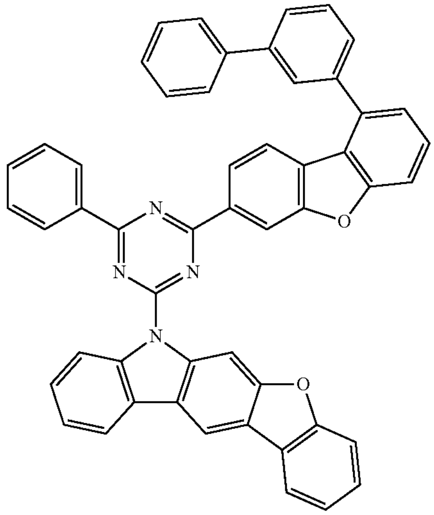
[A-7]
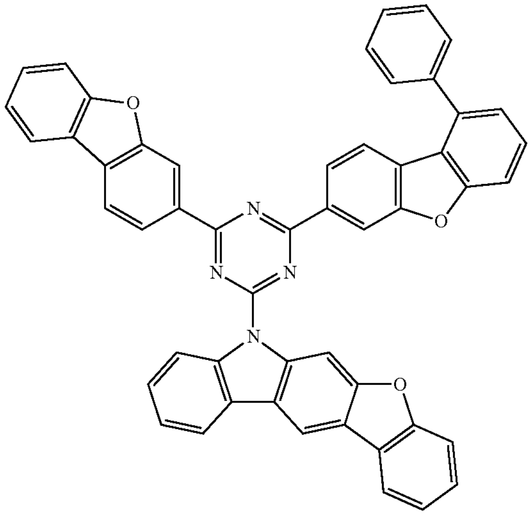

-continued
[A-8]
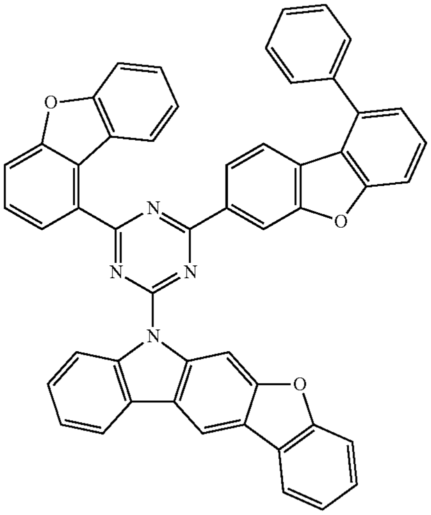
[A-9]
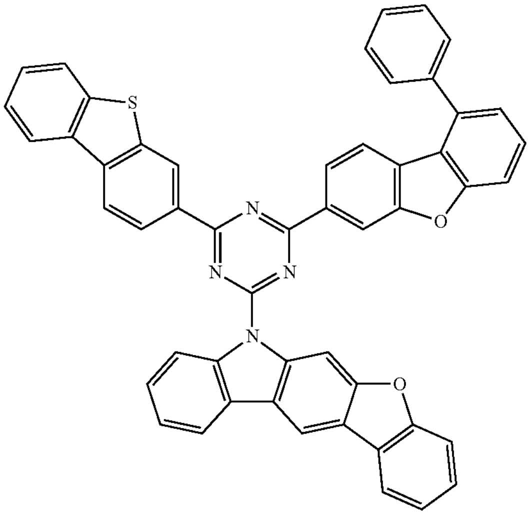
[A-10]
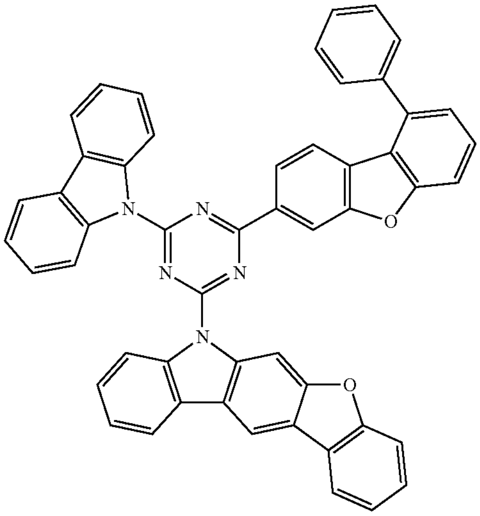
-continued
[A-11]
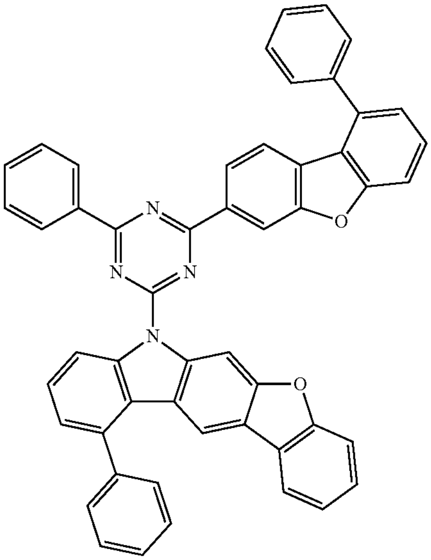
[A-12]
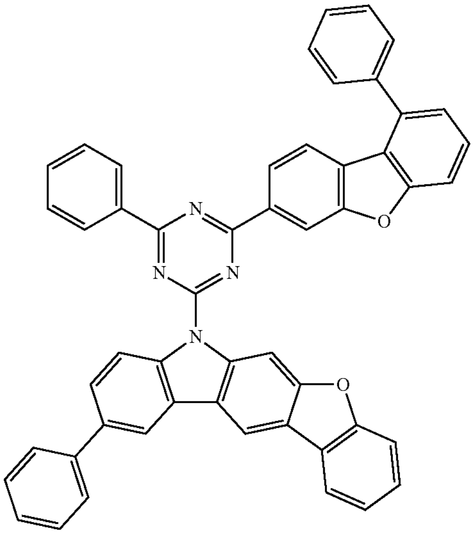
[A-13]
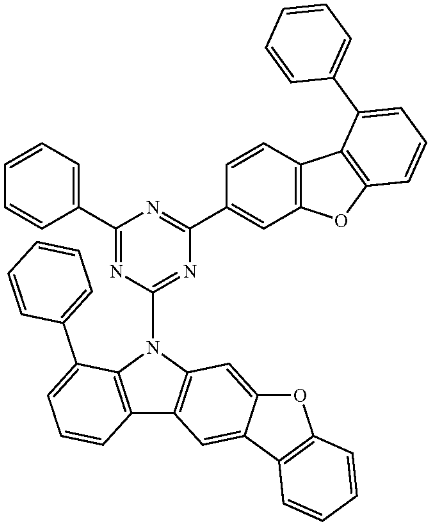

-continued
[A-14]
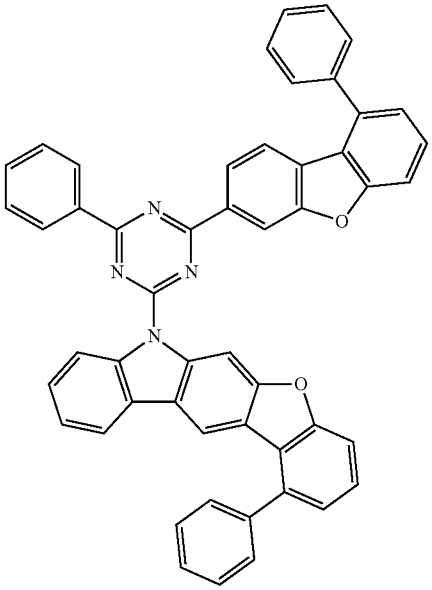
[A-15]
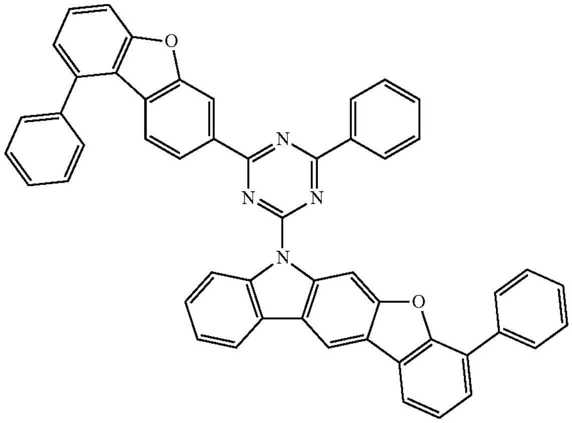
[A-16]
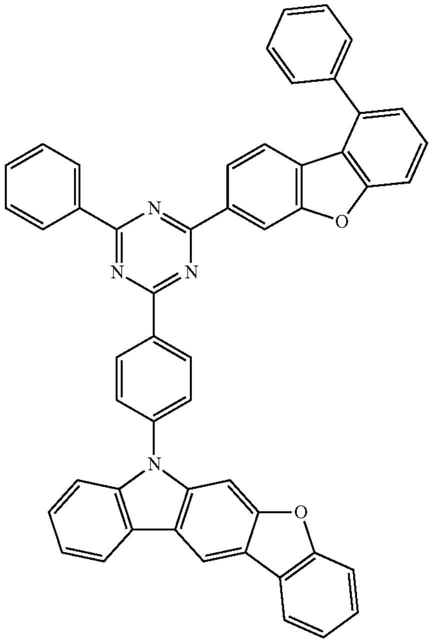
-continued
[A-17]
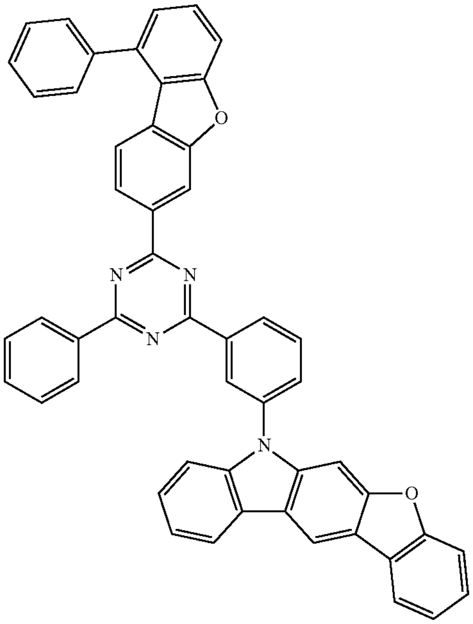
[A-18]
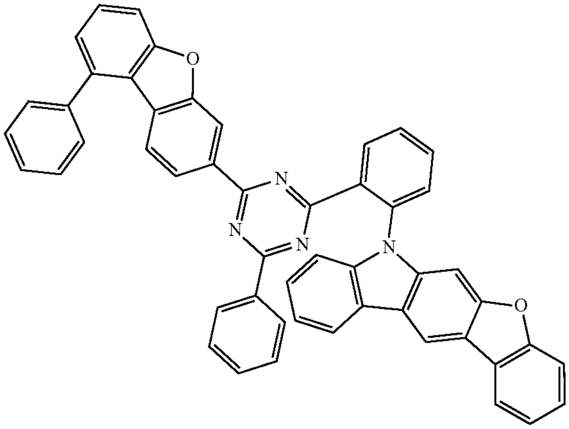

-continued
[A-19]
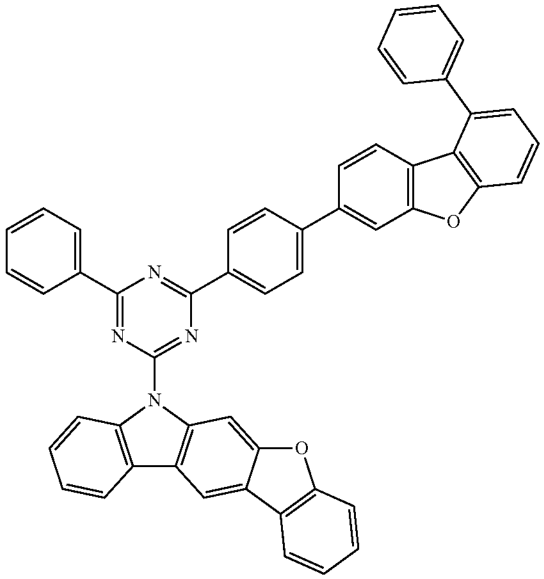
[A-20]
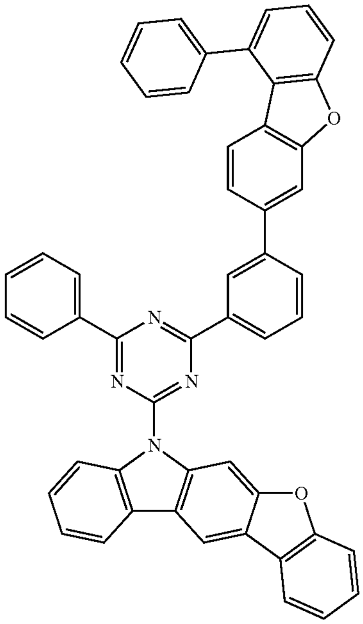
-continued
[A-21]
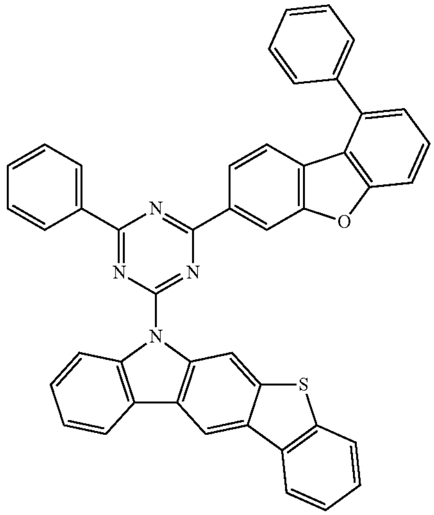
[A-22]
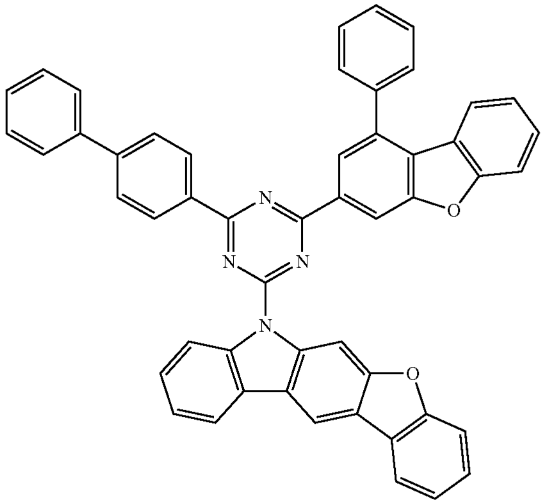
[A-23]
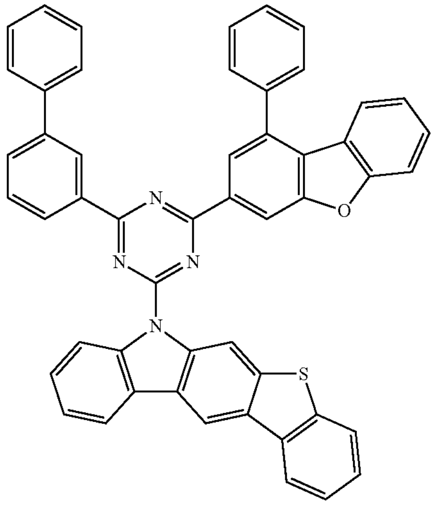

-continued
[A-24]
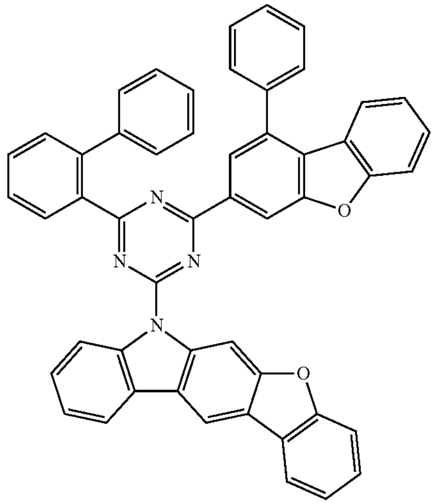
[A-25]
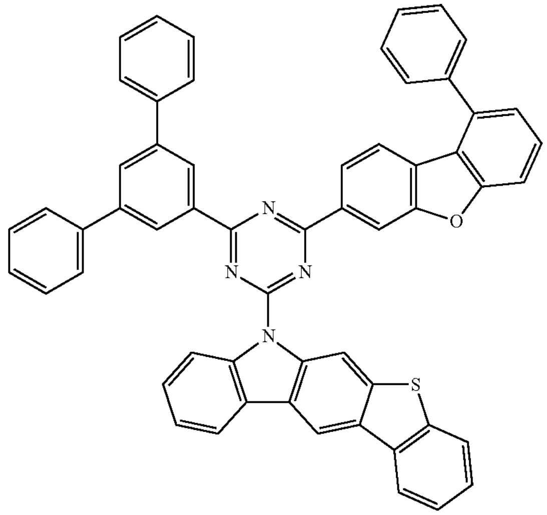
[A-26]
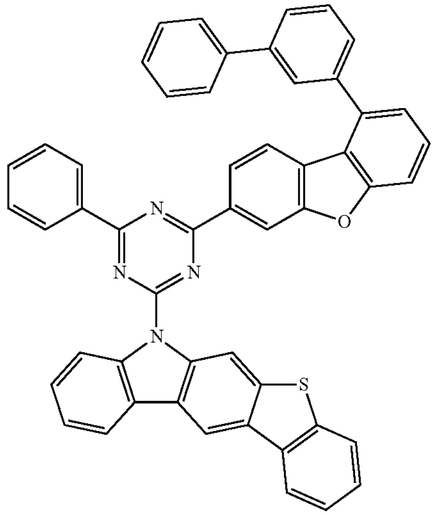
-continued
[A-27]
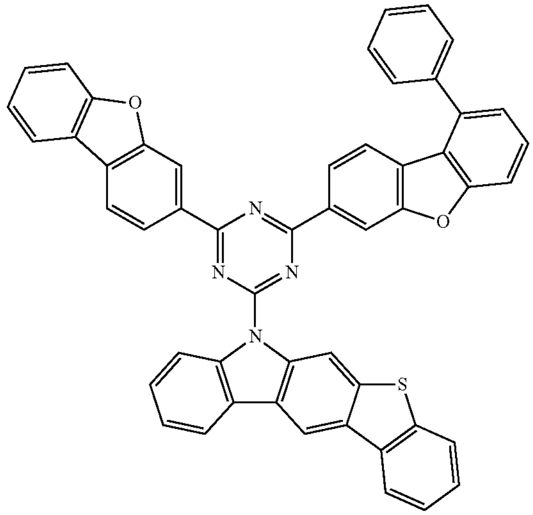
[A-28]
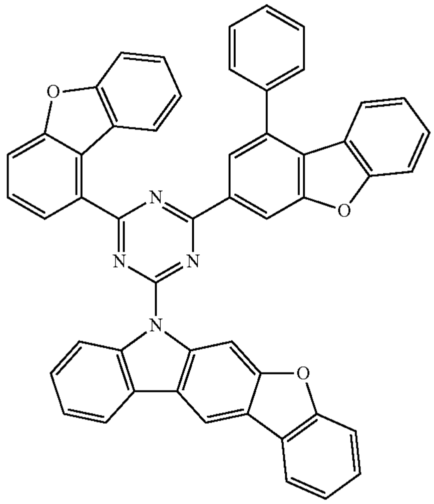
[A-29]
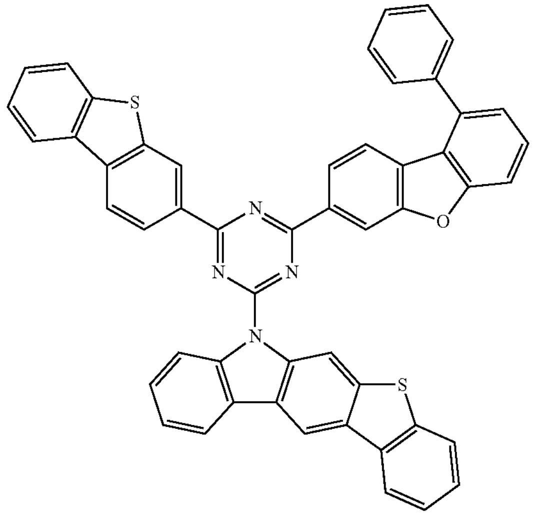

-continued
[A-30]
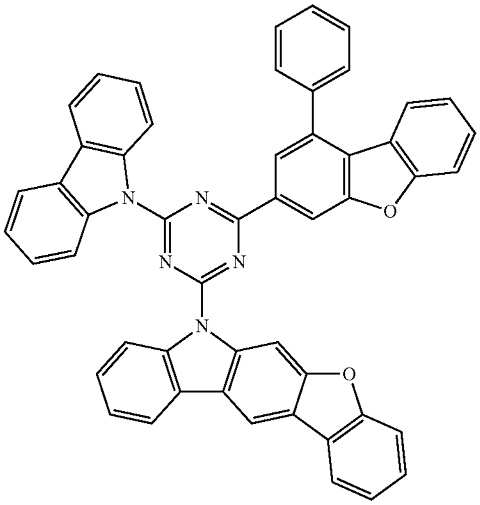
[A-31]
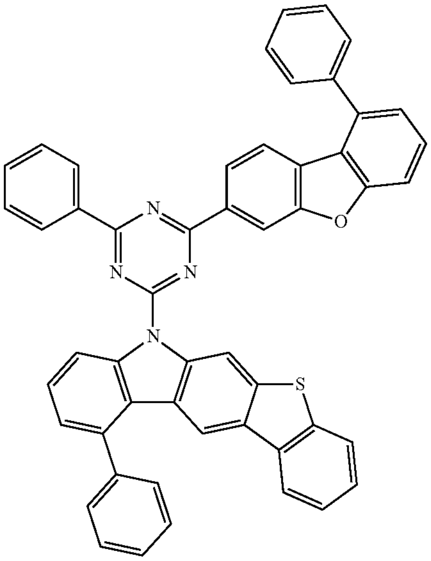
[A-32]
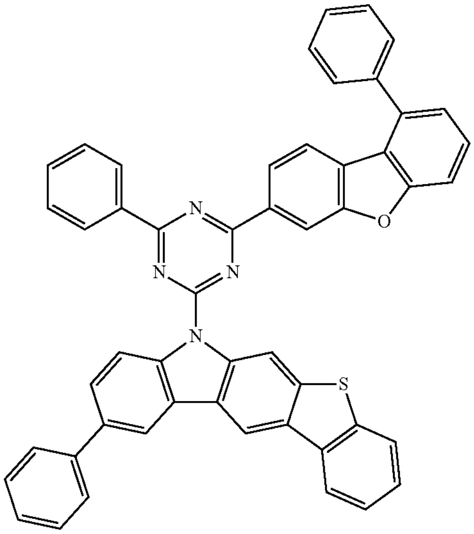
-continued
[A-33]
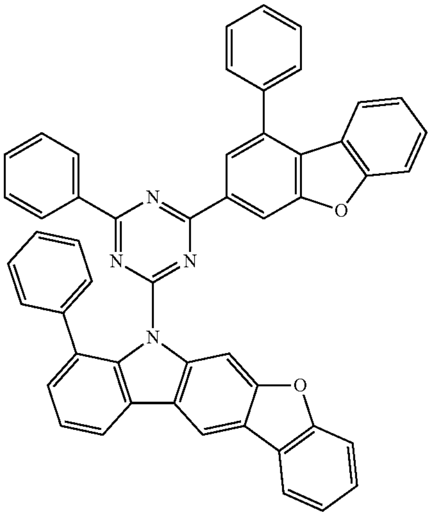
[A-34]
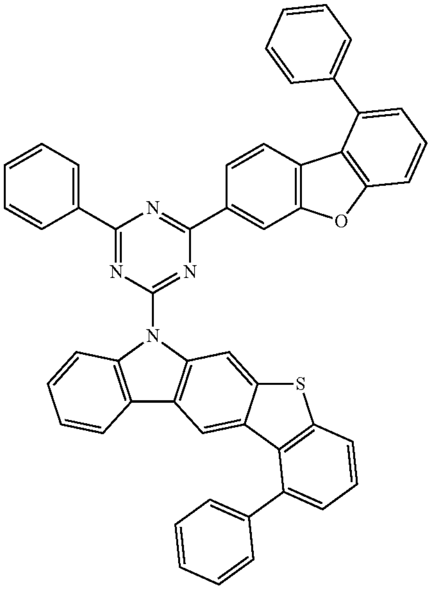
[A-35]
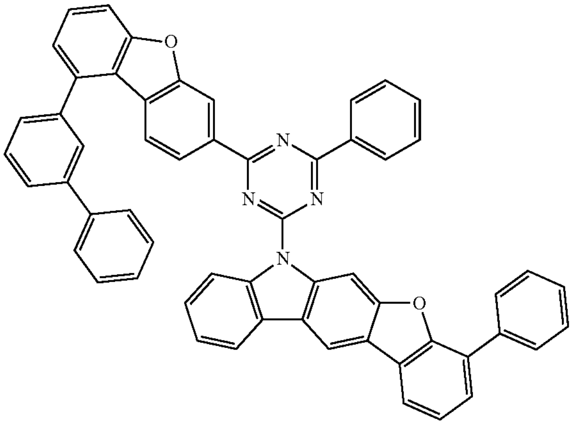

-continued
[A-36]
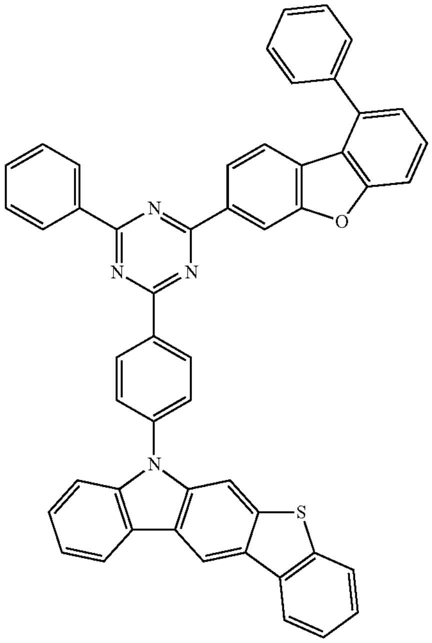
[A-37]
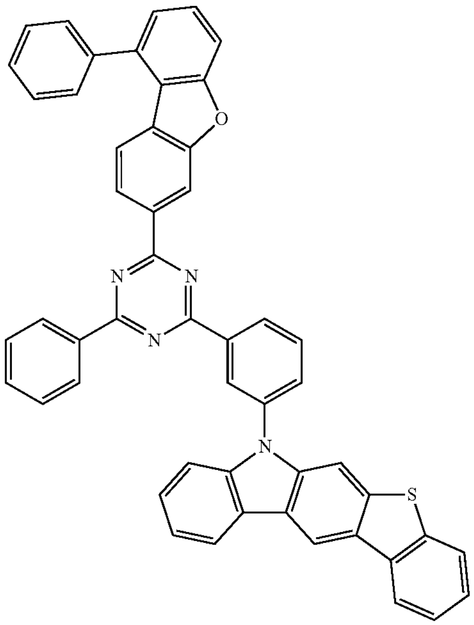
-continued
[A-38]
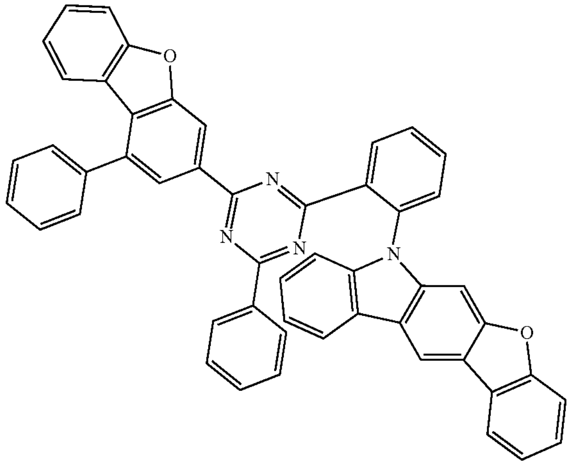
[A-39]
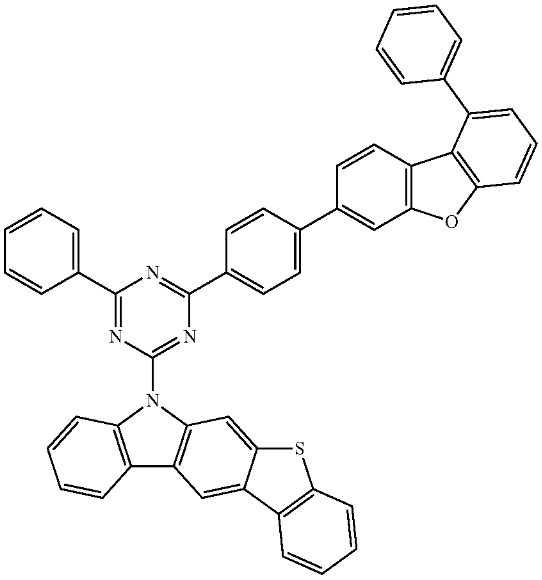

-continued
[A-40]
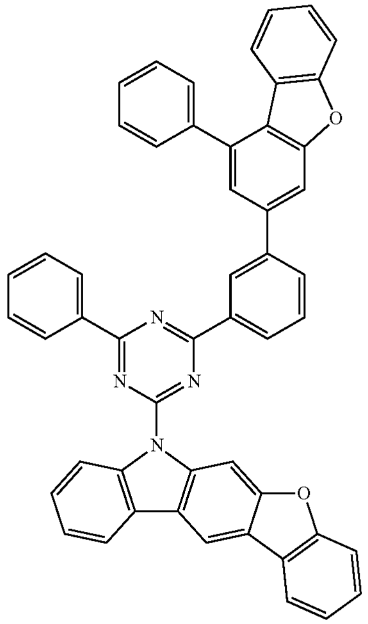
[A-41]
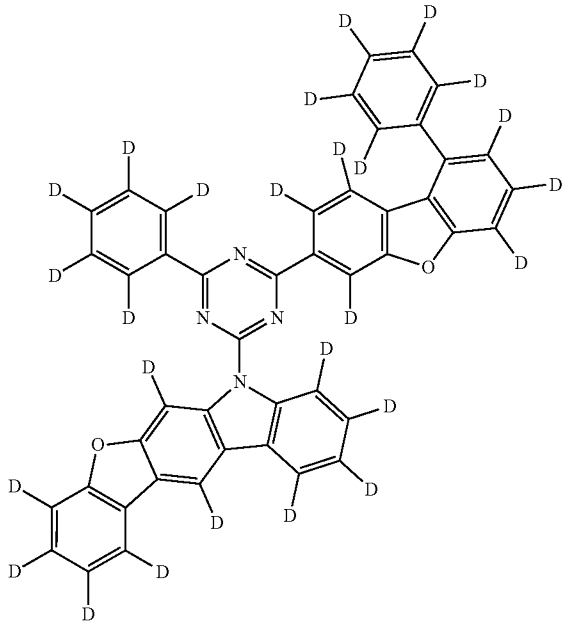
-continued
[A-42]
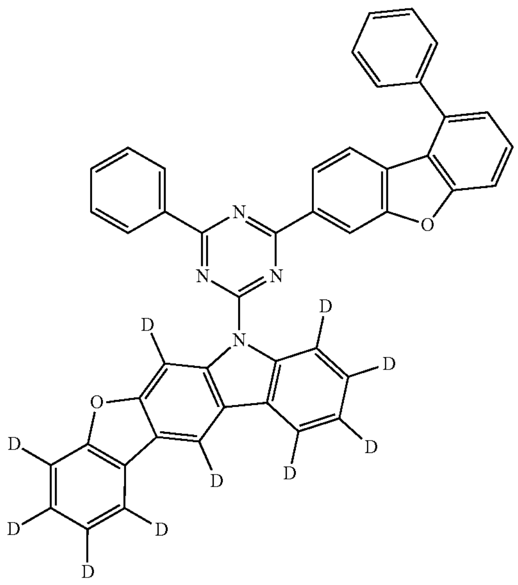
[A-43]
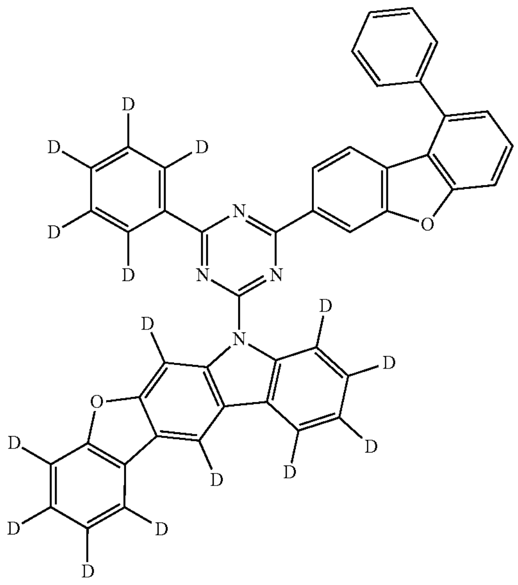

-continued
[A-44]
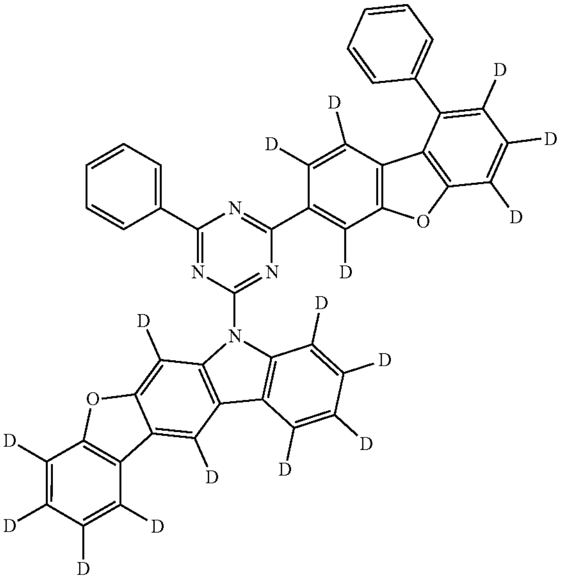
[A-45]
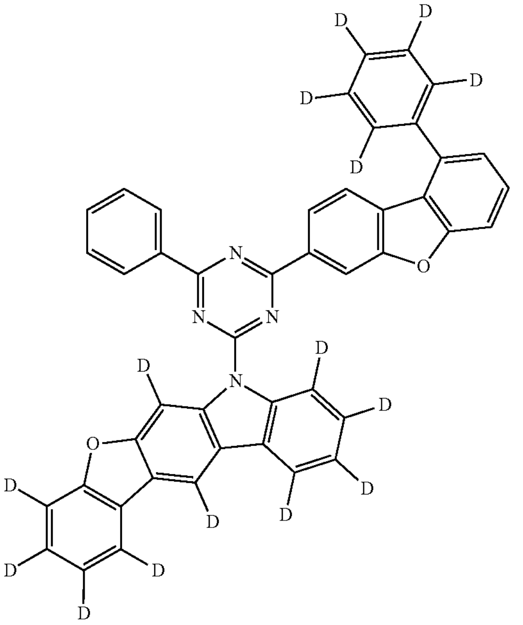
-continued
[A-46]
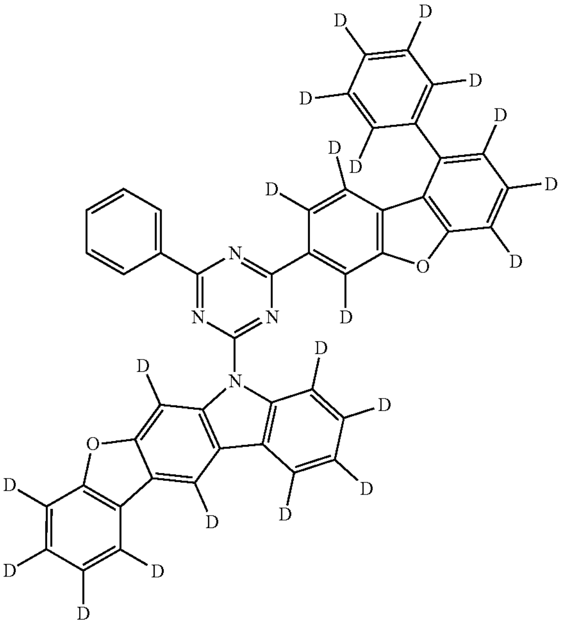
[A-47]
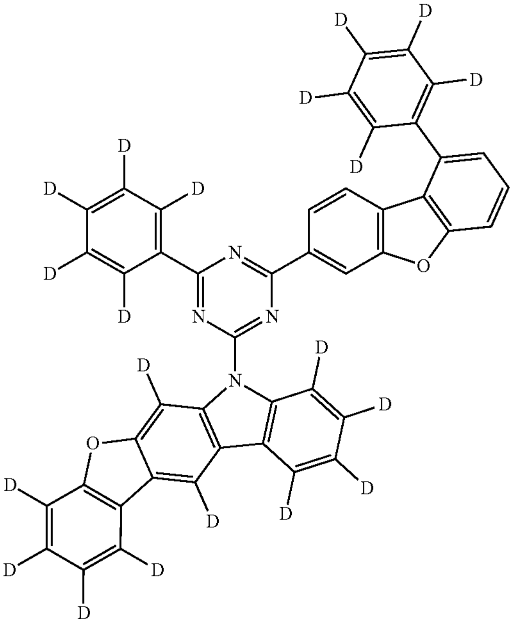

-continued
[A-48]
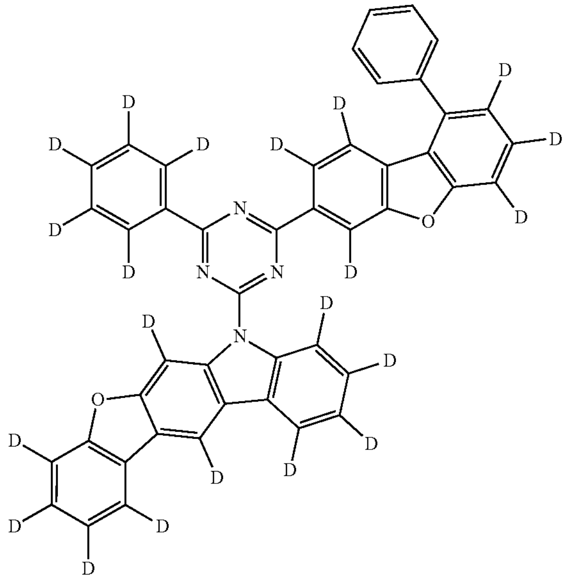
[A-49]
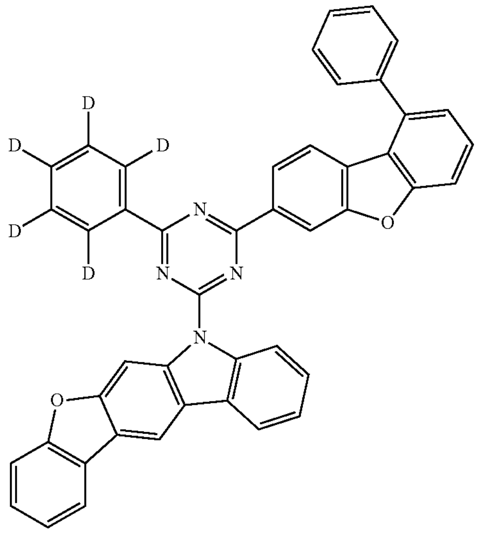
-continued
[A-50]
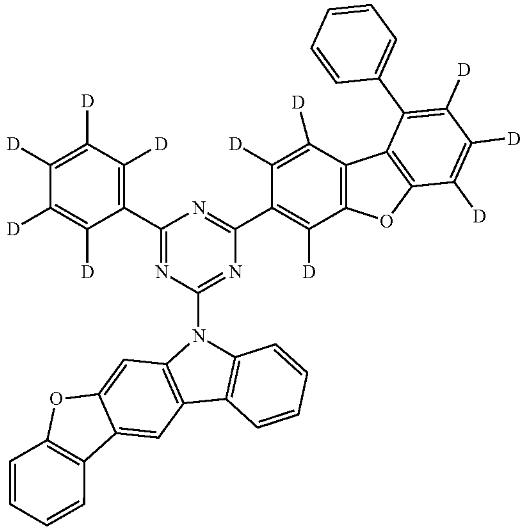
[A-51]
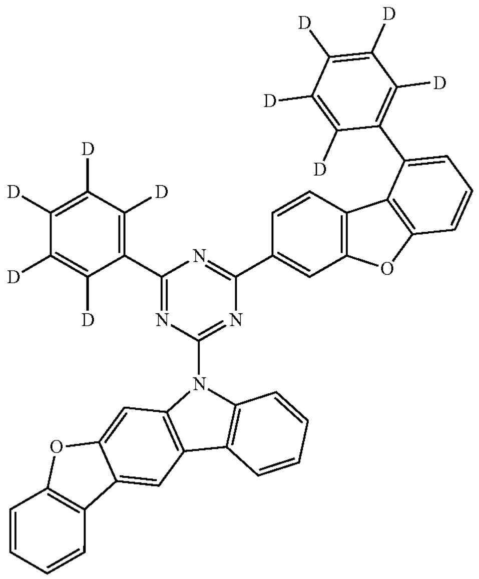

-continued
[A-52]
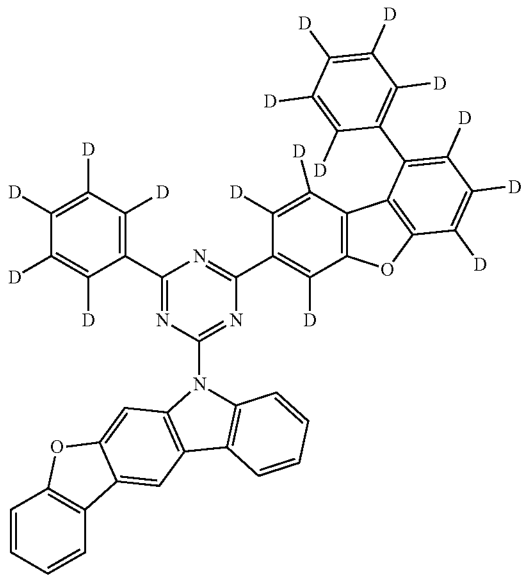
[A-53]
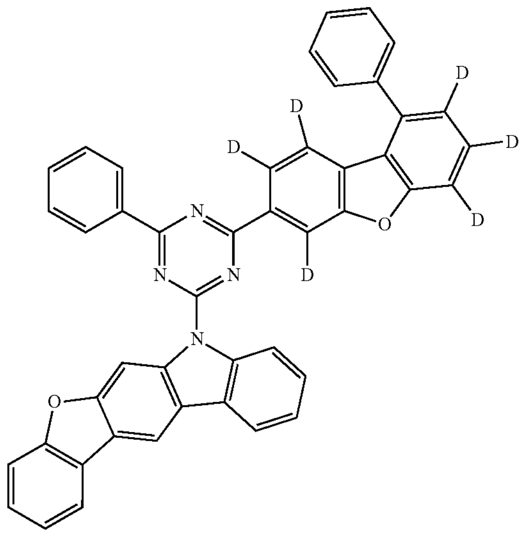
-continued
[A-54]
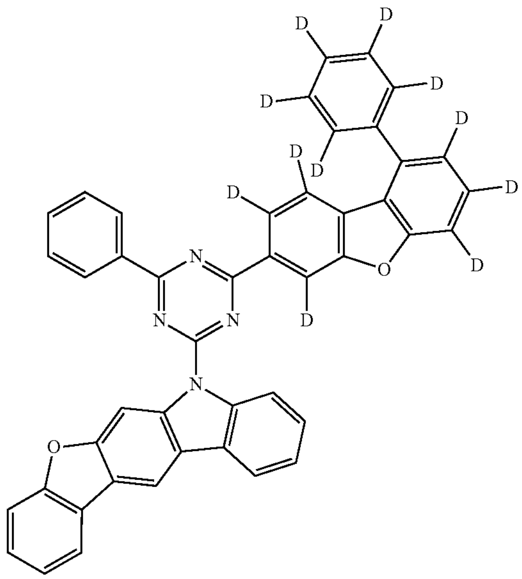
[A-55]
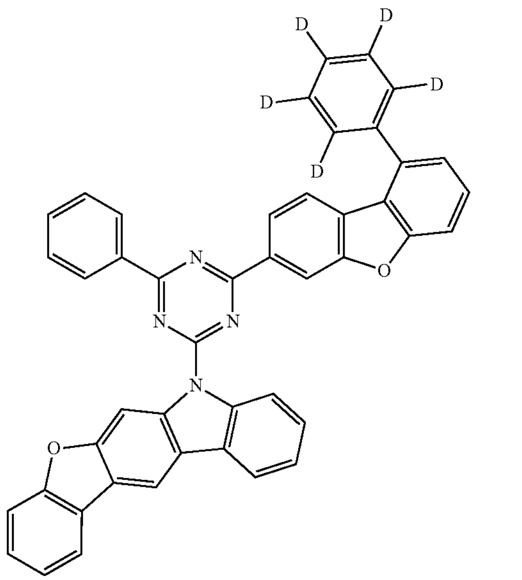

-continued
[A-56]
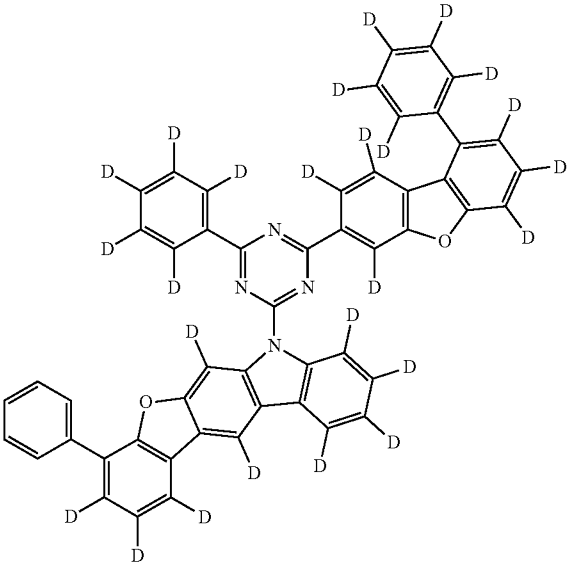
[A-57]
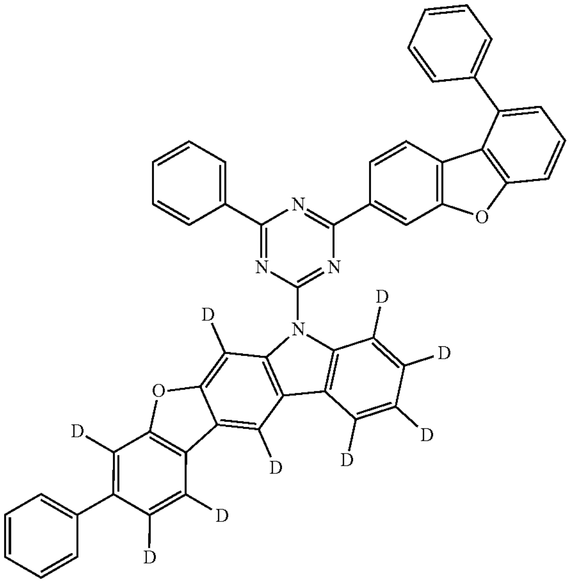
-continued
[A-58]
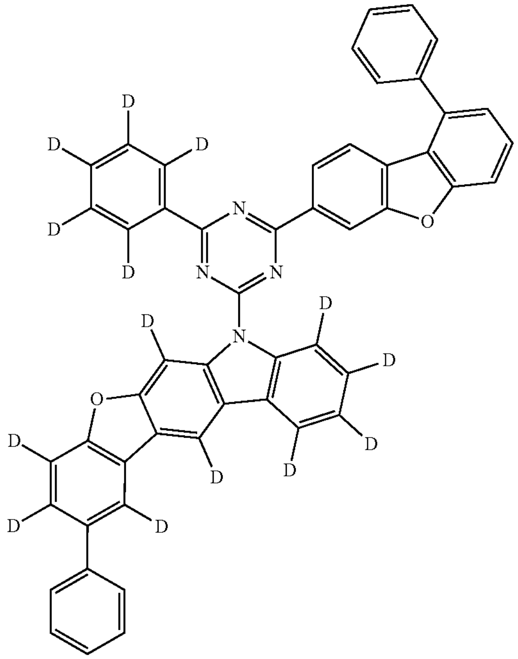
[A-59]
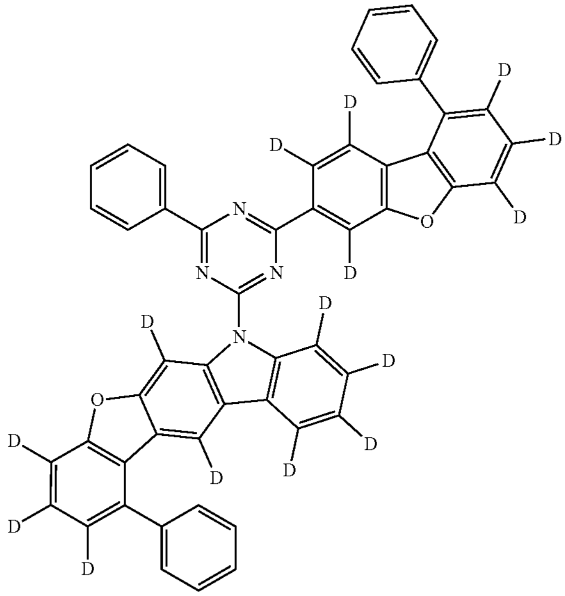

-continued
[A-60]
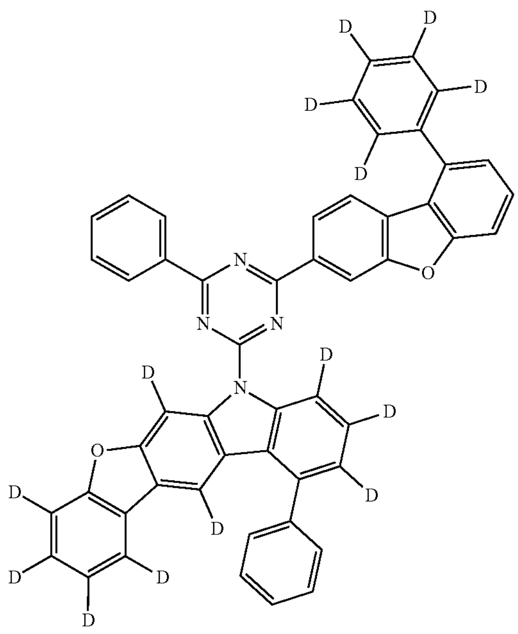
[A-61]
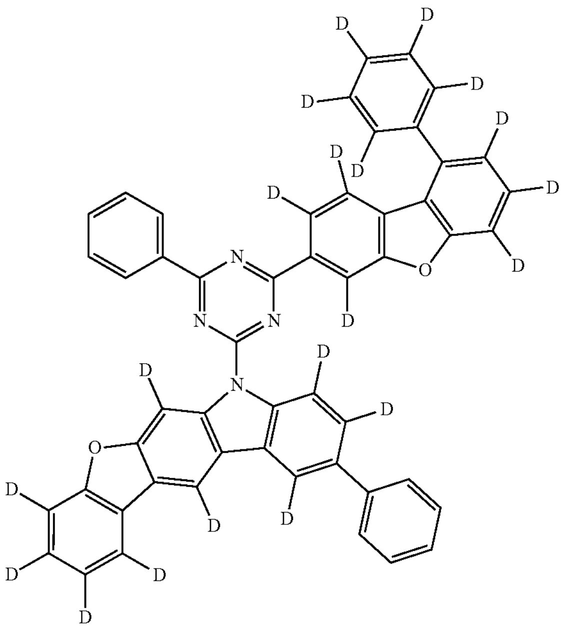
-continued
[A-62]
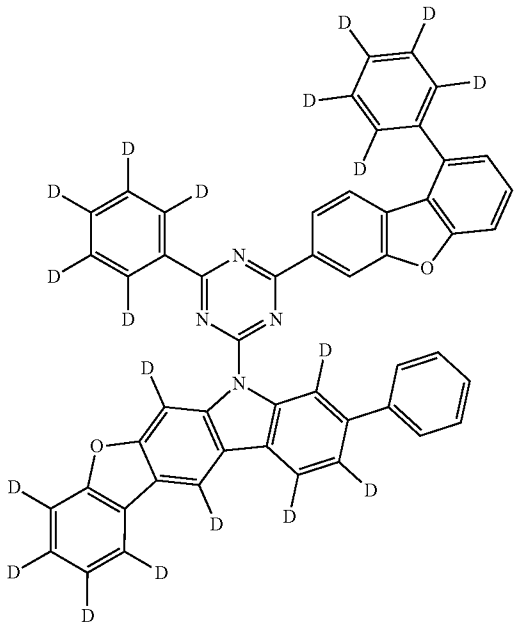
[A-63]
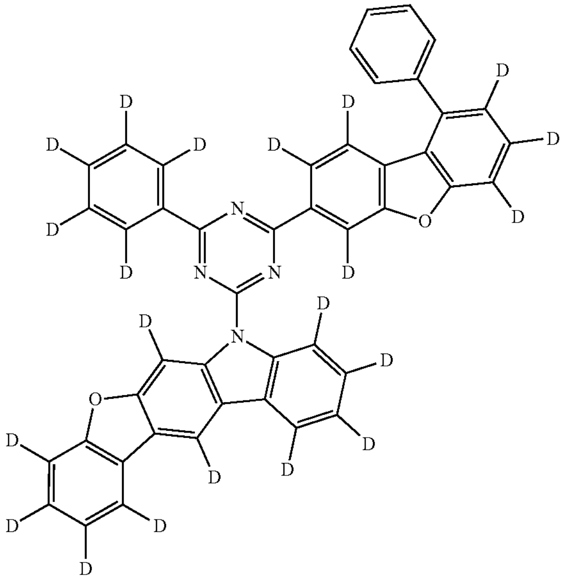

[A-64]
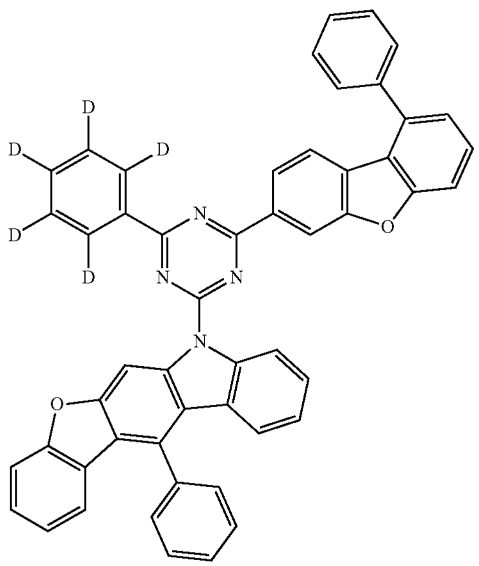
[A-65]
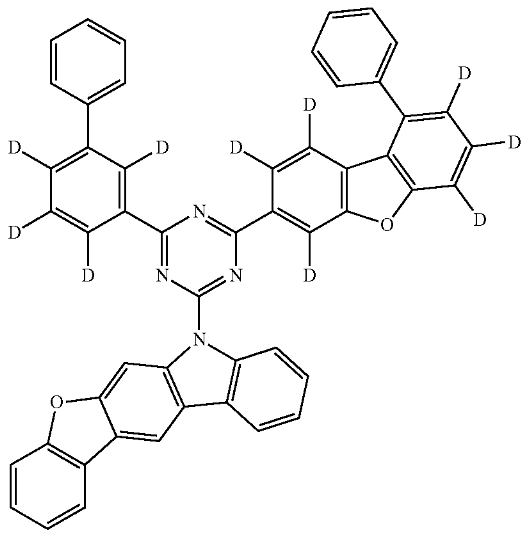
[A-66]
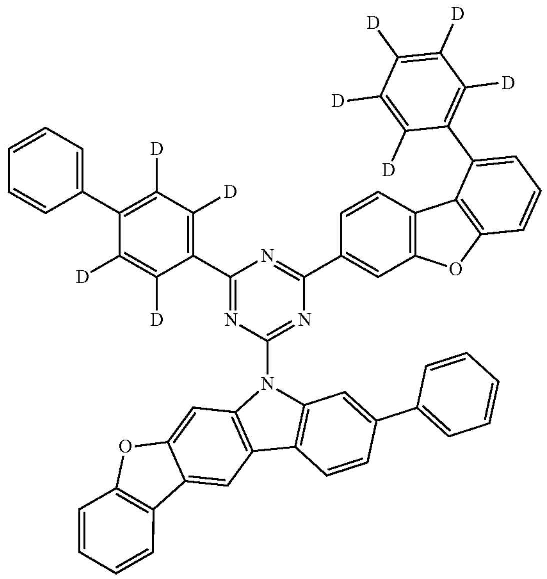
[A-67]
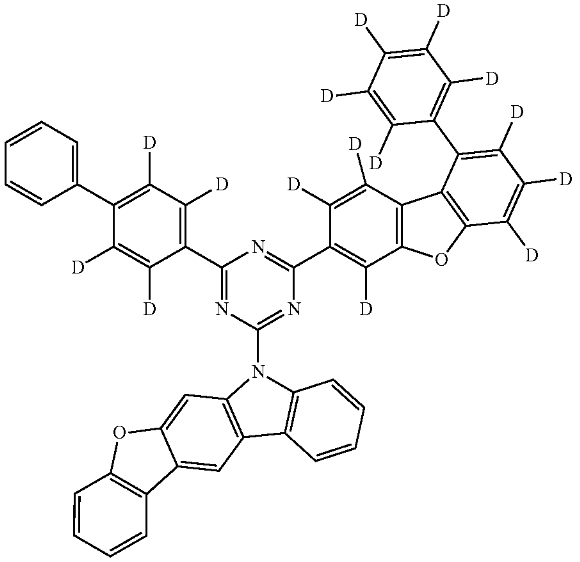

-continued
[A-68]
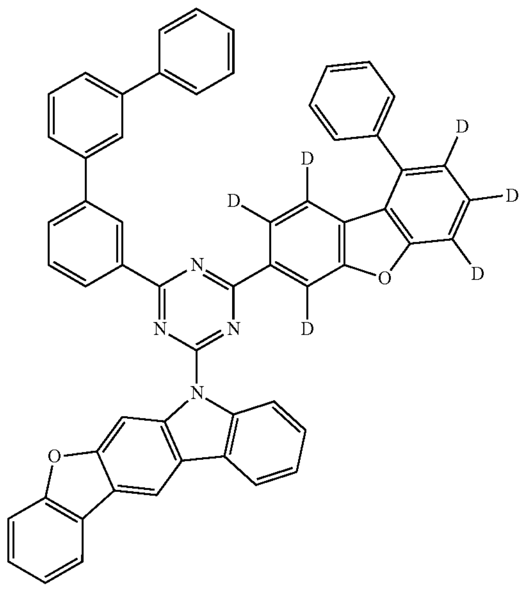
[A-69]
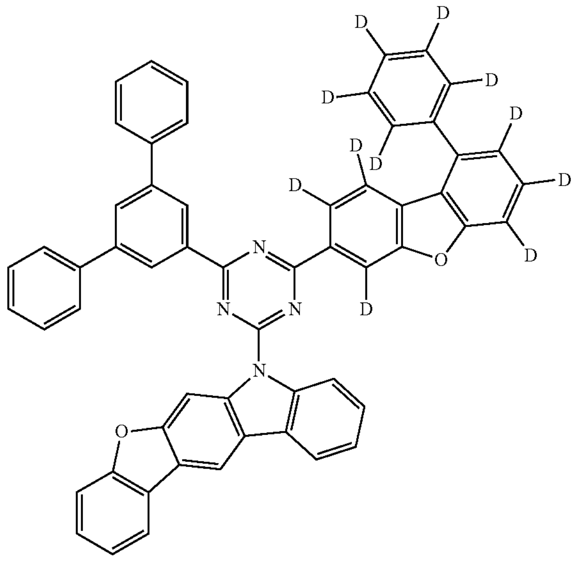
-continued
[A-70]
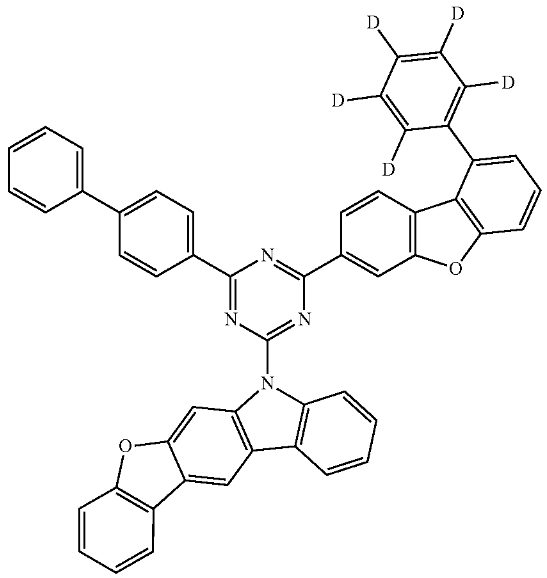
[A-71]
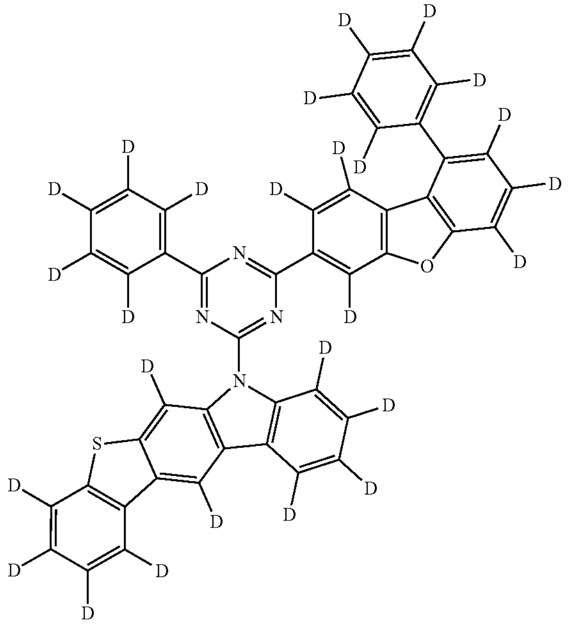

-continued
[A-72]
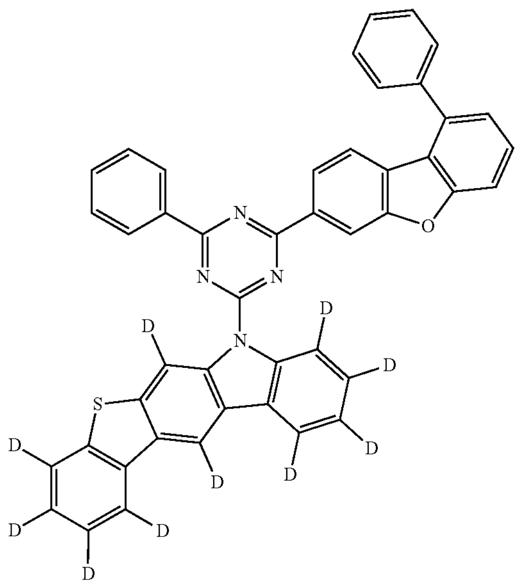
[A-73]
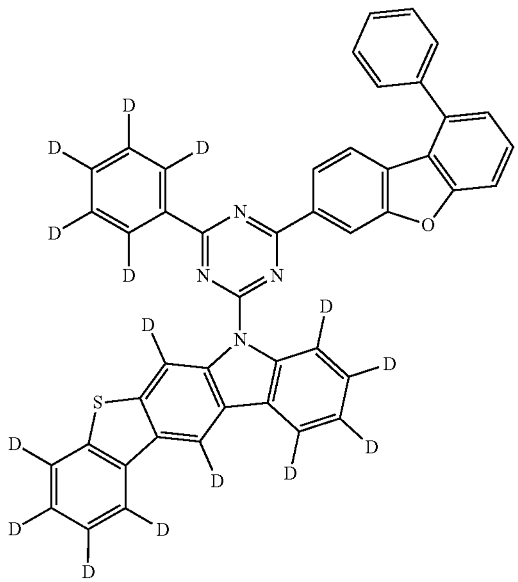
-continued
[A-74]
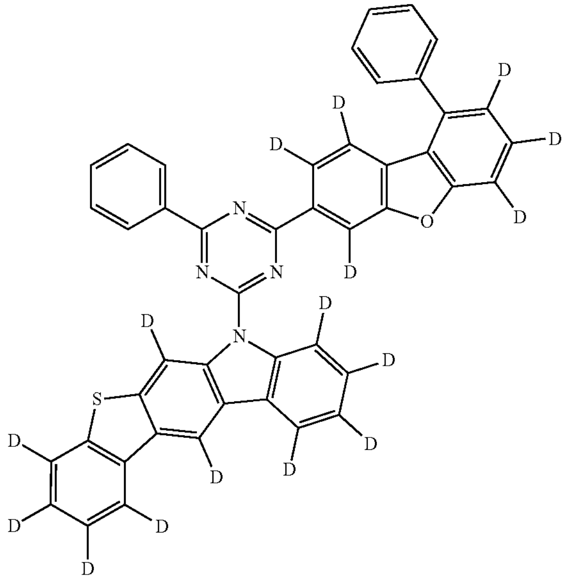
[A-75]
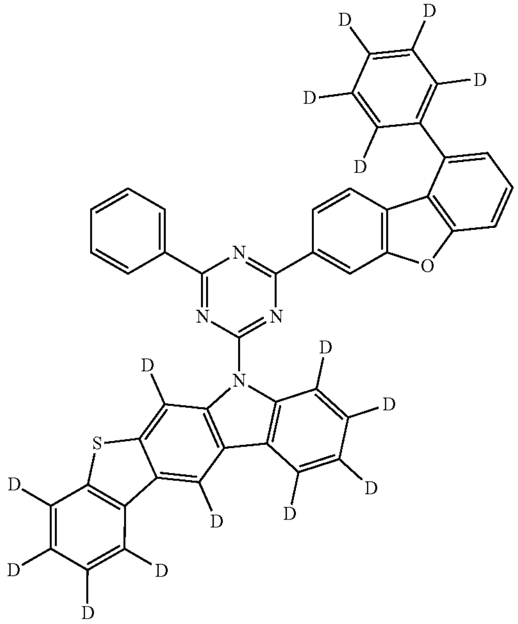

-continued
[A-76]
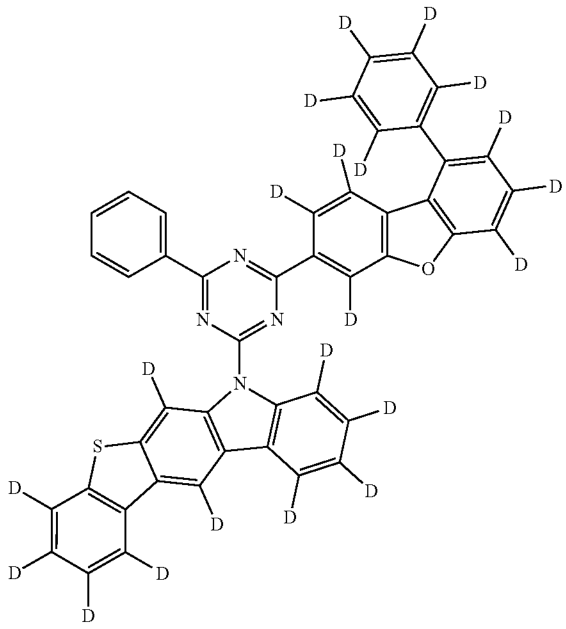
[A-77]
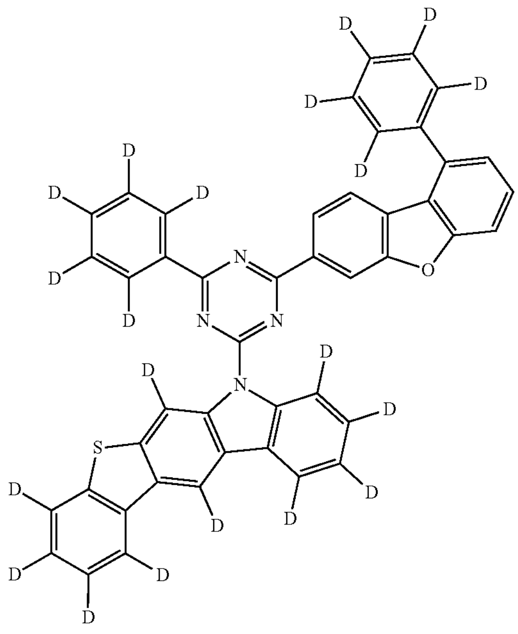
-continued
[A-78]
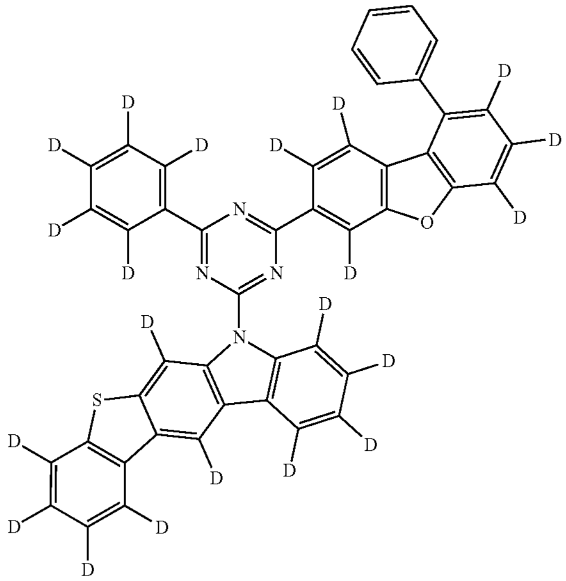
[A-79]
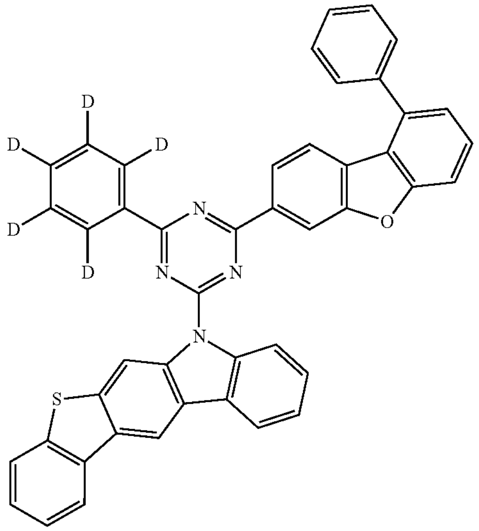

-continued
[A-80]
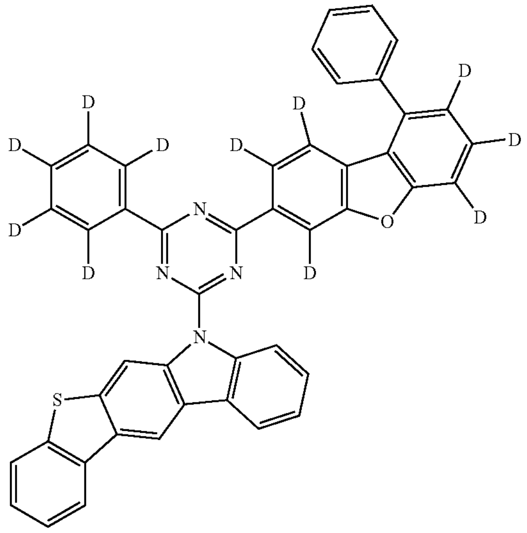
[A-81]
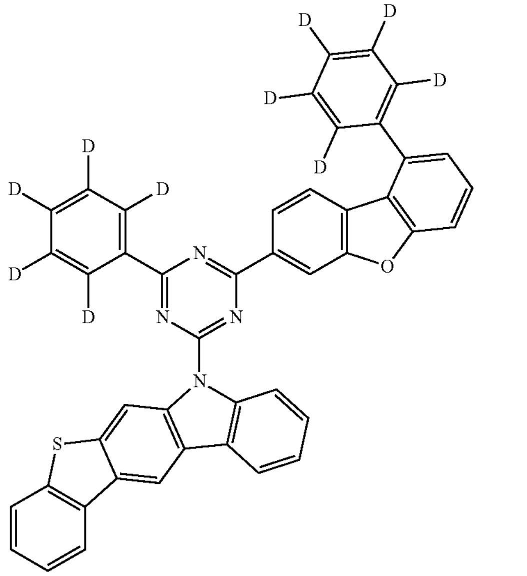
-continued
[A-82]
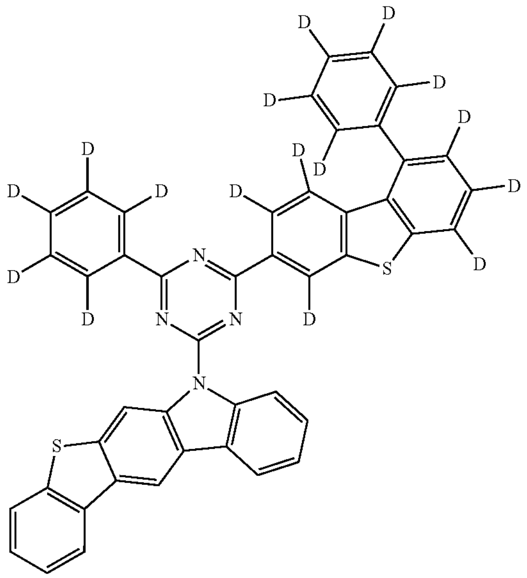
[A-83]
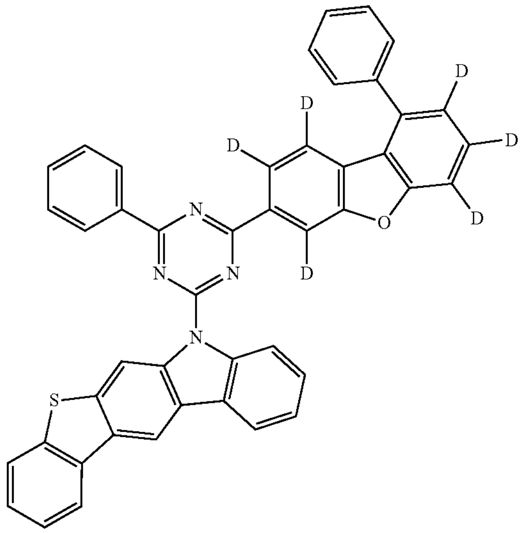

-continued
[A-84]
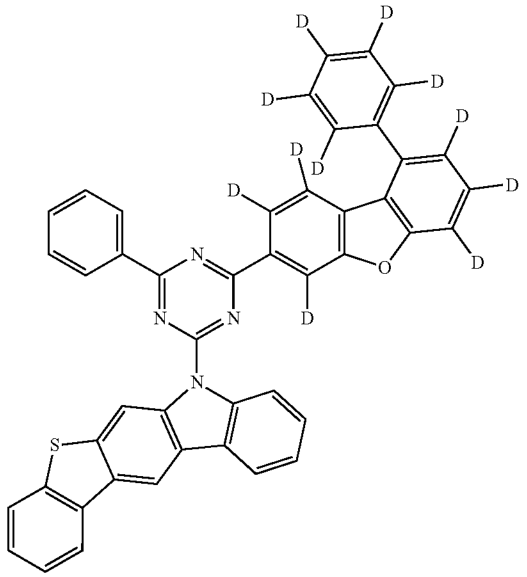
[A-85]
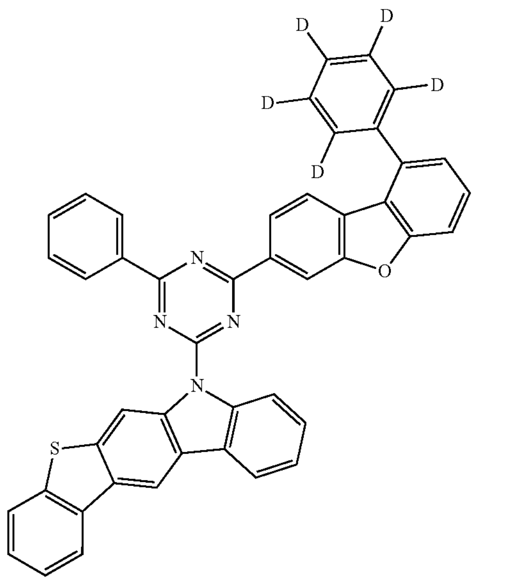
-continued
[A-86]
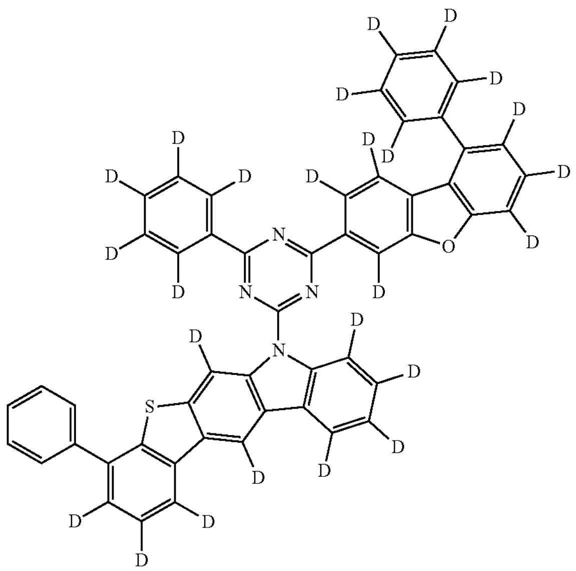
[A-87]
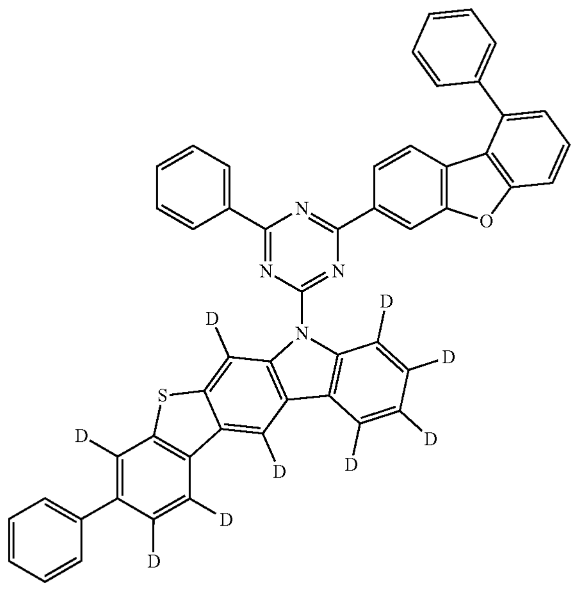

-continued
[A-88]
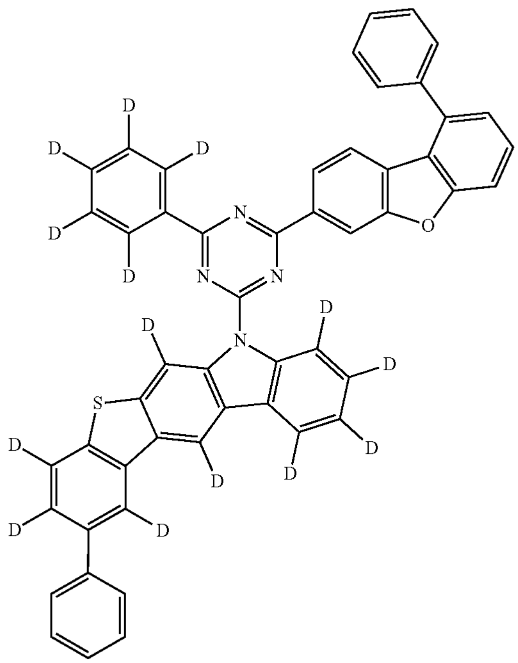
[A-89]
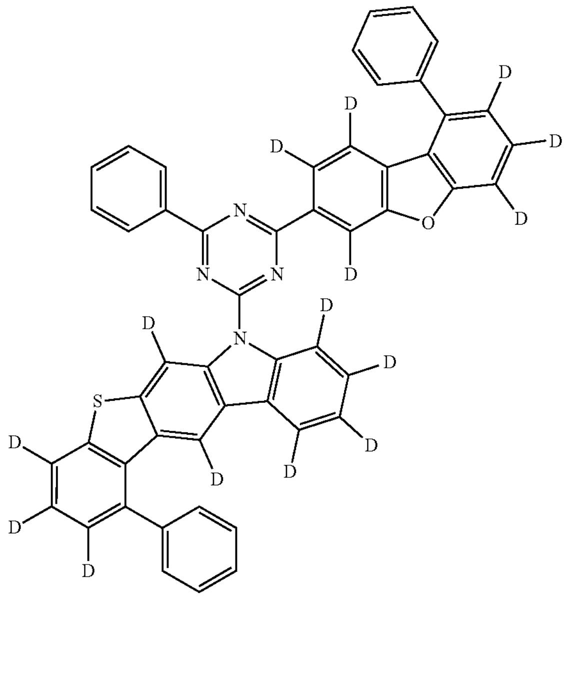
-continued
[A-90]
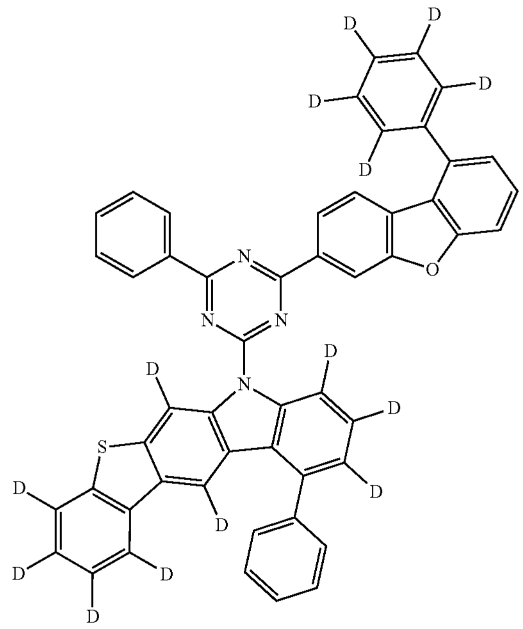
[A-91]
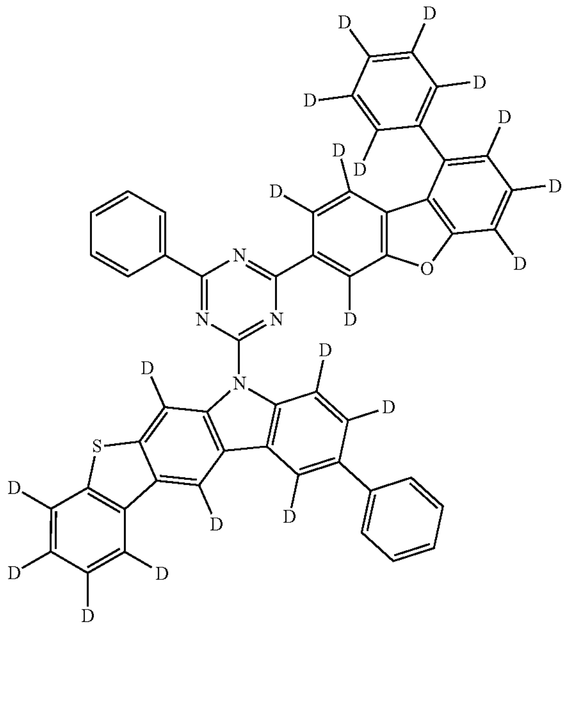

-continued
[A-92]
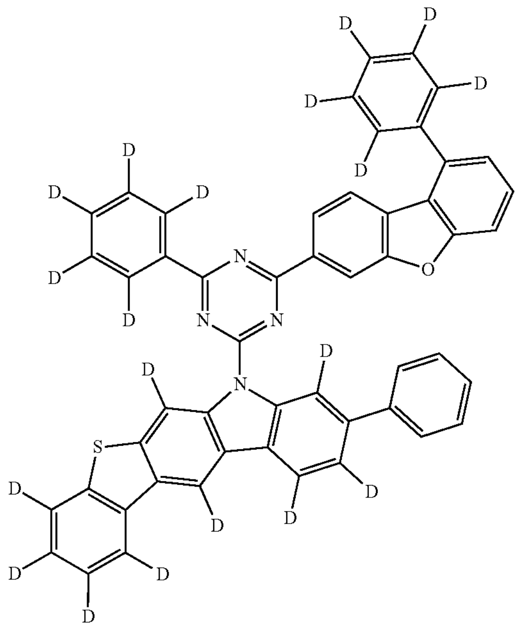
[A-93]
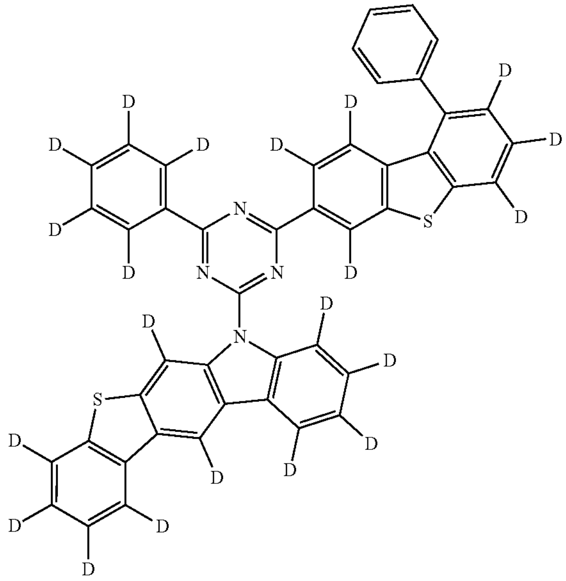
-continued
[A-94]
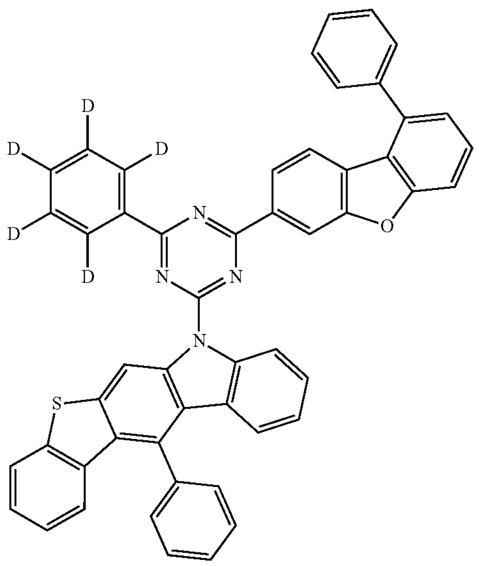
[A-95]
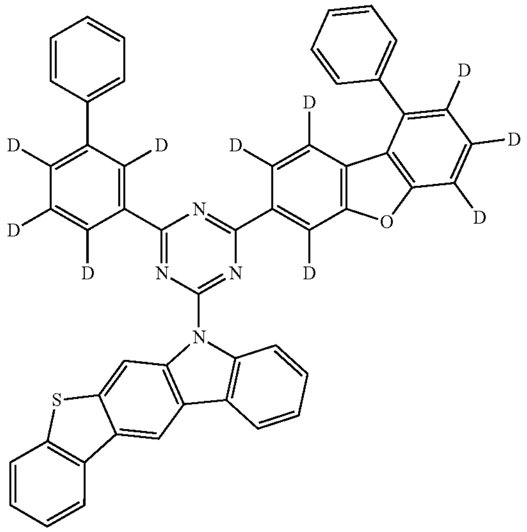

-continued
[A-96]
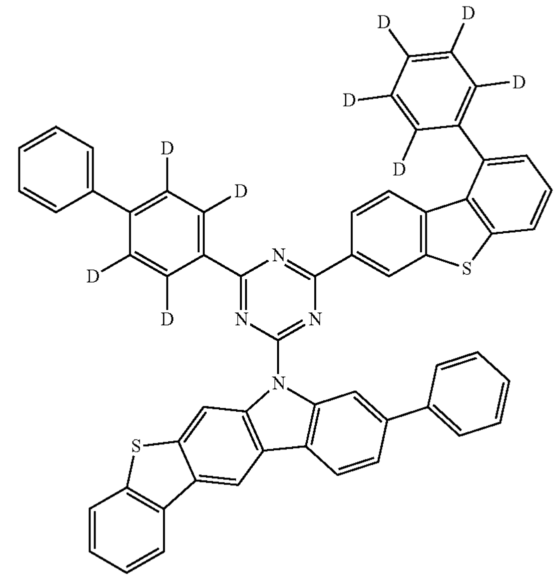
[A-97]
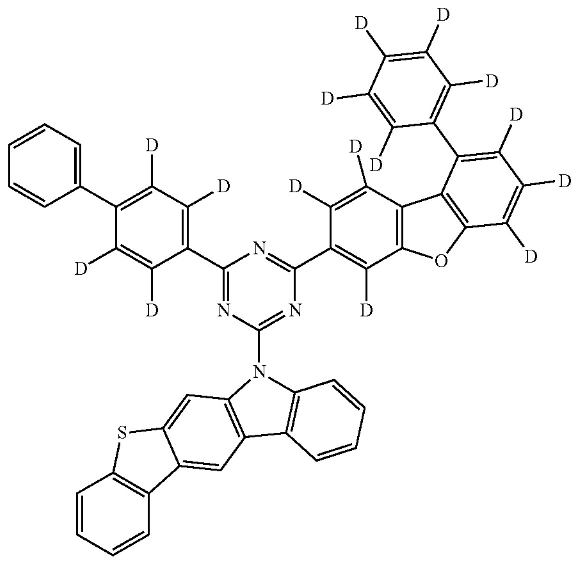
-continued
[A-98]
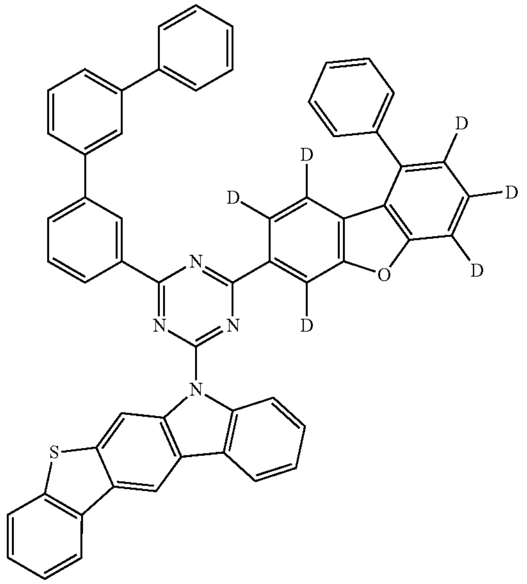
[A-99]
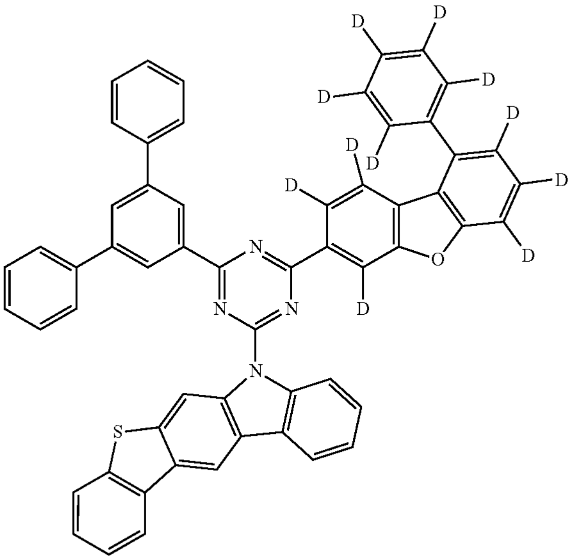

-continued
[A-100]
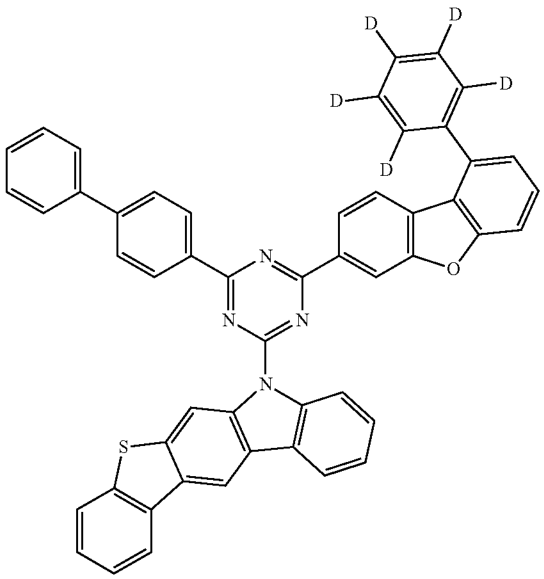
[B-1]
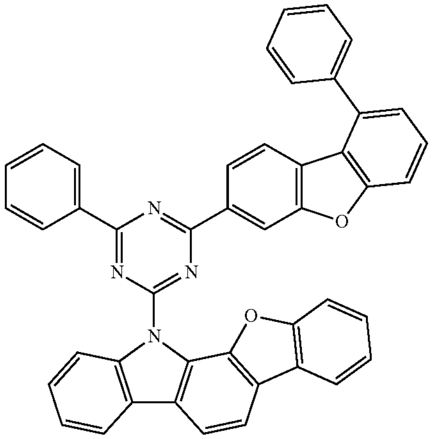
[B-2]
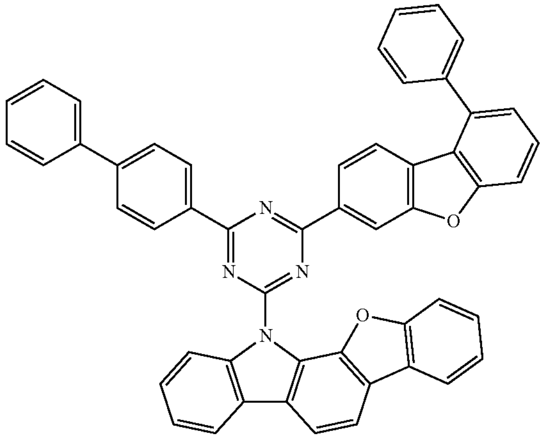
-continued
[B-3]
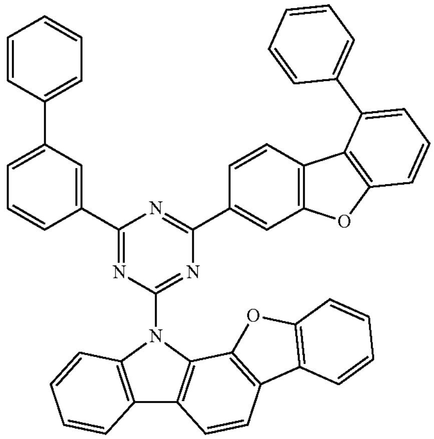
[B-4]
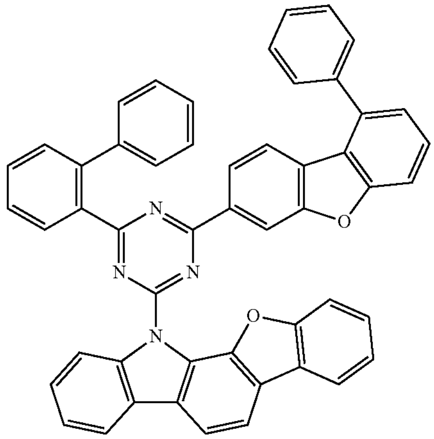
[B-5]
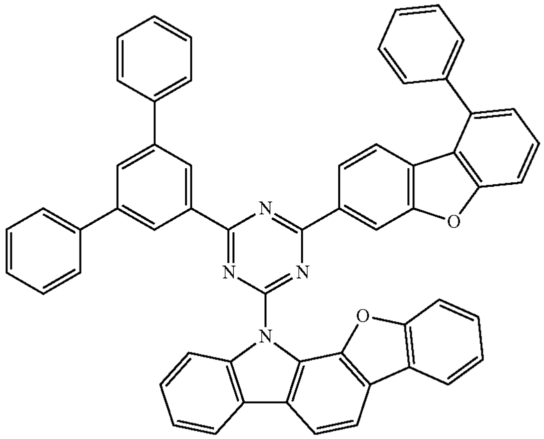

-continued
[B-6]
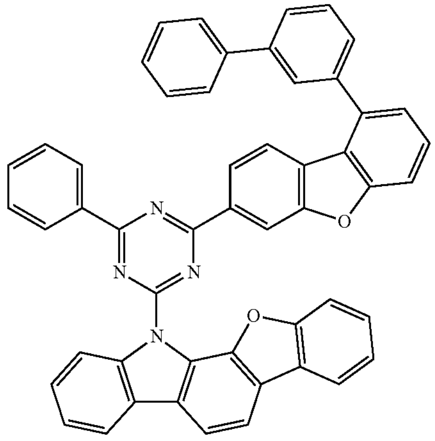
[B-7]
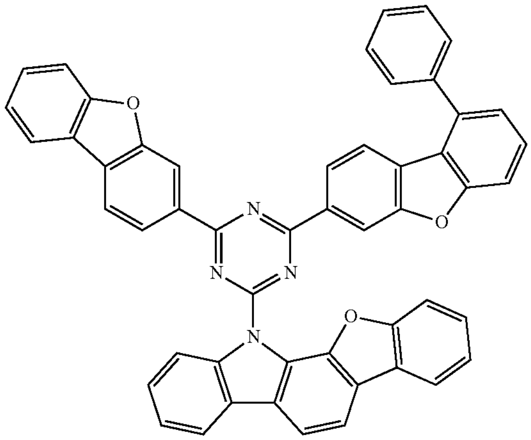
[B-8]
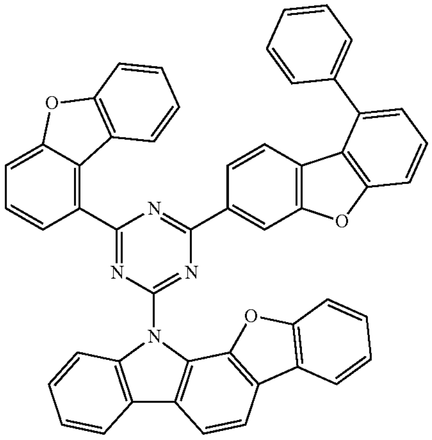
-continued
[B-9]
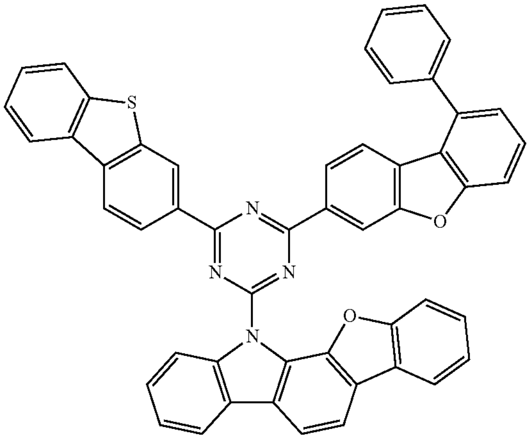
[B-10]
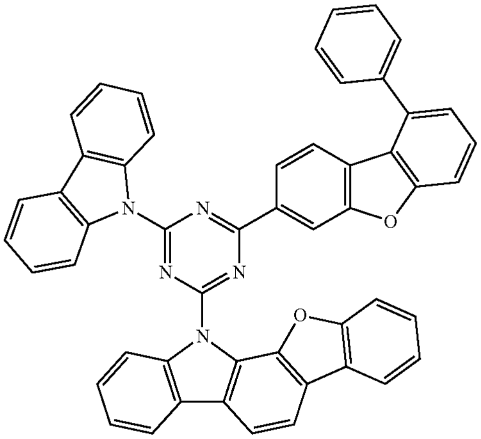
[B-11]
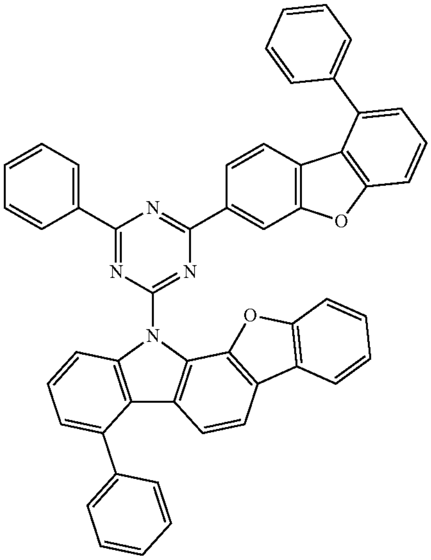

-continued
[B-12]
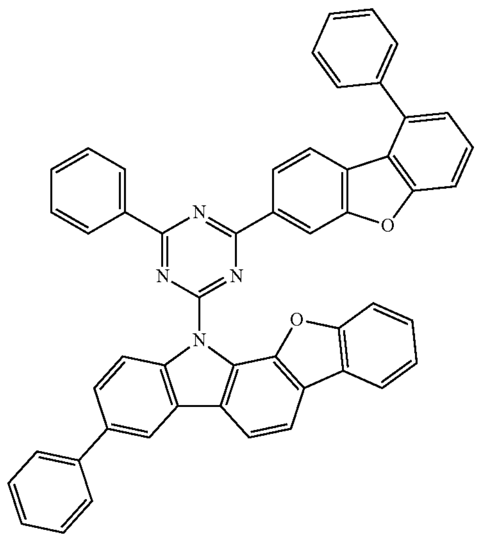
[B-13]
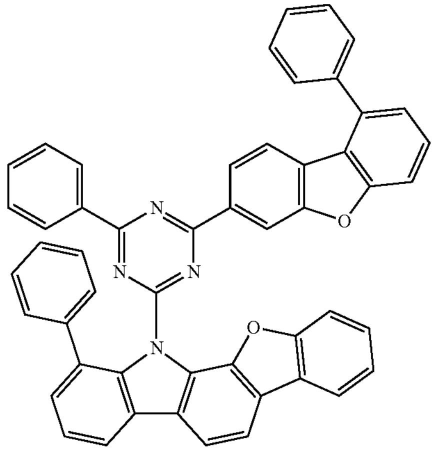
[B-14]
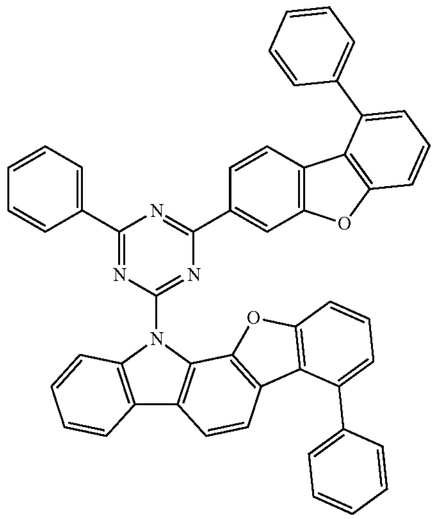
-continued
[B-15]
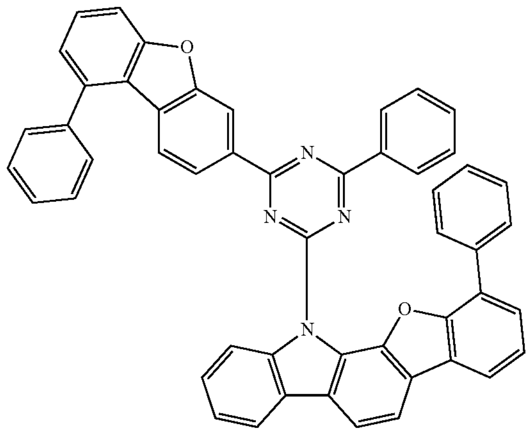
[B-16]
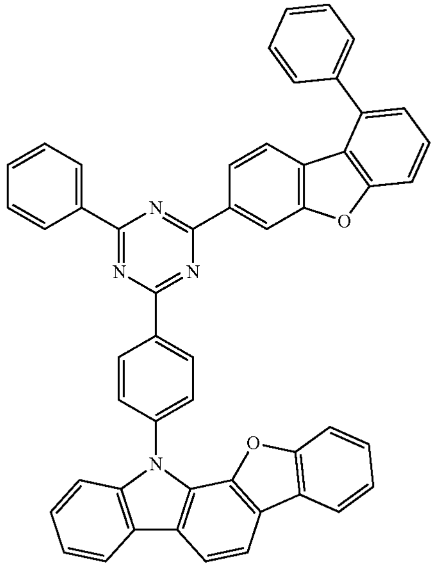
[B-17]
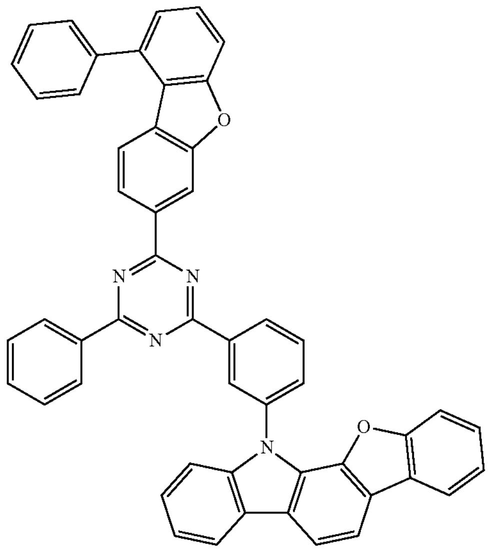

-continued
[B-18]
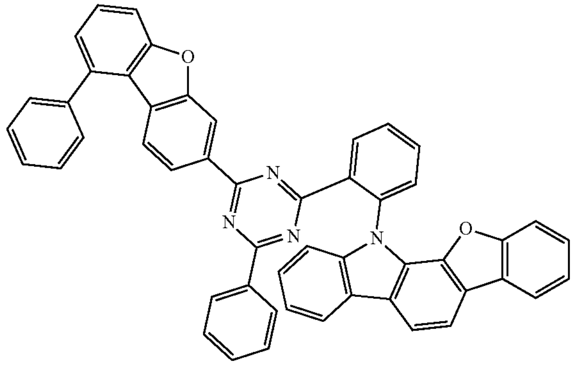
[B-19]
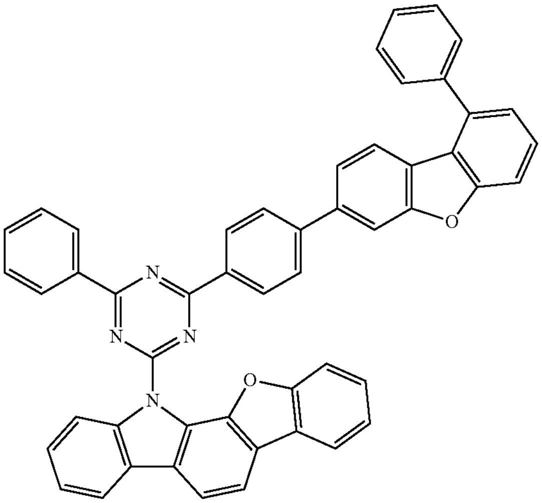
[B-20]
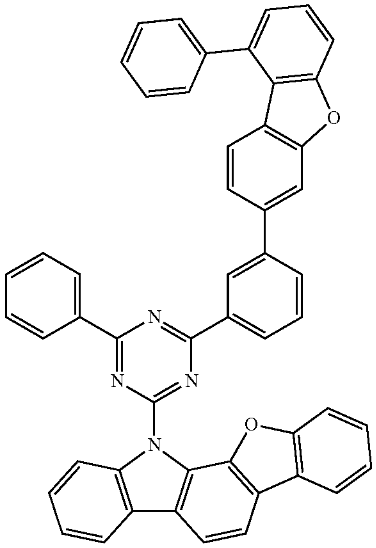
-continued
[B-21]
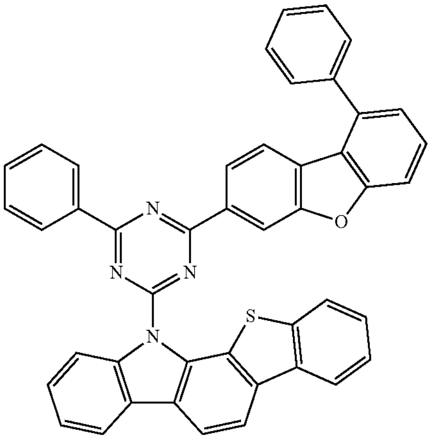
[B-22]
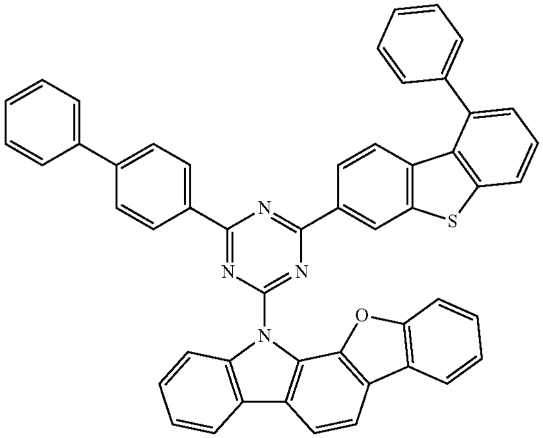
[B-23]
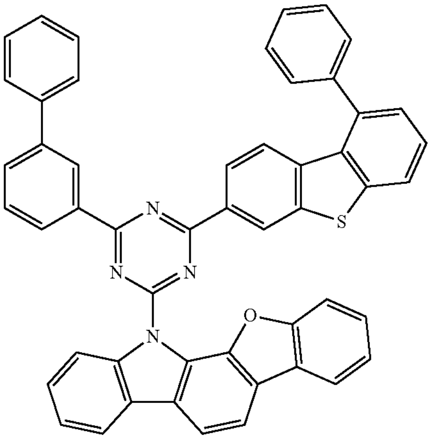

-continued
[B-24]
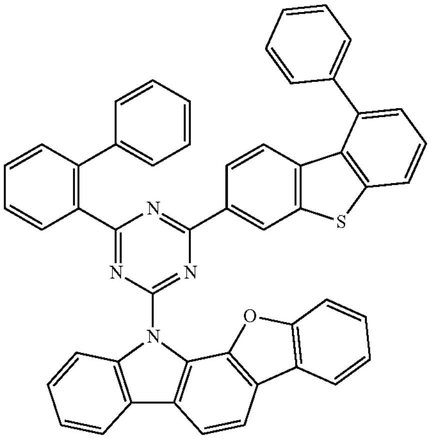
[B-25]
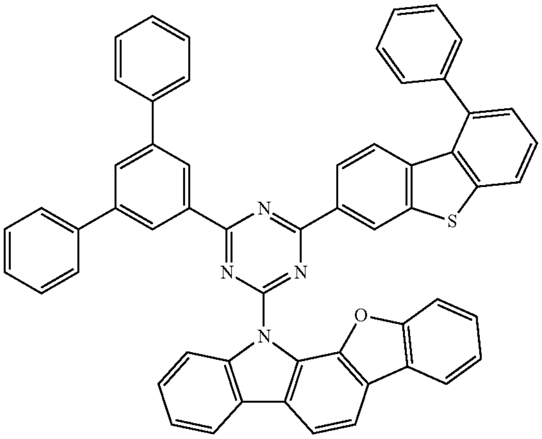
[B-26]
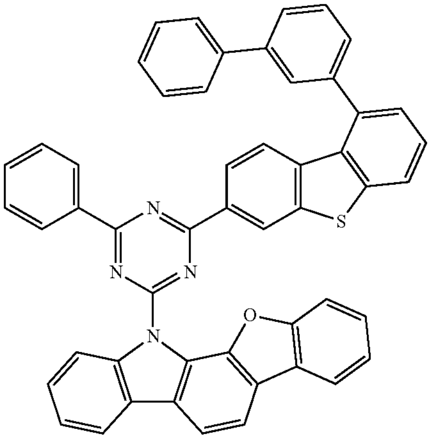
-continued
[B-27]
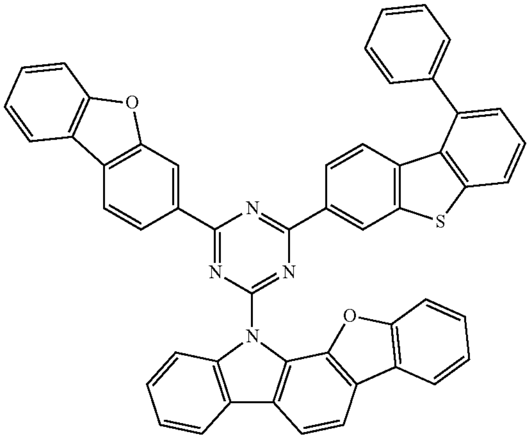
[B-28]
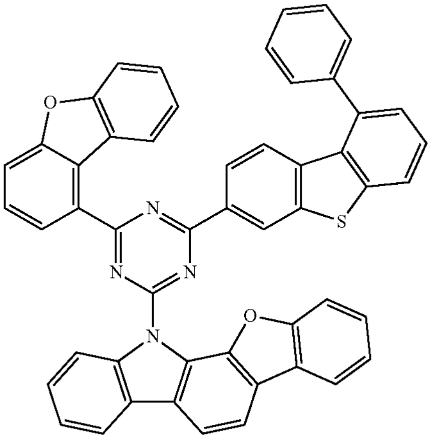
[B-29]
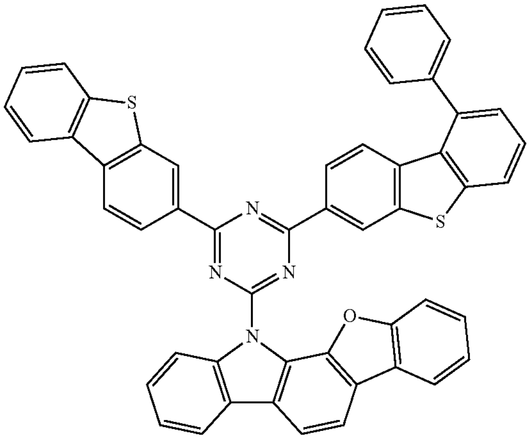

-continued
[B-30]
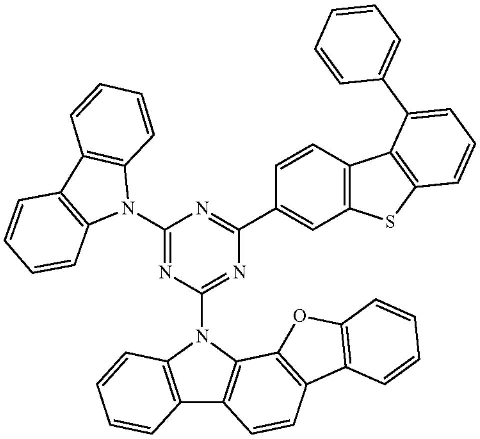
[B-31]
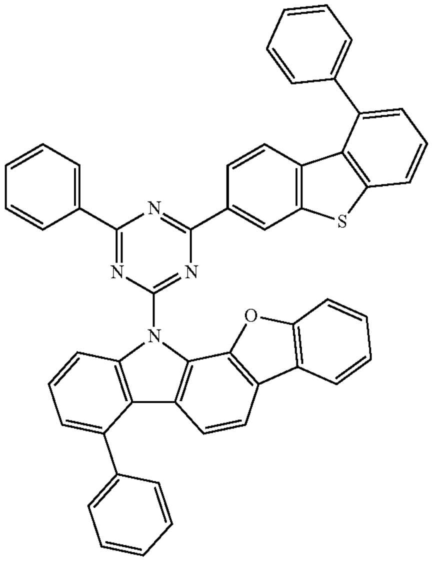
[B-32]
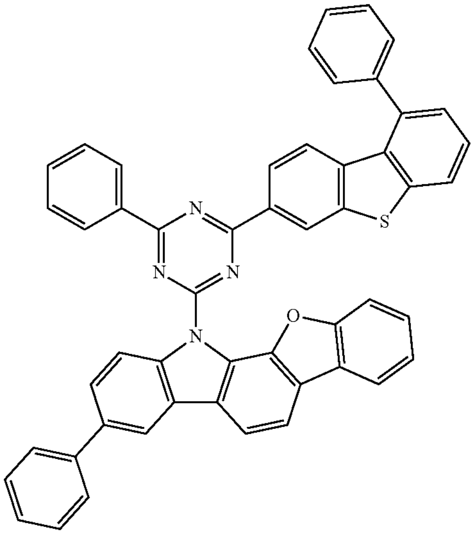
-continued
[B-33]
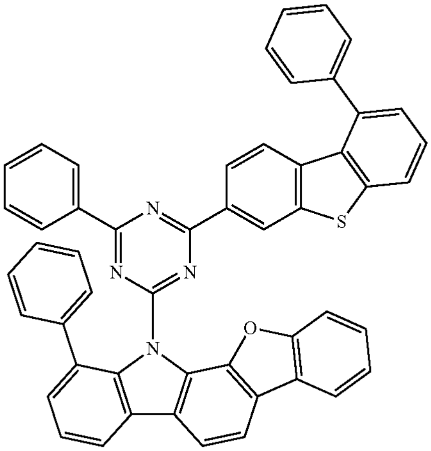
[B-34]
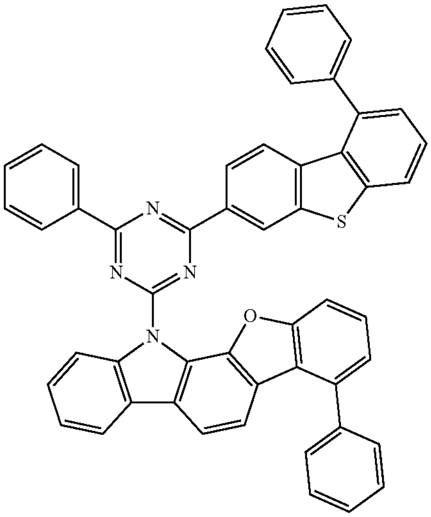
[B-35]
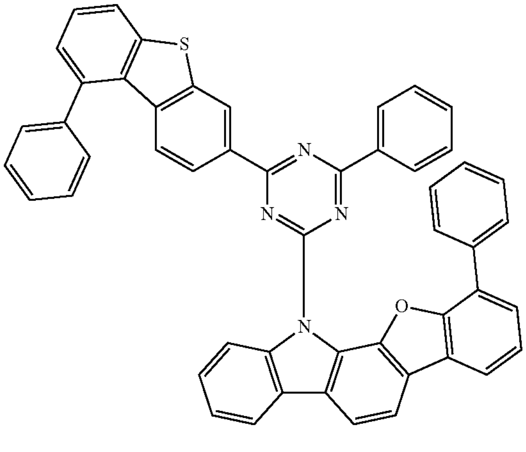

-continued
[B-36]
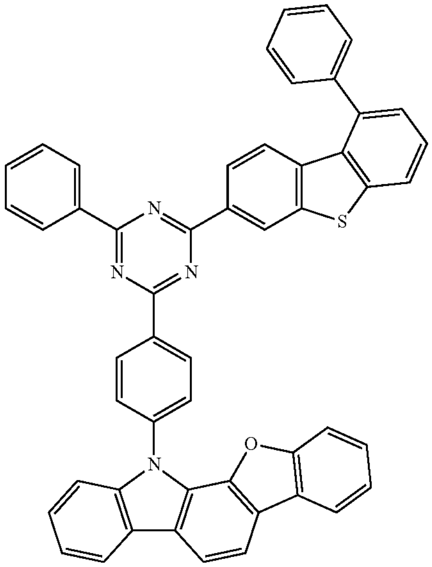
[B-37]
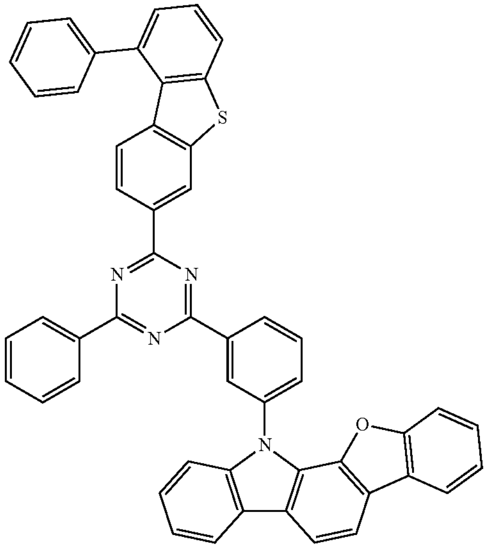
[B-38]
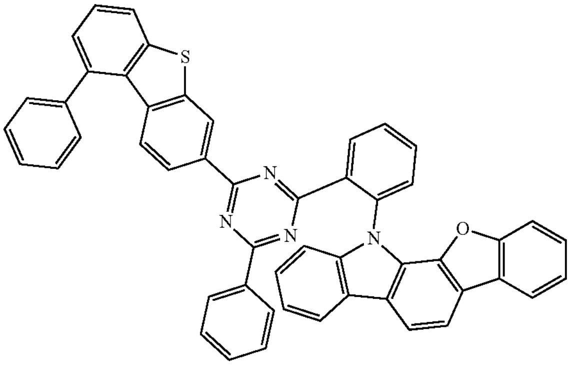
-continued
[B-39]
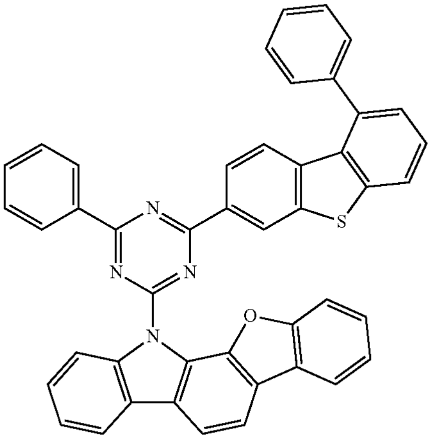
[B-40]
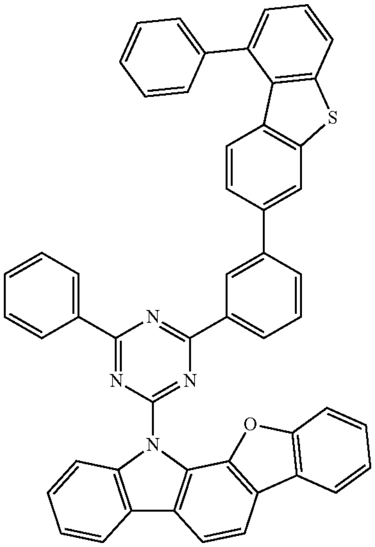
[B-41]
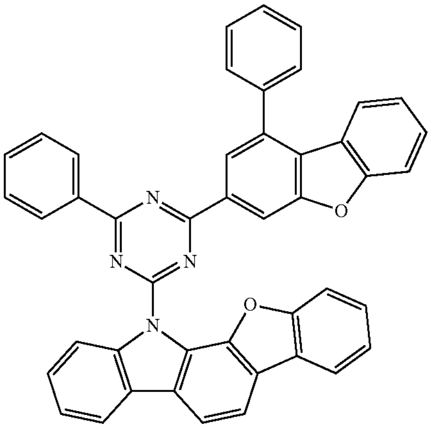

-continued
[B-42]
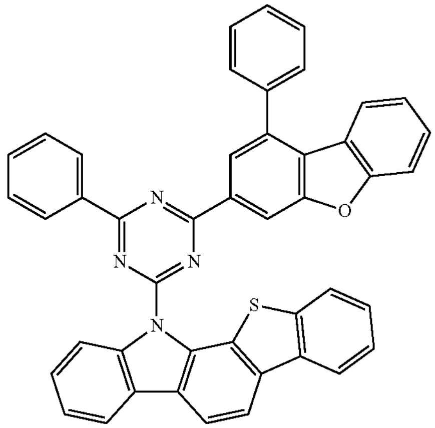
[B-43]
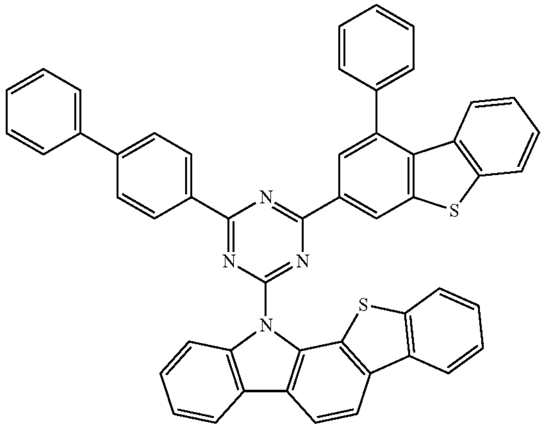
[B-44]
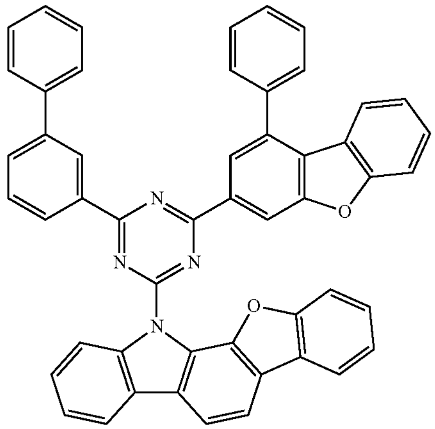
-continued
[B-45]
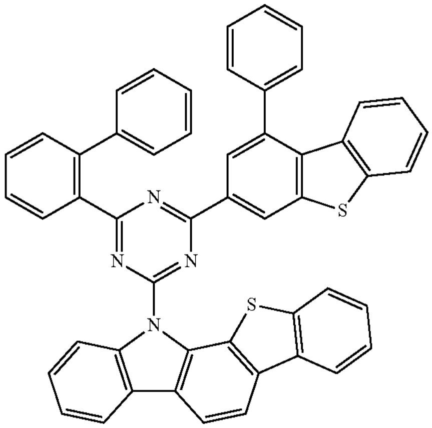
[B-46]
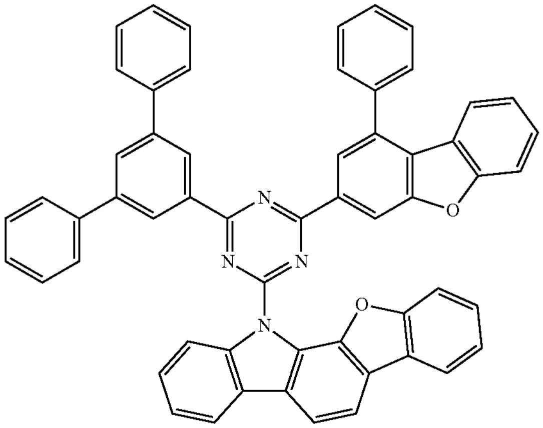
[B-47]
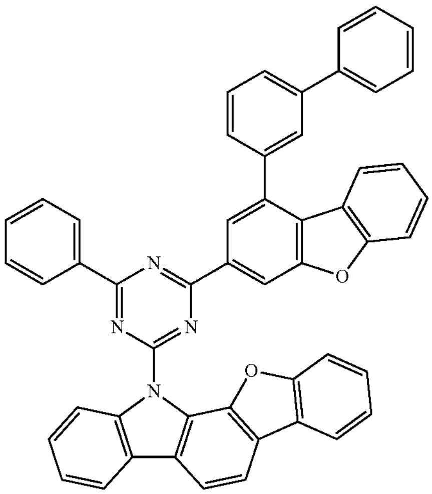

-continued
[B-48]
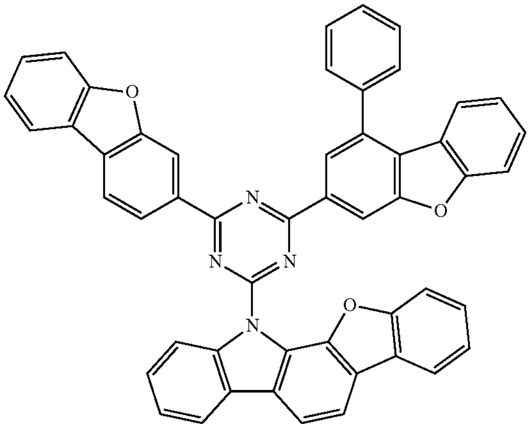
[B-49]
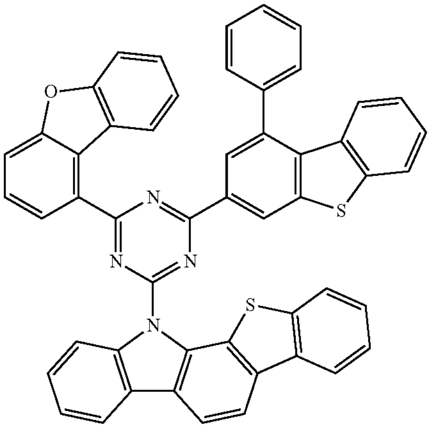
[B-50]
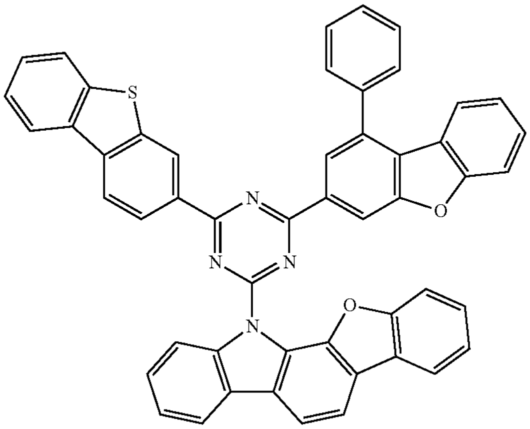
-continued
[B-51]
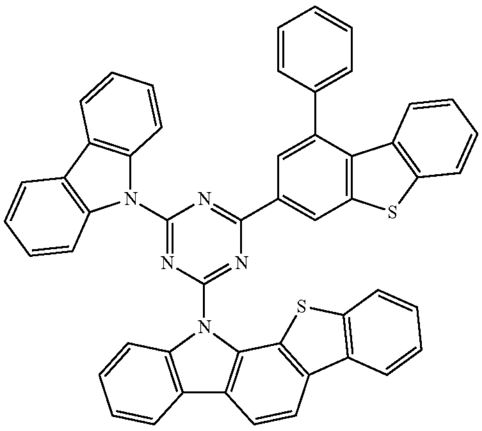
[B-52]
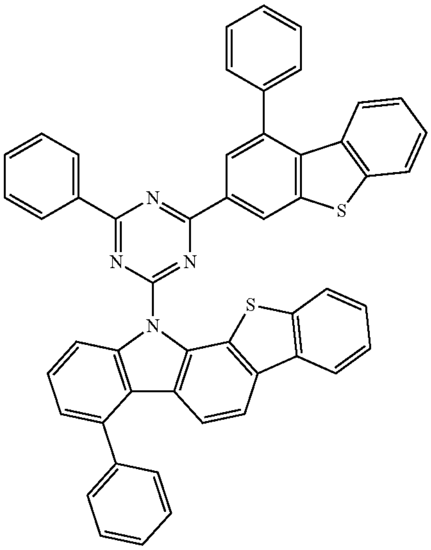
[B-53]
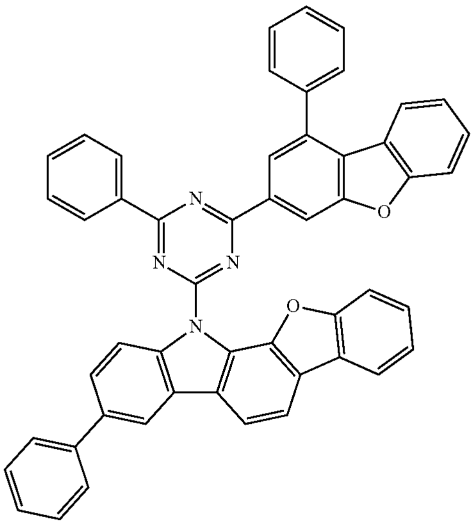

-continued
[B-54]
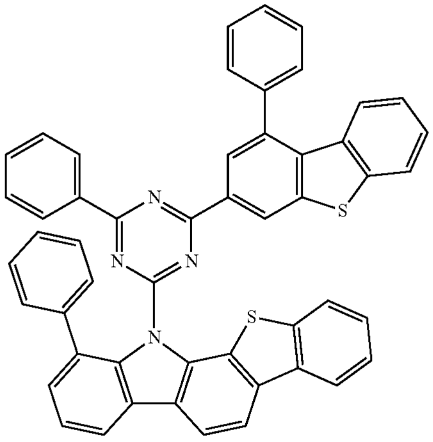
[B-55]
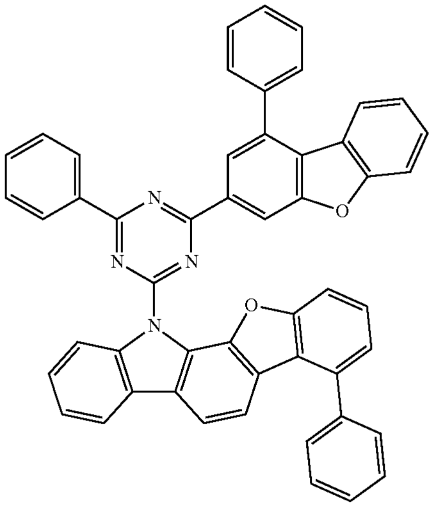
[B-56]
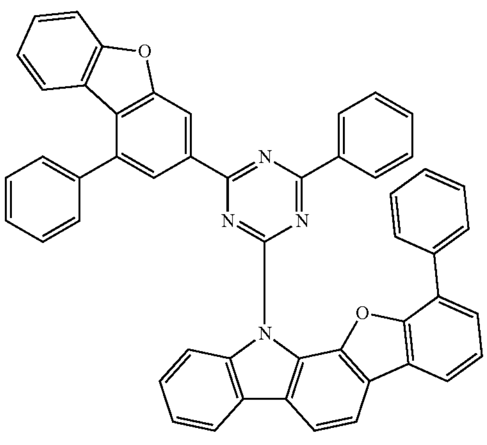
-continued
[B-57]
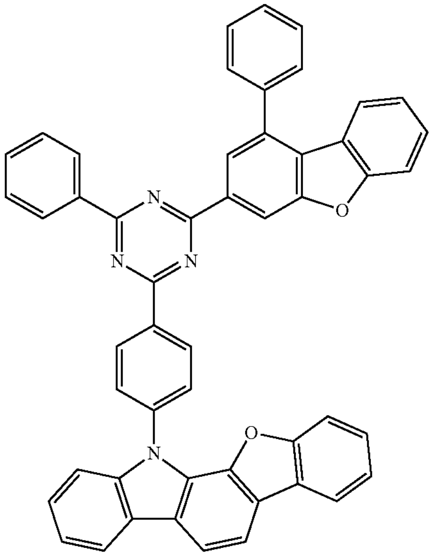
[B-58]
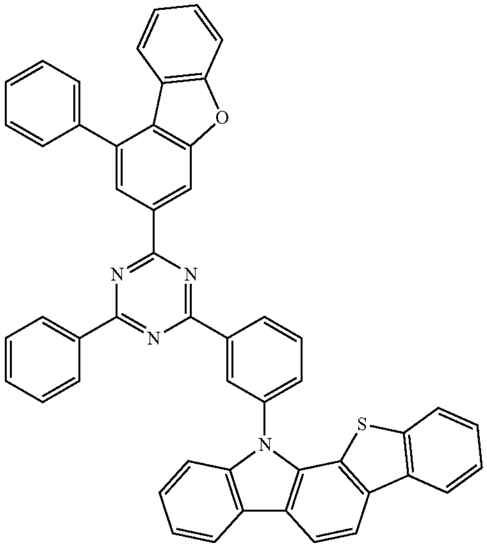
[B-59]
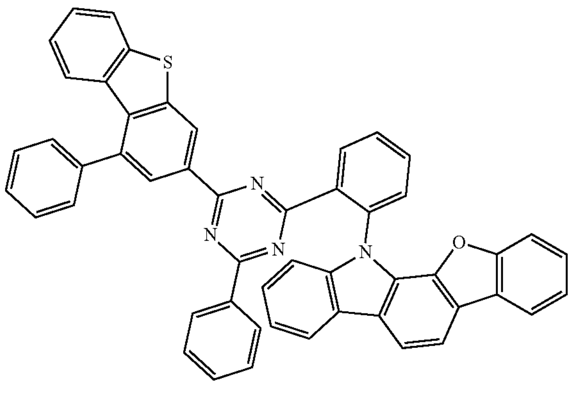

-continued
[B-60]
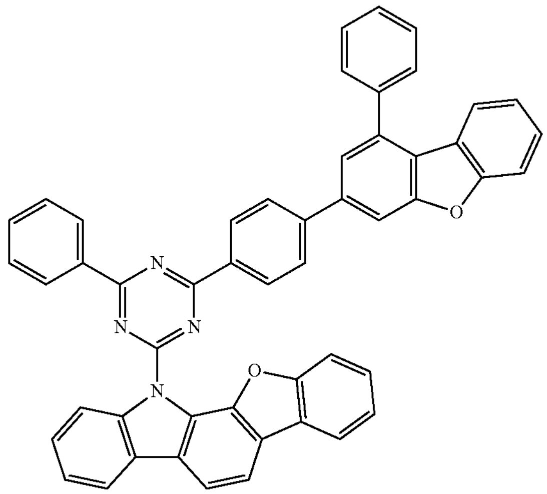
[B-61]
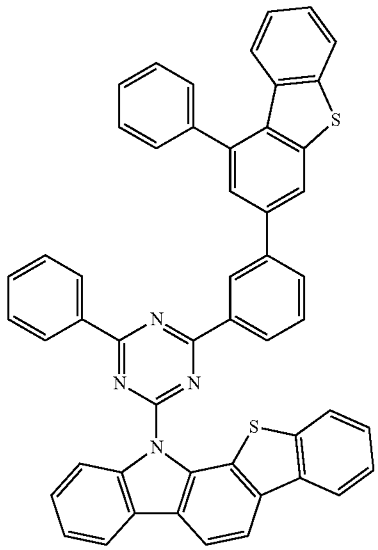
[B-62]
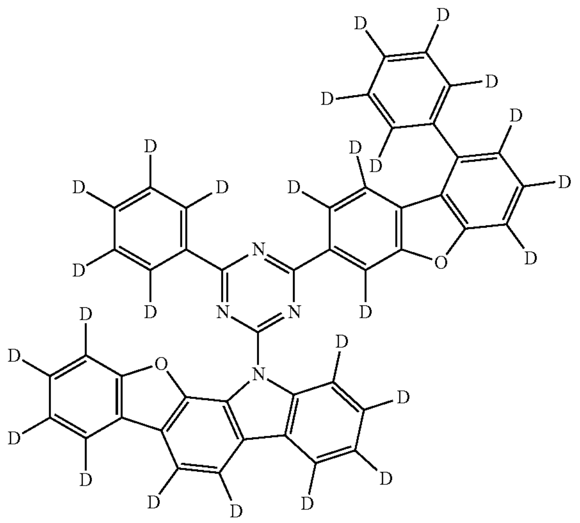
-continued
[B-63]
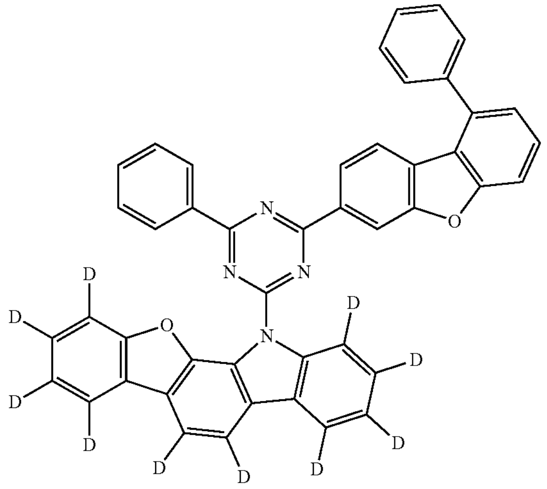
[B-64]
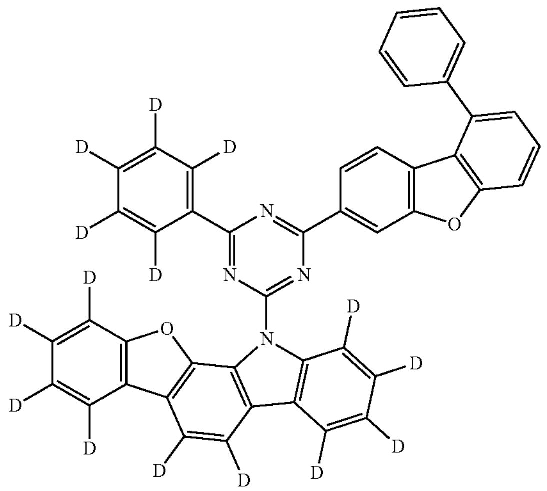
[B-65]
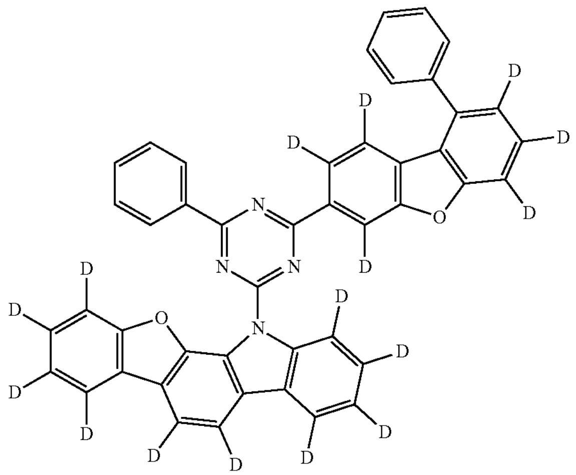

-continued
[B-66]
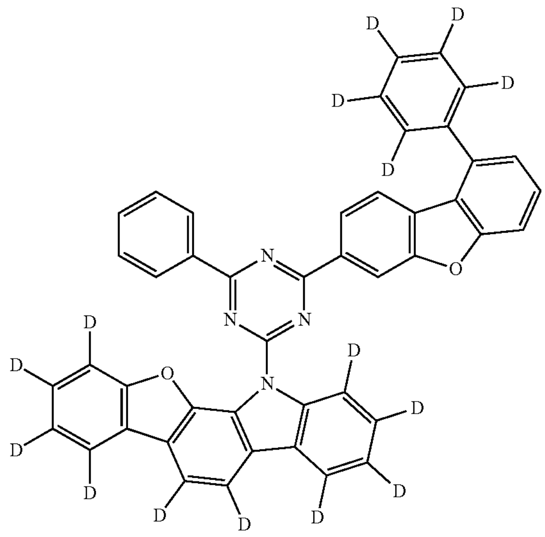
[B-67]
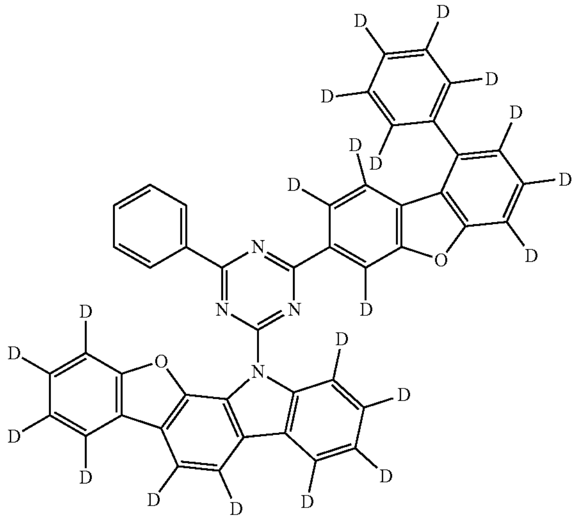
[B-68]
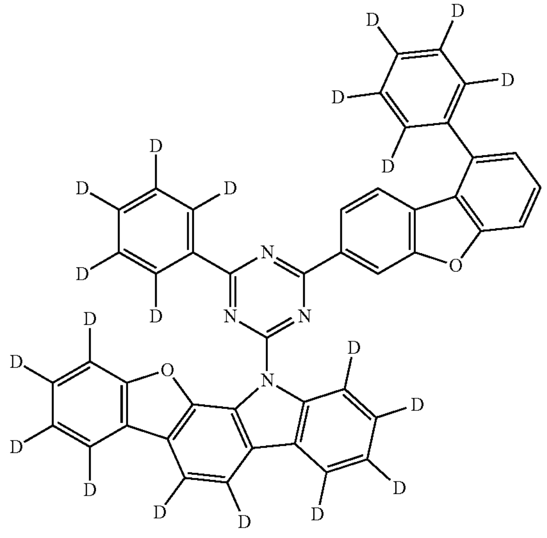
-continued
[B-69]
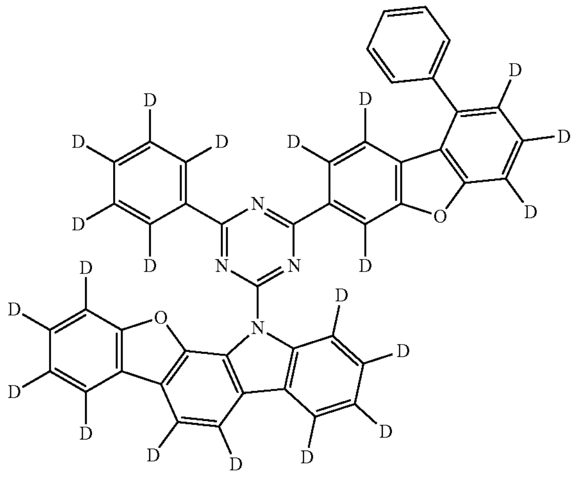
[B-70]
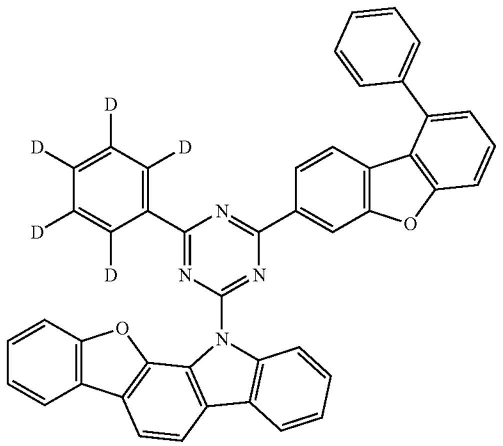
[B-71]
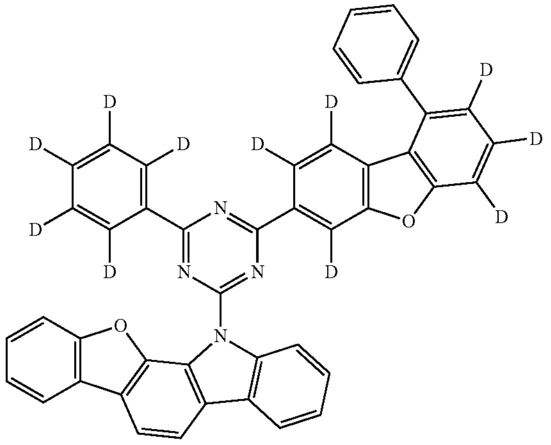

-continued
[B-72]
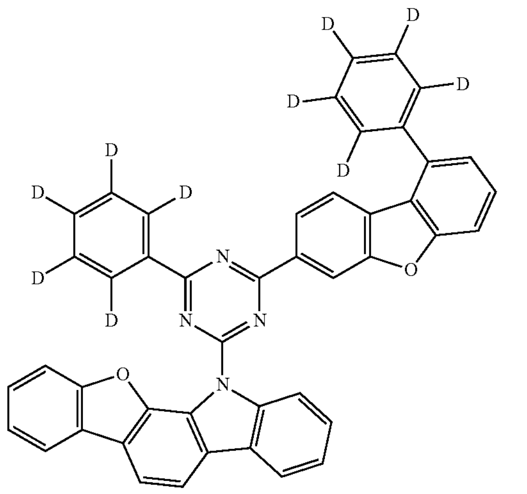
[B-73]
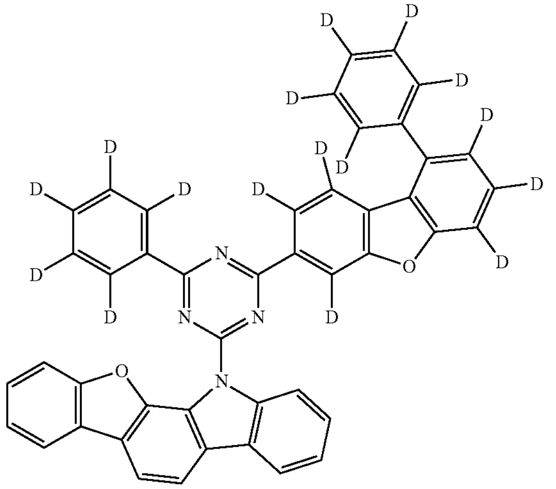
[B-74]
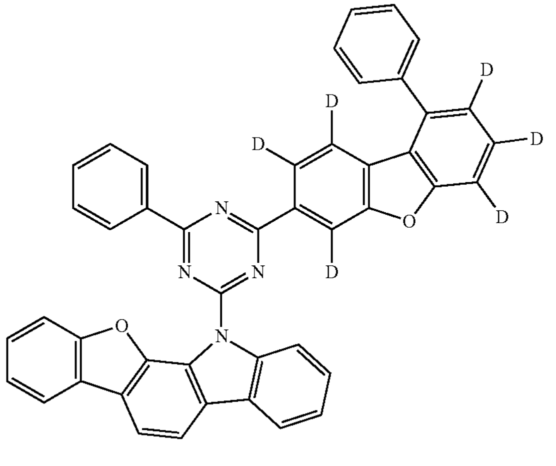
-continued
[B-75]
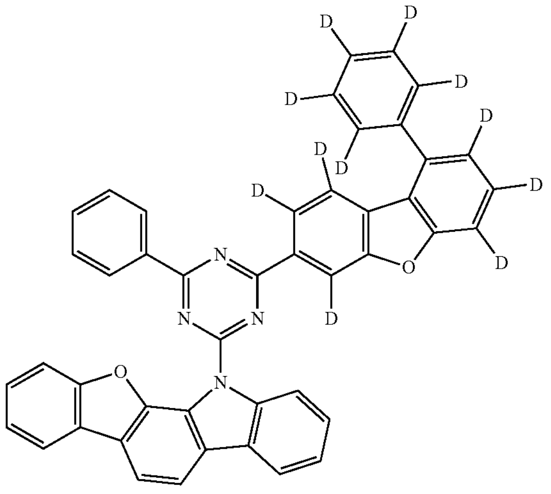
[B-76]
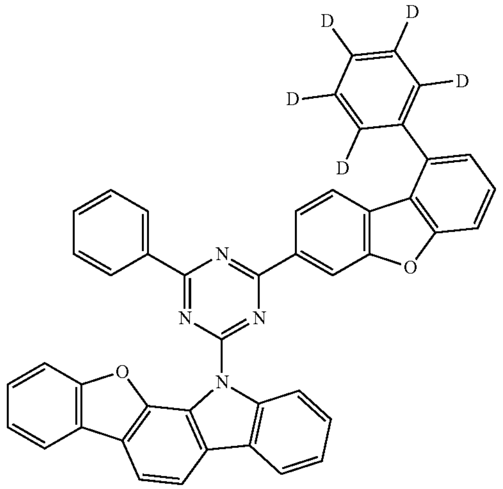
[B-77]
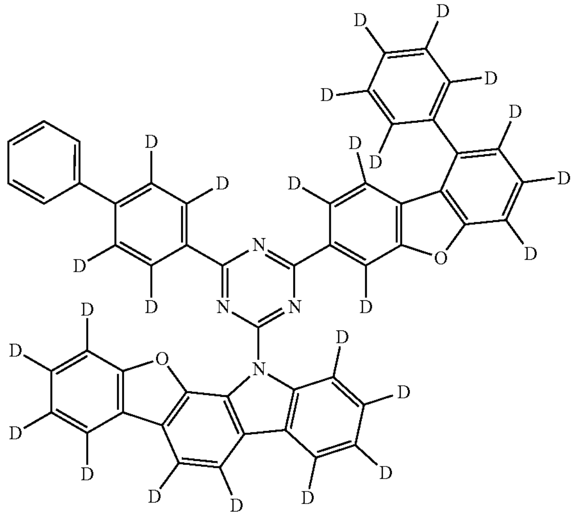

-continued
[B-78]
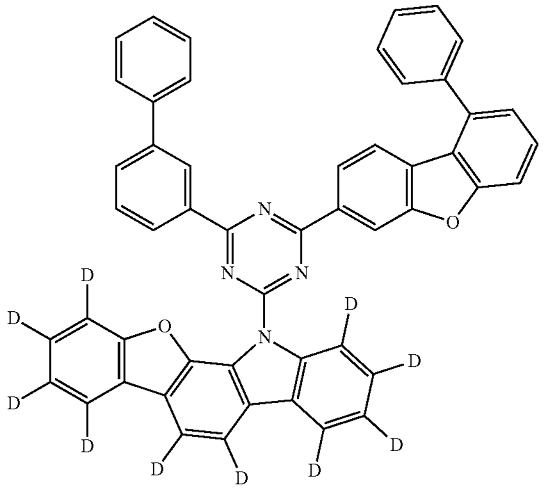
[B-79]
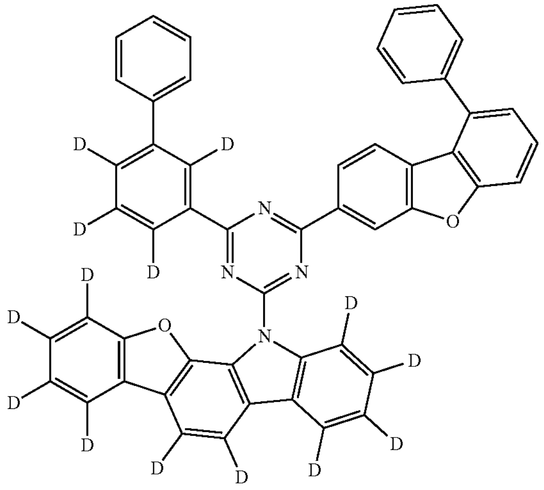
[B-80]
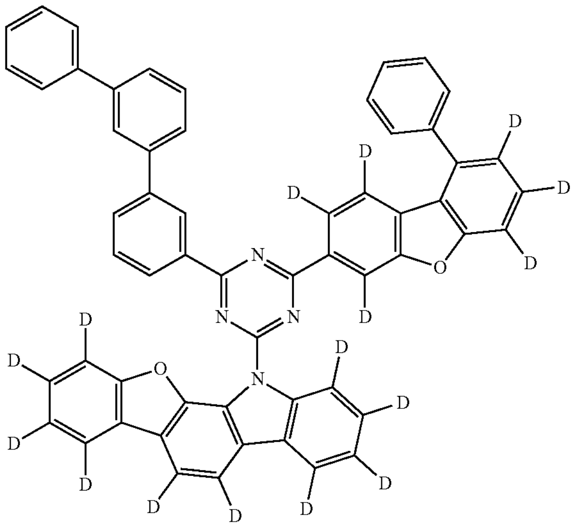
-continued
[B-81]
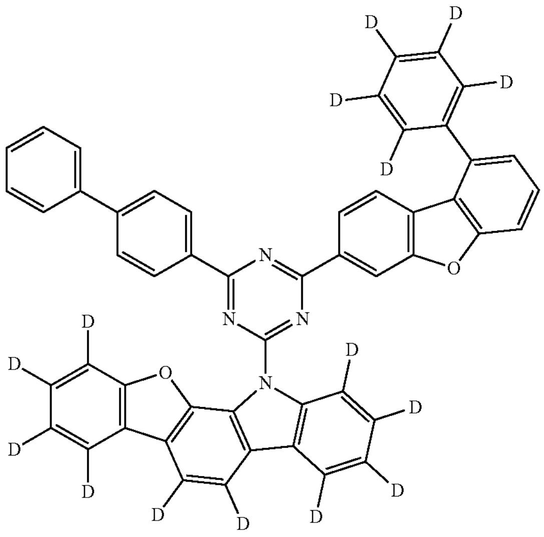
[B-82]
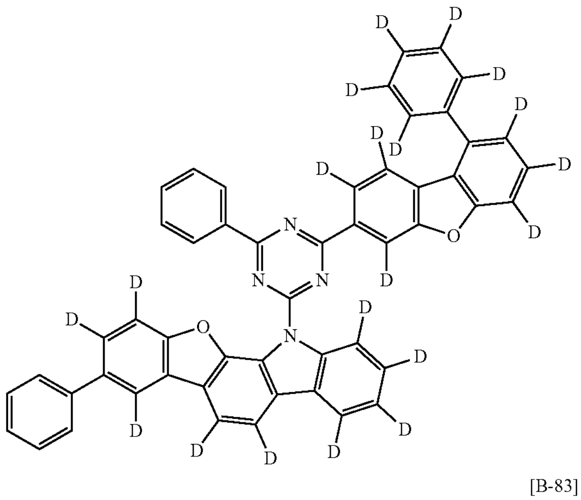
[B-83]
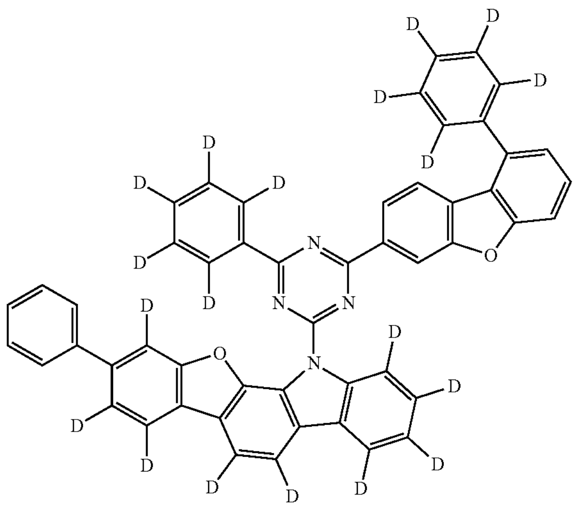

-continued
[B-84]
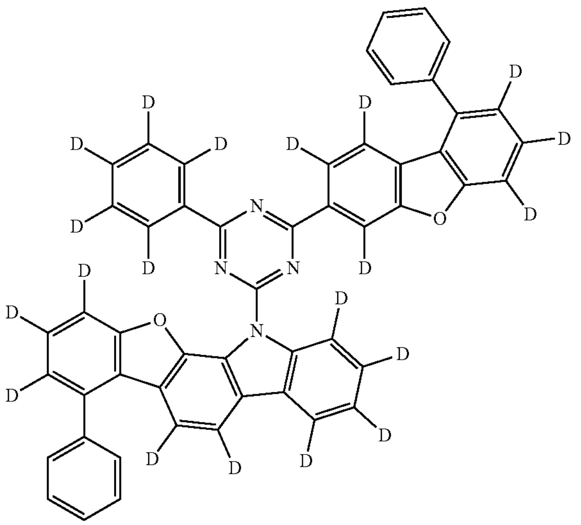
[B-85]
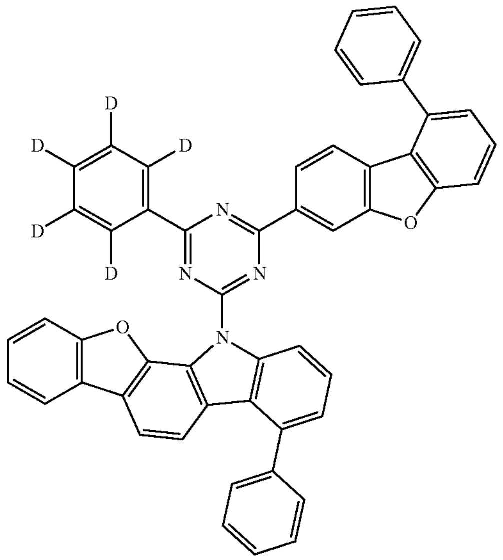
[B-86]
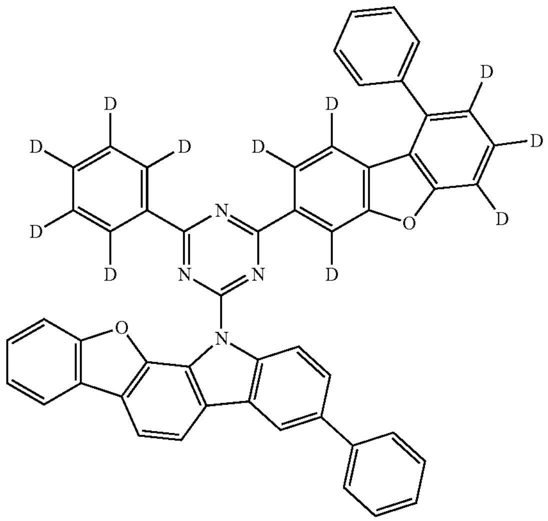
-continued
[B-87]
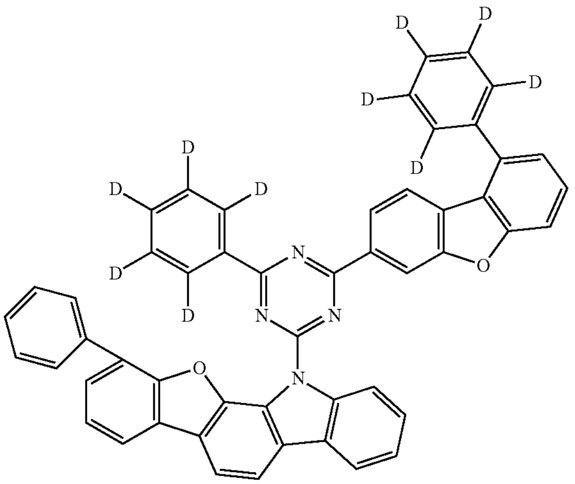
[B-88]
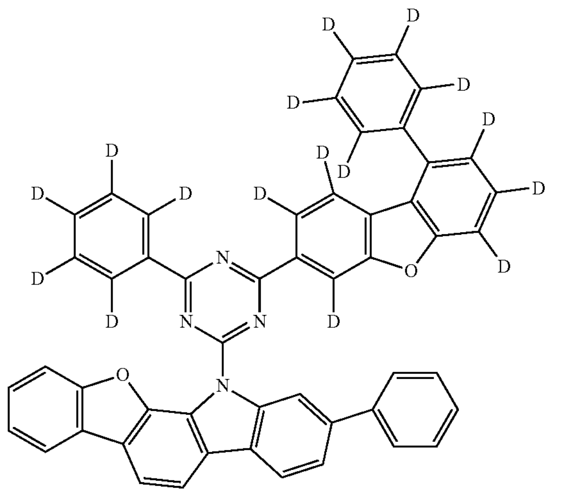
[B-89]
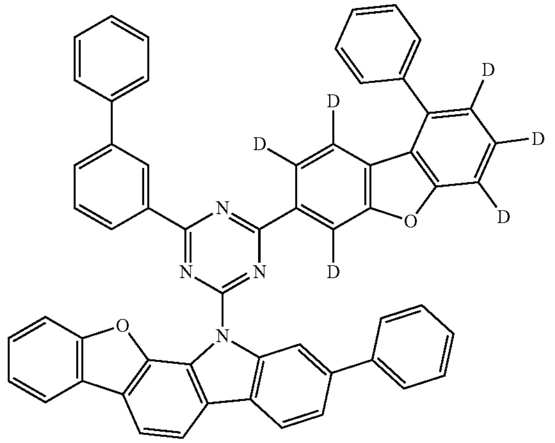

-continued
[B-90]
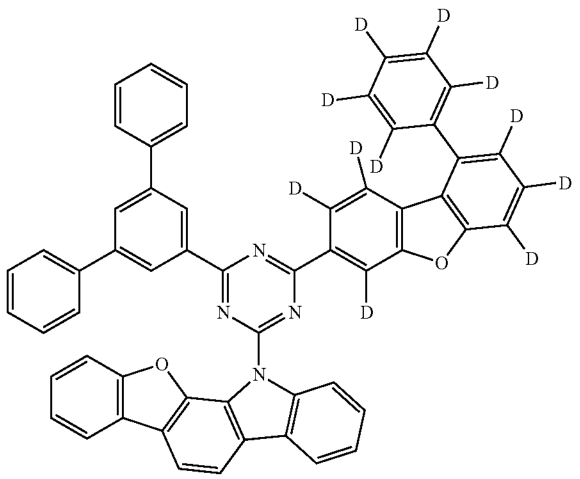
[B-91]
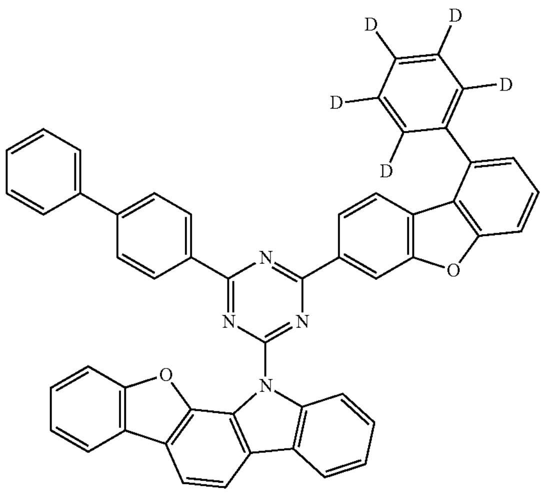
[B-92]
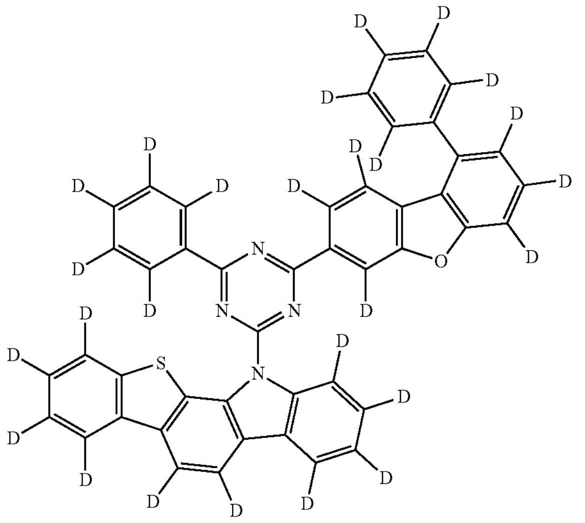
-continued
[B-93]
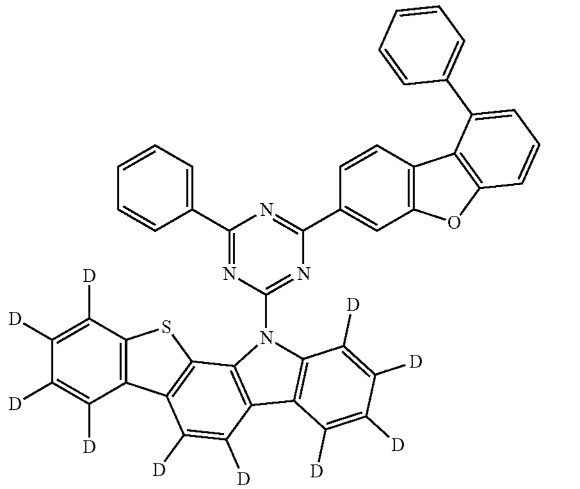
[B-94]
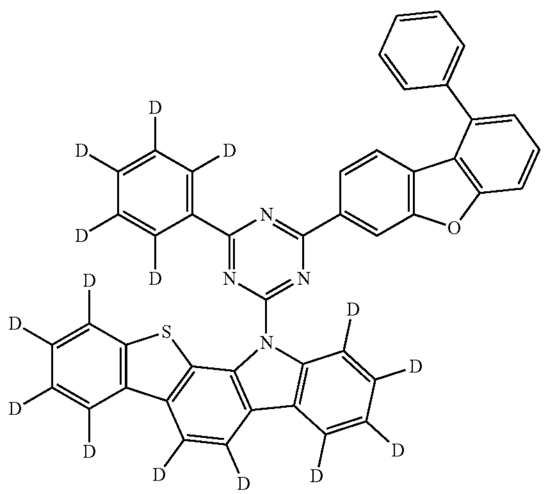
[B-95]
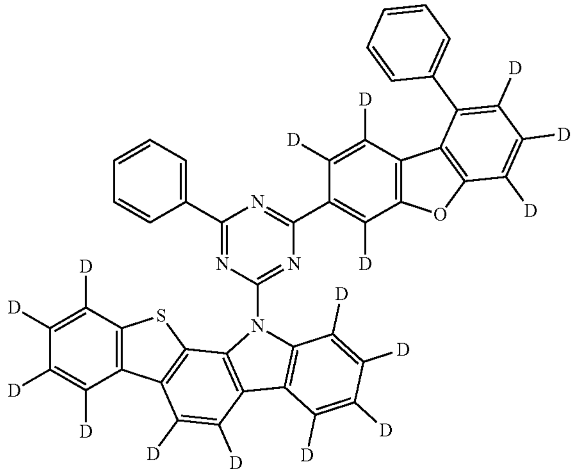

-continued
[B-96]
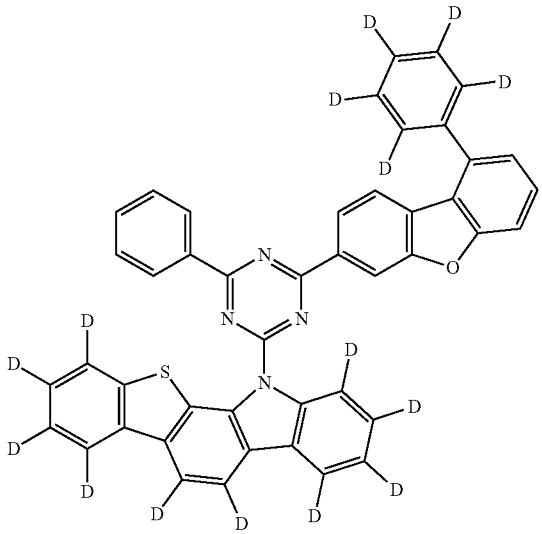
[B-97]
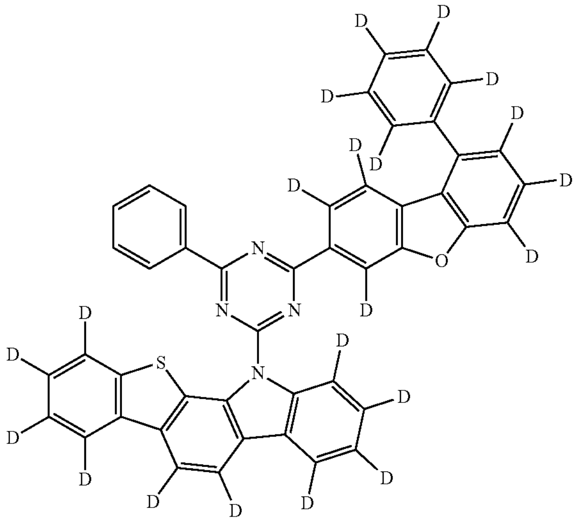
[B-98]
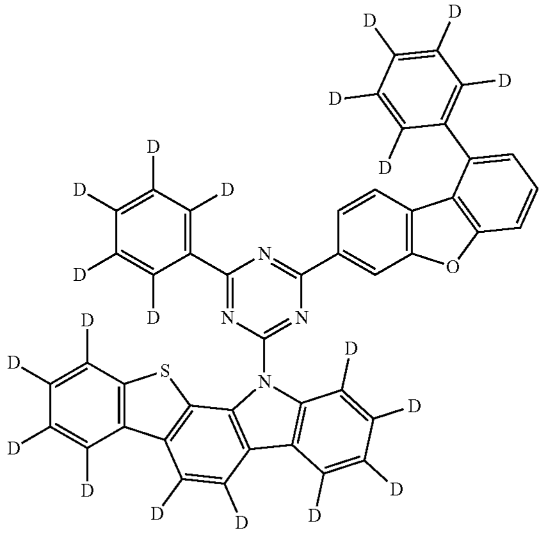
-continued
[B-99]
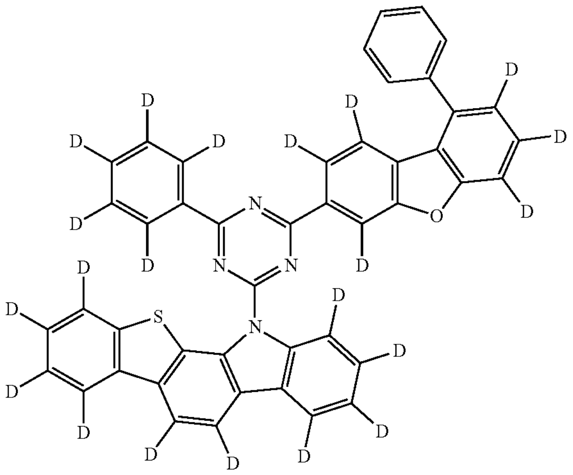
[B-100]
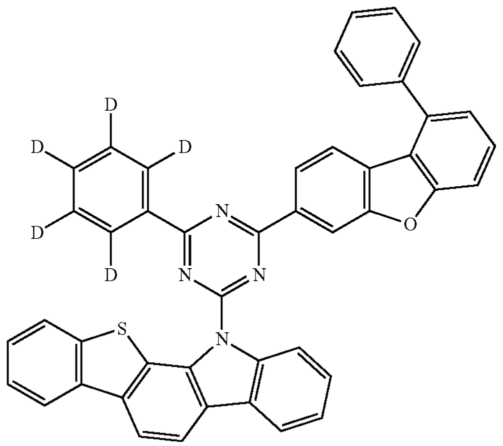
[B-101]
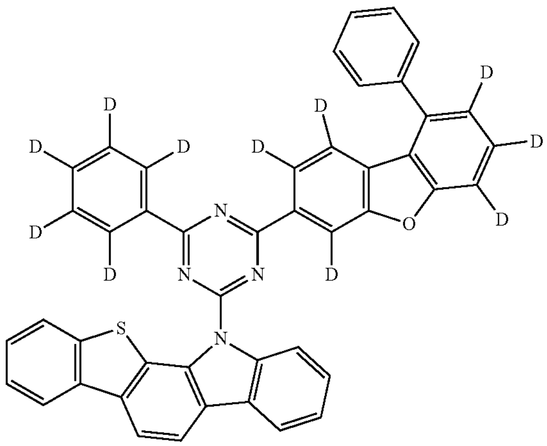

-continued
[B-102]
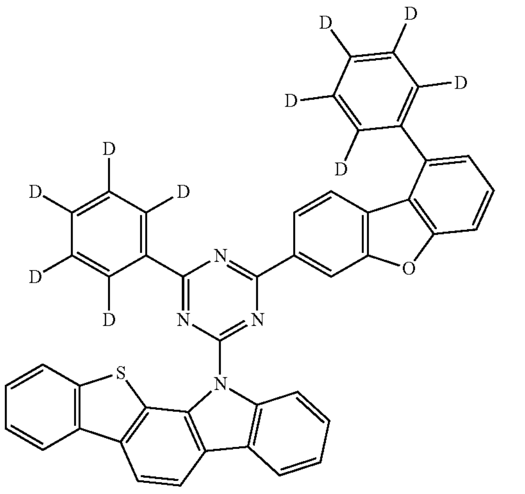
[B-103]
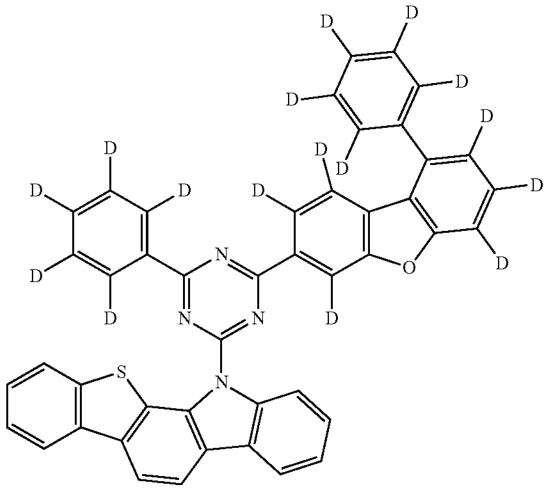
[B-104]
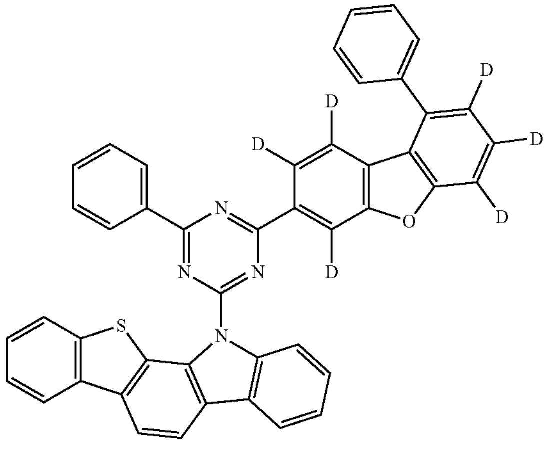
-continued
[B-105]
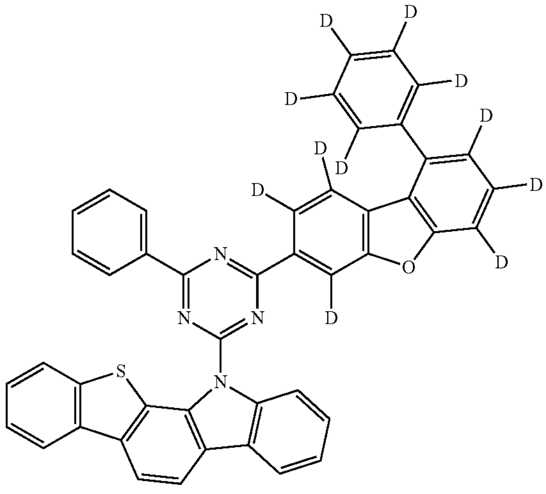
[B-106]
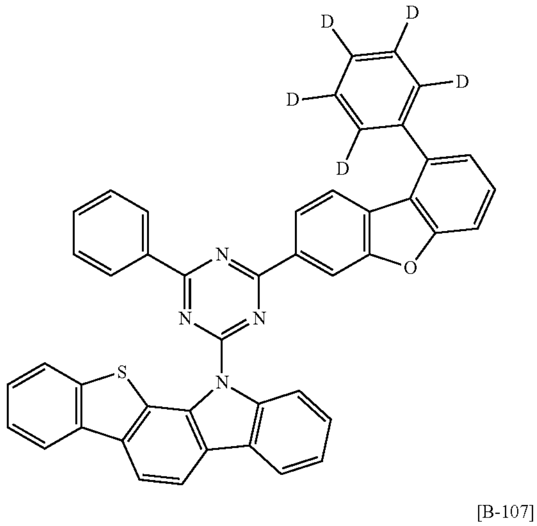
[B-107]
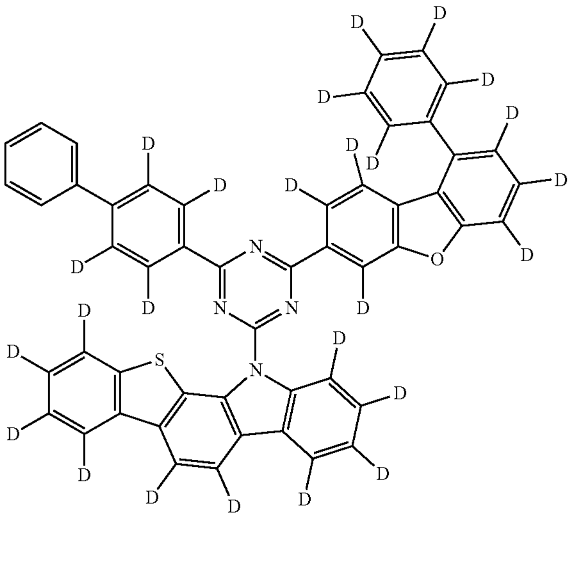

-continued
[B-108]
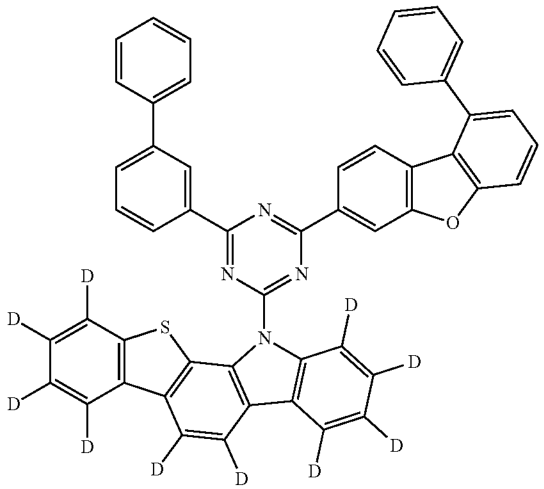
[B-109]
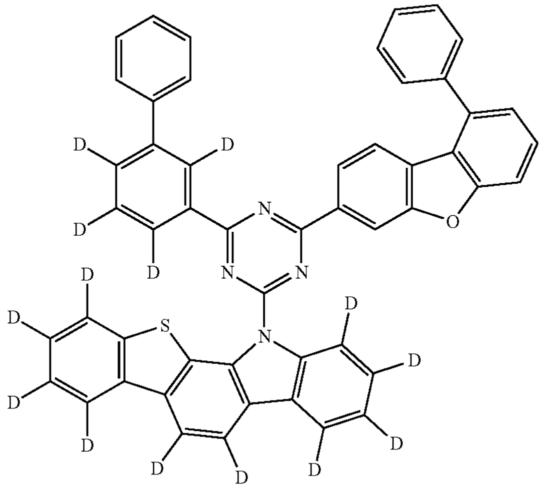
[B-110]
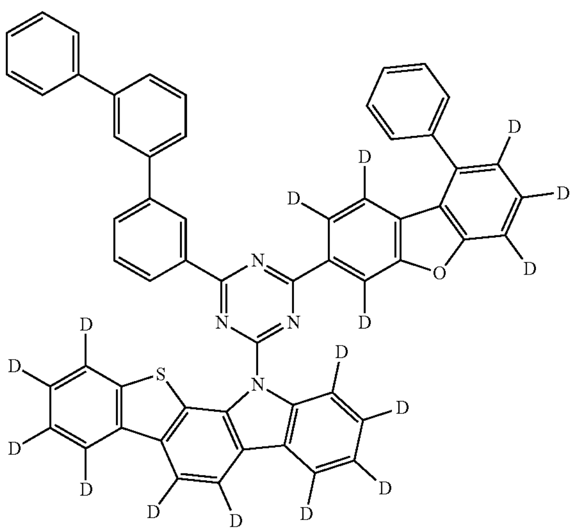
-continued
[B-111]
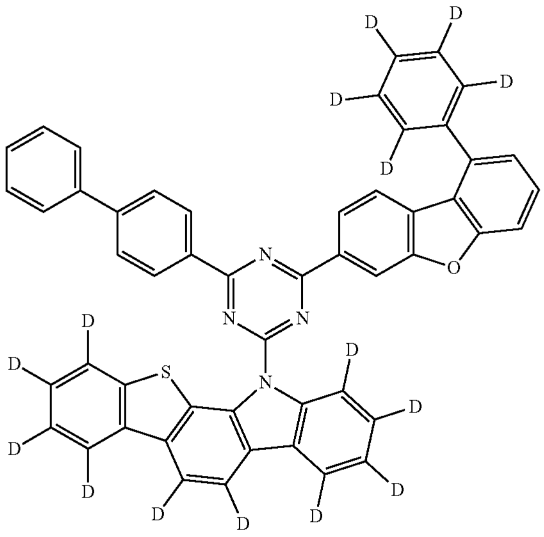
[B-112]
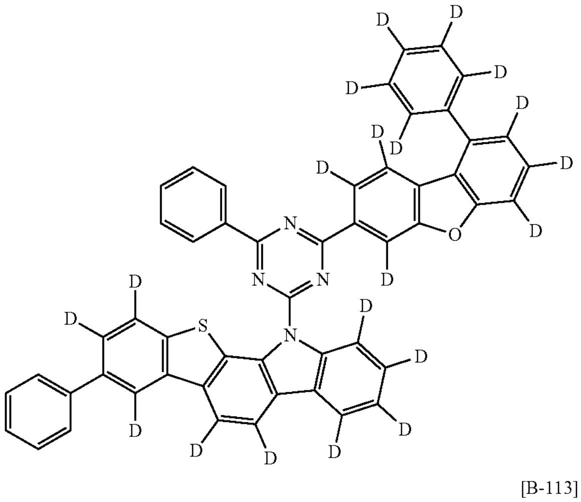
[B-113]
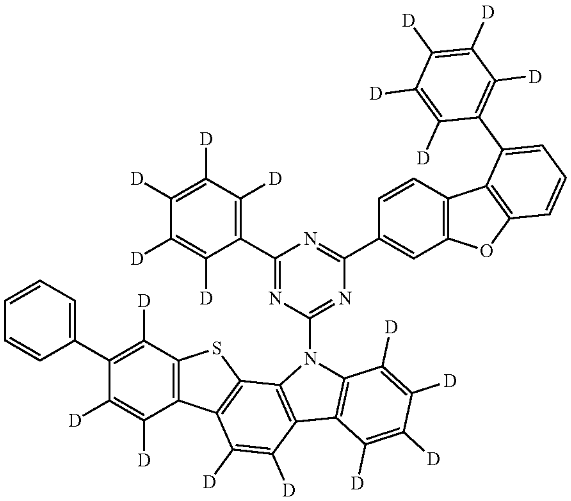

-continued
[B-114]
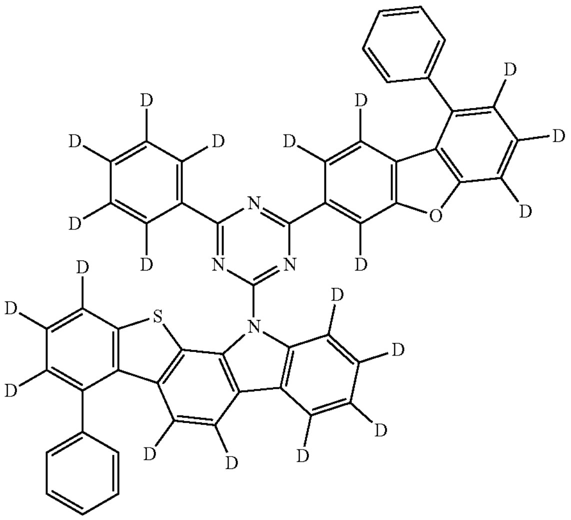
[B-115]
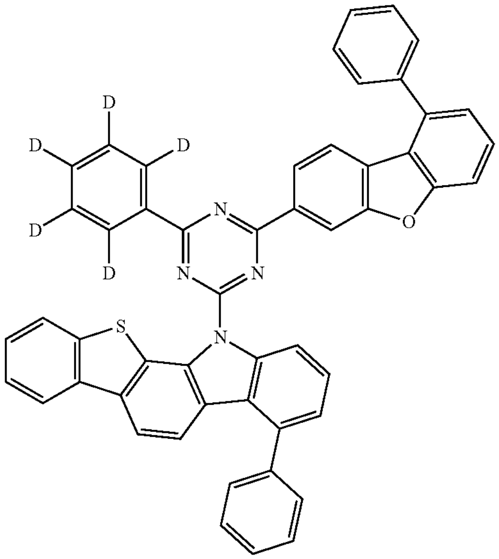
[B-116]
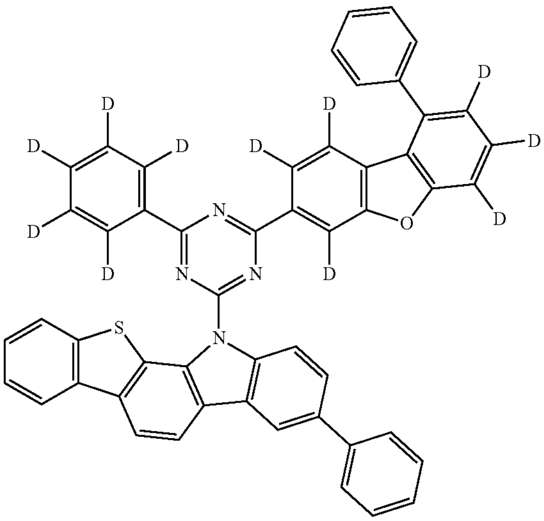
-continued
[B-117]
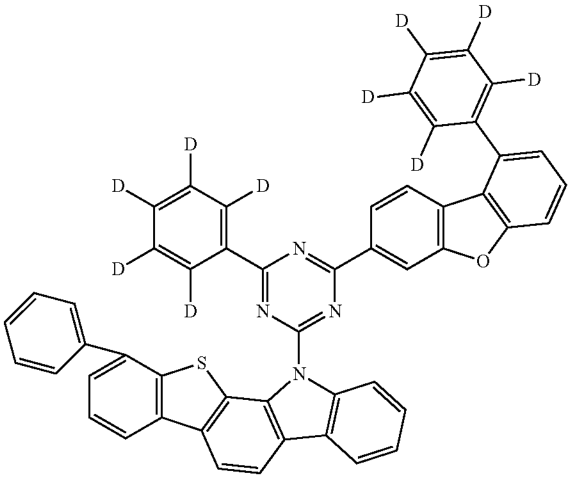
[B-118]
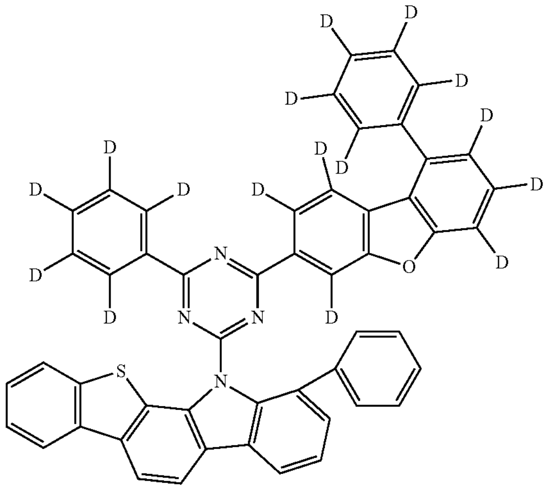
[B-119]
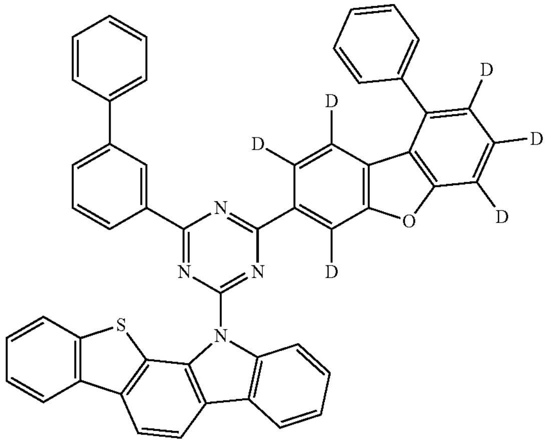

-continued
[B-120]
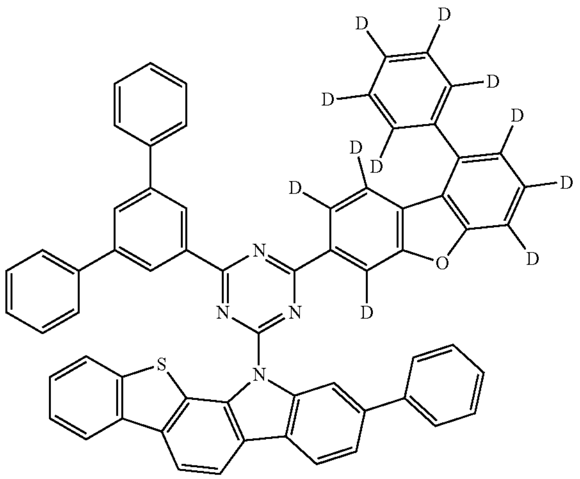
[B-121]
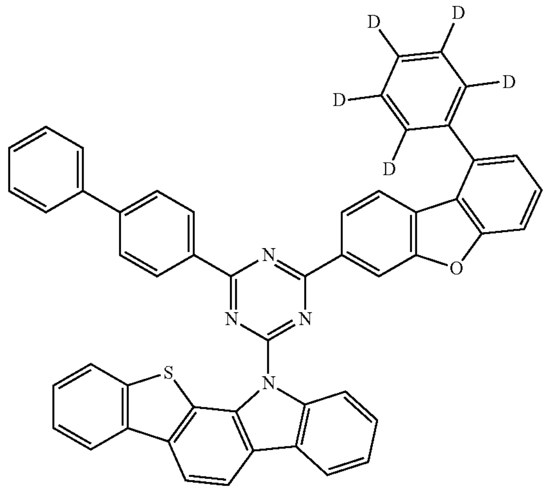
[C-1]
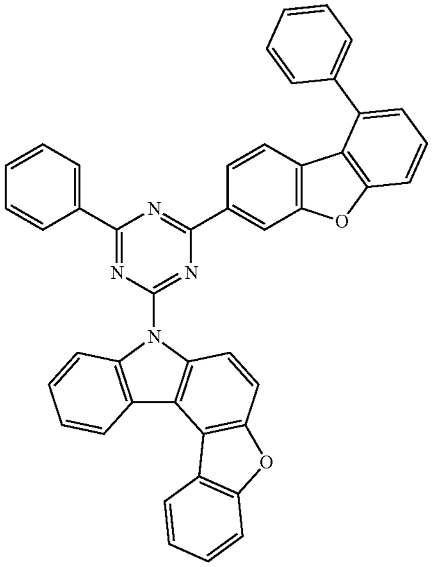
-continued
[C-2]
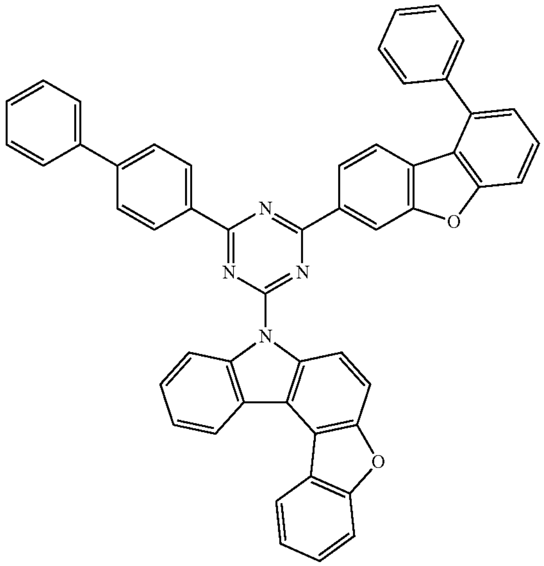
[C-3]
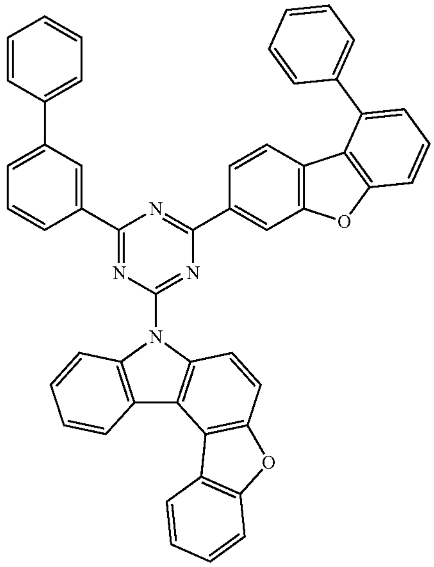

-continued
[C-4]
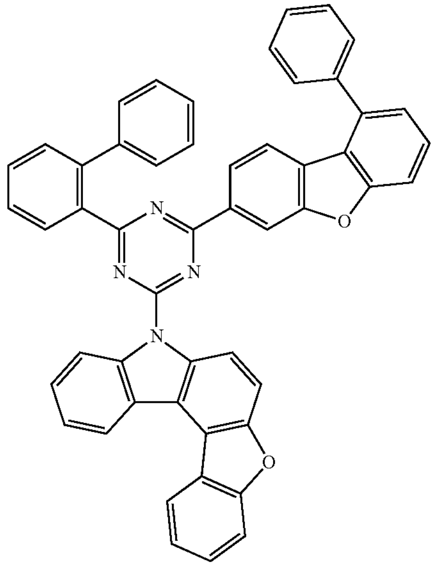
[C-5]
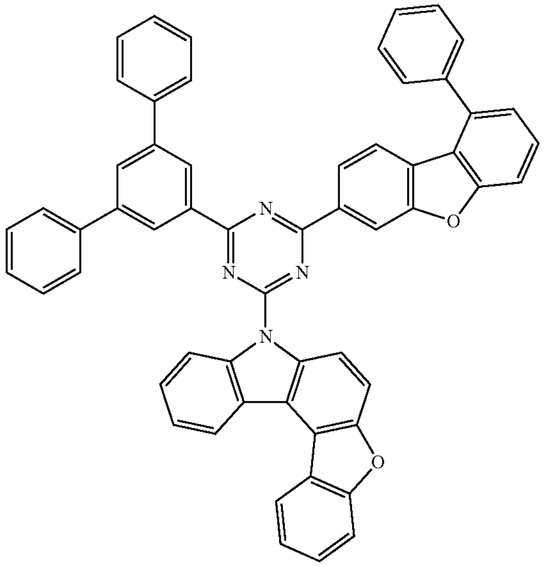
-continued
[C-6]
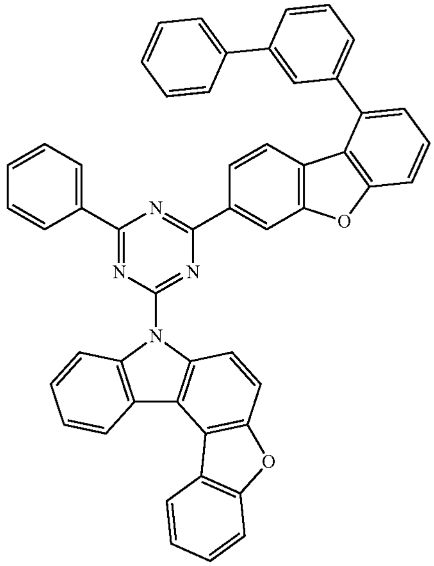
[C-7]
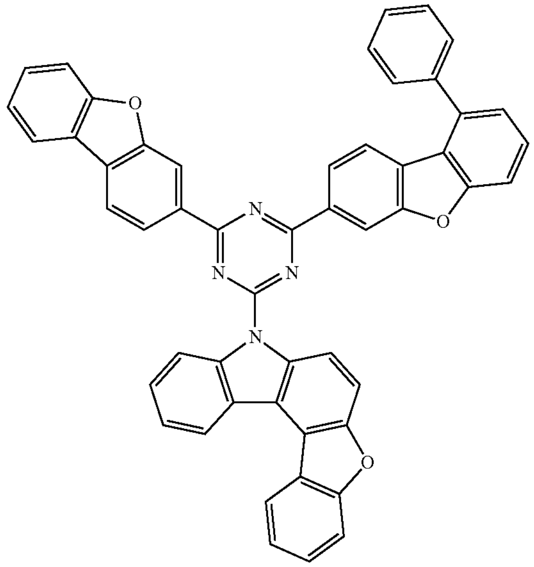

-continued
[C-8]
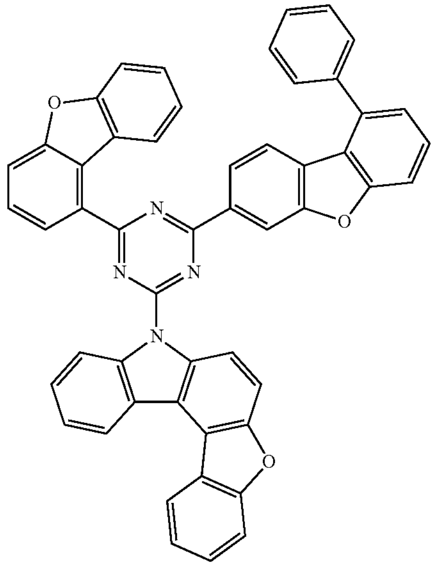
[C-9]
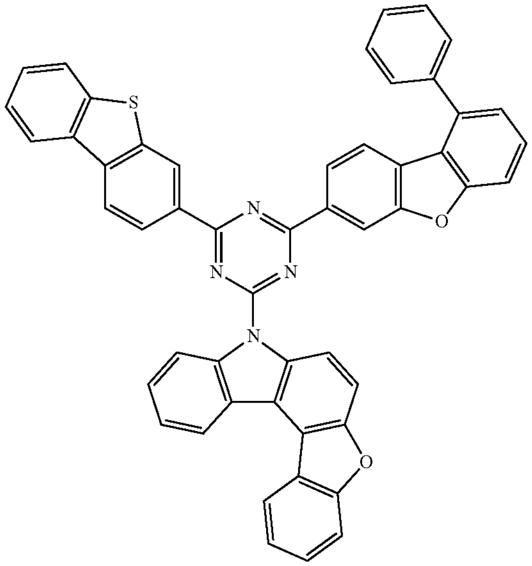
-continued
[C-10]
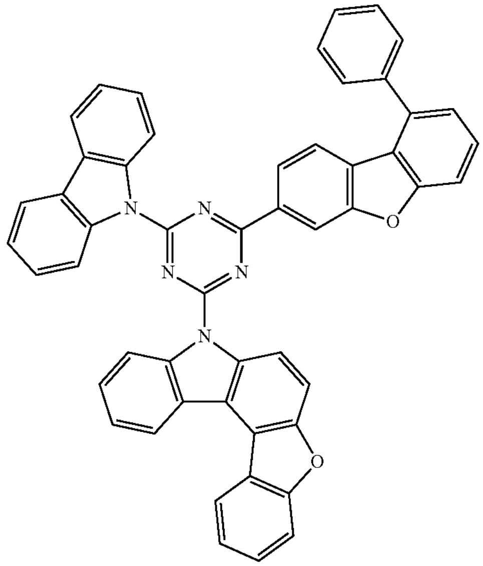
[C-11]
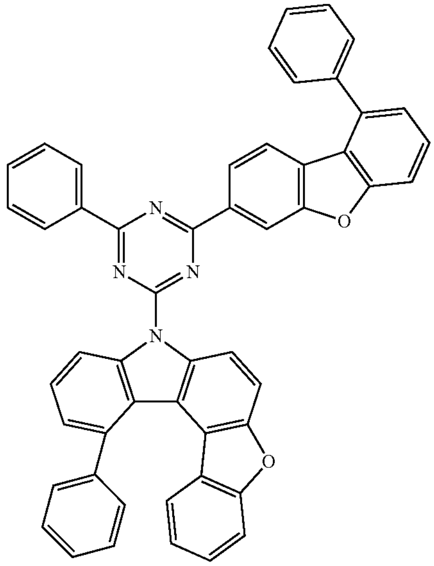

-continued
[C-12]
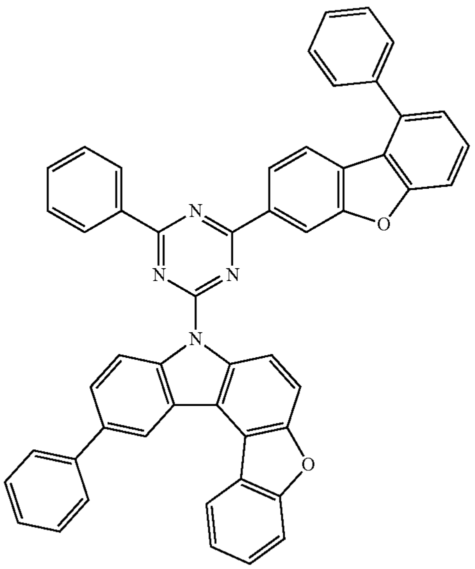
-continued
[C-14]
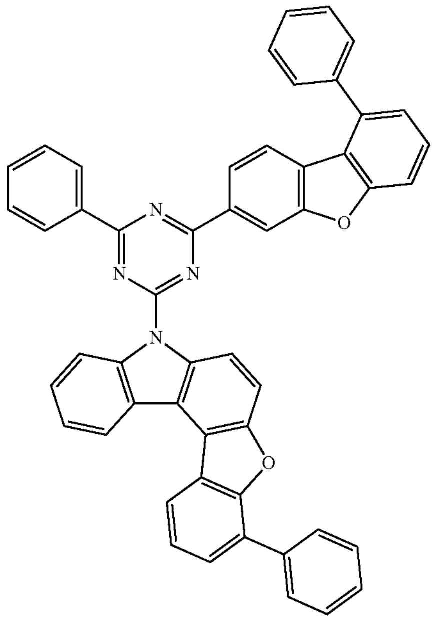
[C-13]
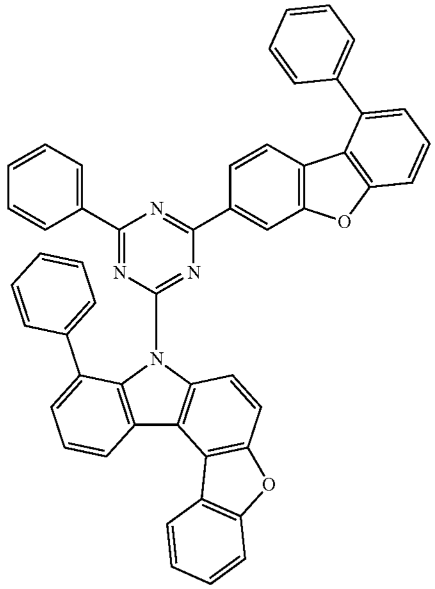
[C-15]
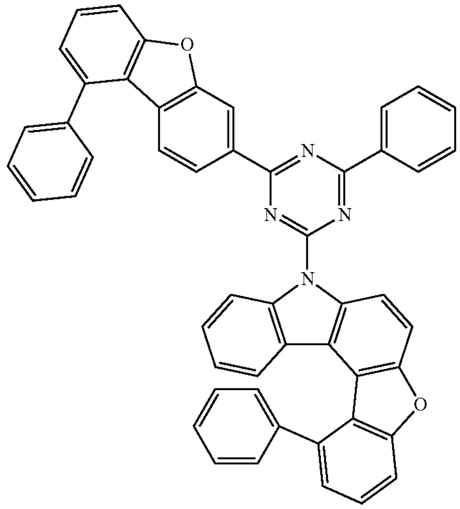

[C-16]
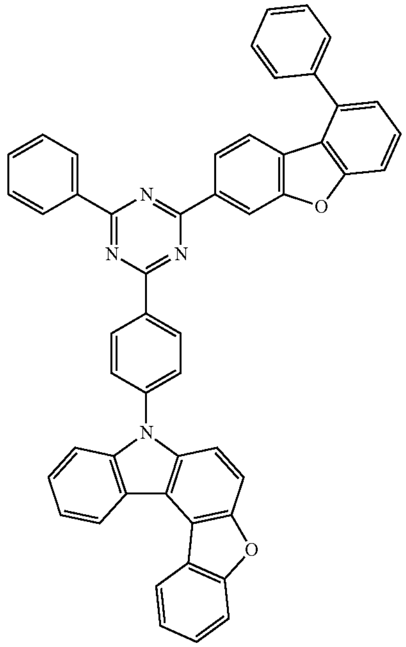
[C-17]
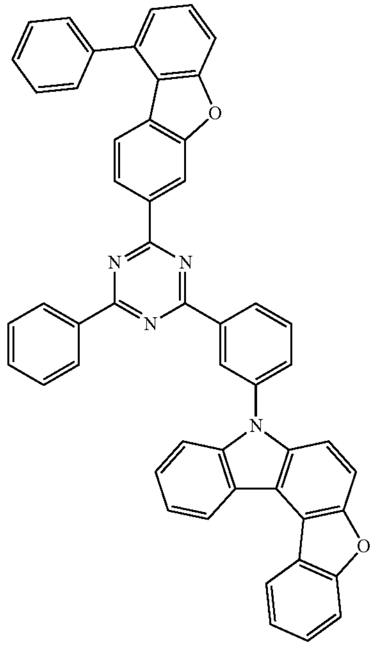
[C-18]
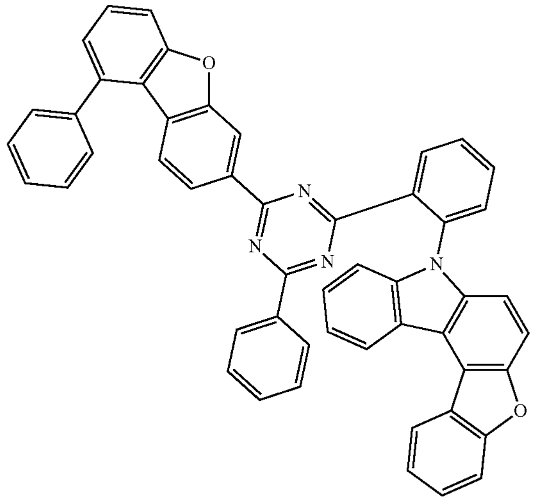
[C-19]
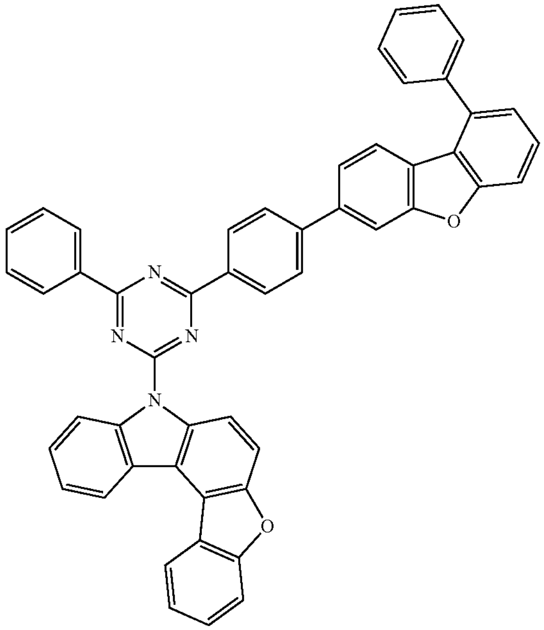

-continued
[C-20]
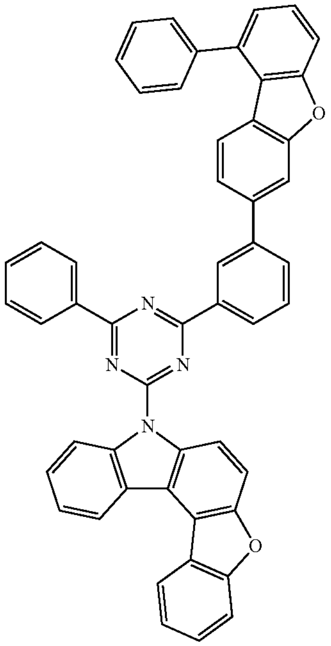
[C-21]
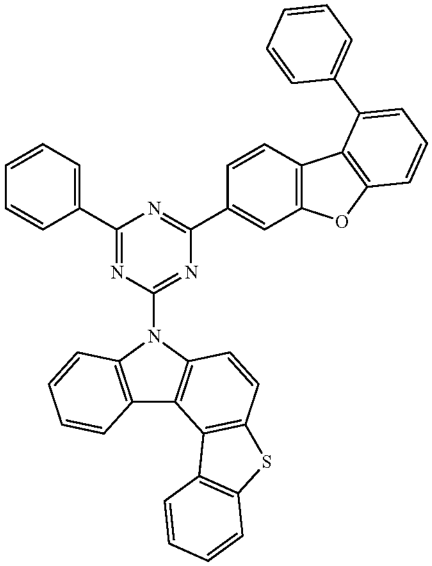
-continued
[C-22]
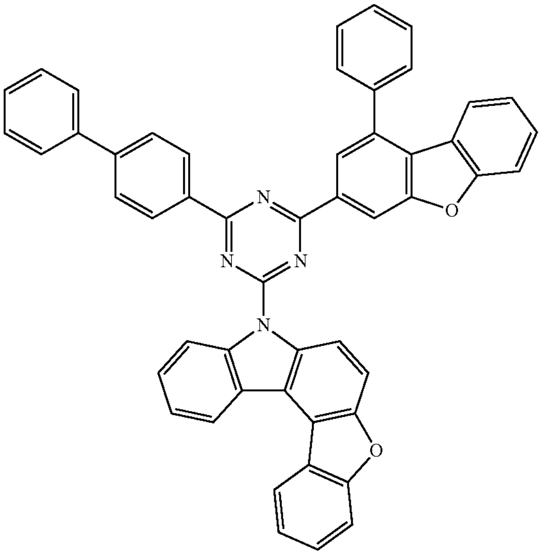
[C-23]
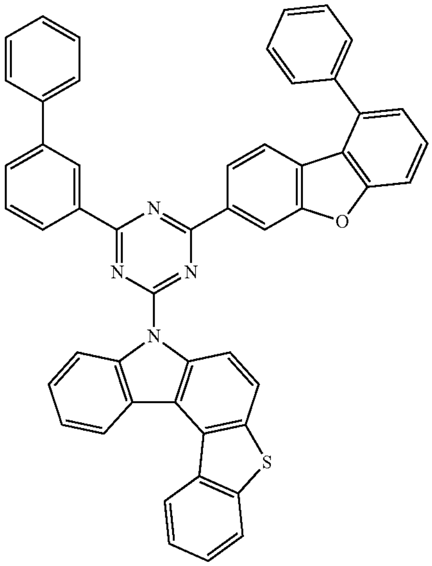

-continued
[C-24]
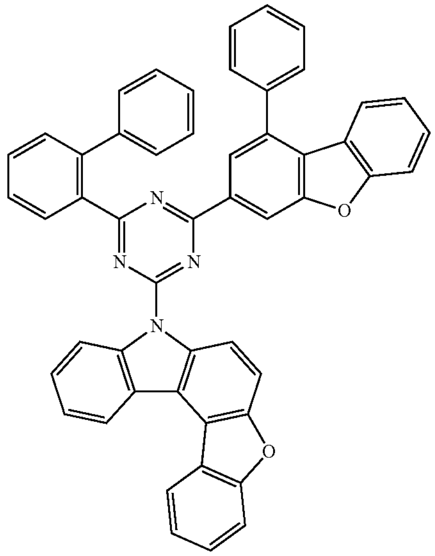
-continued
[C-26]
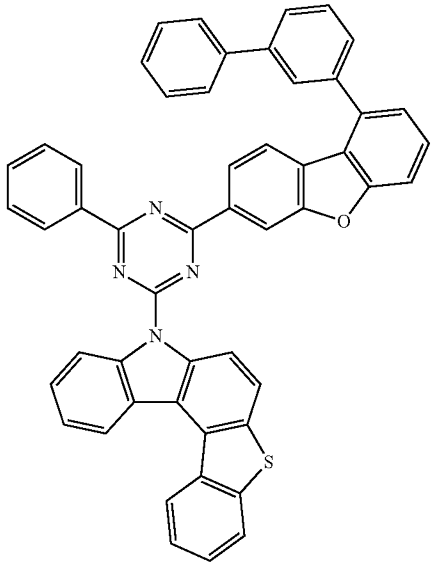
[C-25]
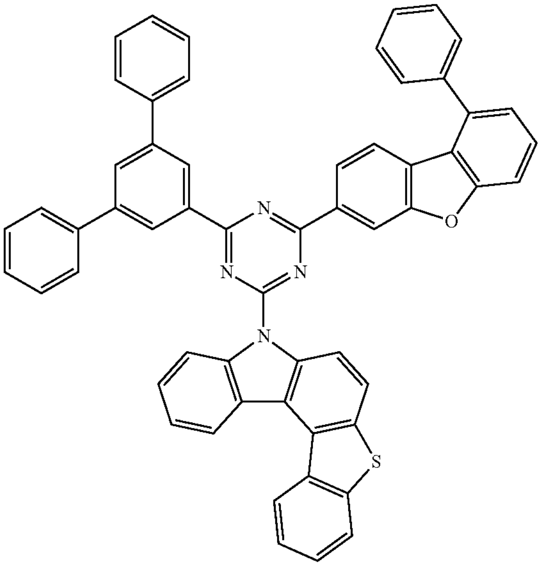
[C-27]
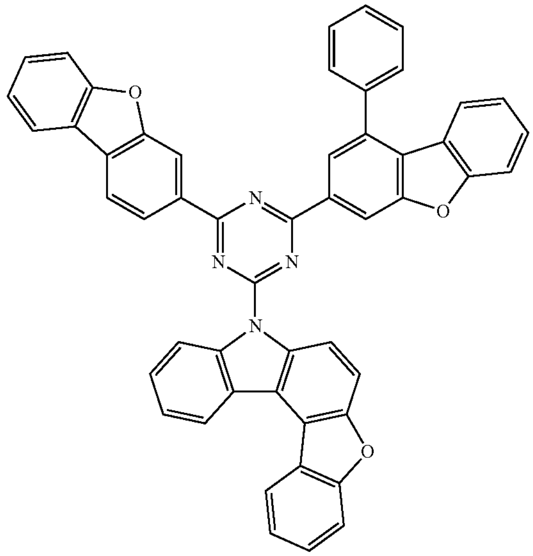

-continued
[C-28]
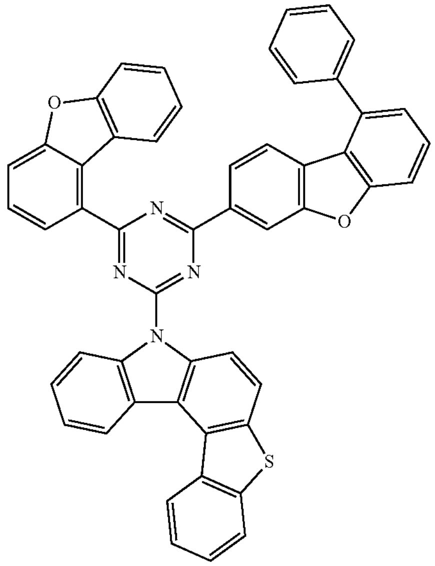
[C-29]
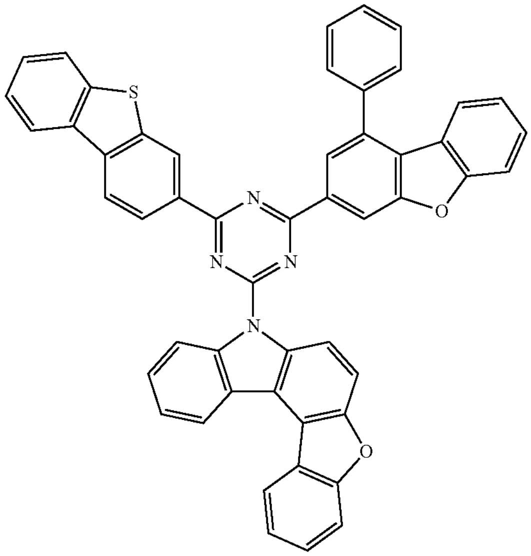
-continued
[C-30]
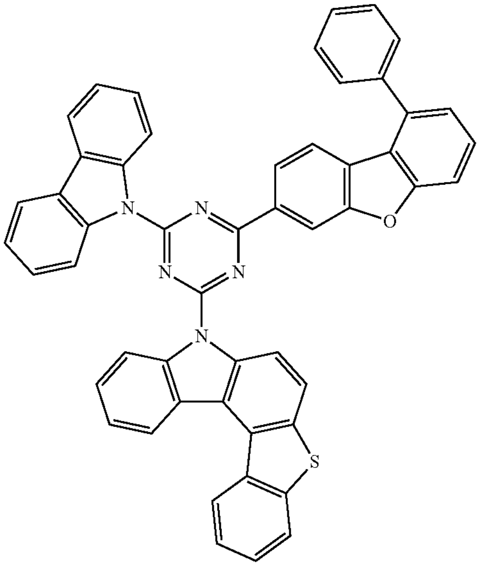
[C-31]
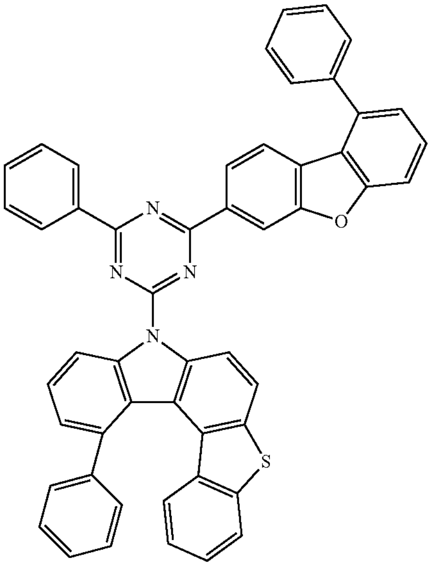

-continued
[C-32]
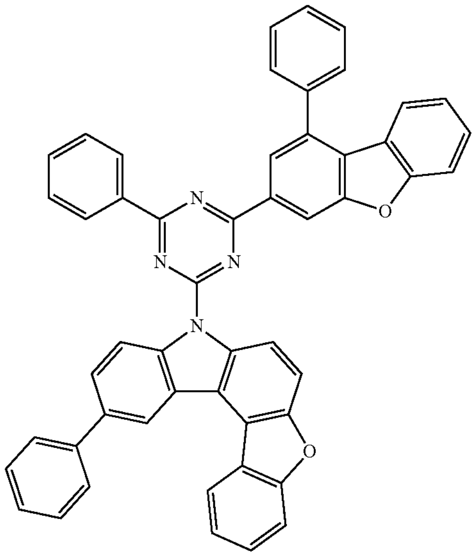
[C-33]
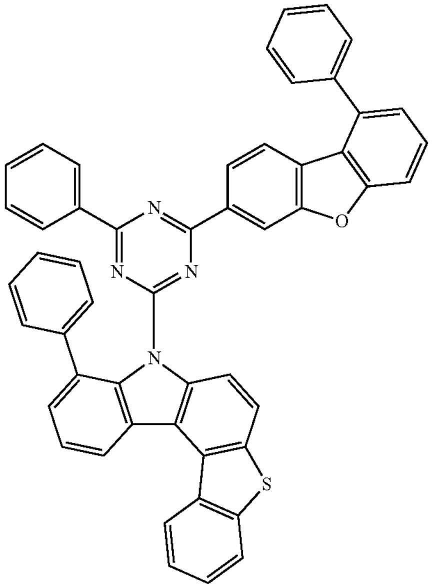
-continued
[C-34]
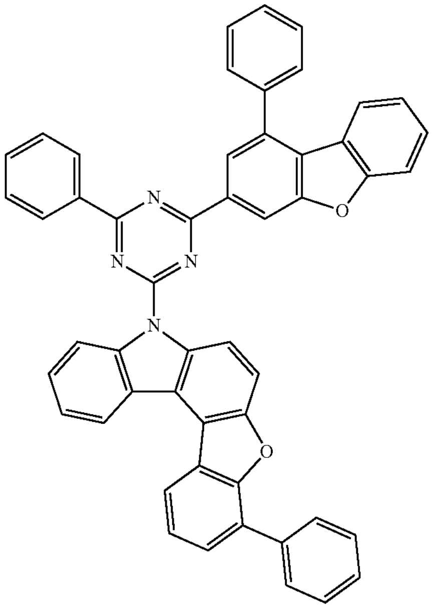
[C-35]
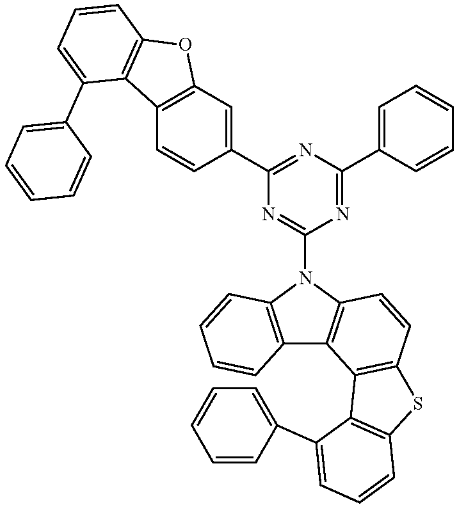

-continued
[C-36]
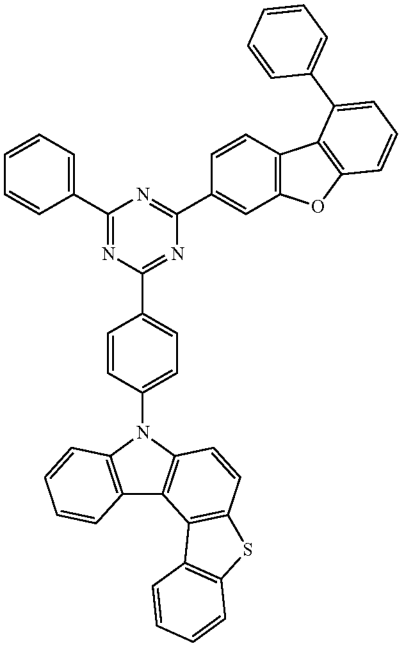
[C-37]
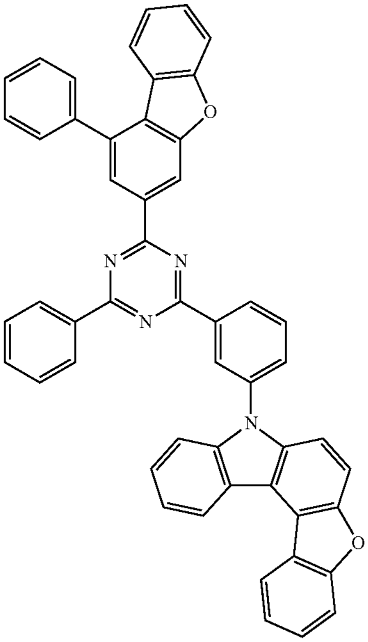
-continued
[C-38]
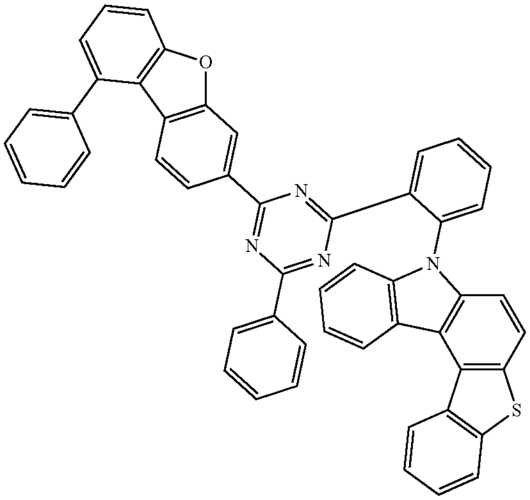
[C-39]
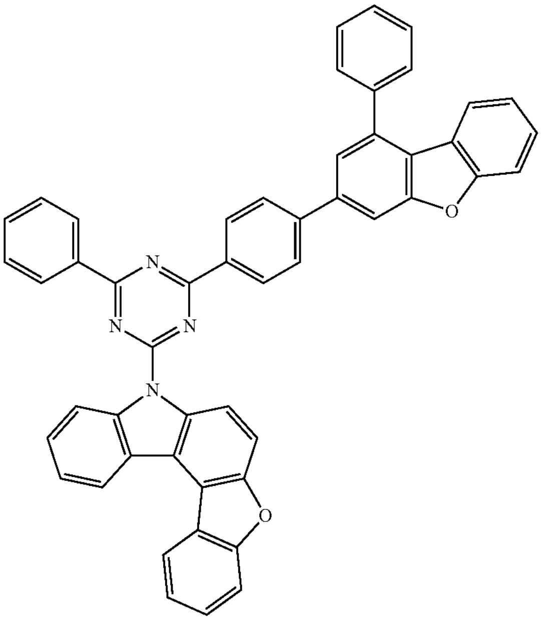

-continued
[C-40]
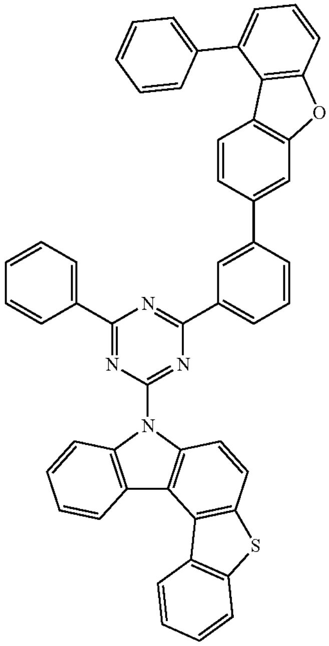
[C-41]
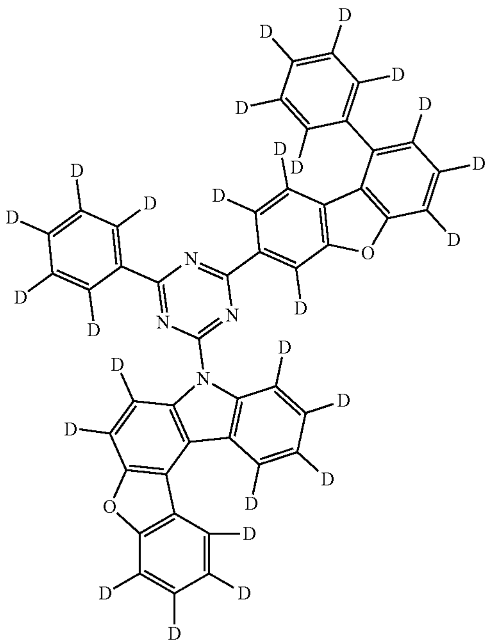
-continued
[C-42]
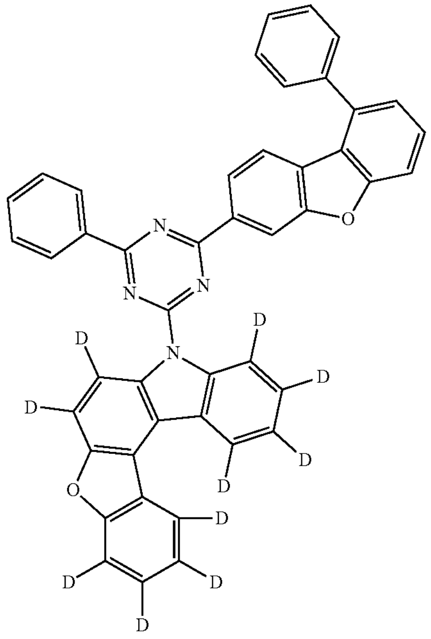
[C-43]
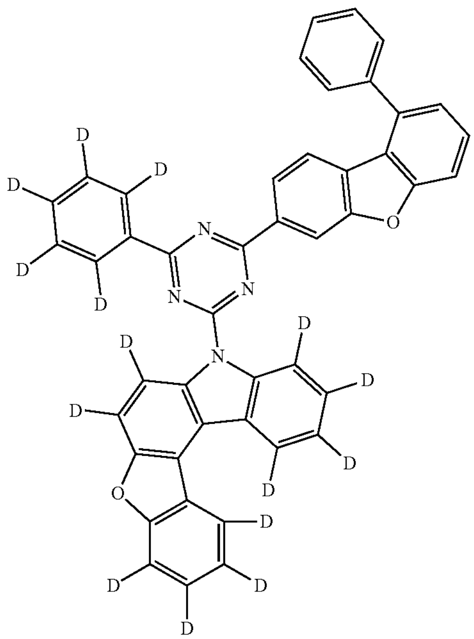

-continued
[C-44]
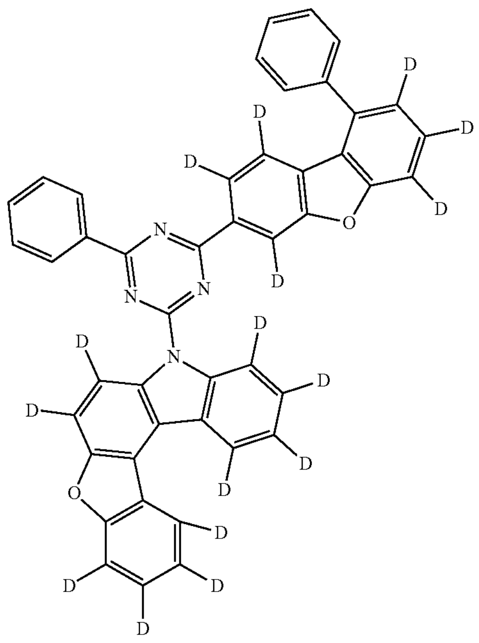
-continued
[C-46]
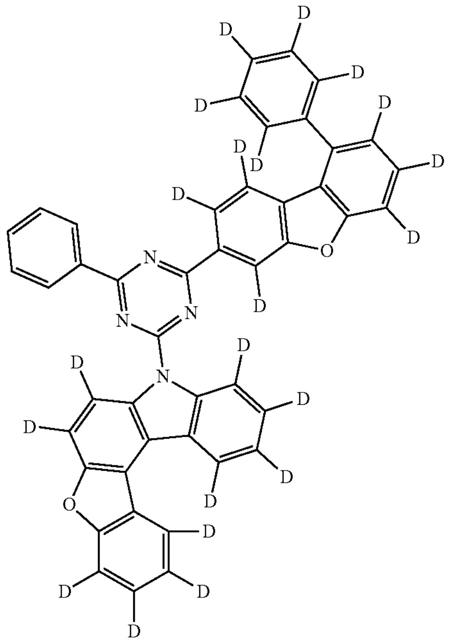
[C-45]
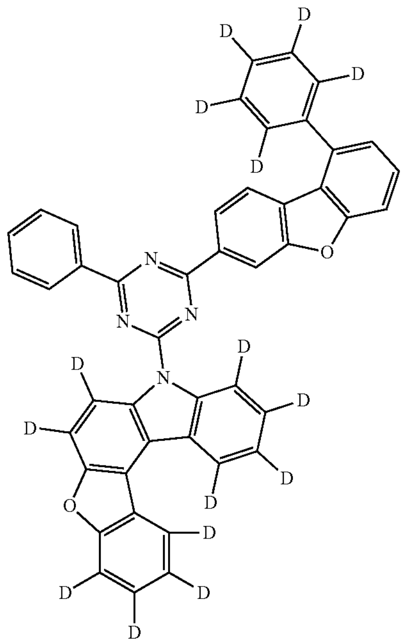
[C-47]
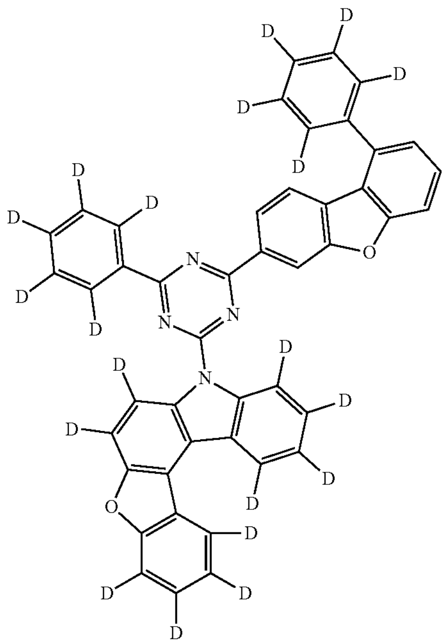

-continued
[C-48]
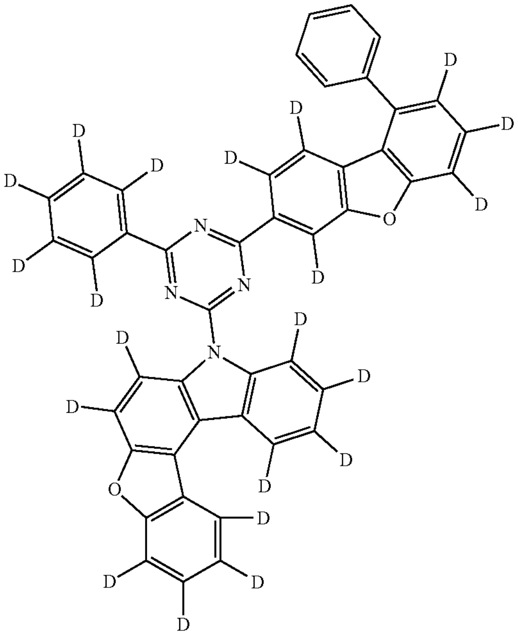
[C-49]
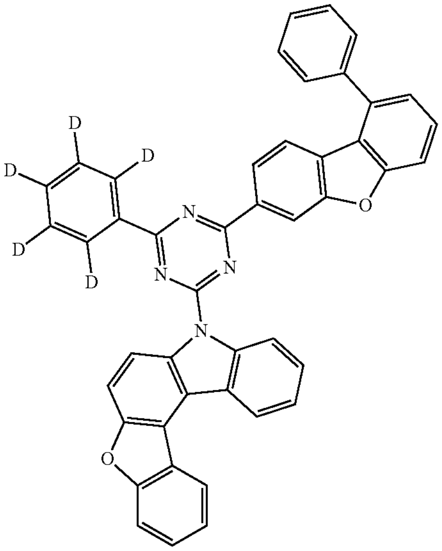
-continued
[C-50]
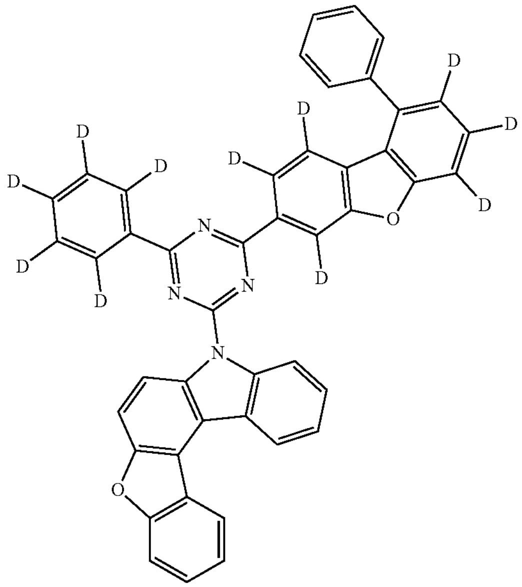
[C-51]
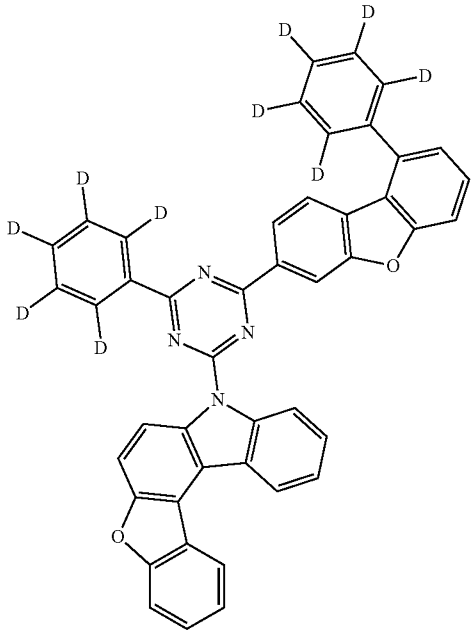

-continued
[C-52]
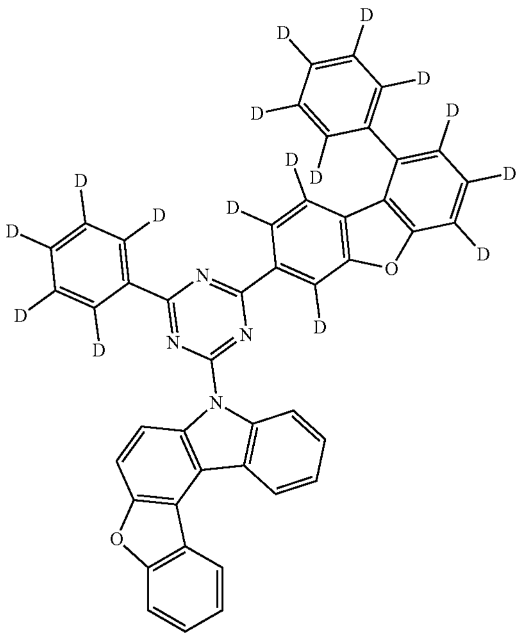
[C-53]
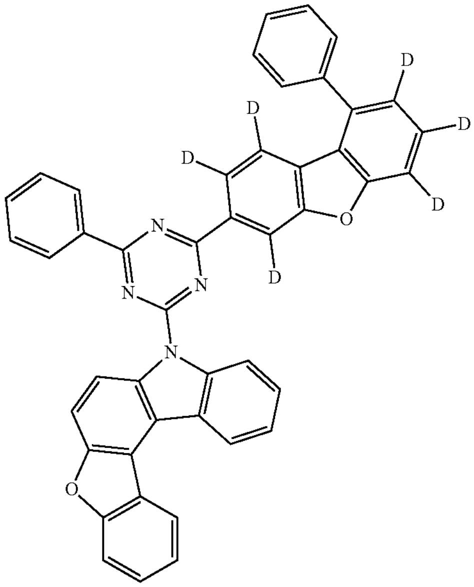
-continued
[C-54]
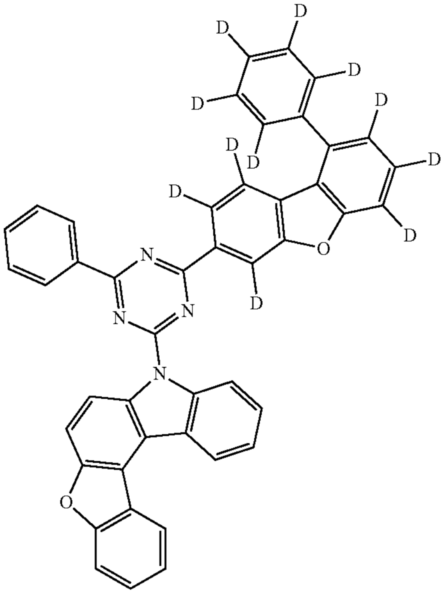
[C-55]
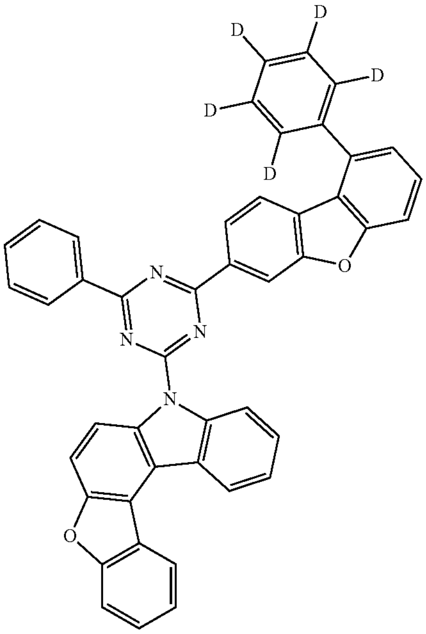

-continued
[C-56]
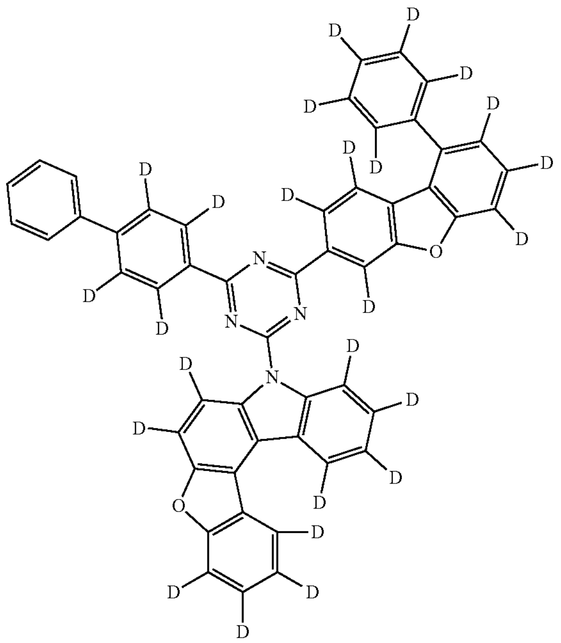
[C-57]
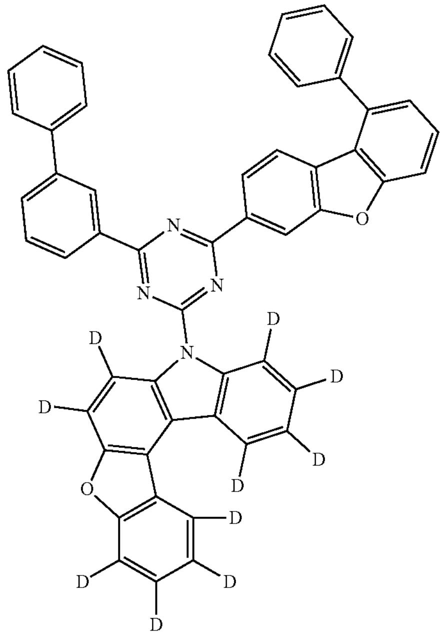
-continued
[C-58]
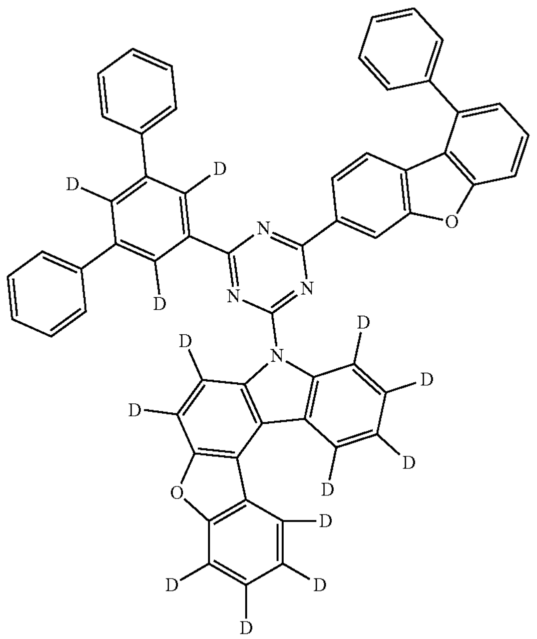
[C-59]
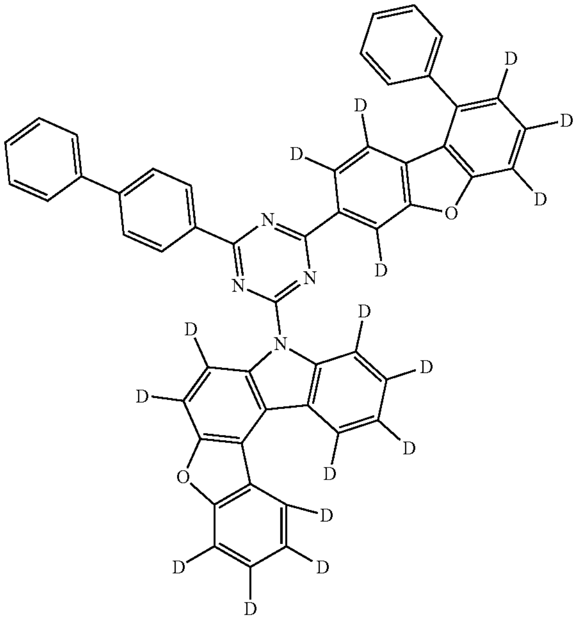

-continued
[C-60]
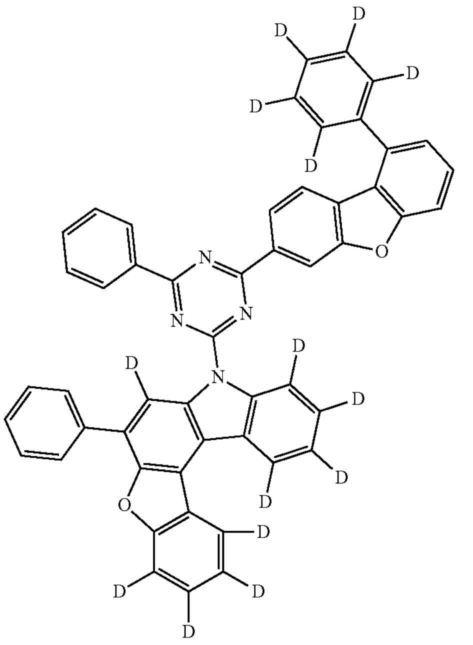
[C-61]
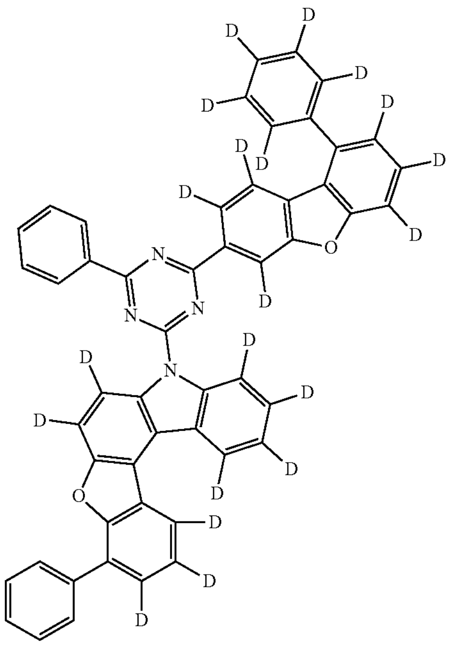
-continued
[C-62]
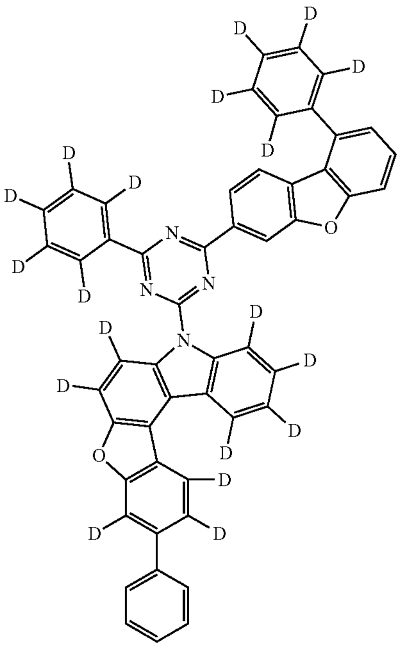
[C-63]
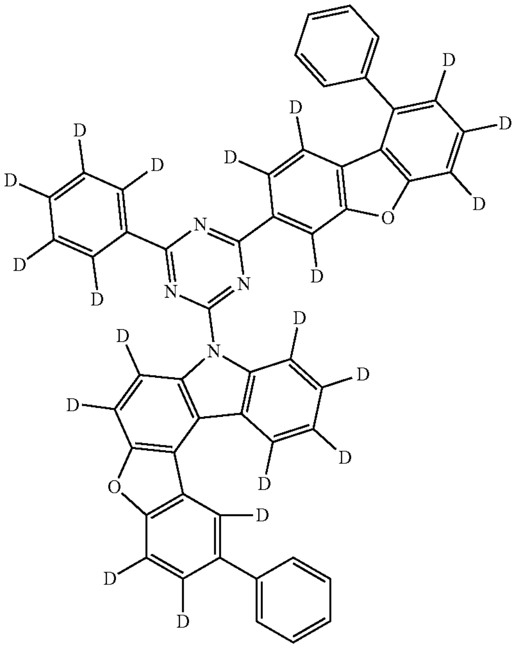

-continued
[C-64]
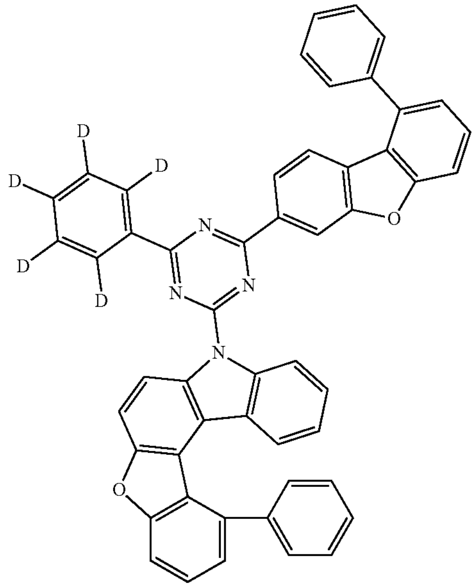
[C-65]
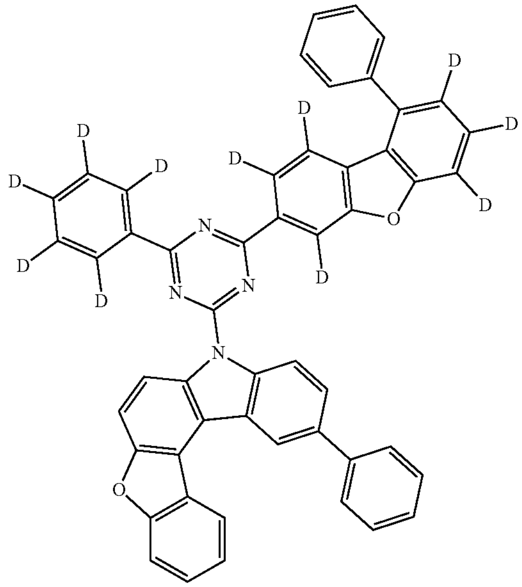
-continued
[C-66]
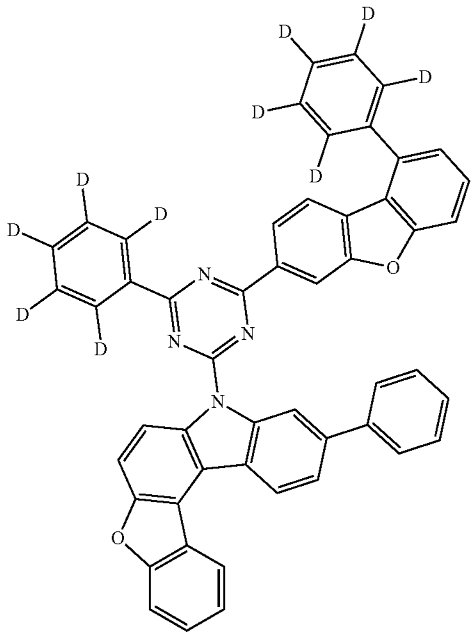
[C-67]
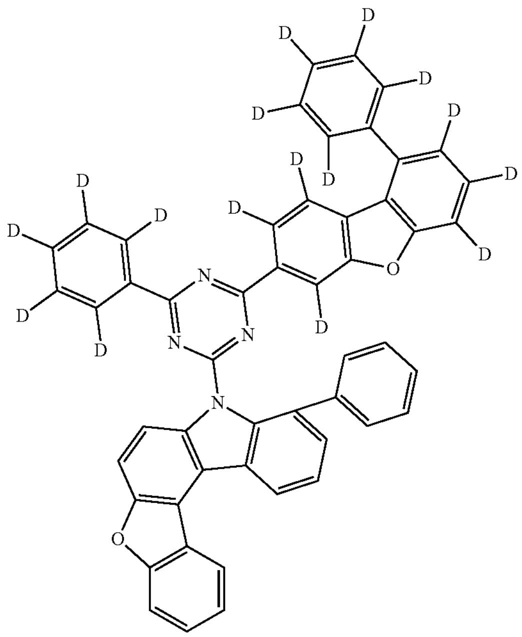

-continued
[C-68]
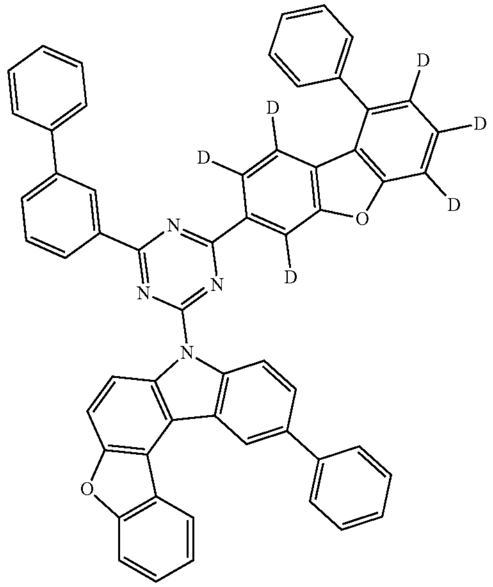
[C-69]
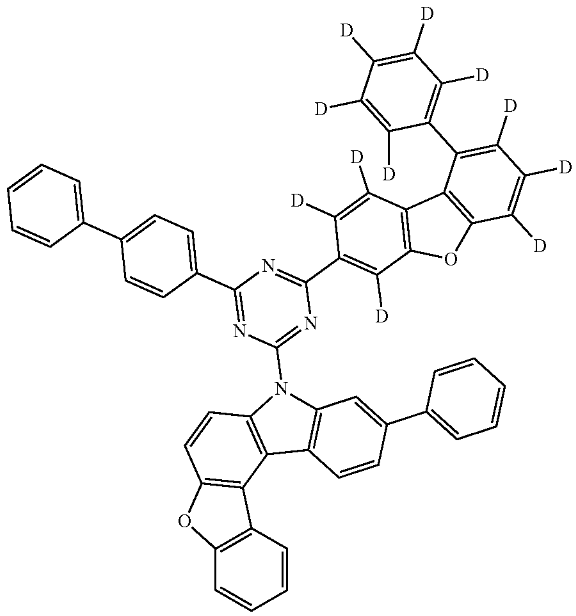
-continued
[C-70]
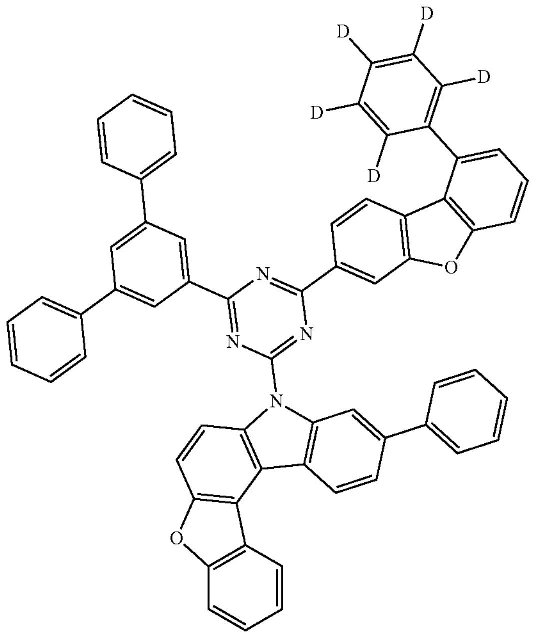
[C-71]
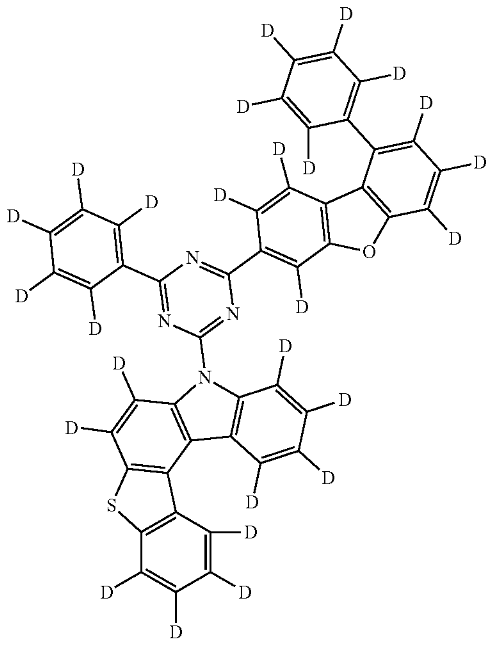

-continued
[C-72]
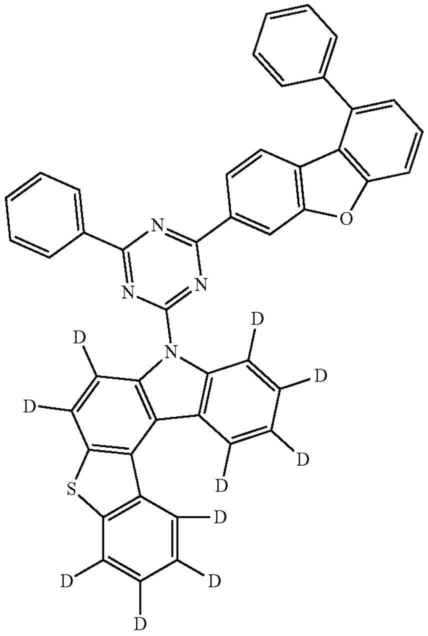
[C-73]
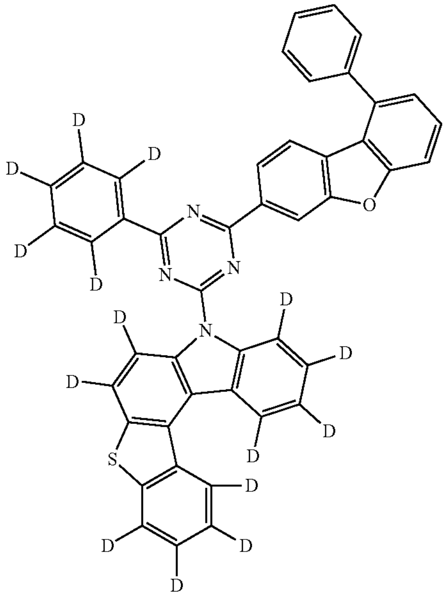
-continued
[C-74]
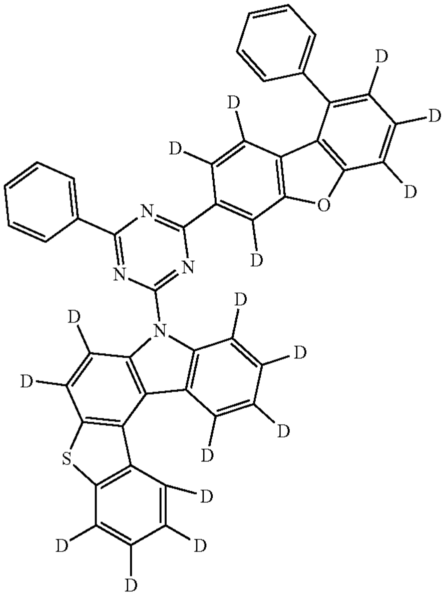
[C-75]
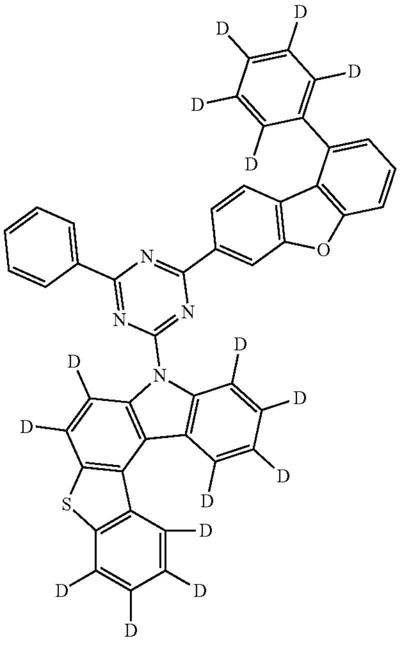

[C-76]
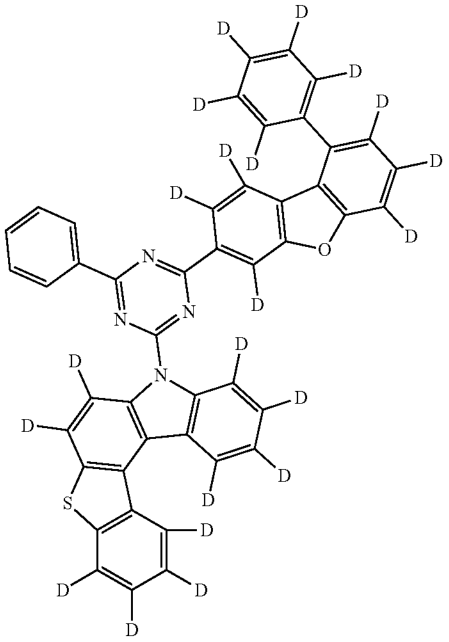
[C-77]
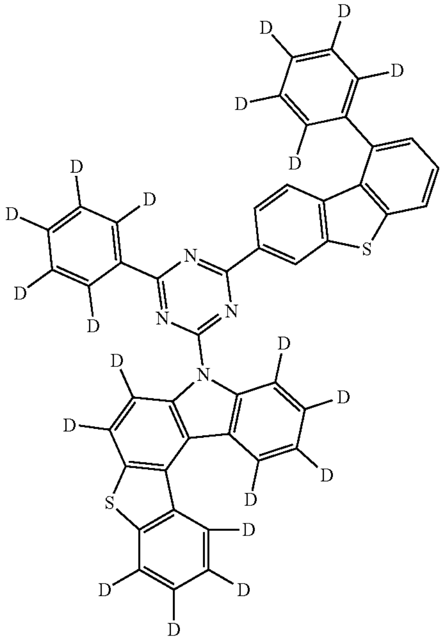
[C-78]
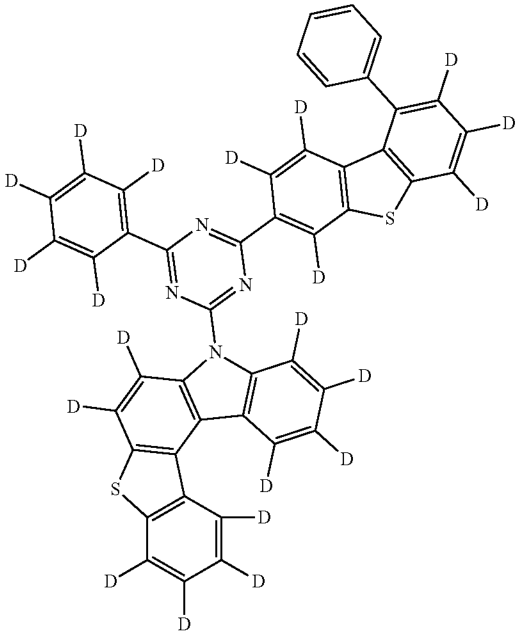
[C-79]
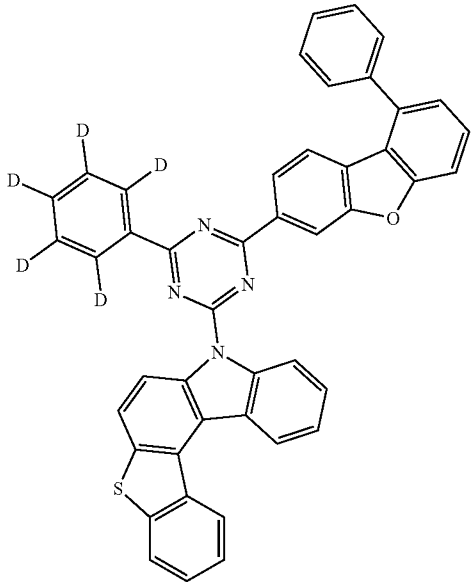

-continued
[C-80]
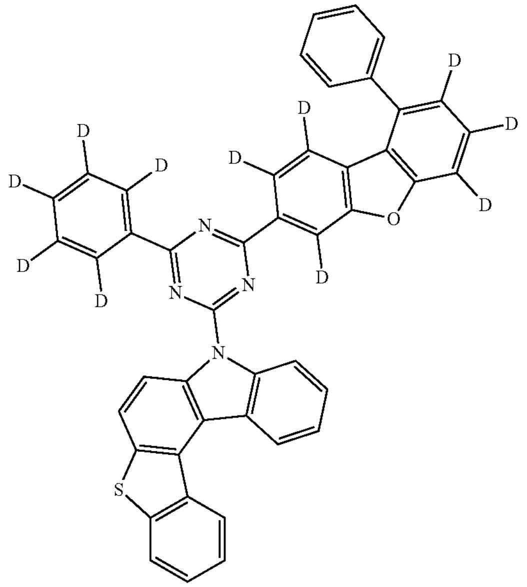
[C-81]
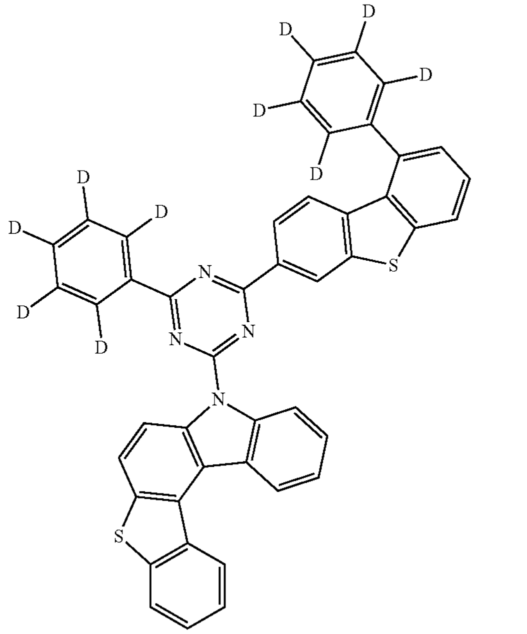
-continued
[C-82]
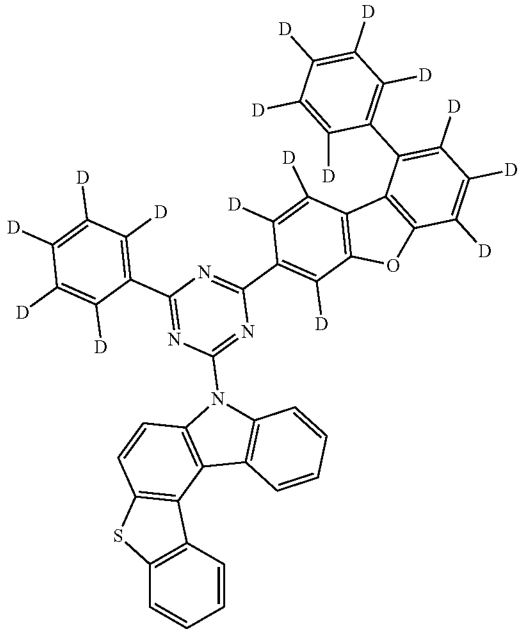
[C-83]
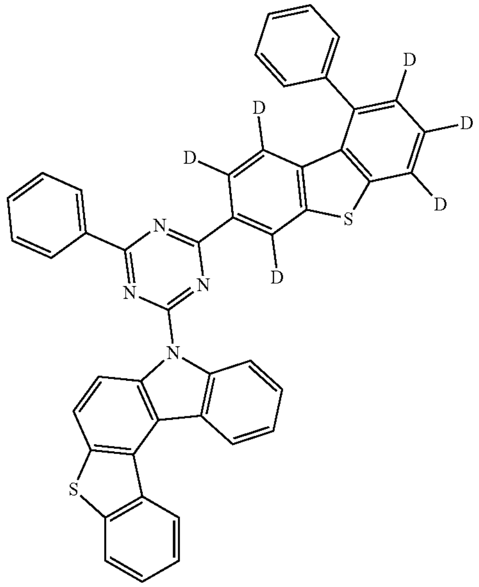

[C-84]
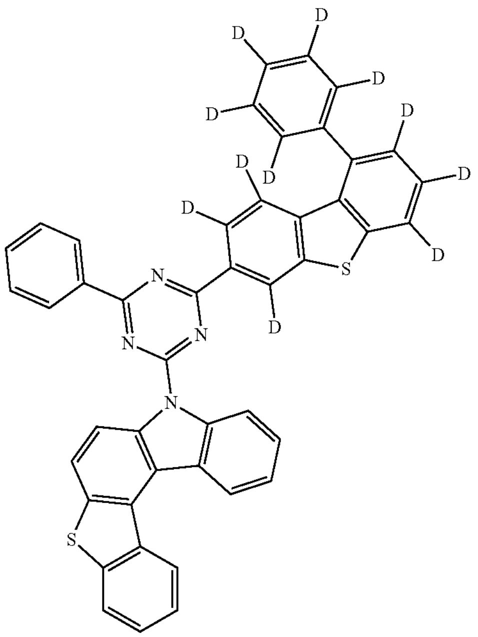
[C-85]
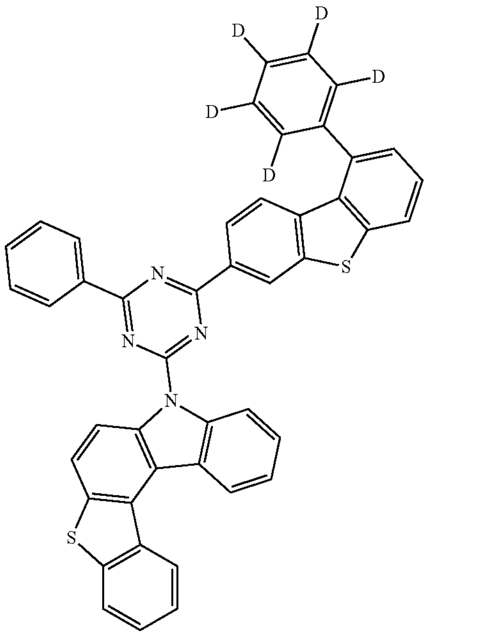
[C-86]
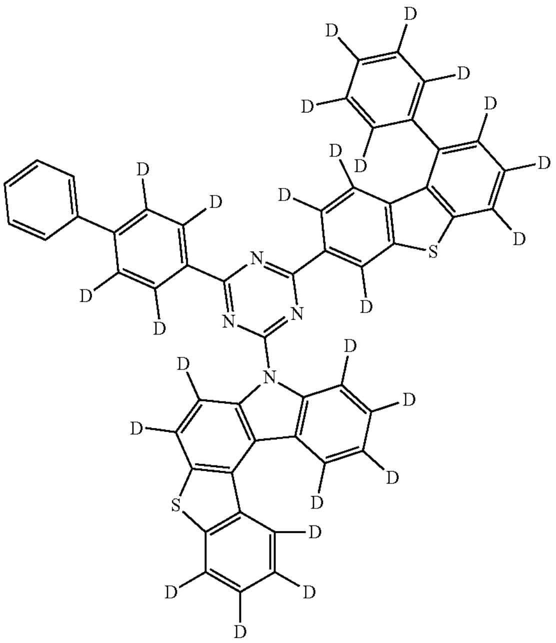
[C-87]
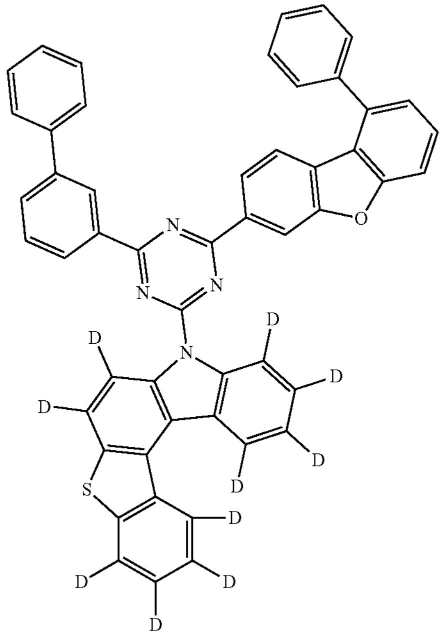

[C-88]
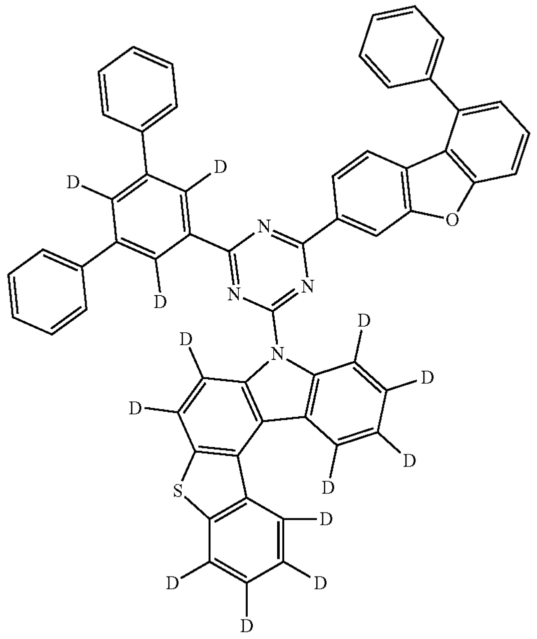
[C-89]
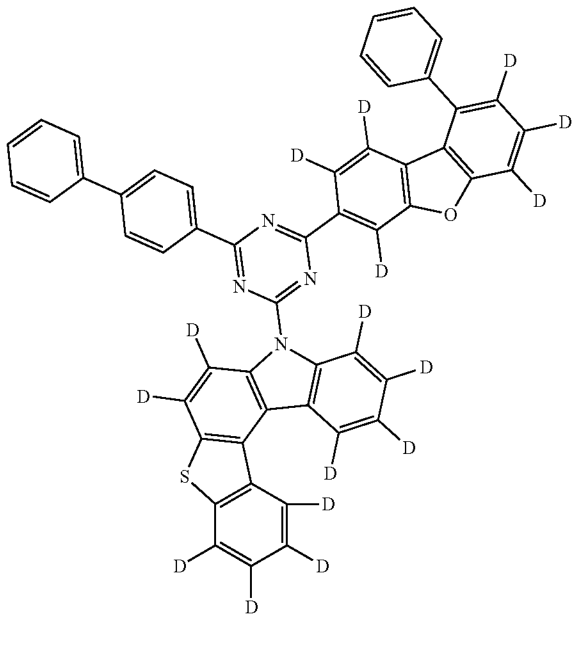
[C-90]
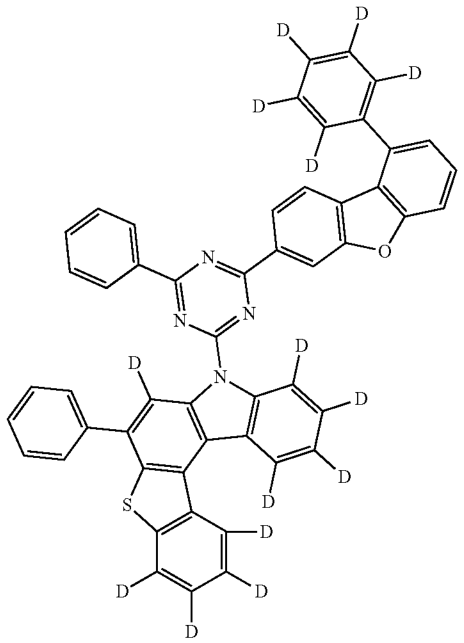
[C-91]
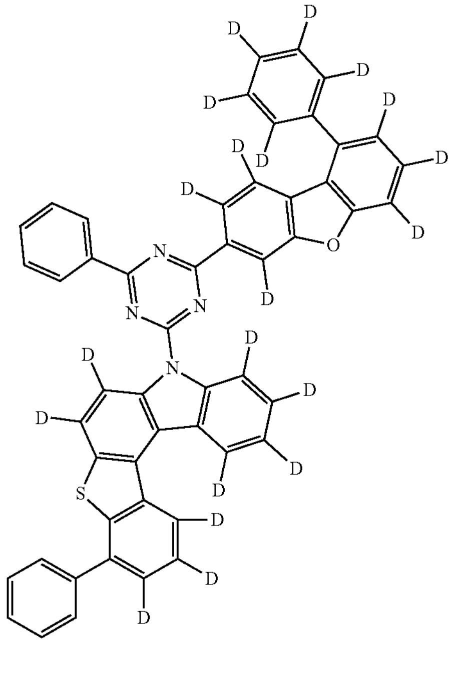

-continued
[C-92]
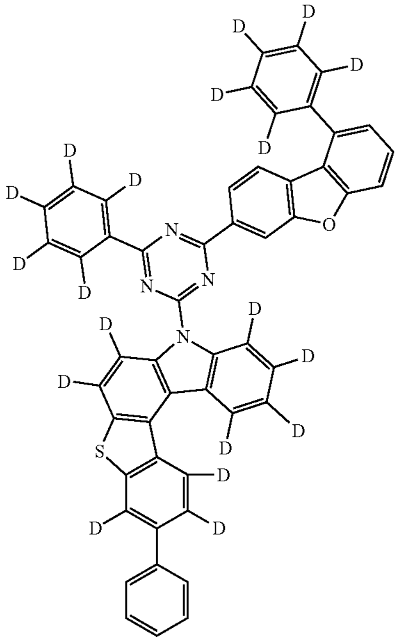
[C-93]
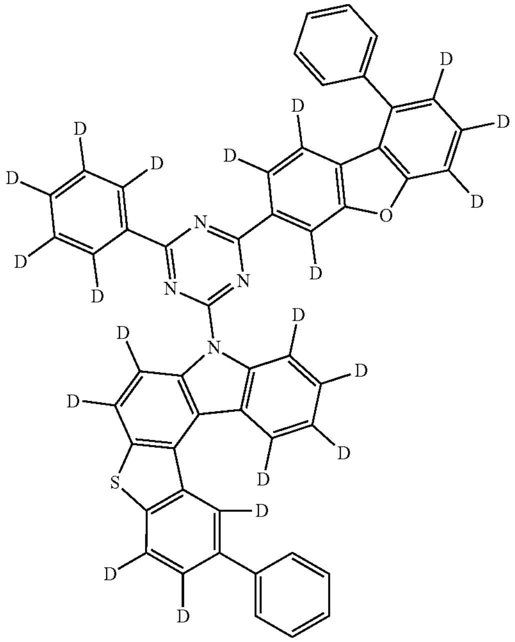
-continued
[C-94]
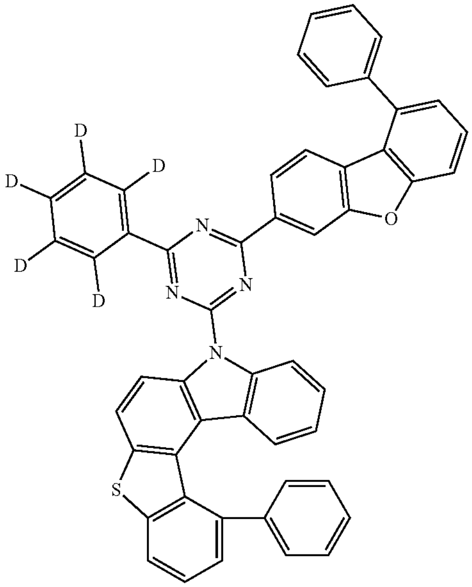
[C-95]
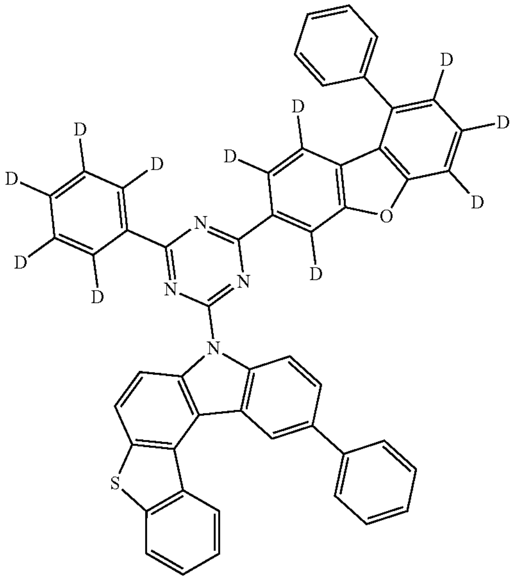

-continued
[C-96]
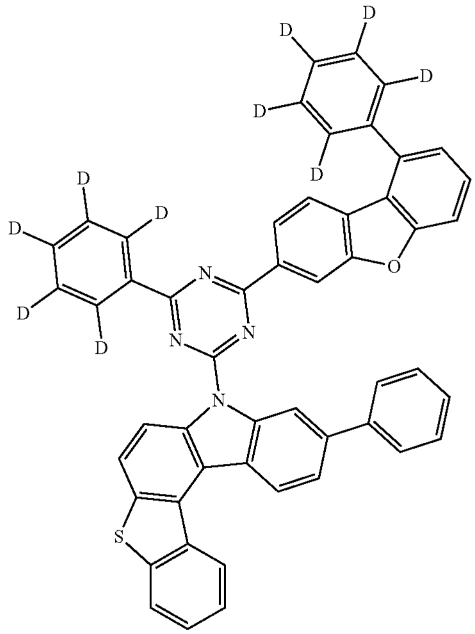
[C-97]
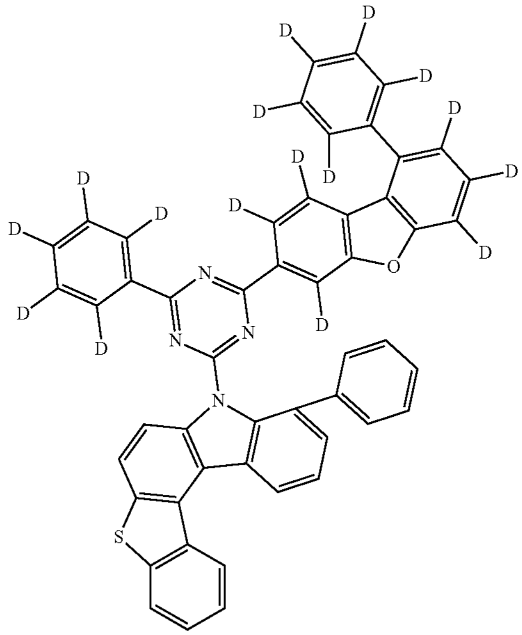
-continued
[C-98]
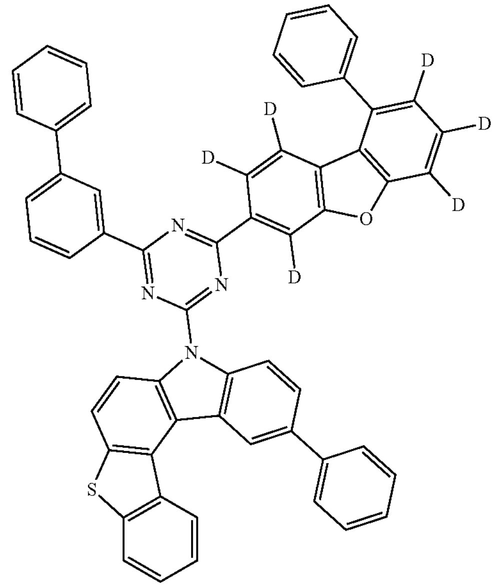
[C-99]
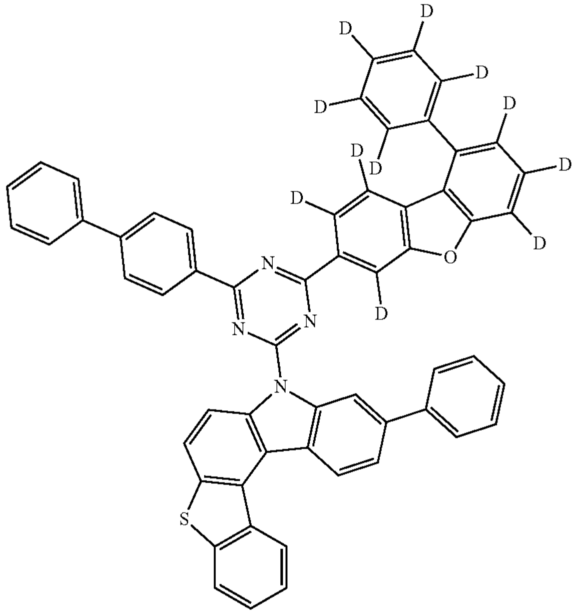

-continued
[C-100]
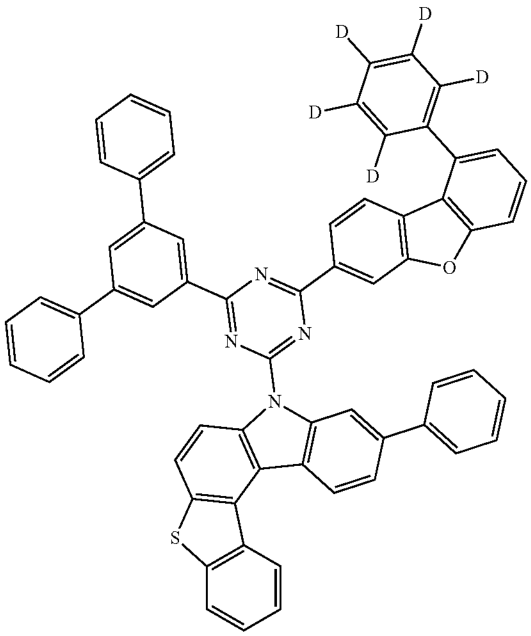
[D-1]
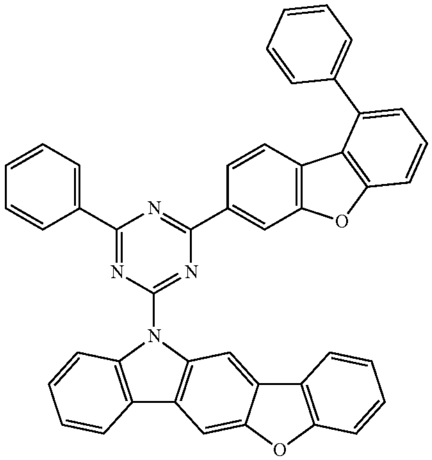
[D-2]
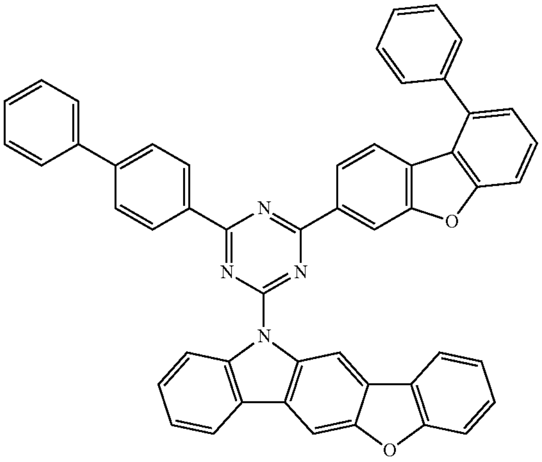
-continued
[D-3]
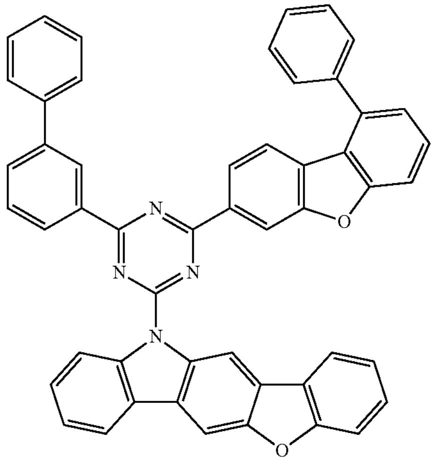
[D-4]
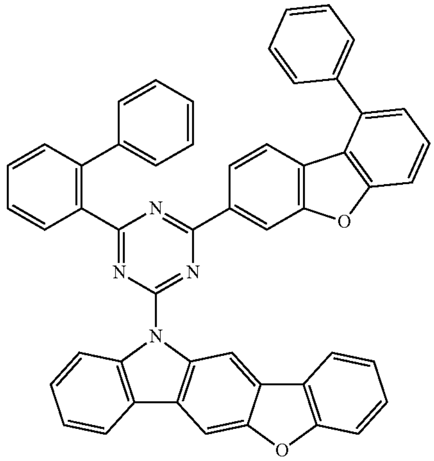
[D-5]
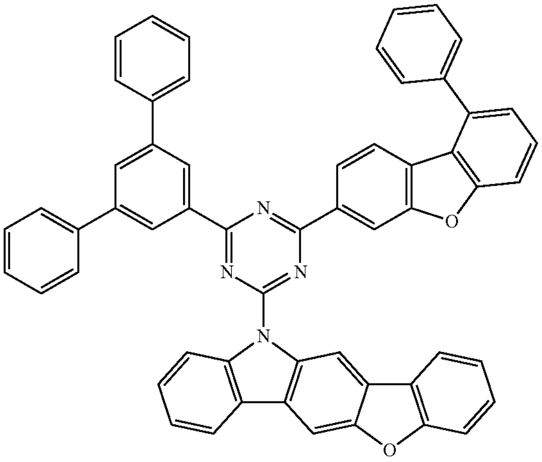

[D-6]
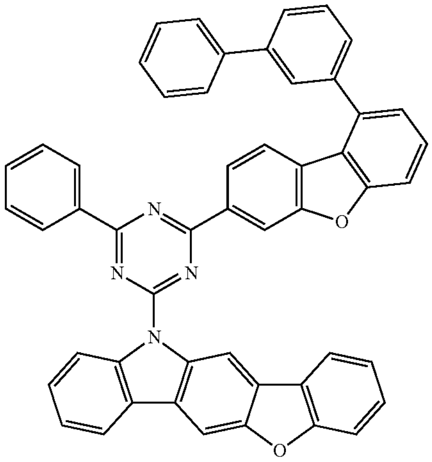
[D-7]
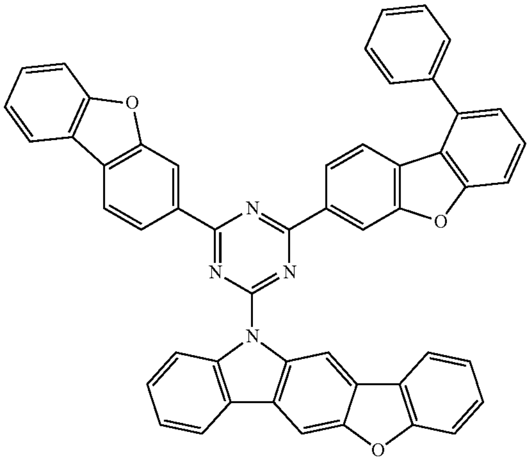
[D-8]
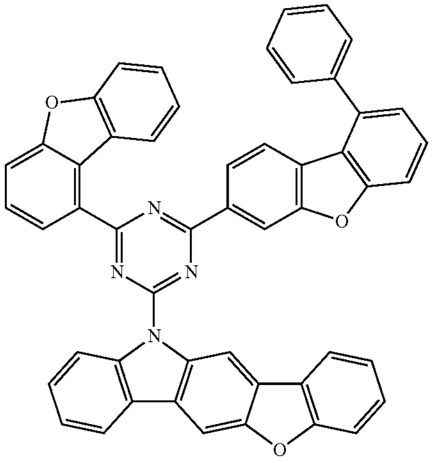
[D-9]
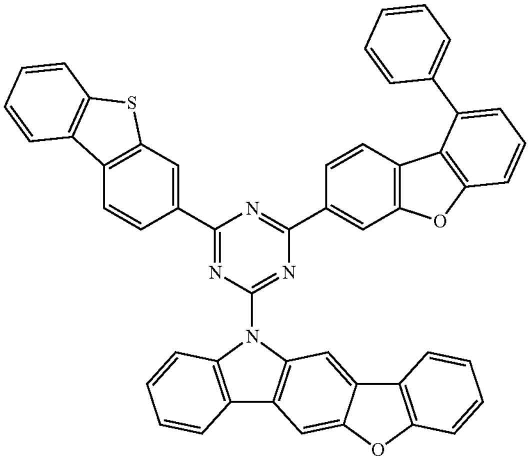
[D-10]
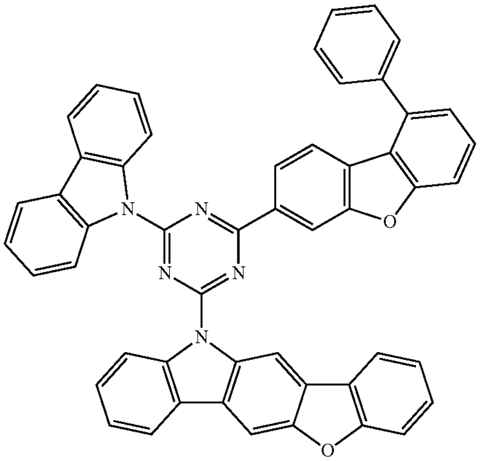
[D-11]
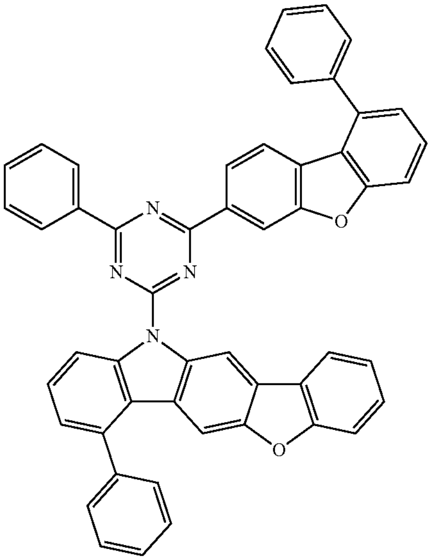

-continued
[D-12]
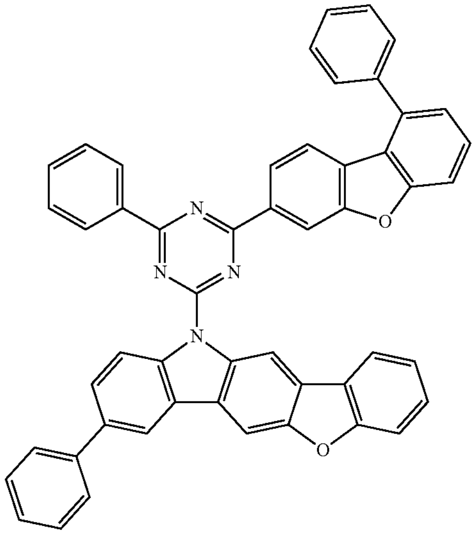
[D-13]
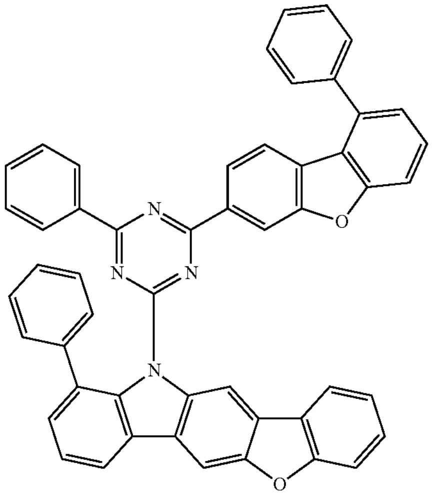
[D-14]
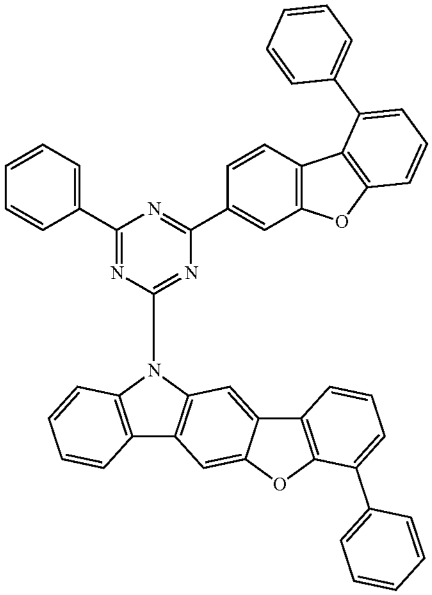
-continued
[D-15]
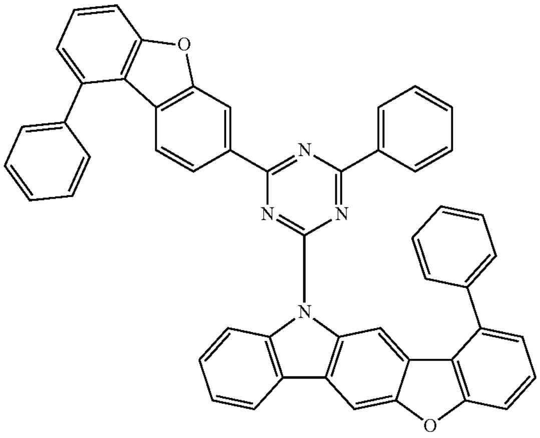
[D-16]
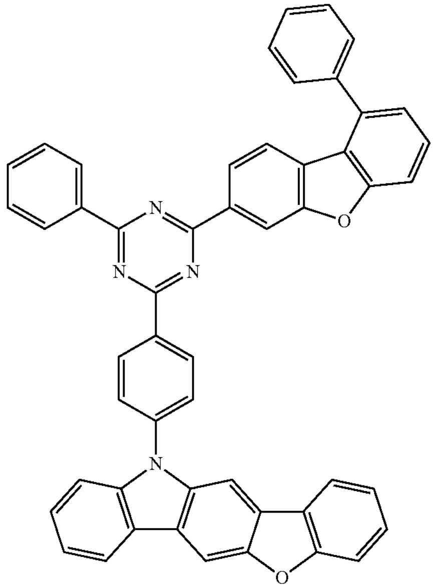
[D-17]
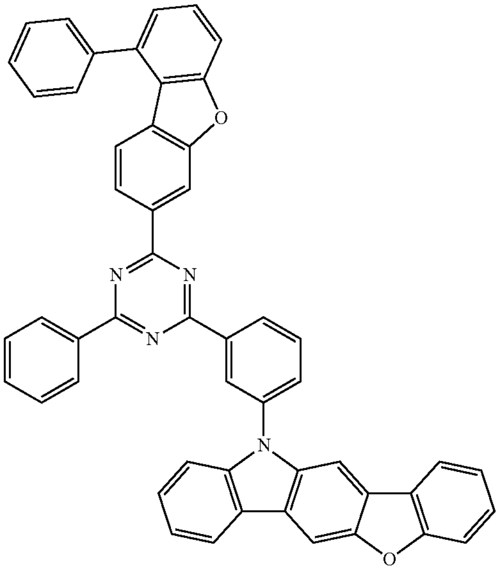

-continued
[D-18]
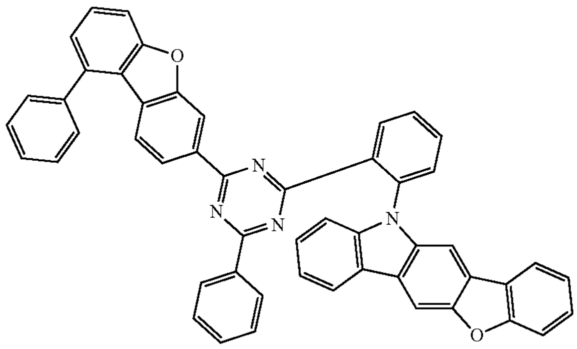
[D-19]
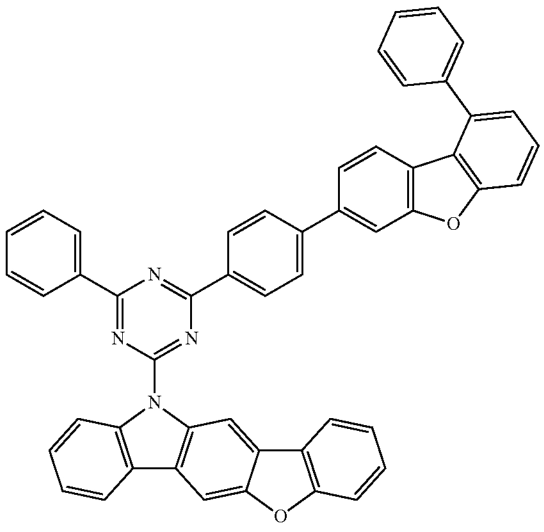
[D-20]
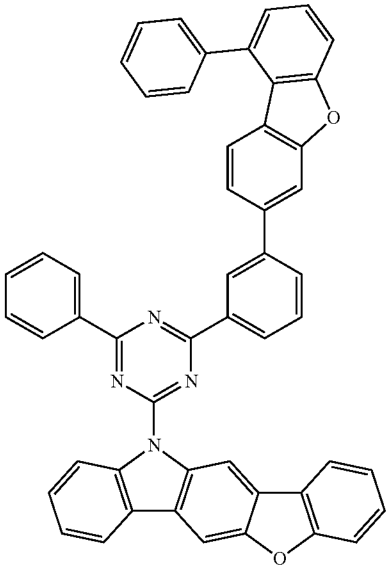
-continued
[D-21]
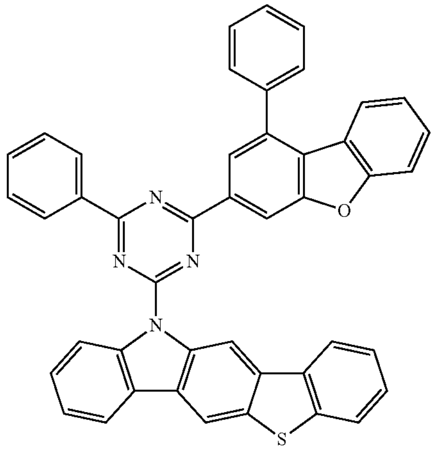
[D-22]
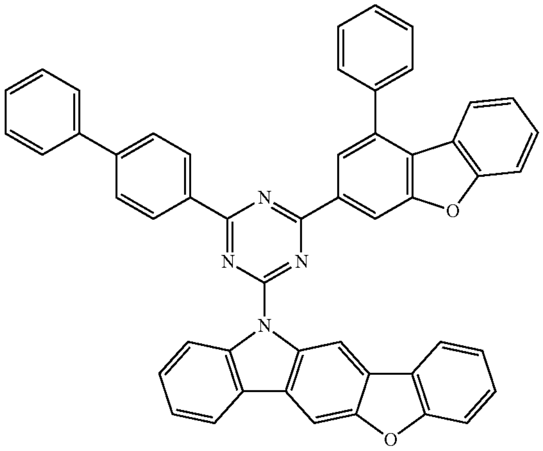
[D-23]
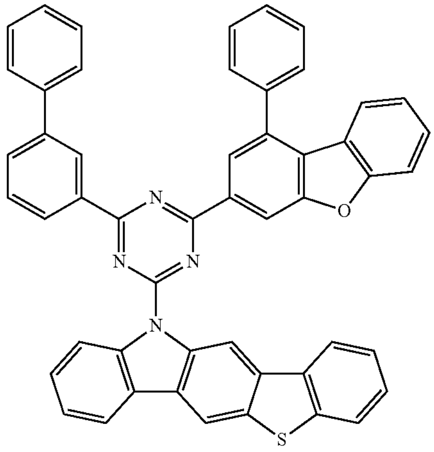

-continued
[D-24]
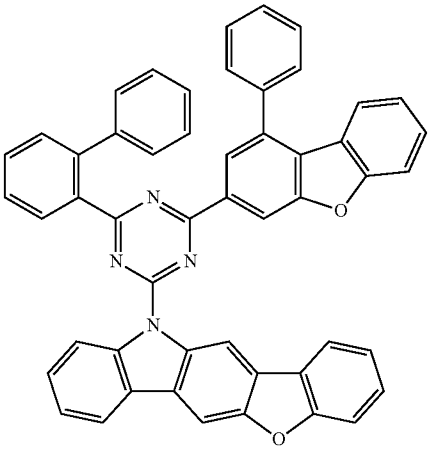
[D-25]
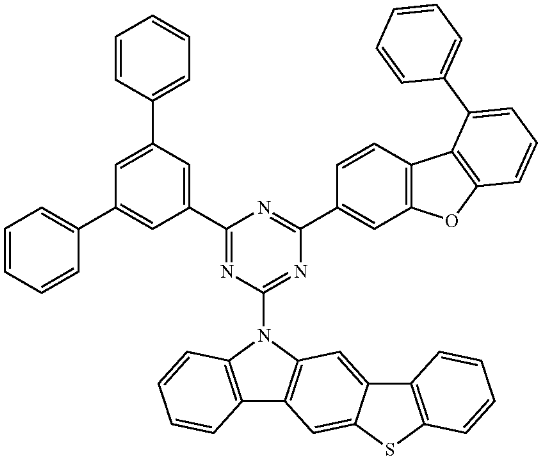
[D-26]
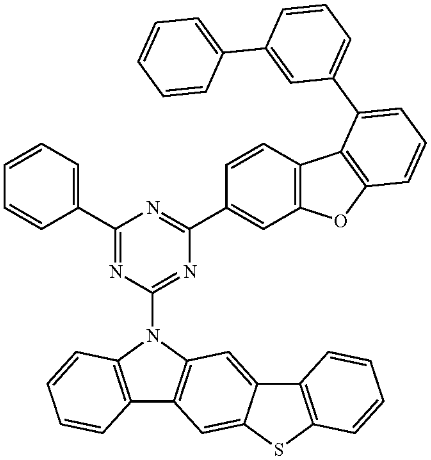
-continued
[D-27]
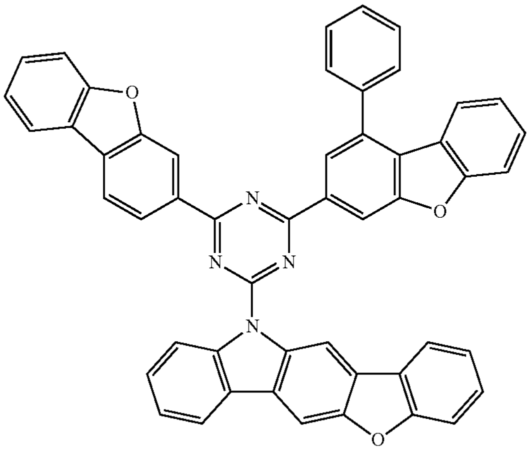
[D-28]
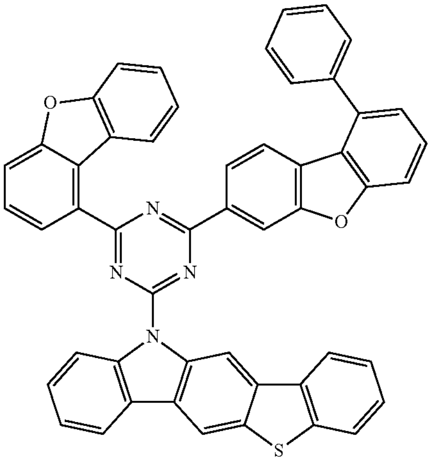
[D-29]
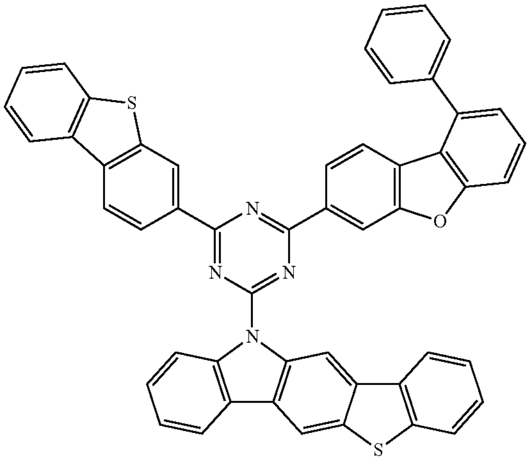

-continued
[D-30]
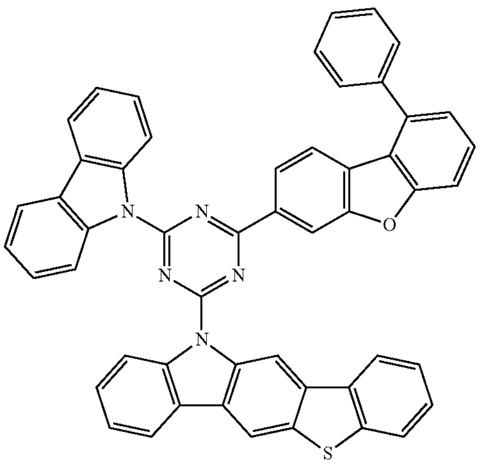
[D-31]
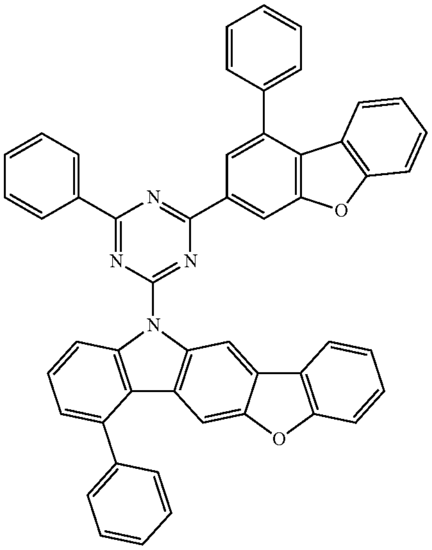
[D-32]
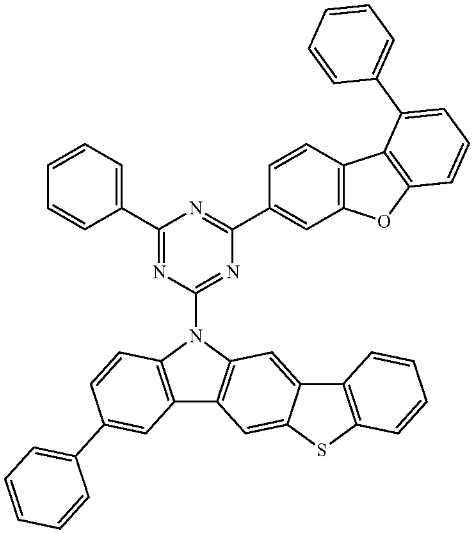
-continued
[D-33]
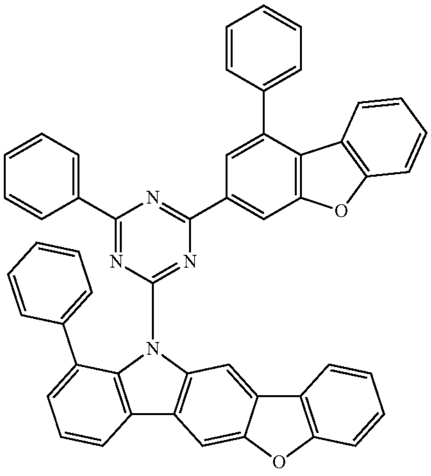
[D-34]
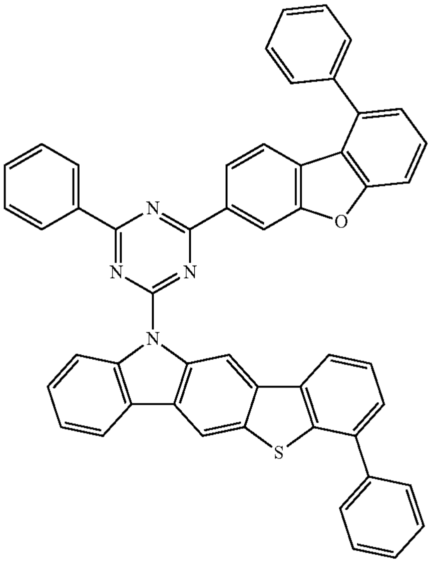
[D-35]
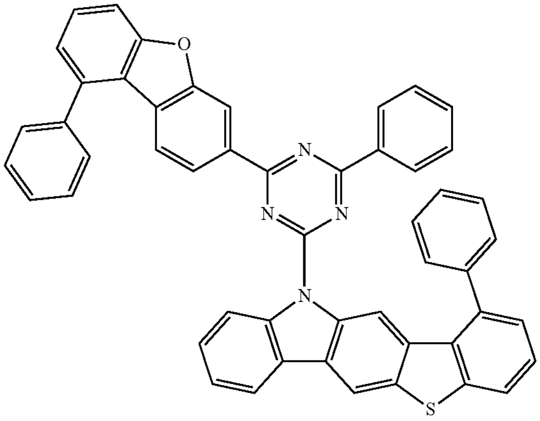

-continued
[D-36]
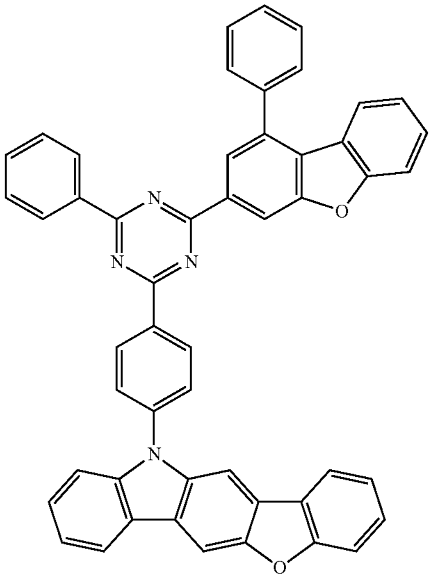
[D-37]
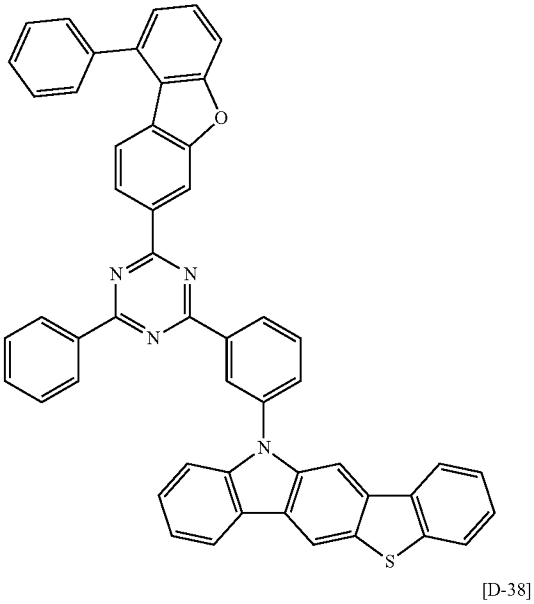
[D-38]
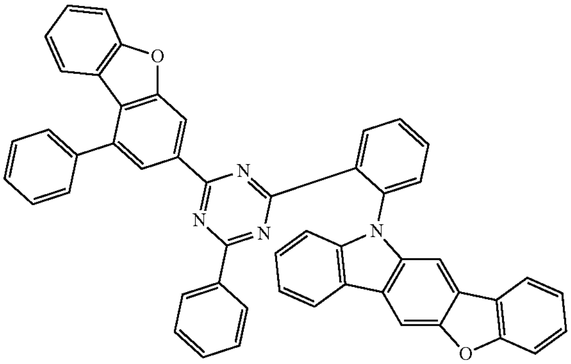
-continued
[D-39]
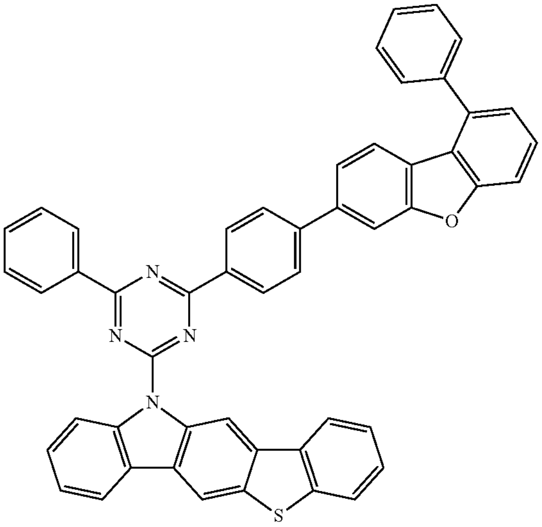
[D-40]
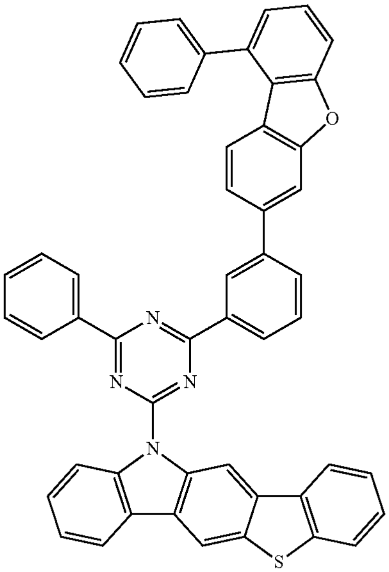

-continued
[D-41]
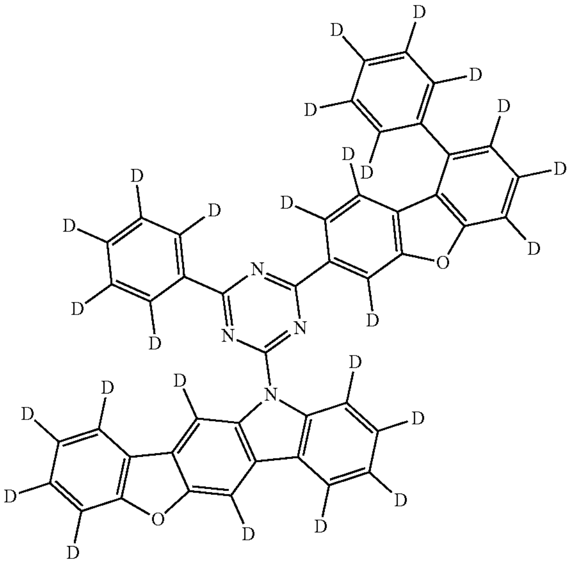
[D-42]
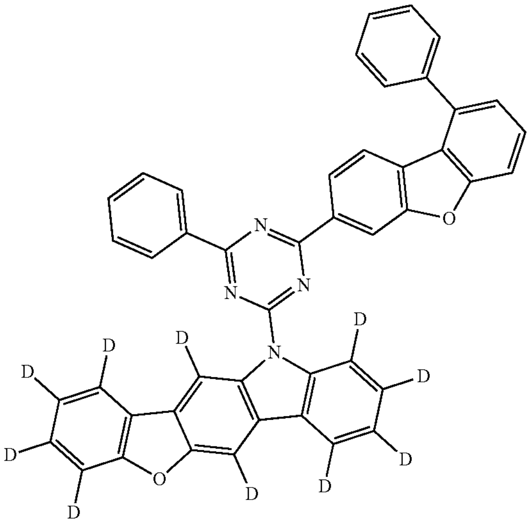
[D-43]
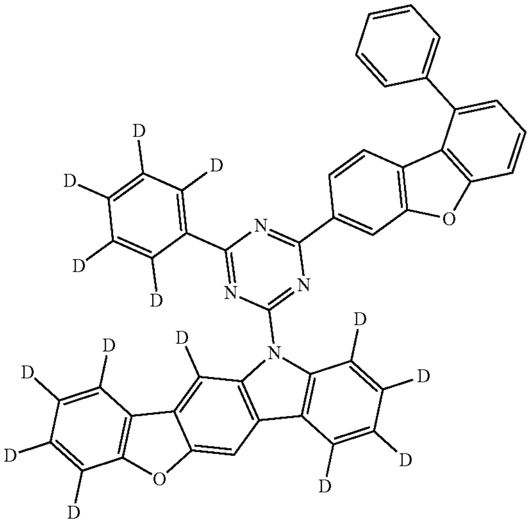
-continued
[D-44]
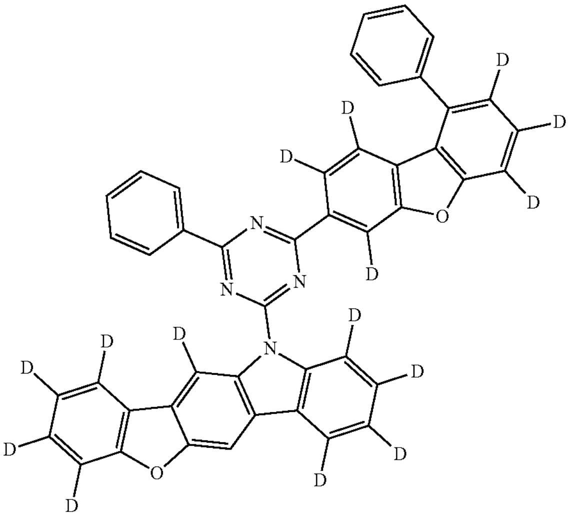
[D-45]
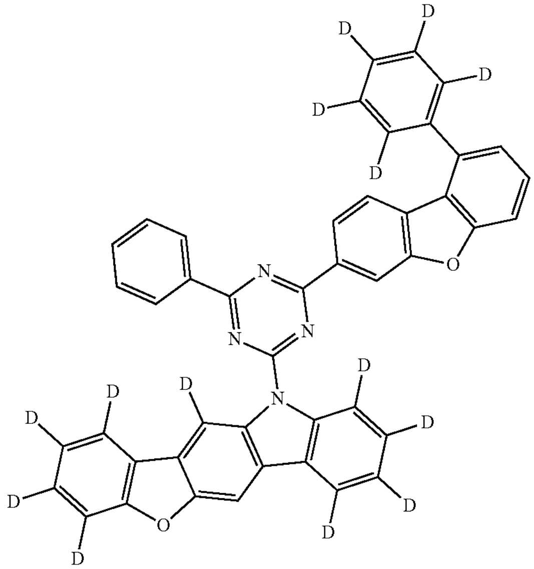

-continued
[D-46]
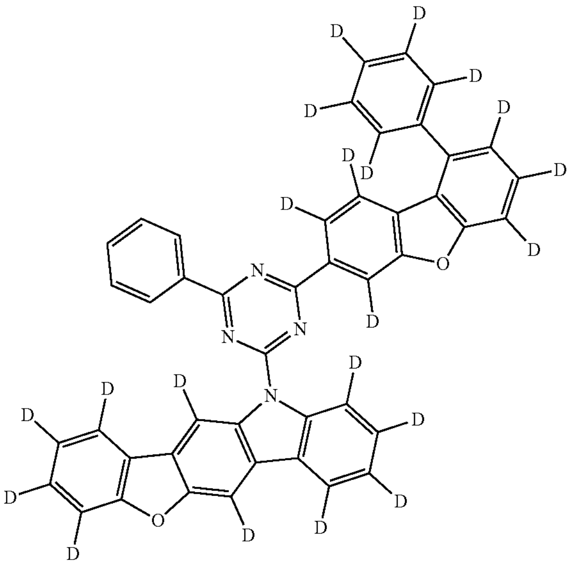
[D-47]
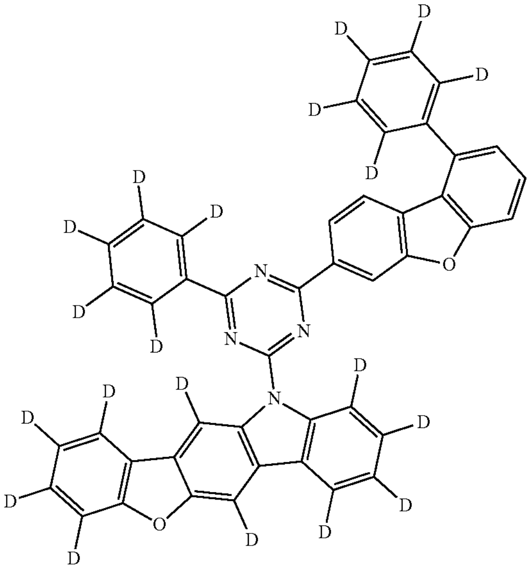
-continued
[D-48]
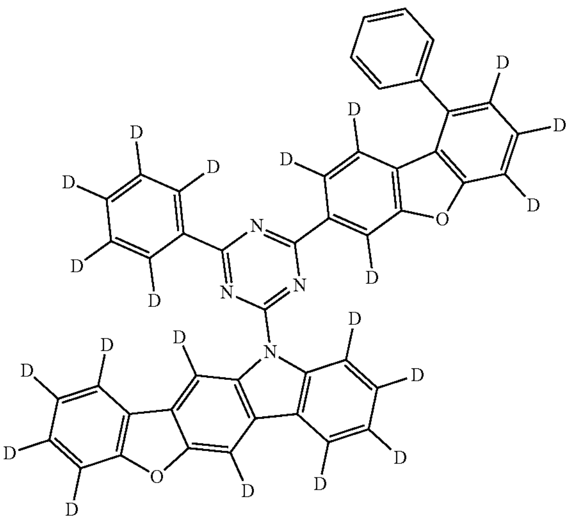
[D-49]
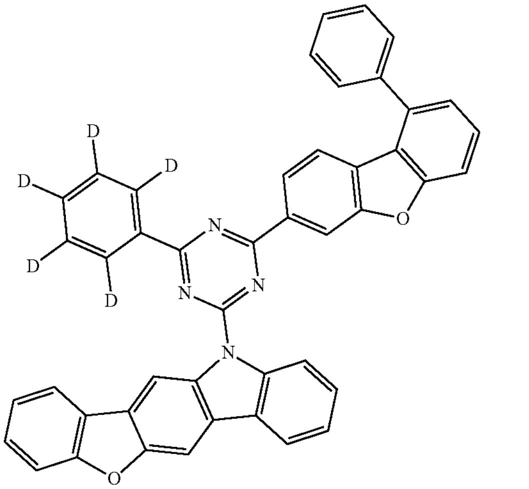
[D-50]
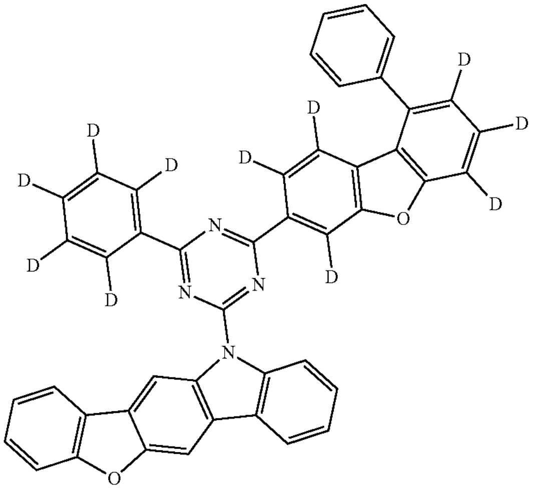

-continued
[D-51]
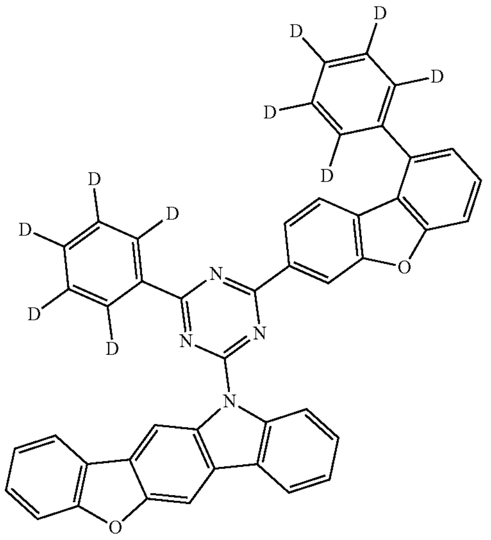
[D-52]
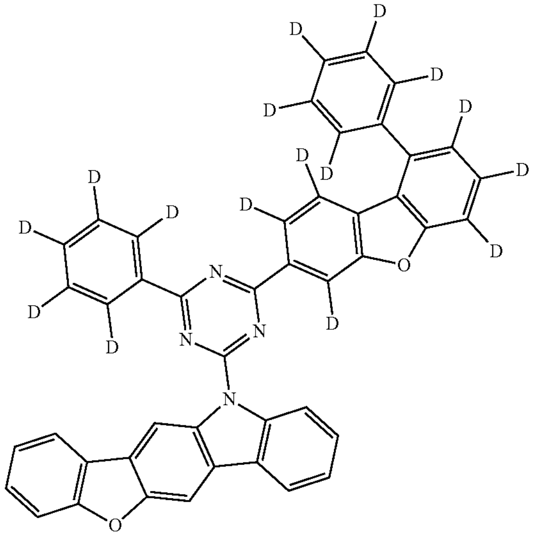
[D-53]
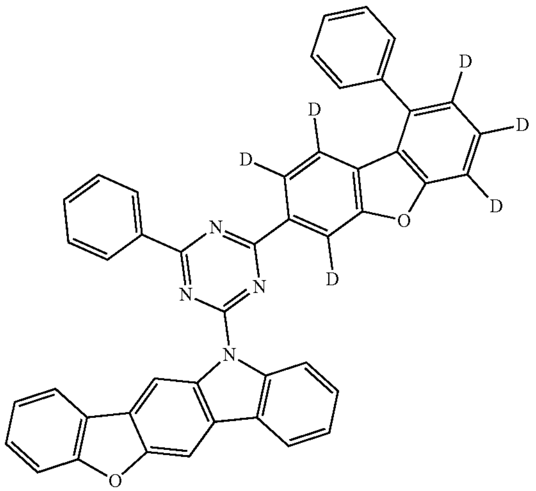
-continued
[D-54]
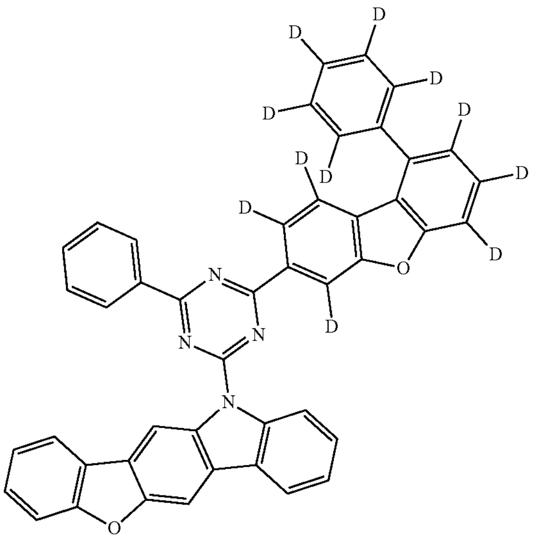
[D-55]
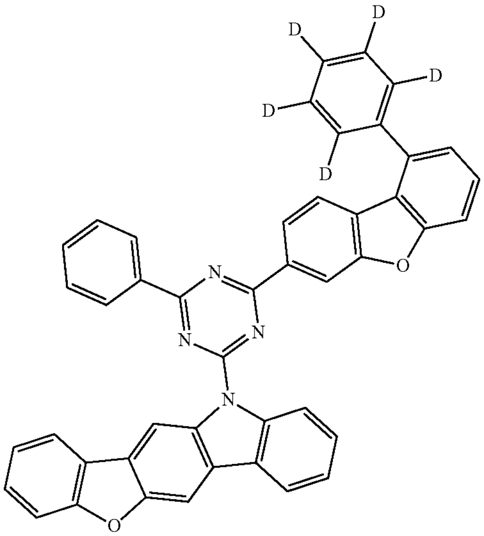

-continued
[D-56]
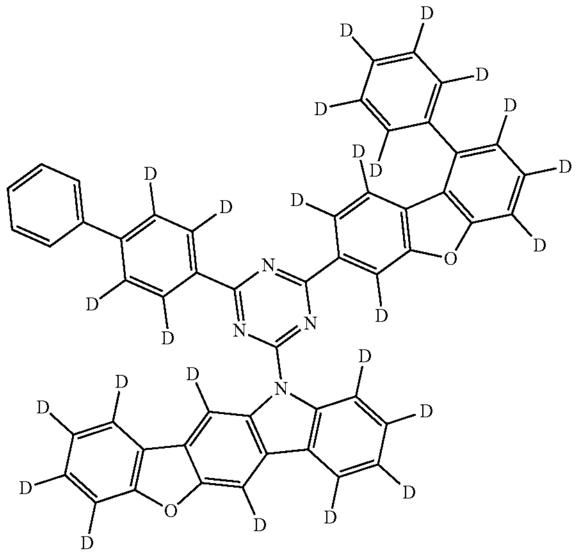
[D-57]
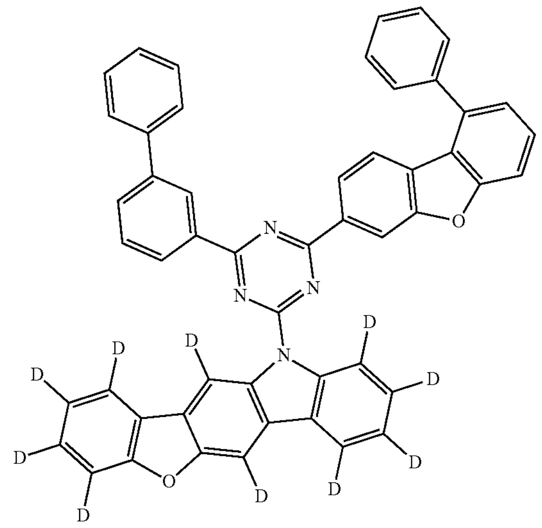
[D-58]
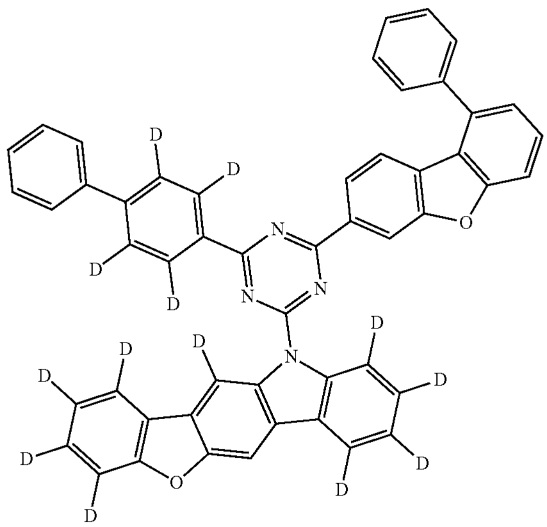
-continued
[D-59]
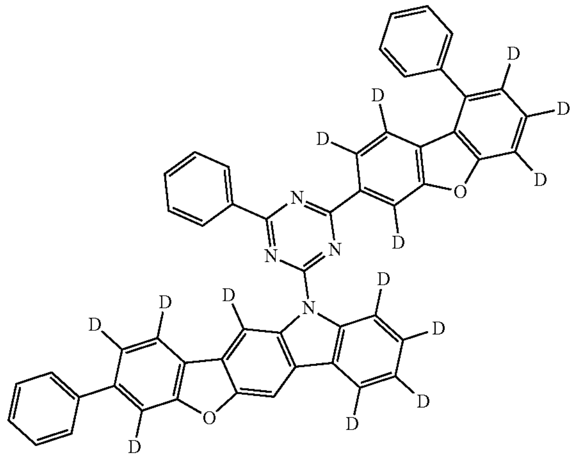
[D-60]
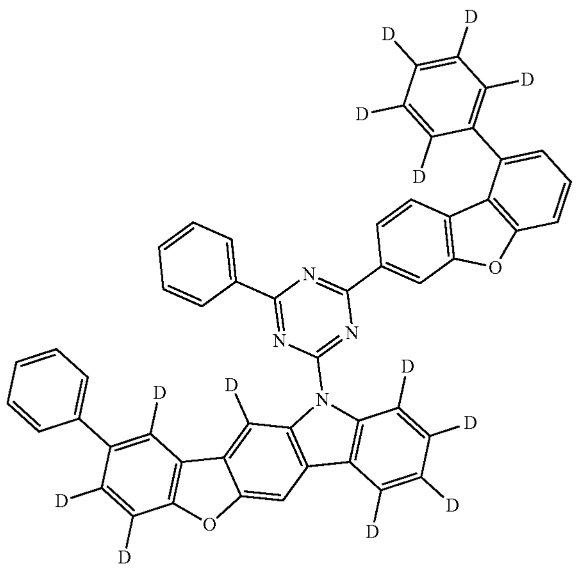

-continued
[D-61]
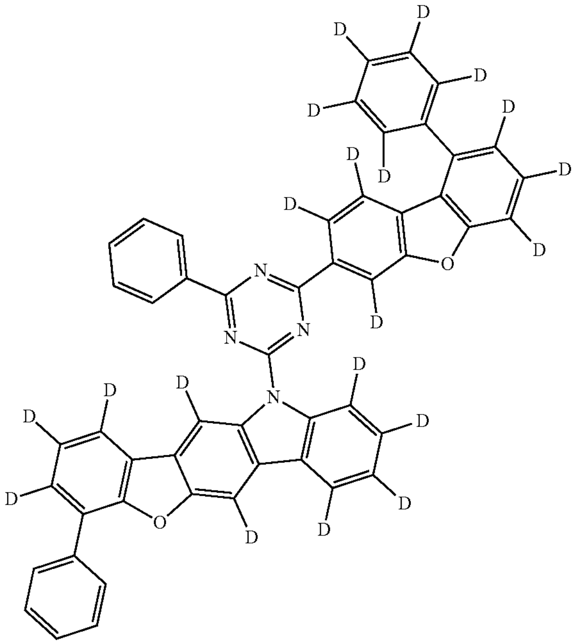
[D-62]
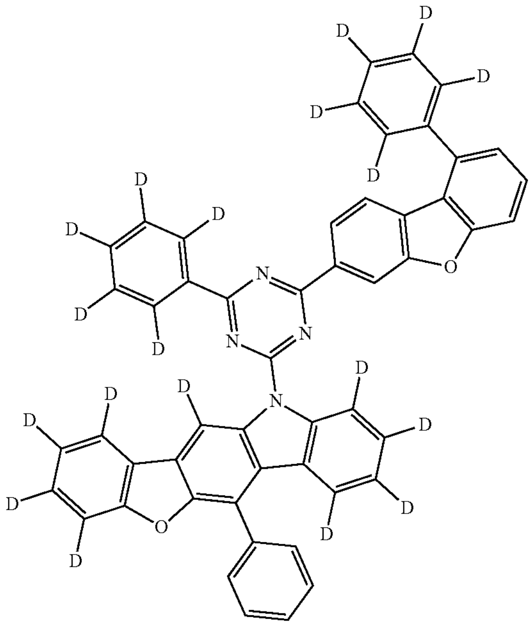
-continued
[D-63]
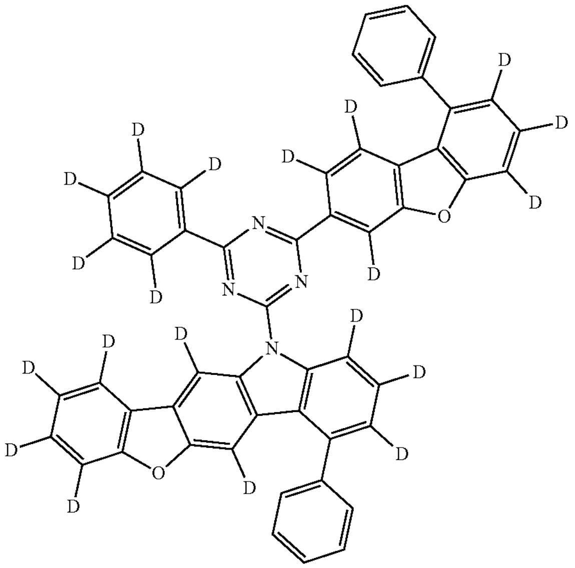
[D-64]
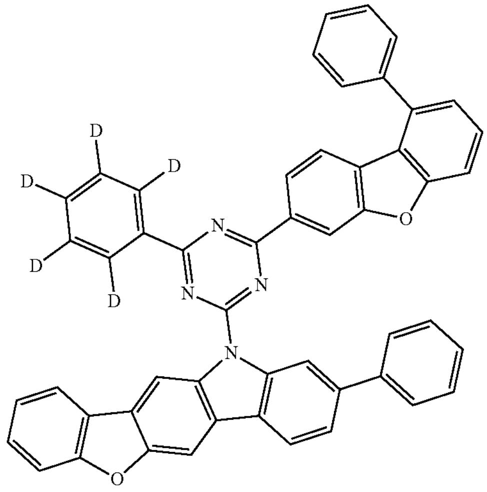
[D-65]
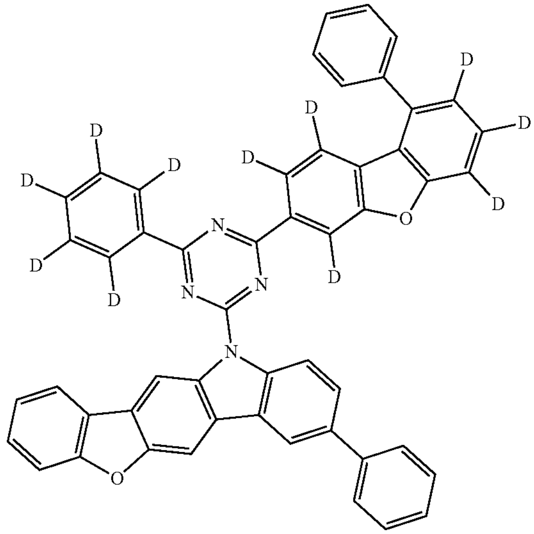

-continued
[D-66]
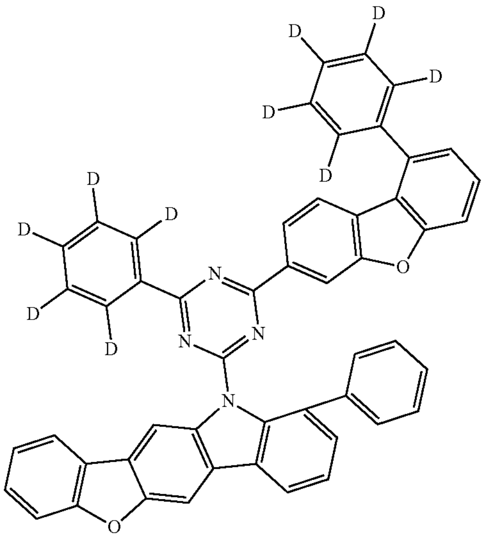
[D-67]
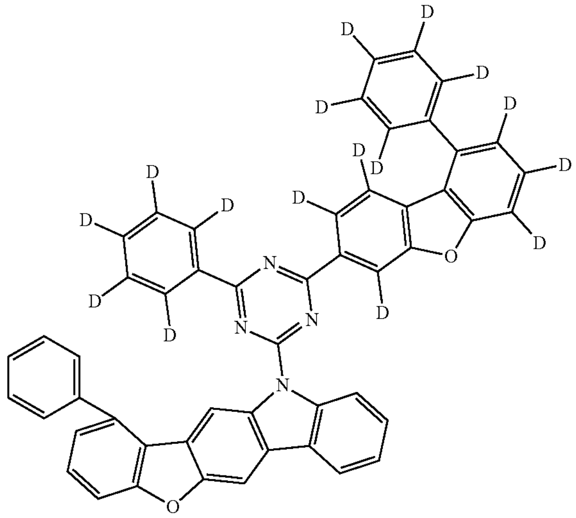
[D-68]
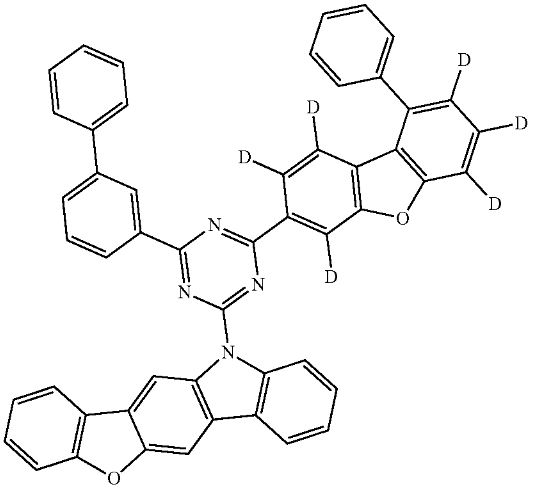
-continued
(D-69)
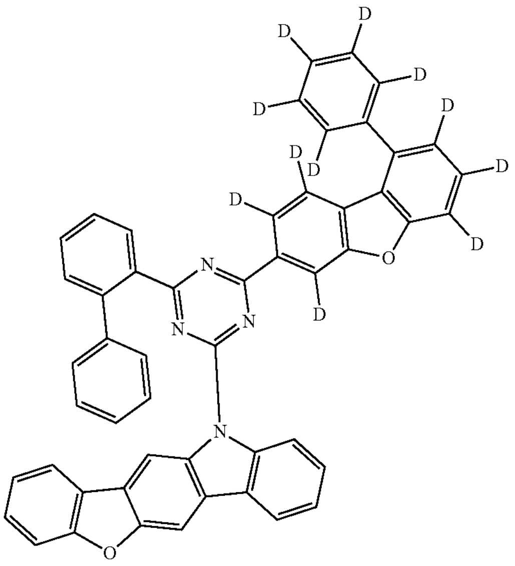
[D-70]
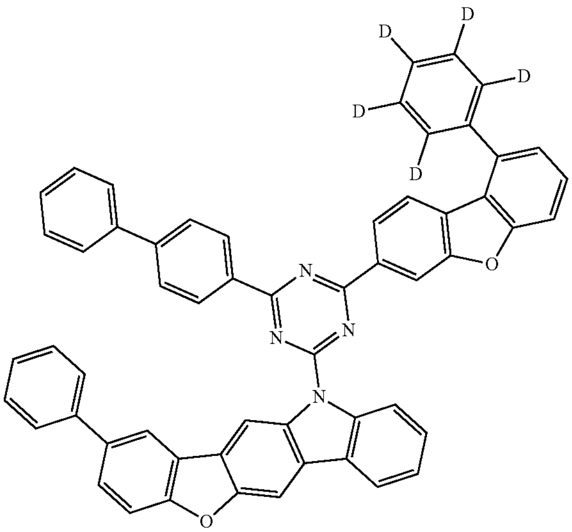

-continued
[D-71]
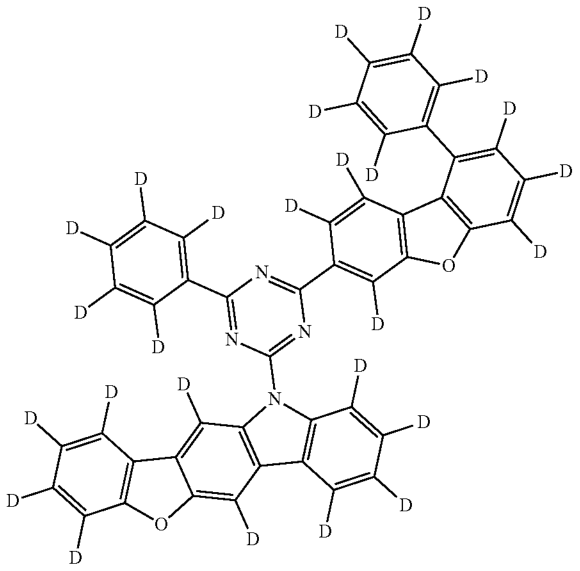
[D-72]
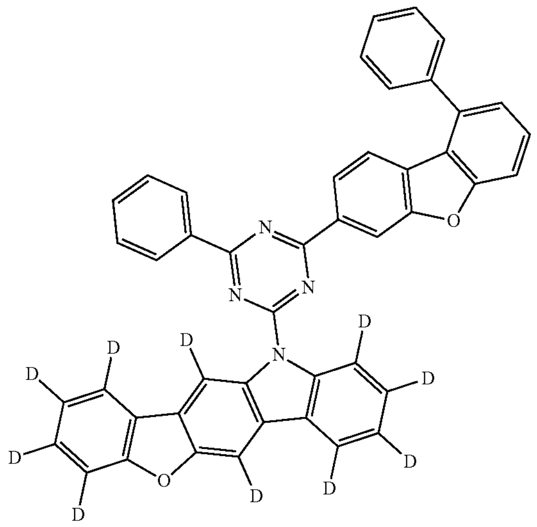
-continued
[D-73]
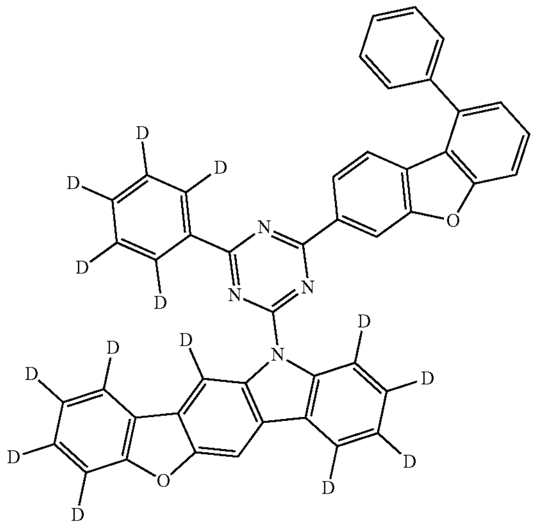
[D-74]
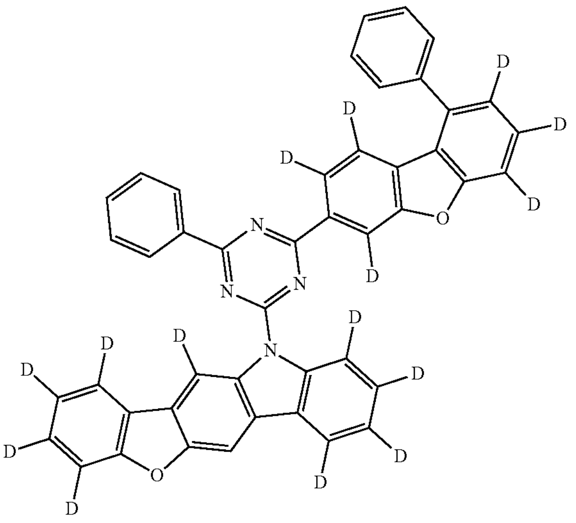

-continued
[D-75]
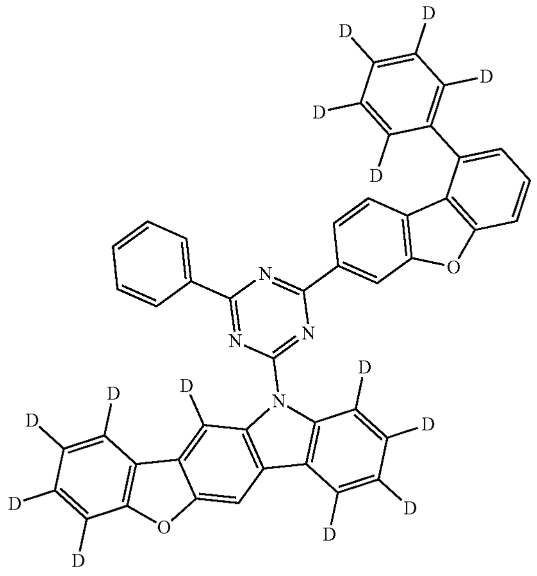
[D-76]
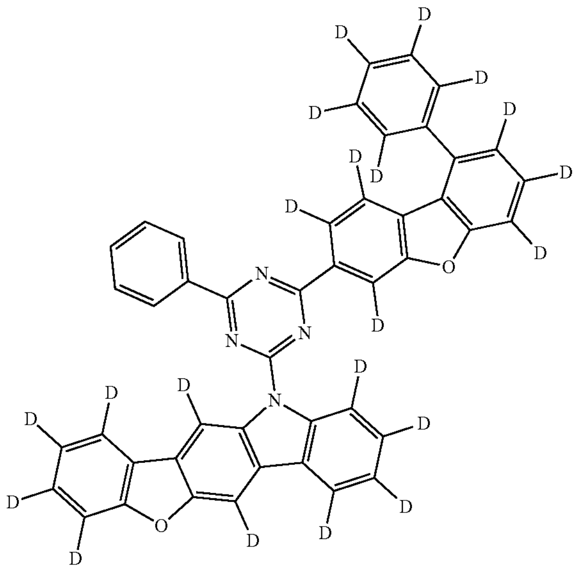
-continued
[D-77]
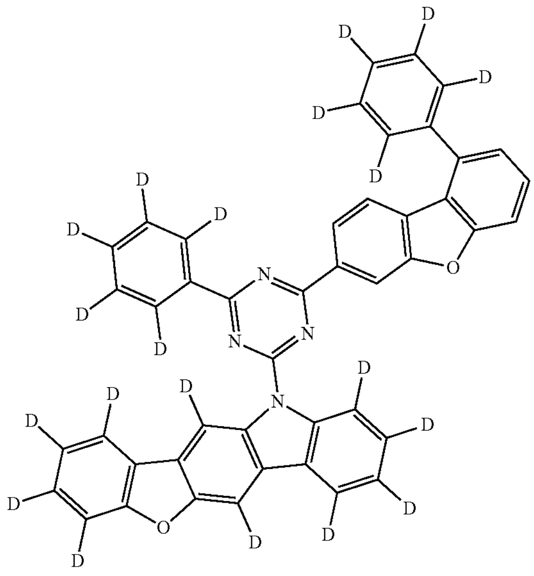
[D-78]
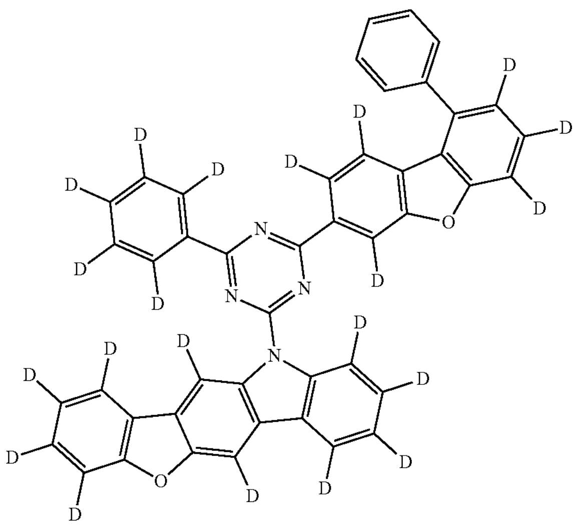
[D-79]
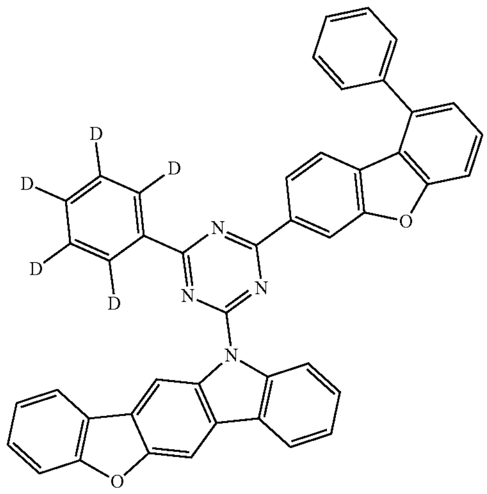

-continued
[D-80]
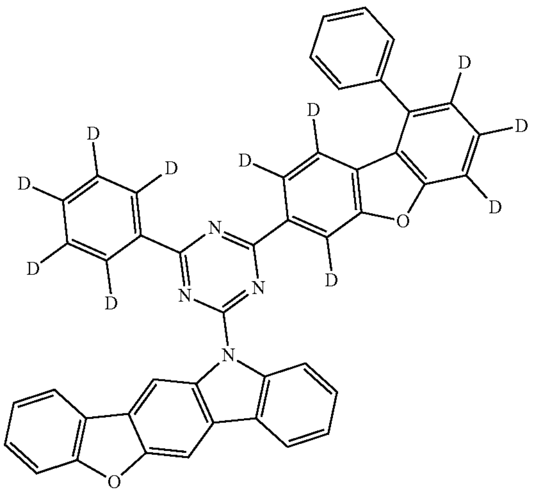
[D-81]
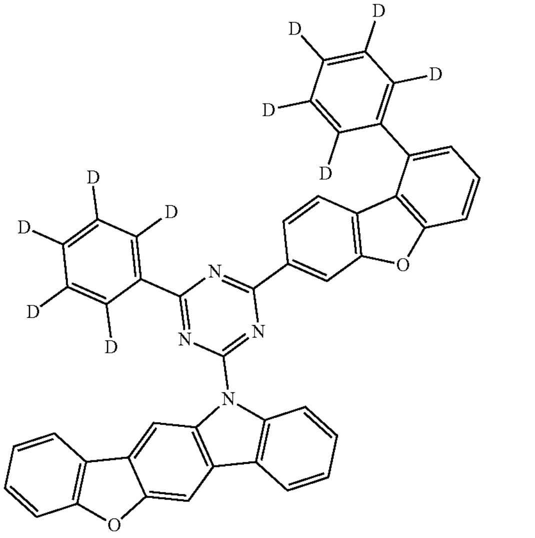
[D-82]
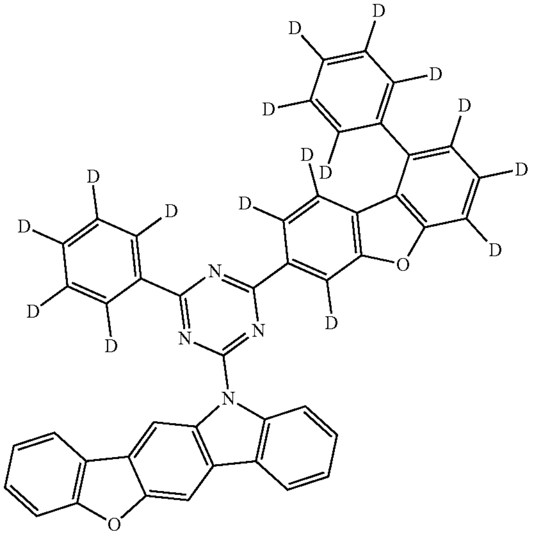
-continued
[D-83]
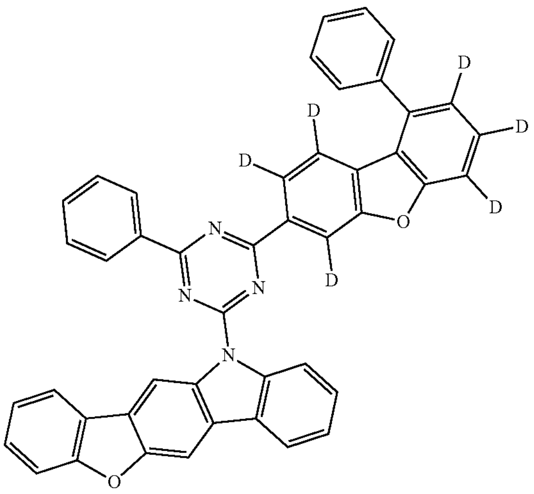
[D-84]
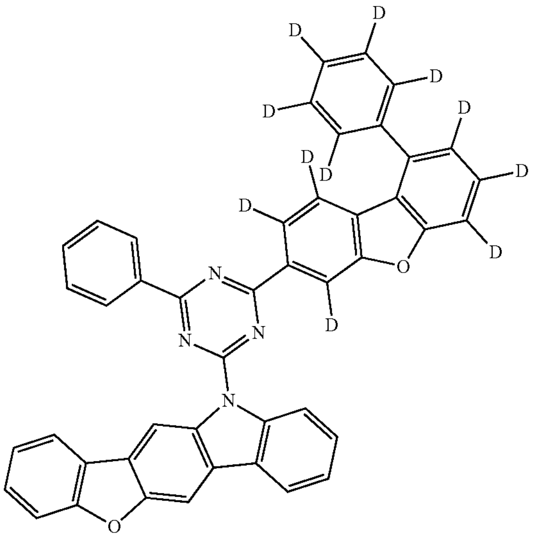
[D-85]
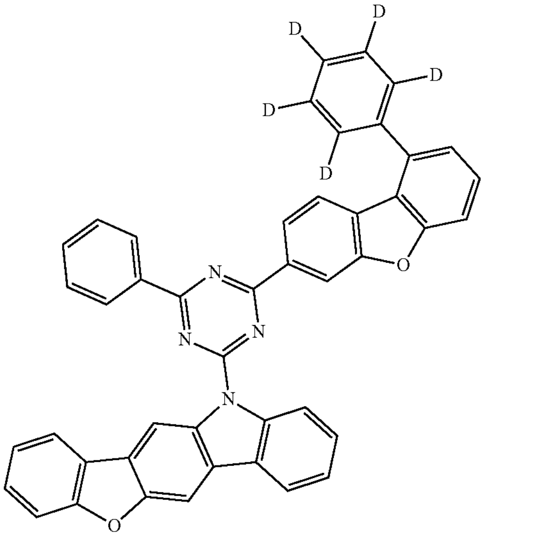

-continued
[D-86]
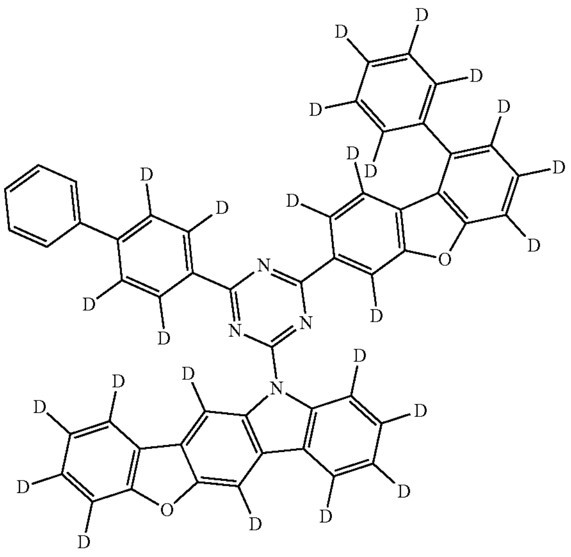
[D-87]
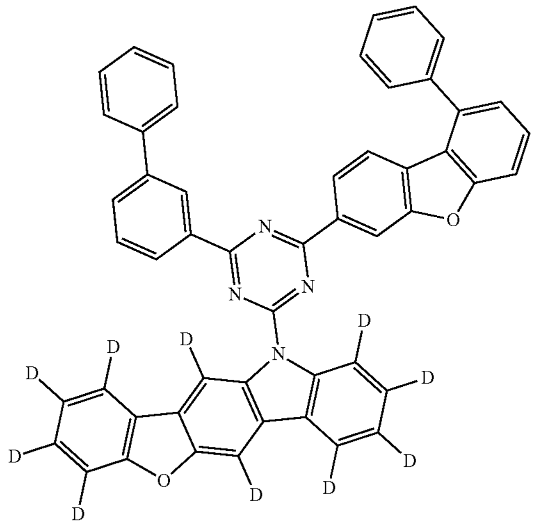
[D-88]
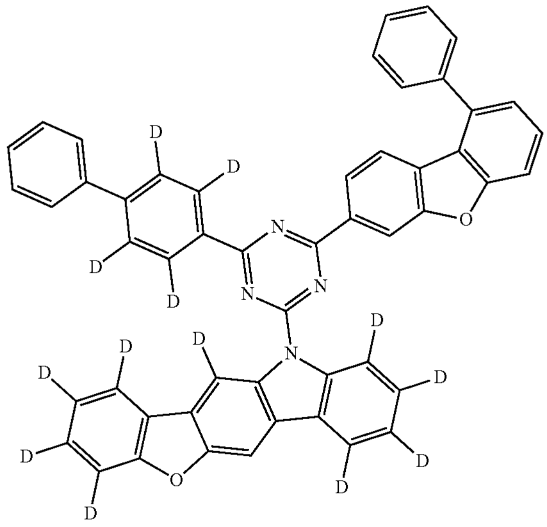
-continued
[D-89]
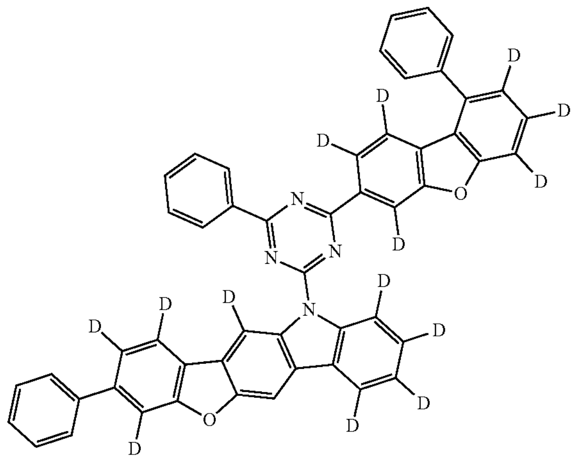
[D-90]
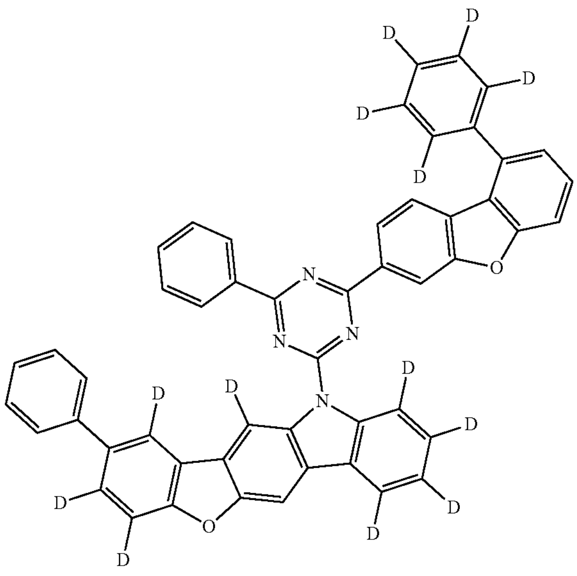

-continued
[D-91]
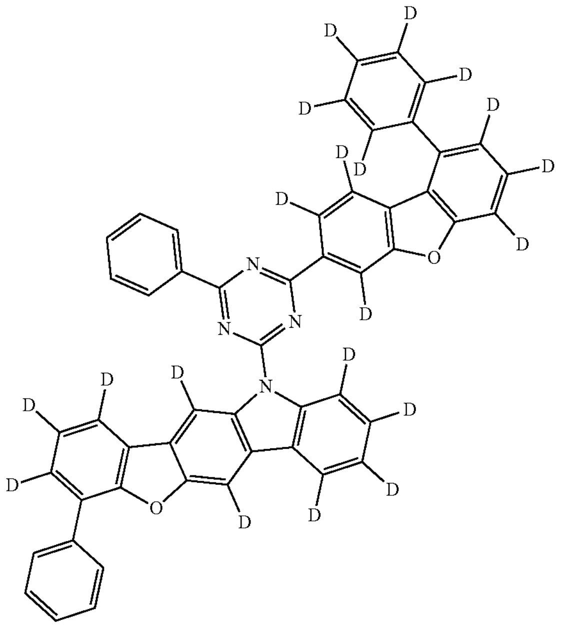
[D-92]
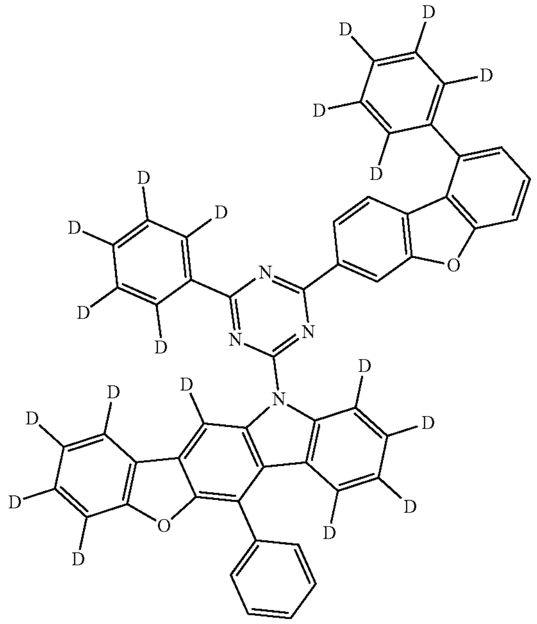
-continued
[D-93]
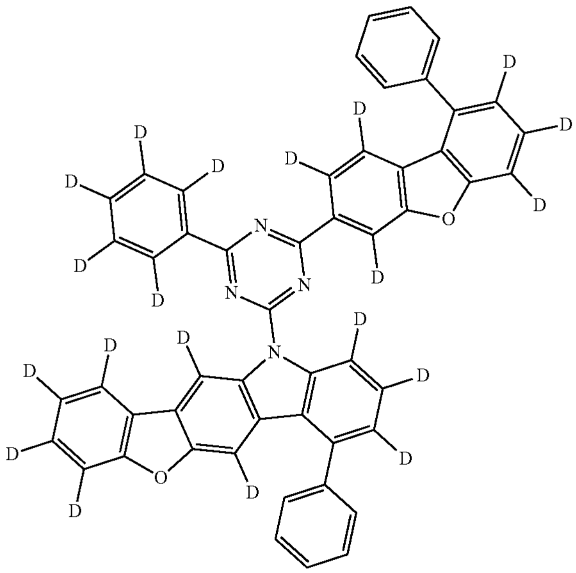
[D-94]
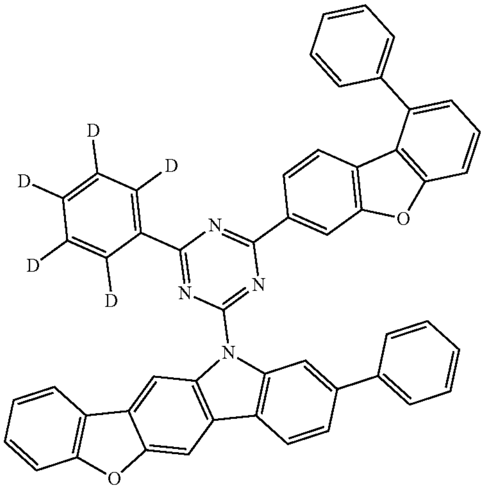
[D-95]
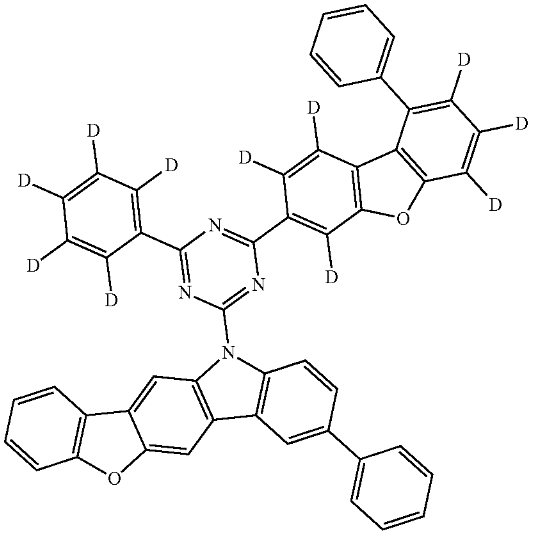

-continued
[D-96]
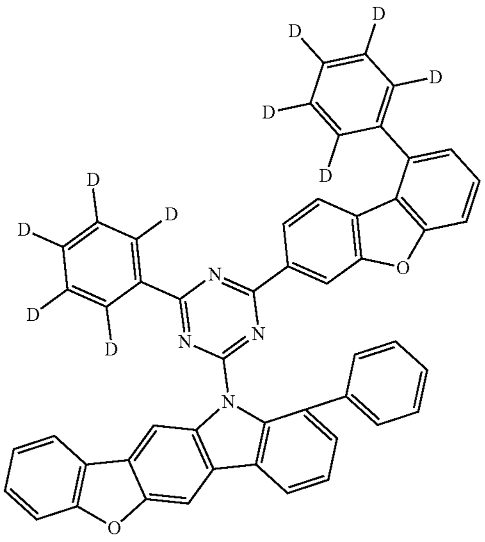
[D-97]
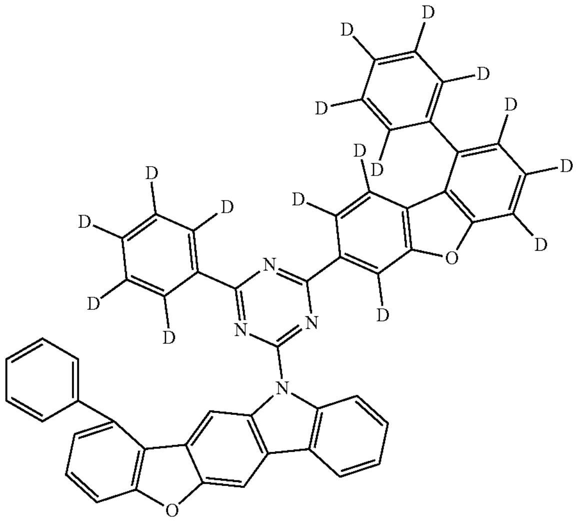
[D-98]
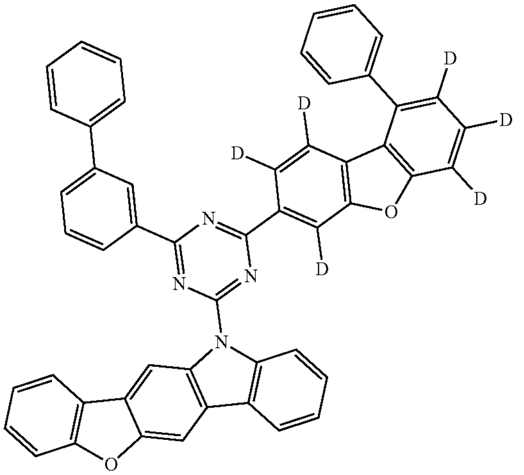
-continued
[D-99]
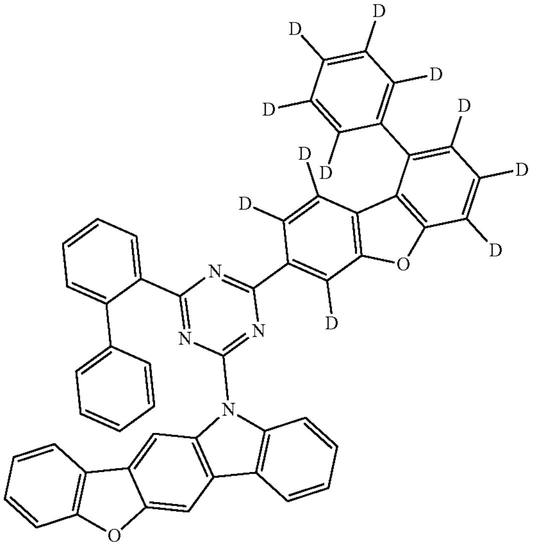
[D-100]
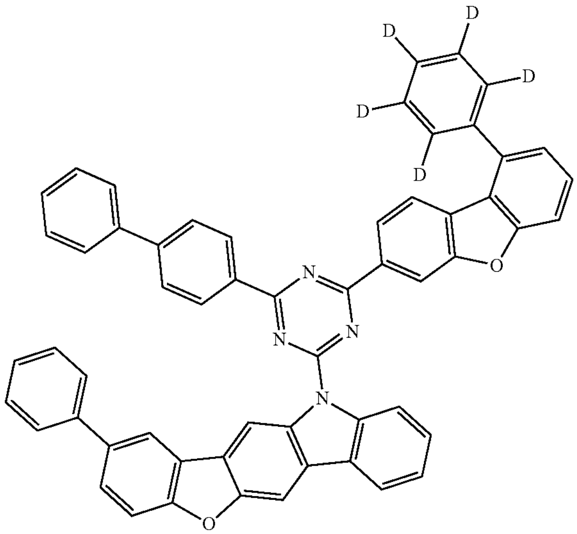
[E-1]
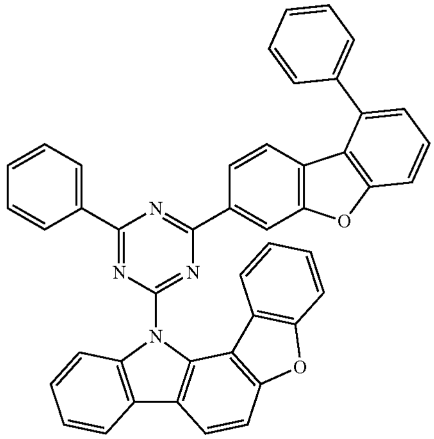

-continued
[E-2]
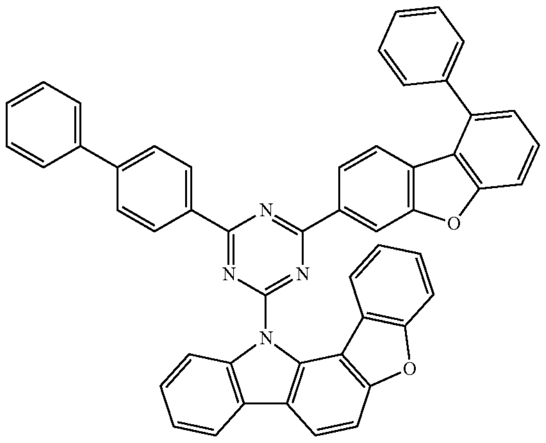
[E-3]
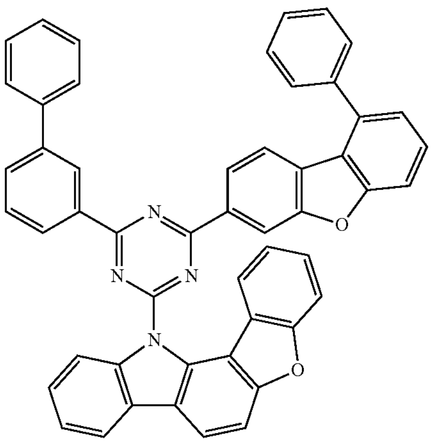
[E-4]
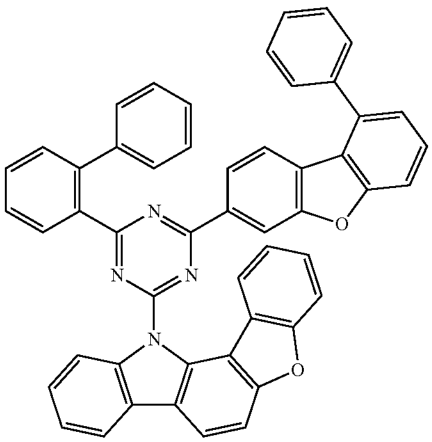
-continued
[E-5]
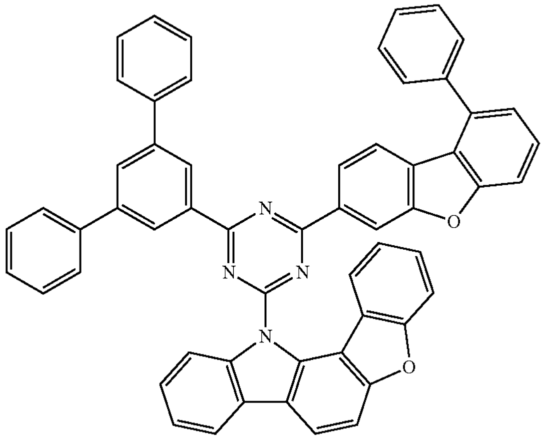
[E-6]
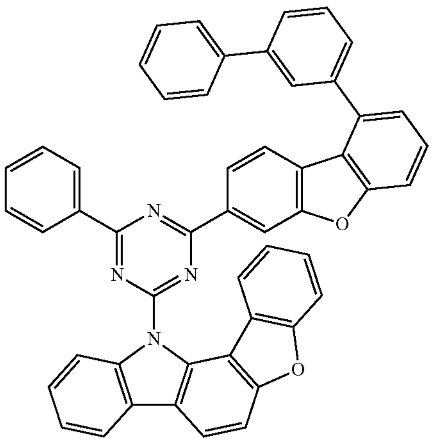
[E-7]
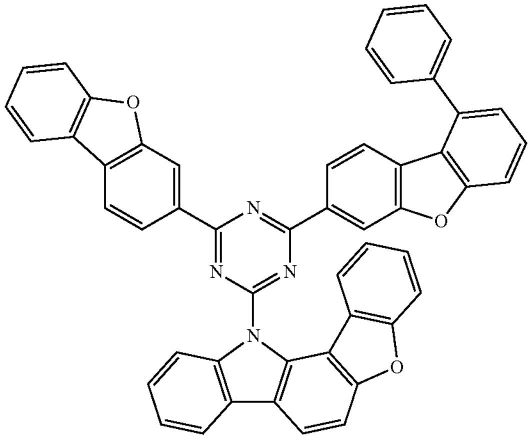

-continued
[E-8]
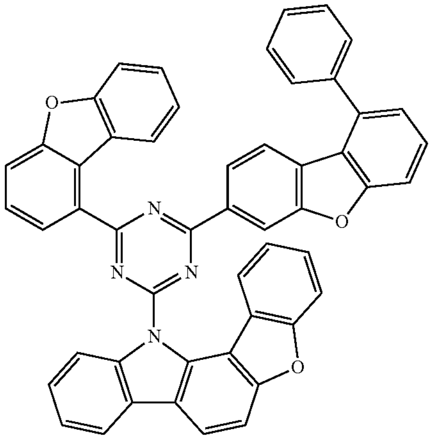
[E-9]
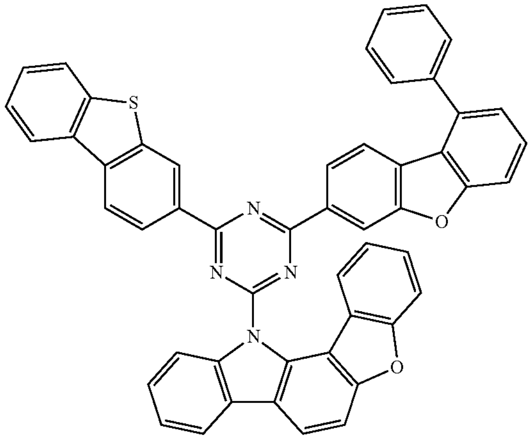
[E-10]
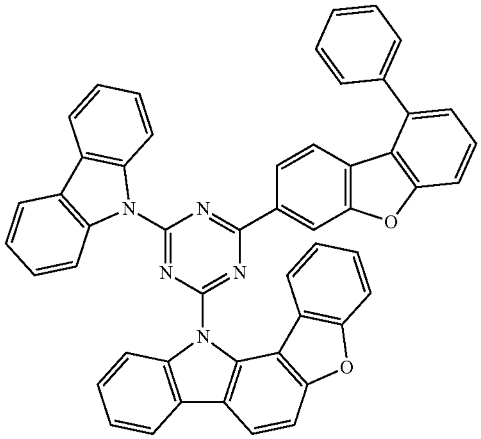
-continued
[E-11]
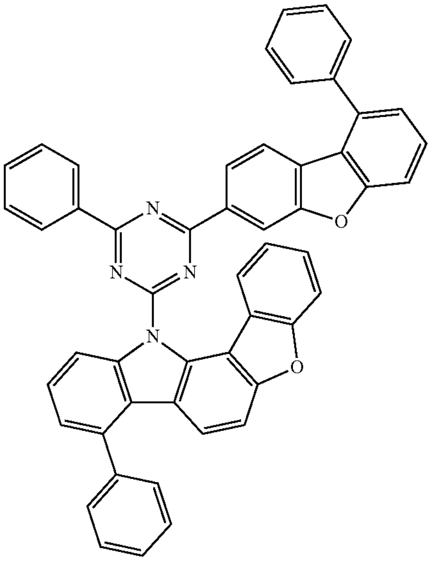
[E-12]
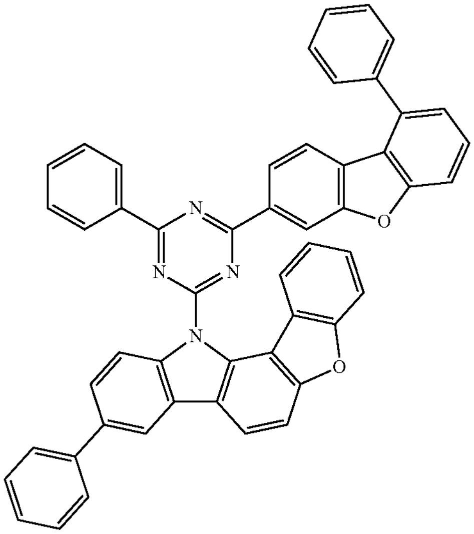
[E-13]
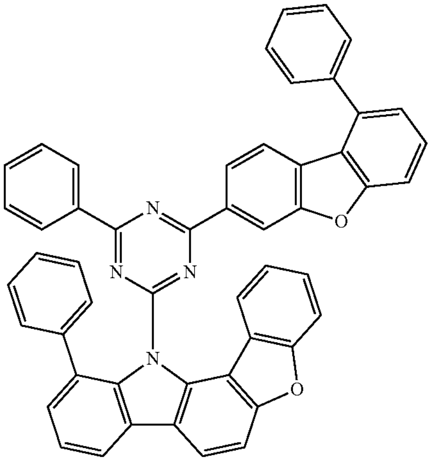

-continued
[E-14]
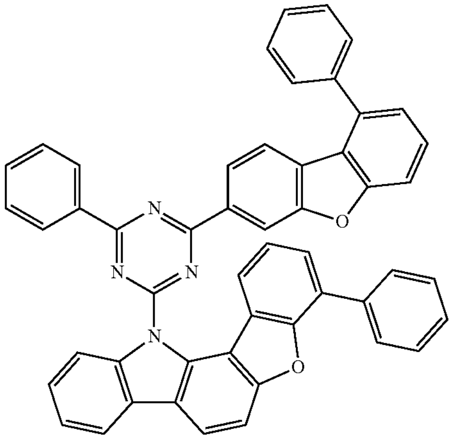
[E-15]
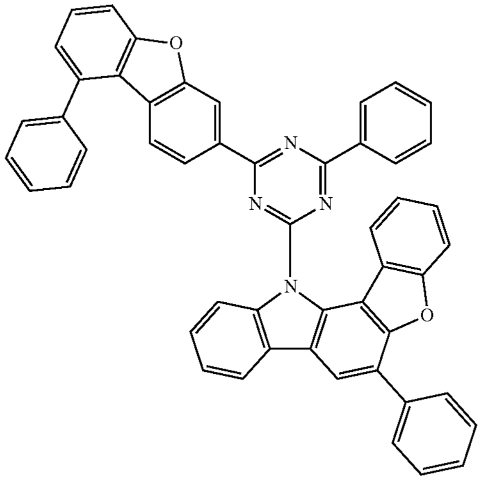
[E-16]
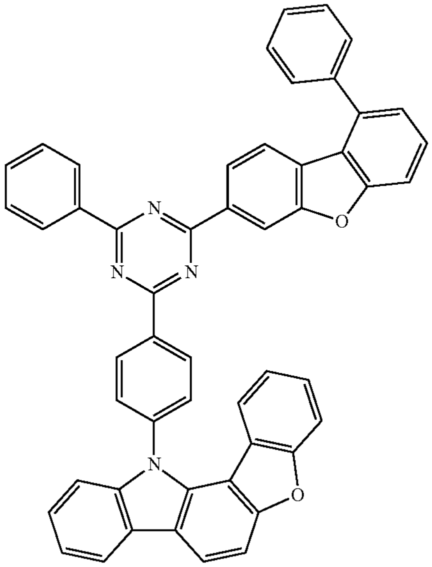
-continued
[E-17]
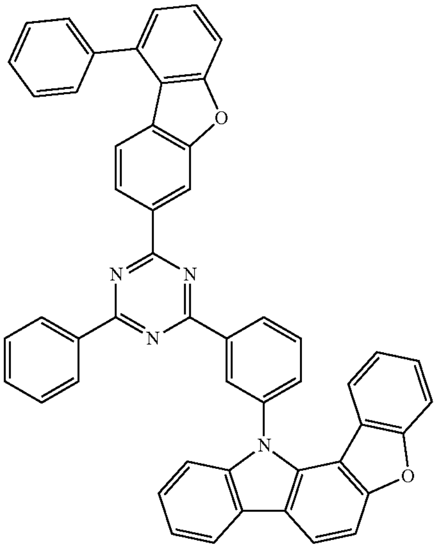
[E-18]
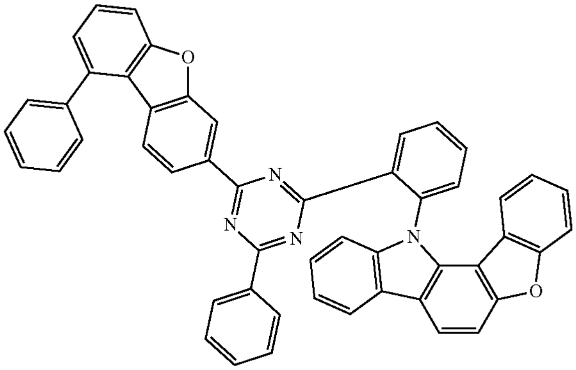
[E-19]
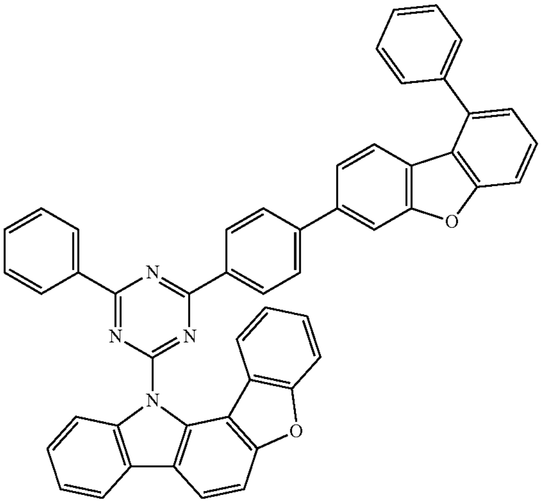

-continued
[E-20]
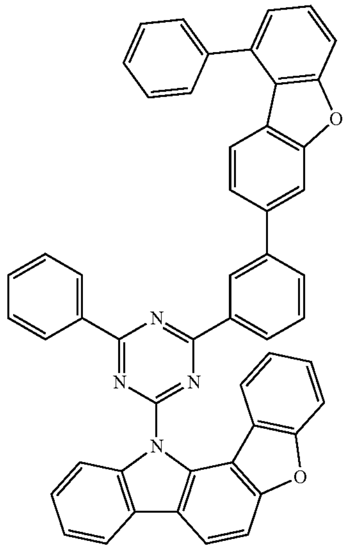
[E-21]
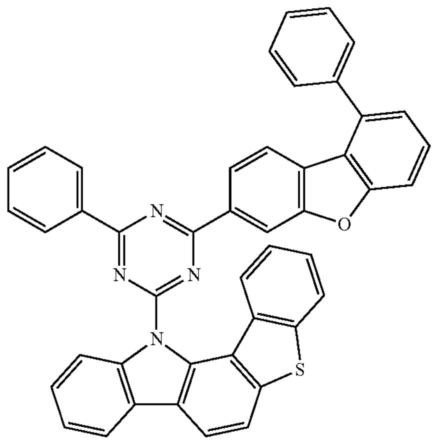
[E-22]
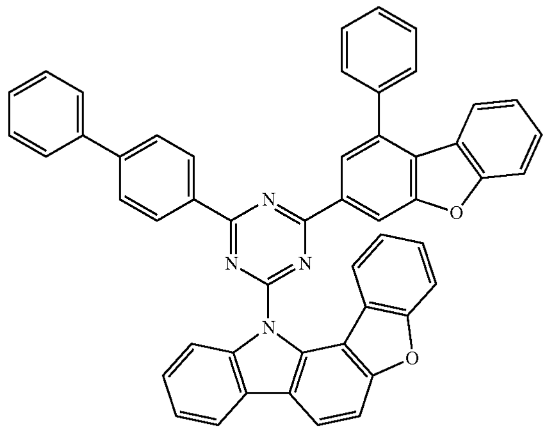
-continued
[E-23]
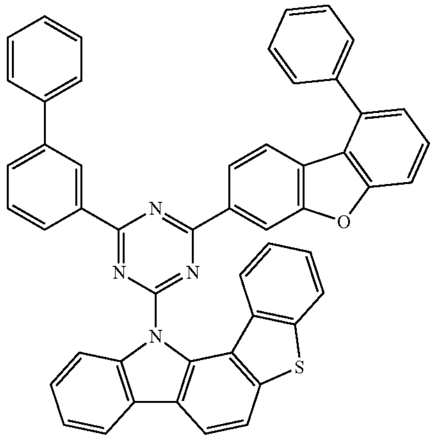
[E-24]
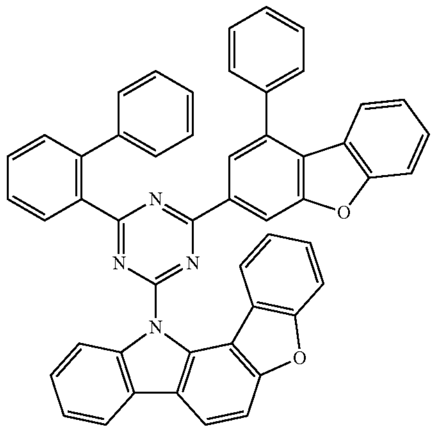
[E-25]
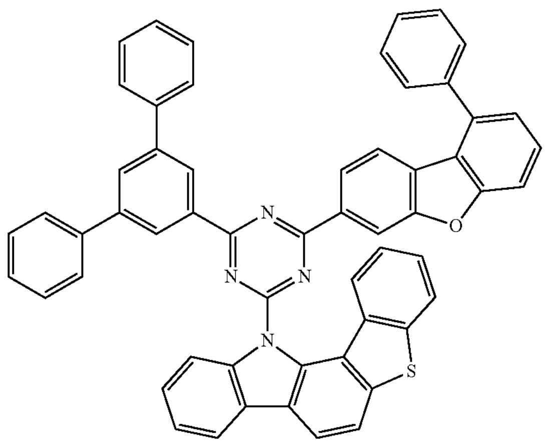

[E-26]
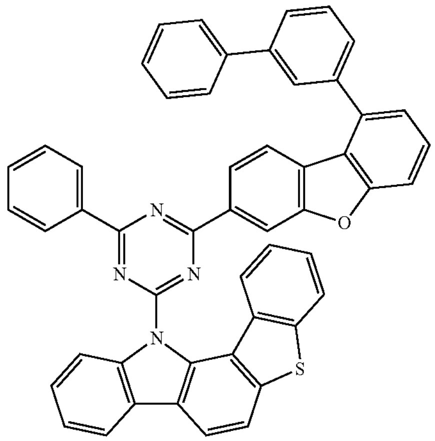
[E-27]
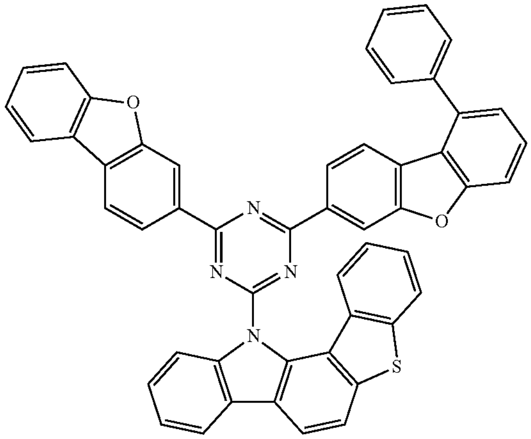
[E-28]
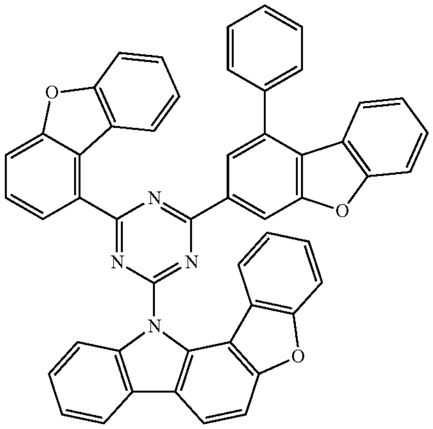
[E-29]
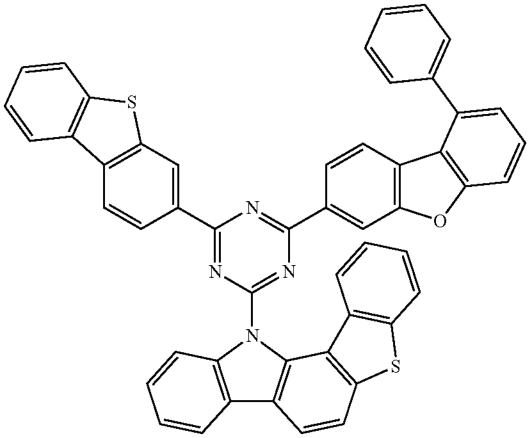
[E-30]
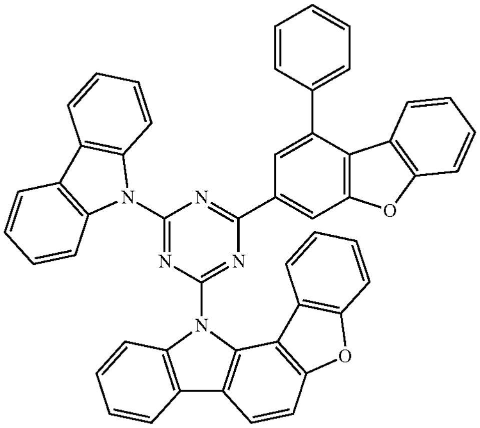
[E-31]
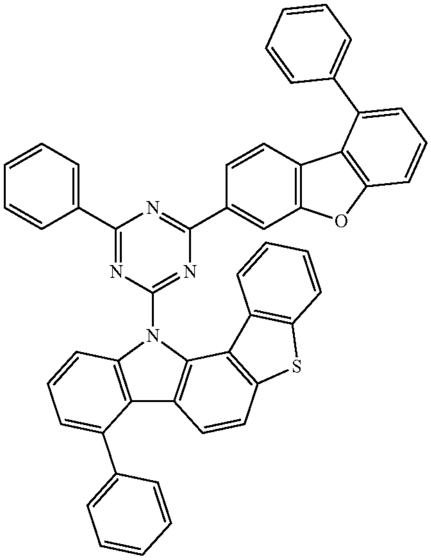

-continued
[E-32]
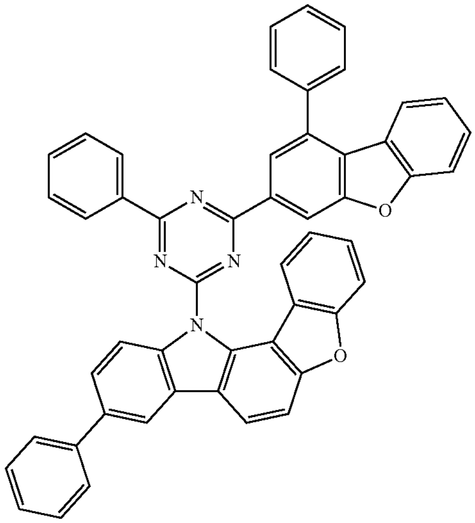
[E-33]
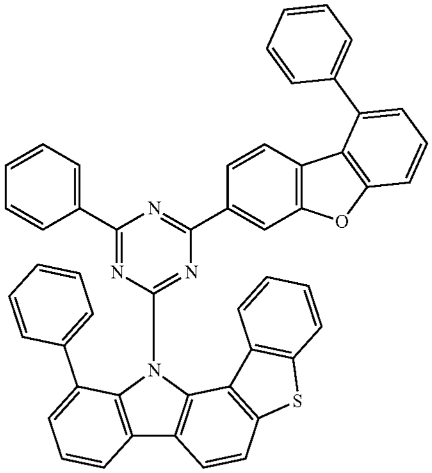
[E-34]
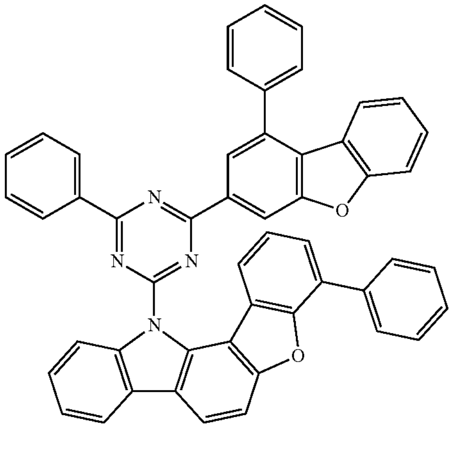
-continued
[E-35]
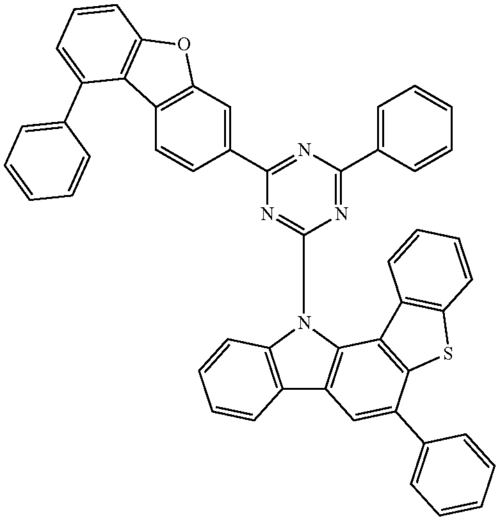
[E-36]
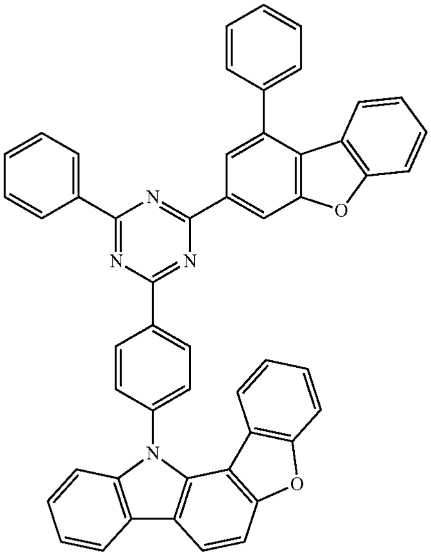
[E-37]
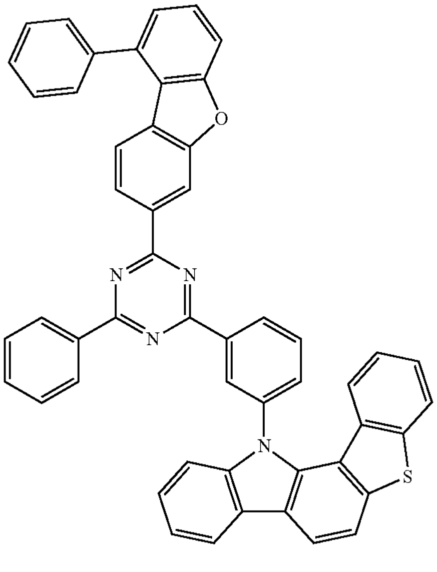

-continued
[E-38]
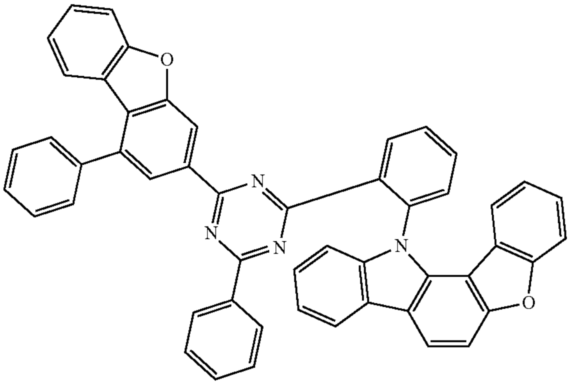
[E-39]
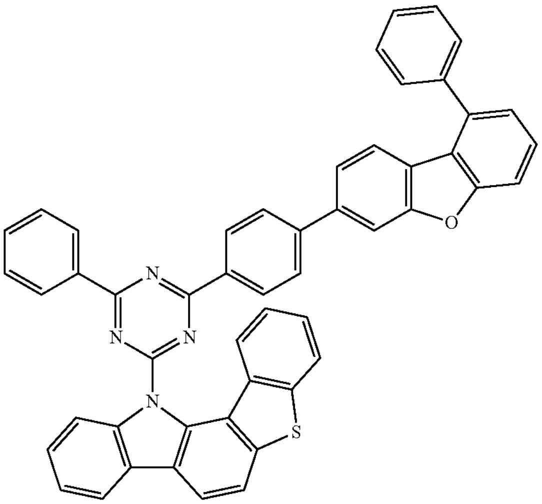
[E-40]
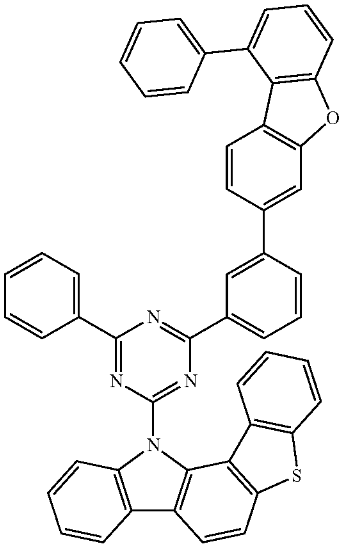
-continued
[E-41]
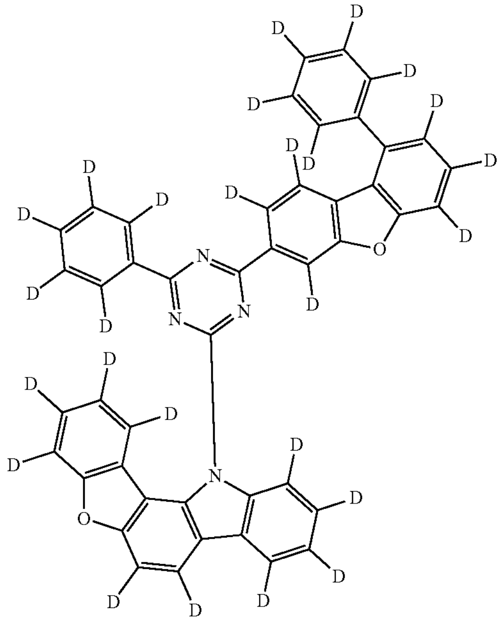
[E-42]
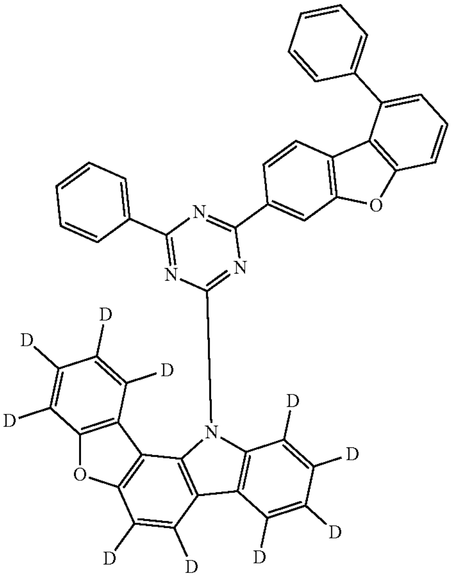

-continued
[E-43]
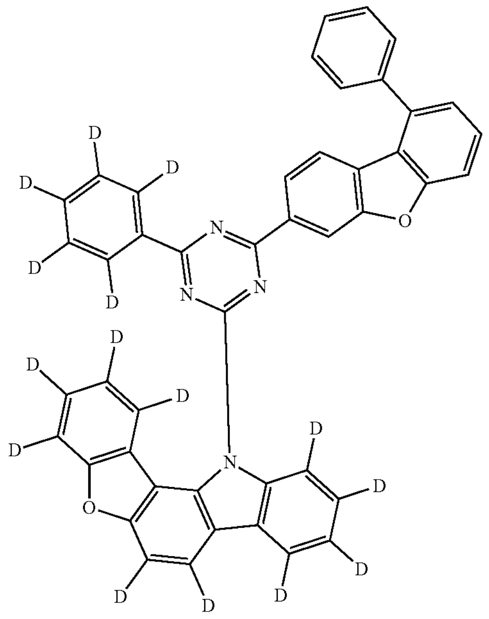
[E-44]
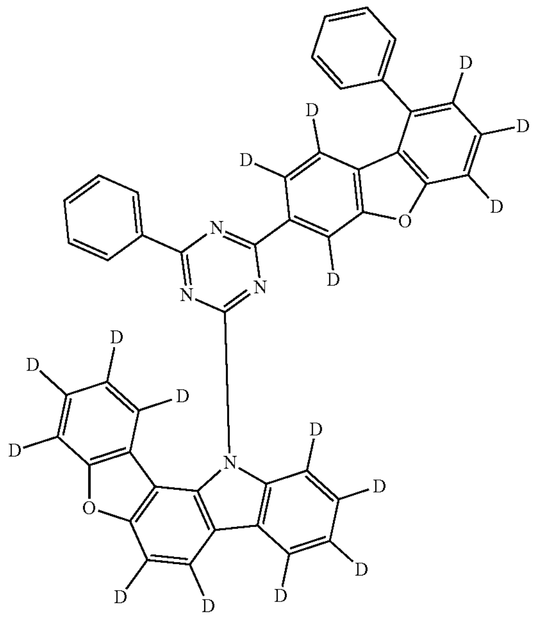
-continued
[E-45]
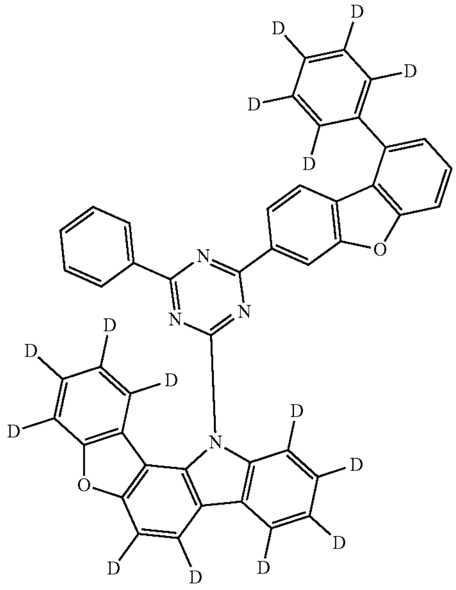
[E-46]
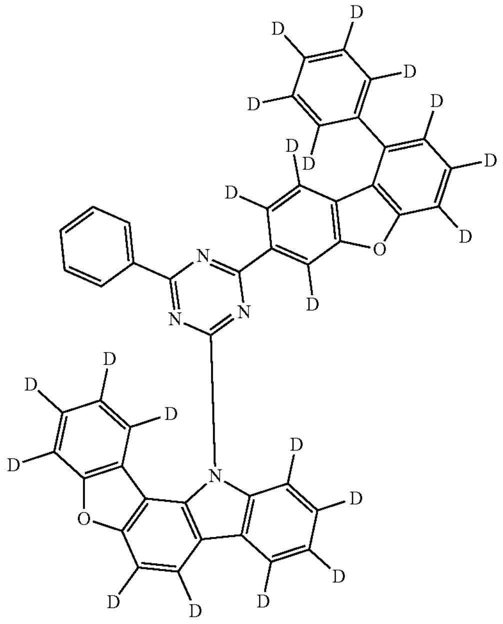

-continued
[E-47]
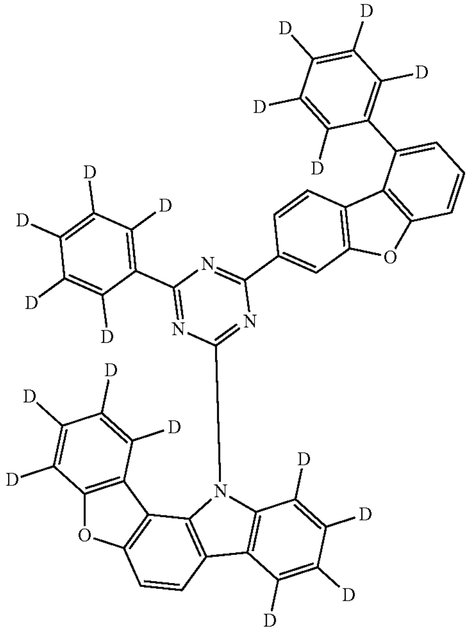
[E-48]
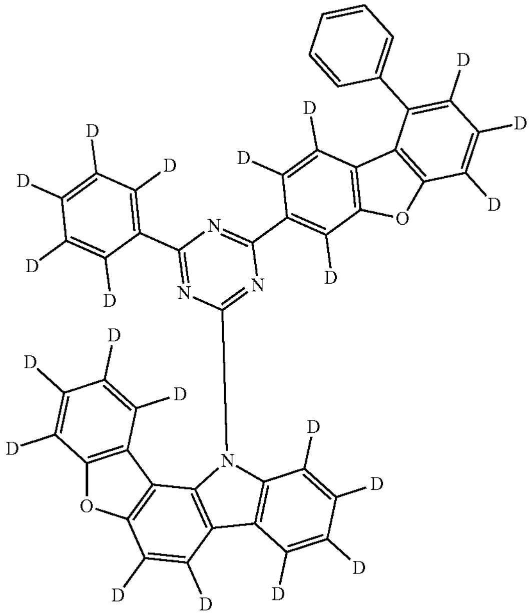
-continued
[E-49]
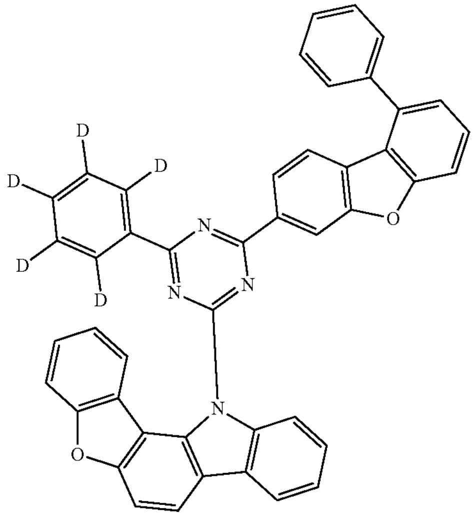
[E-50]
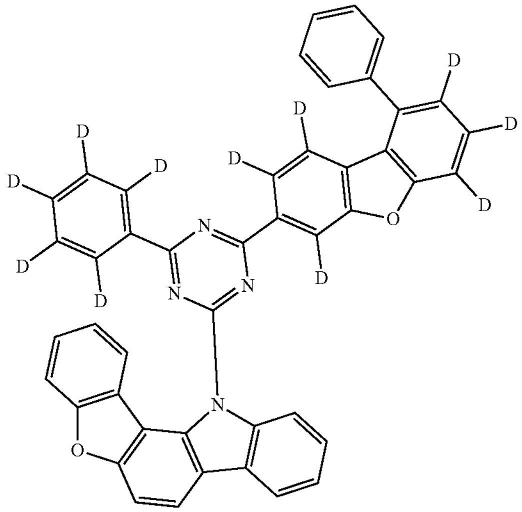
[E-51]
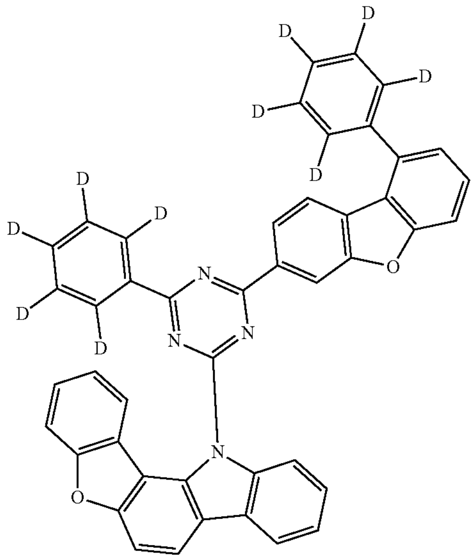

-continued
[E-52]
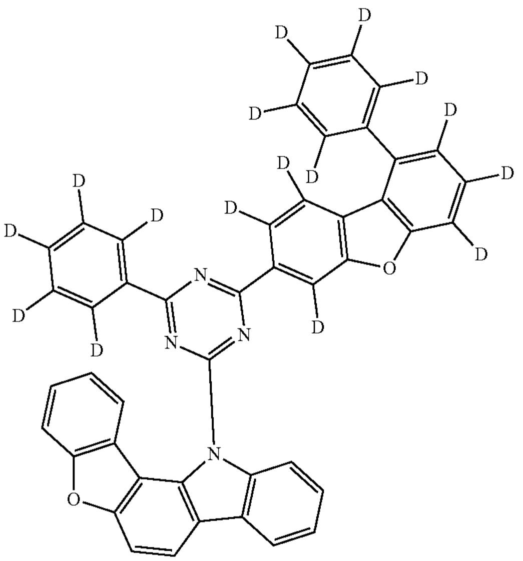
[E-53]
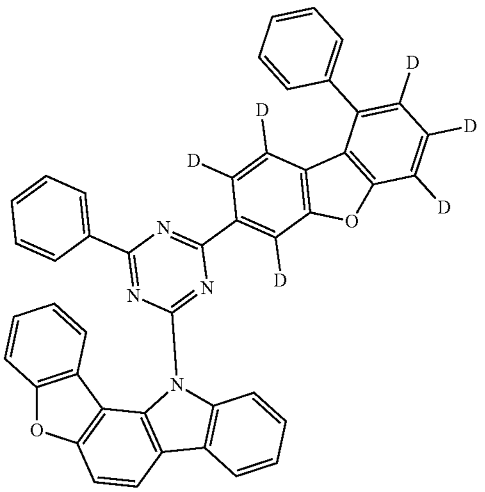
[E-54]
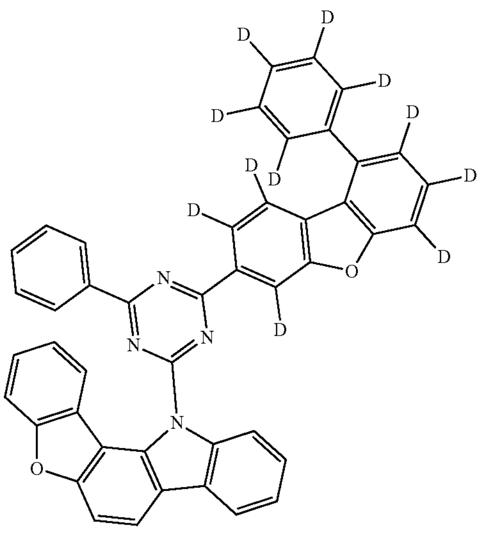
-continued
[E-55]
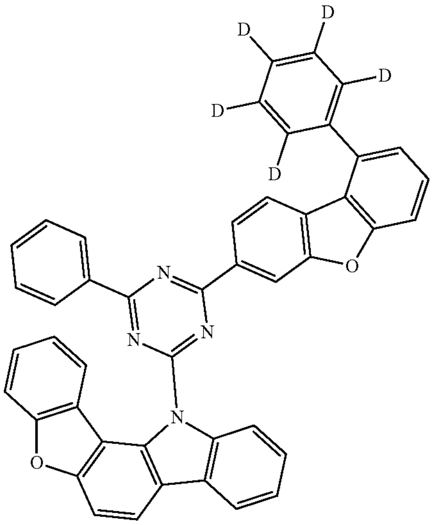
[E-56]
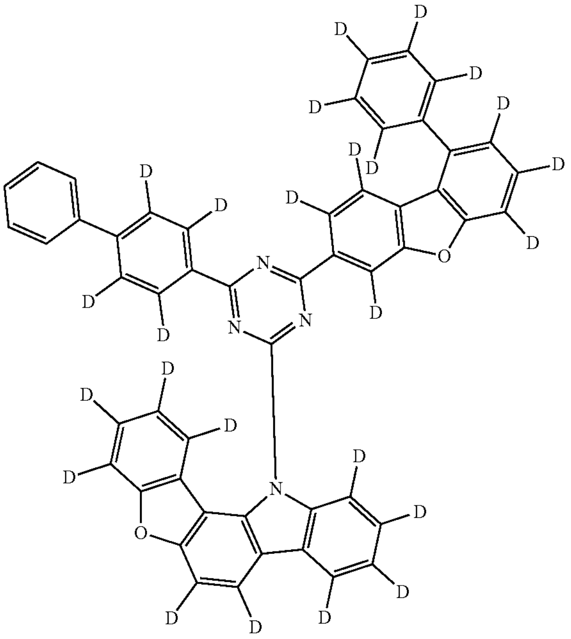

-continued
[E-57]
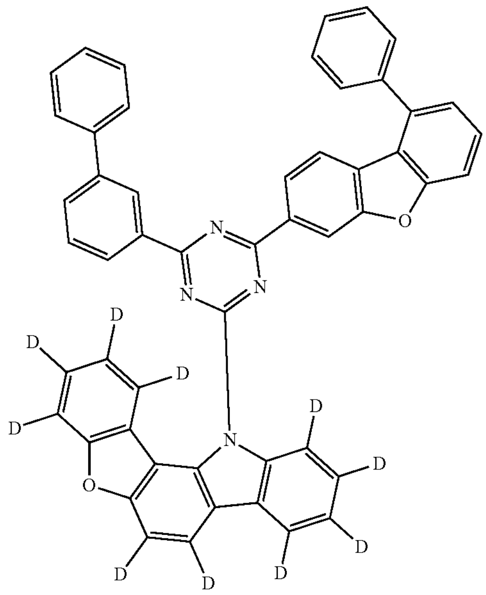
[E-58]
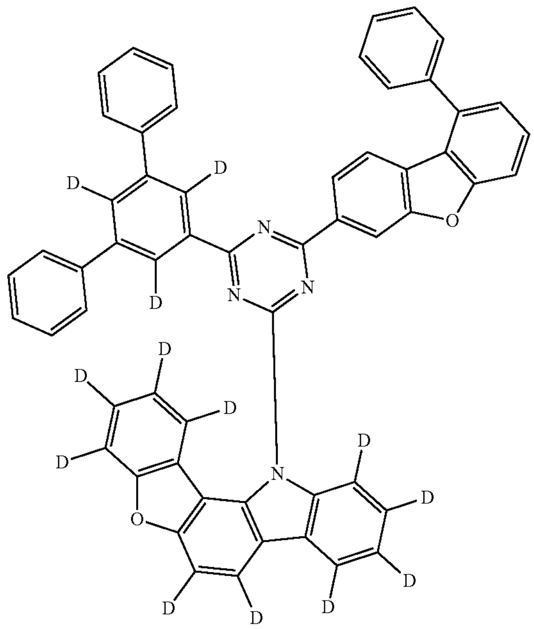
-continued
[E-59]
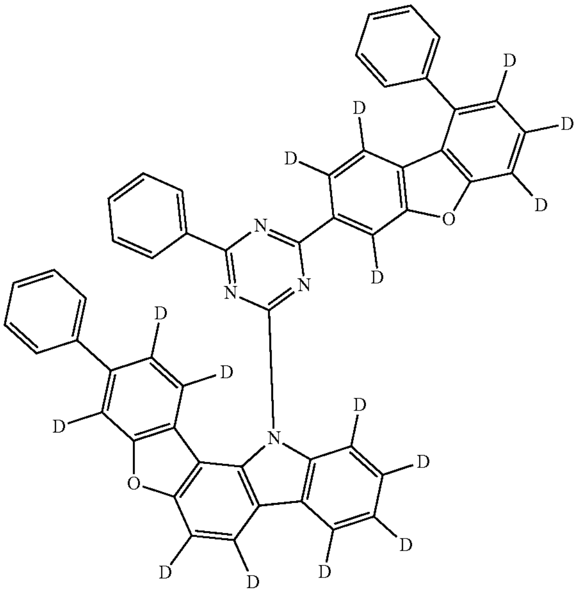
[E-60]
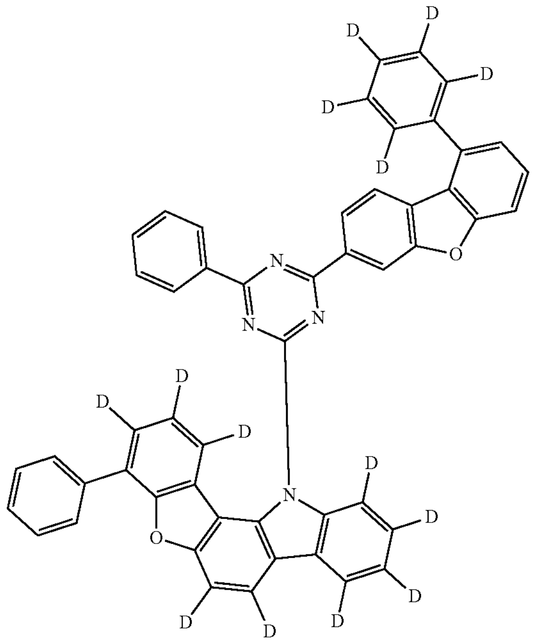

-continued
[E-61]
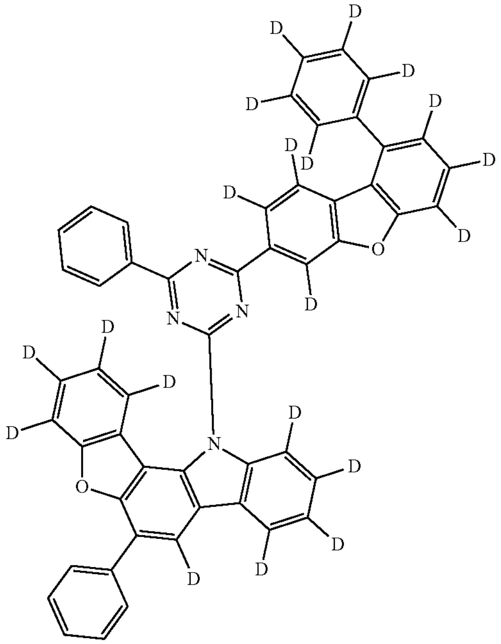
[E-62]
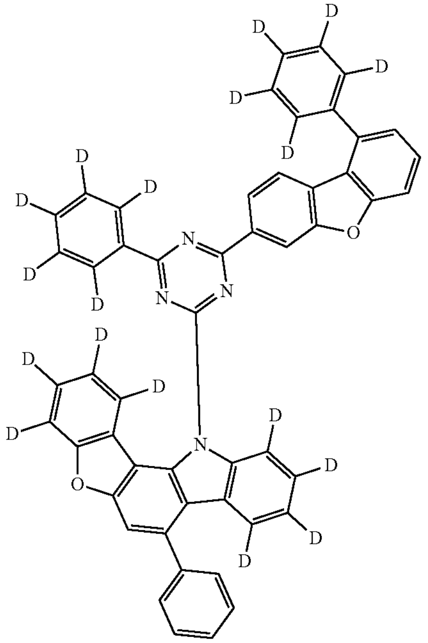
-continued
[E-63]
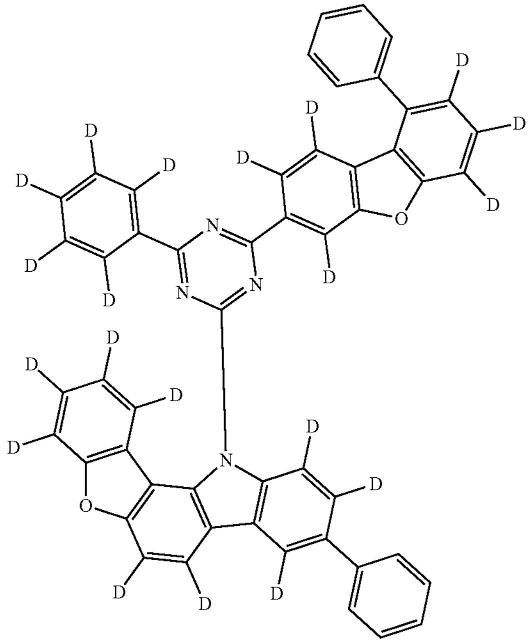
[E-64]
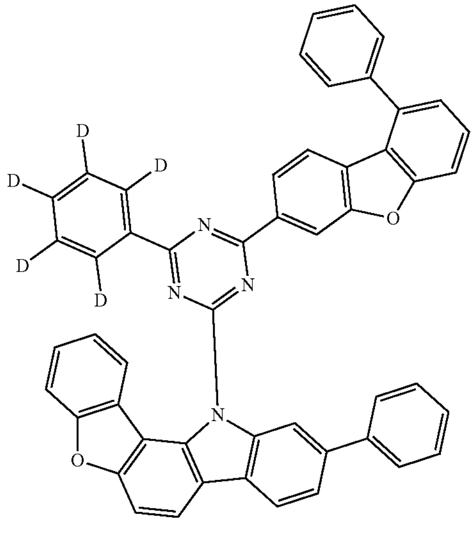

-continued
[E-65]
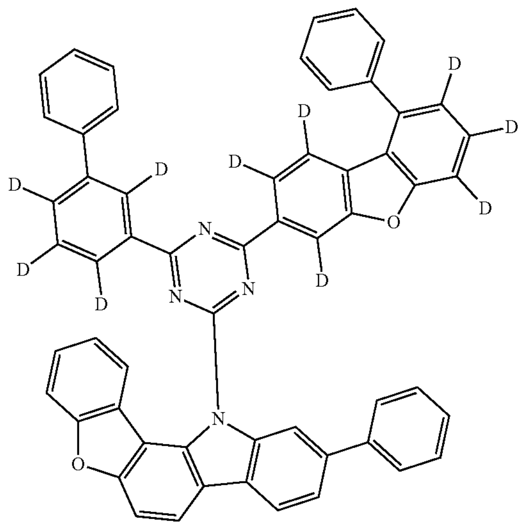
[E-66]
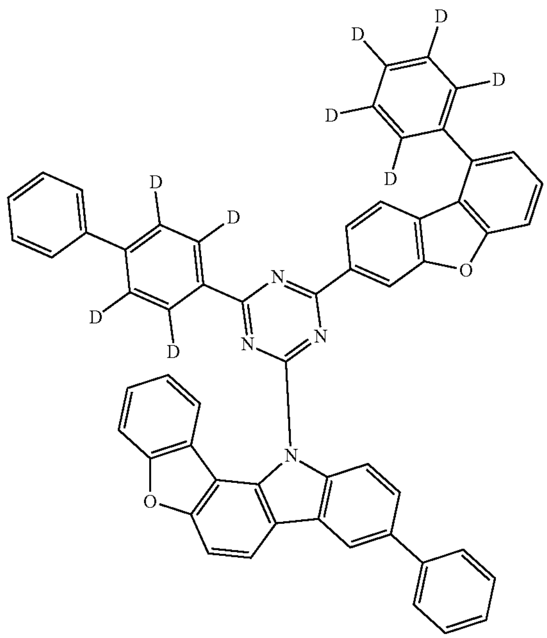
-continued
[E-67]
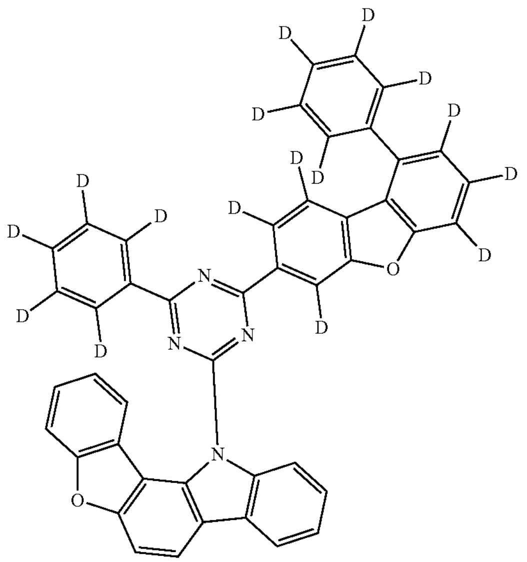
[E-68]
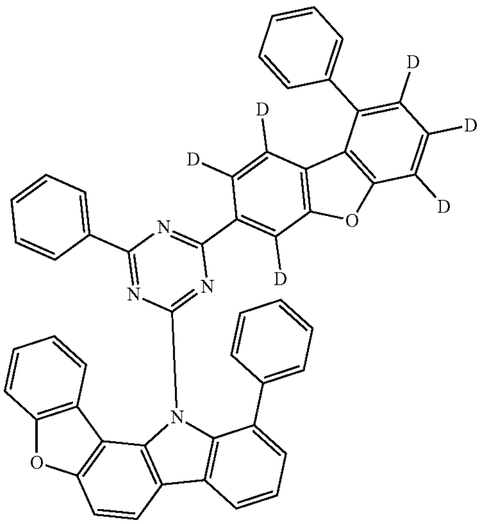

[E-69]
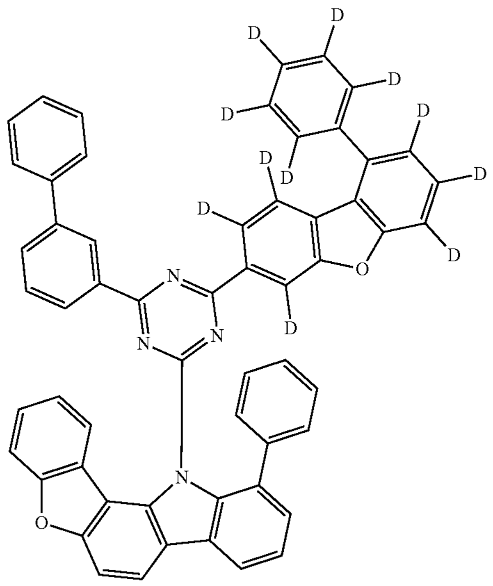
[E-70]
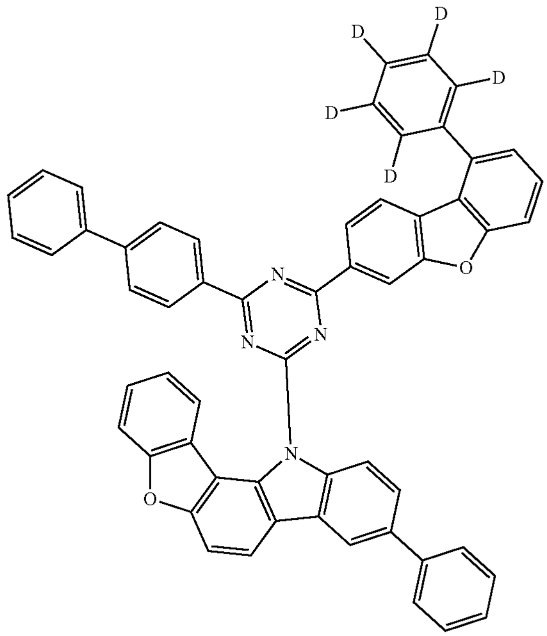
[E-71]
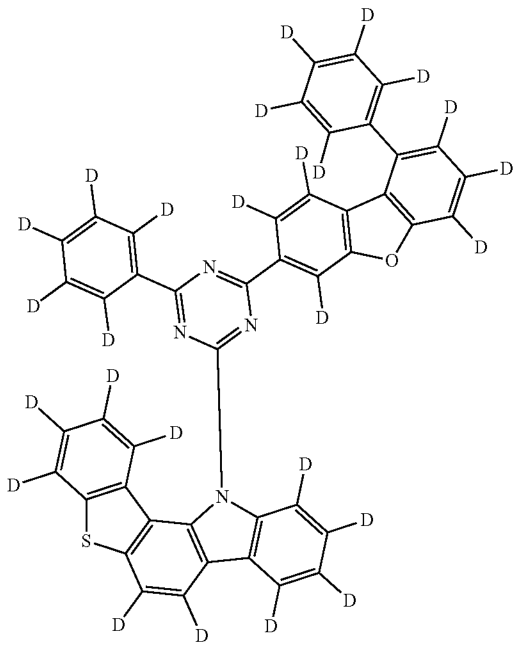
[E-72]
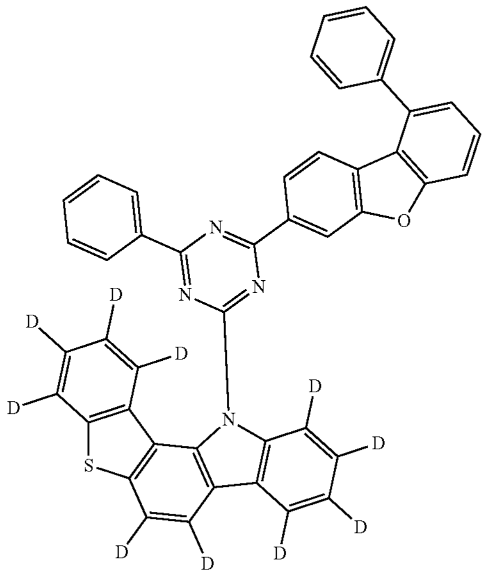

[E-73]
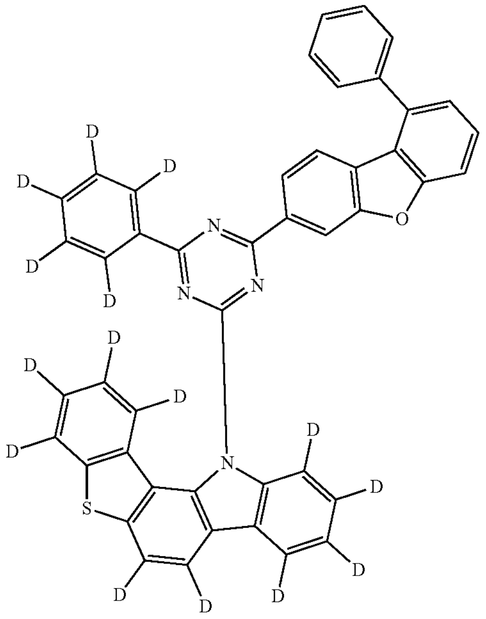
[E-74]
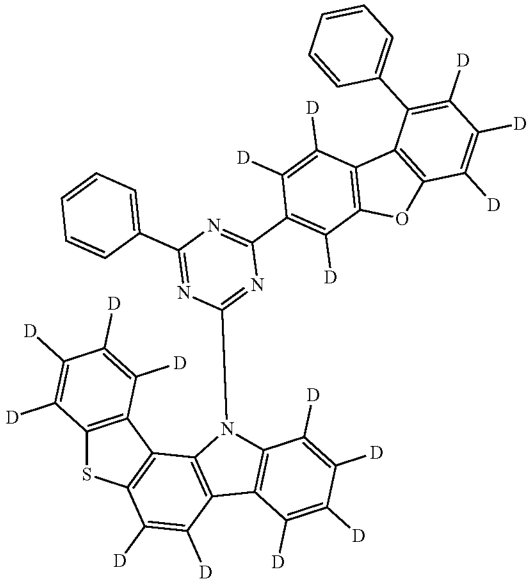
[E-75]
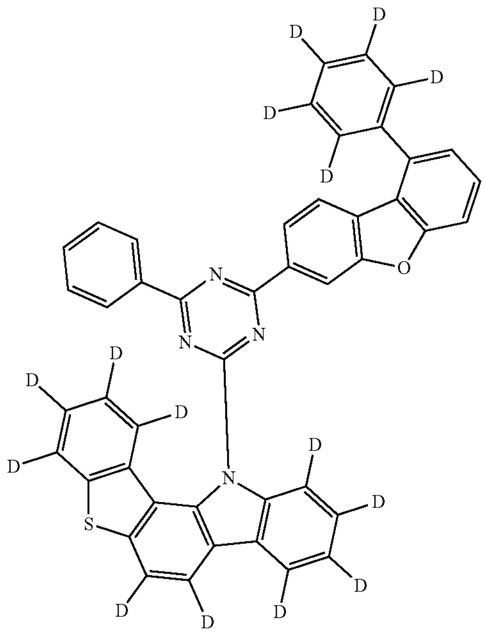
[E-76]
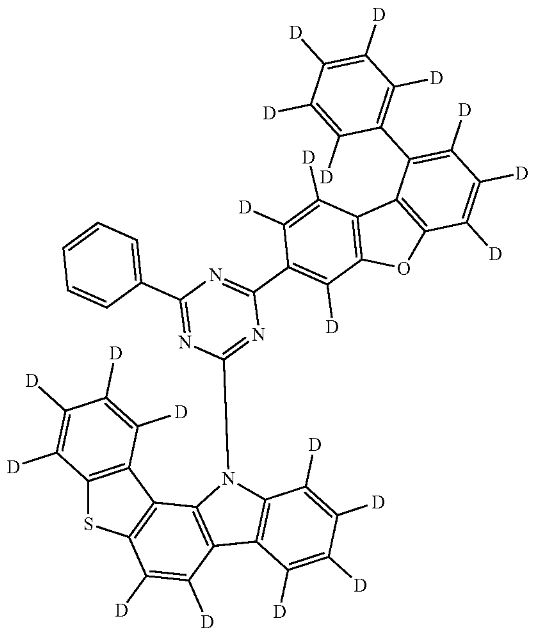

[E-77]
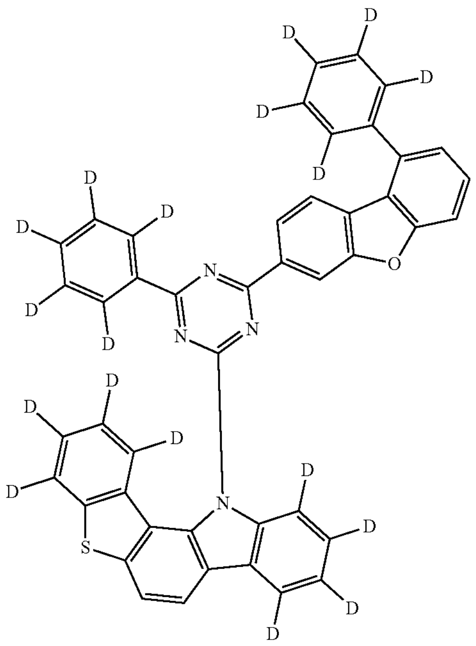
[E-78]
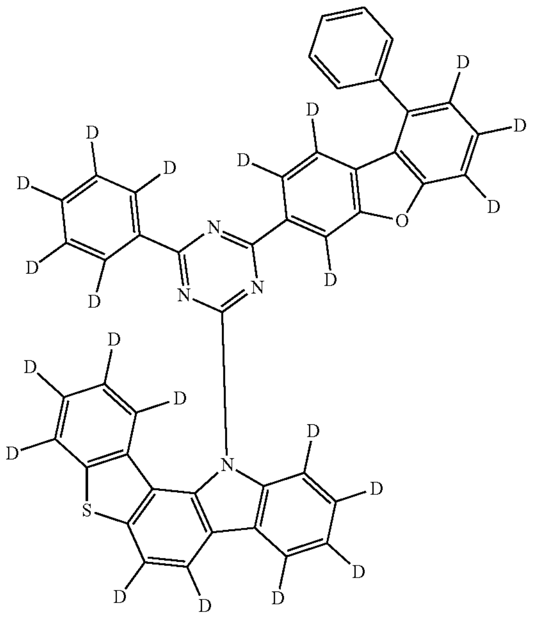
[E-79]
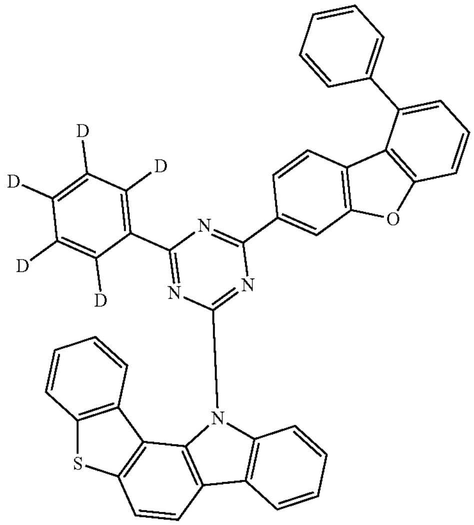
[E-80]
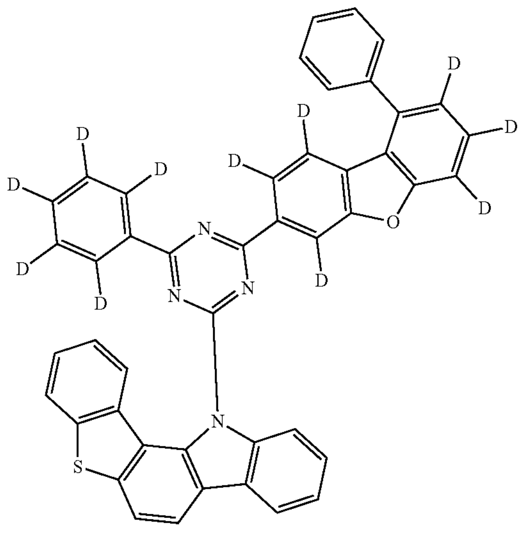

-continued
[E-81]
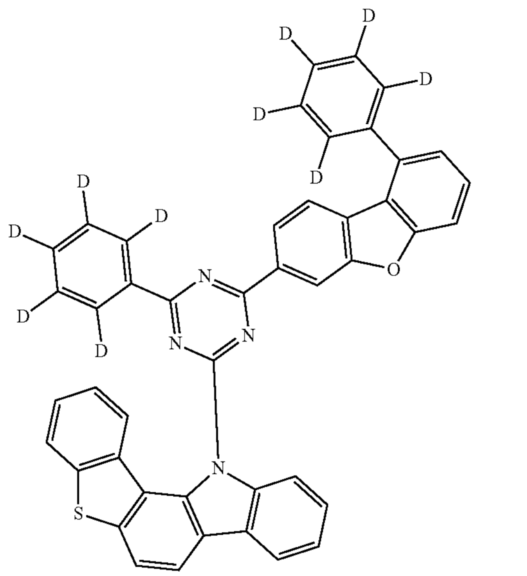
[E-82]
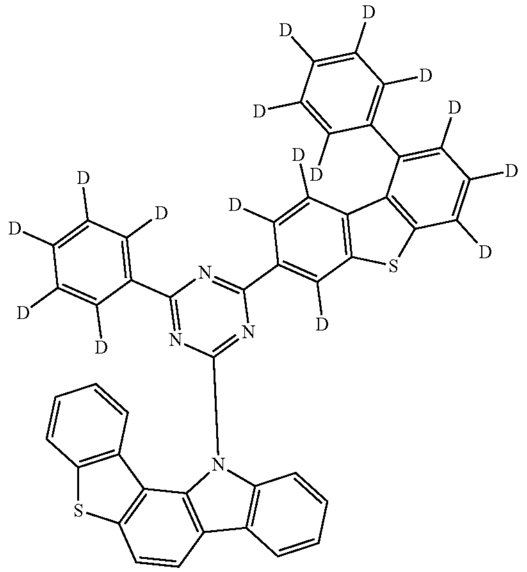
-continued
[E-83]
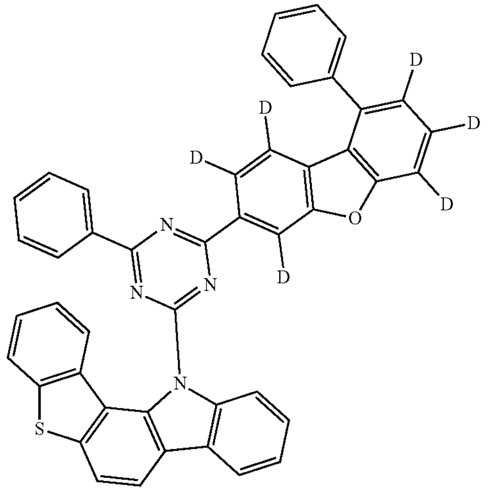
[E-84]
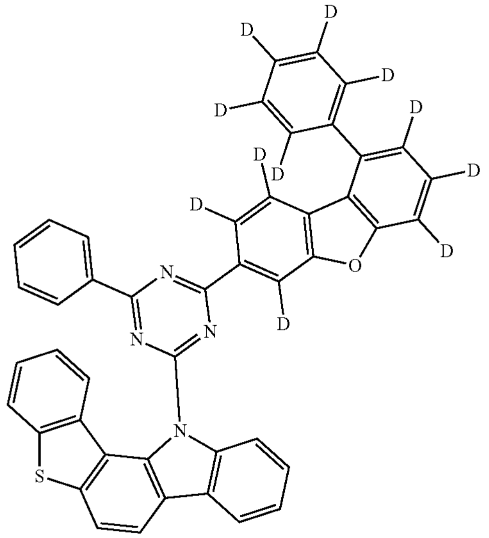
[E-85]
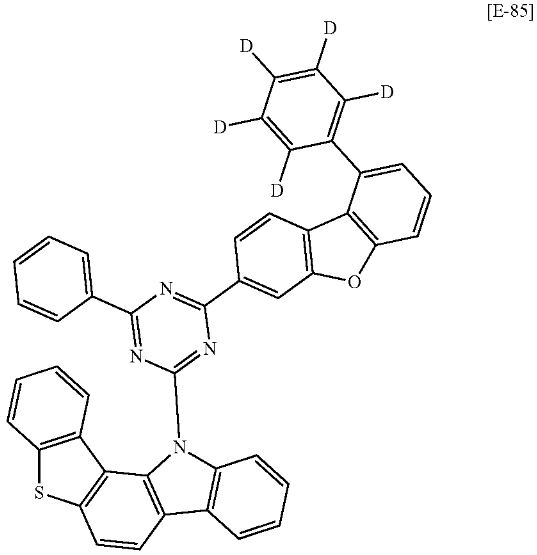

-continued
[E-86]
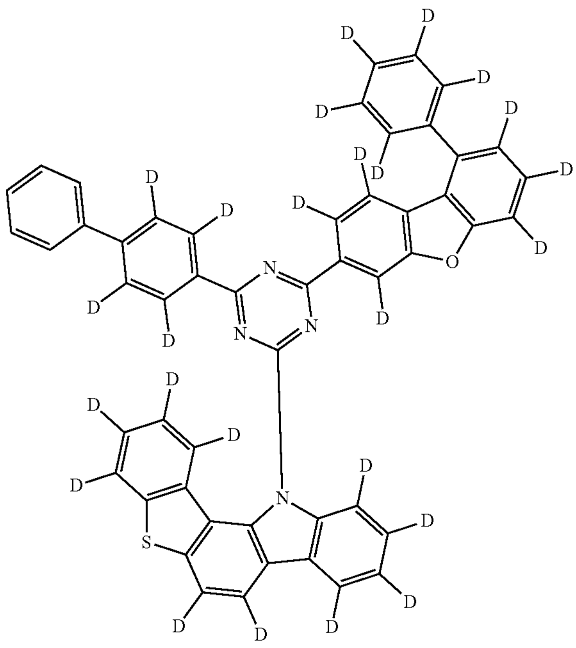
[E-87]
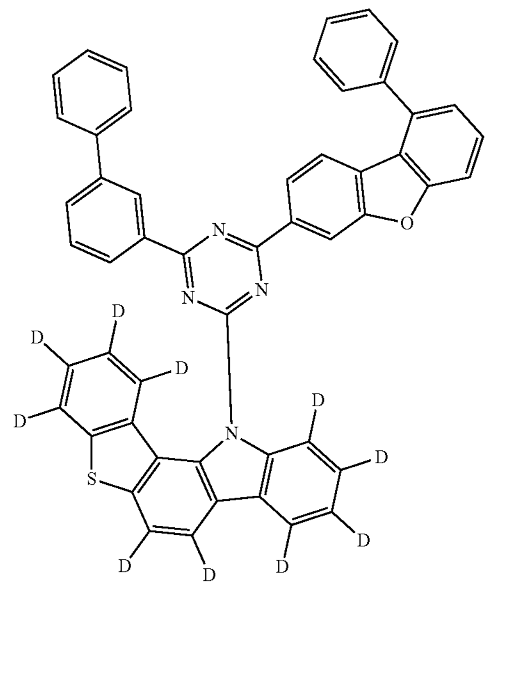
-continued
[E-88]
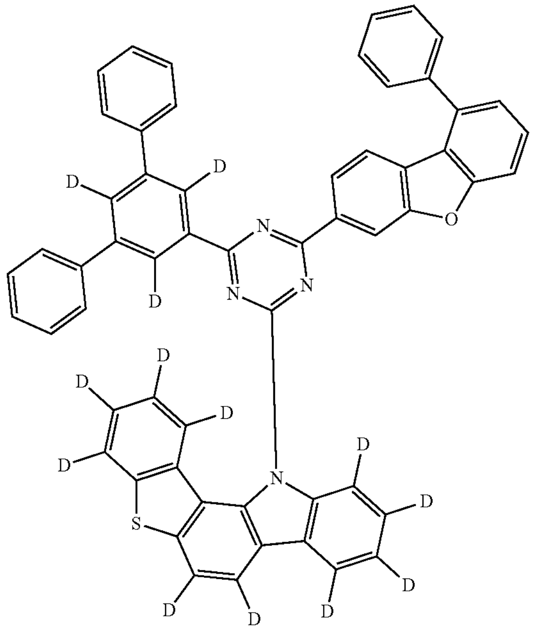
[E-89]
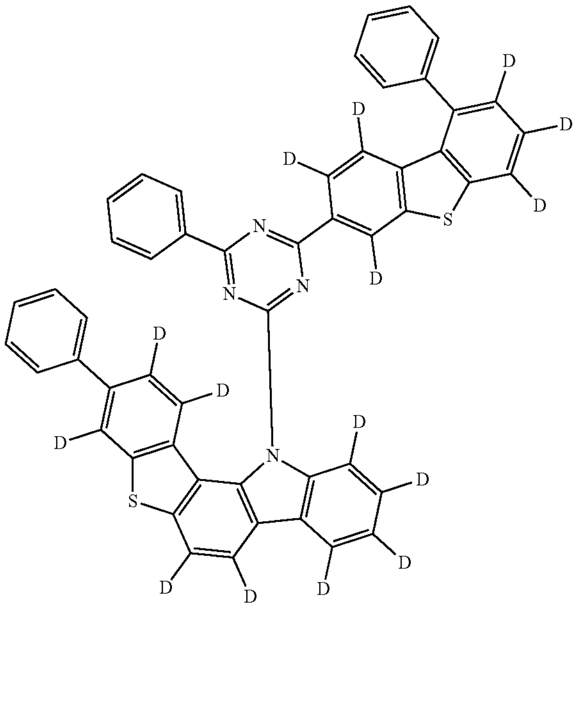

-continued
[E-90]
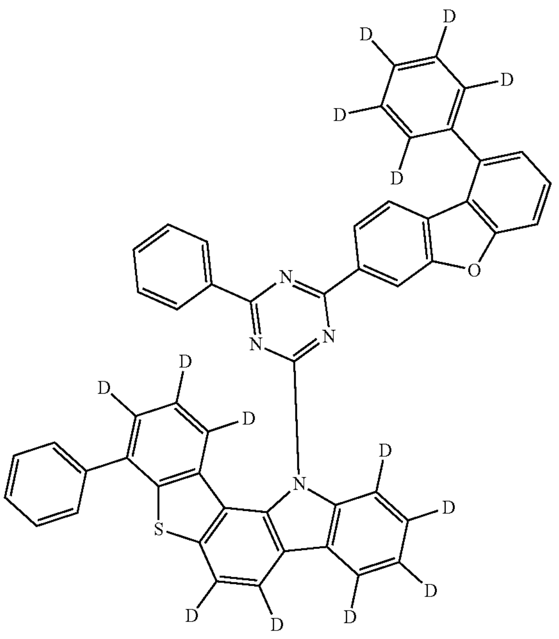
[E-91]
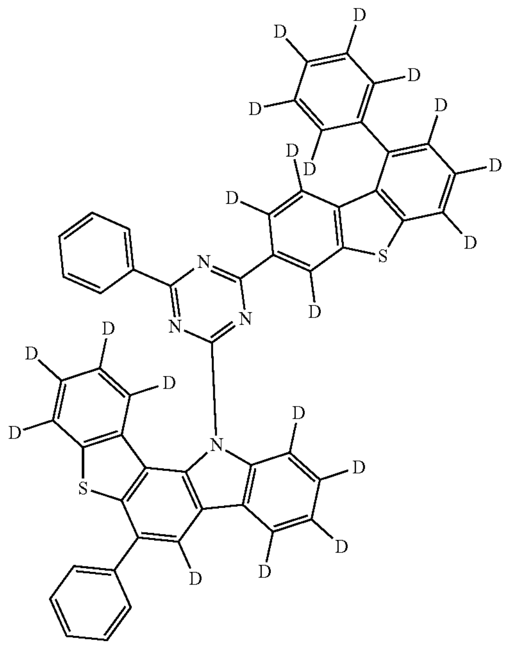
-continued
[E-92]
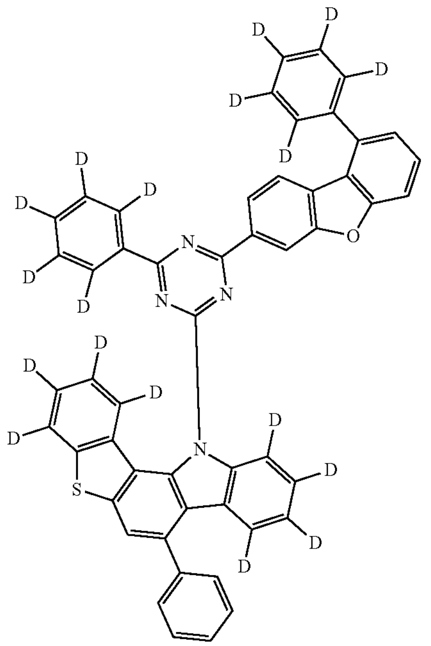
[E-93]
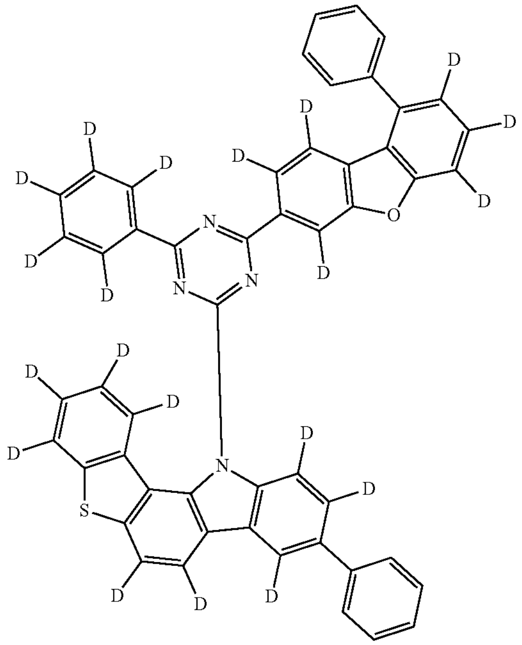

-continued
[E-94]
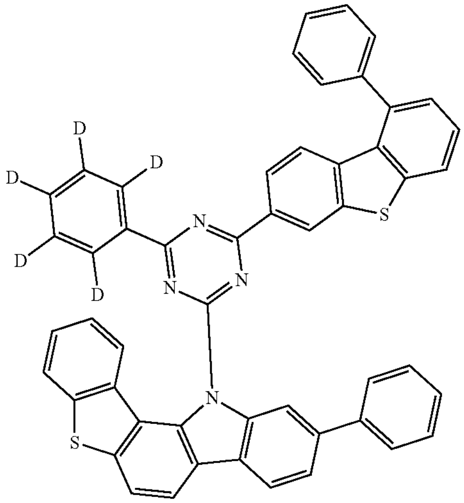
[E-95]
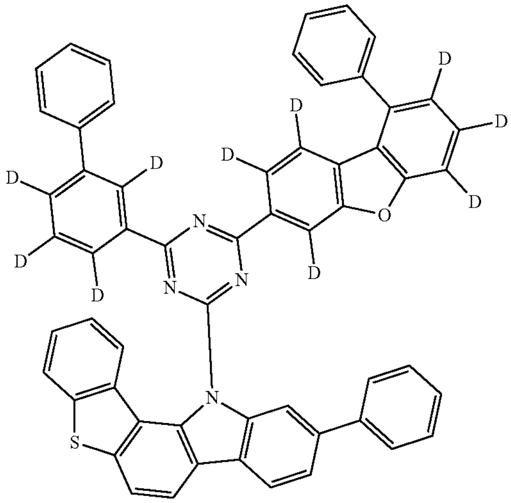
-continued
[E-96]
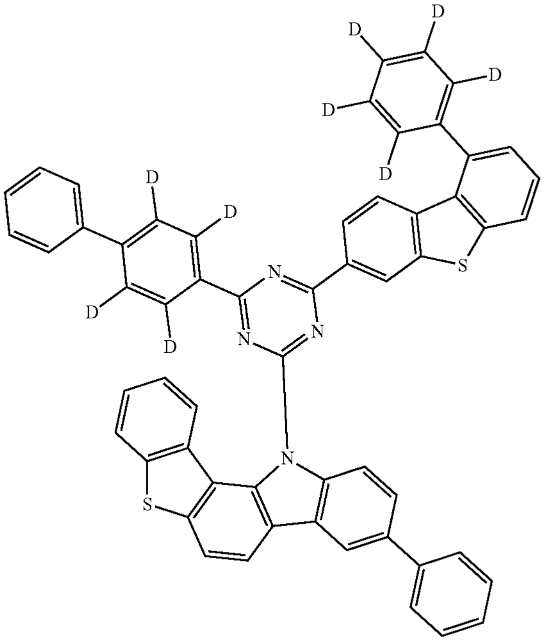
[E-97]
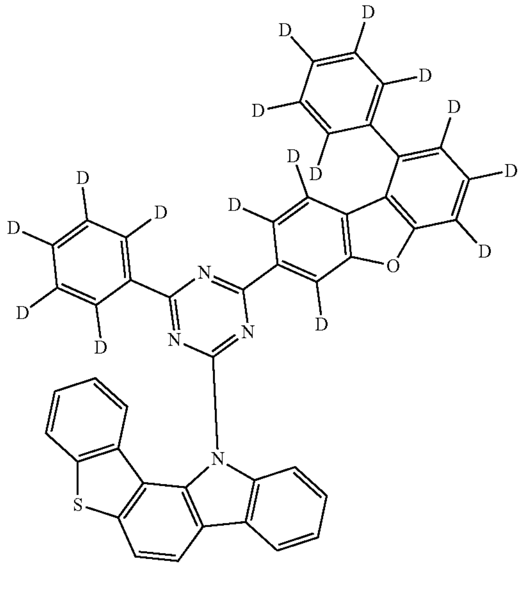

-continued
[E-98]
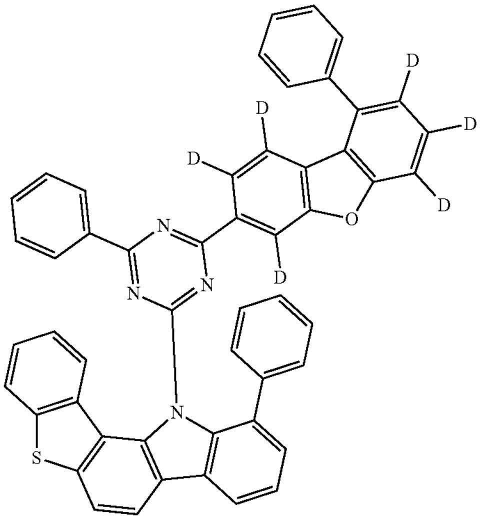
[E-99]
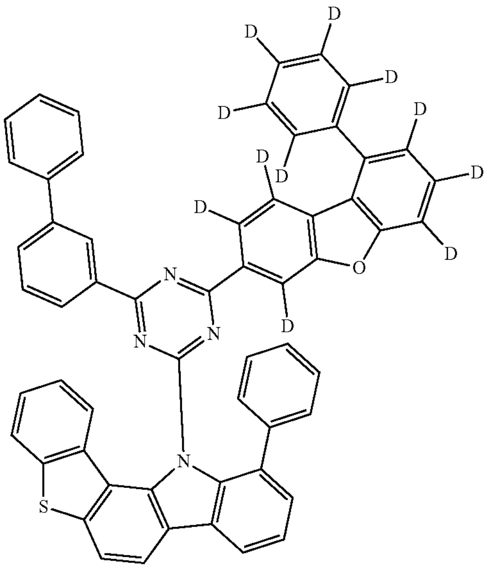
-continued
[E-100]
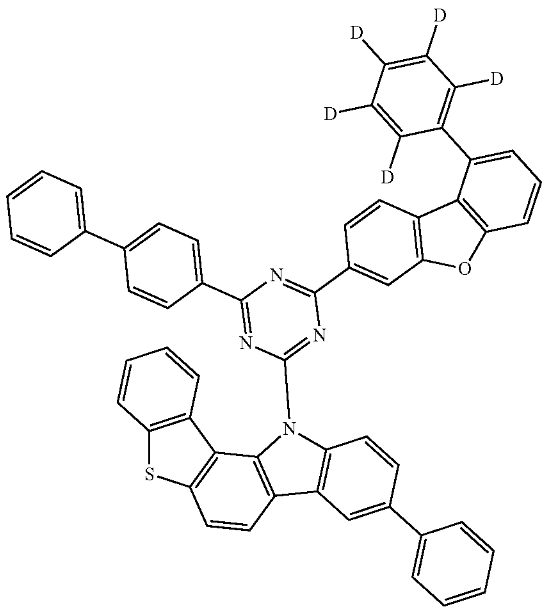
[F-1]
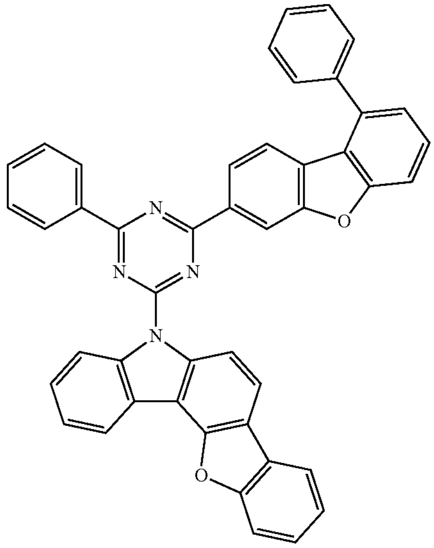

-continued
[F-2]
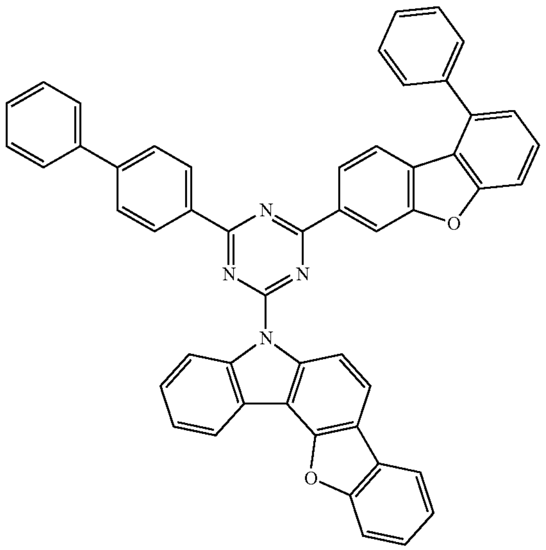
[F-3]
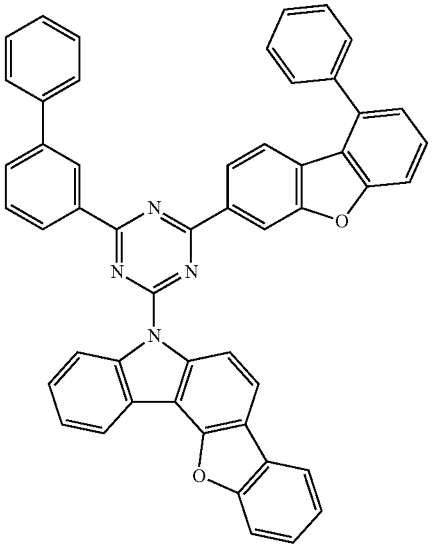
[F-4]
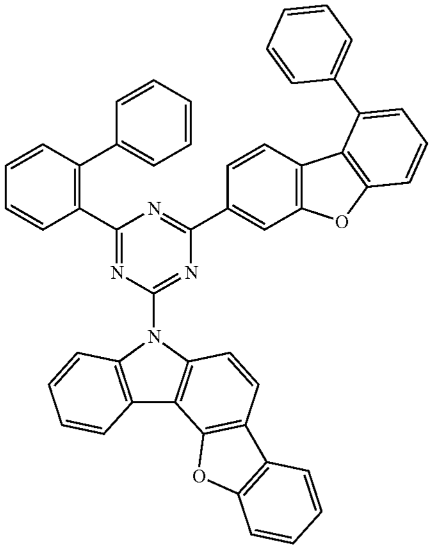
-continued
[F-5]
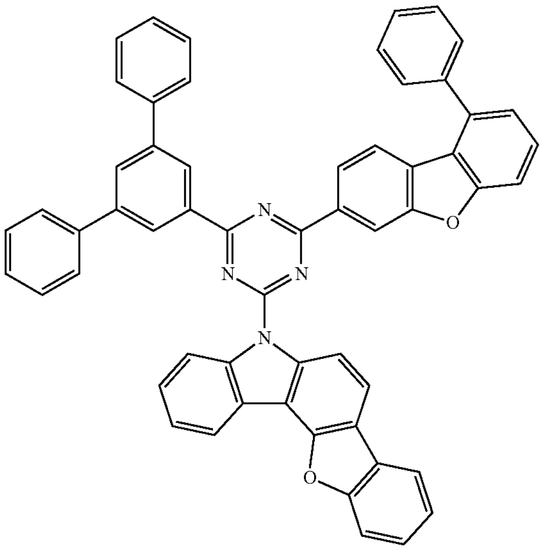
[F-6]
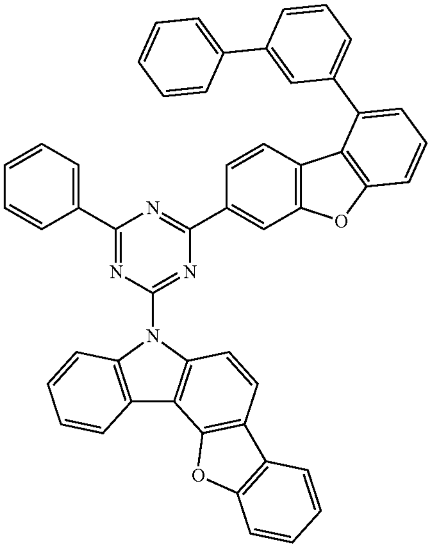

-continued
[F-7]
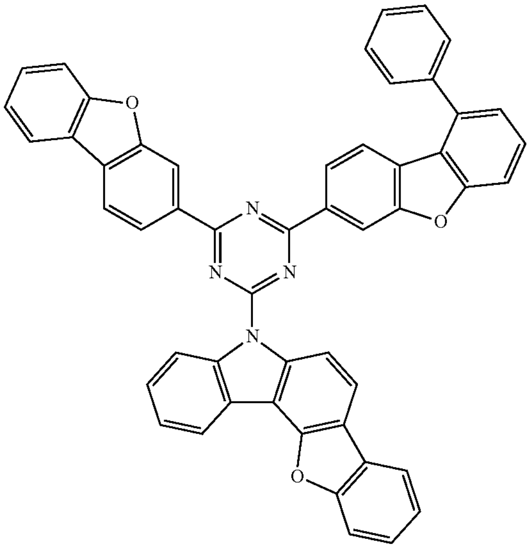
[F-8]
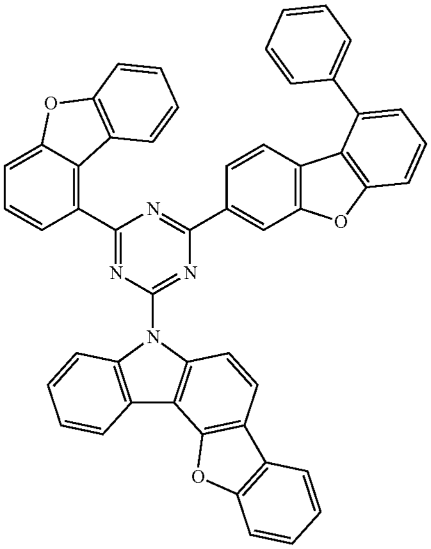
-continued
[F-9]
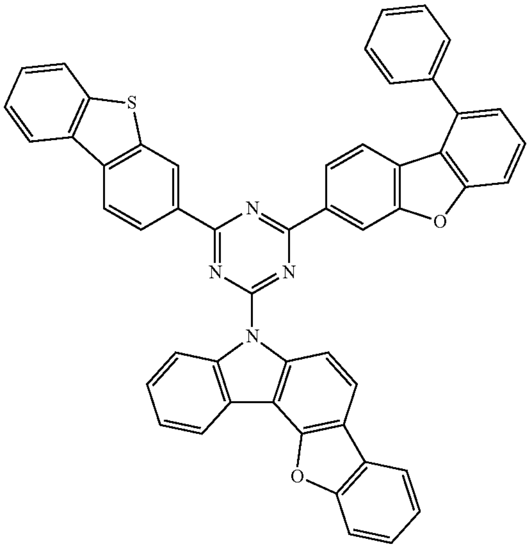
[F-10]
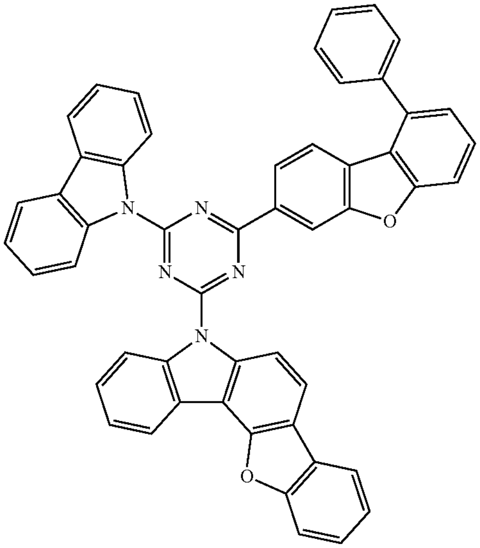

-continued
[F-11]
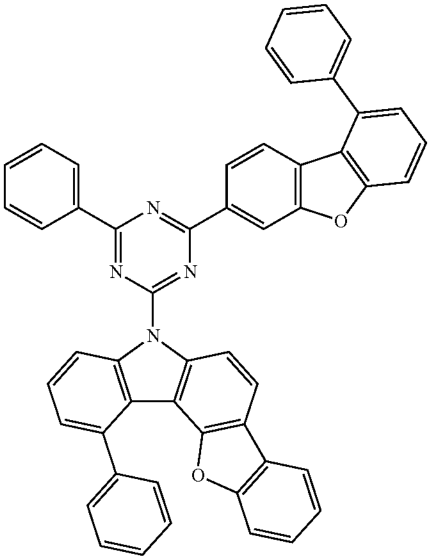
[F-12]
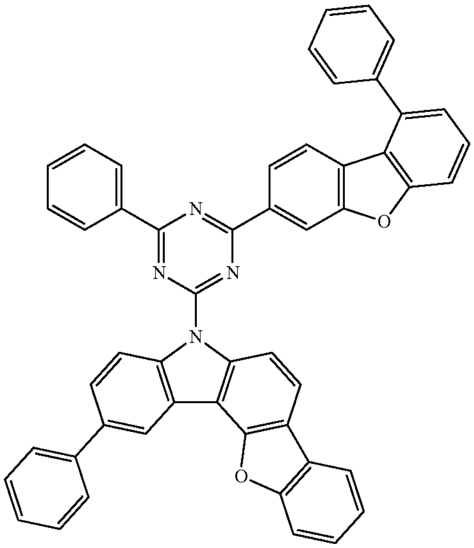
-continued
[F-13]
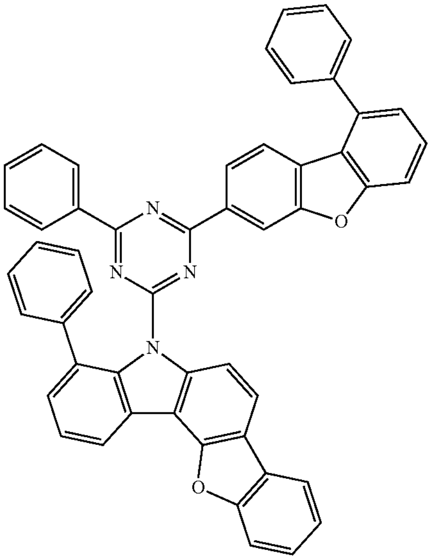
[F-14]
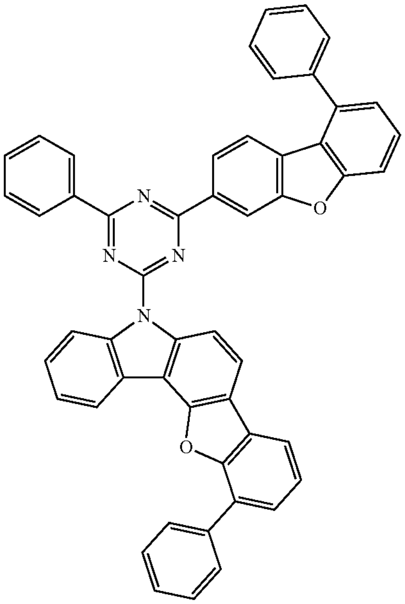

-continued
[F-15]
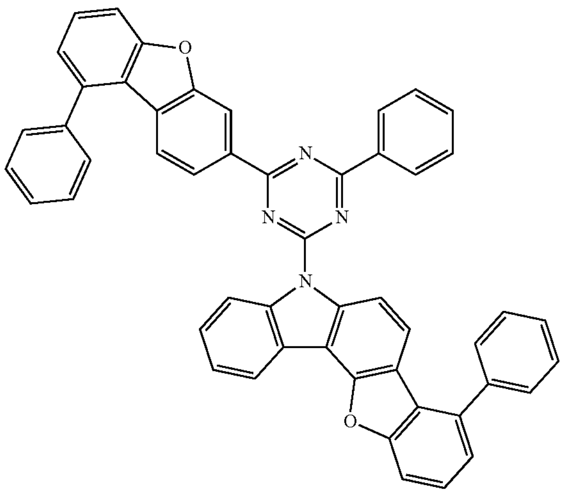
[F-16]
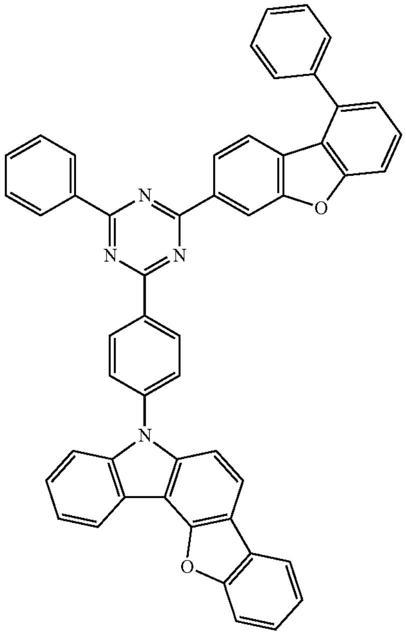
-continued
[F-17]
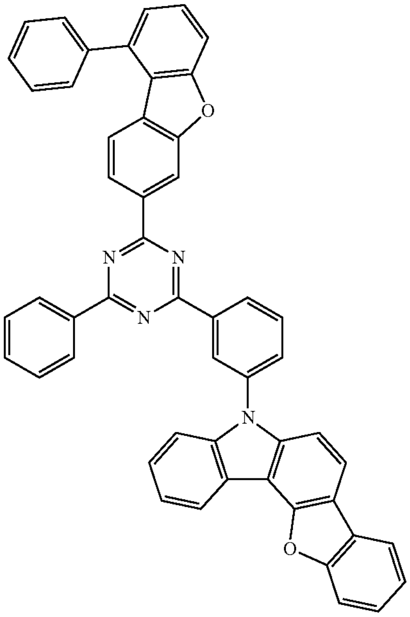
[F-18]
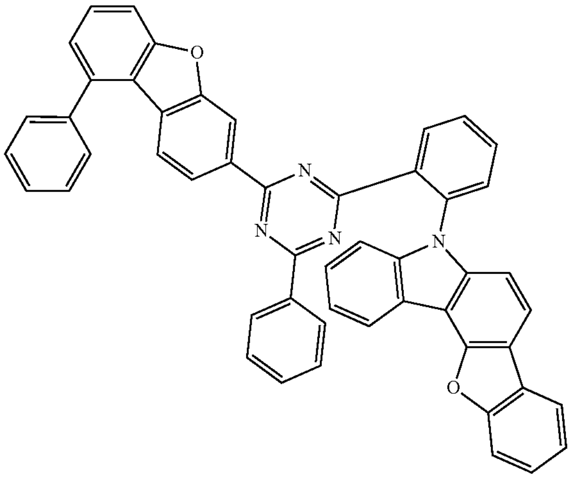

-continued
[F-19]
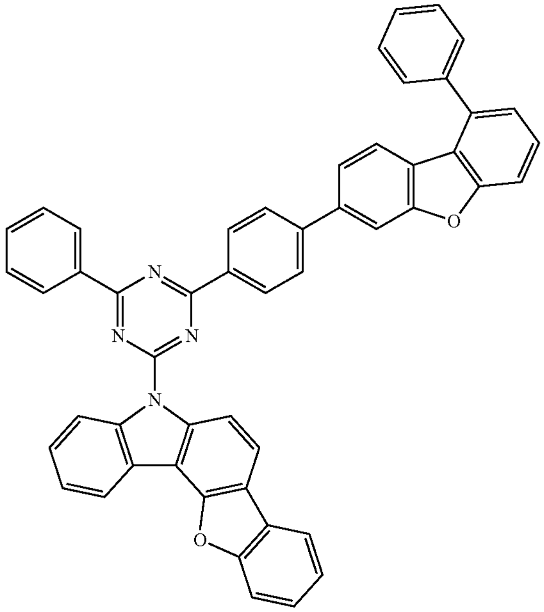
[F-20]
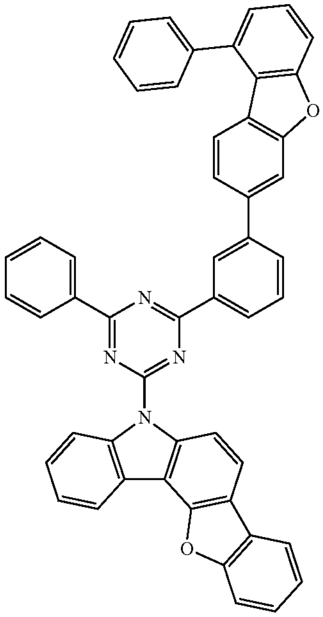
-continued
[F-21]
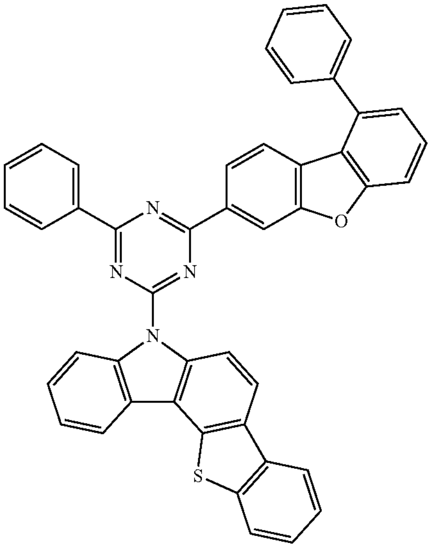
[F-22]
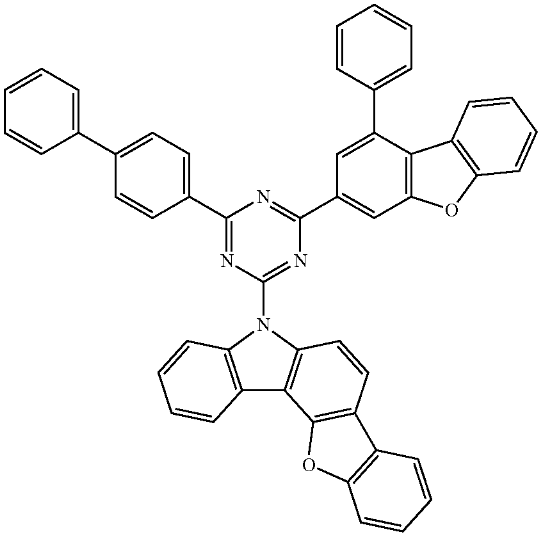
[F-23]
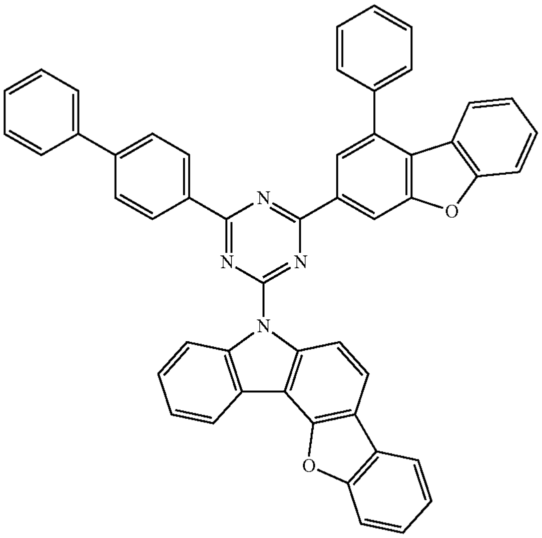

-continued
[F-24]
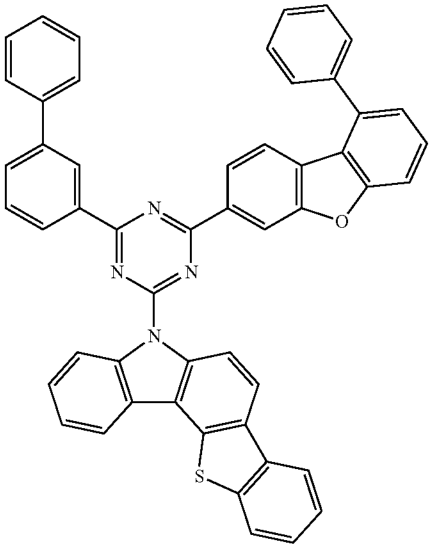
[F-25]
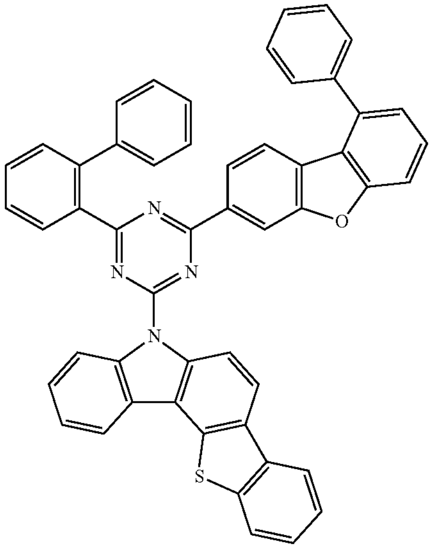
[F-26]
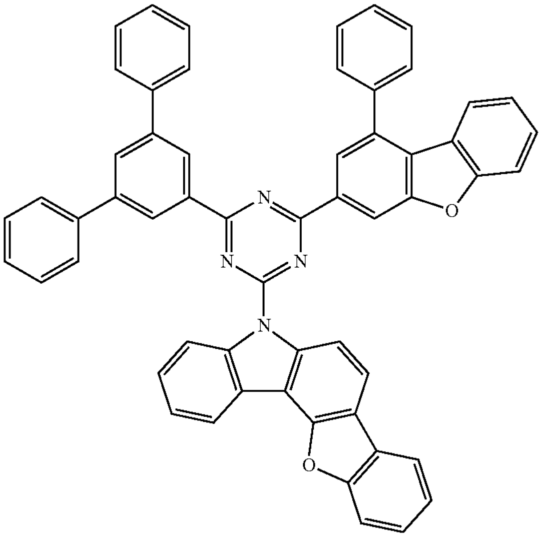
-continued
[F-27]
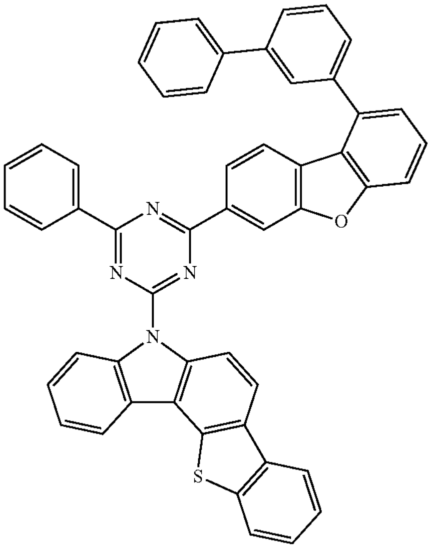
[F-28]
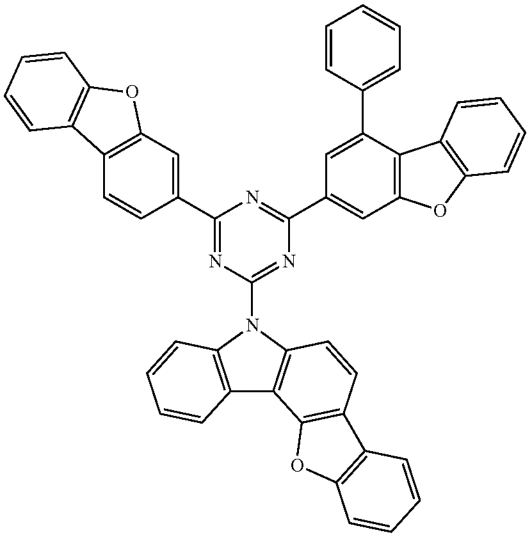
[F-29]
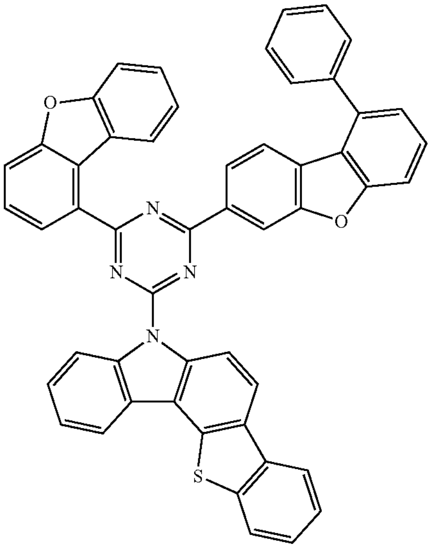

-continued
[F-30]
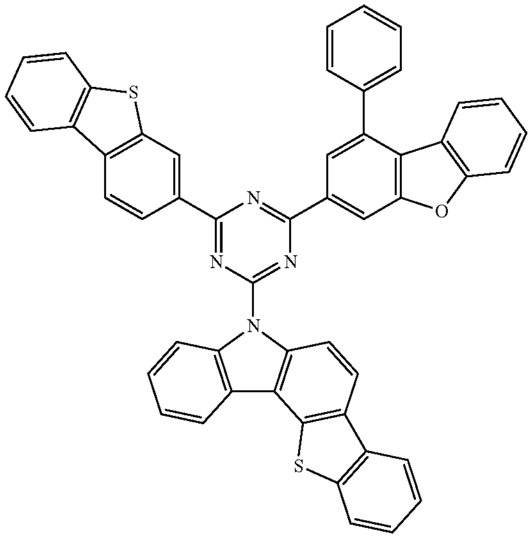
[F-31]
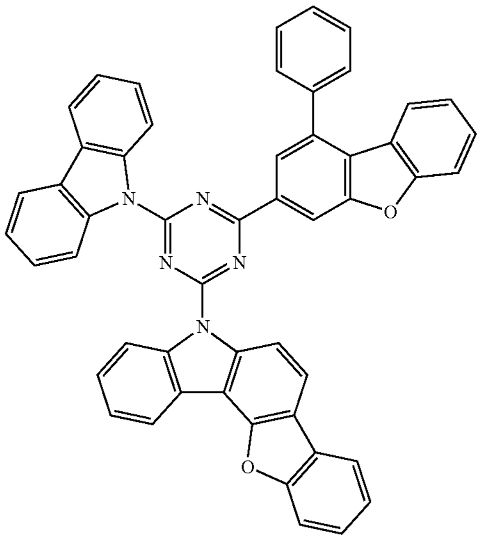
-continued
[F-32]
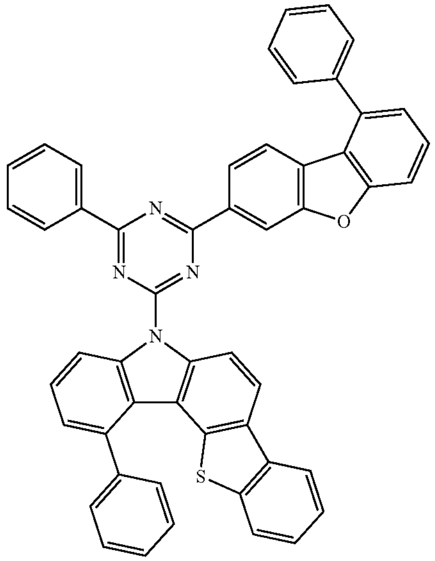
[F-33]
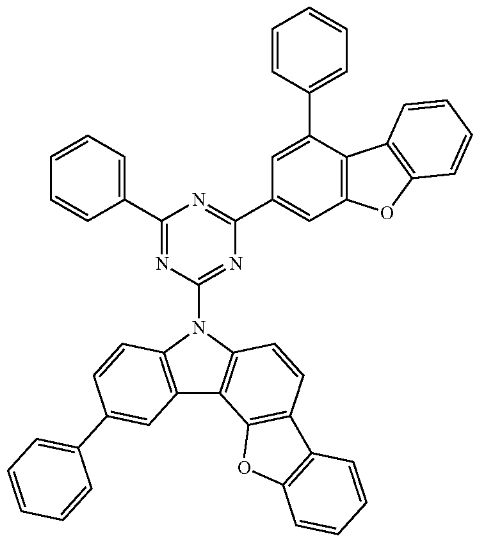

-continued
[F-34]
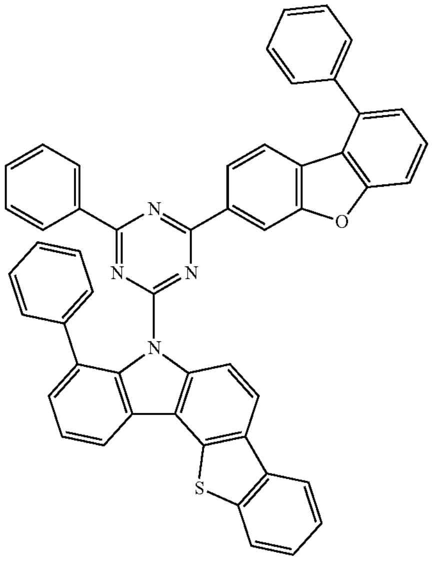
[F-35]
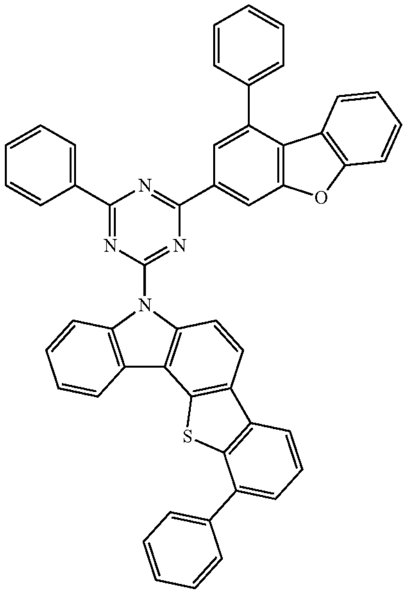
[F-36]
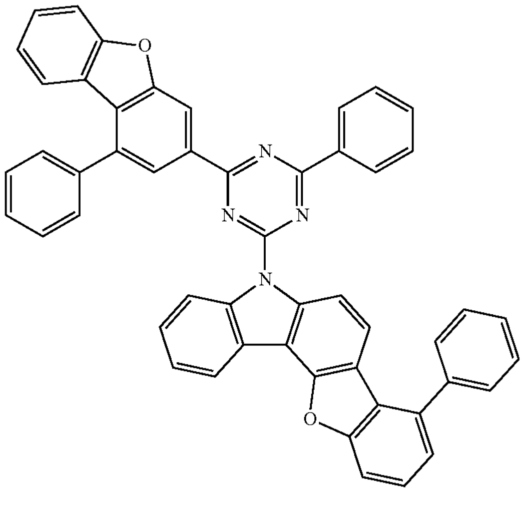
-continued
[F-37]
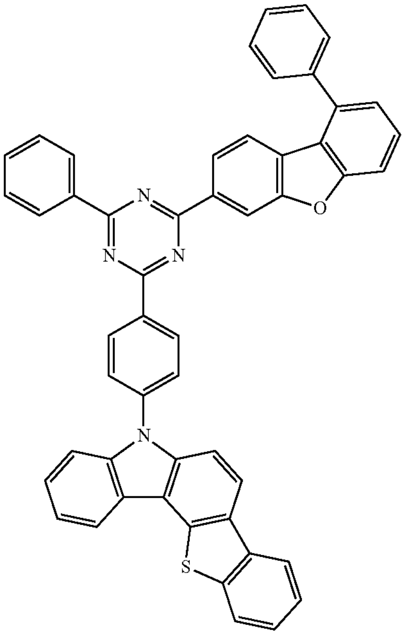
[F-38]
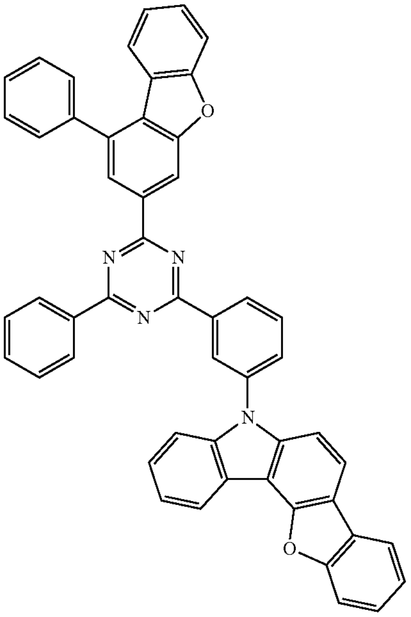

-continued
[F-39]
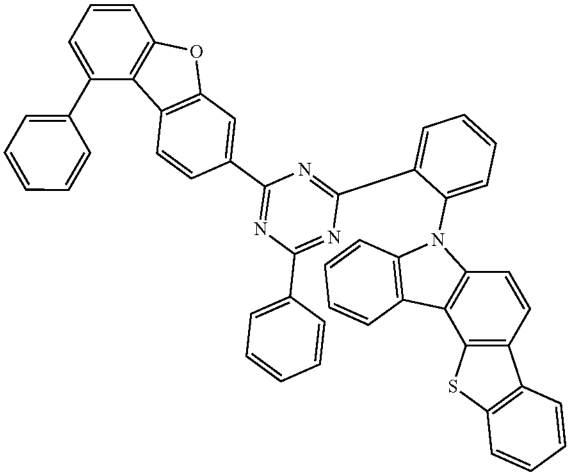
[F-40]
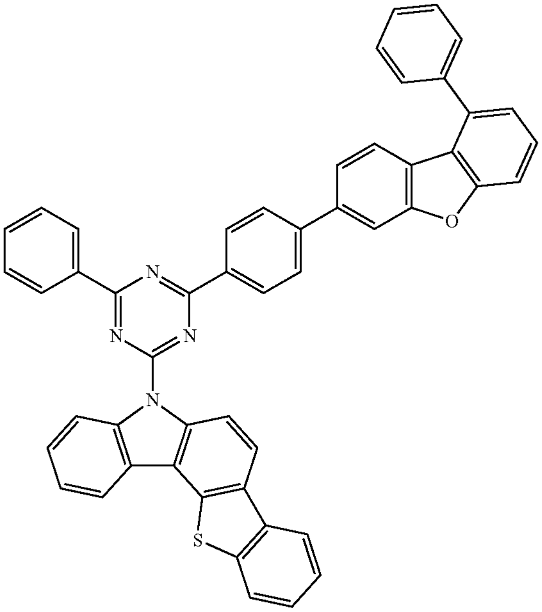
-continued
[F-41]
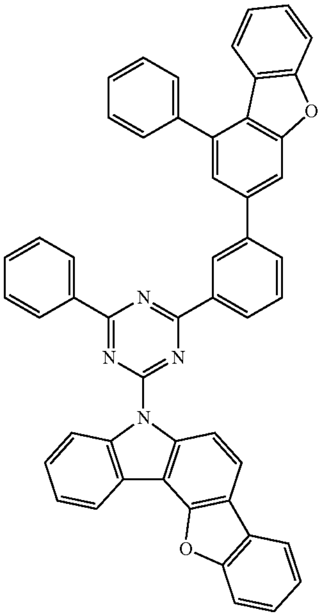
[F-42]
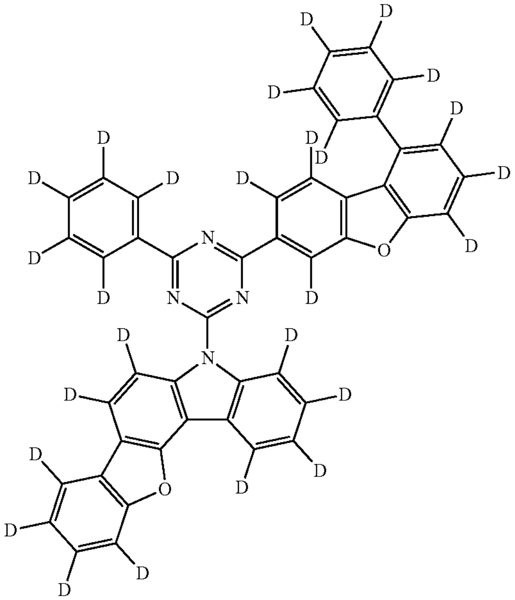

-continued
[F-43]
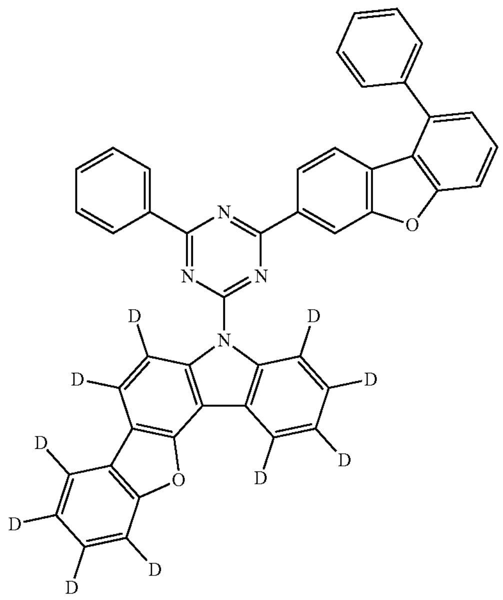
[F-44]
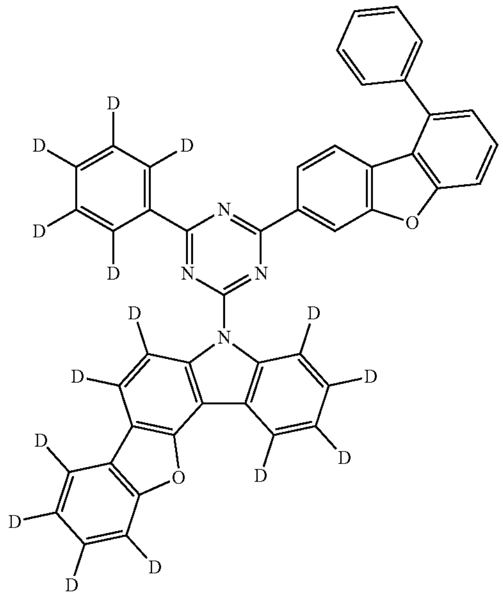
-continued
[F-45]
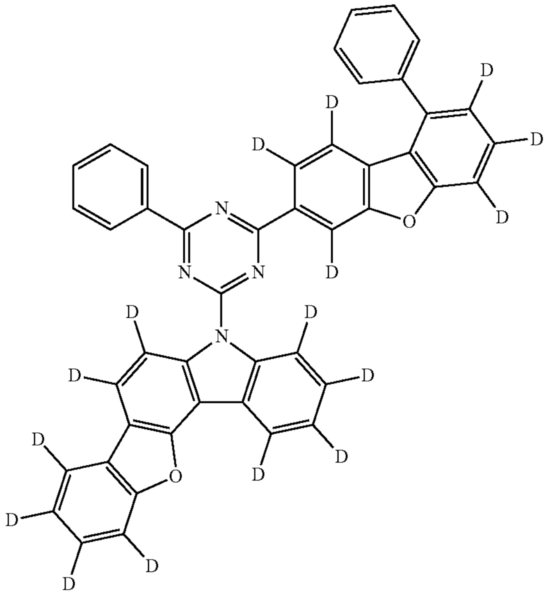
[F-46]
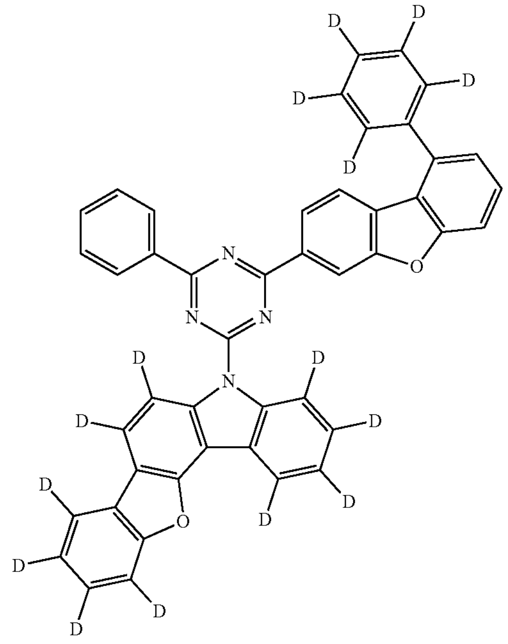

-continued
[F-47]
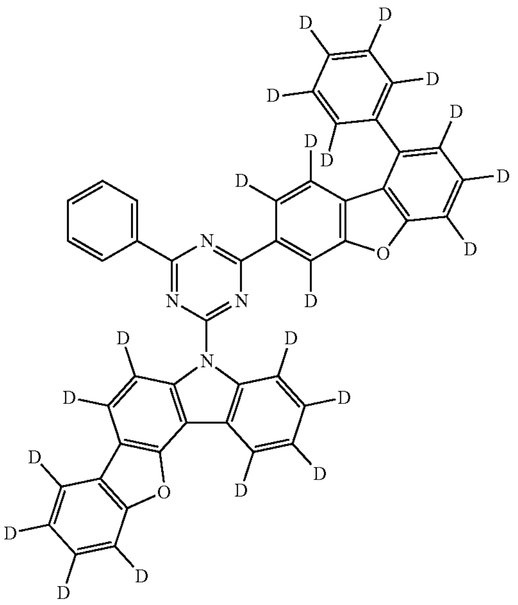
[F-48]
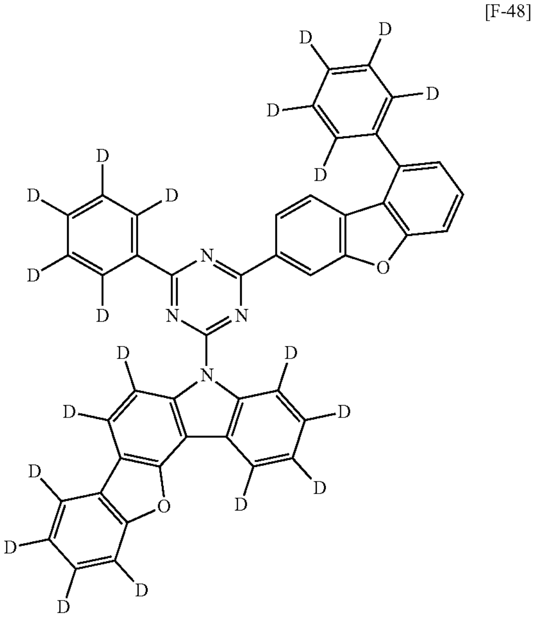
-continued
[F-49]
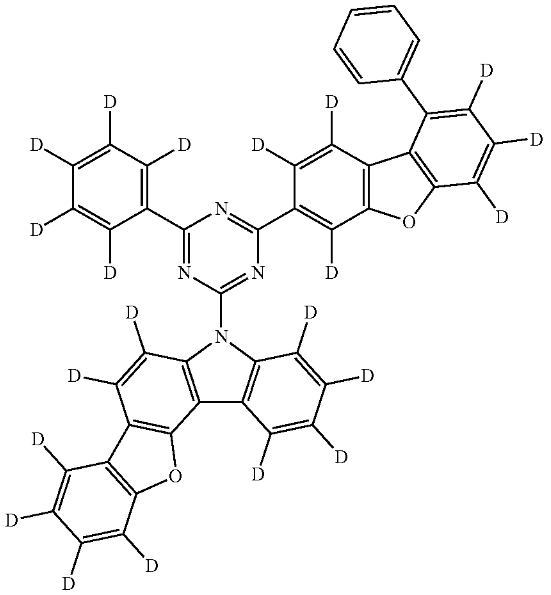
[F-50]
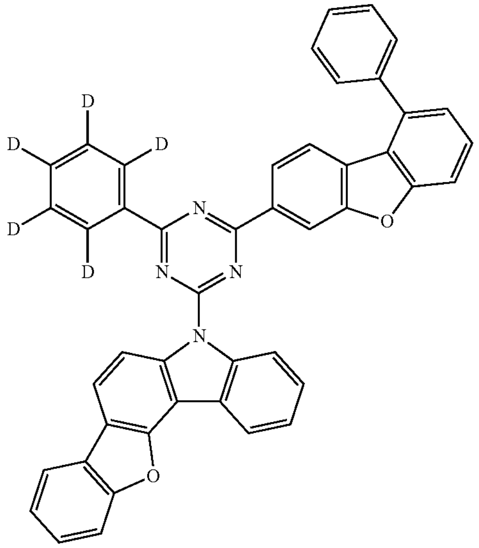

-continued
[F-51]
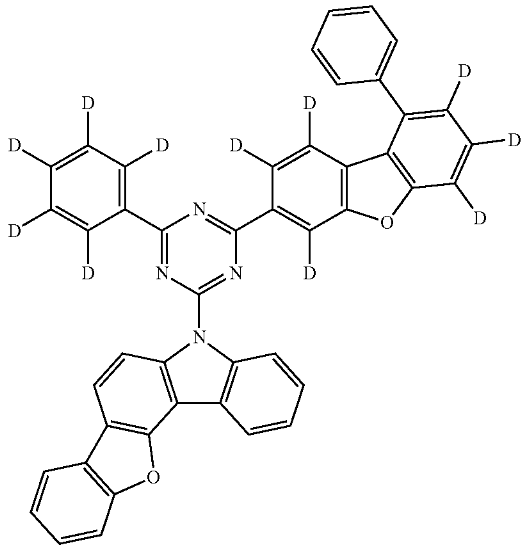
[F-52]
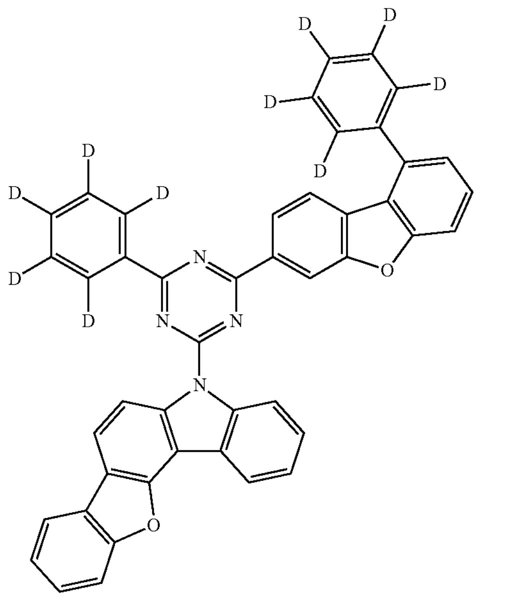
-continued
[F-53]
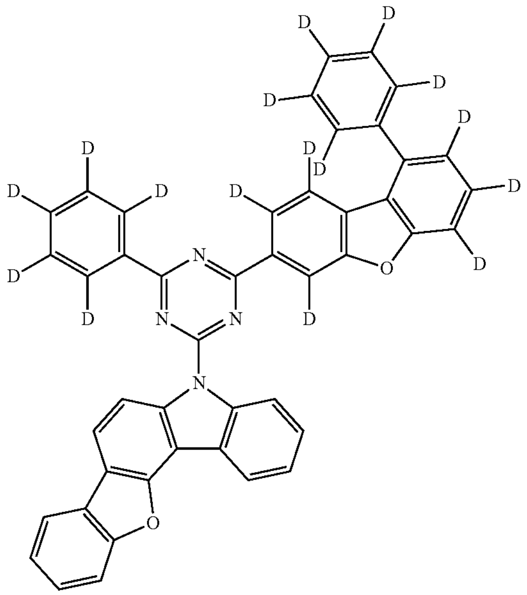
[F-54]
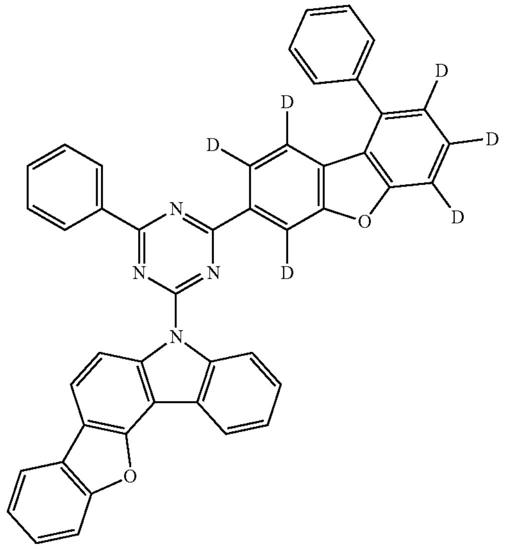

-continued
[F-55]
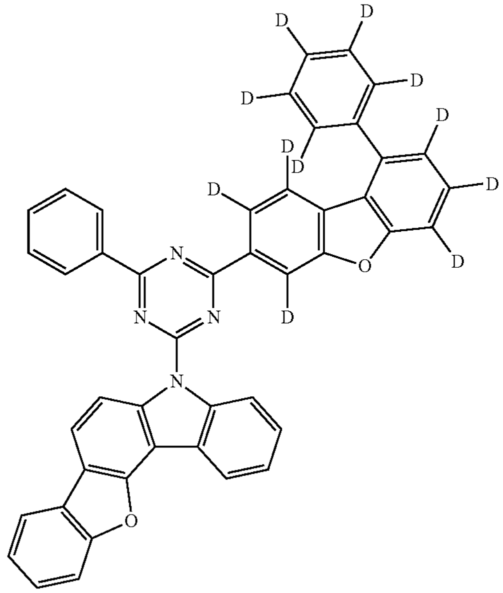
[F-56]
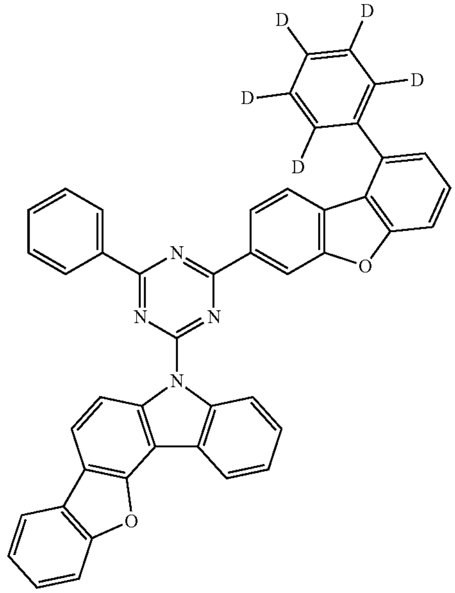
-continued
[F-57]
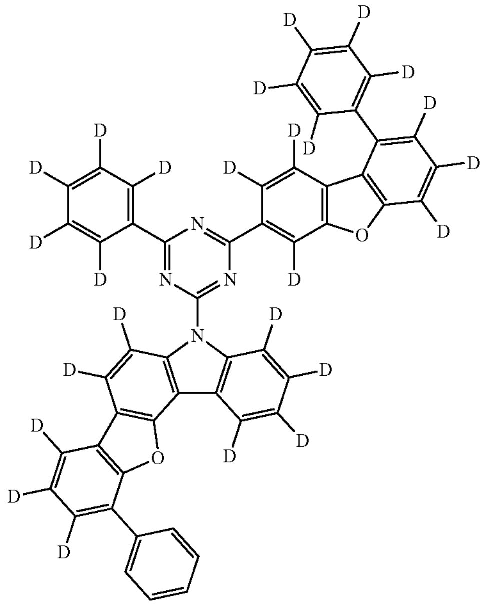
[F-58]
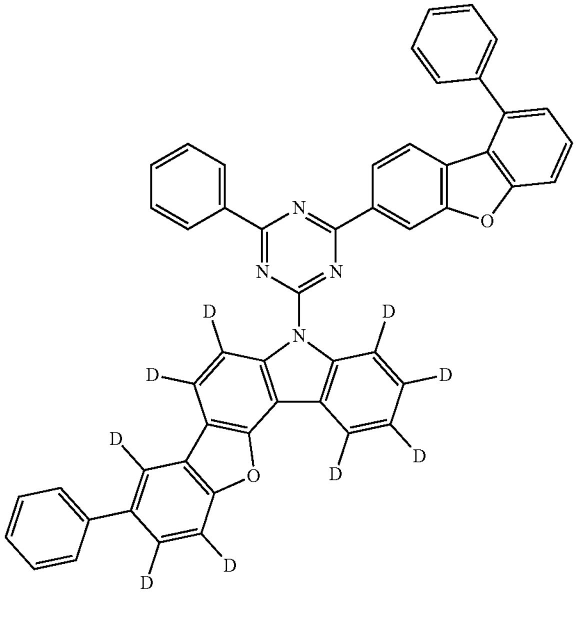

-continued
[F-59]
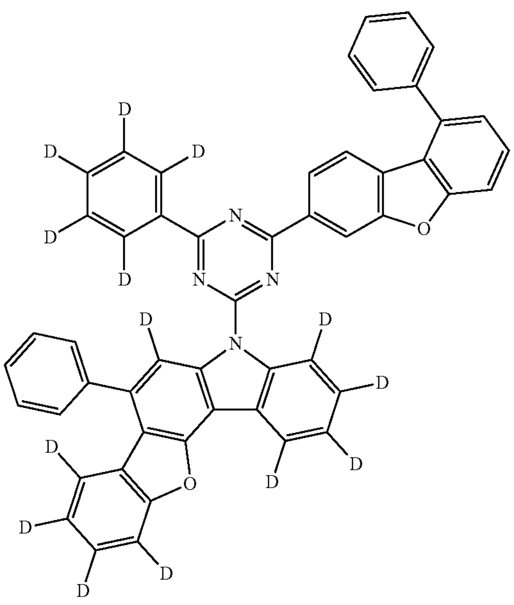
[F-60]
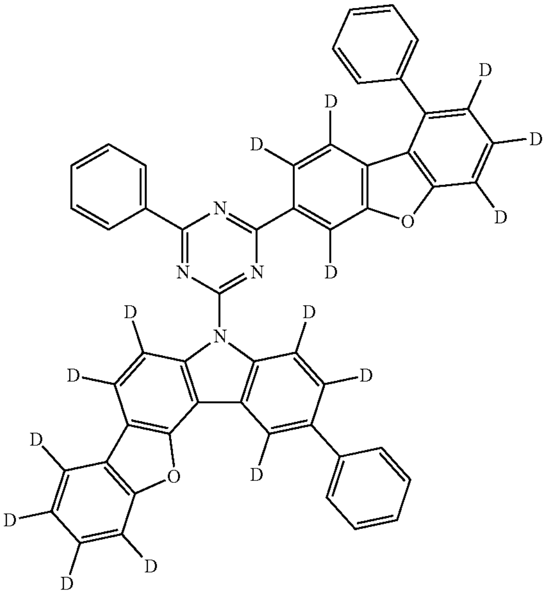
-continued
[F-61]
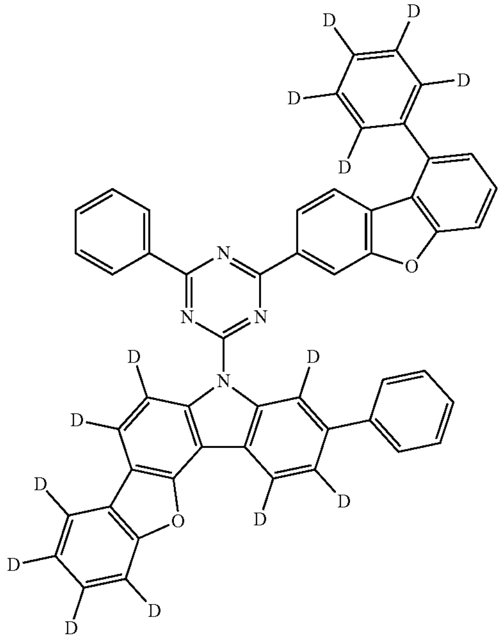
[F-62]
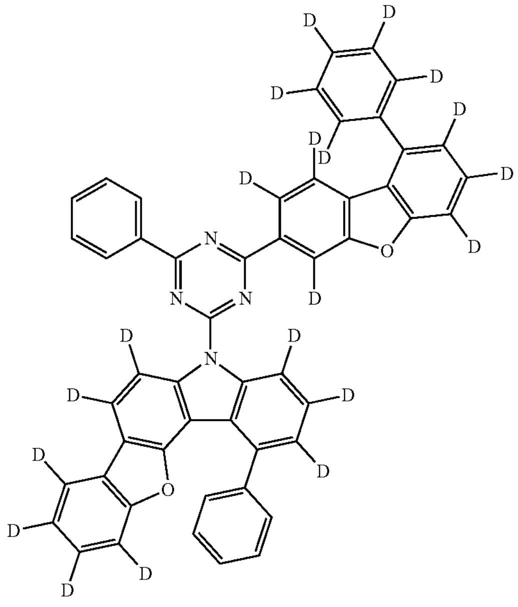

-continued
[F-63]
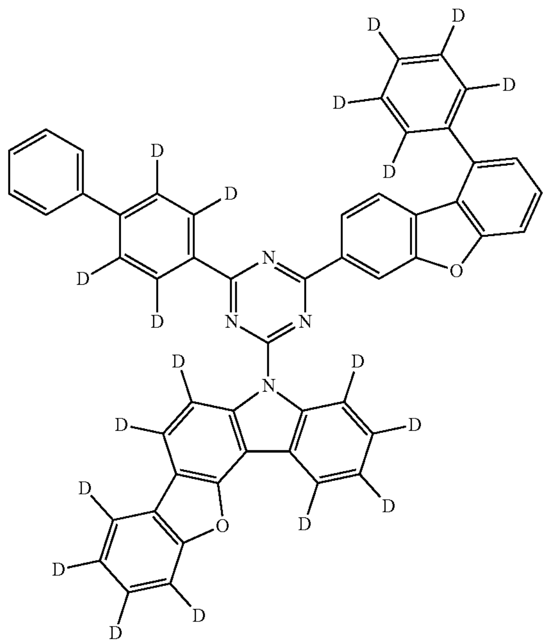
[F-64]
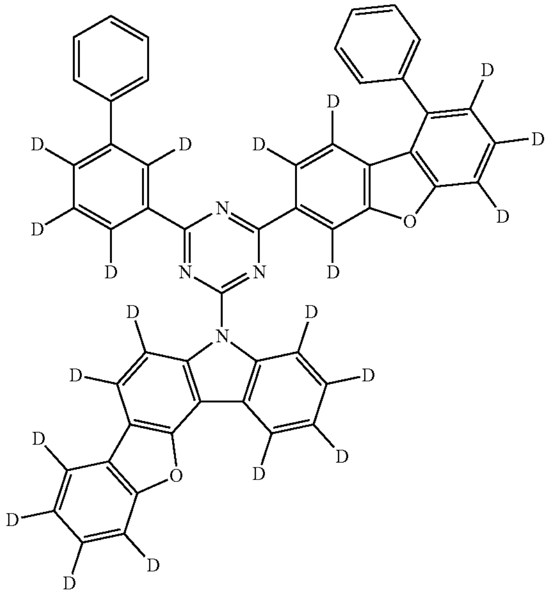
-continued
[F-65]
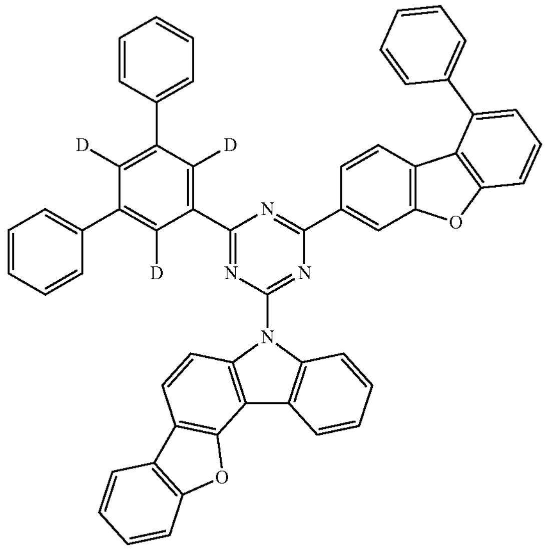
[F-66]
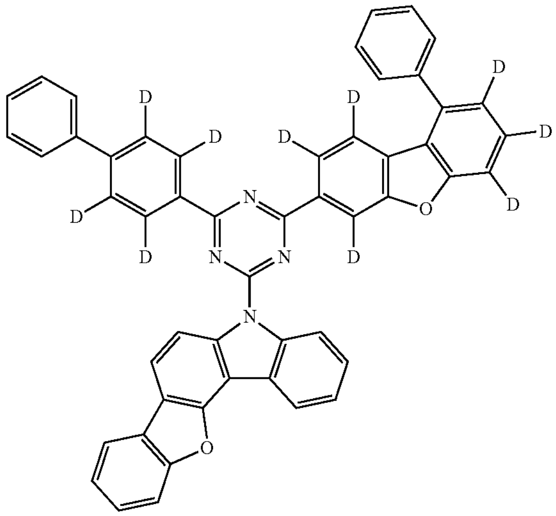

-continued
[F-67]
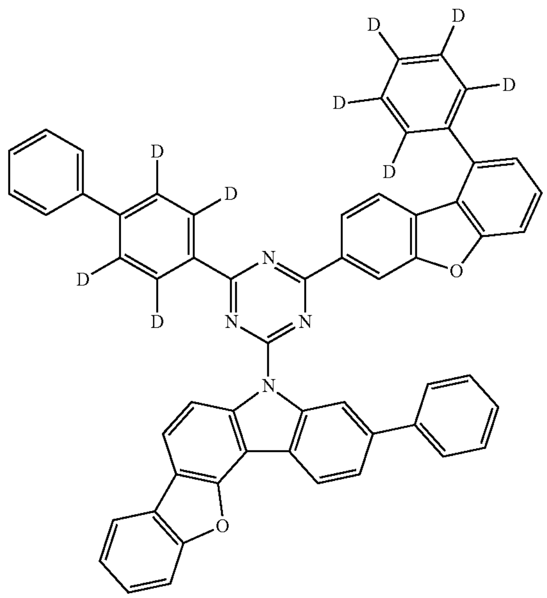
[F-68]
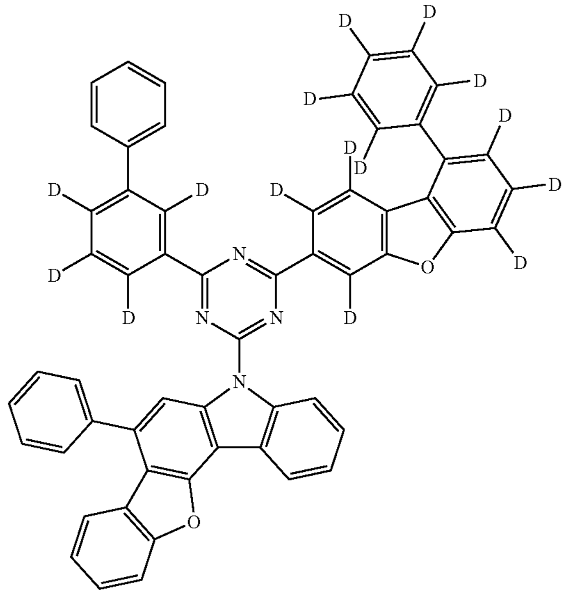
-continued
[F-69]
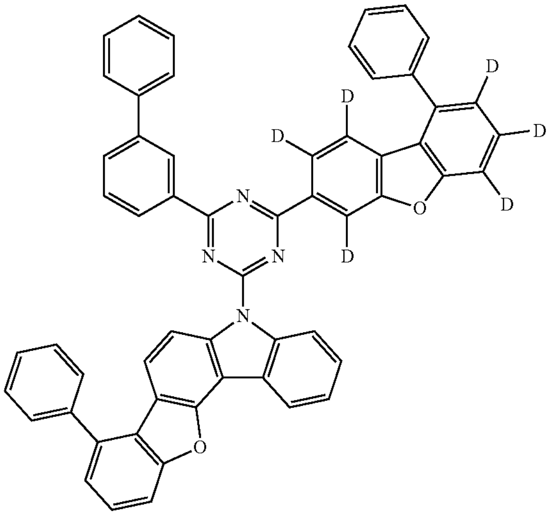
[F-70]
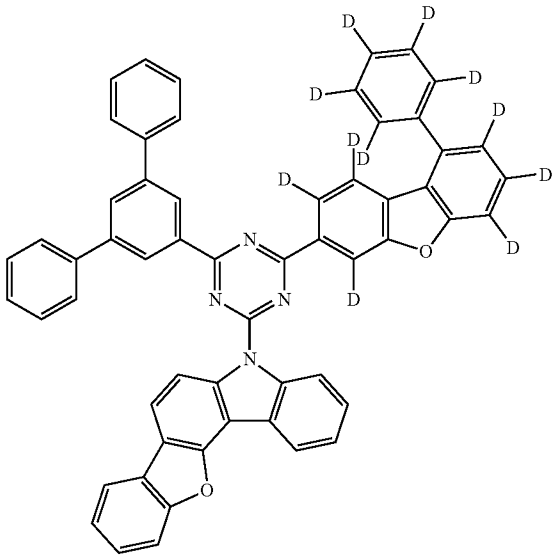

-continued
[F-71]
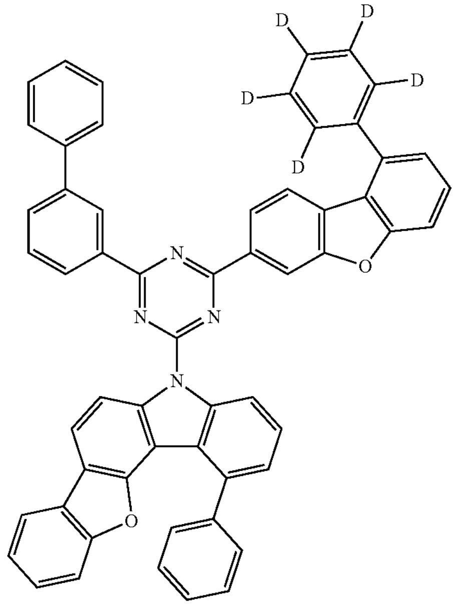
[F-72]
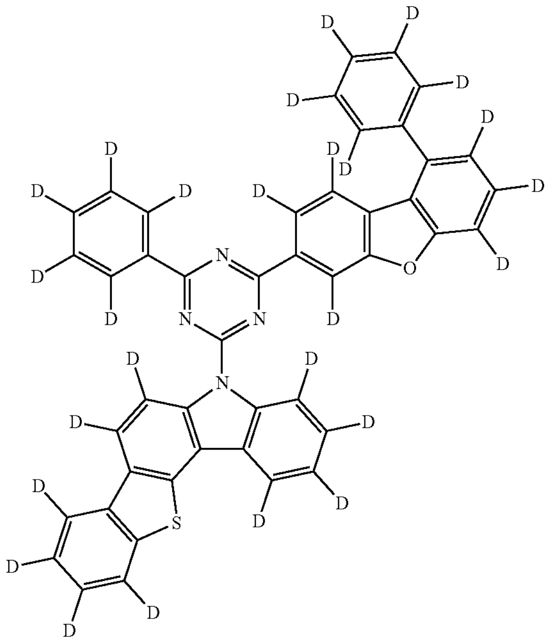
-continued
[F-73]
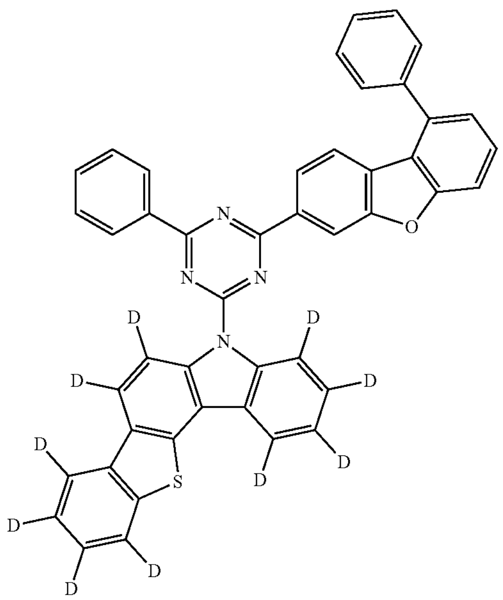
[F-74]
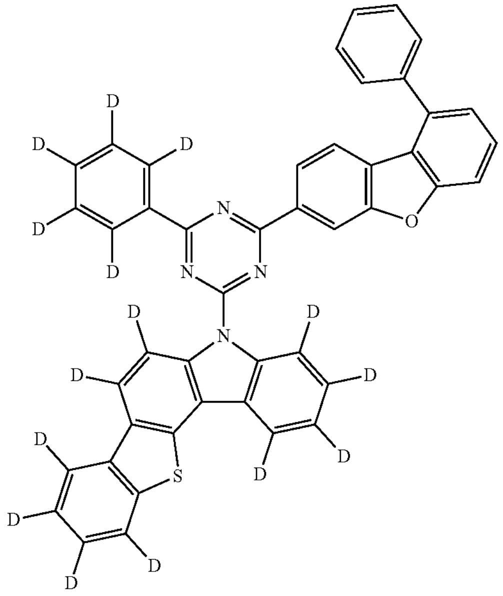

-continued
[F-75]
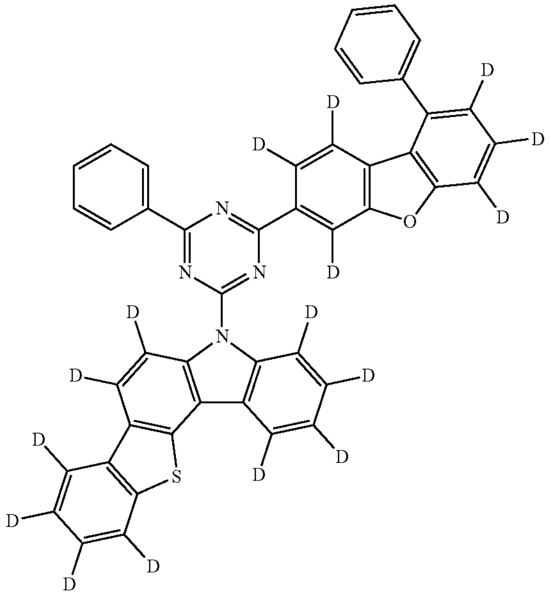
[F-76]
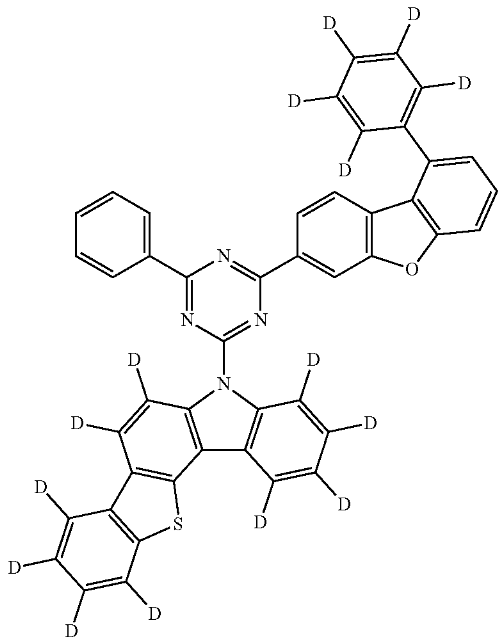
-continued
[F-77]
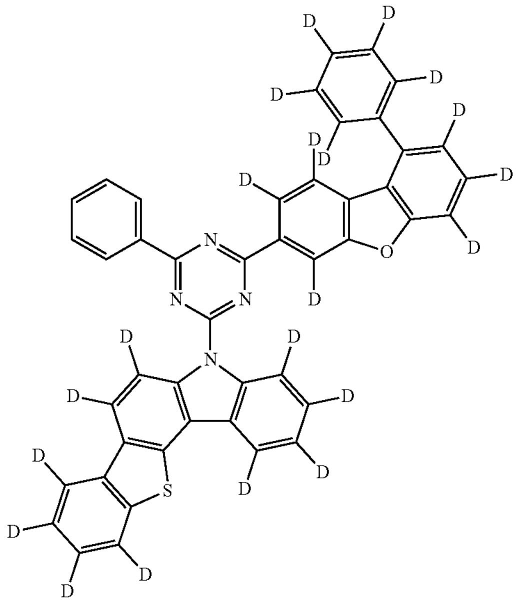
[F-78]
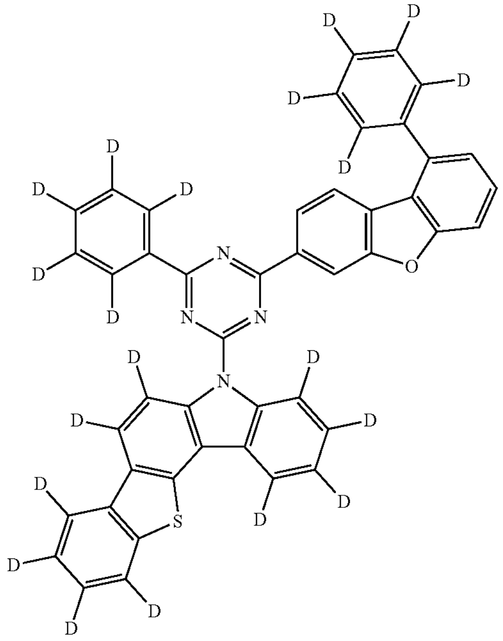

-continued
[F-79]
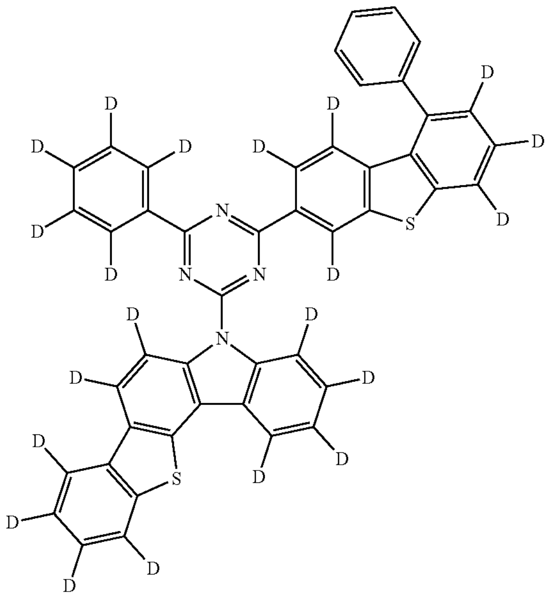
[F-80]
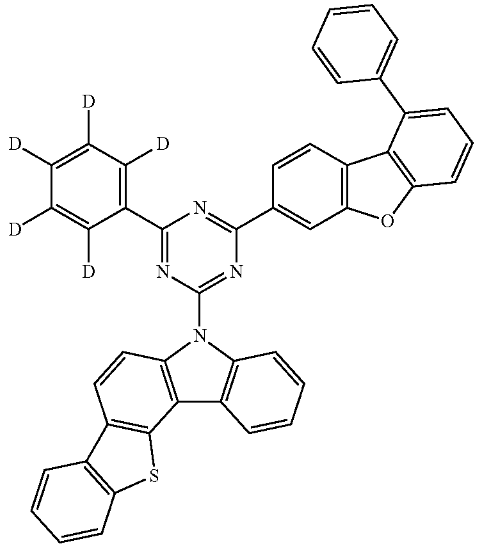
-continued
[F-81]
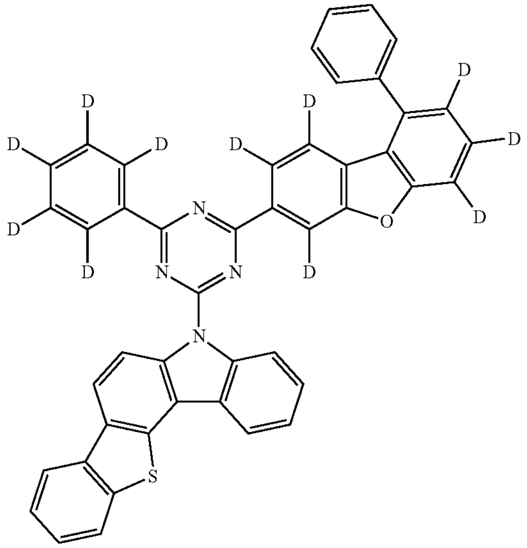
[F-82]
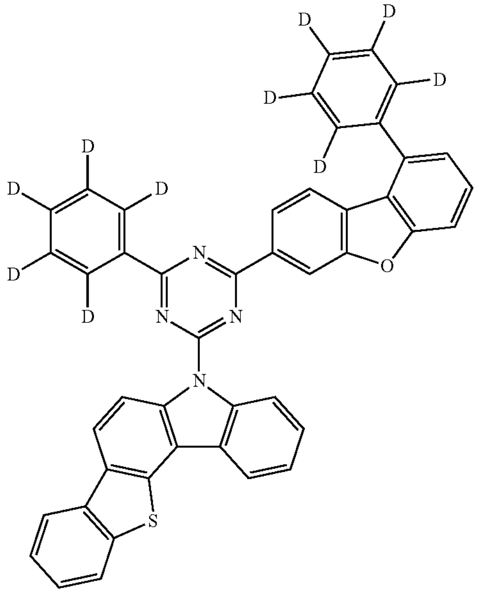

-continued
[F-83]
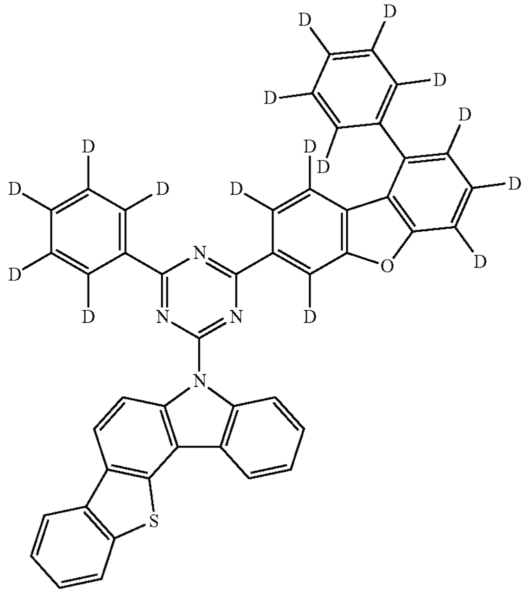
[F-84]
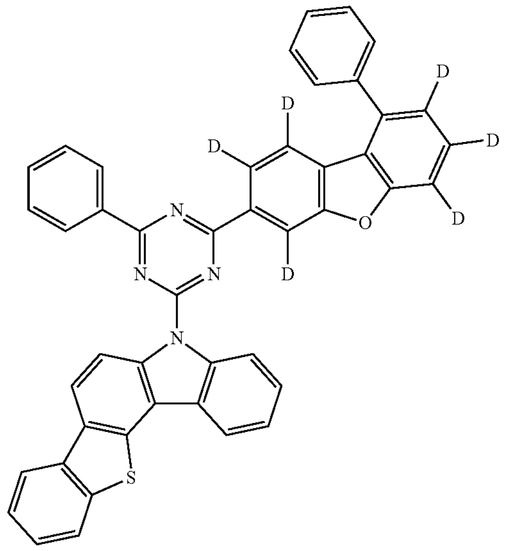
-continued
[F-85]
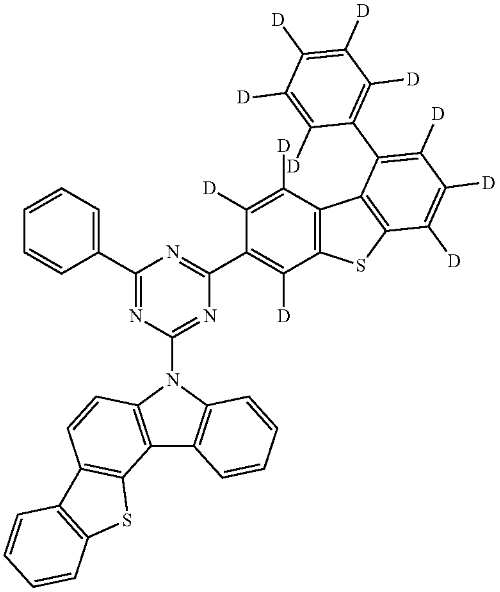
[F-86]
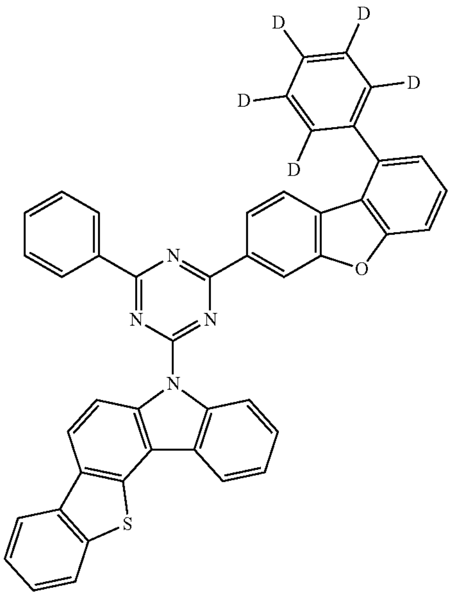

-continued
[F-87]
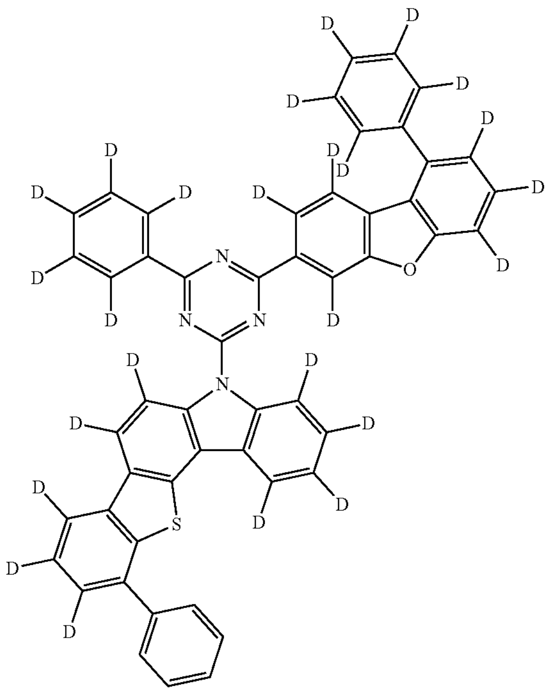
-continued
[F-89]
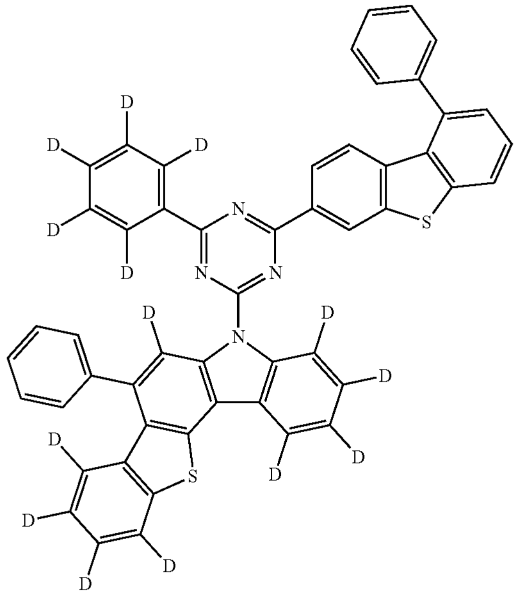
[F-88]
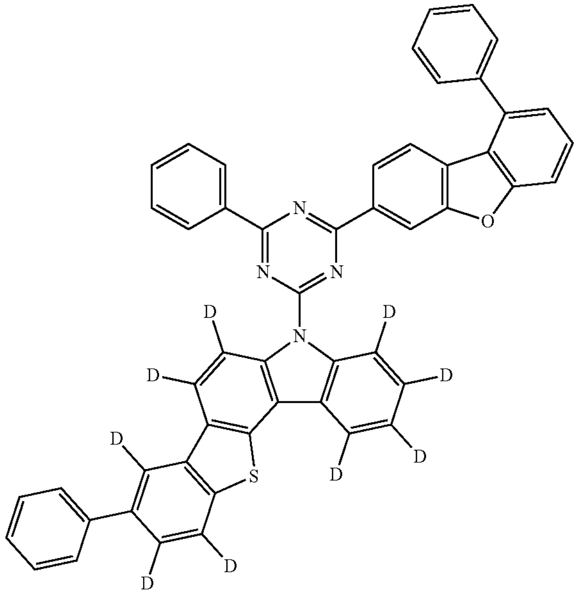
[F-90]
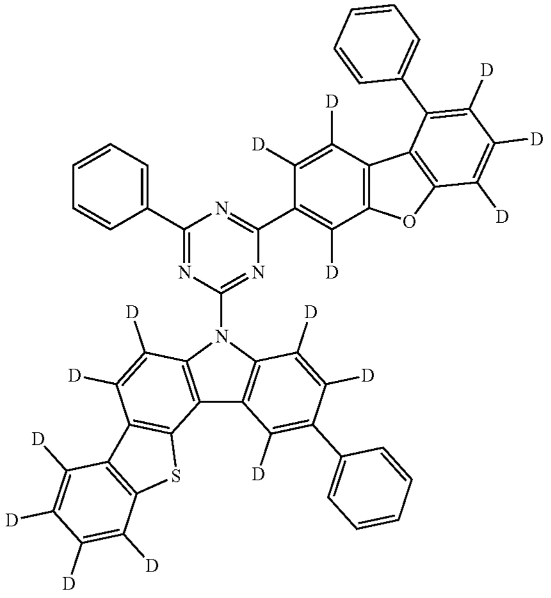

[F-91]
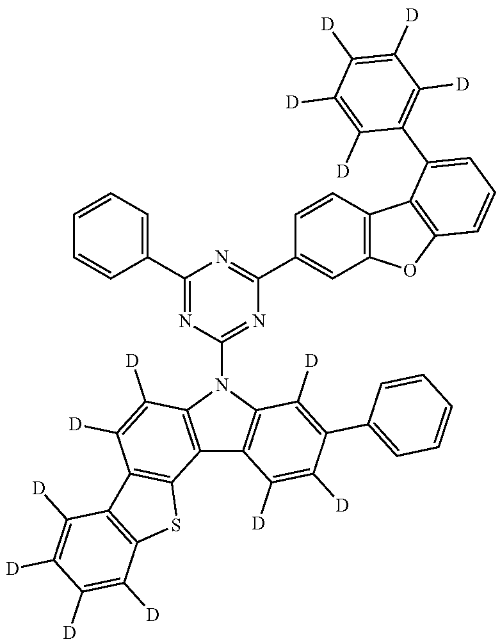
[F-93]
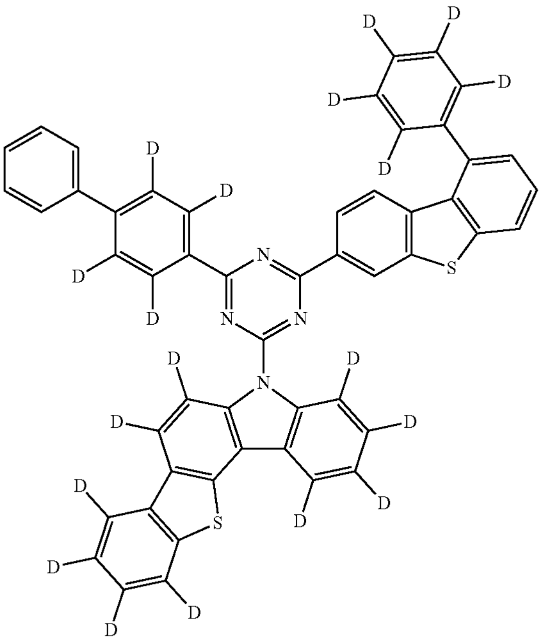
[F-92]
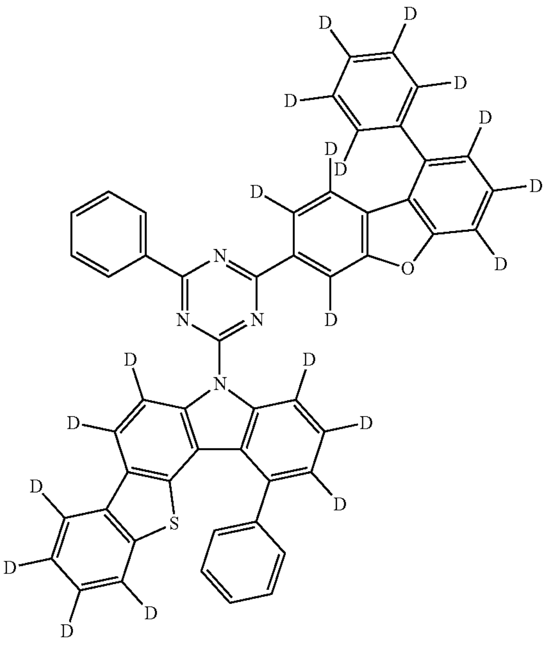
[F-94]
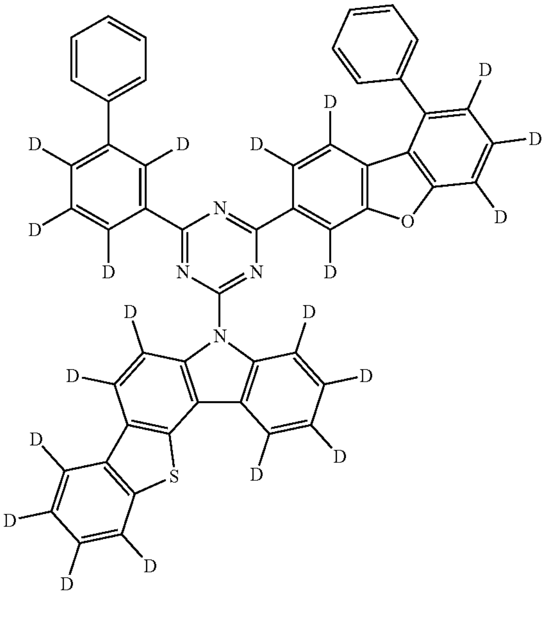

-continued
[F-95]
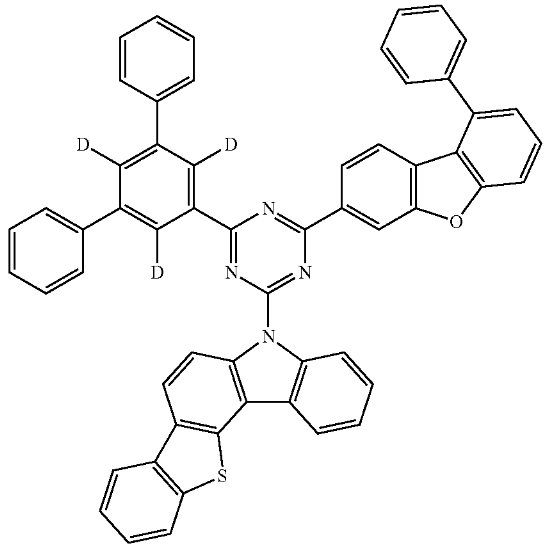
[F-96]
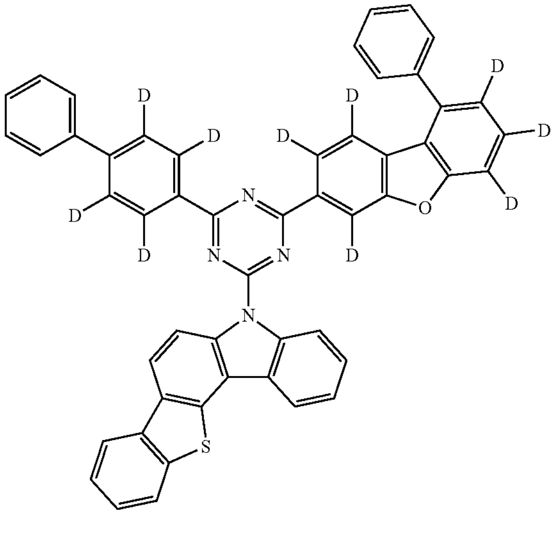
[F-97]
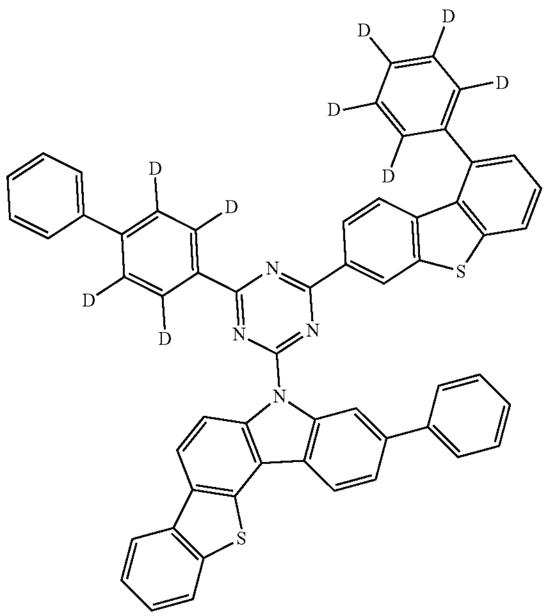
[F-98]
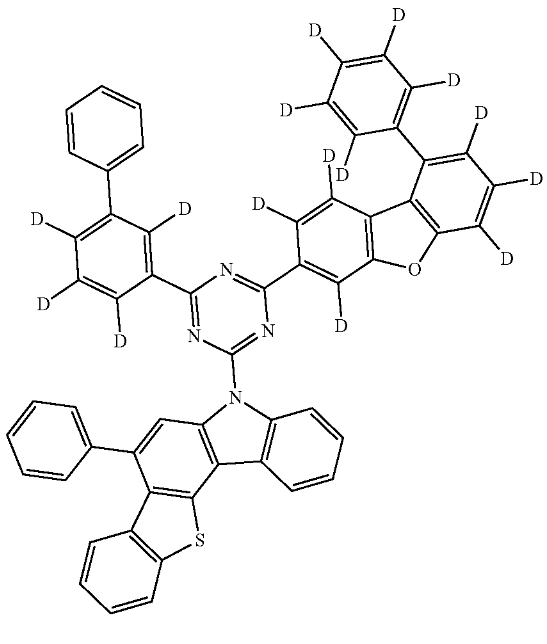

-continued

[F-99]

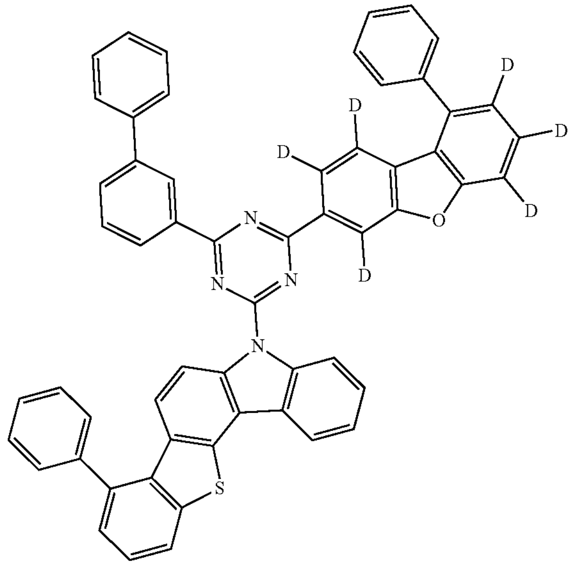

[F-100]

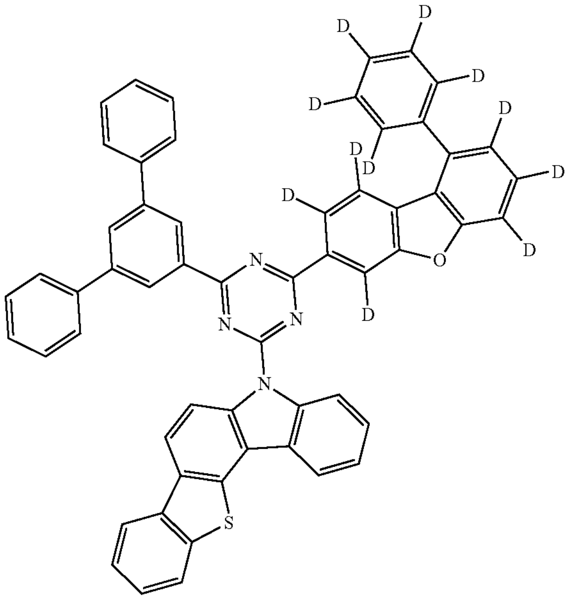

-continued

[F-101]

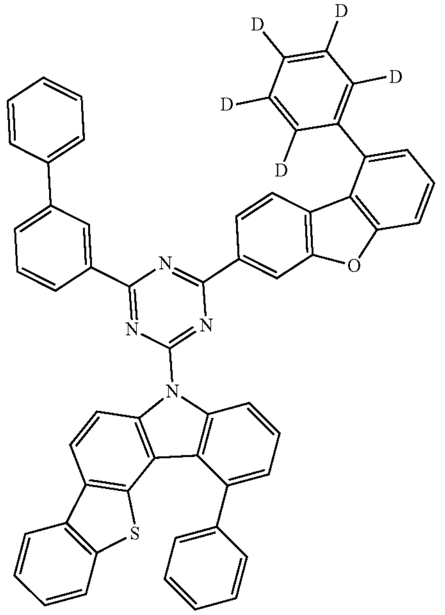

The composition for the organic optoelectronic element according to another embodiment includes the aforementioned compound (hereinafter referred to as "a first compound") and a second compound for an organic optoelectronic element represented by Chemical Formula 4.

[Chemical Formula 4]

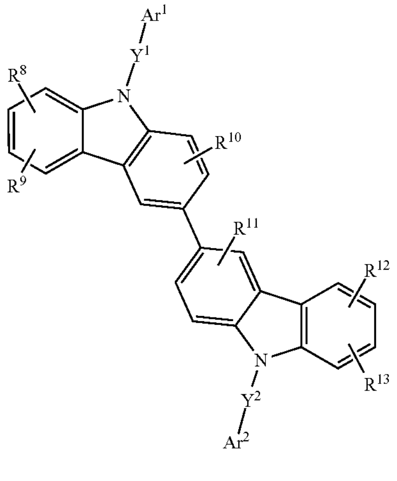

In Chemical Formula 4, $Y^1$ and $Y^2$ are each independently a single bond or a substituted or unsubstituted C6 to C20 arylene group, $Ar^1$ and $Ar^2$ are each independently a substituted or unsubstituted C6 to C20 aryl group, or a substituted or unsubstituted C2 to C30 heterocyclic group, and $R^8$ to $R^{13}$ are each independently hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof.

The second compound for the organic optoelectronic element that is a material having fast and stable hole transport characteristics may be used in the light emitting layer together with the first compound for an organic optoelectronic element having fast and stable electron transport characteristics to balance charges, and thereby it may have a high glass transition temperature relative to its molecular weight, realizing low driving and long life-span characteristics.

In an example embodiment of the present invention, in Chemical Formula 4, $Ar^1$ and $Ar^2$ may each independently be a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted triphenylenyl group, a substituted or unsubstituted carbazolyl group, a substituted or unsubstituted dibenzothiophenyl group, a substituted or unsubstituted dibenzofuranyl group, a substituted or unsubstituted fluorenyl group, or a substituted or unsubstituted pyridinyl group, $Y^1$ and $Y^2$ may each independently be a single bond, a substituted or unsubstituted phenylene group, or a substituted or unsubstituted biphenylene group, and $R^8$ to $R^{13}$ may each independently be hydrogen, deuterium, or a substituted or unsubstituted C6 to C12 aryl group.

In Chemical Formula 4, "substituted" refers to replacement of at least one hydrogen by deuterium, a C1 to C4 alkyl group, a C6 to C18 aryl group, or a C2 to C30 heteroaryl group.

For example, $*—Y^1—Ar^1$ and $*—Y^2—Ar^2$ of Chemical Formula 4 may be one of substituents of Group II.

[Group II]

G-1

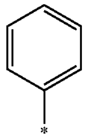

G-2

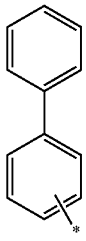

G-3

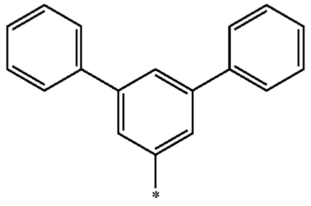

G-4

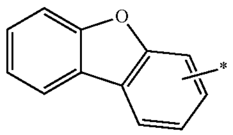

-continued

G-5

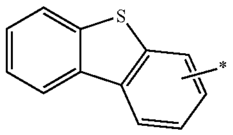

G-6

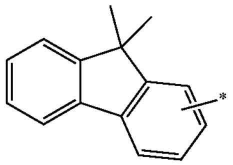

G-7

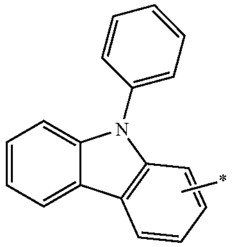

G-8

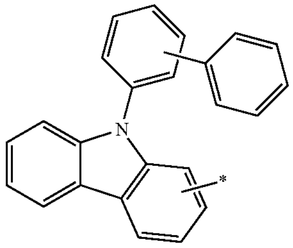

G-9

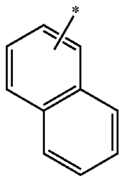

G-10

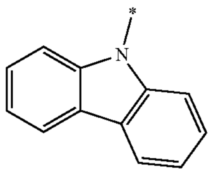

G-11

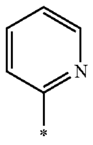

G-12

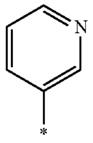

-continued
G-13
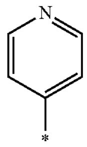
G-14
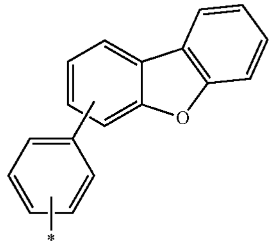
G-15
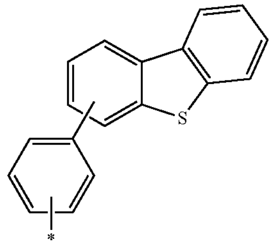
G-16
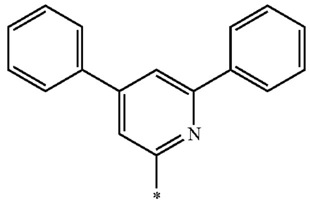
G-17
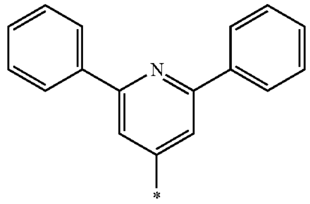
G-18
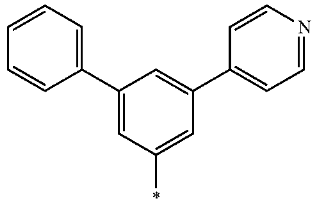
G-19
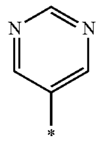
-continued
G-20
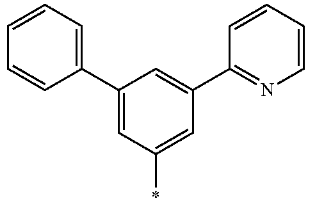
G-21
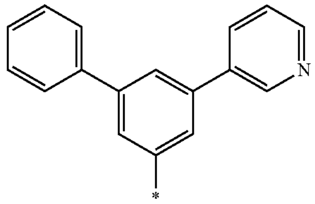
G-22
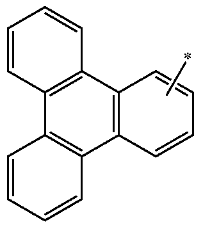
G-23
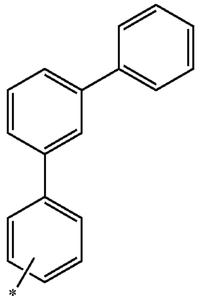
G-24
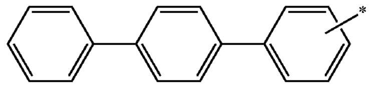
G-25
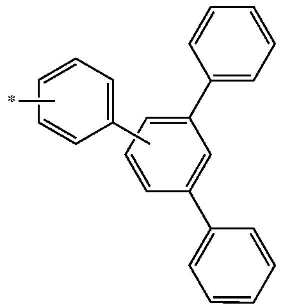
In Group II, * is a linking point.
In an embodiment of the present invention, *—$Y^1$—$Ar^1$ and *—$Y^2$—$Ar^2$ may be any one of G-1 to G-4 of Group II.
For example, the compound represented by Chemical Formula 4 may be one selected from the compounds of Group 2, but is not limited thereto.

[Group 2]
[I-1]
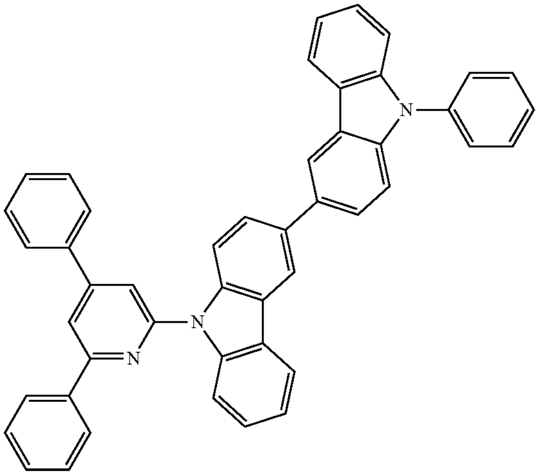
[I-2]
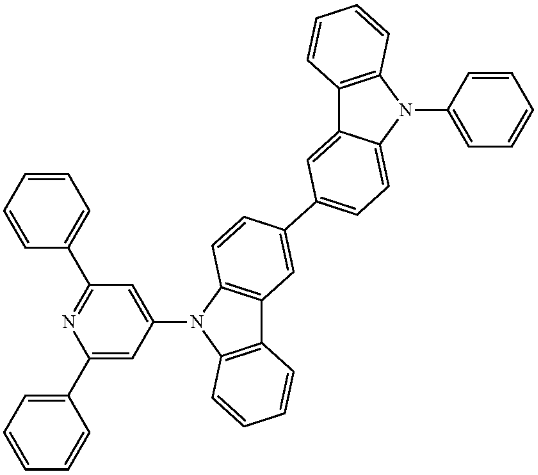
[I-3]
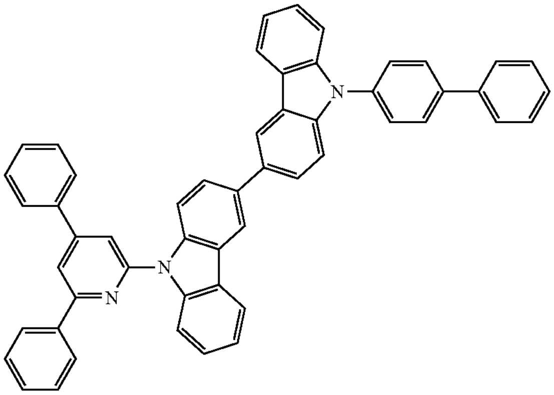
[I-4]
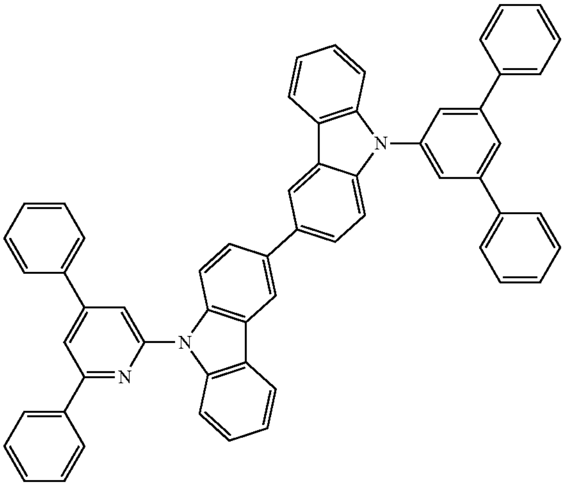
[I-5]
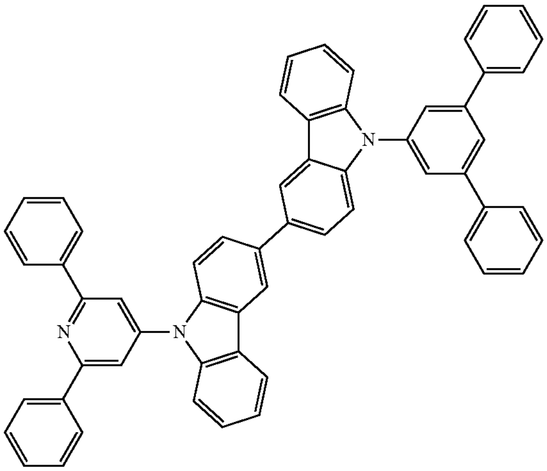
[I-6]
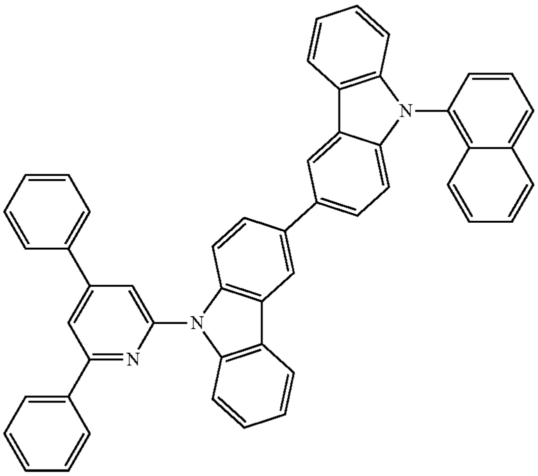

-continued
[I-7]
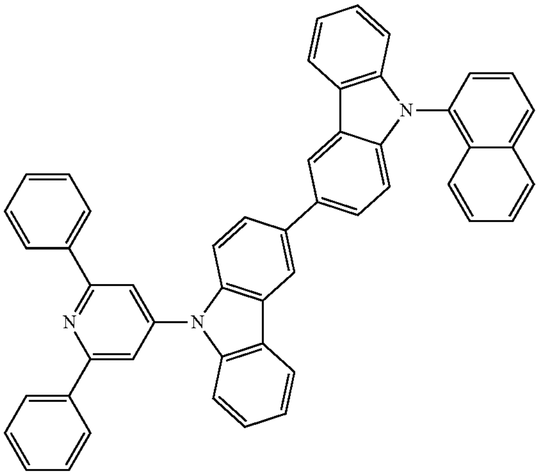
[I-8]
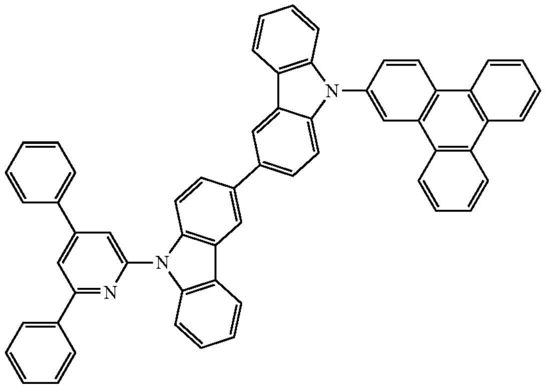
[I-9]
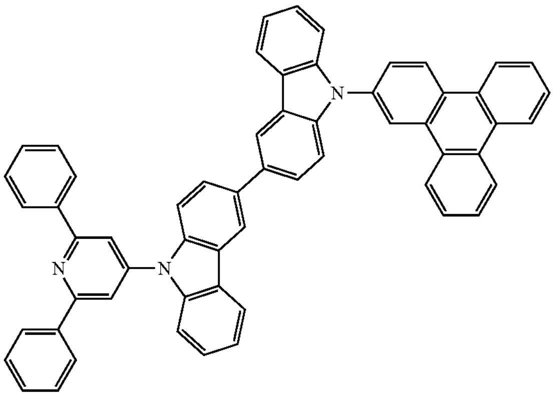
[I-10]
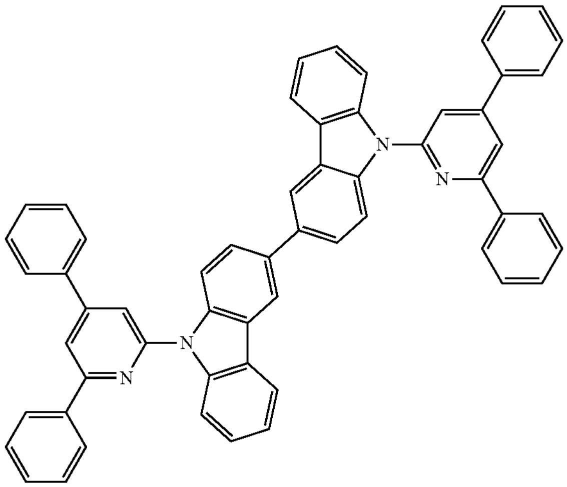
[I-11]
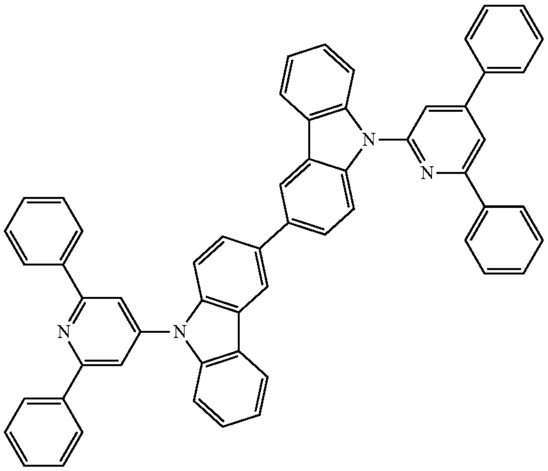
[I-12]
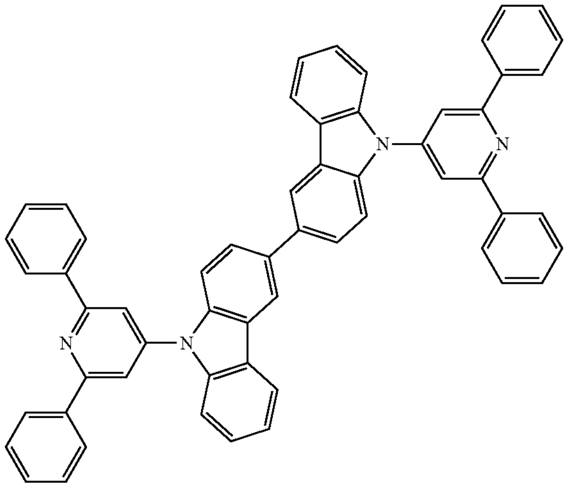

-continued
[I-13]
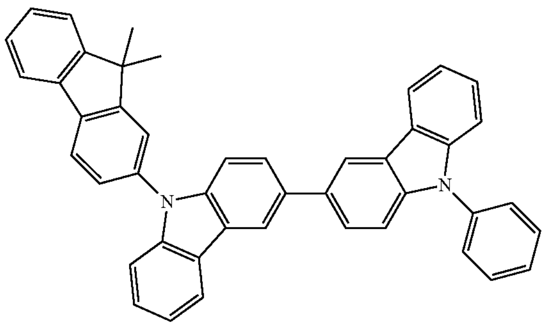
[I-14]
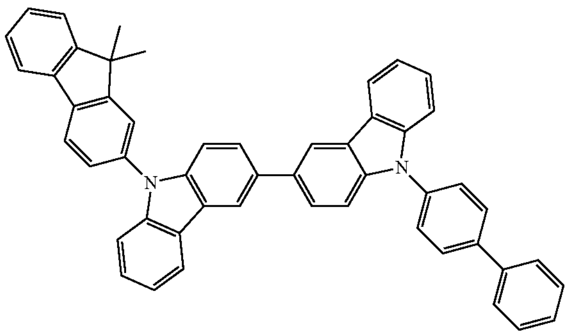
[I-15]
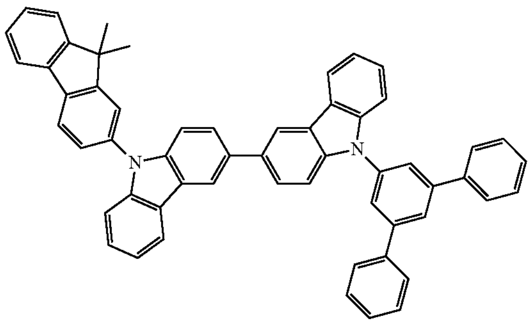
[I-16]
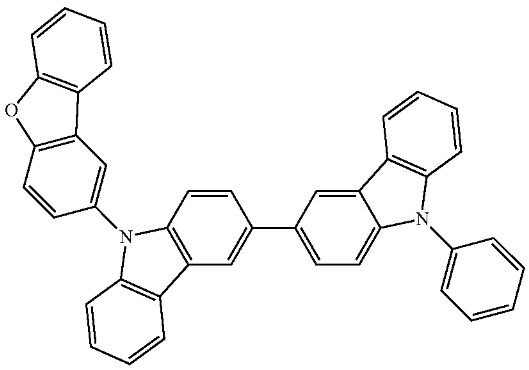
[I-17]
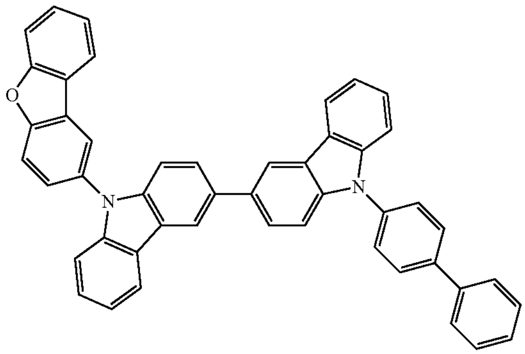
[I-18]
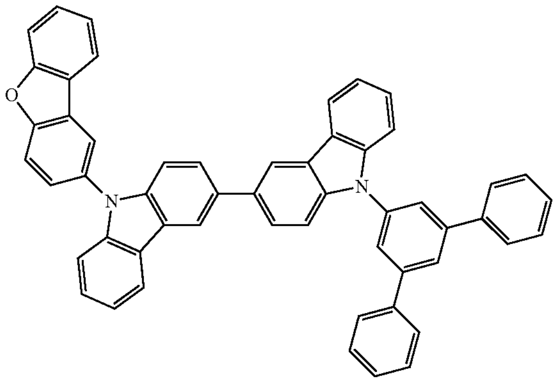
[I-19]
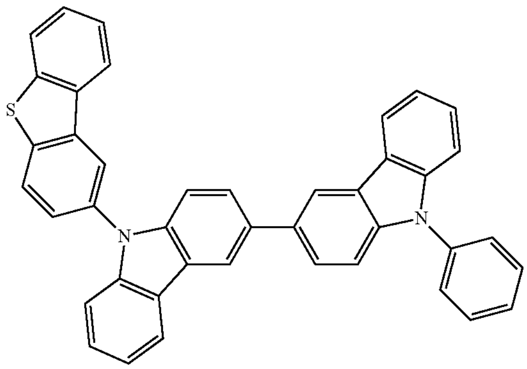
[I-20]
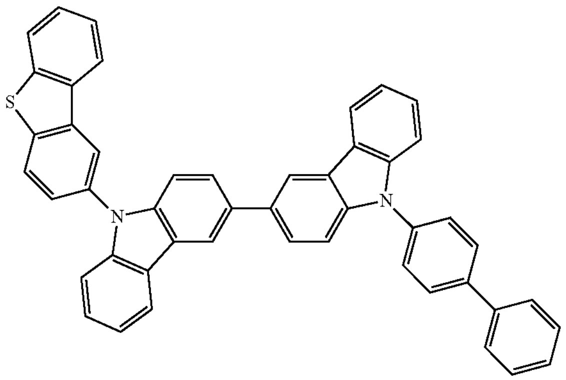

-continued
[I-21]
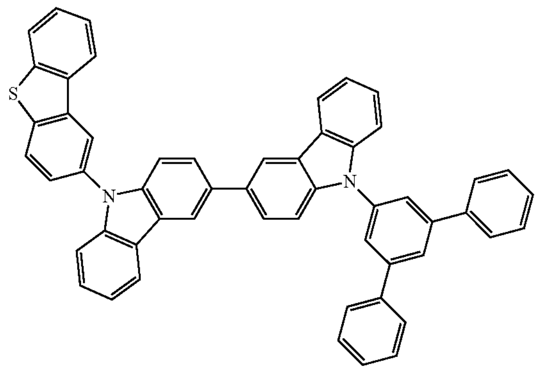
[I-22]
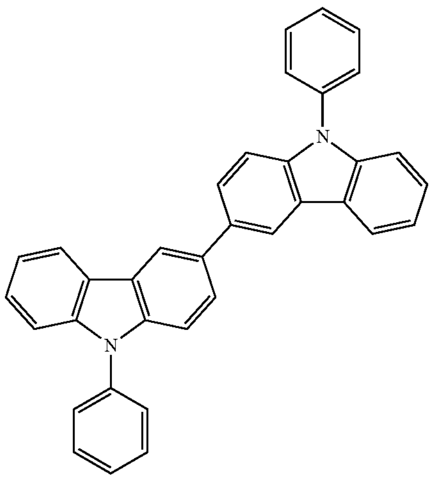
[I-23]
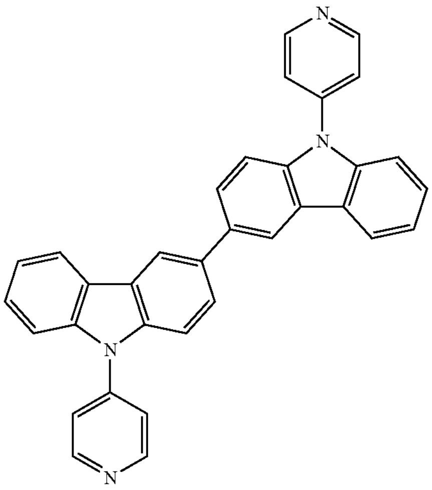
[I-24]
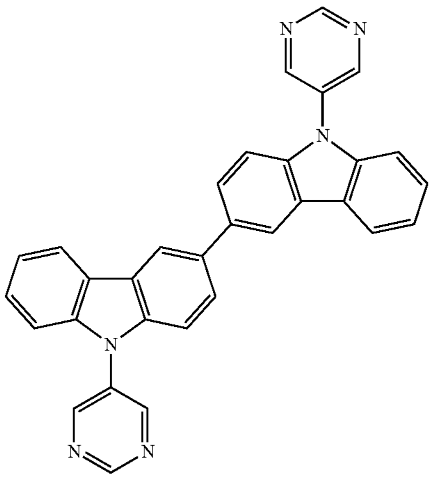
[I-25]
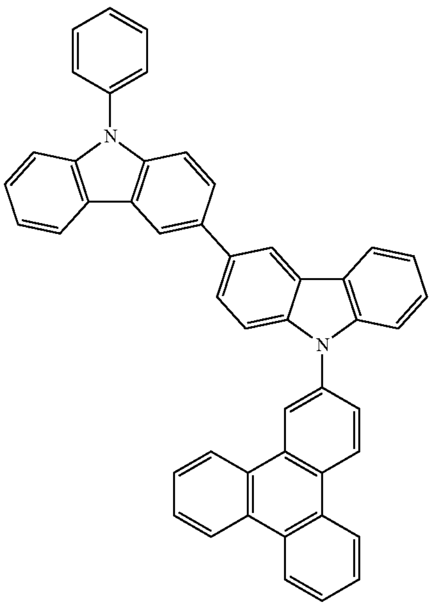
[I-26]
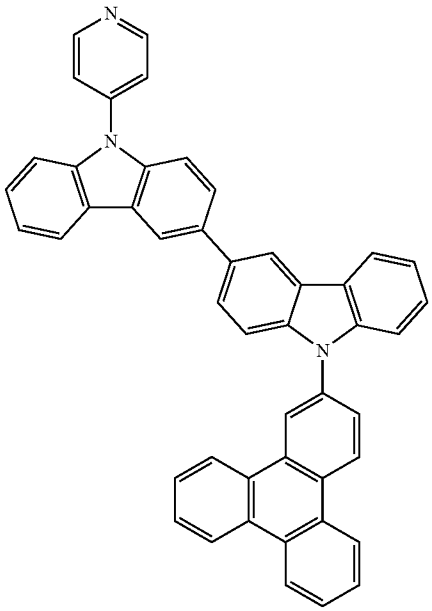

-continued
[I-27]
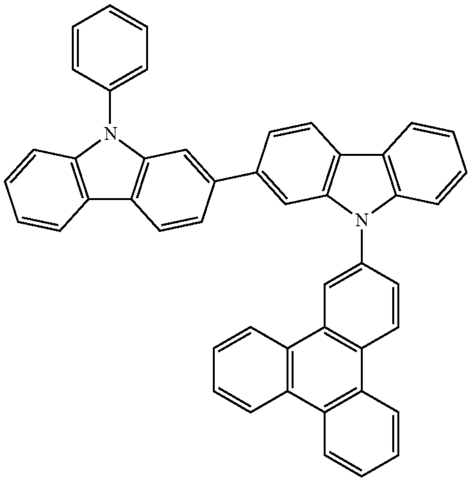
[I-28]
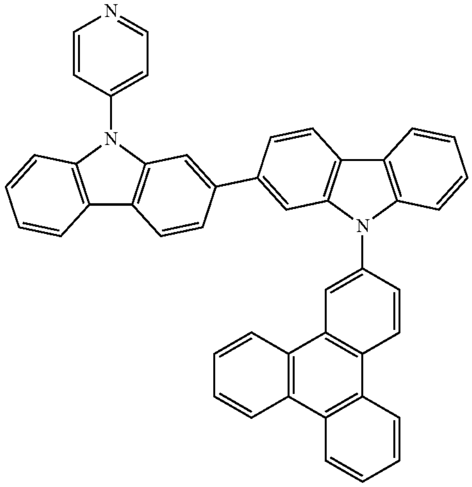
[I-29]
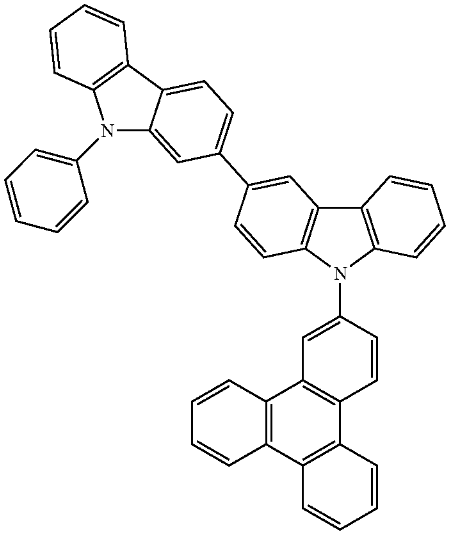
[I-30]
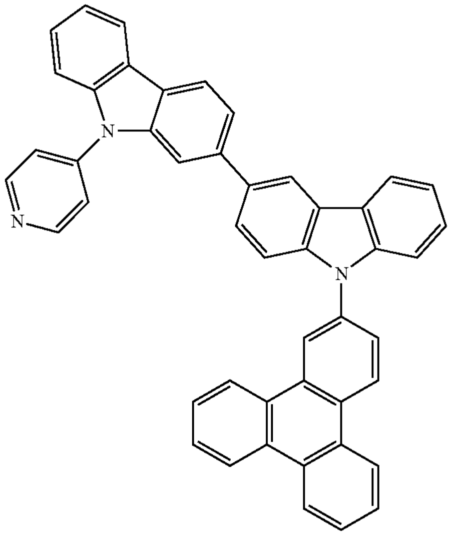
[I-31]
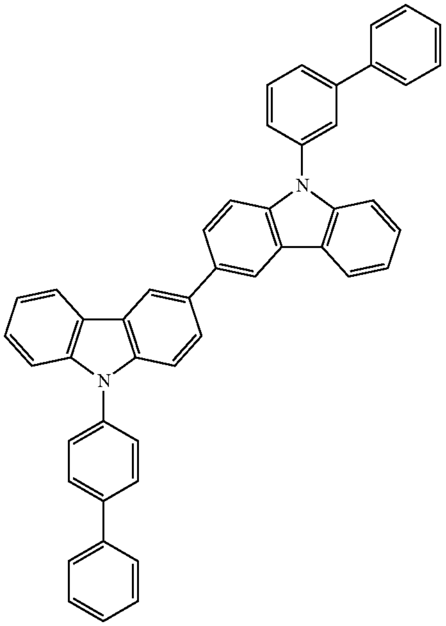
[I-32]
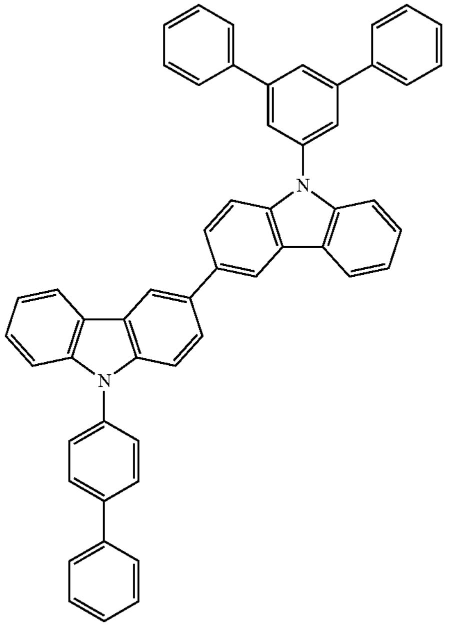

-continued
[I-33]
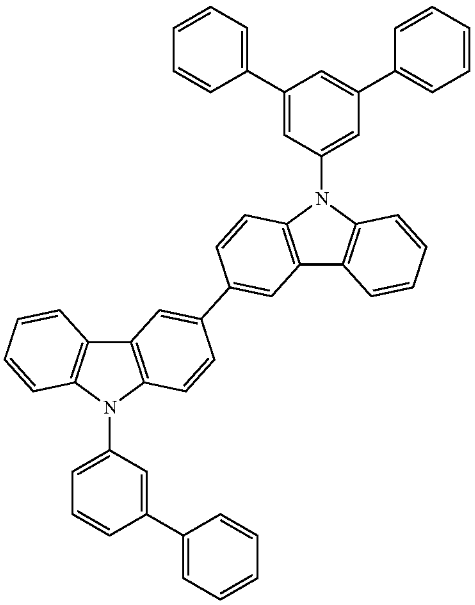
[I-34]
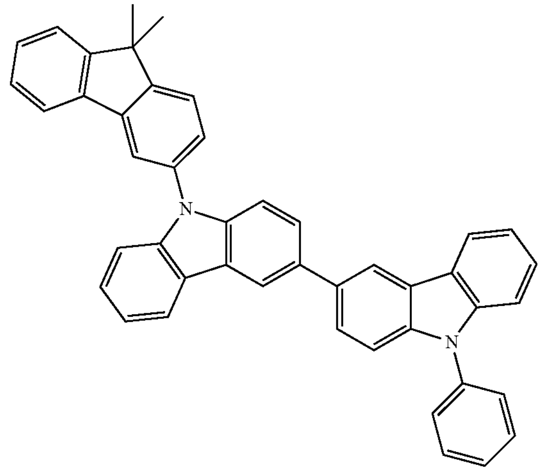
[I-35]
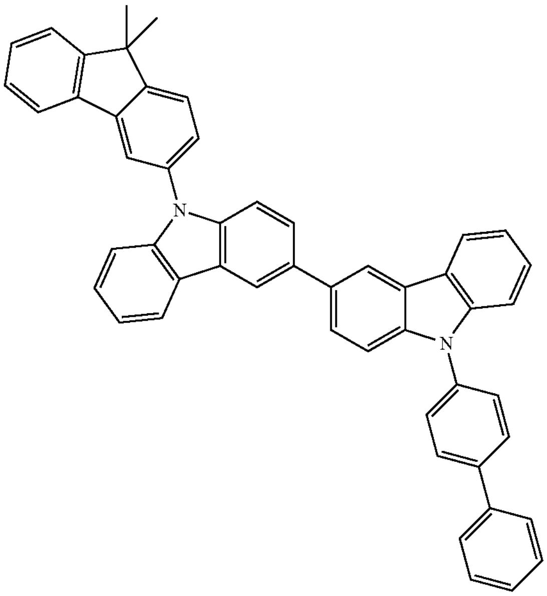
[I-36]
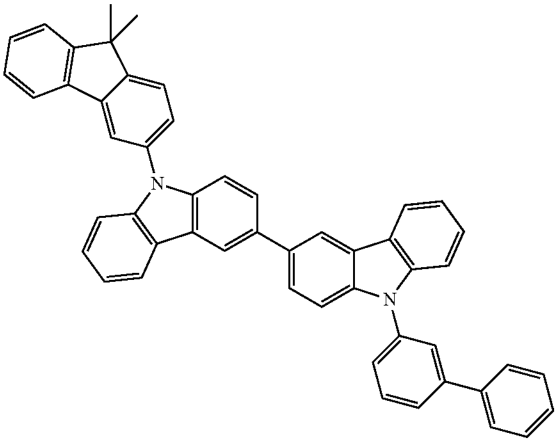

-continued
[I-37]
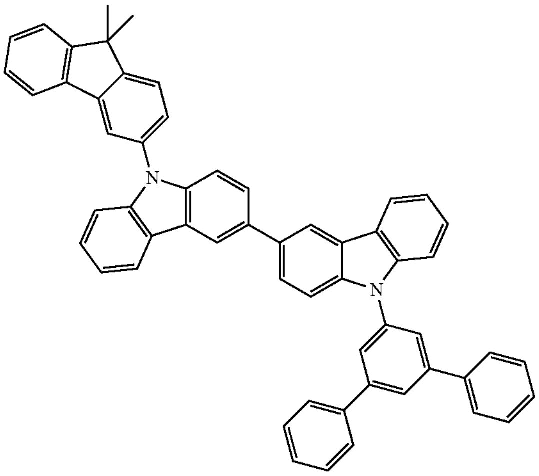
[I-38]
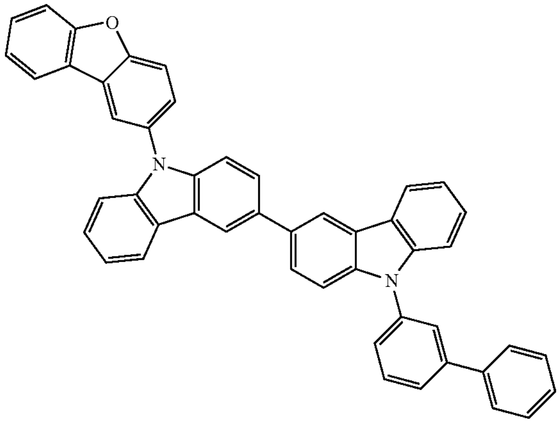
[I-39]
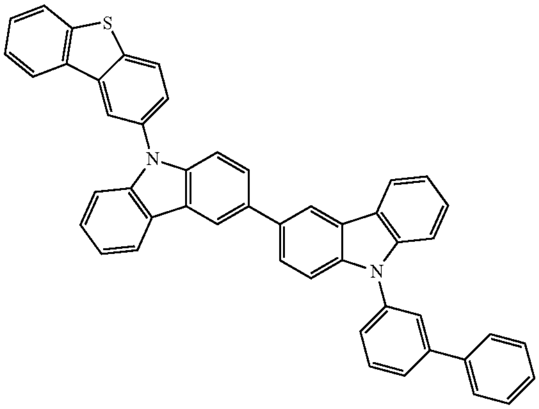
[I-40]
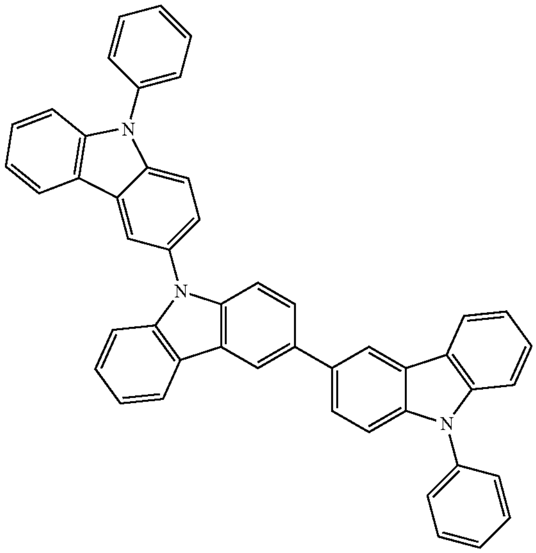
[I-41]
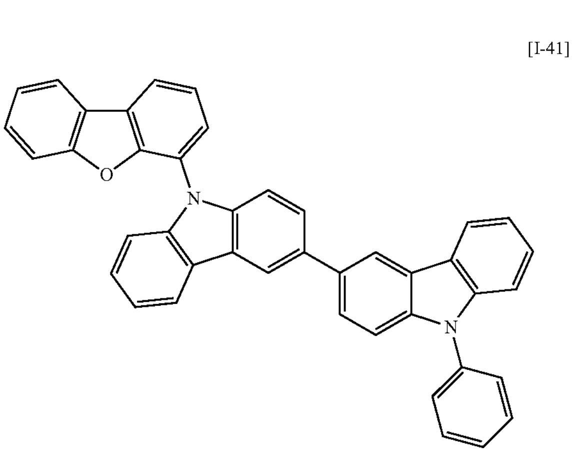
[I-42]
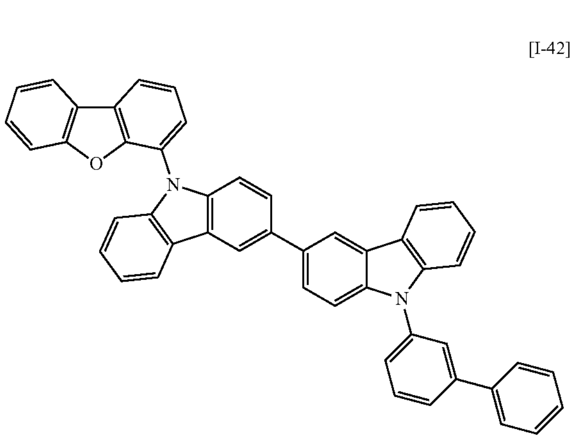

-continued
[I-43]
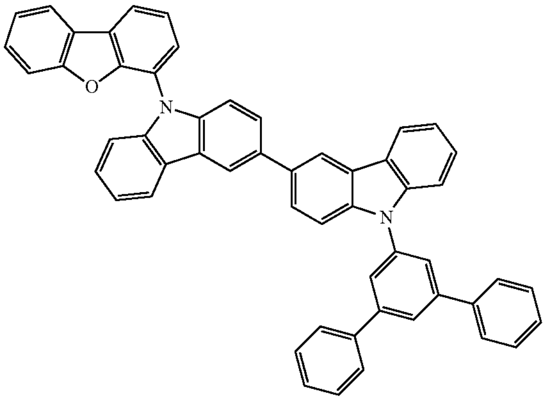
[I-44]
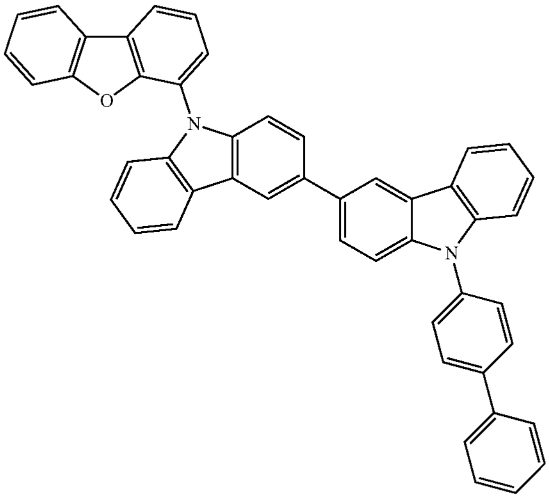
[I-45]
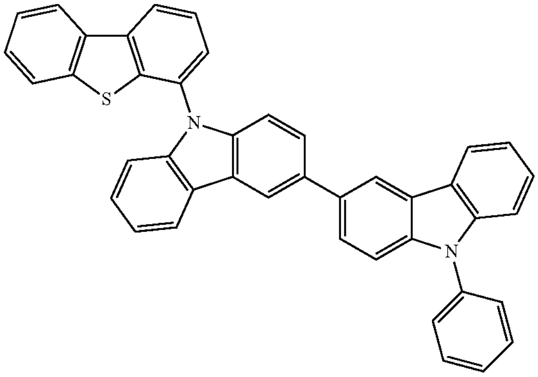
[I-46]
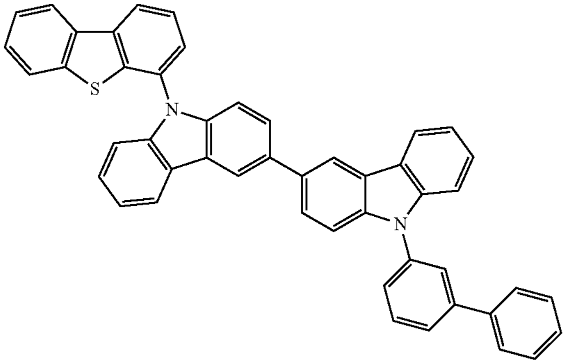
[I-47]
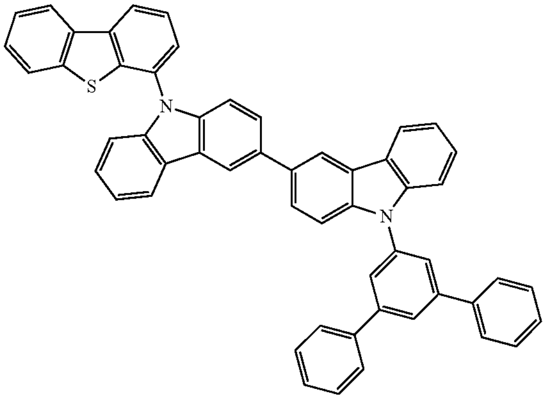
[I-48]
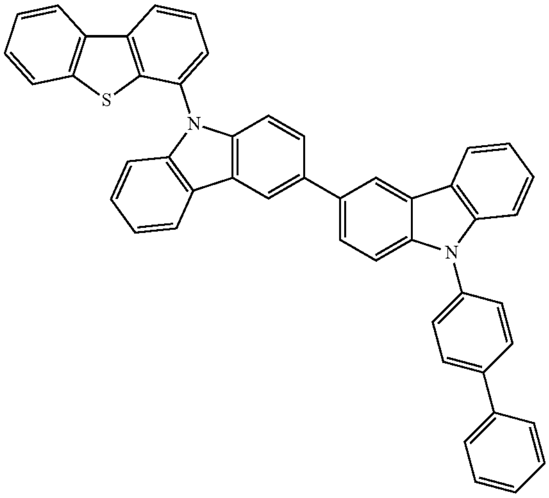

-continued
[I-49]
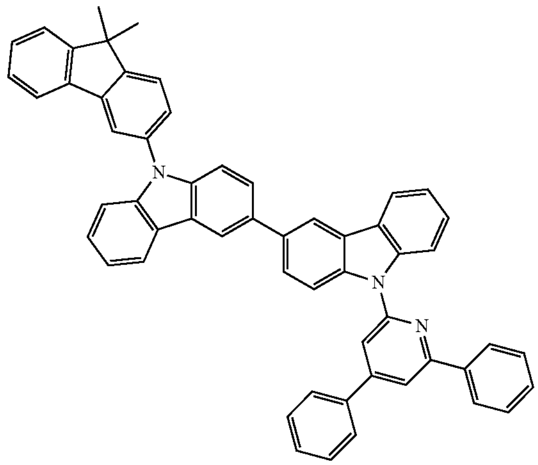
[I-50]
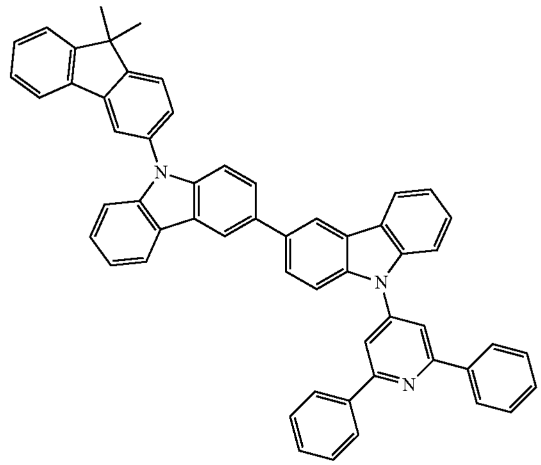
[I-51]
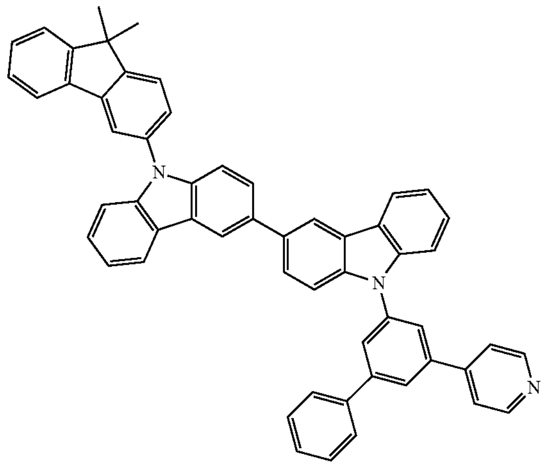
[I-52]
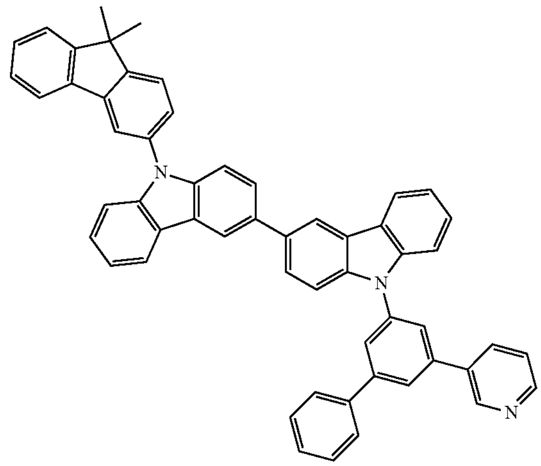
[I-53]
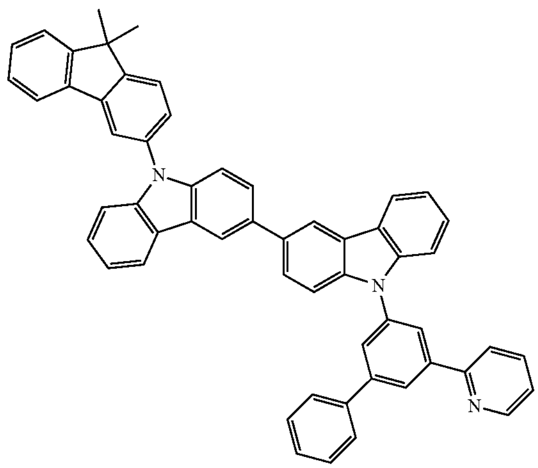
[I-54]
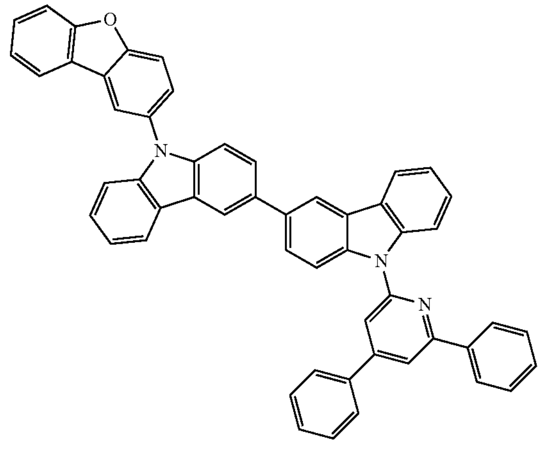

-continued
[I-55]
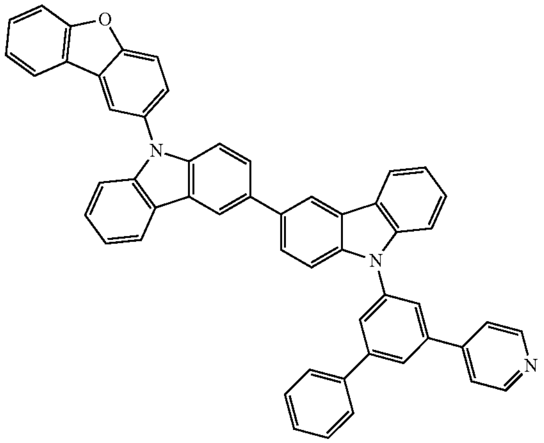
[I-56]
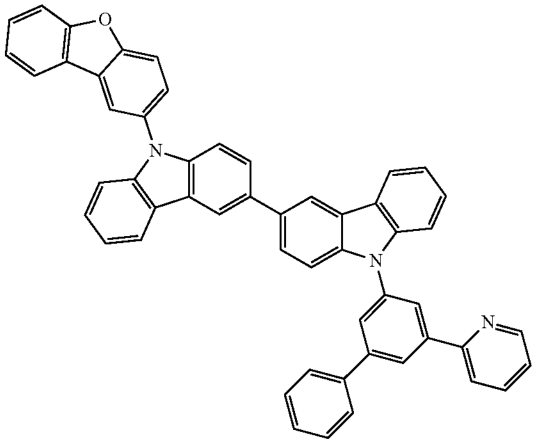
[I-57]
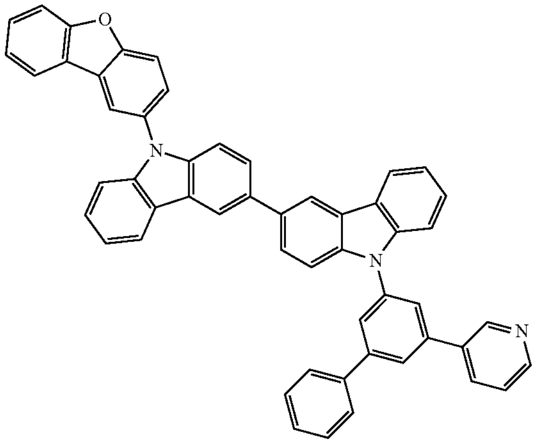
[I-58]
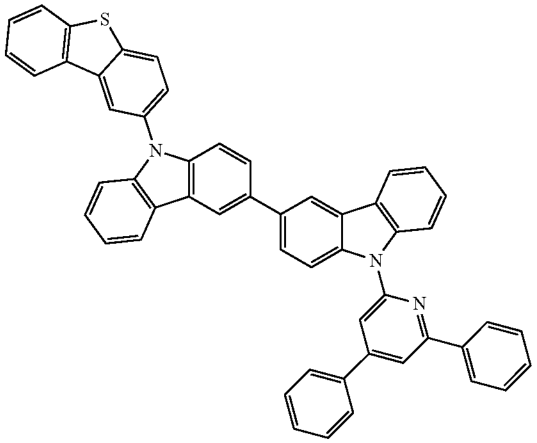
[I-59]
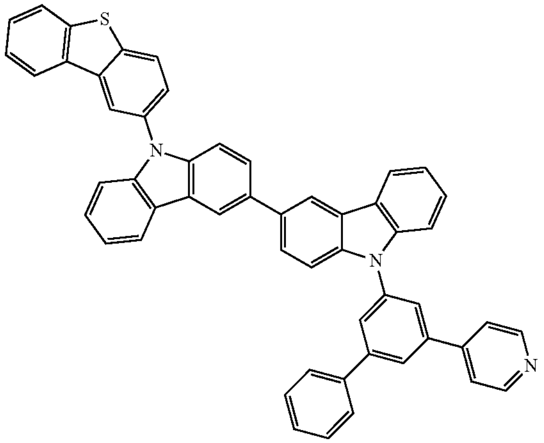
[I-60]
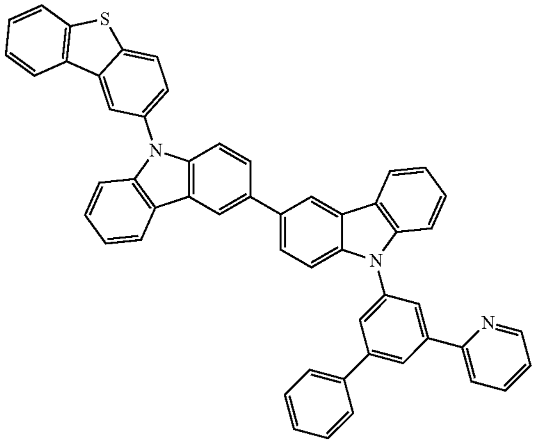

-continued
[I-61]
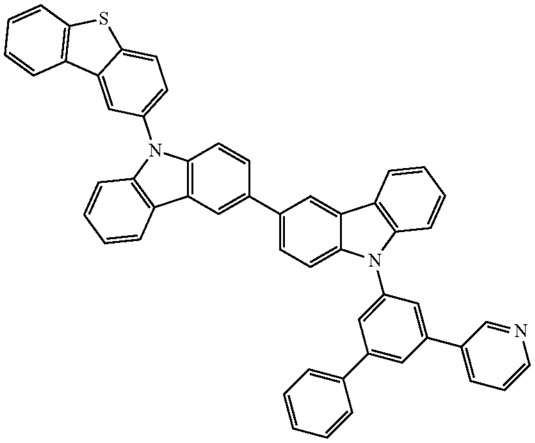
[I-62]
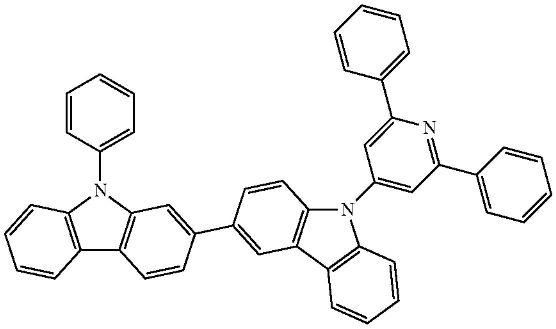
[I-63]
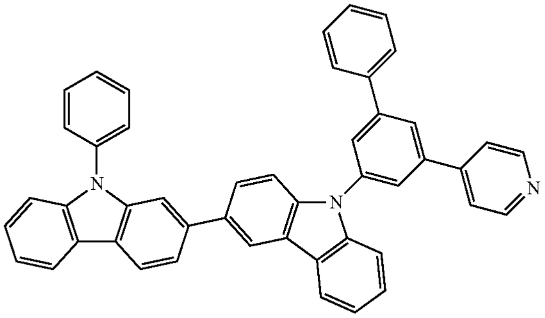
[I-64]
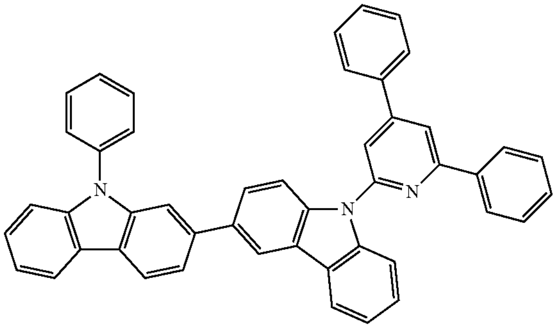
[I-65]
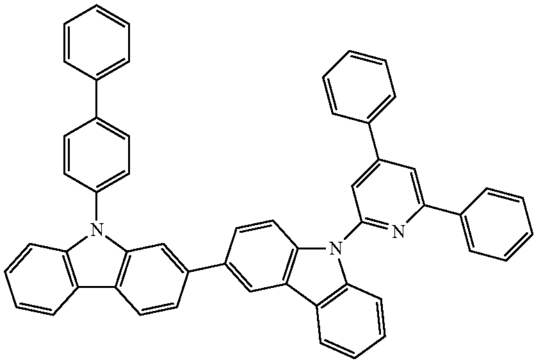
[I-66]
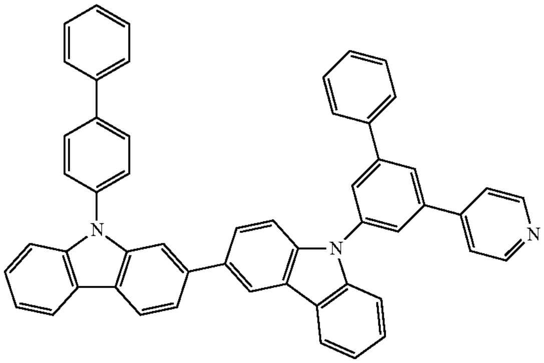
[I-67]
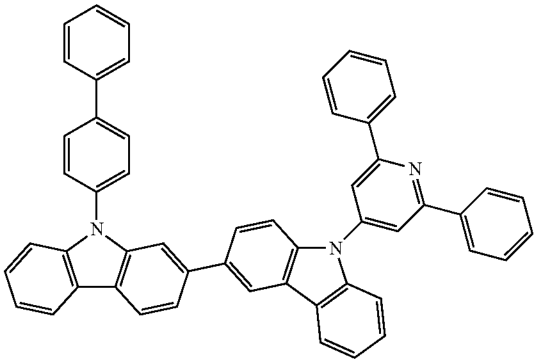
[I-68]
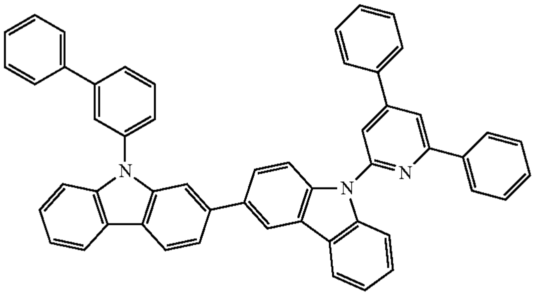

-continued
[I-69]
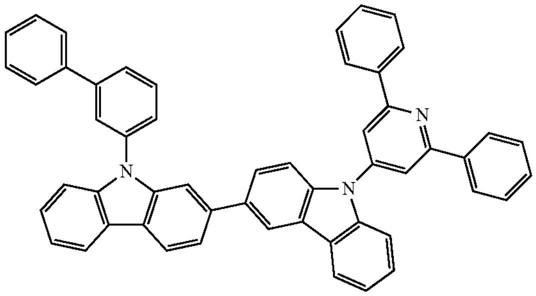
[I-70]
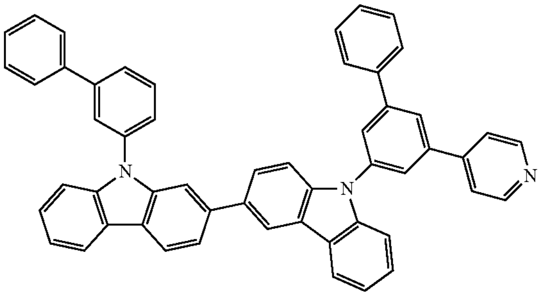
[I-71]
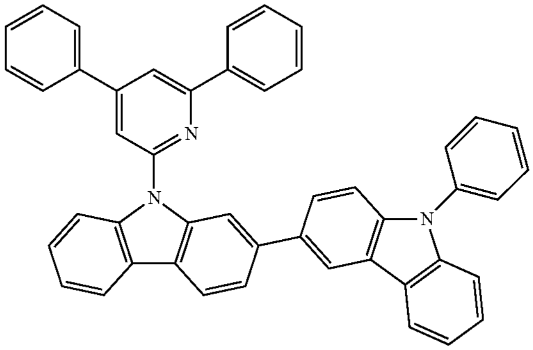
[I-72]
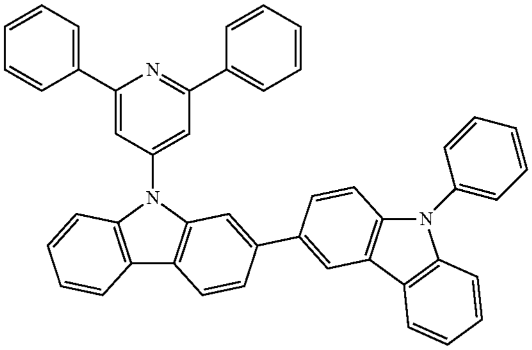
[I-73]
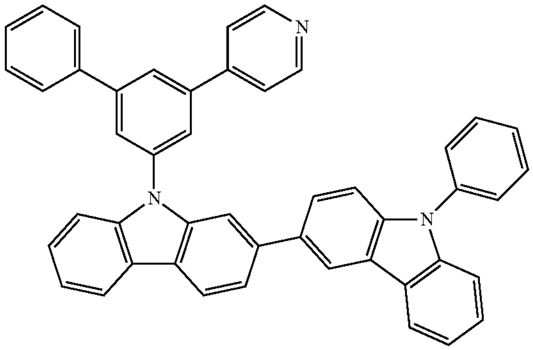
[I-74]
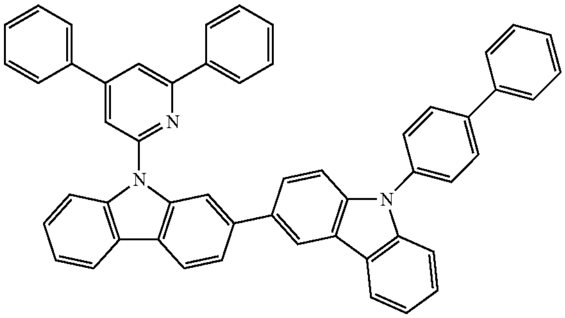
[I-75]
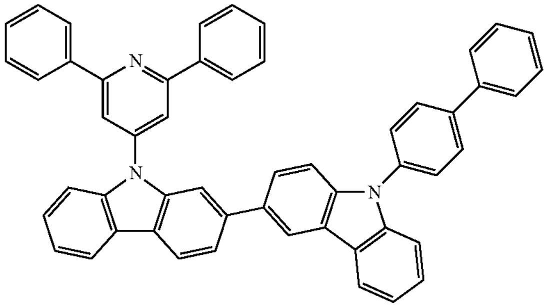
[I-76]
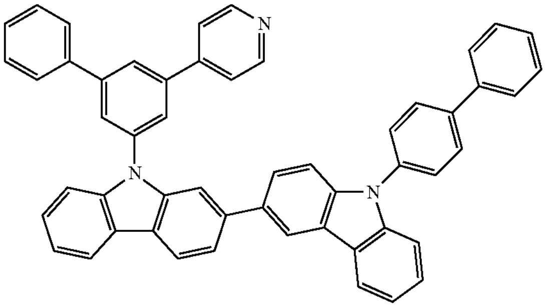

-continued
[I-77]
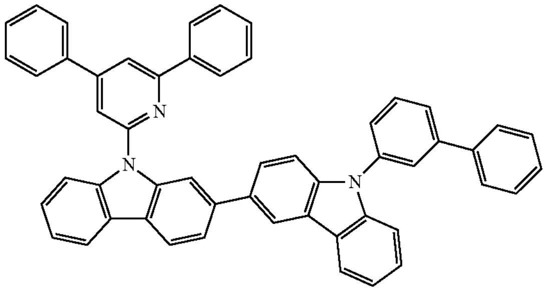
[I-78]
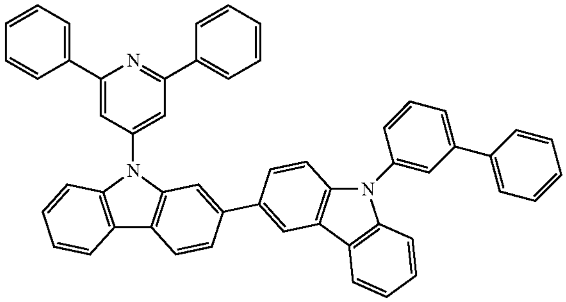
[I-79]
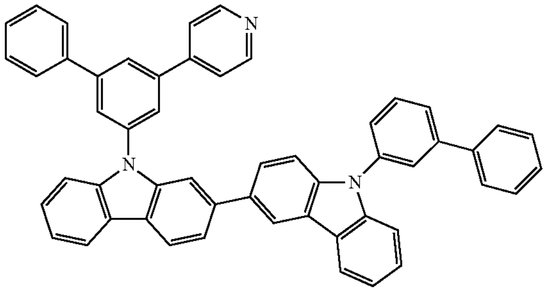
[I-80]
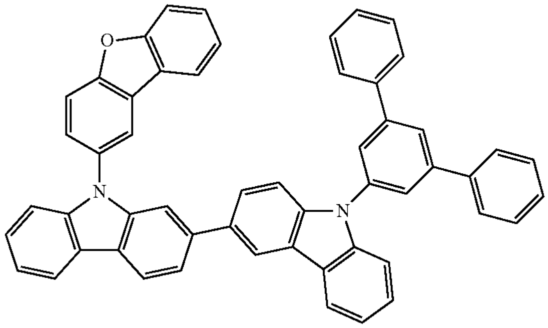
[I-81]
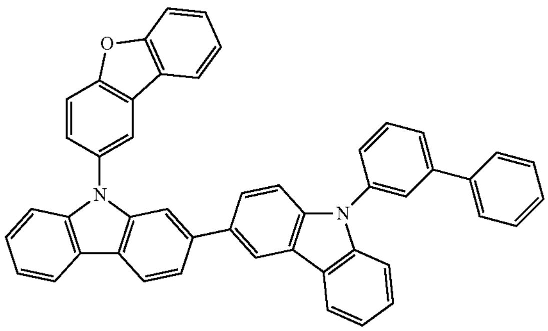
[I-82]
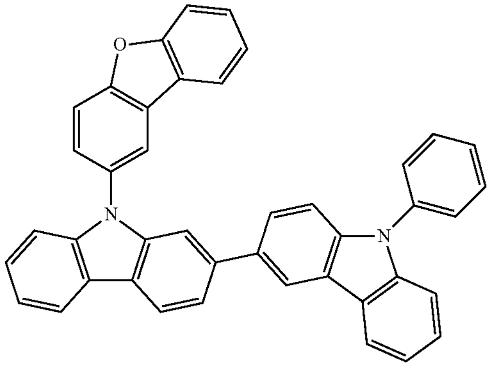
[I-83]
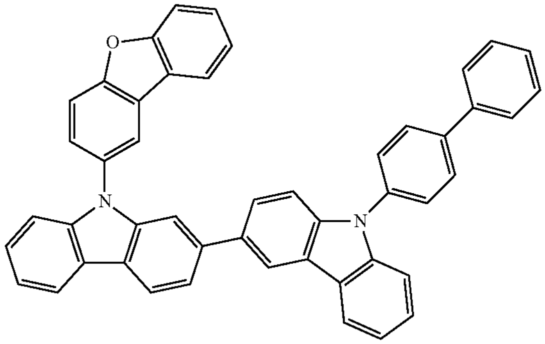
[I-84]
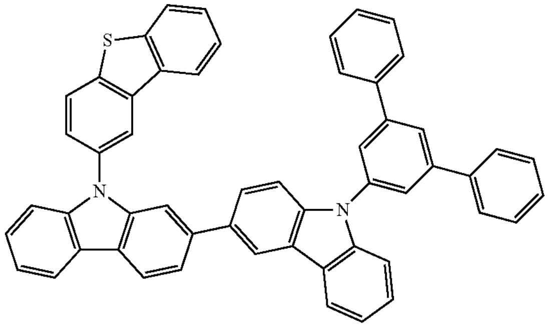

-continued
[I-85]
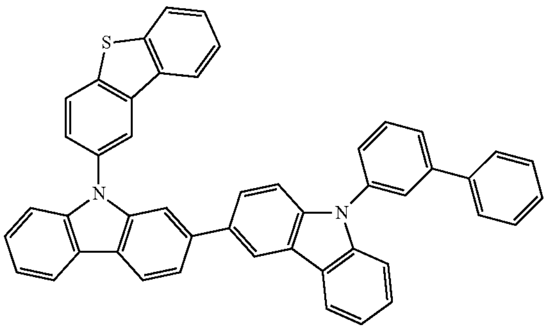
[I-86]
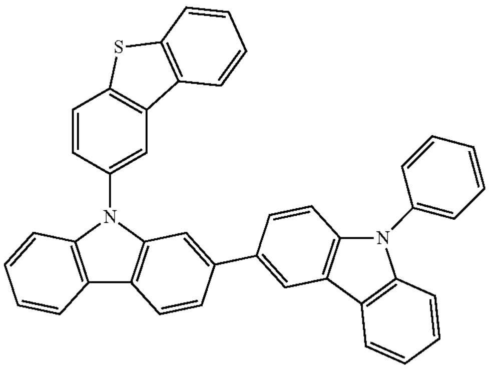
[I-87]
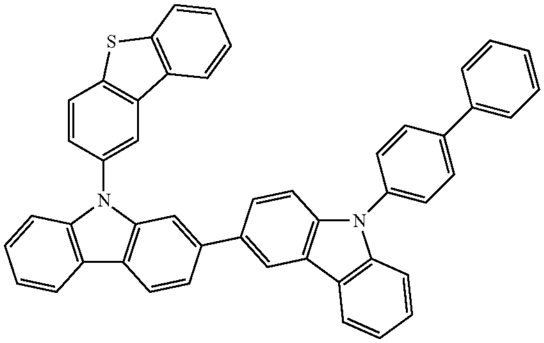
[I-88]
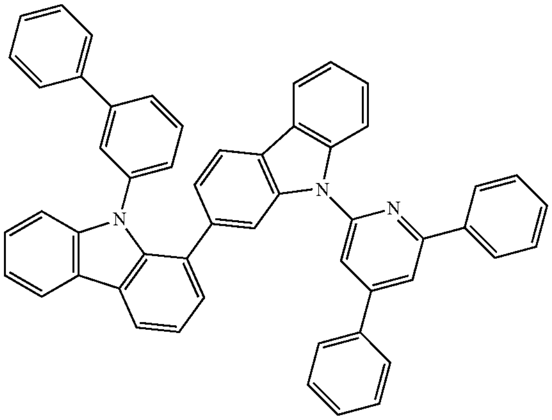
[I-89]
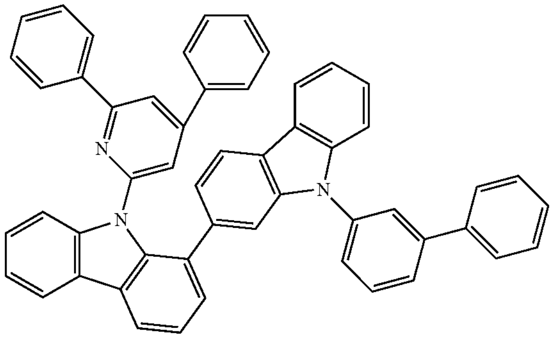
[I-90]
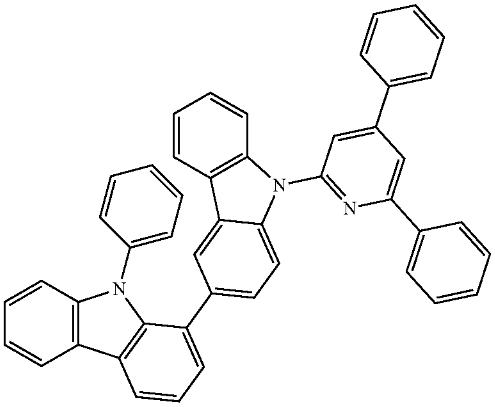
[I-91]
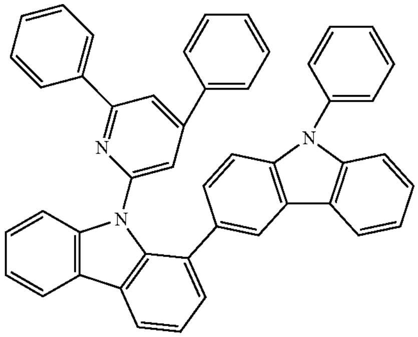
[I-92]
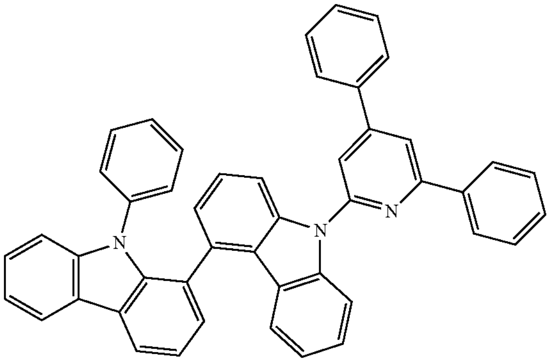

-continued
[I-93]
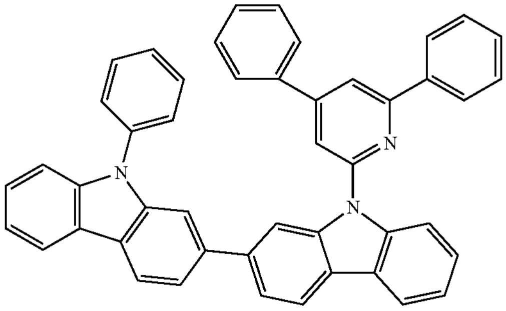
[I-94]
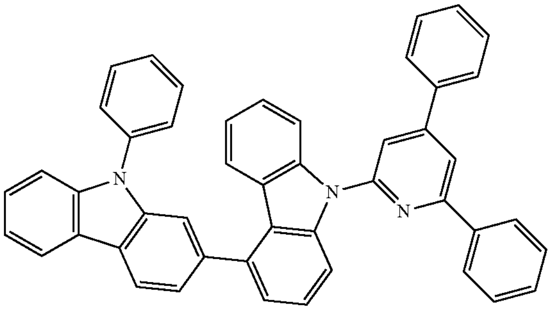
[I-95]
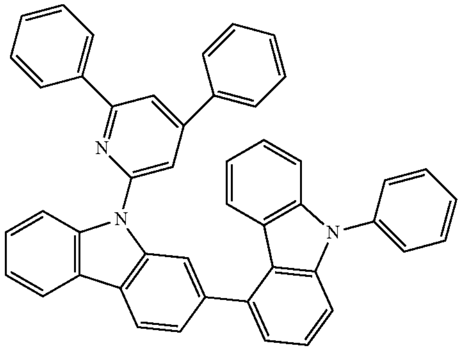
[I-96]
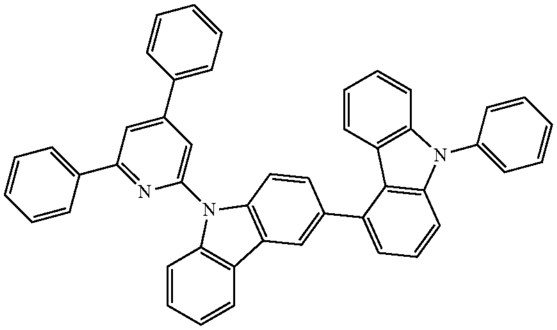
[I-97]
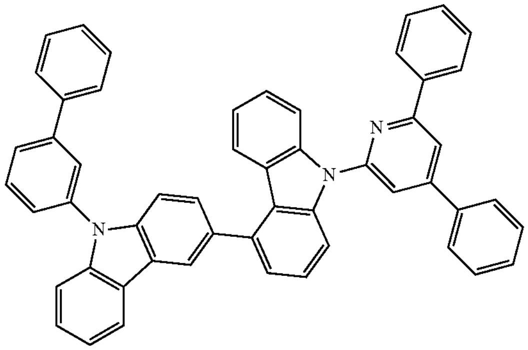
[I-98]
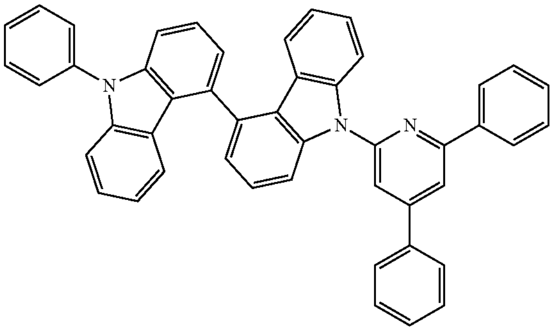

-continued
[I-99]
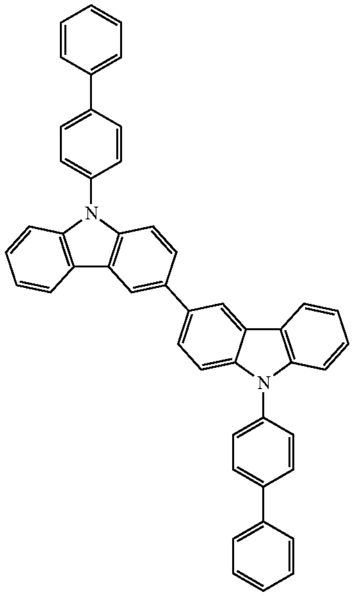
[I-100]
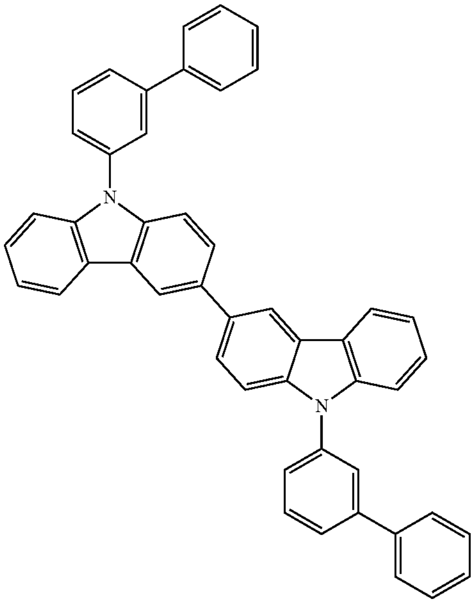
[I-101]
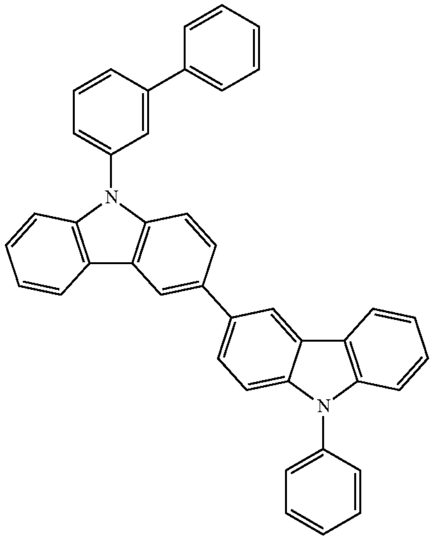
[I-102]
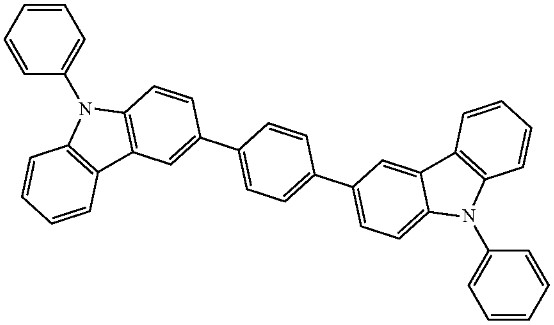
[I-103]
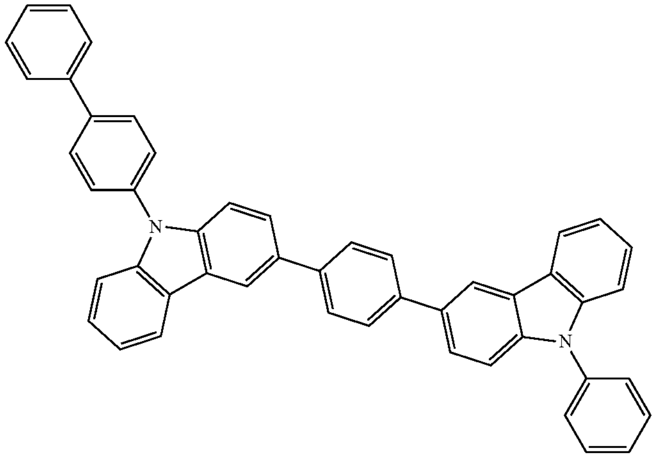

-continued
[I-104]
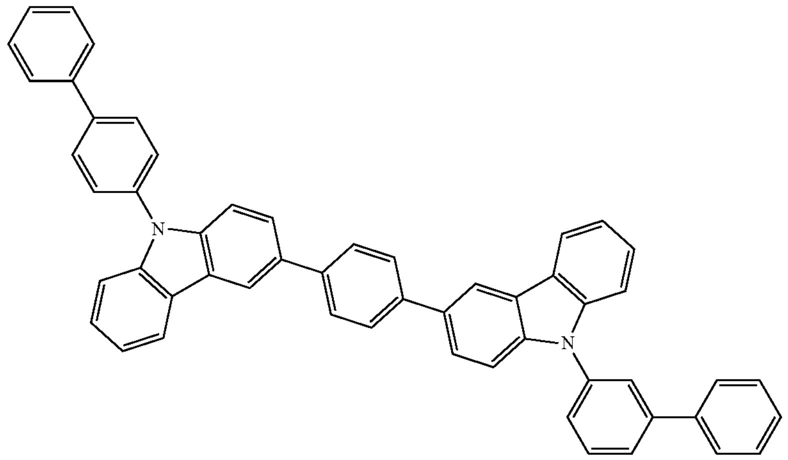
[I-105]
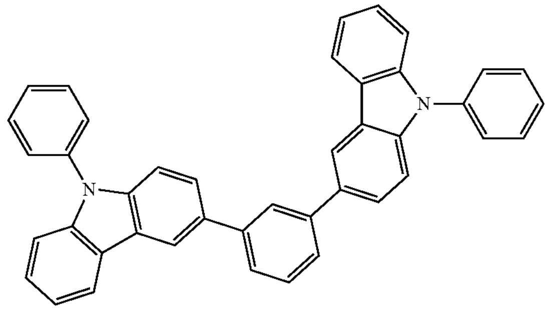
[I-106]
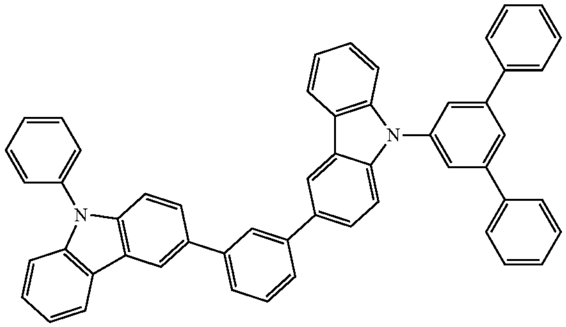
[I-107]
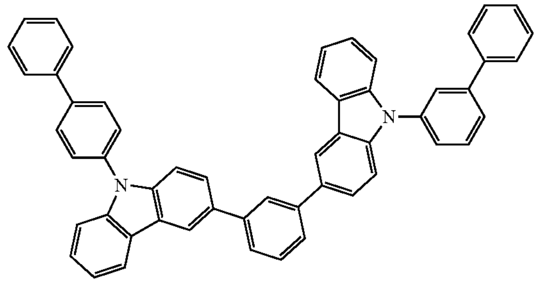
[I-108]
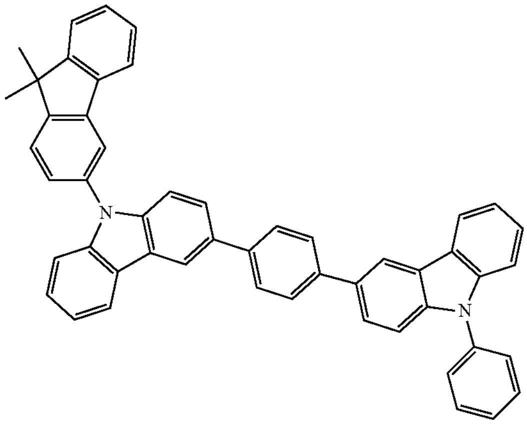

-continued
[I-109]
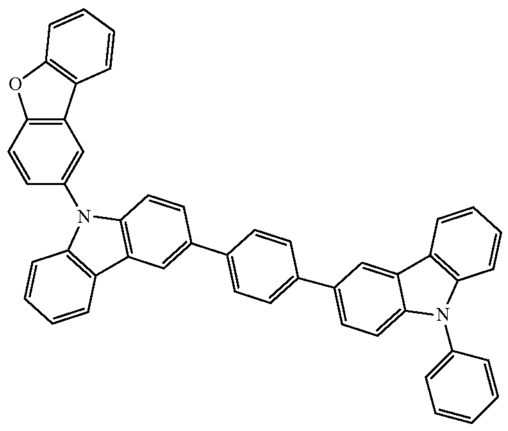
[I-110]
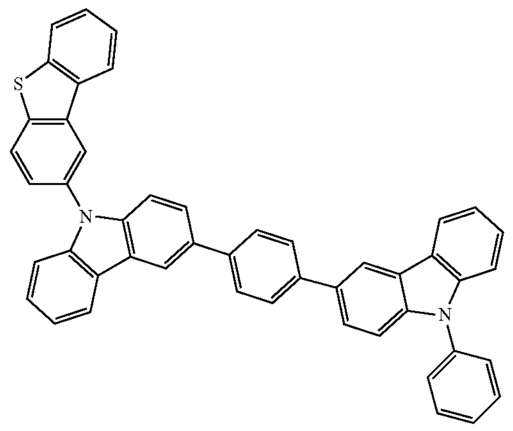
[I-111]
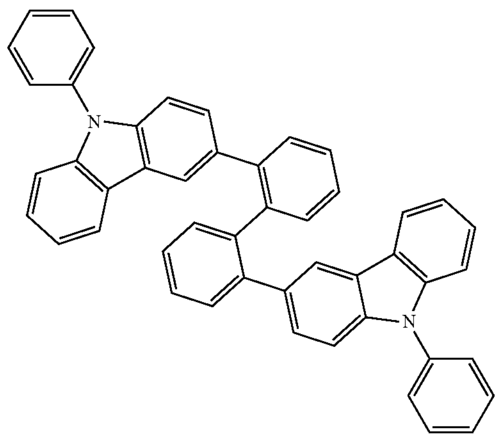
[I-112]
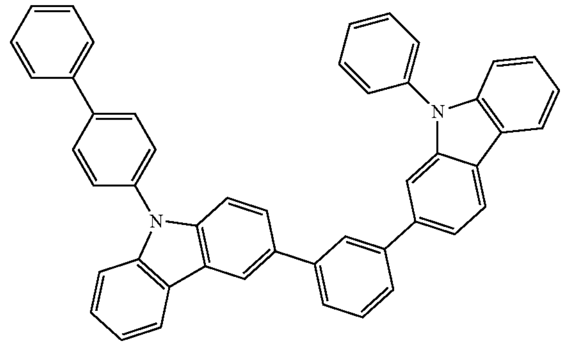
[I-113]
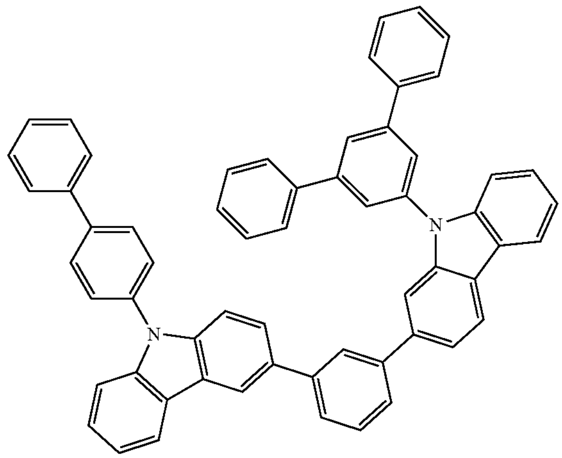
[I-114]
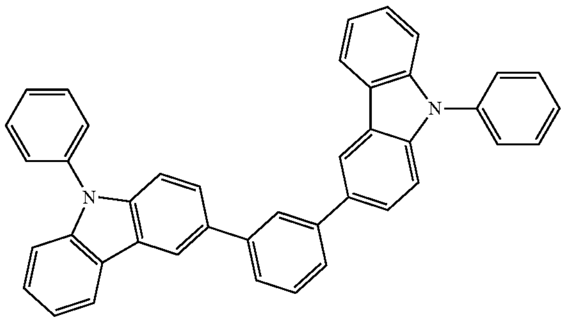

-continued
[I-115]
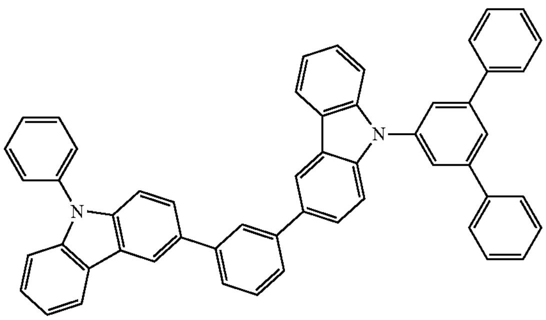
[I-116]
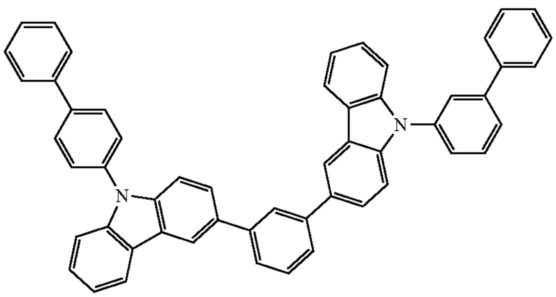
[I-117]
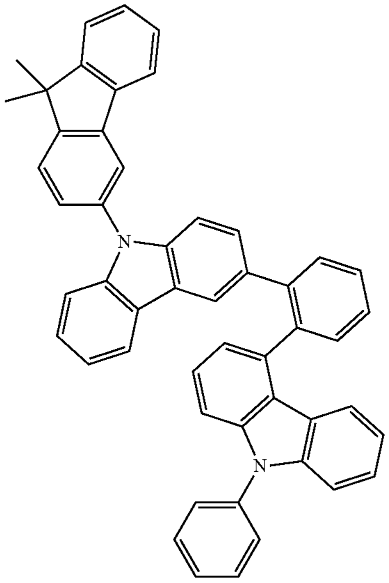
[I-118]
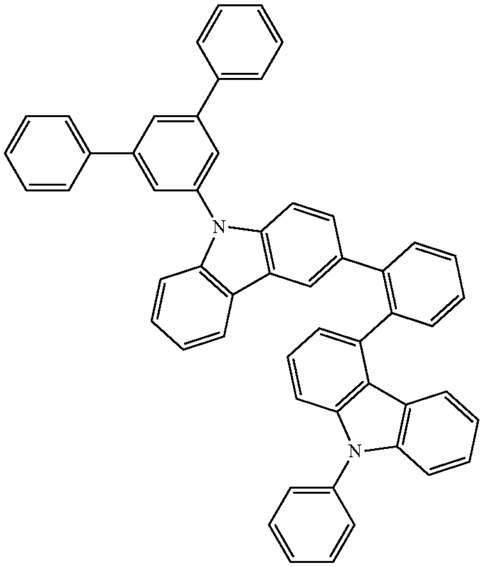
[I-119]
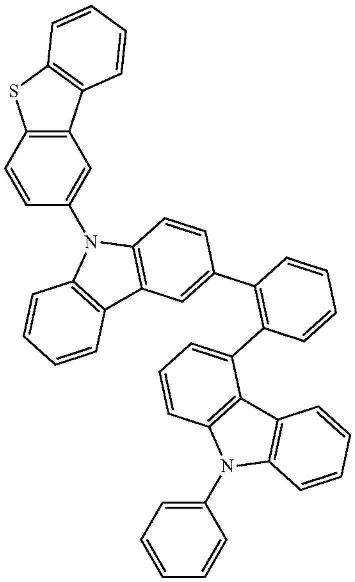
[I-120]
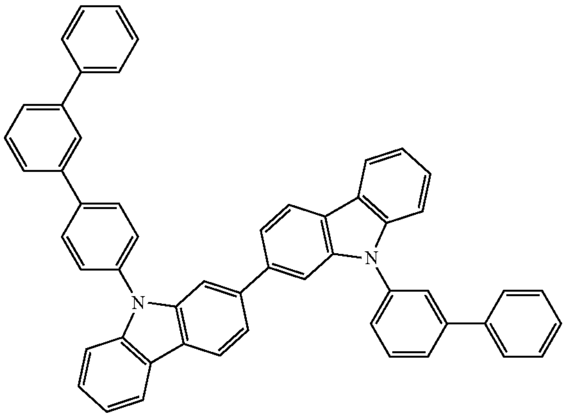

-continued
[I-121]
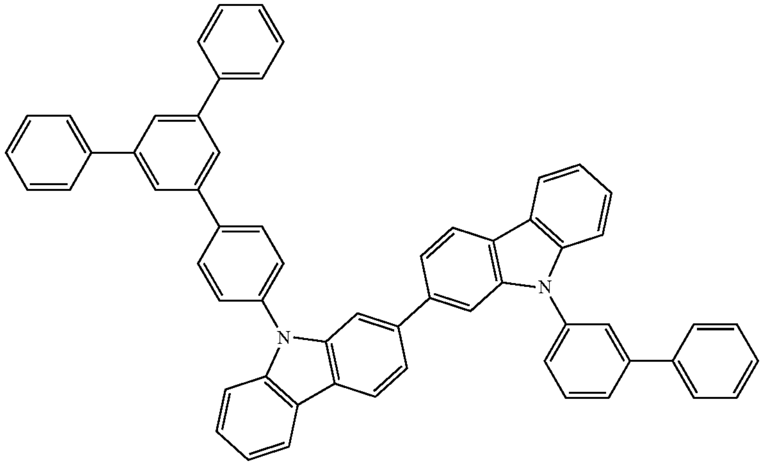
[I-122]
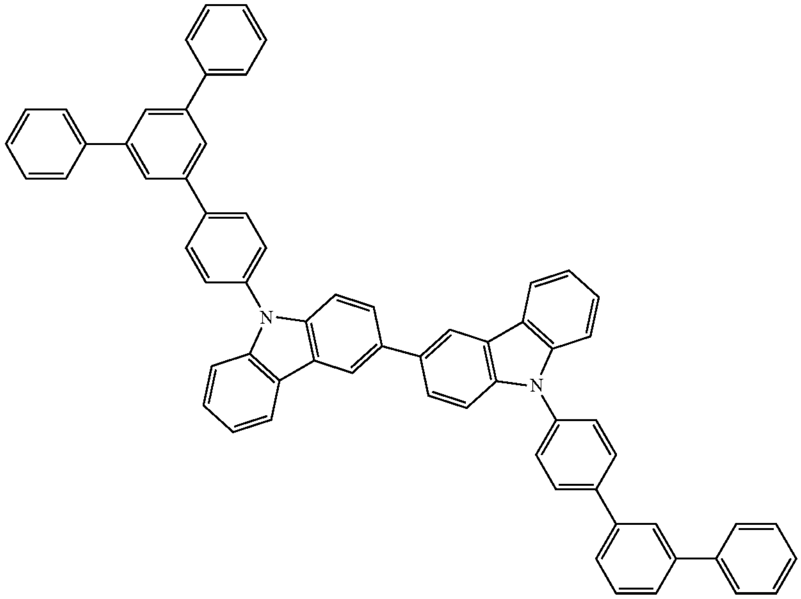
[I-123]
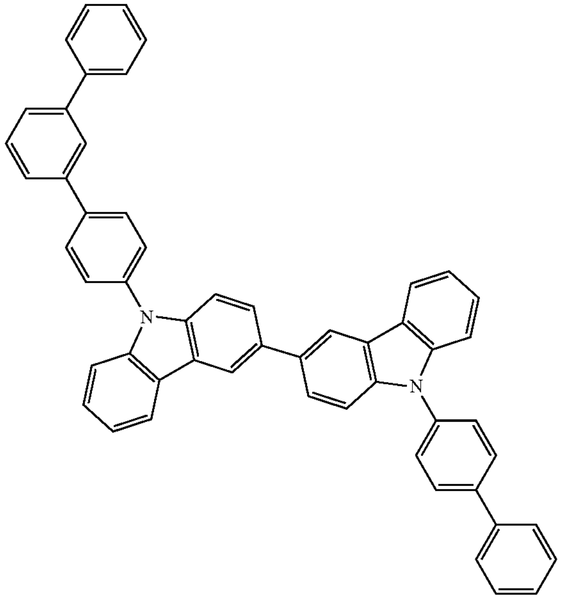

-continued
[I-124]
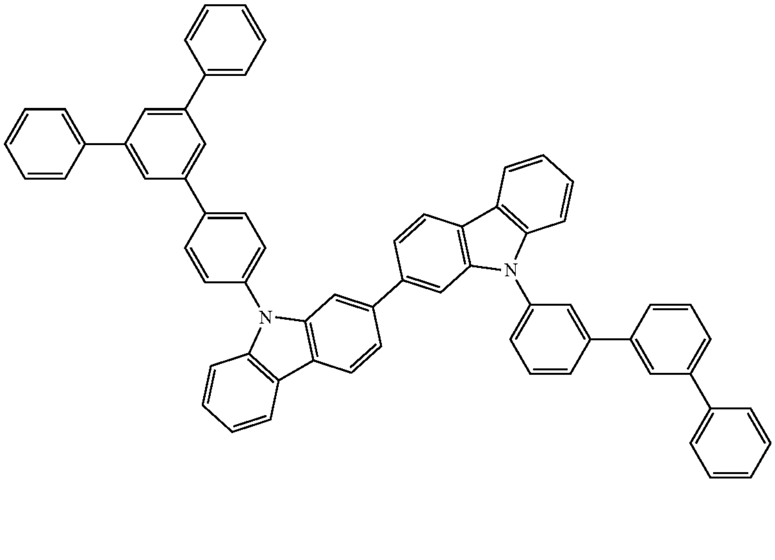
[I-125]
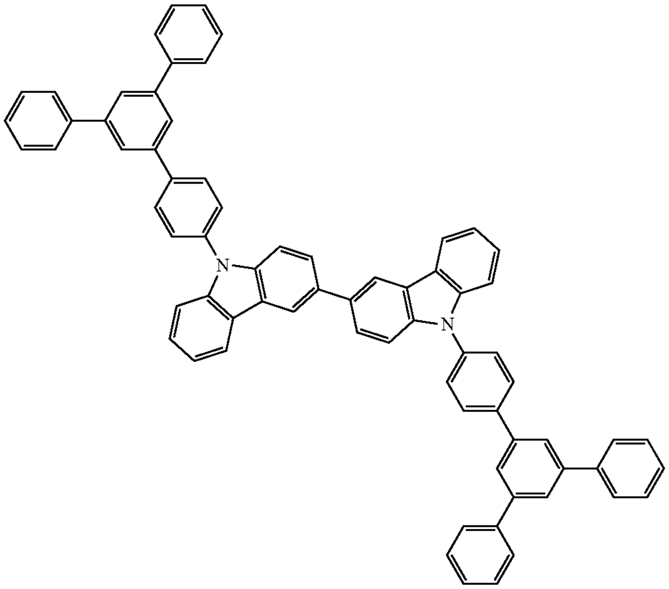

-continued
[I-126]
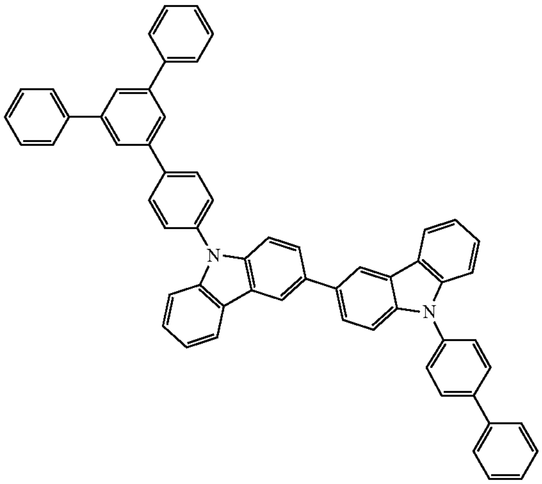
[I-127]
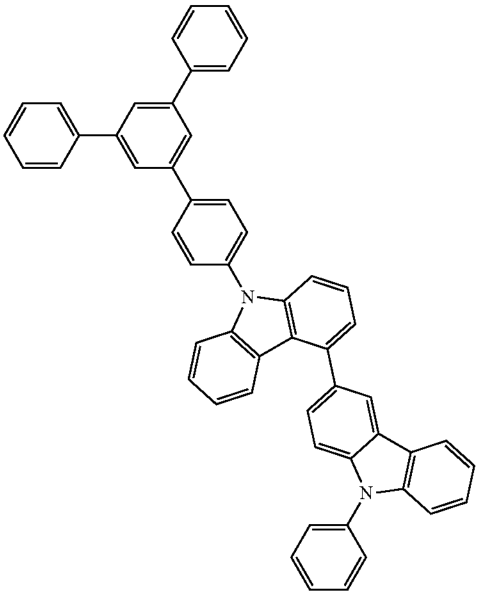
[I-128]
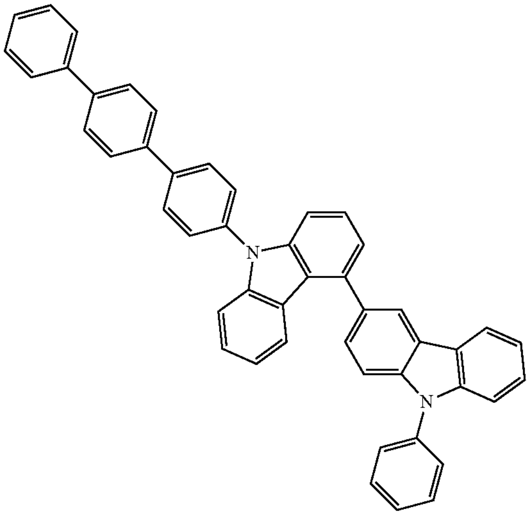
[I-129]
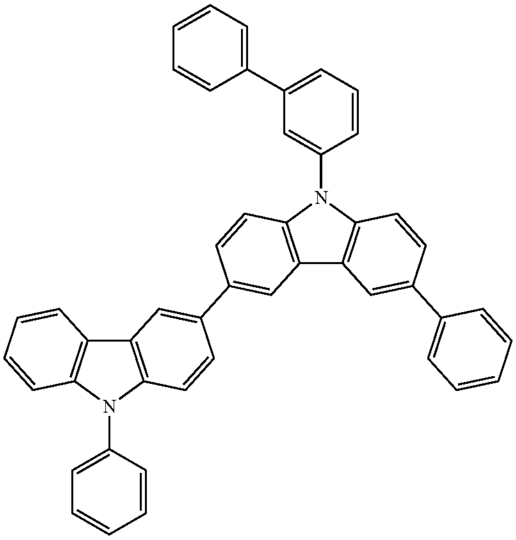

-continued
[I-130]
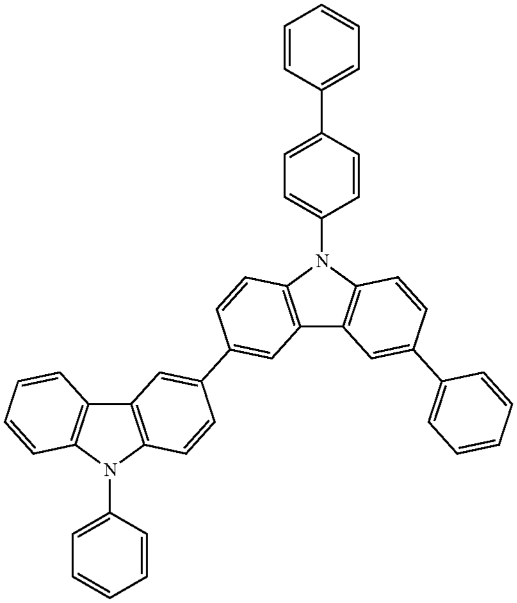
[I-131]
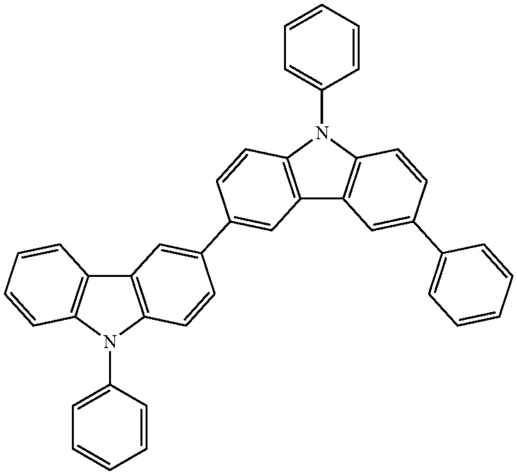
[I-132]
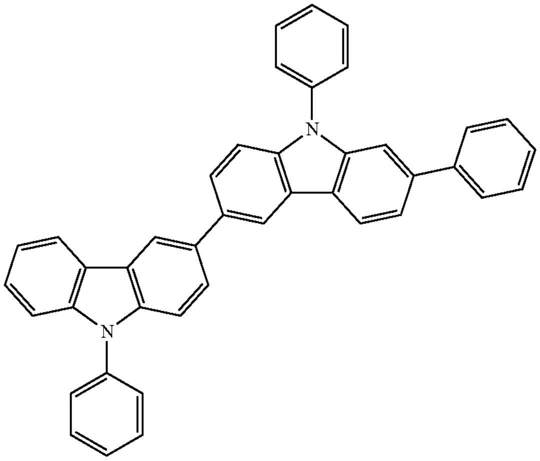
[I-133]
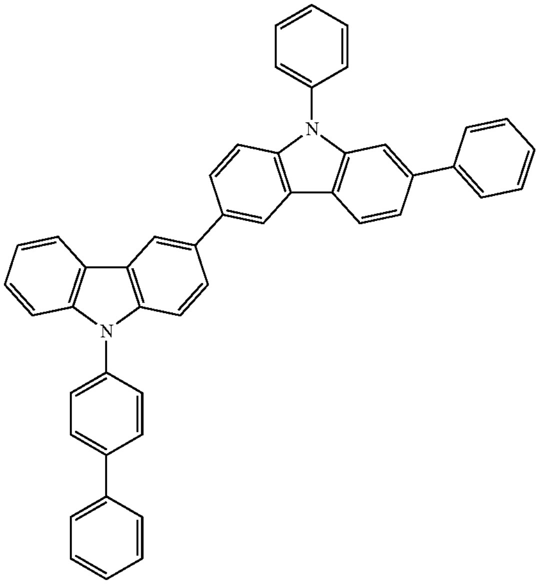

-continued
[I-134]
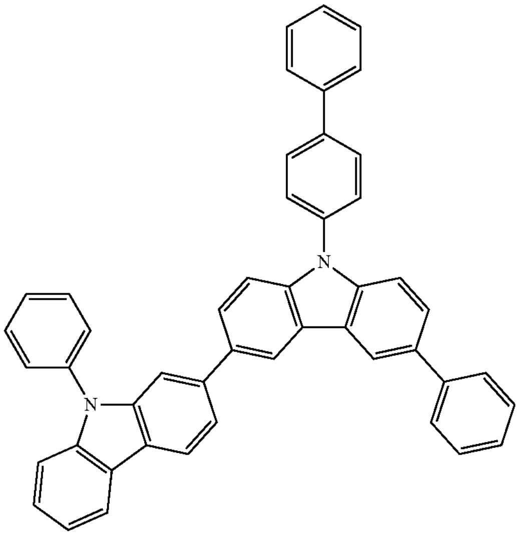
[I-135]
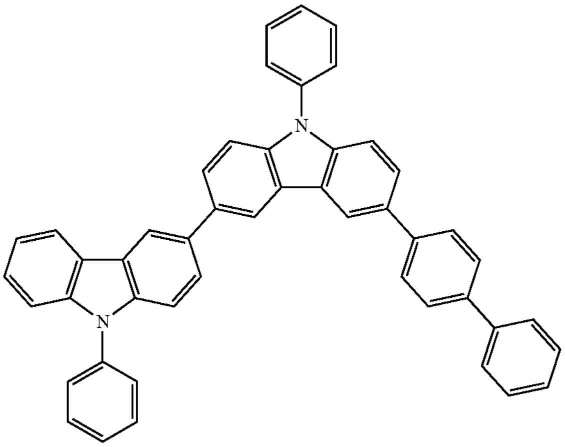
[I-136]
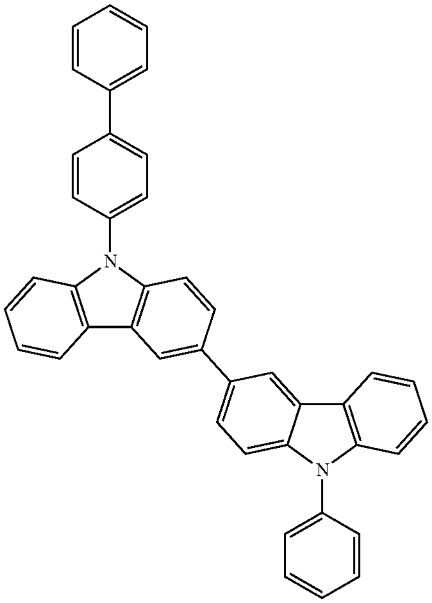
[I-137]
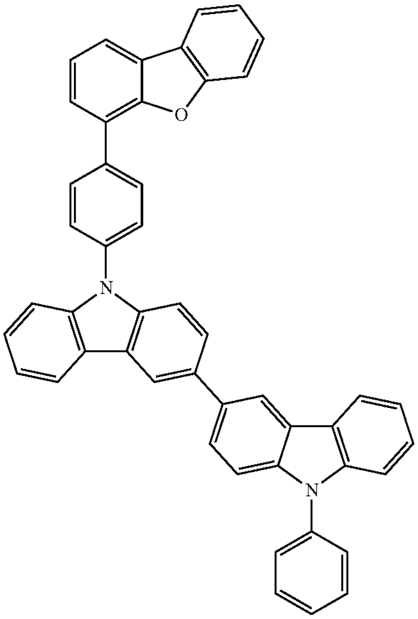

-continued

[I-138]

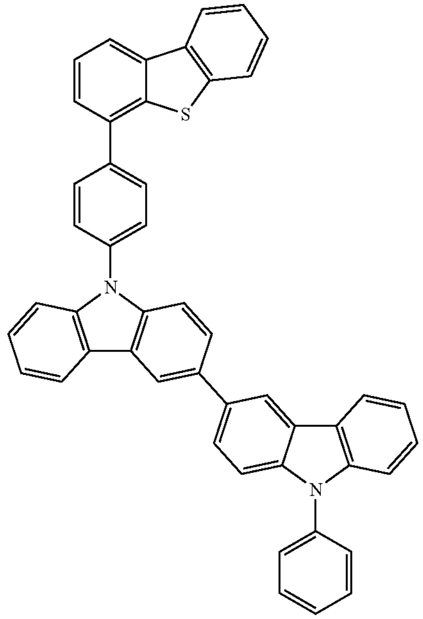

The first compound for the organic optoelectronic element and the second compound for the organic optoelectronic element may be applied in the form of a composition.

For example, the aforementioned compound for the organic optoelectronic element or composition for the organic optoelectronic element may be a host.

The first compound for the organic optoelectronic element and the second compound for the organic optoelectronic element may be included in a weight ratio of 1:99 to 99:1. Within the range, a desirable weight ratio may be adjusted using an electron transport capability of the first compound for the organic optoelectronic element and a hole transport capability of the second compound for the organic optoelectronic element to realize bipolar characteristics and thus to improve efficiency and life-span. Within the range, they may be for example included in a weight ratio of about 10:90 to about 90:10, about 20:80 to about 80:20, for example about 20:80 to about 70:30, about 20:80 to about 60:40, and about 20:80 to about 50:50. For example, they may be included in a weight ratio of 20:80 to 40:60, for example, a weight ratio of 30:70.

In the composition according an embodiment of the present invention, the first compound for the organic optoelectronic element may be represented by one of Chemical Formula 1A-3-2A, Chemical Formula 1A-3-2B, and Chemical Formula 1A-3-2F.

The aforementioned compound for the organic optoelectronic element or composition for an organic optoelectronic element may further include a dopant. The dopant may be, for example, a phosphorescent dopant, such as a red, green, or blue phosphorescent dopant, and may be, for example, a red or green phosphorescent dopant.

The dopant is a material mixed in a trace amount to cause light emission and may be generally a material such as a metal complex that emits light by multiple excitation into a triplet or more. The dopant may be, for example an inorganic, organic, or organic-inorganic compound, and one or more types thereof may be used.

Examples of the dopant may be a phosphorescent dopant and examples of the phosphorescent dopant may be an organic metal compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$L^3MX^A$ [Chemical Formula Z]

In Chemical Formula Z, M is a metal, and $L^3$ and $X^A$ are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the $L^3$ and $X^A$ may be for example a bidendate ligand.

The aforementioned compound for the organic optoelectronic element or composition for the organic optoelectronic element may be formed by a dry film formation method such as chemical vapor deposition (CVD).

Hereinafter, an organic optoelectronic element including the aforementioned compound for the organic optoelectronic element or composition for the organic optoelectronic element is described.

The organic optoelectronic element may be any device to convert electrical energy into photoenergy and vice versa without particular limitation, and may be, for example an organic photoelectric device, an organic light emitting diode, an organic solar cell, and an organic photo conductor drum.

Herein, an organic light emitting diode as one example of an organic optoelectronic element is described referring to drawings.

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 disposed between the anode 120 and cathode 110.

The anode 120 may be made of a conductor having a large work function to help hole injection, and may be for example a metal, a metal oxide and/or a conductive polymer. The anode 120 may be, for example a metal such as nickel, platinum, vanadium, chromium, copper, zinc, gold, and the like or an alloy thereof; a metal oxide such as zinc oxide, indium oxide, indium tin oxide (ITO), indium zinc oxide (IZO), and the like; a combination of a metal and an oxide such as ZnO and Al or $SnO_2$ and Sb; a conductive polymer such as poly(3-methylthiophene), poly(3,4-(ethylene-1,2-dioxy)thiophene) (PEDOT), polypyrrole, and polyaniline, but is not limited thereto.

The cathode 110 may be made of a conductor having a small work function to help electron injection, and may be for example a metal, a metal oxide and/or a conductive polymer. The cathode 110 may be for example a metal such as magnesium, calcium, sodium, potassium, titanium, indium, yttrium, lithium, gadolinium, aluminum silver, tin, lead, cesium, barium, and the like, or an alloy thereof; a multi-layer structure material such as LiF/Al, $LiO_2$/Al, LiF/Ca, LiF/Al, and $BaF_2$/Ca, but is not limited thereto.

The organic layer 105 may include the aforementioned compound or composition.

The light emitting layer 130 may include, for example, the aforementioned compound or composition.

Referring to FIG. 2, an organic light emitting diode 200 further includes a hole auxiliary layer 140 in addition to the light emitting layer 130. The hole auxiliary layer 140 further increases hole injection and/or hole mobility and blocks electrons between the anode 120 and the light emitting layer 130. The hole auxiliary layer 140 may be, for example, a hole transport layer, a hole injection layer, and/or an electron blocking layer and may include at least one layer.

The hole auxiliary layer 140 may include for example at least one of compounds of Group K.

Specifically, the hole auxiliary layer 140 may include a hole transport layer between the anode 120 and the light emitting layer 130 and a hole transport auxiliary layer between the light emitting layer 130 and the hole transport layer, and at least one of compounds of Group K may be included in the hole transport auxiliary layer.

[Group K]

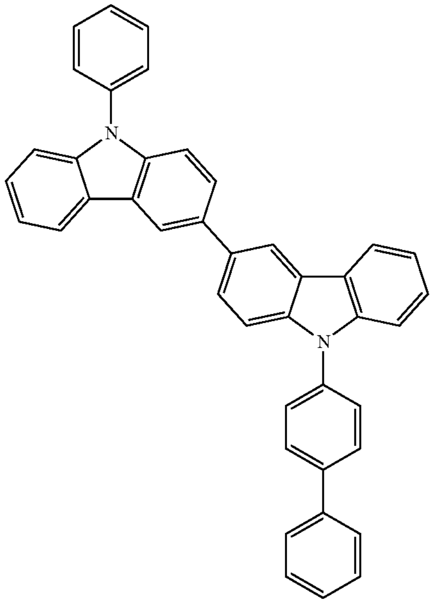

-continued

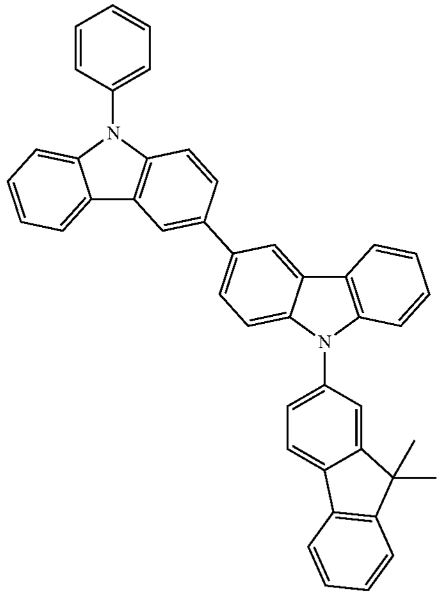

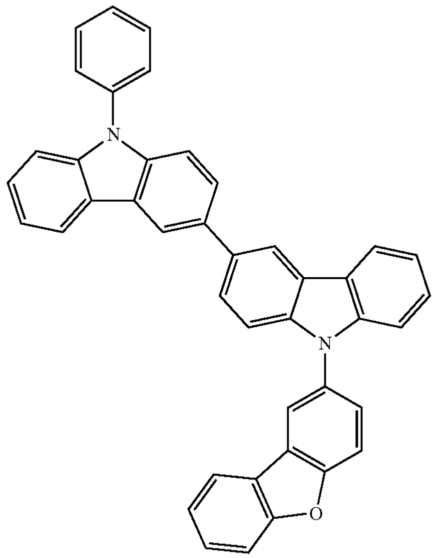

-continued
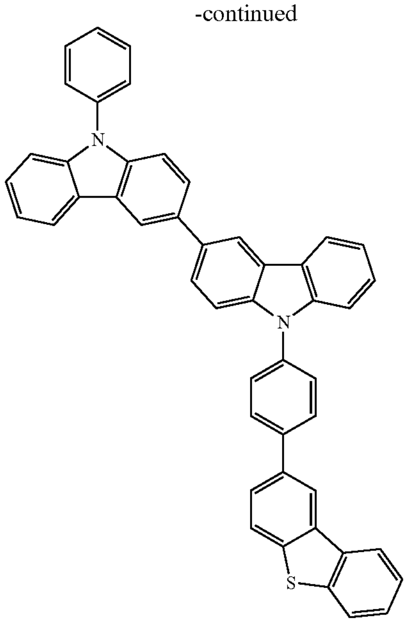
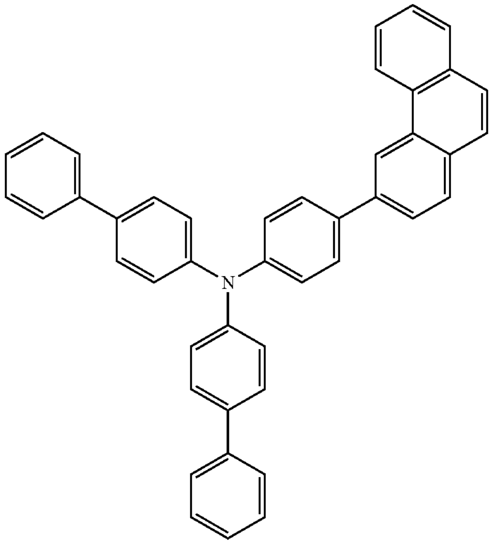
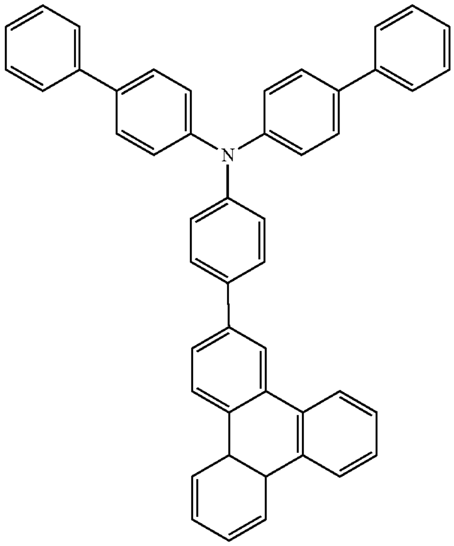
-continued
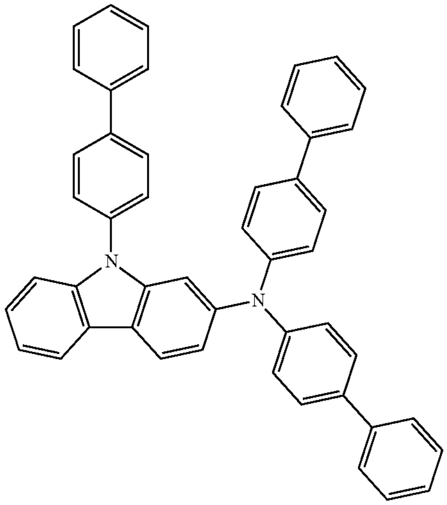
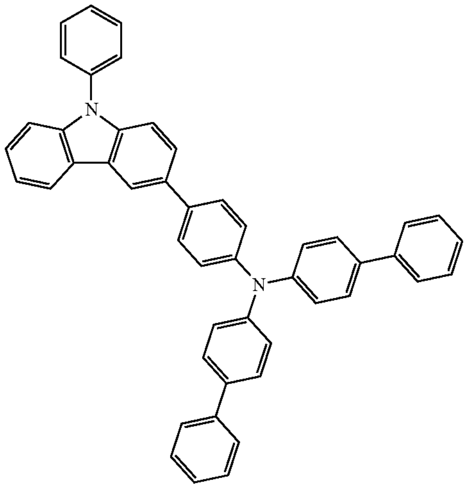
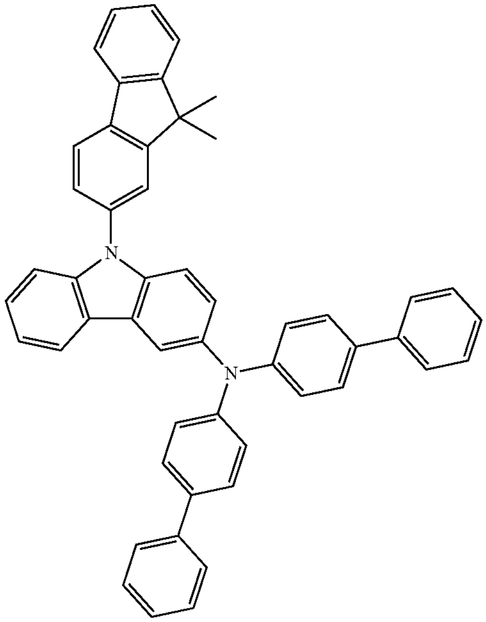

-continued
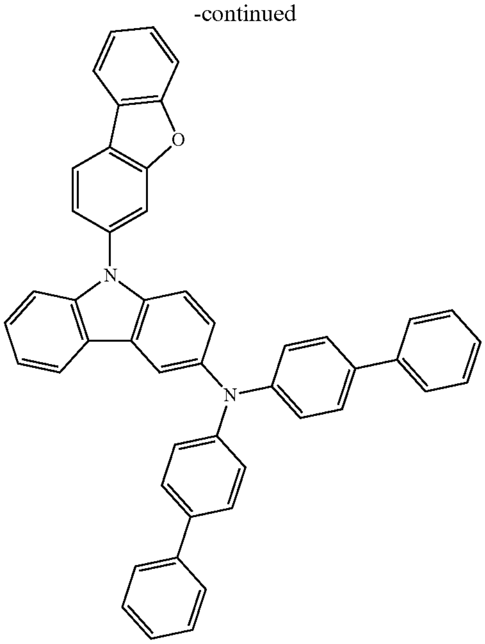
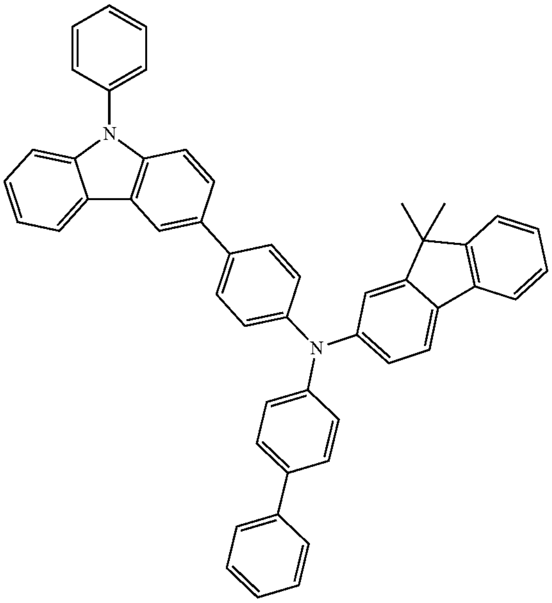
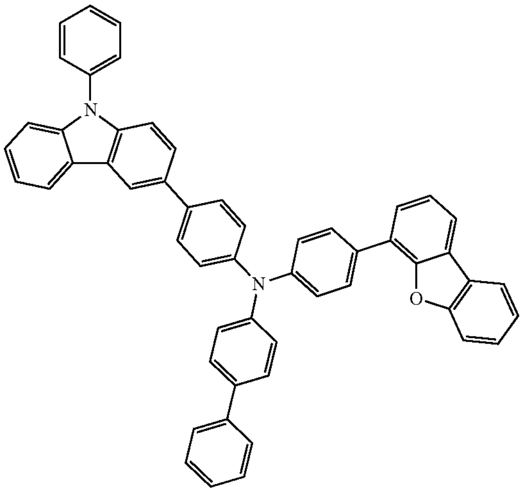
-continued
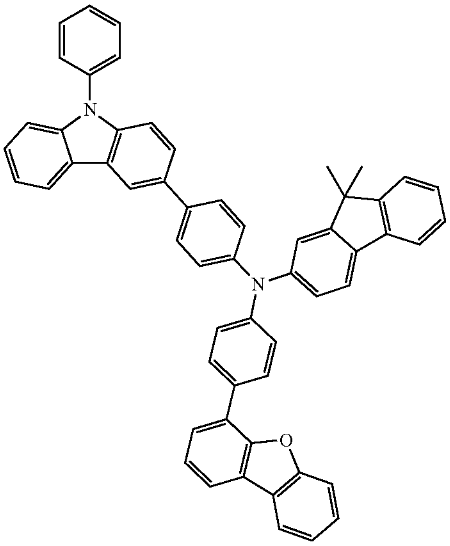
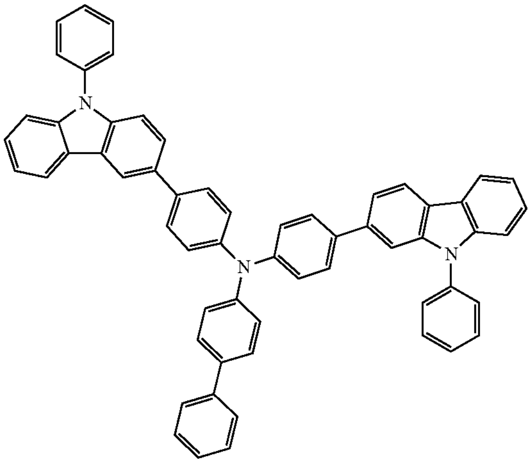
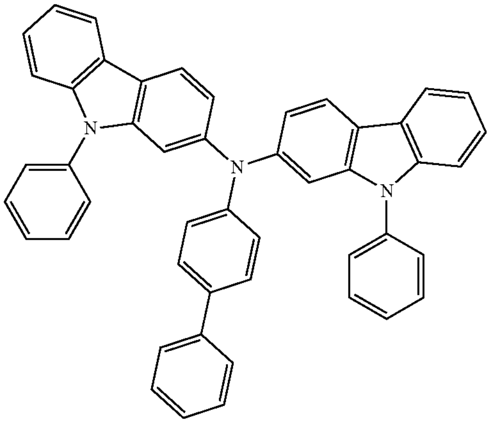

-continued
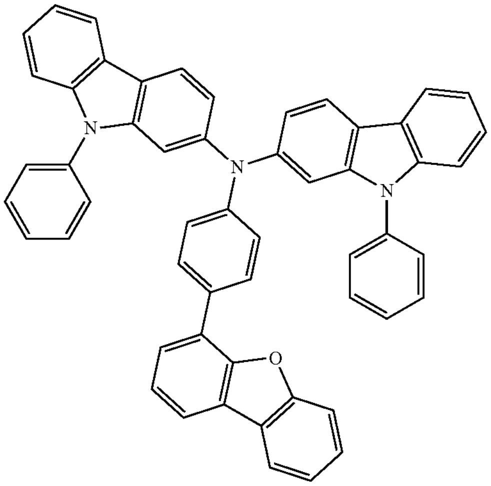
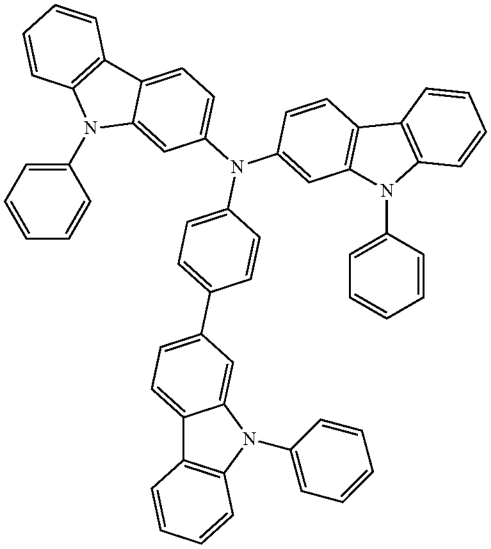
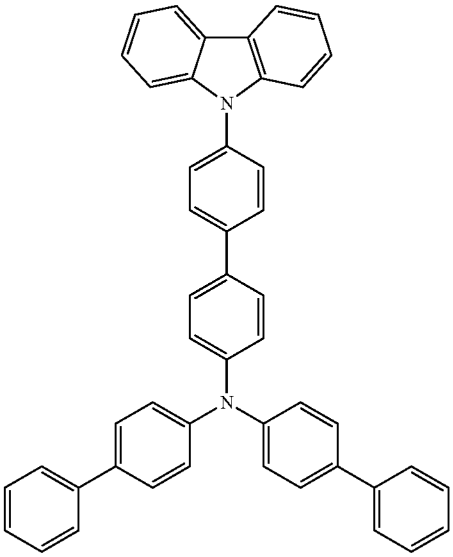
-continued
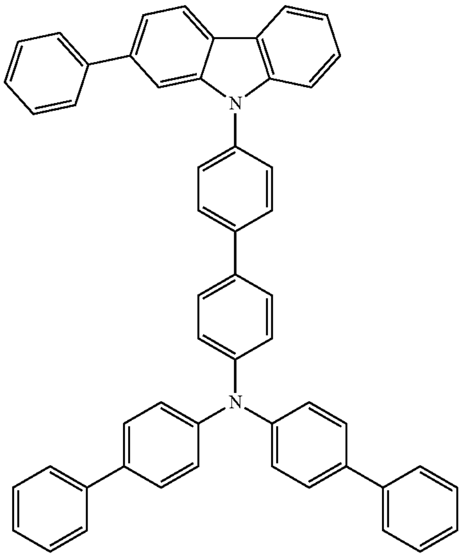
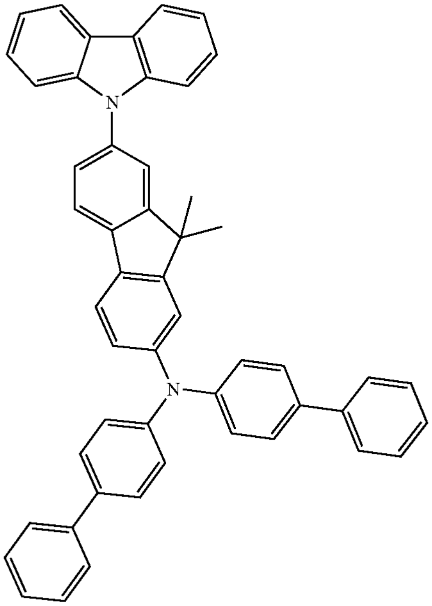
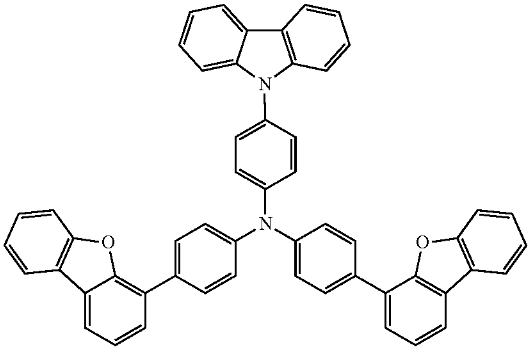

-continued
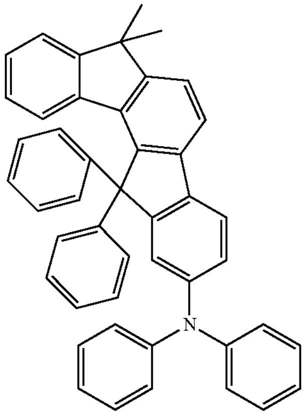
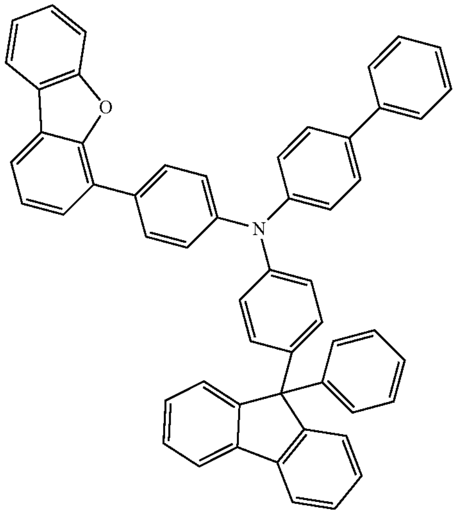
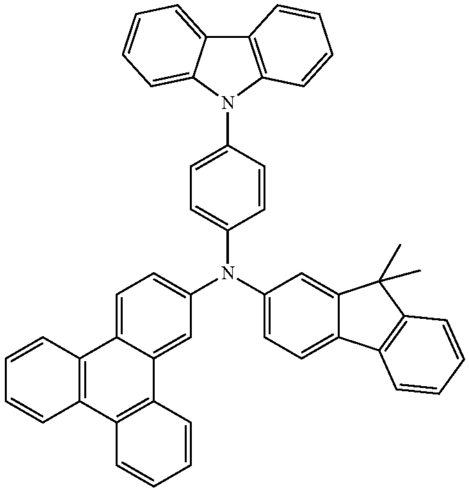
-continued
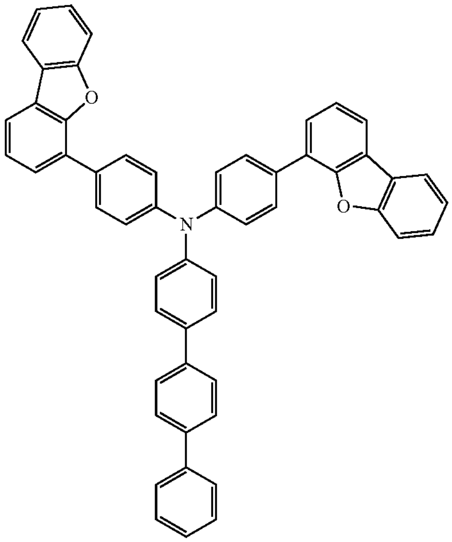
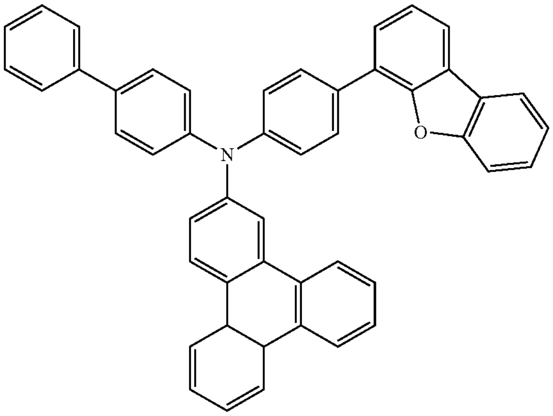
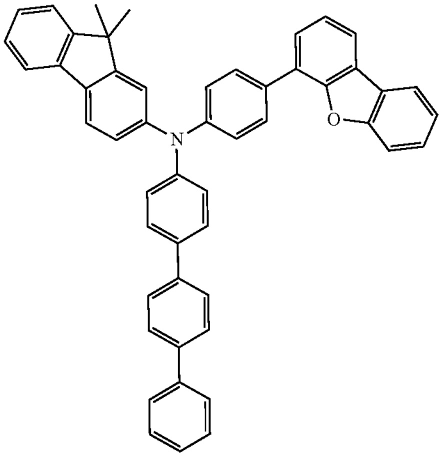

-continued
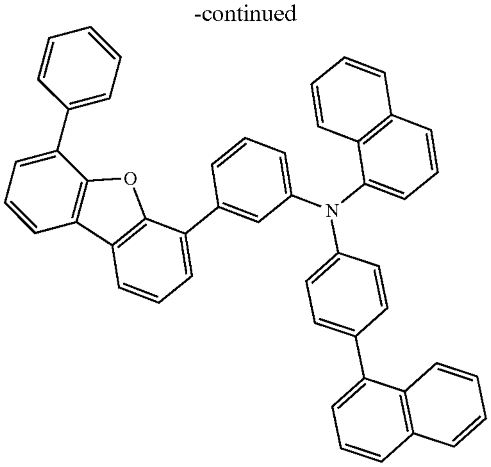
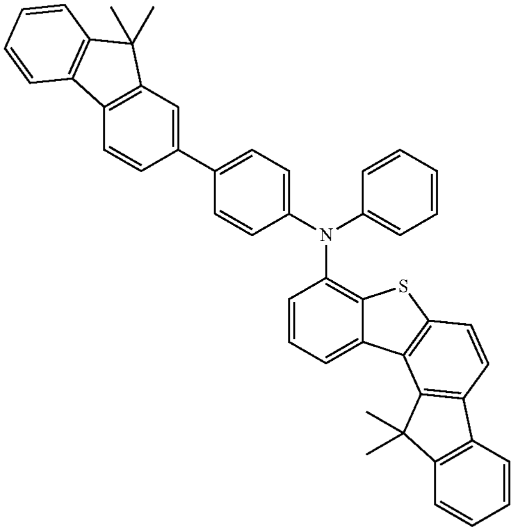
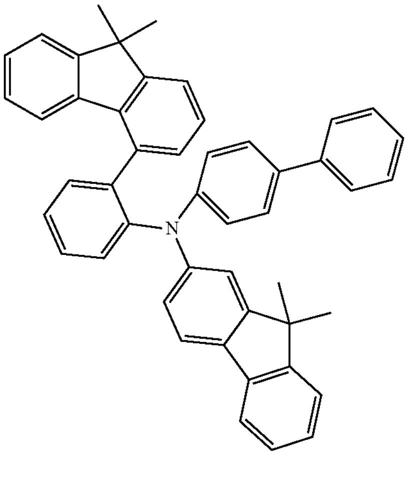
-continued
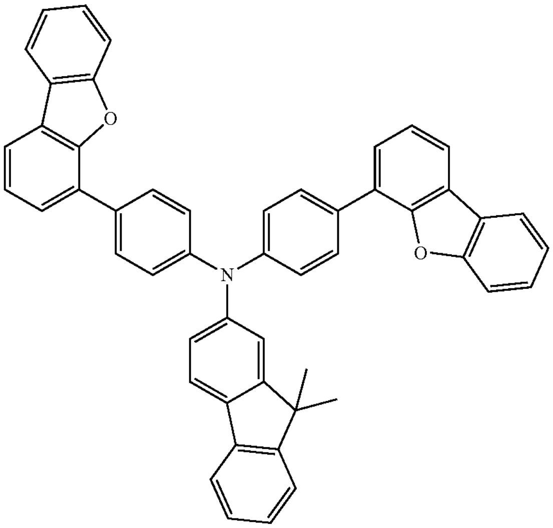
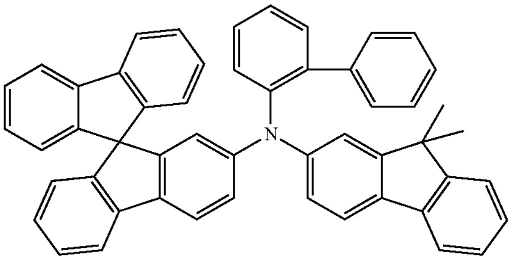
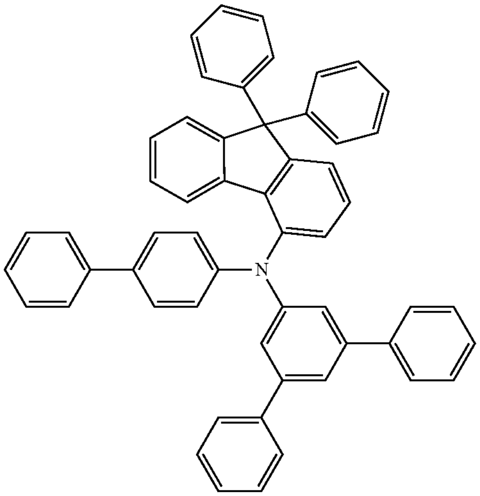
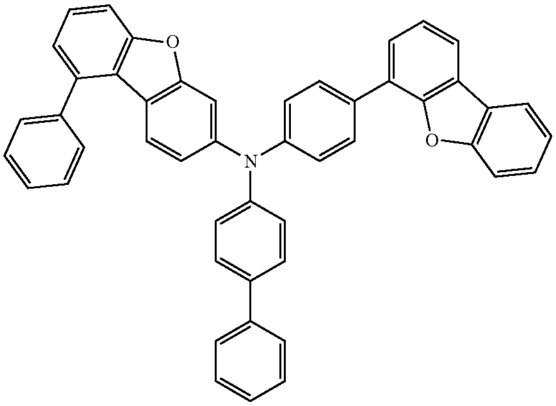

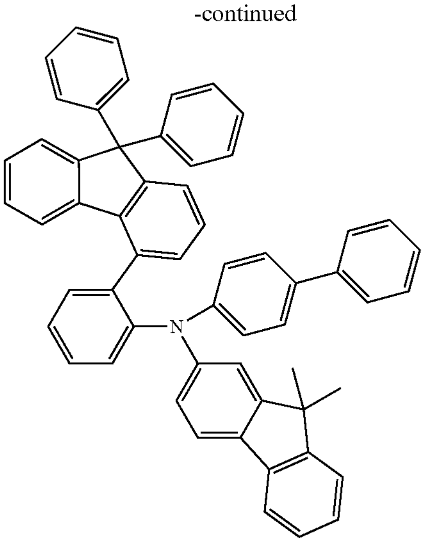
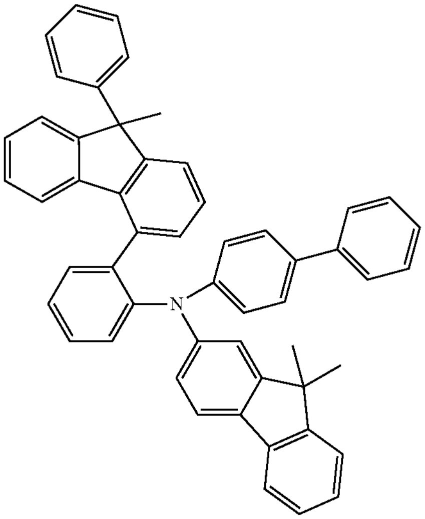
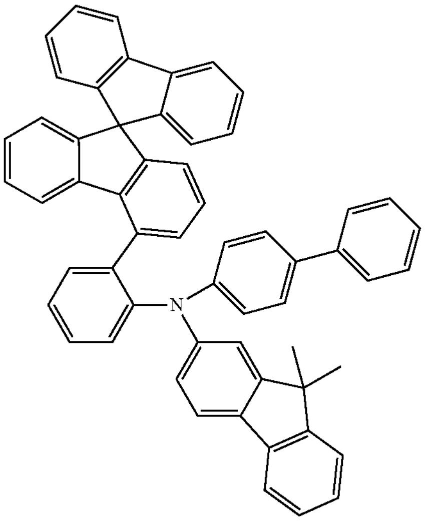
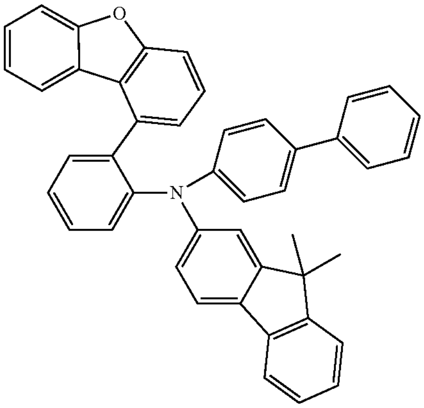
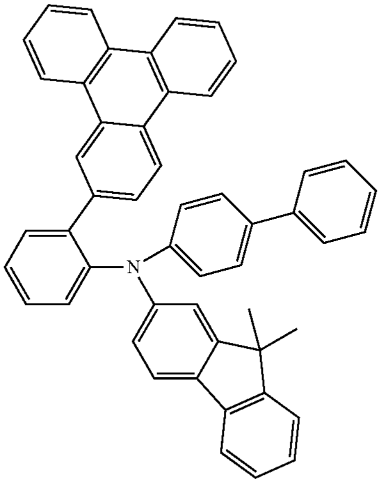
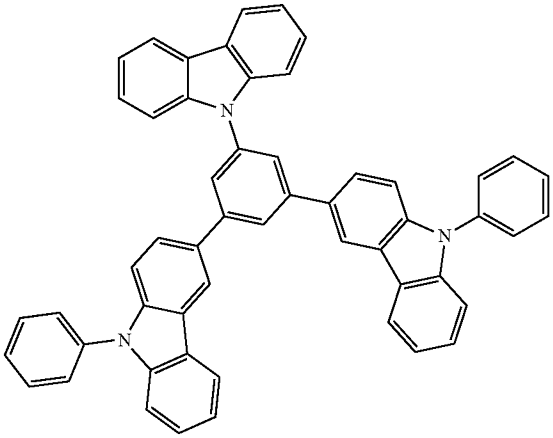
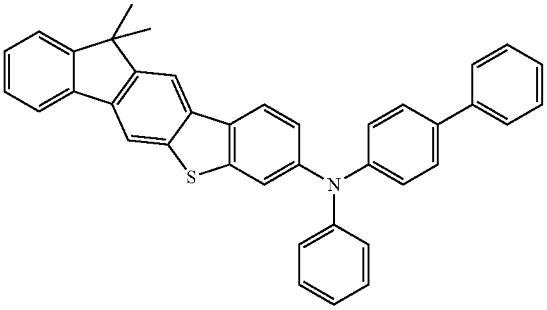

-continued
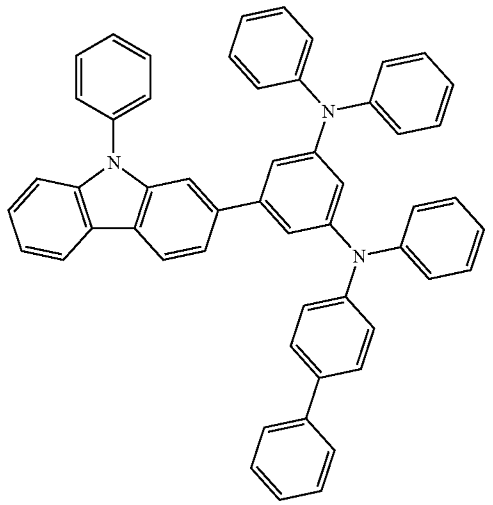
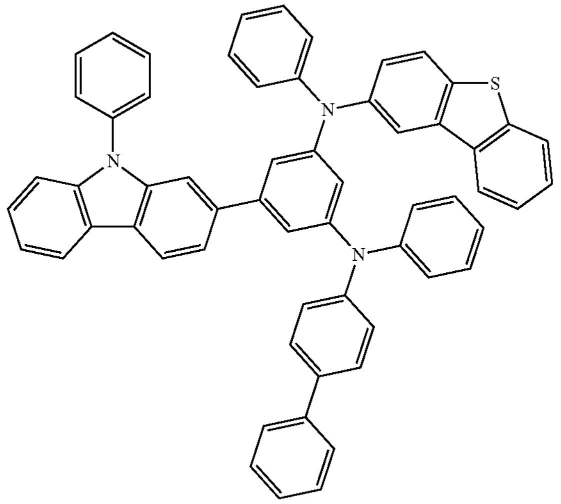
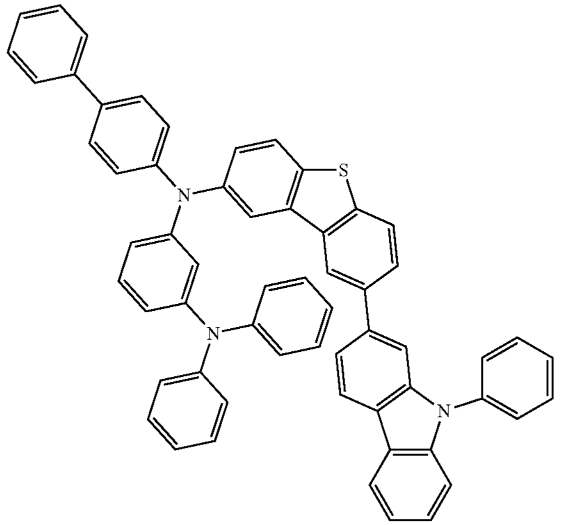
-continued
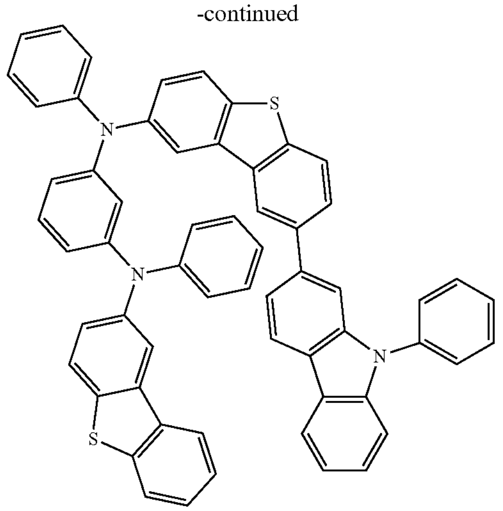
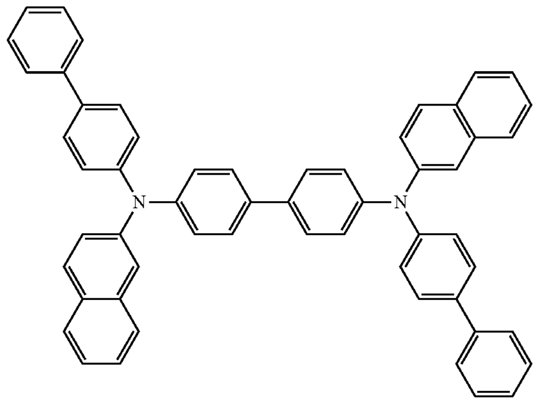
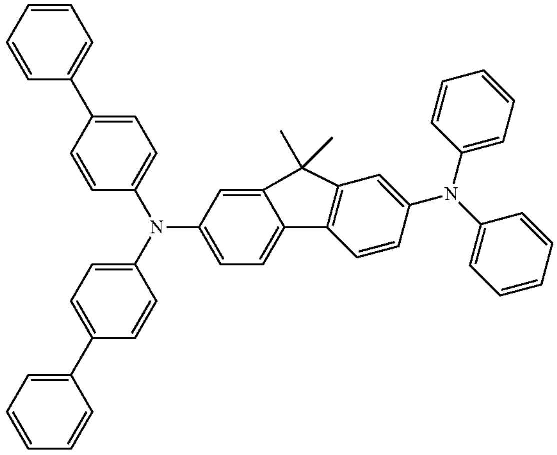

-continued
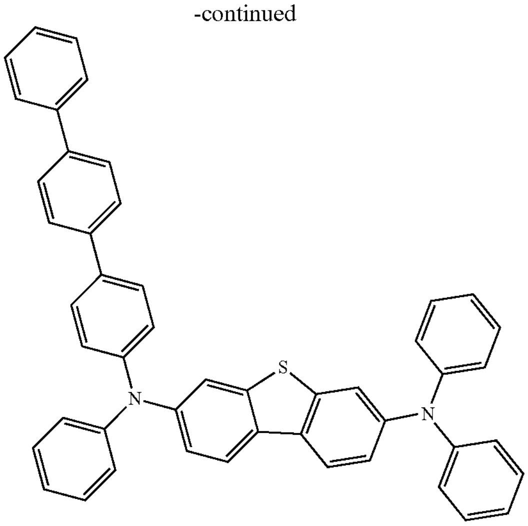
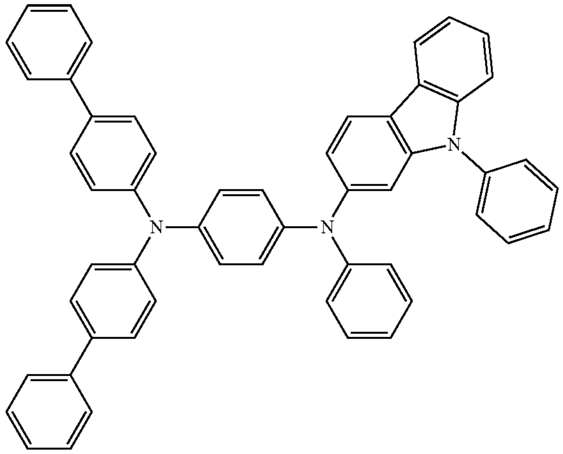
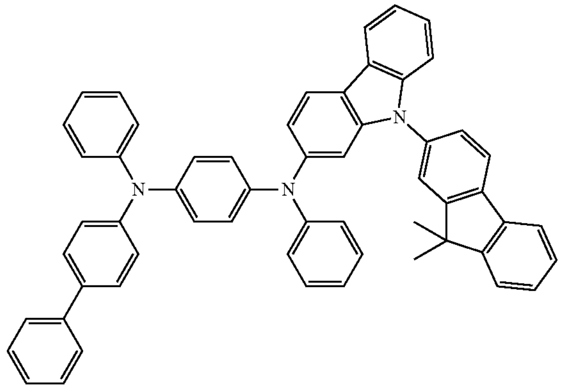
-continued
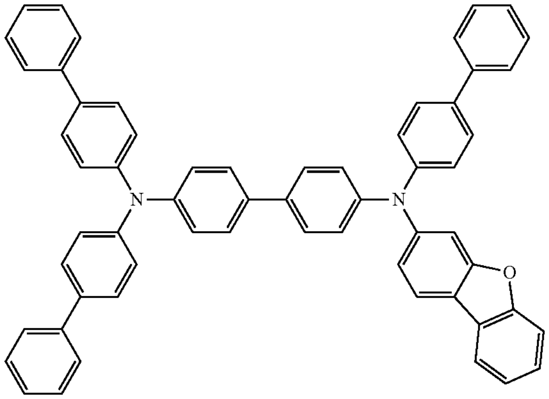
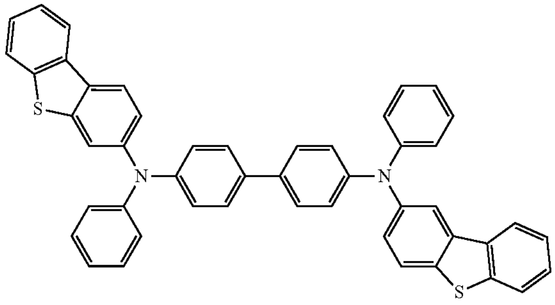
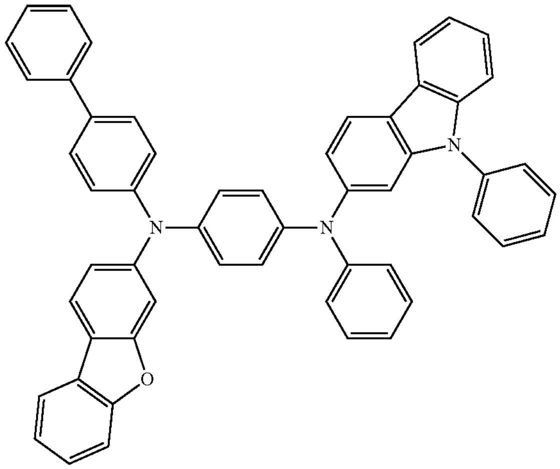
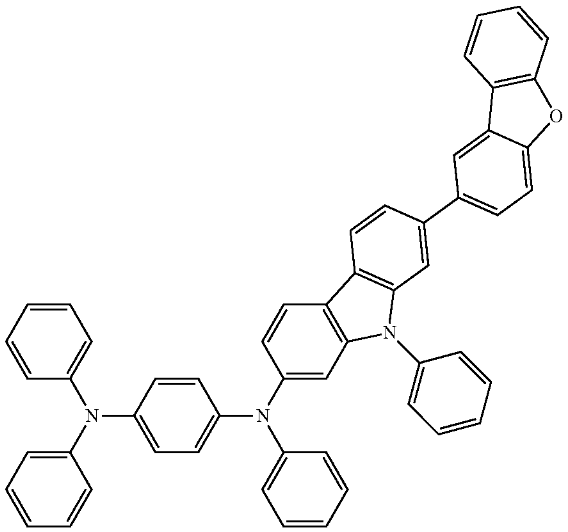

-continued
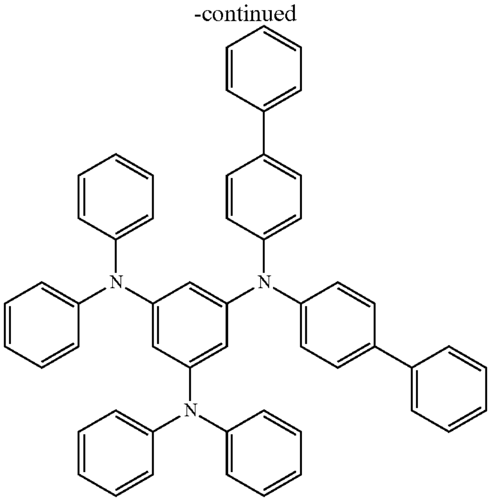
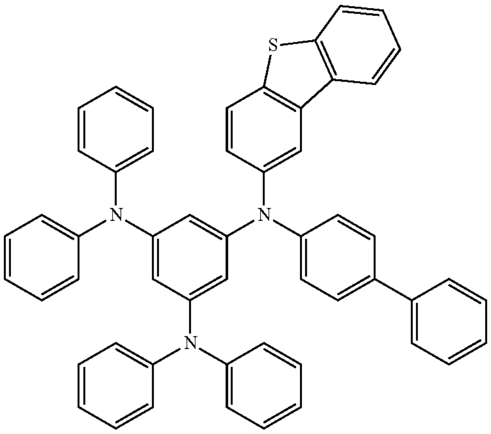
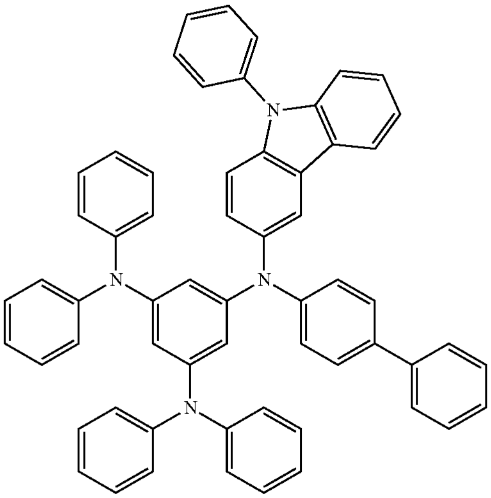
-continued
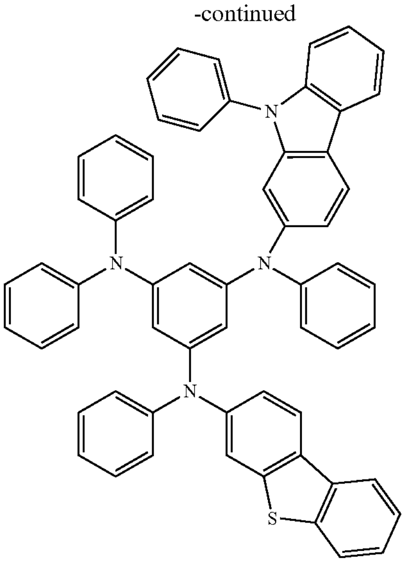
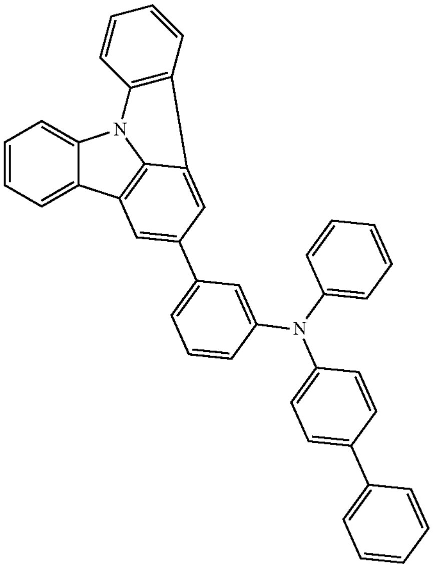
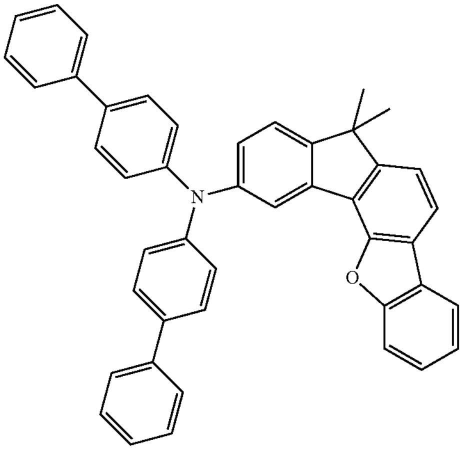

-continued
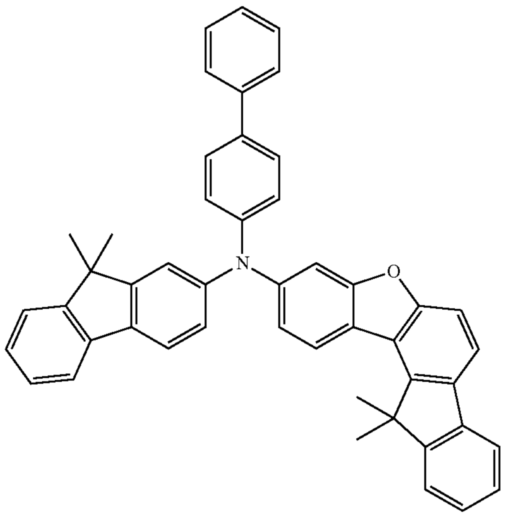
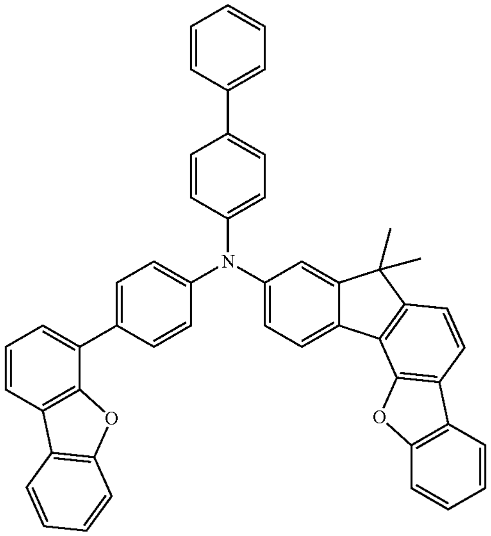
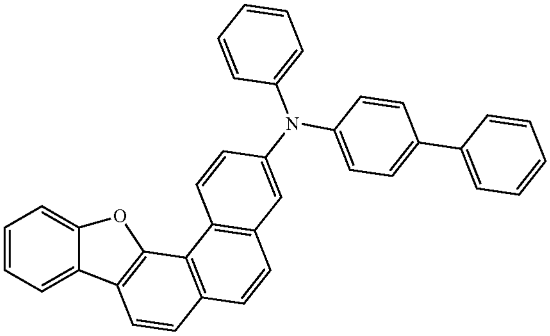
-continued
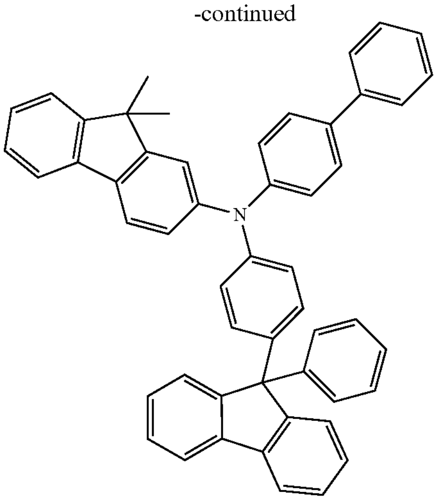
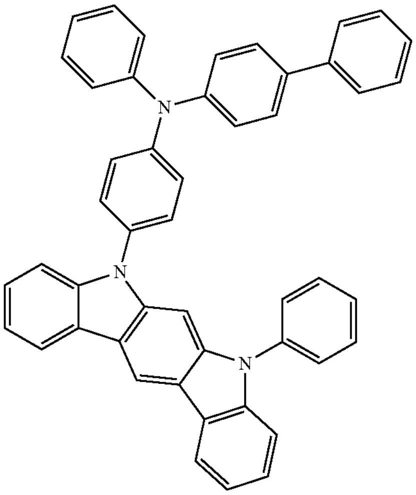
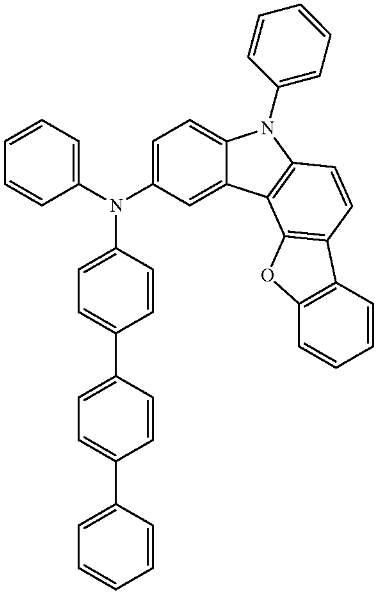

-continued

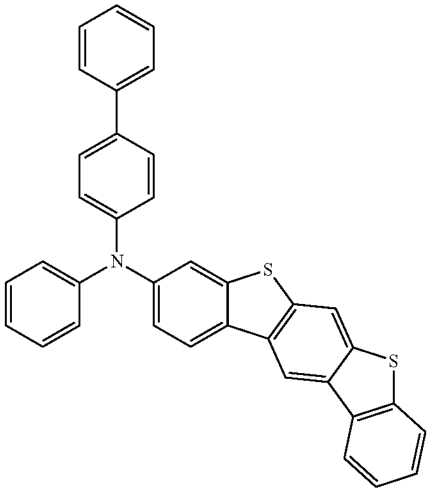

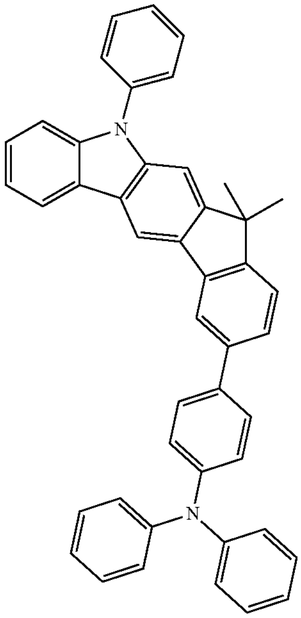

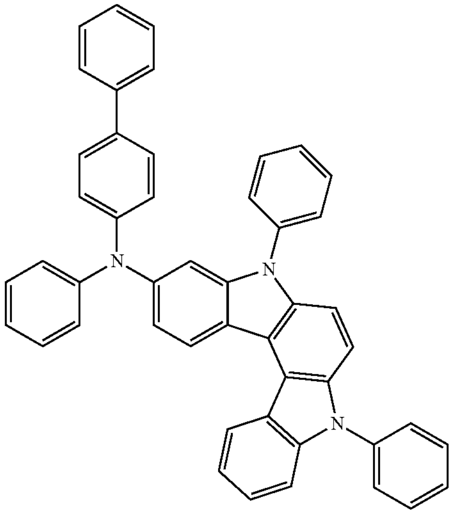

-continued

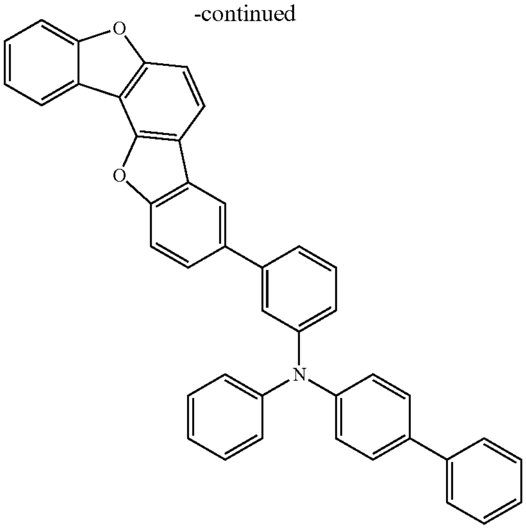

In the hole transport auxiliary layer, known compounds disclosed in U.S. Pat. No. 5,061,569A, JP1993-009471A, WO1995-009147A1, JP1995-126615A, JP1998-095972A and the like and compounds similar thereto may be used in addition to the compound.

In an embodiment, in FIG. 1 or 2, an organic light emitting diode may further include an electron transport layer, an electron injection layer, or a hole injection layer as the organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, starting materials and reactants used in examples and synthesis examples were purchased from Sigma-Aldrich Co. Ltd., TCI Inc., Tokyo chemical industry or P&H tech as far as there in no particular comment or were synthesized by known methods.

(Preparation of Compound for Organic Optoelectronic Device)

The compounds as one specific examples of the present invention were synthesized through the following steps.

(Preparation of First Compound for Organic Optoelectronic Device)

<Synthesis of Core 1>

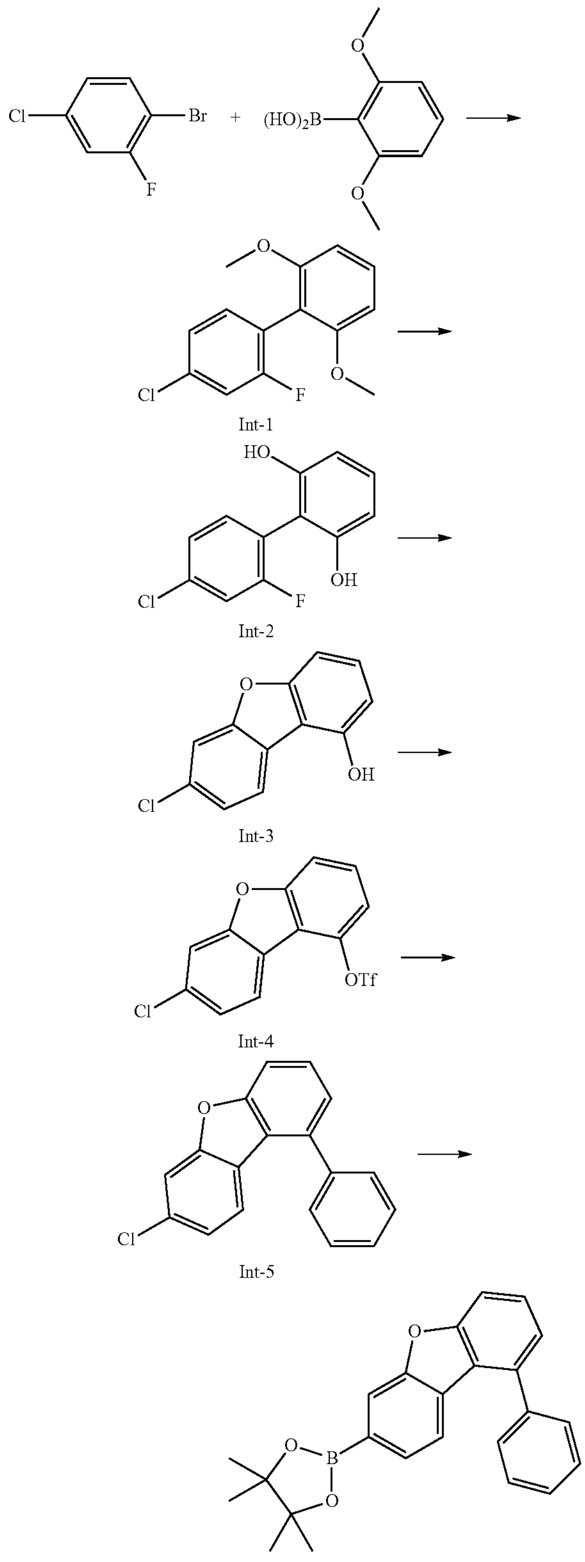

Int-1 Int-2 Int-3 Int-4 Int-5 Int-6

Synthesis Example 1: Synthesis of Intermediate Int-1

[Reaction Scheme 1]

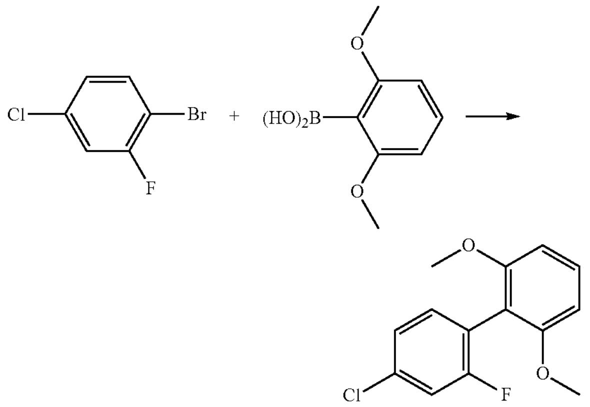

Int-1

1-bromo-4-chloro-2-fluorobenzene (61 g, 291 mmol), 2,6-dimethoxyphenylboronic acid (50.4 g, 277 mmol), $K_2CO_3$ (60.4 g, 437 mmol), and $Pd(PPh_3)_4$ (10.1 g, 8.7 mmol) were dissolved in THF (500 ml) and distilled water (200 ml) in a round-bottomed flask and then, stirred under reflux at 60° C. for 12 hours. When a reaction was completed, after removing an aqueous layer therefrom, column chromatography (hexane:DCM (20%)) was conducted, obtaining 38 g (51%) of Intermediate Int-1.

Synthesis Example 2: Synthesis of Intermediate Int-2

[Reaction Scheme 2]

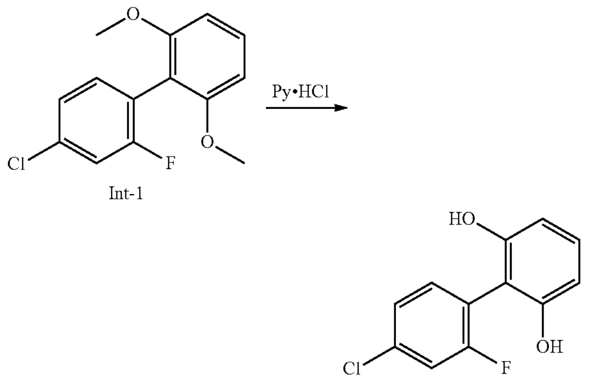

Int-1

Int-2

Intermediate Int-1 (38 g, 142 mmol) and pyridine hydrochloride (165 g, 1425 mmol) were placed in a round-bottomed flask and stirred under reflux at 200° C. for 24 hours. When a reaction was completed, the resultant was cooled to room temperature and slowly poured into distilled water and then, stirred for 1 hour. A solid was filtered therefrom, obtaining 23 g (68%) of Intermediate Int-2.

Synthesis Example 3: Synthesis of Intermediate Int-3

[Reaction Scheme 3]

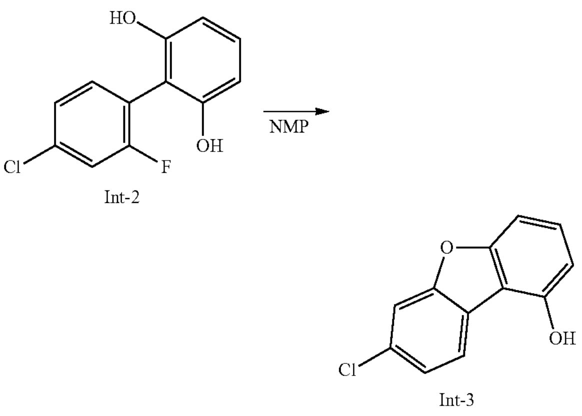

Intermediate Int-2 (23 g, 96 mmol) and $K_2CO_3$ (20 g, 144 mmol) were dissolved in NMP (100 ml) in a round bottomed flask and then, stirred under reflux at 180° C. for 12 hours. When a reaction was completed, the mixture was poured into an excessive amount of distilled water. Subsequently, a solid was filtered therefrom, dissolved in ethyl acetate, and dried with $MgSO_4$, and a solvent was removed from an organic layer under a reduced pressure. Column chromatography (hexane:ethyl acetate 30%) was performed, obtaining 16 g (76%) of Intermediate Int-3.

Synthesis Example 4: Synthesis of Intermediate Int-4

[Reaction Scheme 4]

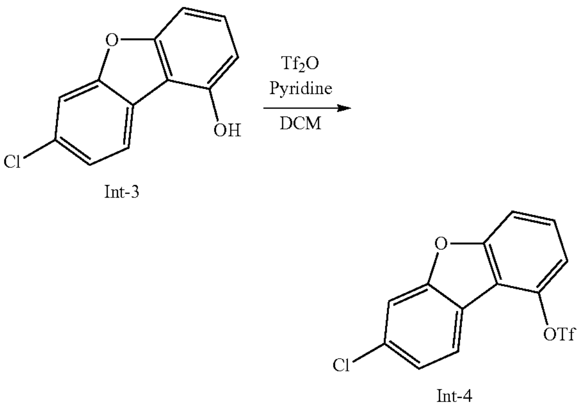

Intermediate Int-3 (16 g, 73 mmol) and pyridine (12 ml, 146 mmol) were dissolved in DCM (200 ml) in a round-bottomed flask. After lowering the temperature to 0° C., trifluoromethanesulfonic anhydride (14.7 ml, 88 mmol) was slowly added thereto in a dropwise fashion. After stirring the obtained mixture for 6 hours, when a reaction was completed, an excessive amount of distilled water was added thereto and then, stirred for 30 minutes and extracted with DCM. After removing an organic solvent under a reduced pressure, the rest was vacuum-dried, obtaining 22.5 g (88%) of Intermediate Int-4.

Synthesis Example 5: Synthesis of Intermediate Int-5

[Reaction Scheme 5]

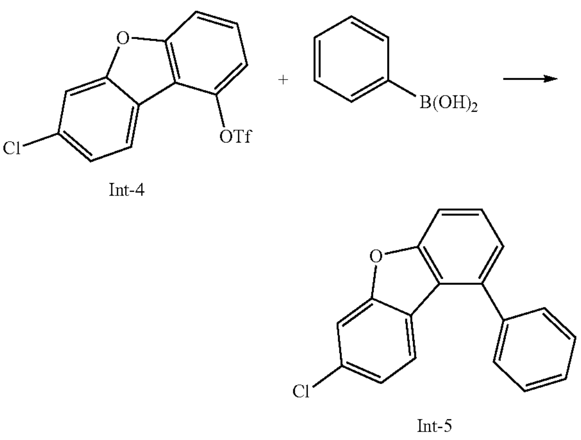

14.4 g (81%) of Intermediate Int-5 was synthesized in the same manner as Synthesis Example 1 except that Intermediate Int-4 (22.5 g, 64 mmol), phenylboronic acid (7.8 g, 64 mmol), $K_2CO_3$ (13.3 g, 96 mmol), and $Pd(PPh_3)_4$ (3.7 g, 3.2 mmol) were used.

Synthesis Example 6: Synthesis of Intermediate Int-6

[Reaction Scheme 6]

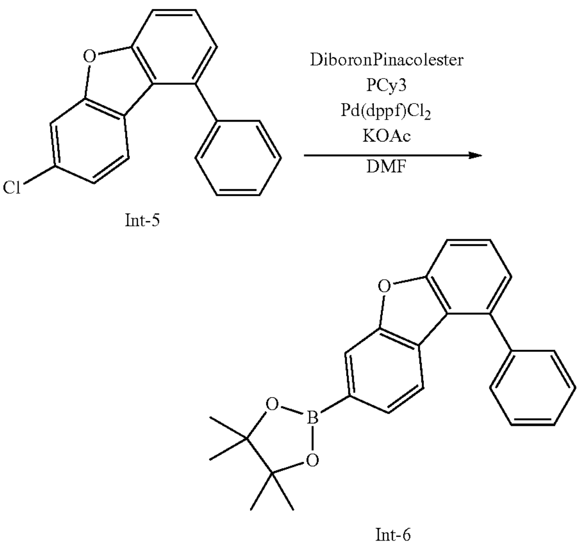

Intermediate Int-5 (22.5 g, 80 mmol), bis(pinacolato) diboron (24.6 g, 97 mmol), $Pd(dppf)Cl_2$ (2 g, 2.4 mmol), tricyclohexylphosphine (3.9 g, 16 mmol), and potassium acetate (16 g, 161 mmol) were dissolved in DMF (320 ml)

in a round-bottomed flask. The mixture was stirred under reflux at 120° C. for 10 hours. When a reaction was completed, the mixture was poured into an excessive amount of distilled water and then, stirred for 1 hour. A solid was filtered therefrom and then, dissolved in DCM. $MgSO_4$ was used to remove moisture therefrom, and an organic solvent was filtered with a silica gel pad and removed under a reduced pressure. The solid was recrystallized with ethyl acetate and hexane, obtaining 26.9 g (90%) of Intermediate Int-6.

<Synthesis of Core 2>

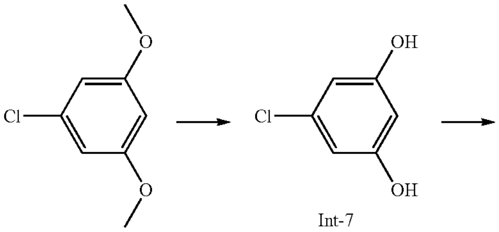

Int-7

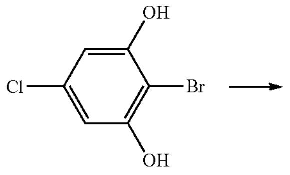

Int-8

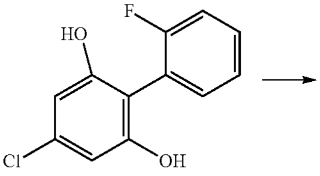

Int-9

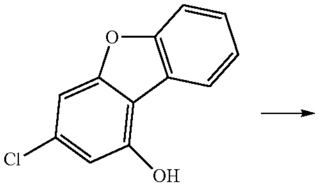

Int-10

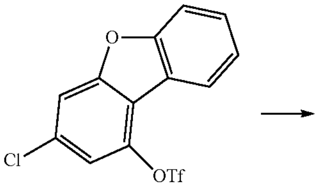

Int-11

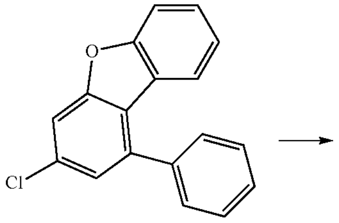

Int-12

-continued

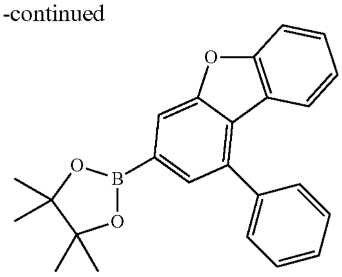

Int-13

Synthesis Example 7: Synthesis of Intermediate Int-7

[Reaction Scheme 7]

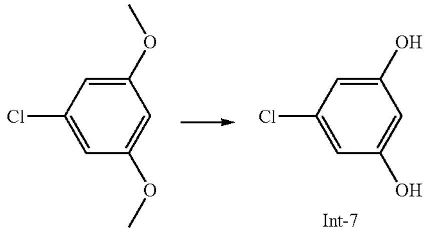

Int-7

1-chloro-3,5-dimethoxybenzene (70 g, 406 mmol) and pyridine hydrochloride (468 g, 4055 mmol) were placed in a round-bottomed flask and stirred under reflux at 200° C. for 24 hours. When a reaction was completed, the resultant was cooled to room temperature and slowly poured into distilled water and then, stirred for 1 hour. A solid was filtered therefrom, obtaining 51.6 g (88%) of Intermediate Int-7.

Synthesis Example 8: Synthesis of Intermediate Int-8

[Reaction Scheme 8]

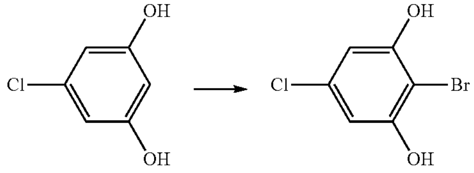

Int-7 Int-8

Intermediate Int-7 (51.6 g, 357 mmol) and p-toluenesulfonic acid monohydrate (6.8 g, 36 mmol) were placed in a round-bottomed flask and dissolved in methanol (500 ml). A solution prepared by dissolving NBS (63.5 g, 357 mmol) in 1 L of methanol was slowly added thereto in a dropwise fashion at 0° C. for 30 minutes. After stirring the obtained mixture for 1 hour at room temperature, when a reaction was completed, a sodium thiosulfate saturated solution was poured thereinto and then, stirred. After adding DCM thereto for extraction, a solvent was removed therefrom under a reduced pressure. Flash column chromatography was conducted, separating and obtaining 72 g (90%) of Intermediate Int-8.

Synthesis Example 9: Synthesis of Intermediate Int-9

[Reaction Scheme 9]

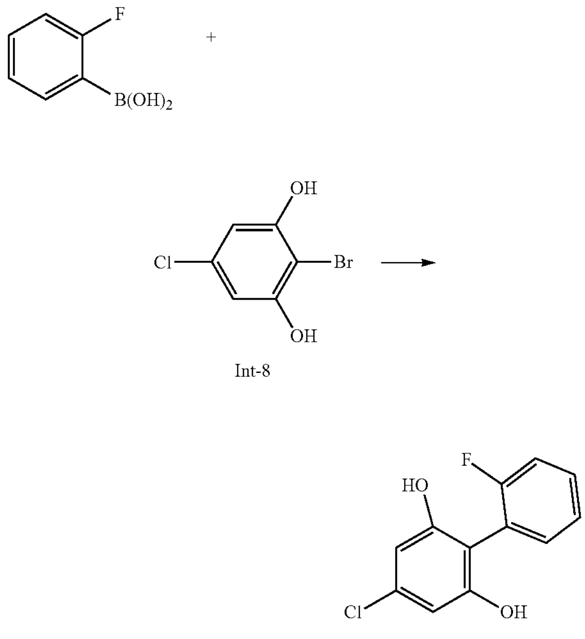

Int-8

Int-9

34.5 g (45%) of Intermediate Int-9 was synthesized in the same manner as Synthesis Example 1 except that 2-fluorophenylboronic acid (45 g, 322 mmol), Intermediate Int-8 (72 g, 322 mmol), $K_2CO_3$ (97.8 g, 708 mmol), and $Pd(PPh_3)_4$ (11.2 g, 9.7 mmol) were used under a nitrogen condition in a round-bottomed flask.

Synthesis Example 10: Synthesis of Intermediate Int-10

[Reaction Scheme 10]

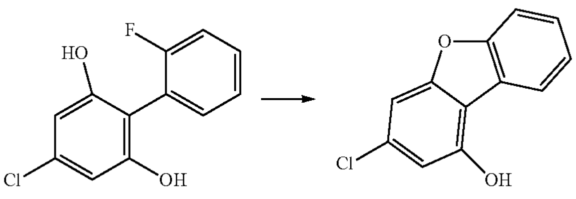

Int-9

Int-10

26.9 g (85%) of Intermediate Int-10 was synthesized in the same manner as Synthesis Example 3 except that Intermediate Int-9 (34.5 g, 145 mmol) and $K_2CO_3$ (26 g, 188 mmol) were dissolved in NMP (450 ml) in a round-bottomed flask.

Synthesis Example 11: Synthesis of Intermediate Int-11

[Reaction Scheme 11]

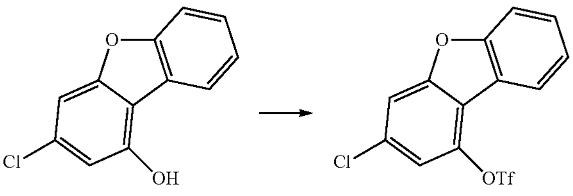

Int-10

Int-11

Intermediate Int-10 (26.9 g, 123 mmol) and pyridine (20 ml, 246 mmol) were dissolved in DCM (300 ml) in a round-bottomed flask. After lowering the temperature to 0° C., trifluoromethanesulfonic anhydride (24.7 ml, 148 mmol) was slowly added thereto in a dropwise fashion. After stirring the obtained mixture for 6 hours, when a reaction was completed, an excessive amount of distilled water was added thereto and then, stirred for 30 minutes and extracted with DCM. After removing an organic solvent therefrom under a reduced pressure, the rest was vacuum-dried, obtaining 36.2 g (84%) of Intermediate Int-11.

Synthesis Example 12: Synthesis of Intermediate Int-12

[Reaction Scheme 12]

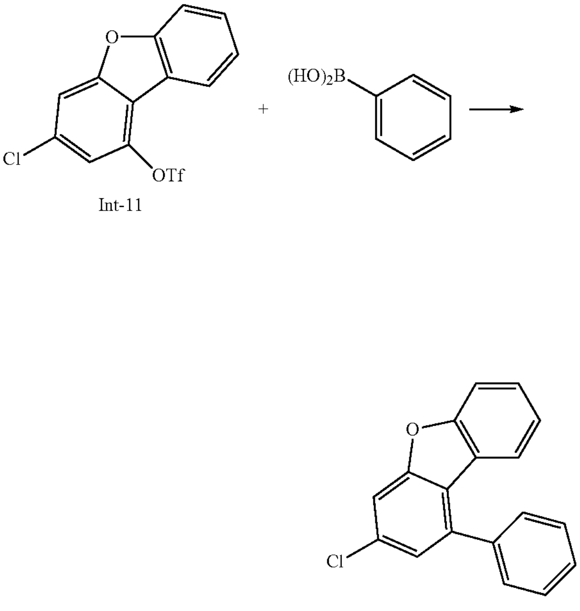

Int-11

Int-12

25.9 g (90%) of Intermediate Int-12 was synthesized in the same manner as Synthesis Example 1 except that Intermediate Int-11 (36.2 g, 103 mmol), phenylboronic acid (12.6 g, 103 mmol), $K_2CO_3$ (21.4 g, 155 mmol), and $Pd(PPh_3)_4$ (5.9 g, 5 mmol) were used.

Synthesis Example 13: Synthesis of Intermediate Int-13

[Reaction Scheme 13]

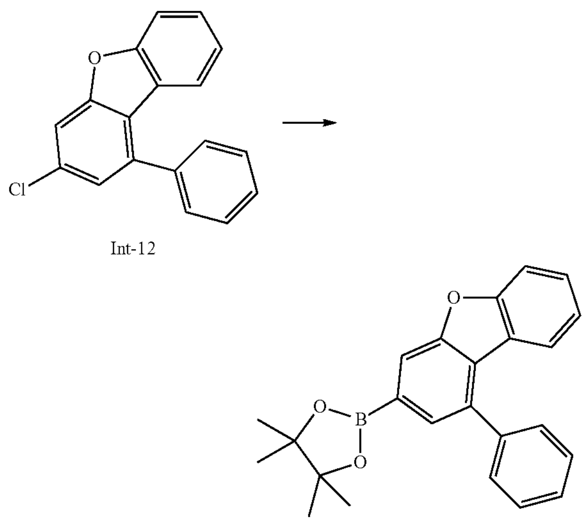

Int-12

Int-13

25.8 g (75%) of Intermediate Int-13 was obtained in the same manner as Synthesis Example 6 except that Intermediate Int-12 (25.9 g, 93 mmol), bis(pinacolato)diboron (28.3 g, 112 mmol), $Pd(dppf)Cl_2$ (2.3 g, 2.8 mmol), tricyclohexylphosphine (4.5 g, 18.6 mmol), and potassium acetate (18.2 g, 186 mmol) were dissolved in DMF (350 ml) in a round-bottomed flask.

Synthesis Example 14: Synthesis of Intermediate Int-14

[Reaction Scheme 14]

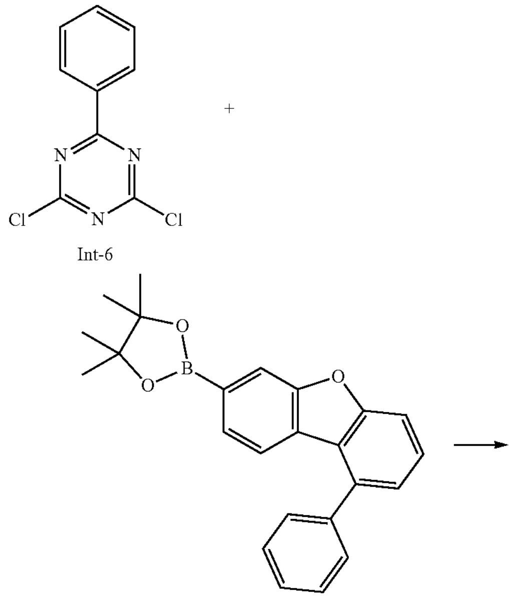

Int-6

+

Int-14

-continued

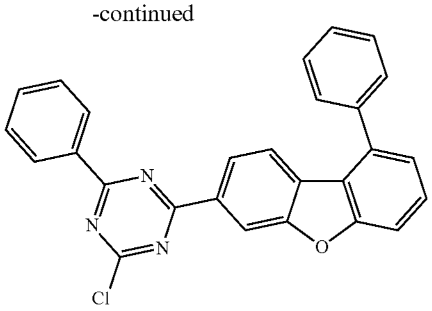

2,4-dichloro-6-phenyl-1,3,5-triazine (36.63 g, 162.05 mmol), Intermediate Int-6 (40 g, 108.04 mmol), $K_2CO_3$ (44.79 g, 324.11 mmol), and $Pd(PPh_3)_4$ (5.9 g, 5 mmol) were dissolved in THE (500 ml) and distilled water (200 ml) in a round-bottomed flask and then, stirred under reflux at 60° C. for 12 hours. When a reaction was completed, after removing an aqueous layer therefrom, a solid was obtained by removing an organic solvent therefrom under a reduced pressure. The obtained solid was placed in a hexane solvent and then, filtered and stirred for 30 minutes. Subsequently, the solid was vacuum-dried, obtaining 24 g (51%) of Intermediate Int-14.

Intermediates Int-15, Int-16, Int-17, Int-18, and Int-19 were obtained in the same manner as Synthesis Example 14 except that the triazine intermediate was changed.

Int-15

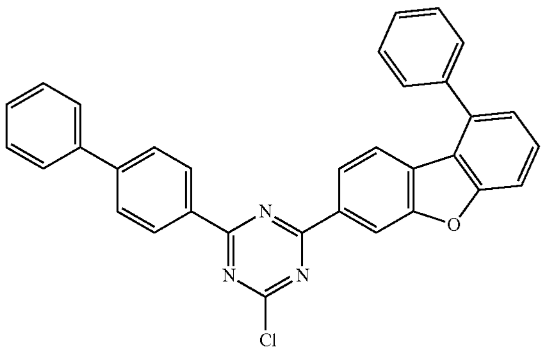

Int-16

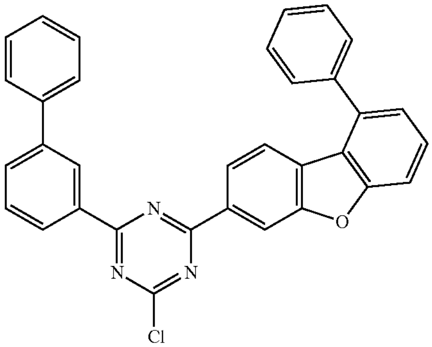

-continued

Int-17

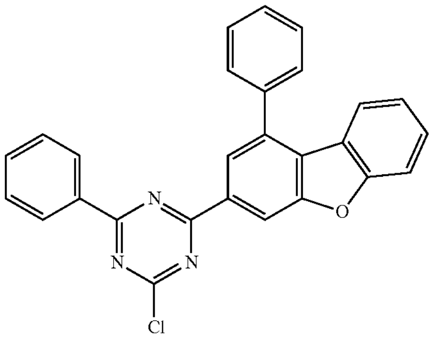

Int-18

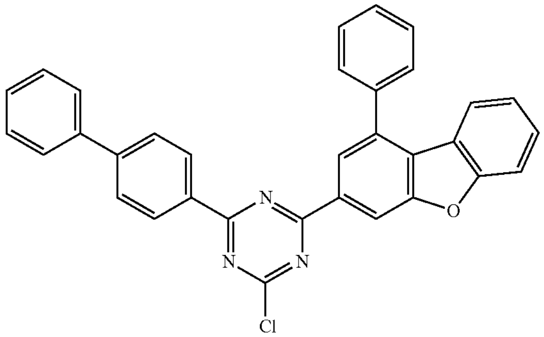

Int-19

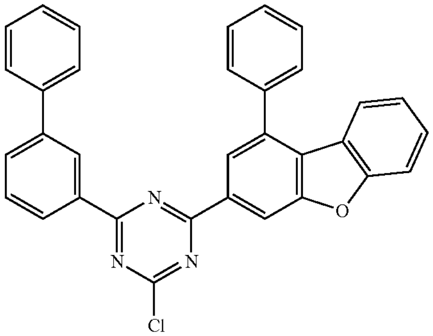

<Synthesis of Core 3>

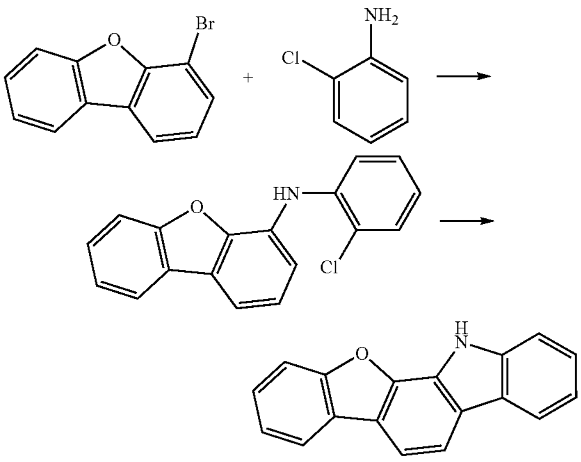

Int-20 Int-21

Synthesis Example 15: Synthesis of Intermediate Int-20

[Reaction Scheme 15]

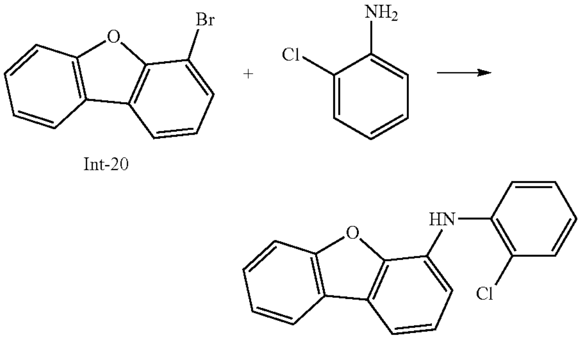

4-bromodibenzofuran (50 g, 202.36 mmol), 2-chloroaniline (38.72 g, 303.53 mmol), $Pd_2(dba)_3$ (9.26 g, 10.12 mmol), $P(t\text{-}bu)_3$ (7.39 ml, 30.35 mmol), and NaO(t-Bu) (29.17 g, 303.53 mmol) were dissolved in toluene (650 ml) in a round-bottomed flask and then, stirred under reflux at 130° C. for 12 hours. When a reaction was completed, after removing an aqueous layer therefrom, column chromatography (hexane:DCM 20%) was conducted, obtaining 38 g (64%) of Intermediate Int-20.

Synthesis Example 16: Synthesis of Intermediate Int-21

[Reaction Scheme 16]

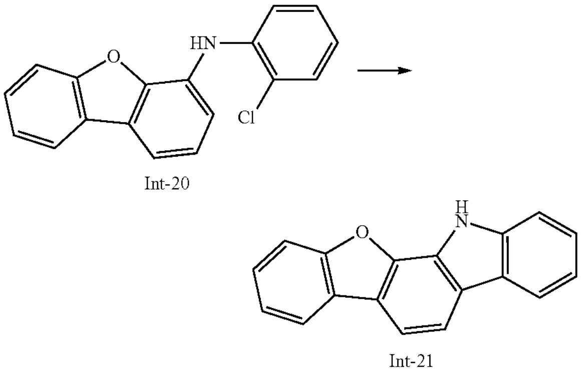

Intermediate Int-20 (50 g, 170.21 mmol), $Pd_2(dba)_3$ (7.79 g, 8.51 mmol), $CS_2CO_3$ (110.91 g, 340.43 mmol), and PCy3·H·$BF_4$ (6.27 g, 17.02 mmol) were dissolved in DMAc (550 ml) under a nitrogen condition and then, stirred under reflux at 160° C. for 12 hours. When a reaction was completed, an excessive amount of distilled water was poured thereinto and then, stirred for 1 hour. A solid therein was filtered and dissolved in MCB of a high temperature. After removing moisture with $MgSO_4$ and filtering an organic solvent by using a silica gel pad, a filtrate therefrom was stirred. A solid produced therein was filtered and vacuum-dried, obtaining 26.9 g (62%) of Intermediate Int-21.

Intermediates Int-22, Int-23, Int-24, Int-25, Int-26, Int-27, Int-28, and Int-29 were obtained in the same manner as Synthesis Examples 15 and 16 except that the dibenzofuran intermediate was changed.

Int-22

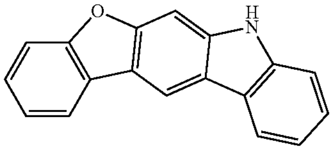

Int-23

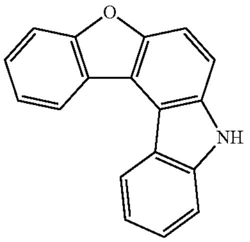

Int-24

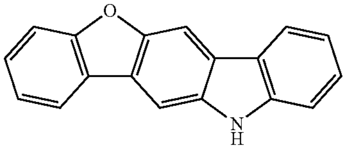

Int-25

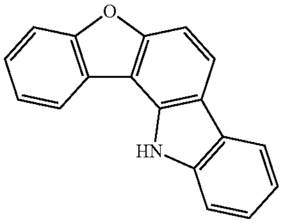

Int-26

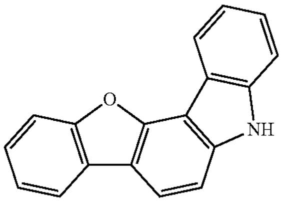

Int-27

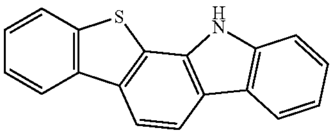

Int-28

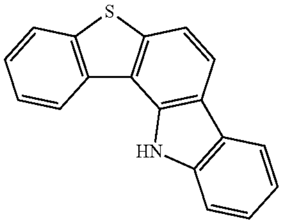

-continued

Int-29

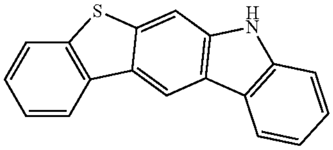

Synthesis Example 17: Synthesis of Compound B-1

[Reaction Scheme 17]

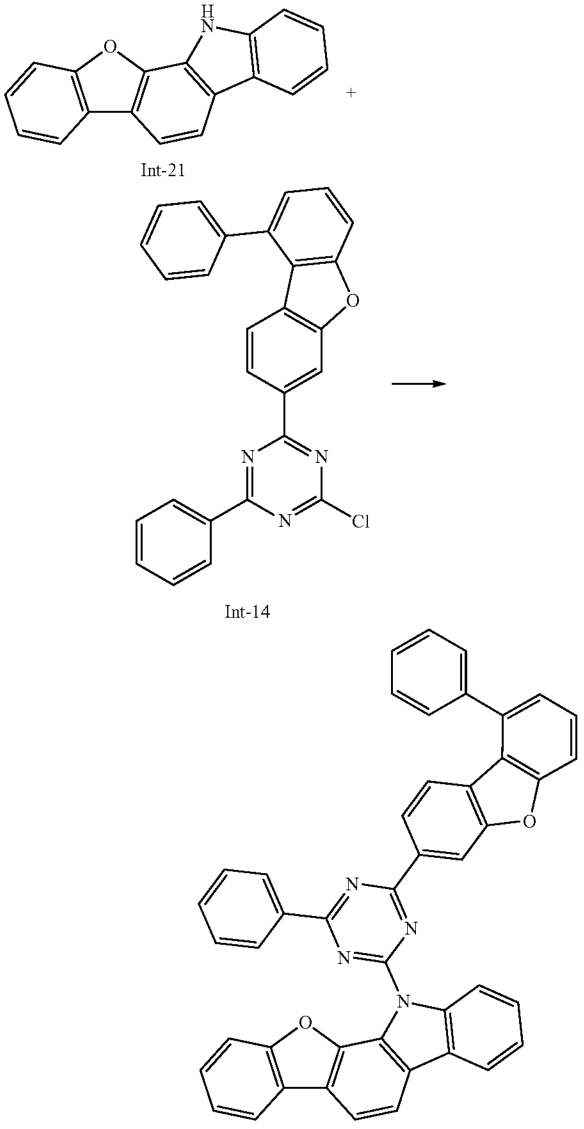

Int-21

Int-14

B-1

Intermediate Int-21 (11.5 g, 44.7 mmol), Intermediate Int-14 (20.94 g, 48.27 mmol), and NaH (2.36 g, 98.33 mmol) were dissolved in DMF (150 ml) in a round-bottomed flask under a nitrogen condition and then, stirred under reflux at room temperature for 12 hours. When a reaction was completed, an excessive amount of distilled water was poured thereinto and then, stirred for 1 hour. A solid was filtered therefrom and then, dissolved in MCB of a high temperature. After removing moisture with $MgSO_4$ and filtering an organic solvent with a silica gel pad, a filtrate therefrom was stirred. A solid produced therein was filtered and vacuum-dried, obtaining 27 g (92%) of Compound B-1.

The following compound was synthesized in the same manner as Synthesis Example 17 except that the intermediate was changed.

TABLE 1

| Synthesis Examples | Intermediate 1 | Intermediate 2 | Amount (yield) | Final product |
|---|---|---|---|---|
| Synthesis Example 18 | 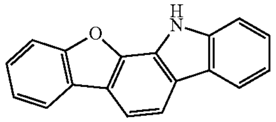 Int-21 | 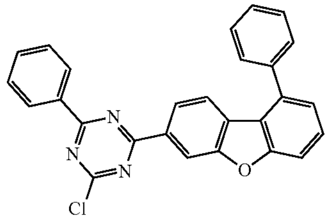 Int-14 | 27.0 g (92%) | 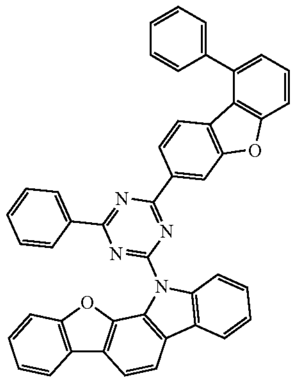 B-1 |
| Synthesis Example 19 | 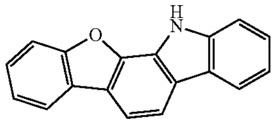 Int-21 | 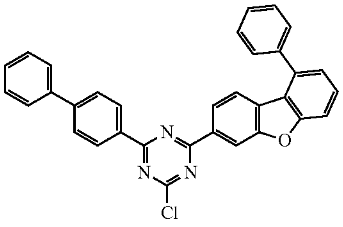 Int-15 | 24.1 g (84%) | 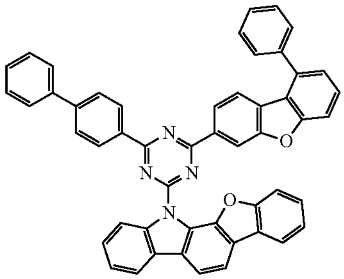 B-2 |
| Synthesis Example 20 | 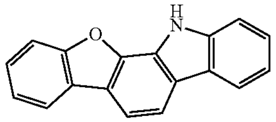 Int-21 | 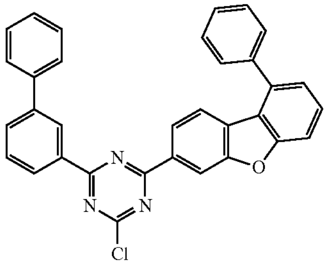 Int-16 | 5.2 g (74%) | 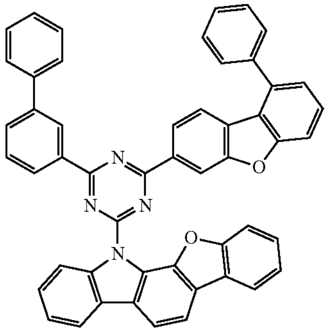 B-3 |
| Synthesis Example 21 | 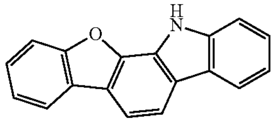 Int-21 | 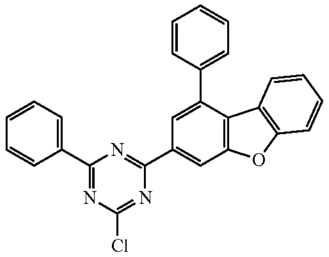 Int-17 | 6.8 g (85%) | 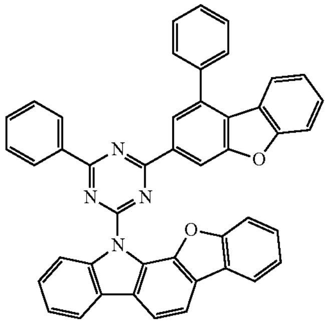 B-41 |

TABLE 1-continued
| Synthesis Examples | Intermediate 1 | Intermediate 2 | Amount (yield) | Final product |
|---|---|---|---|---|
| Synthesis Example 22 | 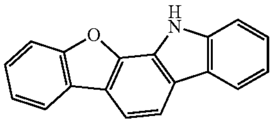 Int-21 | 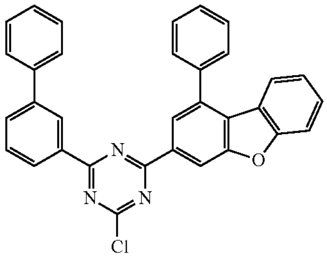 Int-19 | 10.3 g (87%) | 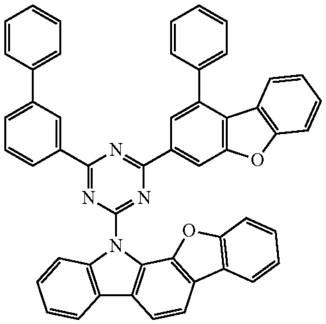 B-44 |
| Synthesis Example 23 | 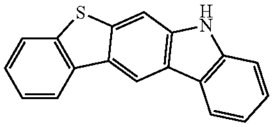 Int-29 | 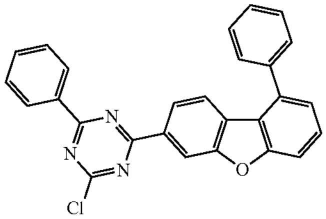 Int-14 | 12.6 g (91%) | 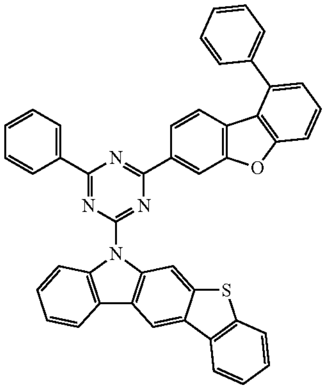 A-21 |
| Synthesis Example 24 | 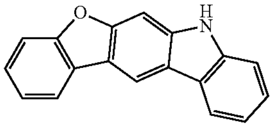 Int-22 | 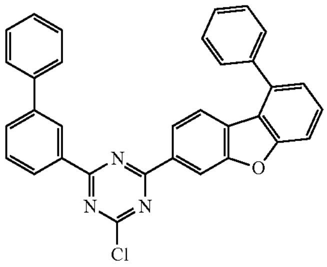 Int-16 | 15.3 g (68%) | 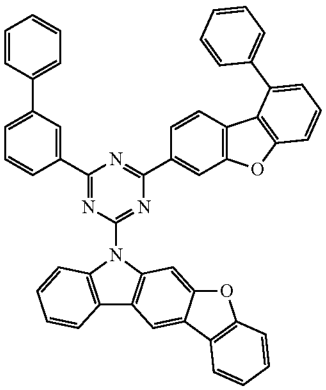 A-3 |

TABLE 1-continued
| Synthesis Examples | Intermediate 1 | Intermediate 2 | Amount (yield) | Final product |
|---|---|---|---|---|
| Synthesis Example 25 | 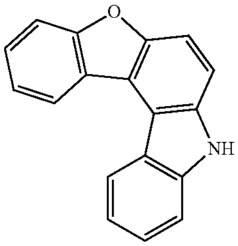 Int-23 | 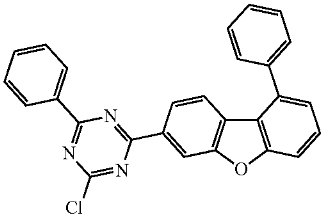 Int-14 | 16.2 g (78%) | 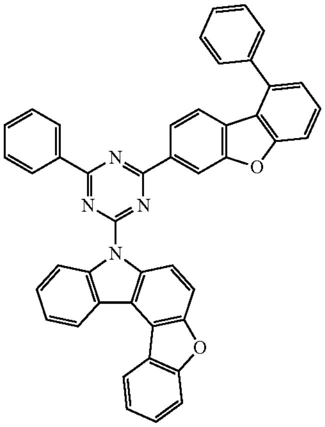 C-1 |
| Synthesis Example 26 | 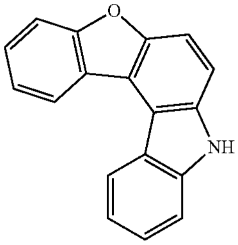 Int-23 | 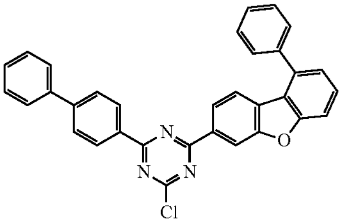 Int-15 | 25.3 g (69%) | 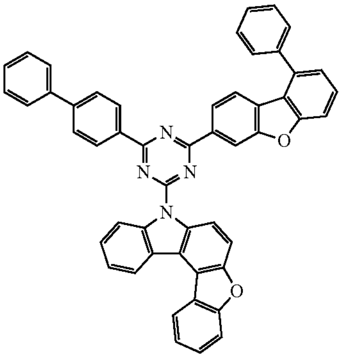 C-2 |
| Synthesis Example 27 | 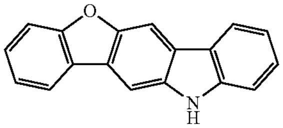 Int-24 | 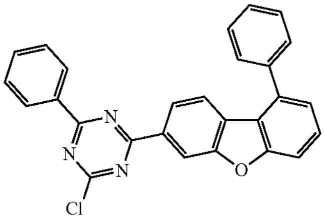 Int-14 | 10.5 g (90%) | 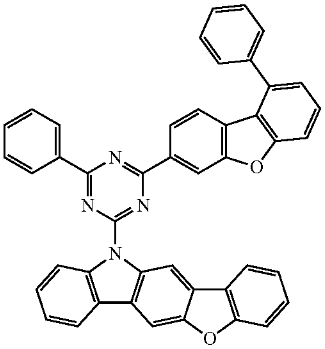 D-1 |
| Synthesis Example 28 | 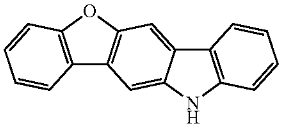 Int-24 | 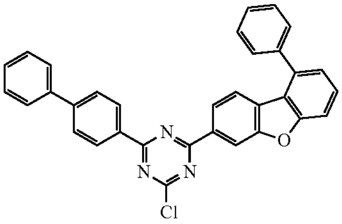 Int-15 | 6.8 g (64%) | 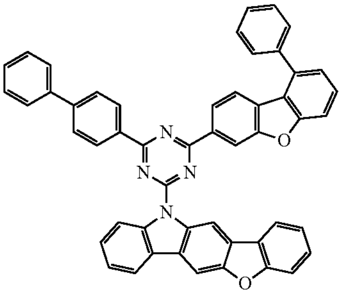 D-2 |

TABLE 1-continued
| Synthesis Examples | Intermediate 1 | Intermediate 2 | Amount (yield) | Final product |
|---|---|---|---|---|
| Synthesis Example 29 | 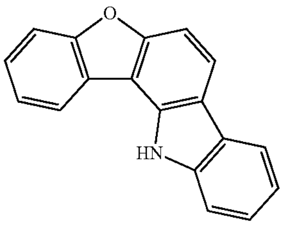 Int-25 | 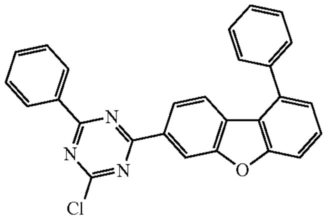 Int-14 | 20.4 g (91%) | 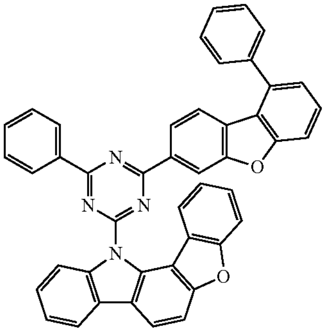 E-1 |
| Synthesis Example 30 | 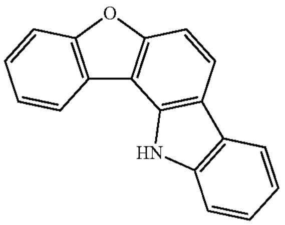 Int-25 | 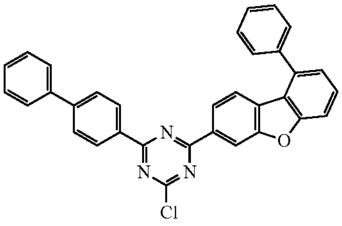 Int-15 | 16.9 g (88%) | 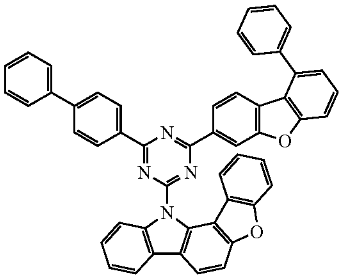 E-2 |
| Synthesis Example 31 | 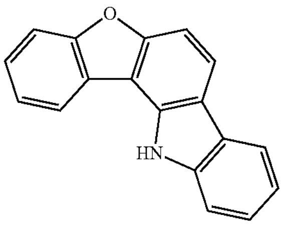 Int-25 | 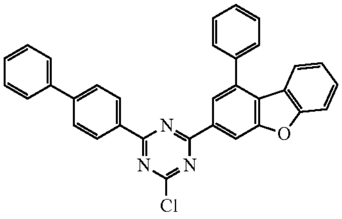 Int-18 | 7.6 g (84%) | 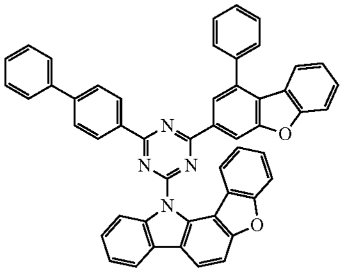 E-22 |
| Synthesis Example 32 | 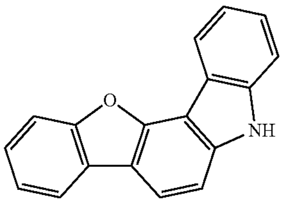 Int-26 | 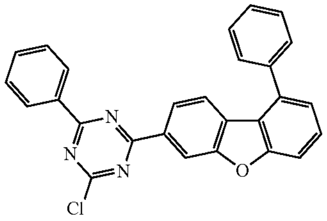 Int-14 | 13.6 g (95%) | 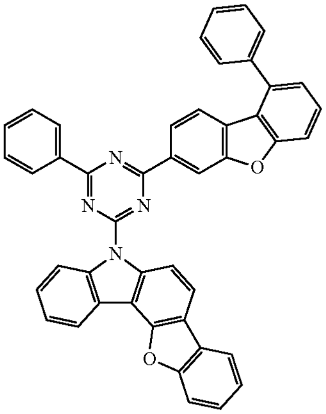 F-1 |

TABLE 1-continued
| Synthesis Examples | Intermediate 1 | Intermediate 2 | Amount (yield) | Final product |
|---|---|---|---|---|
| Synthesis Example 33 | 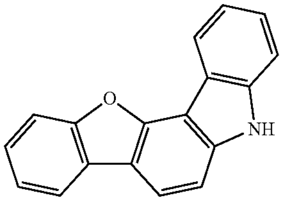 Int-26 | 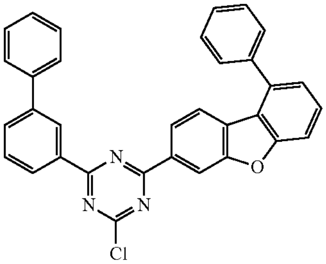 Int-16 | 15.2 g (70%) | 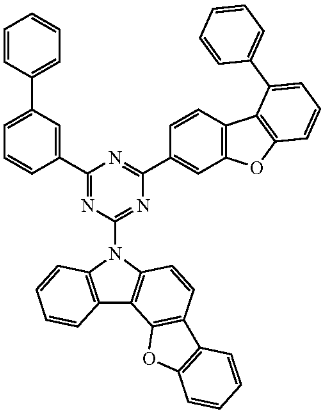 F-3 |
| Synthesis Example 34 | 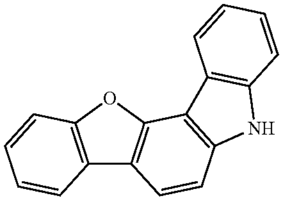 Int-26 | 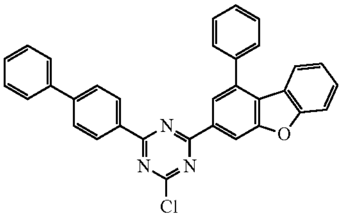 Int-18 | 17.2 g (62%) | 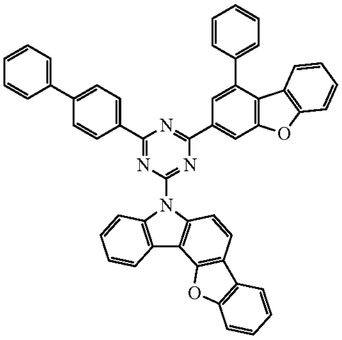 F-23 |
| Synthesis Example 35 | 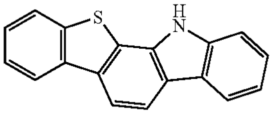 Int-27 | 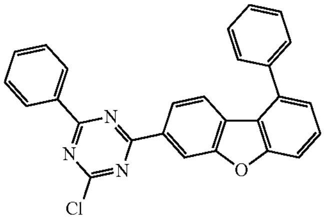 Int-14 | 14.2 g (72%) | 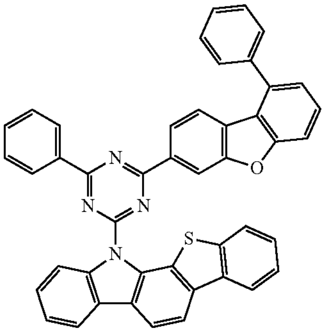 B-21 |
| Synthesis Example 36 | 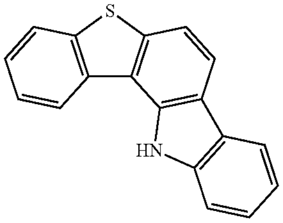 Int-28 | 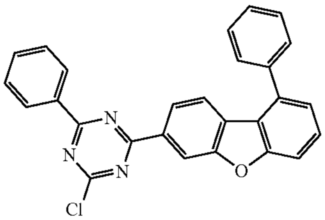 Int-14 | 17.1 g (76%) | 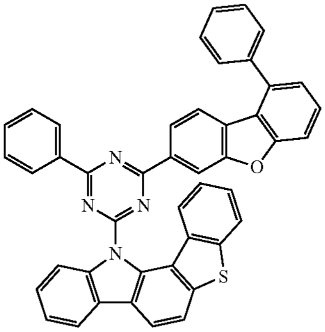 E-21 |

(Preparation of Second Compound)

Compound H-1 and Compound H-2 were synthesized in the same manner as known in KR2015-0070860.

H-1

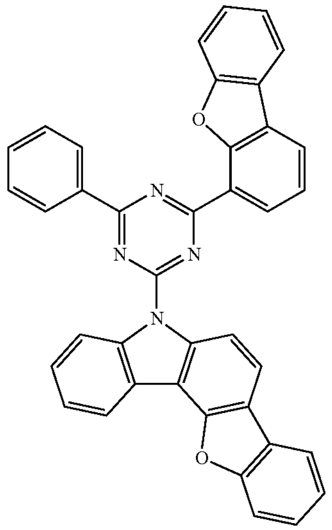

H-2

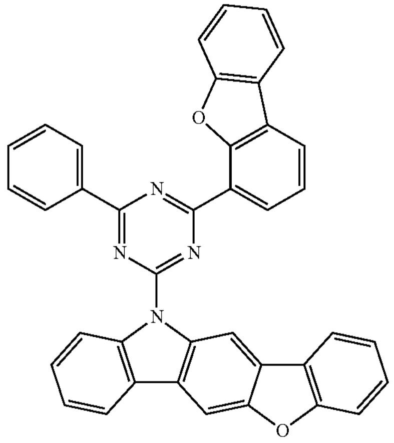

Compound H-3 was synthesized in the same manner as in JP5795896.

H-3

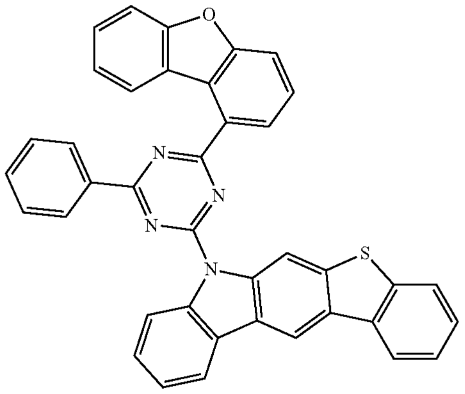

Compound H-4 was synthesized in the same manner as known in KR2019-0001357A.

H-4

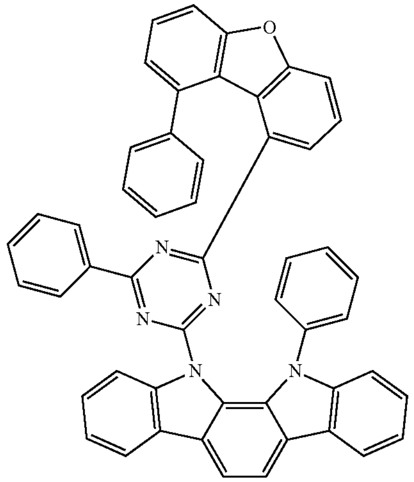

(Manufacture of Organic Light Emitting Diode)

Example 1

The glass substrate coated with ITO (Indium tin oxide) at a thickness of 1,500 Å was washed with ultrasonic waves. After washing with the distilled water, the glass substrate was washed with a solvent such as isopropyl alcohol, acetone, methanol, and the like ultrasonically and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, and Compound B was deposited to be 50 Å-thick on the injection layer, and then Compound C was deposited to be 1,020 Å-thick to form a hole transport layer. On the hole transport layer, 400 Å-thick light emitting layer was formed by using Compound F-1 obtained in Synthesis Example 32 as a host and doping 7 wt % of PhGD as a dopant by a vacuum-deposition. Subsequently, on the light emitting layer, a 300 Å-thick electron transport layer was formed by simultaneously vacuum-depositing Compound D and Liq in a ratio of 1:1, and on the electron transport layer, Liq and Al were sequentially vacuum-deposited to be 15 Å-thick and 1,200 Å-thick, manufacturing an organic light emitting diode.

The organic light emitting diode had a five-layered organic thin layer, and specifically the following structure.

ITO/Compound A (700 Å)/Compound B (50 Å)/Compound C (1,020 Å)/EML [Compound F-1: PhGD (7 wt %)] (400 Å)/Compound D:Liq (300 Å)/Liq (15 Å)/Al (1200 Å)

Compound A: N4,N4'-diphenyl-N4,N4'-bis(9-phenyl-9H-carbazol-3-yl)biphenyl-4,4'-diamine Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine Compound D: 8-(4-(4,6-di(naphthalen-2-yl)-1,3,5-triazin-2-yl)phenyl)quinoline

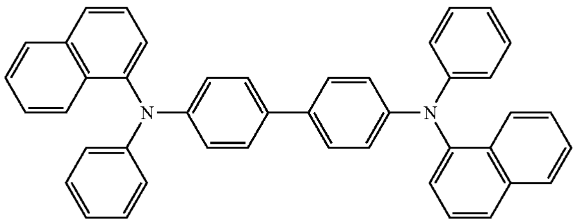

[NPB]

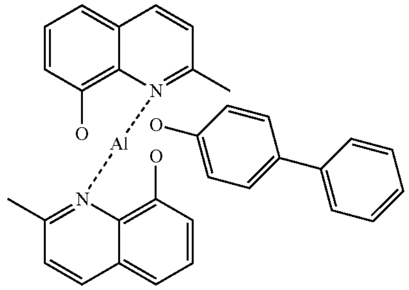

[BAlq]

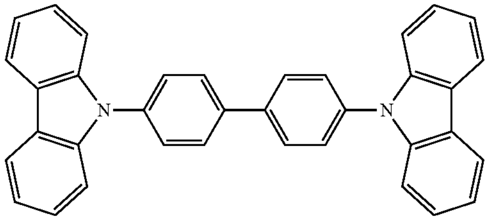

[CBP]

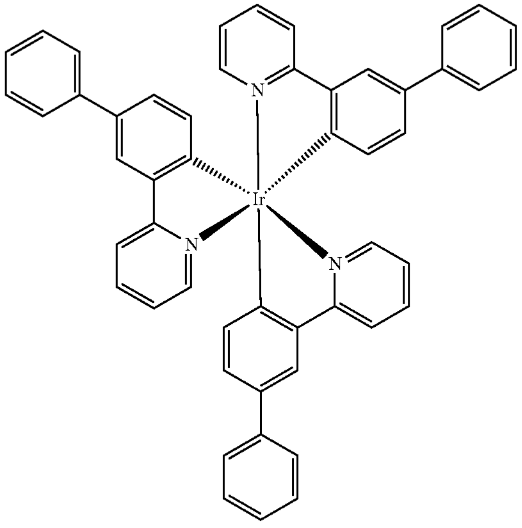

PhGD

Examples 2 to 6 and Comparative Examples 1 to 6

As described in Tables 2 to 7, each diode of Examples 2 to 6 and Comparative Examples 1 to 6 was manufactured according to the same method as Example 1 except that a host and a ratio thereof were changed.

Evaluation

Driving voltage, luminous efficiency, and life-span characteristics of the organic light emitting diodes of Examples 1 to 6 and Comparative Examples 1 to 6 were evaluated.

Specific measurement methods are as follows, and the results are shown in Tables 2 to 7.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Power Efficiency

Power efficiency (cd/A) at the same current density (10 mA/cm$^2$) were calculated by using the luminance and current density from the items (1) and (2).

(4) Measurement of Life-Span

The results were obtained by measuring a time when power efficiency (cd/A) was decreased down to 95%, while luminance (cd/m$^2$) was maintained to be 24,000 cd/m$^2$.

(5) Measurement of Driving Voltage

A driving voltage of each diode was measured using a current-voltage meter (Keithley 2400) at 15 mA/cm$^2$.

(6) Calculation of T95 Life-Span Ratio (%)

Relative values of T95 (h) of single hosts or the examples of mixed hosts (applying a first compound for an organic optoelectronic element as a first host) and the comparative examples of the mixed hosts (applying a comparative compound as a first host), which were all prepared by applying the same second host, were evaluated.

$$T95\text{ life-span ratio (\%)} = \{[T95(h)\text{ of Example or Comparative Example (applying a first compound for an organic optoelectronic element or a comparative compound as a single host or as a first host of a mixed host)}]/[T95(h)\text{ of reference data (applying the comparative compound as a single host or a first host of the mixed host)}]\}\times 100$$

(7) Calculation of Driving Voltage Ratio (%)

Relative values of the single hosts or the mixed hosts of the examples (applying a first compound for an organic optoelectronic element as a first host) and the comparative examples (applying a comparative compound as a first host), which were all prepared by applying the same second host, were evaluated.

$$\text{Driving voltage ratio (\%)} = \{[\text{driving voltage (V) of Example or Comparative Example (applying a first compound for an organic optoelectronic element or a comparative compound as single host or as first host of mixed host)}]/[\text{driving voltage (V) of reference data (applying the comparative compound as a single host or a first host of a mixed host)}]\}\times 100$$

(8) Calculation of Power Efficiency Ratio (%)

Relative values of the single hosts or the examples of the mixed hosts (applying a first compound for an organic optoelectronic element as a first host) or the comparative examples (applying a comparative compound as a first host), which were all prepared by applying the same second host, were evaluated.

Power efficiency ratio (%) = {[electric power efficiency ($Cd/A$) of Example or Comparative Example (applying a first compound for an organic optoelectronic element as a single host or as a first host of a mixed host)]/[electric power efficiency ($Cd/A$) of reference data (applying the comparative compound as a single host or as a first host of a mixed host)]}×100

TABLE 2

| | Single host | Power efficiency ratio (%) | T95 life-span ratio (%) |
|---|---|---|---|
| Example 1 | F-1 | 107% | 182% |
| Comparative Example 1 | H-1 | 100% | 100% |

TABLE 3

| | Single host | Driving voltage ratio (%) | T95 life-span ratio (%) |
|---|---|---|---|
| Example 2 | D-1 | 97% | 144% |
| Comparative Example 2 | H-2 | 100% | 100% |

TABLE 4

| | Single host | Driving voltage ratio (%) | T95 life-span ratio (%) |
|---|---|---|---|
| Example 3 | A-21 | 96% | 151% |
| Comparative Example 3 | H-3 | 100% | 100% |

TABLE 5

| | Host | | | Driving voltage ratio (%) | T95 life-span ratio (%) |
|---|---|---|---|---|---|
| | First host | Second host | Ratio of First and Second hosts | | |
| Example 4 | B-1 | I-99 | 3:7 | 94% | 130% |
| Comparative Example 4 | H-4 | I-99 | 3:7 | 100% | 100% |

TABLE 6

| | Host | | | T95 life-span ratio (%) |
|---|---|---|---|---|
| | First host | Second host | Ratio of First and Second hosts | |
| Example 5 | F-1 | I-99 | 3:7 | 210% |
| Comparative Example 5 | H-1 | I-99 | 3:7 | 100% |

TABLE 7

| | Host | | | | |
|---|---|---|---|---|---|
| | First host | Second host | Ratio of First and Second hosts | Driving voltage ratio (%) | T95 life-span ratio (%) |
| Example 6 | A-21 | I-99 | 3:7 | 96% | 162% |
| Comparative Example 6 | H-3 | I-99 | 3:7 | 100% | 100% |

Referring to Tables 2 to 7, the present invention had structural similarity to Comparative Examples 1, 2, 3, 4, 5, and 6 in terms of including dibenzofuran but had a difference therefrom in that the dibenzofuran was substituted with an aryl at the $1^{st}$ position of the dibenzofuran, and accordingly, the material of the present invention had significantly changed molecular properties and stability and thus greatly increased a life-span and improved electric power efficiency or a driving voltage.

In addition, the present invention included benzofuran (benzothiophene)carbazole instead of the indolocarbazole, which is different from Comparative Example 4, and accordingly, the material of the present invention had optimal balance between holes and electrons, slightly pulled the driving voltage, and greatly improved a life-span.

This effect appeared in the same manner in a mixed host as well as a single host.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound for an organic optoelectronic element represented by a combination of Chemical Formula 1 to Chemical Formula 3:

[Chemical Formula 1]

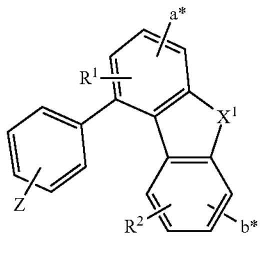

-continued

[Chemical Formula 2]

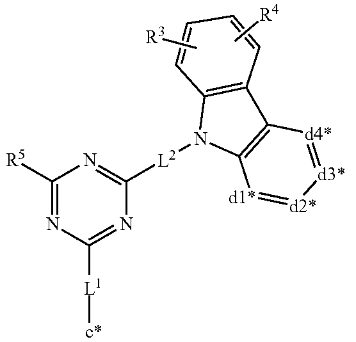

[Chemical Formula 3]

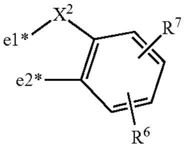

wherein, in Chemical Formula 1 to Chemical Formula 3, $X^1$ and $X^2$ are each independently O or S, Z is hydrogen, deuterium, a substituted or unsubstituted C1 to C10 alkyl group, or a substituted or unsubstituted phenyl group, $L^1$ and $L^2$ are each independently a single bond or a substituted or unsubstituted C6 to C20 arylene group, a* or b* of Chemical Formula 1 is linked to c* of Chemical Formula 2, two adjacent ones of $d_1$* to $d_4$* of Chemical Formula 2 are linking carbons linked at $e_1$* and $e_2$* of Chemical Formula 3, respectively, the remaining a* or b*, not linked to c* of Chemical Formula 2, is $R^a$, the remaining two of $d_1$* to $d_4$* of Chemical Formula 2, not linked at $e_1$* and $e_2$* of Chemical Formula 3, are each independently $CR^b$, and $R^a$, $R^b$, and $R^1$ to $R^7$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

2. The compound as claimed in claim 1, wherein:

the combination of Chemical Formulas 1 and 2 is represented by Chemical Formula 1A or Chemical Formula 1B:

[Chemical Formula 1A]

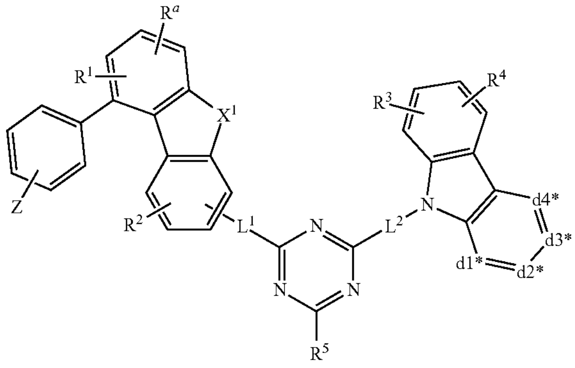

-continued

[Chemical Formula 1B]

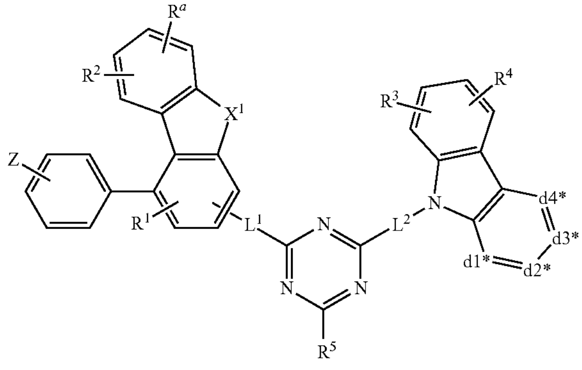

in Chemical Formula 1A and Chemical Formula 1B, $X^1$, Z, $L^1$, $L^2$, $R^a$, $R^1$ to $R^5$, and $d_1$* to $d_4$* are defined the same as those of Chemical Formula 1 and Chemical Formula 2.

3. The compound as claimed in claim 1, wherein:

the combination of Chemical Formulas 1 and 2 is represented by Chemical Formula Chemical Formula 1A-3 or Chemical Formula 1B-2:

[Chemical Formula 1A-3]

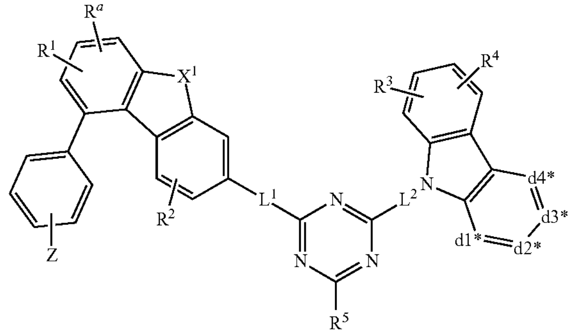

[Chemical Formula 1B-2]

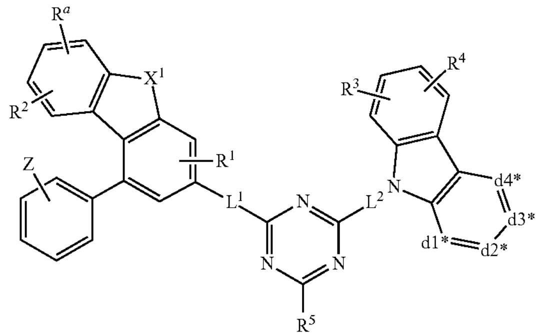

in Chemical Formula 1A-3 and Chemical Formula 1B-2, $X^1$, Z, $L^1$, $L^2$, $R^a$, $R^1$ to $R^5$, and $d_1$* to $d_4$* are defined the same as those of Chemical Formula 1 and Chemical Formula 2.

4. The compound as claimed in claim 3, wherein the combination of Chemical Formulas 1 and 2 is represented by Chemical Formula 1A-3.

5. The compound as claimed in claim 1, wherein the combination of Chemical Formulas 2 and 3 is represented by one of Chemical Formula 2A to Chemical Formula 2F:

[Chemical Formula 2A]

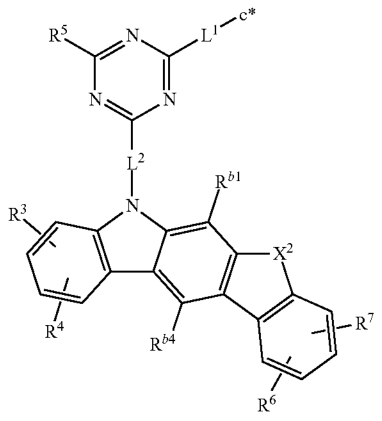

[Chemical Formula 2B]

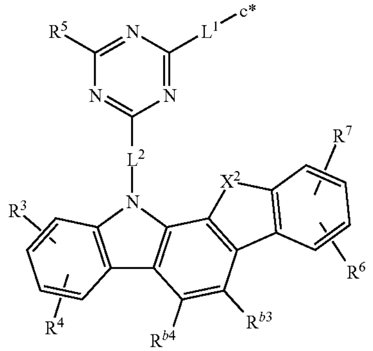

[Chemical Formula 2C]

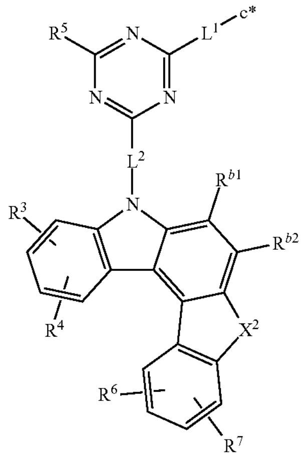

[Chemical Formula 2D]

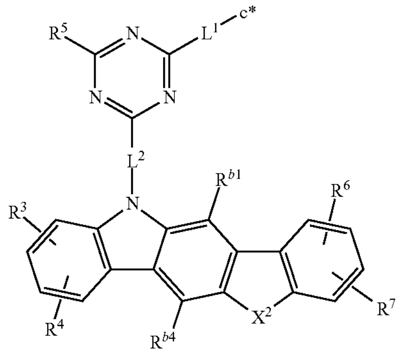

-continued

[Chemical Formula 2E]

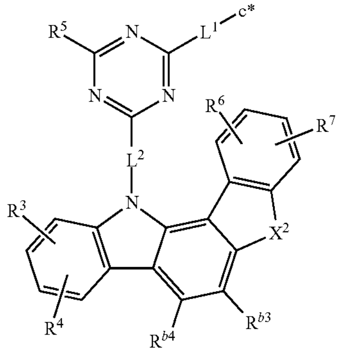

[Chemical Formula 2F]

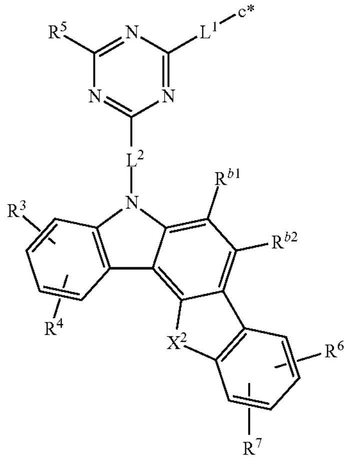

wherein, in Chemical Formula 2A to Chemical Formula 2F, $X^2$, $L^1$, $L^2$, c*, and $R^3$ to $R^7$ are defined the same as in claim 1, those of Chemical Formula 2 and Chemical Formula 3, and $R^{b1}$ to $R^{b4}$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

6. The compound as claimed in claim 5, wherein the combination of Chemical Formulas 2 and 3 is represented by one of Chemical Formula 2A, Chemical Formula 2B, Chemical Formula 2D, and Chemical Formula 2F.

7. The compound as claimed in claim 1, wherein the combination of Chemical Formulas 1 to 3 is represented by one of Chemical Formula 1A-3-2A, Chemical Formula 1A-3-2B, Chemical Formula 1A-3-2D, and Chemical Formula 1A-3-2F:

[Chemical Formula 1A-3-2A]

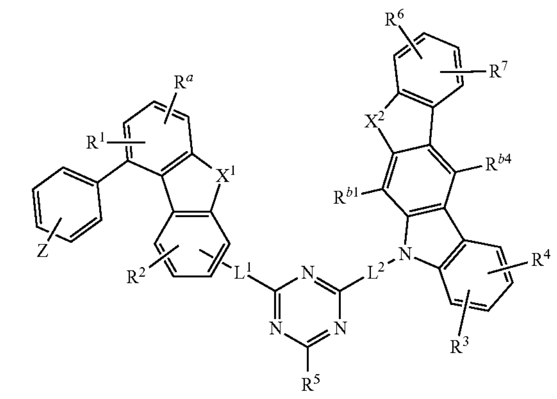

[Chemical Formula 1A-3-2B]

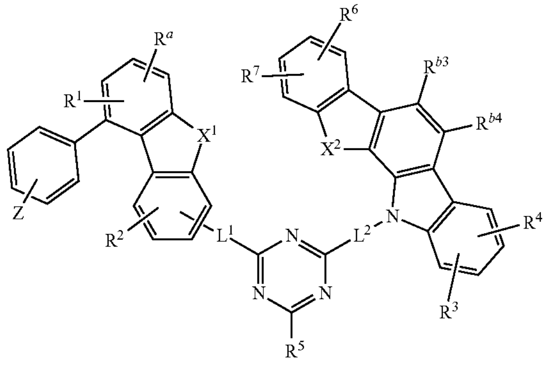

[Chemical Formula 1A-3-2D]

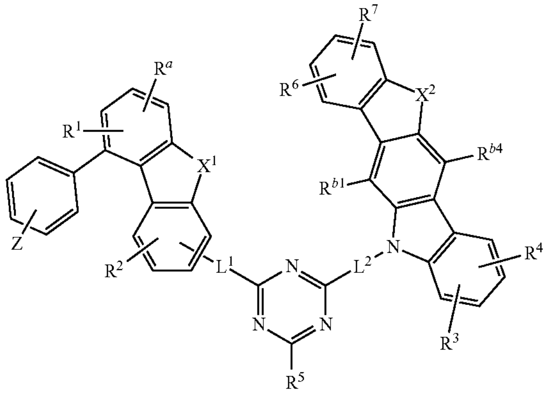

-continued

[Chemical Formula 1A-3-2F]

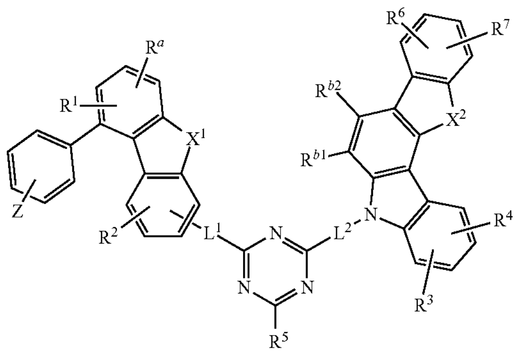

wherein, in Chemical Formula 1A-3-2A, Chemical Formula 1A-3-2B, Chemical Formula 1A-3-2D, and Chemical Formula 1A-3-2F, $X^1$, $X^2$, Z, $L^1$, $L^2$, $R^a$, and $R^1$ to $R^7$ are the same as in claim 1, defined the same as those of Chemical Formula 1 to Chemical Formula 3, and $R^{b1}$, $R^{b3}$, and $R^{b4}$ are each independently hydrogen, deuterium, a substituted or unsubstituted C1 to C10 alkyl group, a substituted or unsubstituted C6 to C20 aryl group, or a substituted or unsubstituted C2 to C30 heterocyclic group.

8. The compound as claimed in claim 1, wherein:

Z is hydrogen or a phenyl group, $L^1$ and $L^2$ are each independently a single bond or a phenylene group, and $R^a$, $R^b$, $R^1$ to $R^4$, $R^6$, and $R^7$ are each independently hydrogen or a substituted or unsubstituted phenyl group.

9. The compound as claimed in claim 1, wherein $R^5$ is a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, a substituted or unsubstituted dibenzothiophenyl group, or a substituted or unsubstituted carbazolyl group.

10. The compound as claimed in claim 1, wherein the compound is a compound of Group 1:

[Group 1]

[A-1]

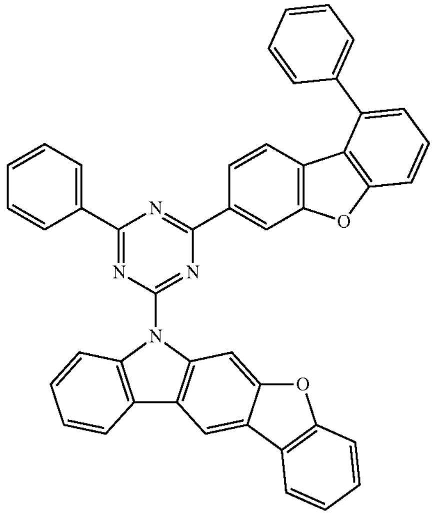

-continued
[A-2]
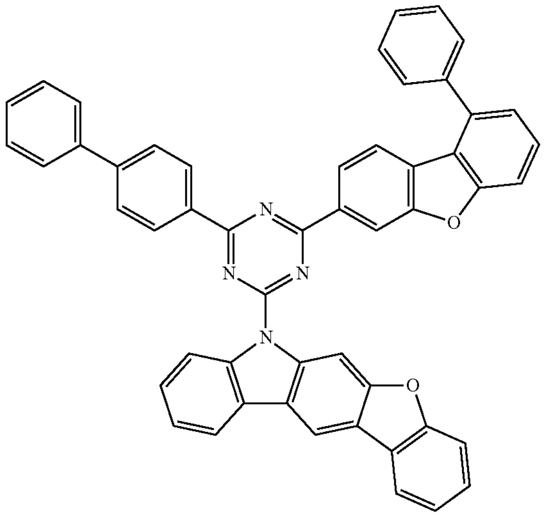
[A-3]
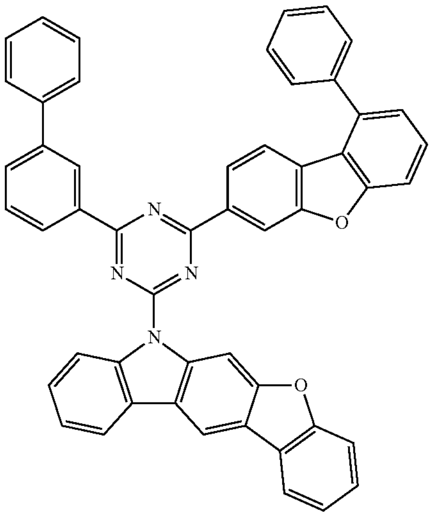
[A-4]
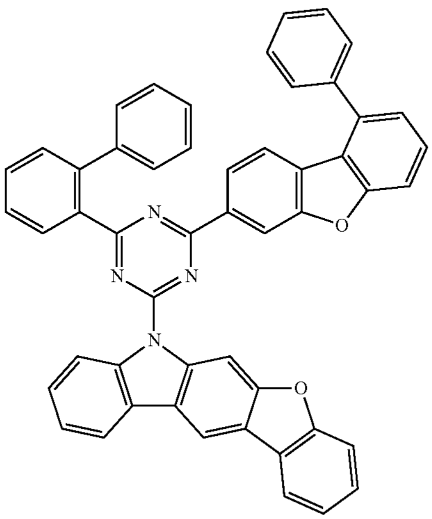
-continued
[A-5]
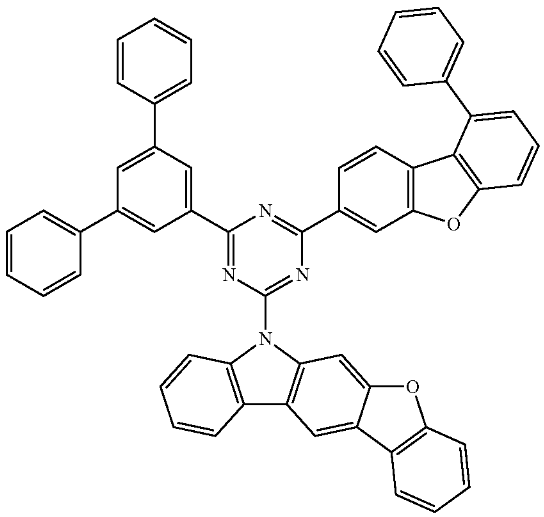
[A-6]
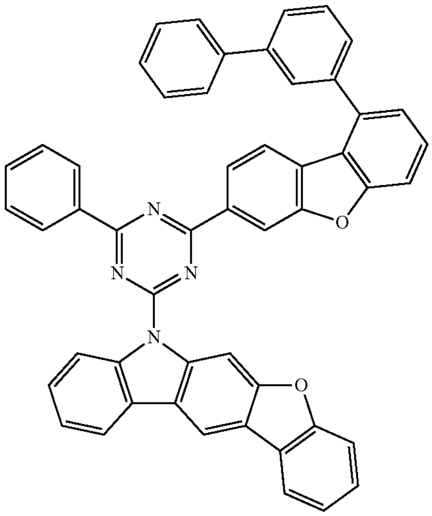
[A-7]
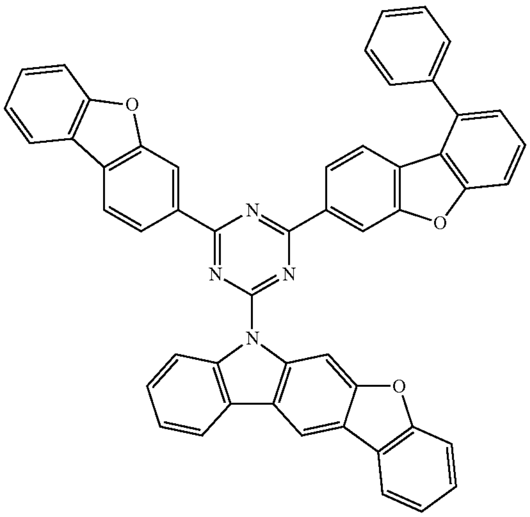

-continued
[A-8]
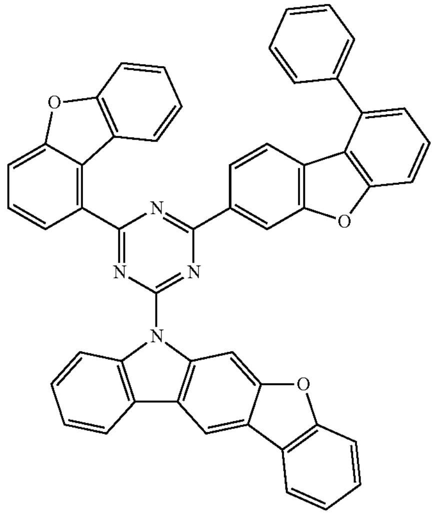
[A-9]
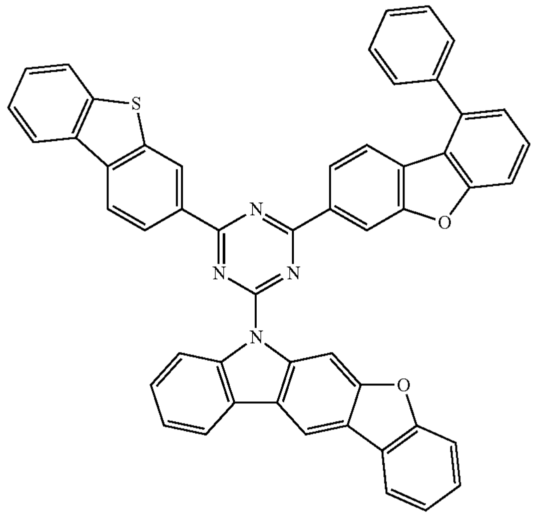
[A-10]
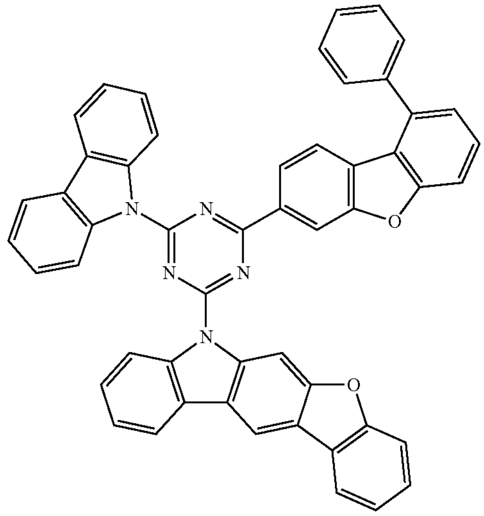
-continued
[A-11]
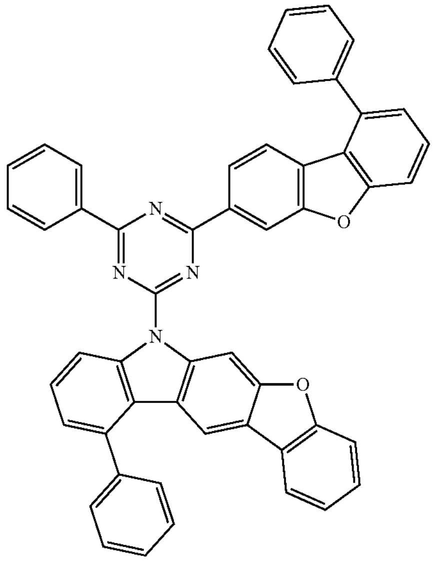
[A-12]
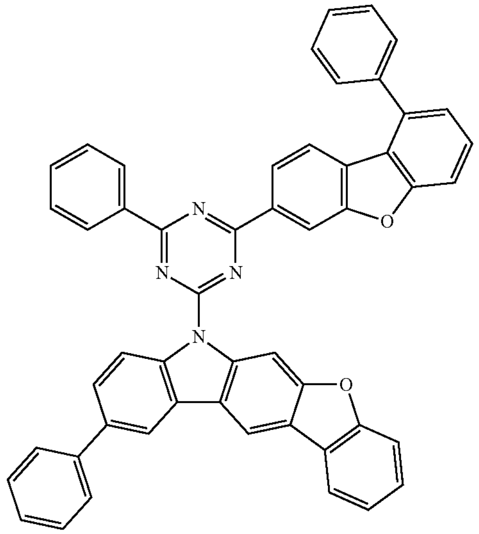
[A-13]
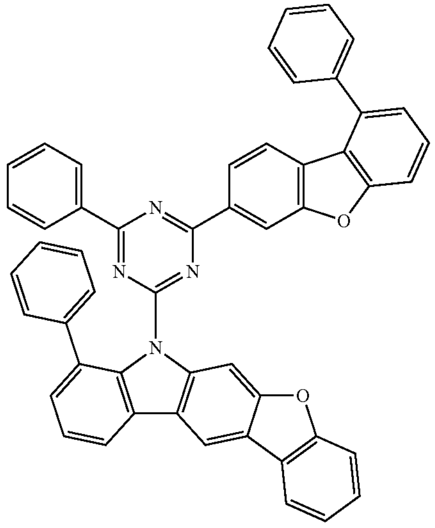

-continued
[A-14]
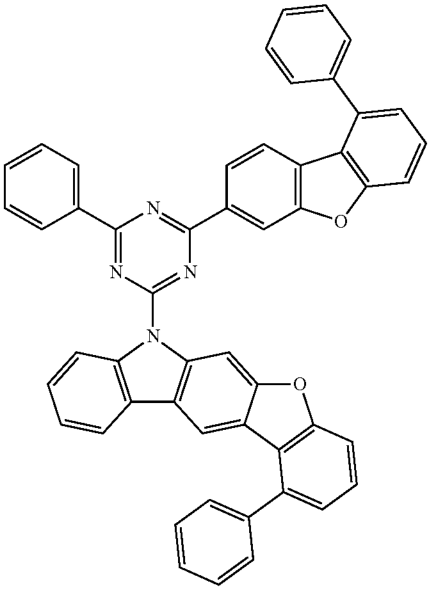
[A-15]
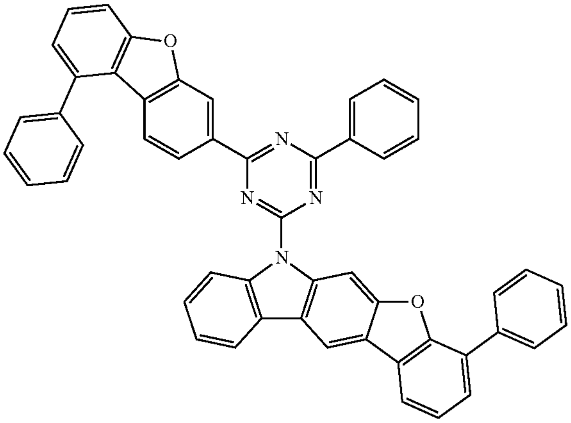
[A-16]
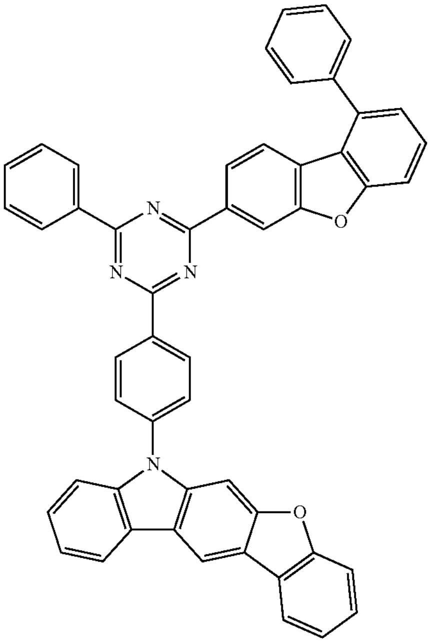
-continued
[A-17]
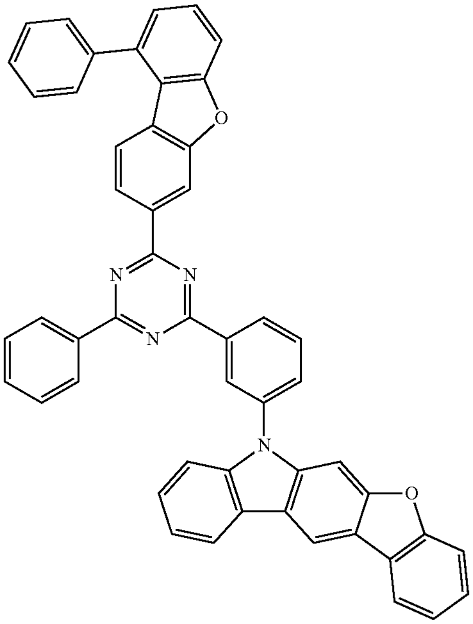
[A-18]
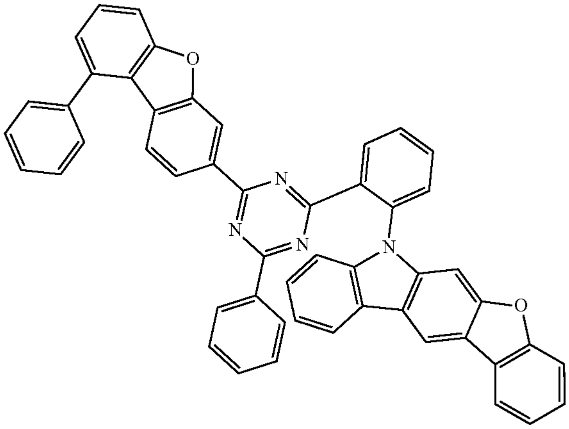

-continued
[A-19]
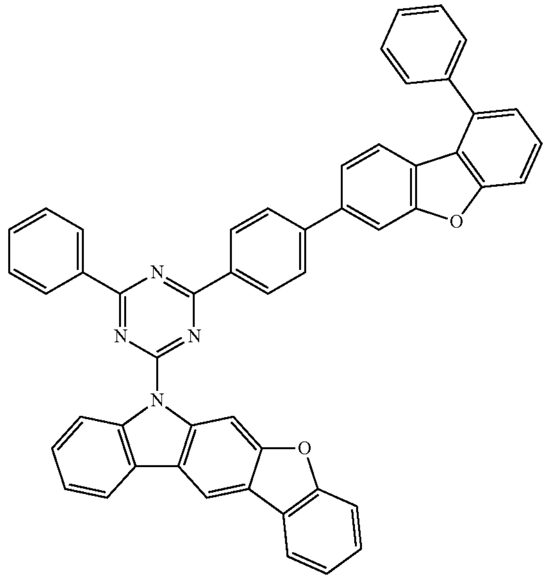
[A-20]
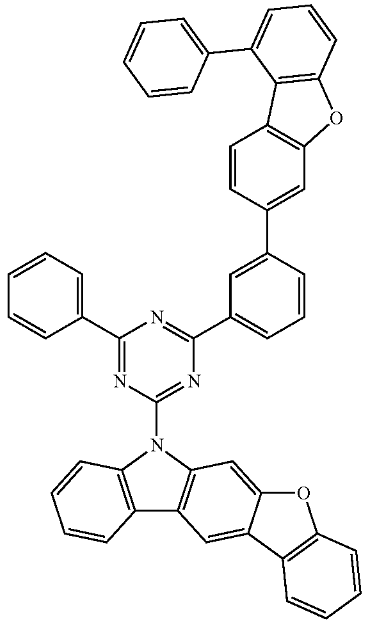
-continued
[A-21]
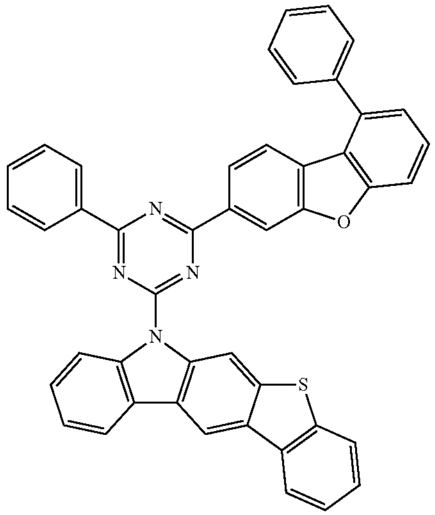
[A-22]
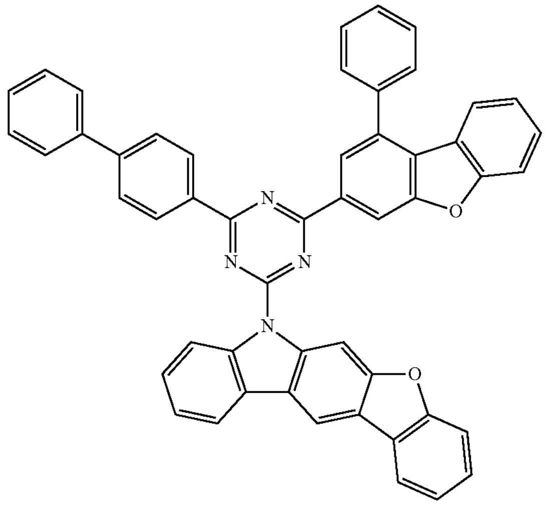
[A-23]
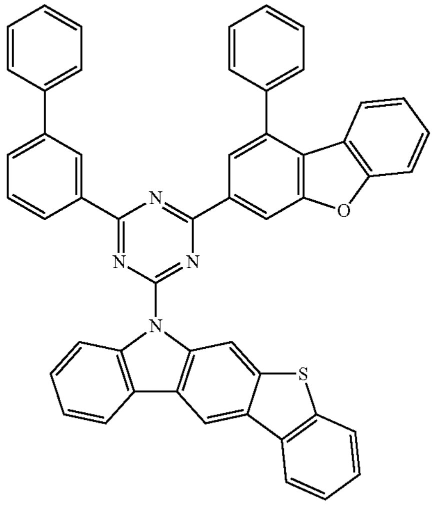

-continued
[A-24]
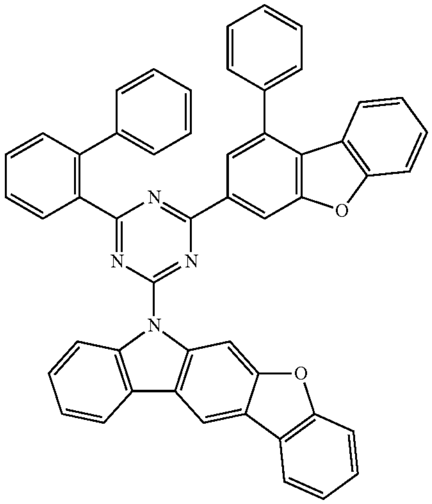
[A-25]
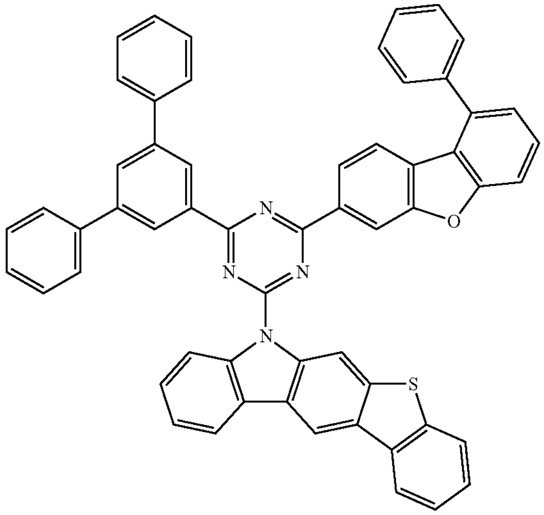
[A-26]
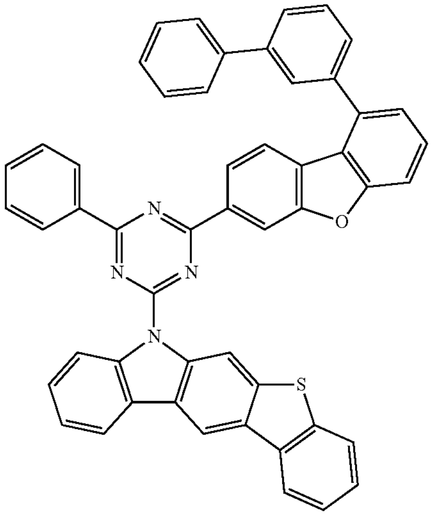
-continued
[A-27]
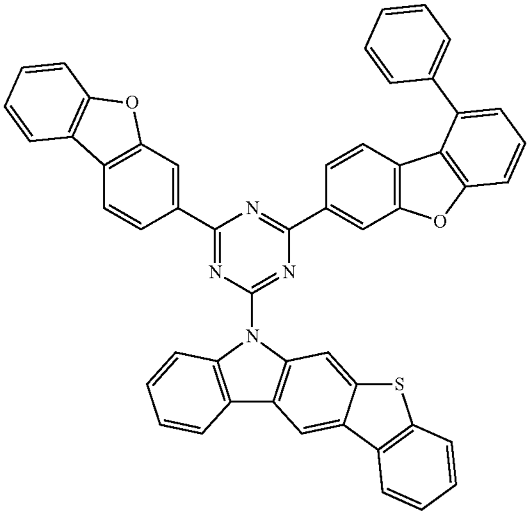
[A-28]
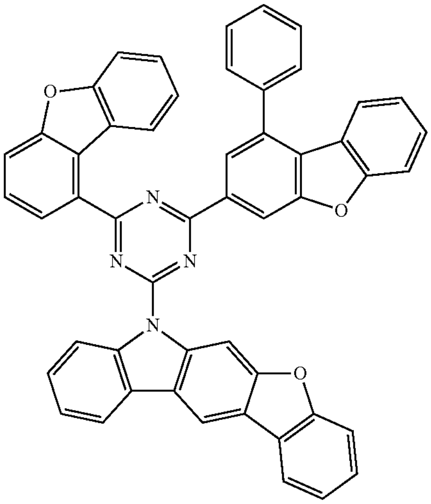
[A-29]
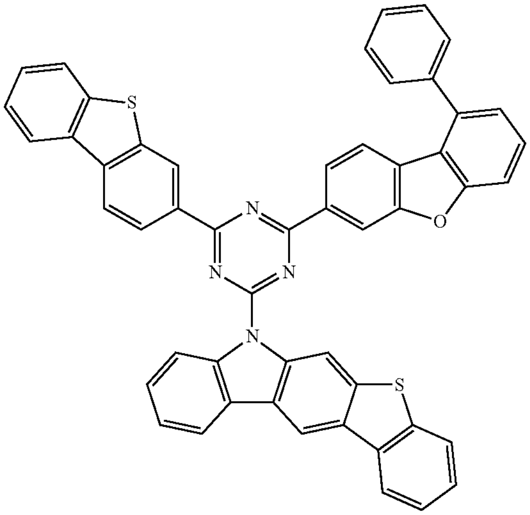

-continued
[A-30]
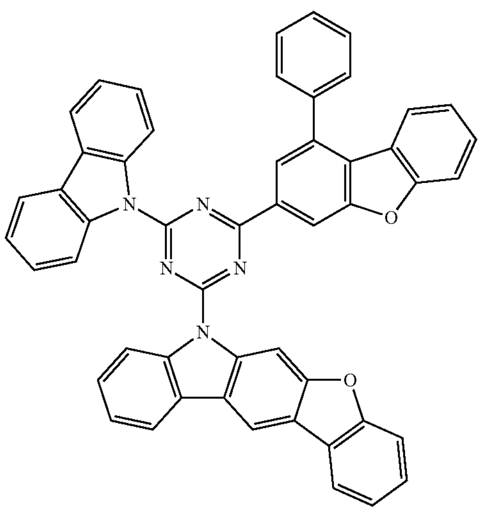
[A-31]
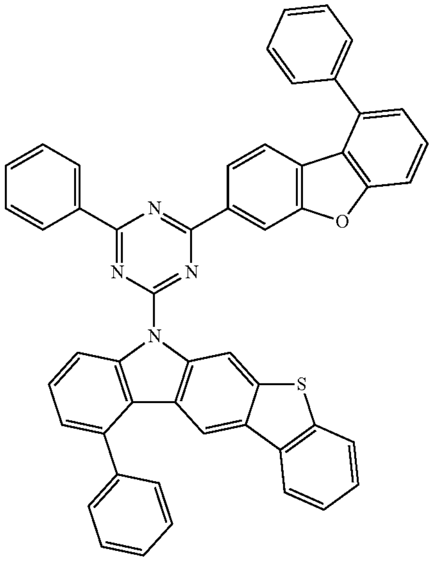
[A-32]
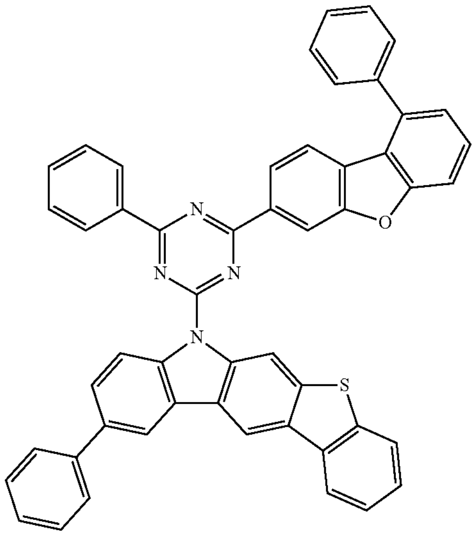
-continued
[A-33]
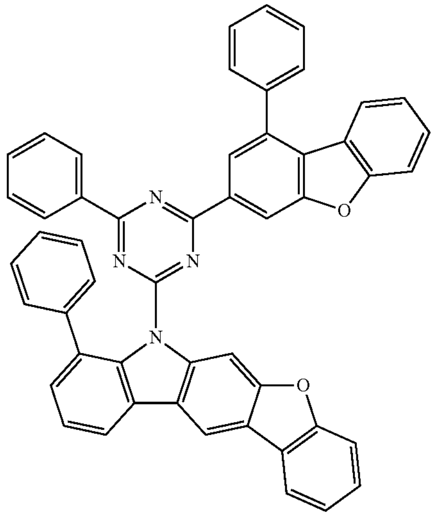
[A-34]
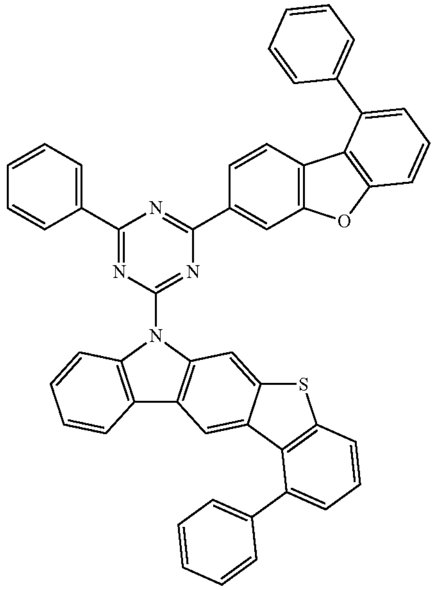
[A-35]
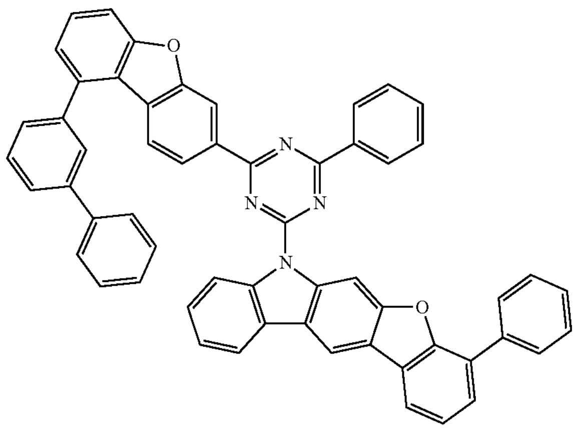

-continued
[A-36]
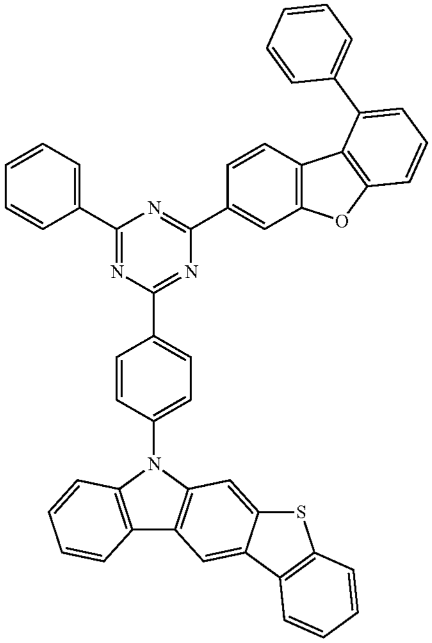
[A-37]
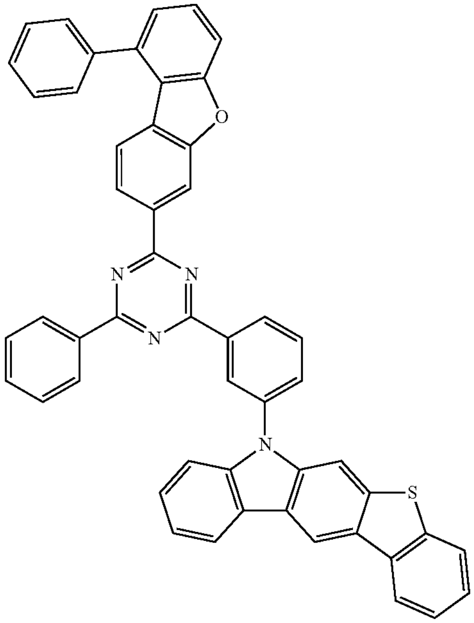
-continued
[A-38]
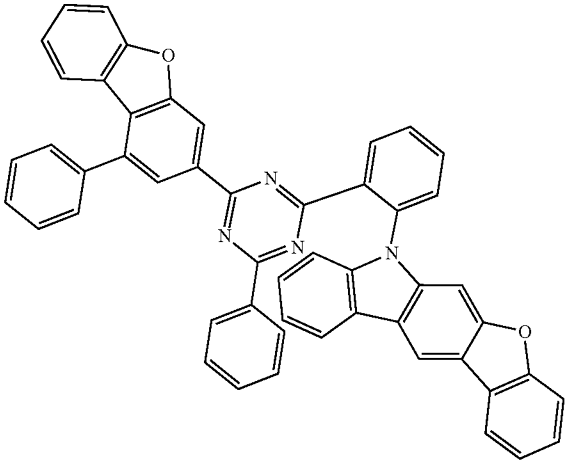
[A-39]
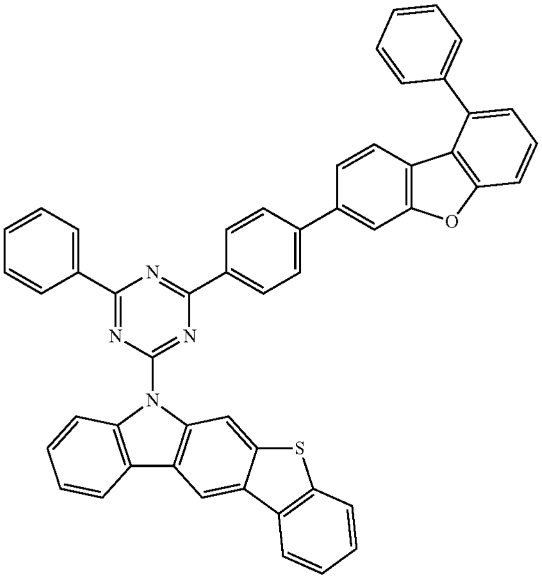

-continued
[A-40]
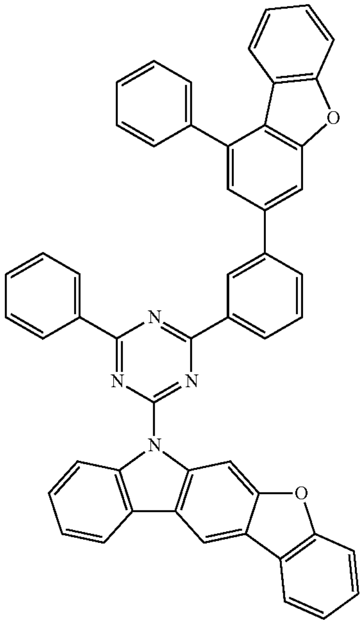
[A-41]
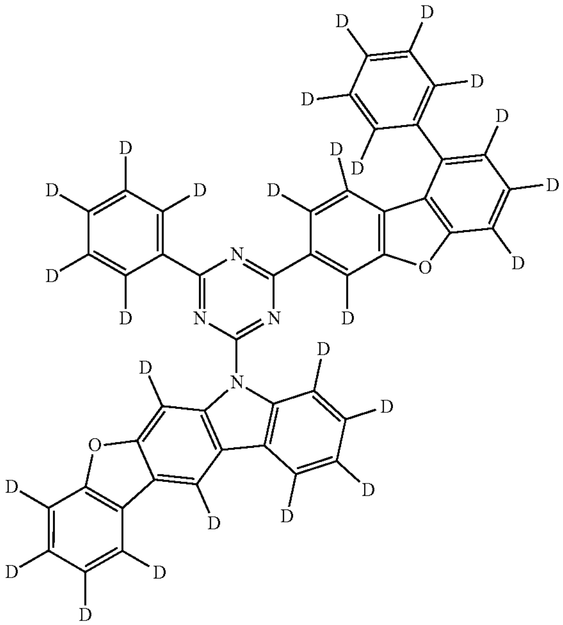
-continued
[A-42]
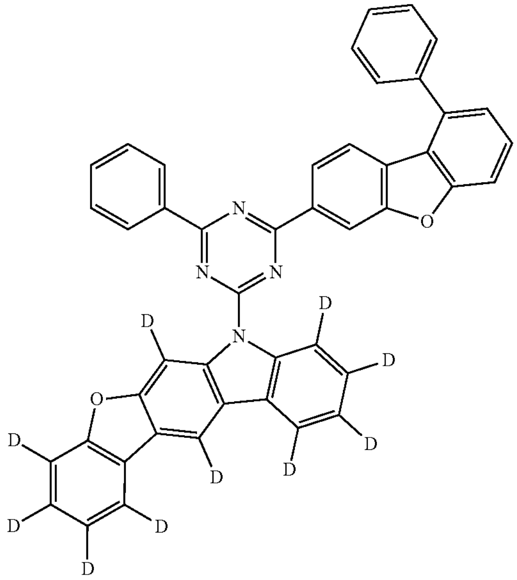
[A-43]
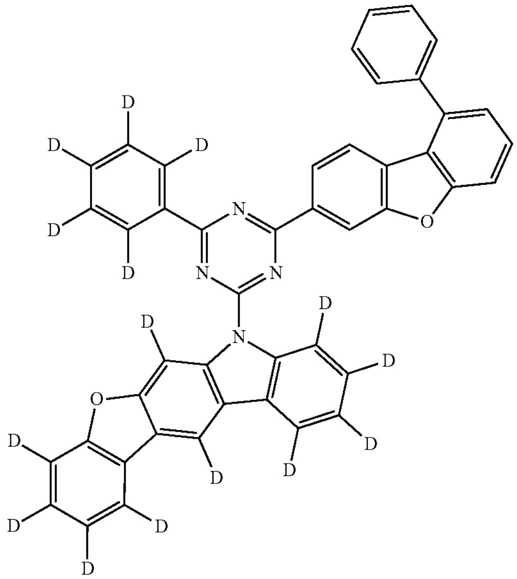

-continued
[A-44]
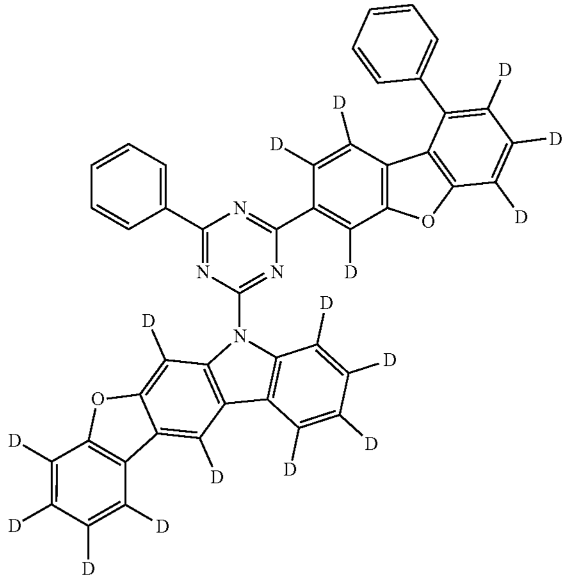
[A-45]
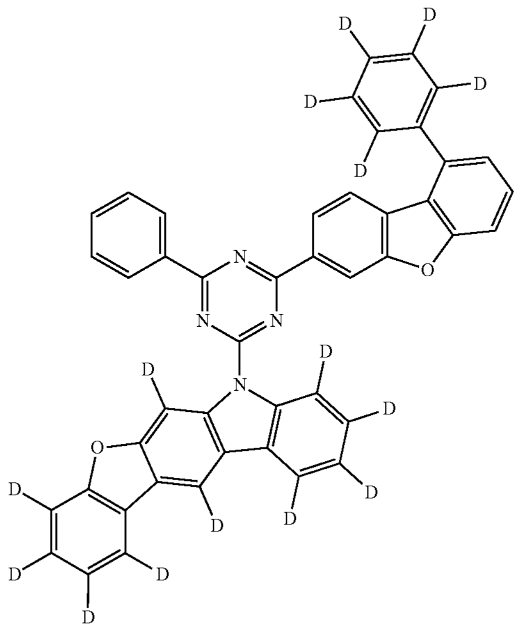
-continued
[A-46]
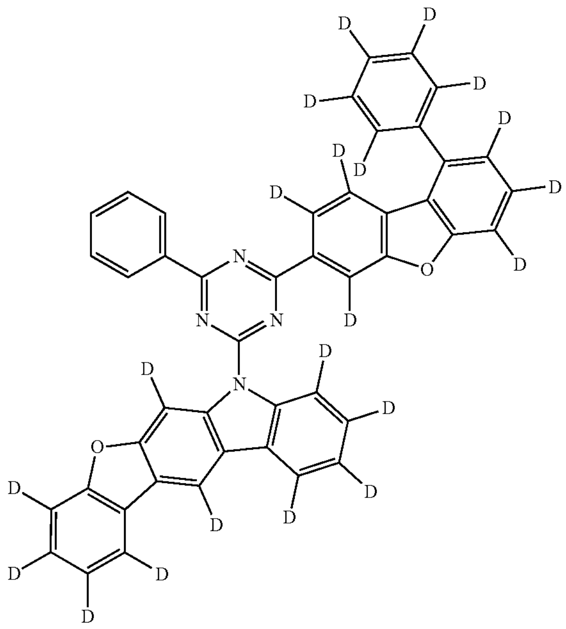
[A-47]
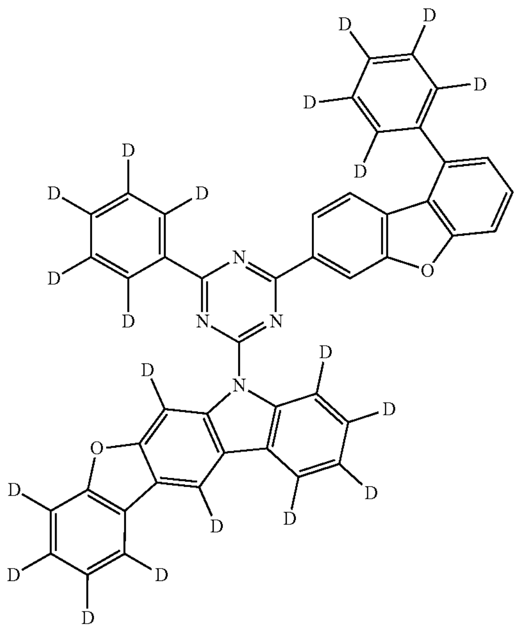

-continued
[A-48]
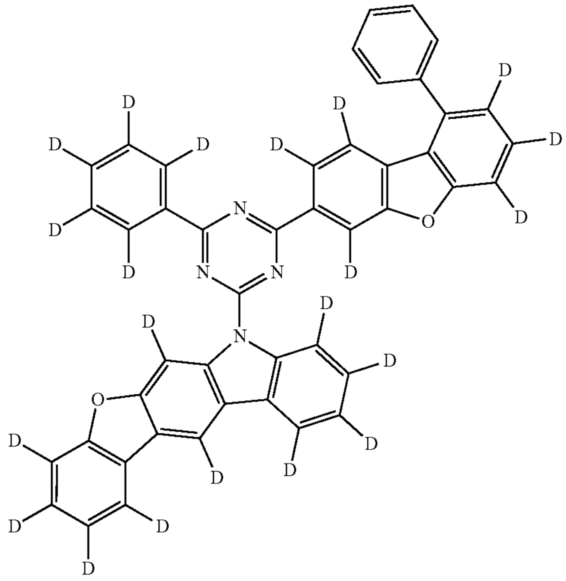
[A-49]
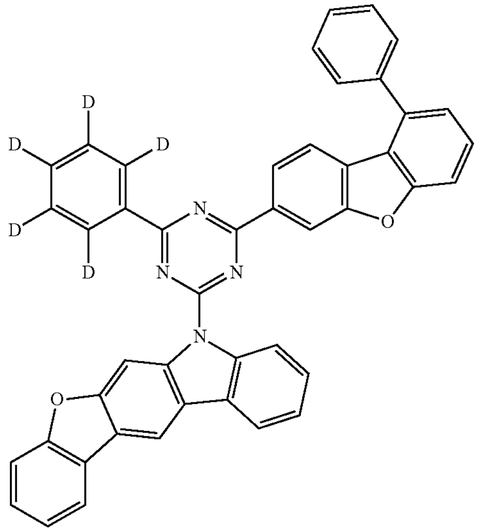
-continued
[A-50]
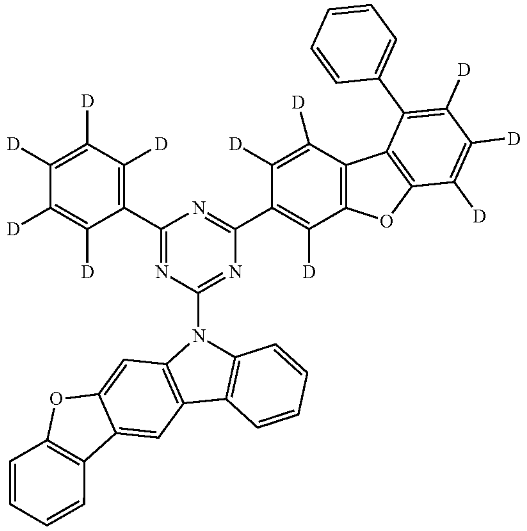
[A-51]
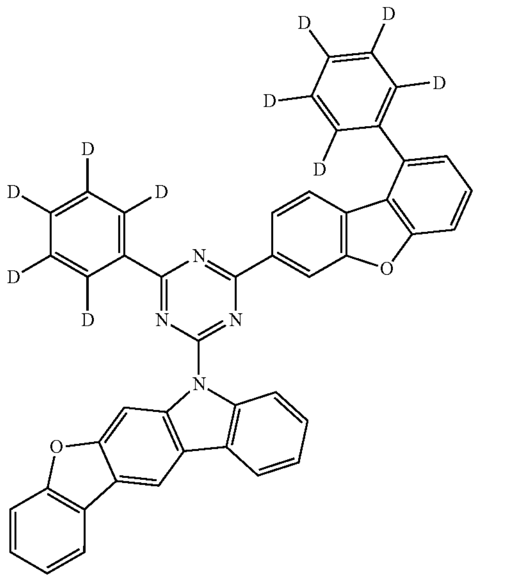

-continued
[A-52]
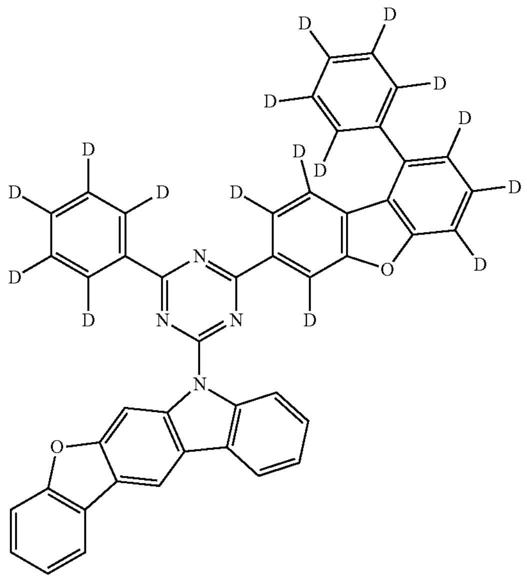
[A-53]
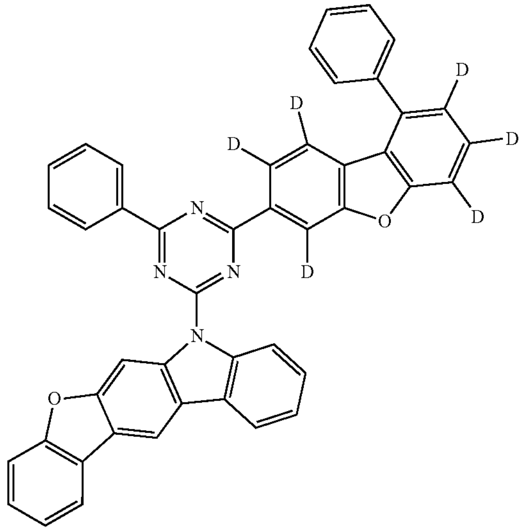
-continued
[A-54]
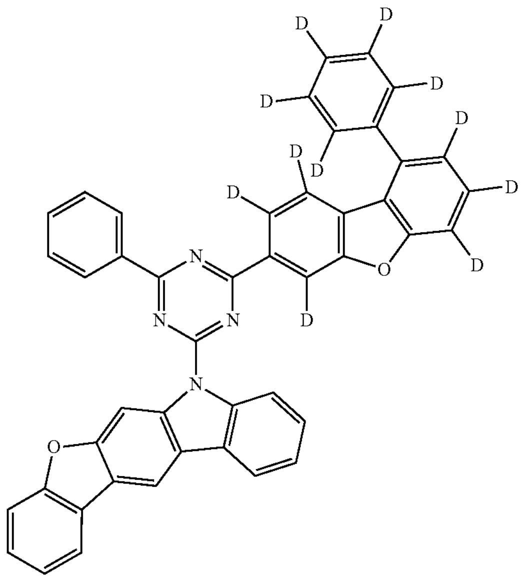
[A-55]
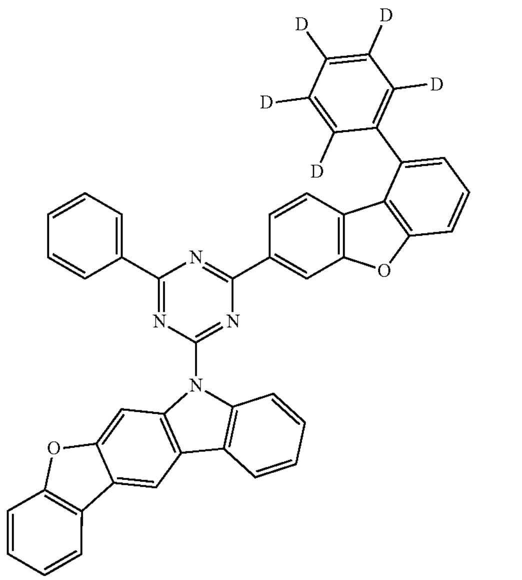

-continued
[A-56]
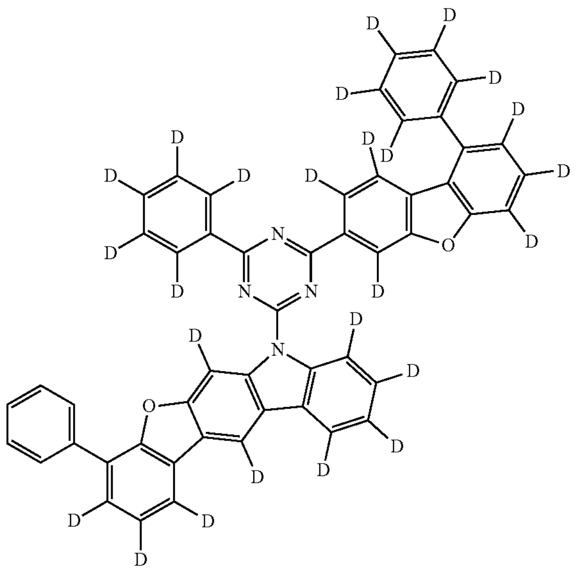
[A-57]
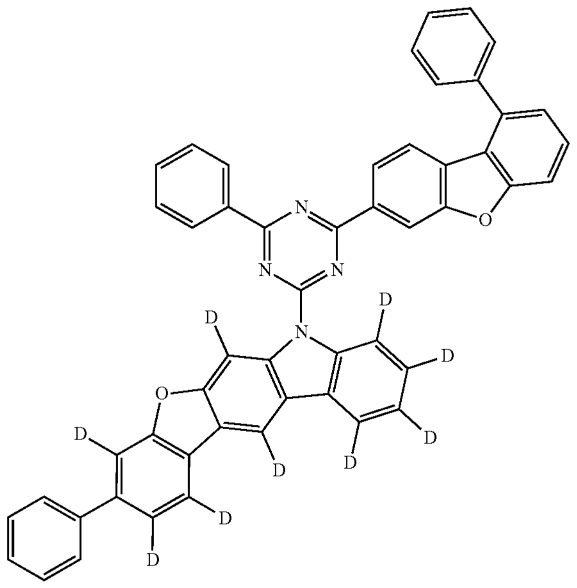
-continued
[A-58]
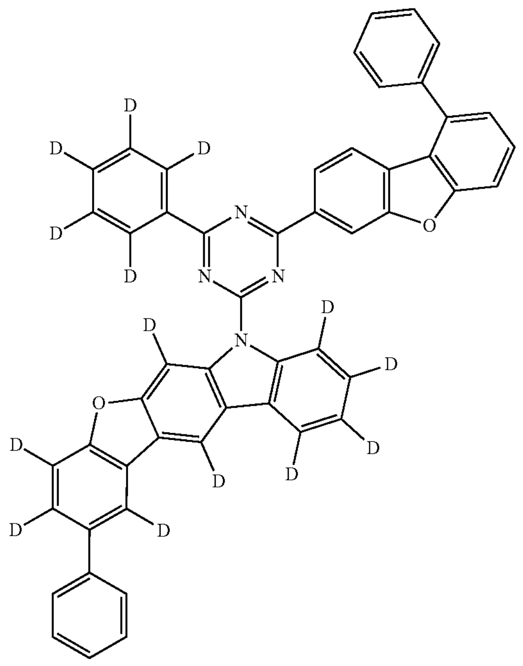
[A-59]
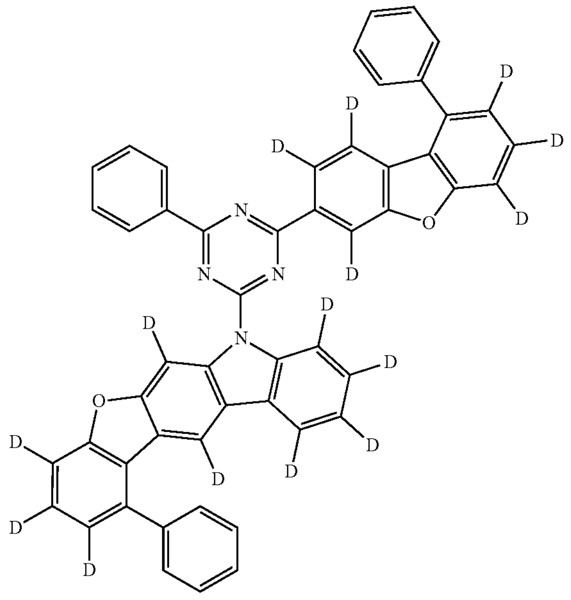

-continued
[A-60]
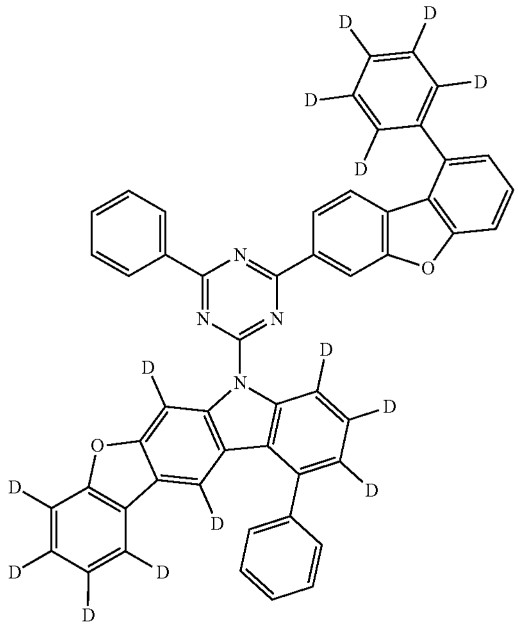
[A-61]
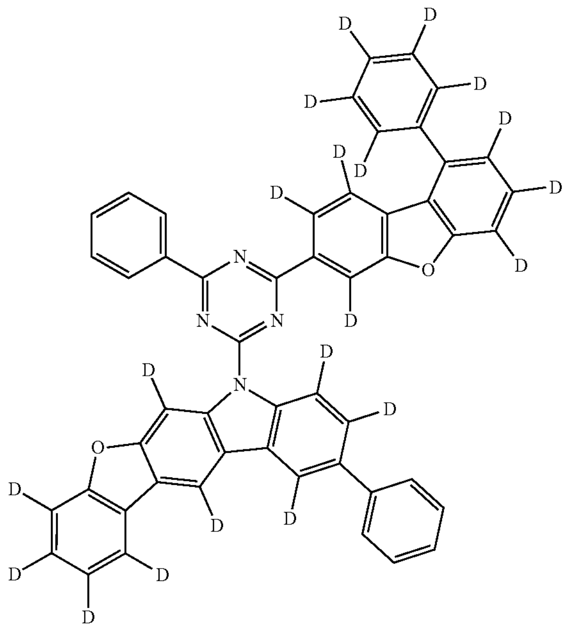
-continued
[A-62]
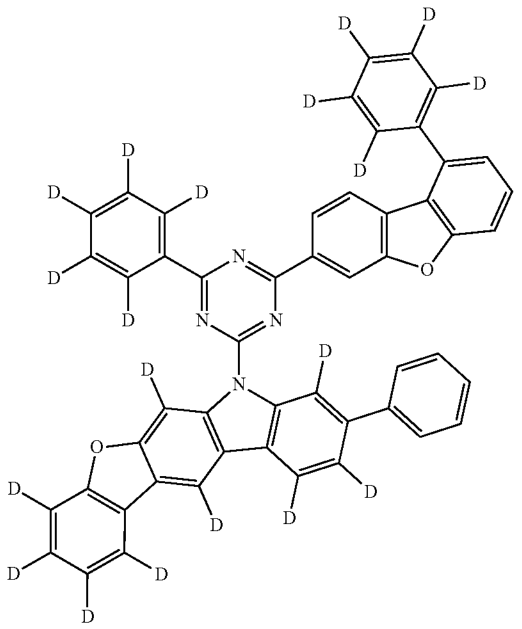
[A-63]
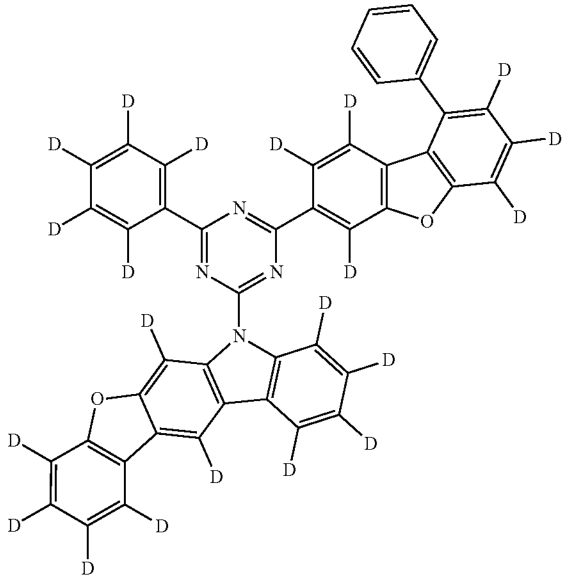

-continued
[A-64]
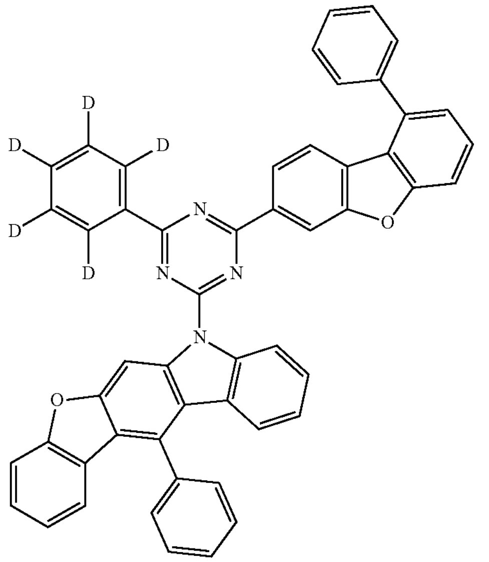
[A-65]
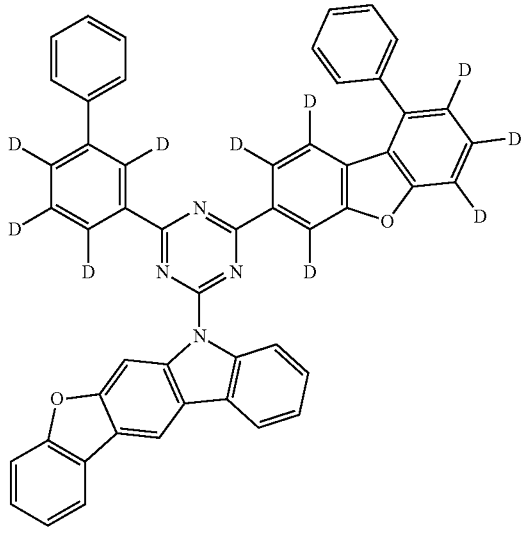
-continued
[A-66]
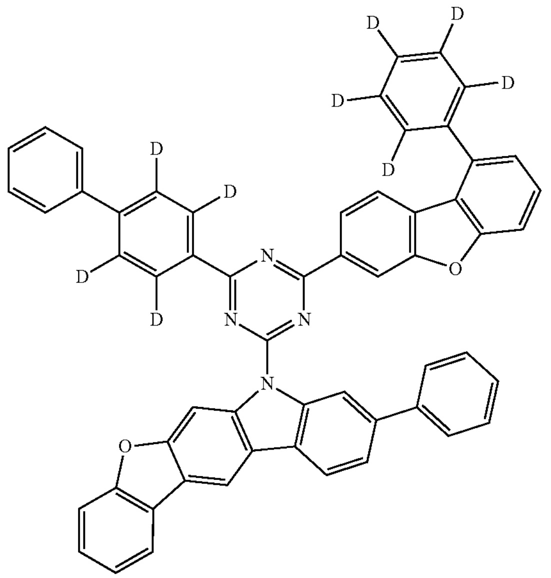
[A-67]
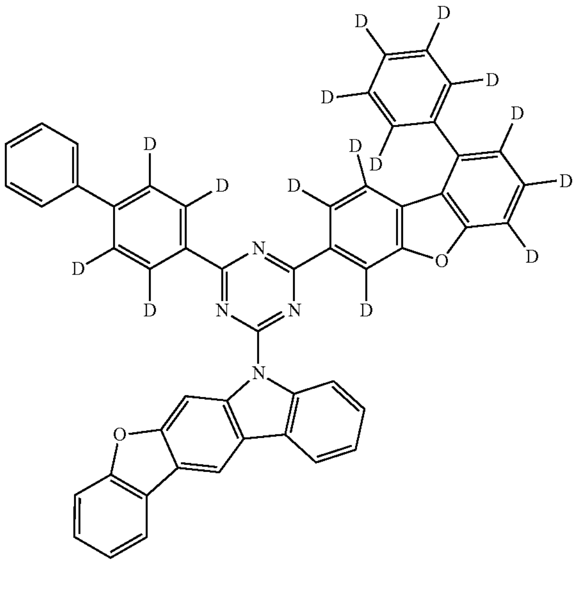

-continued
[A-68]
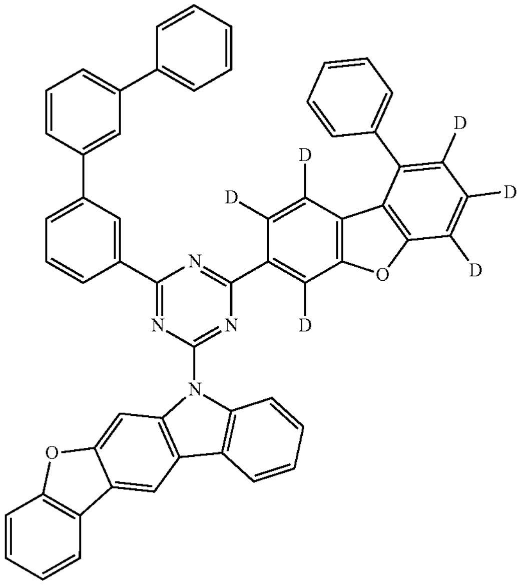
[A-69]
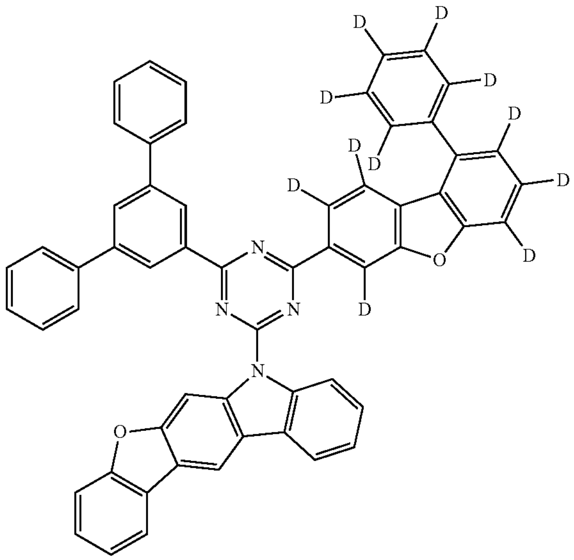
-continued
[A-70]
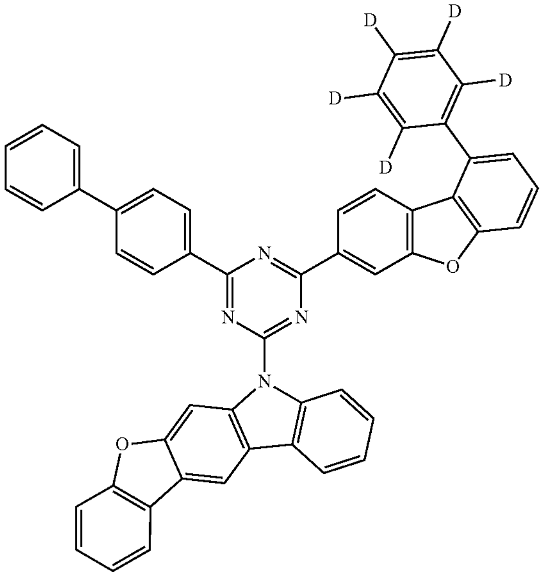
[A-71]
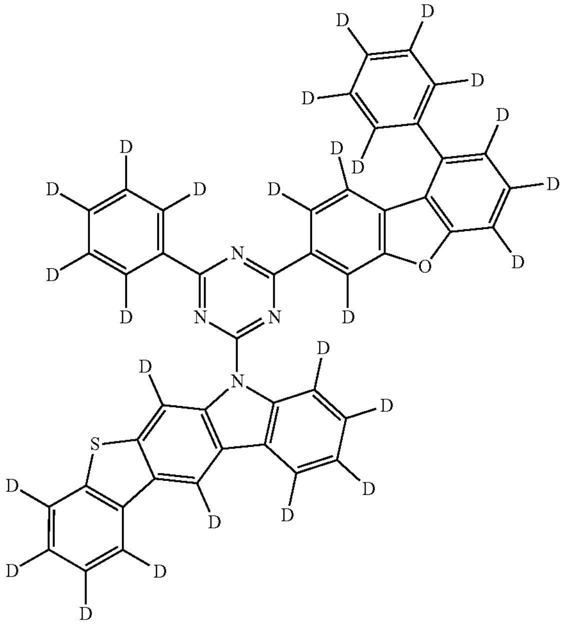

-continued
[A-72]
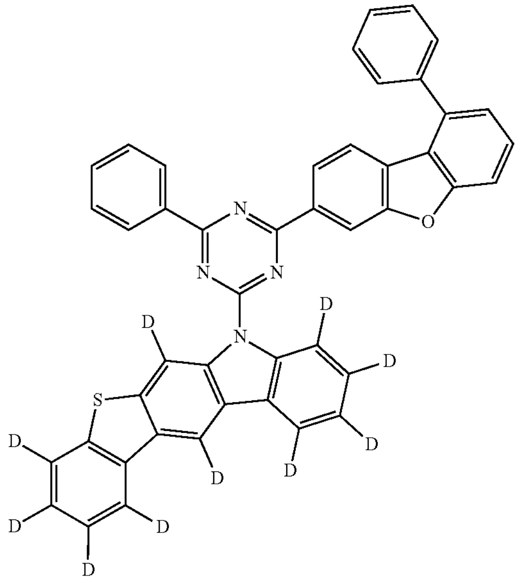
[A-73]
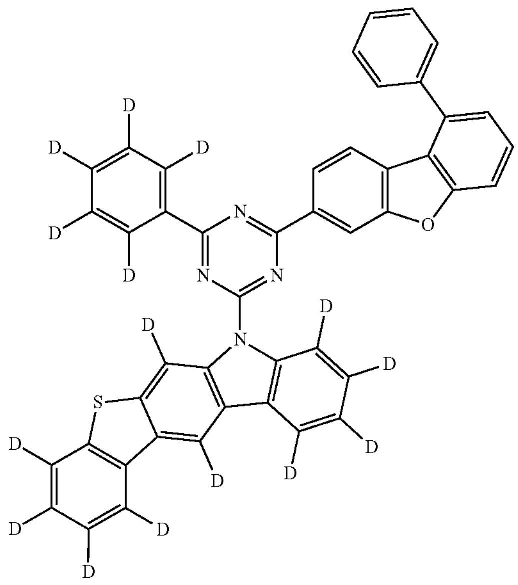
-continued
[A-74]
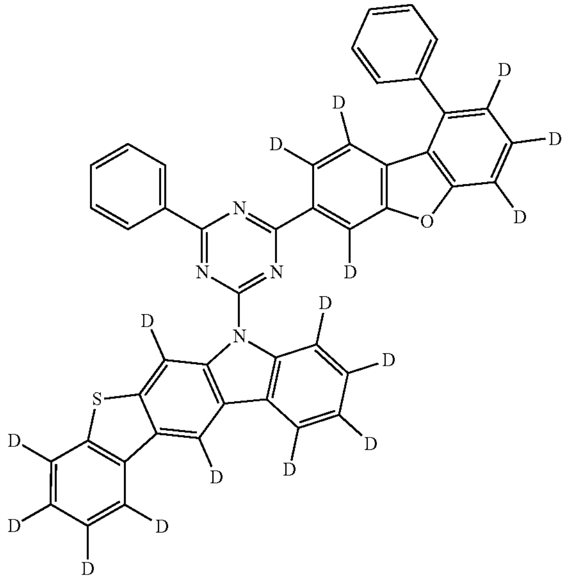
[A-75]
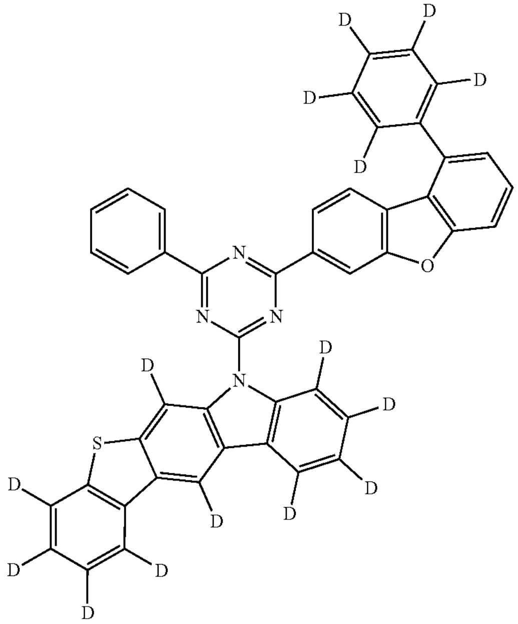

[A-76]
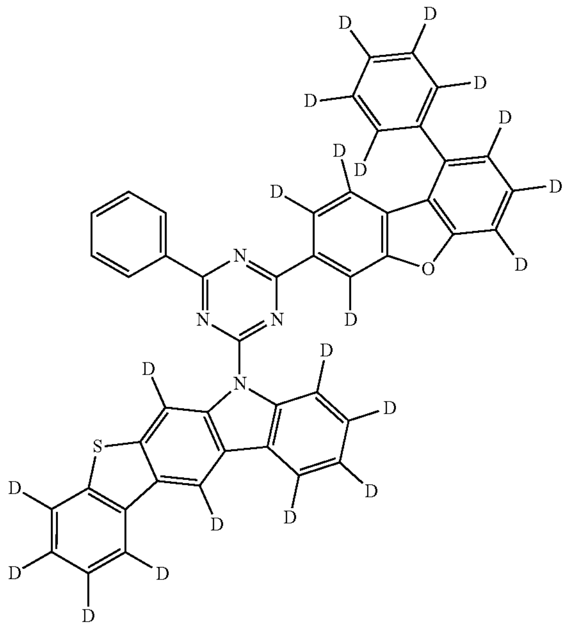
[A-77]
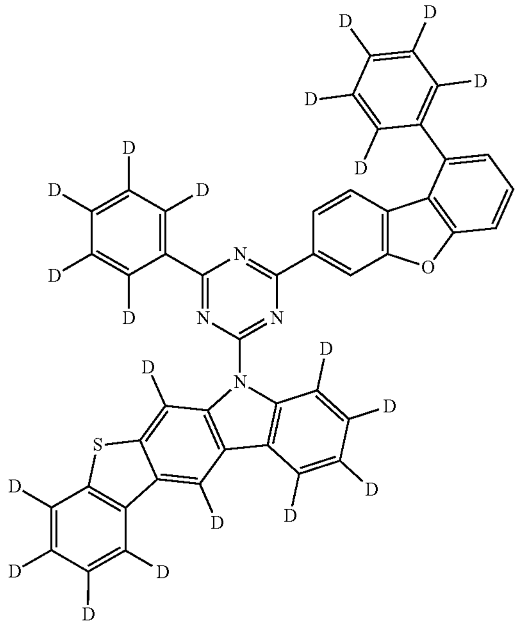
[A-78]
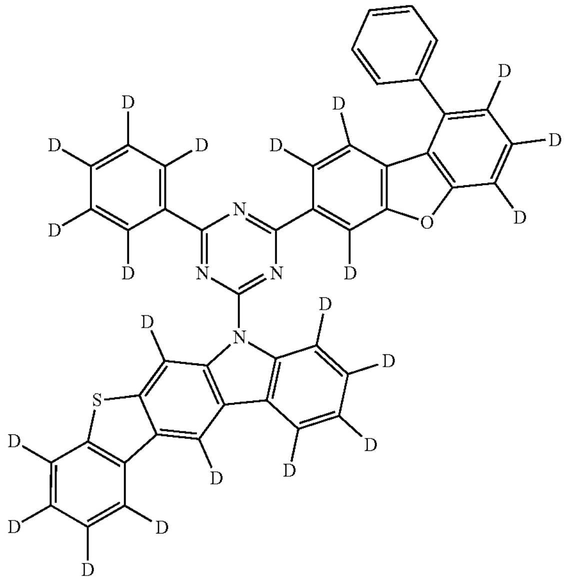
[A-79]
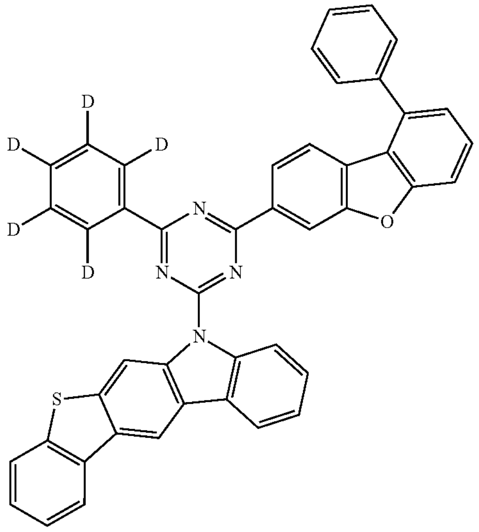

-continued
[A-80]
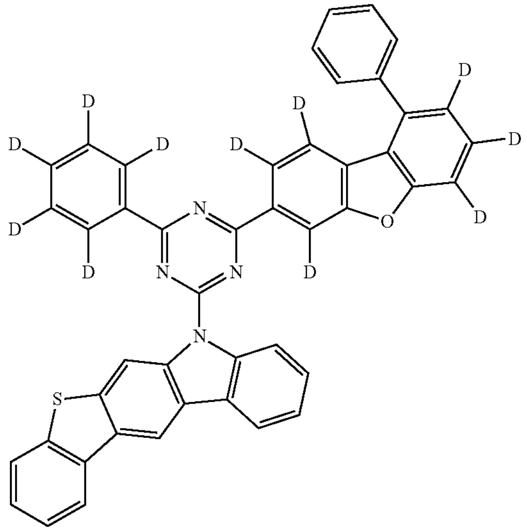
[A-81]
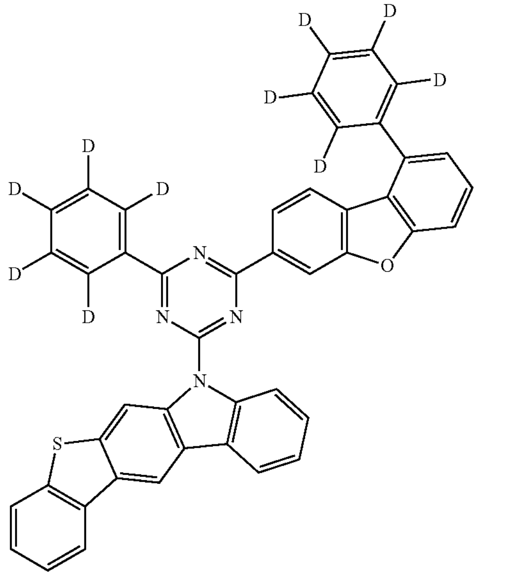
-continued
[A-82]
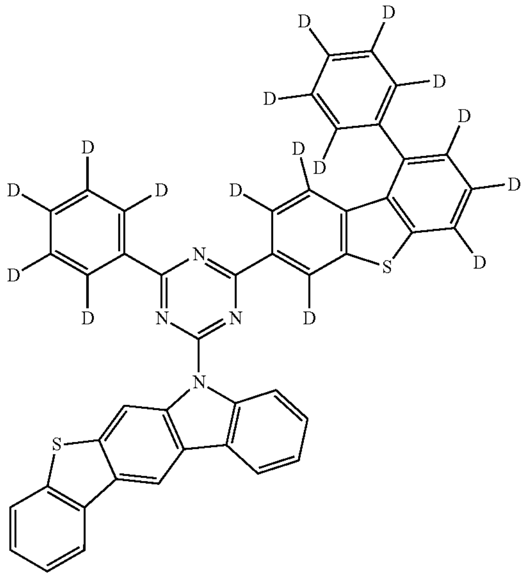
[A-83]
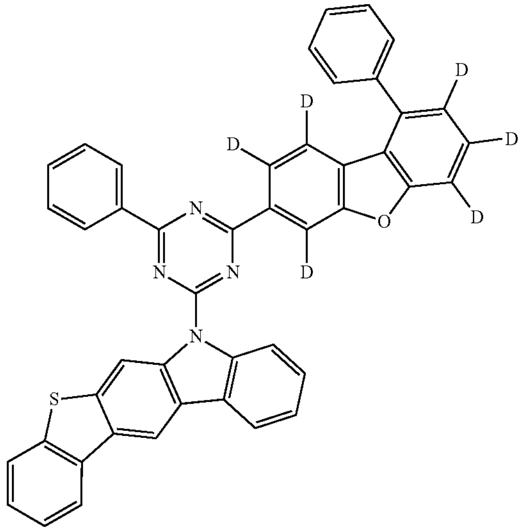

-continued
[A-84]
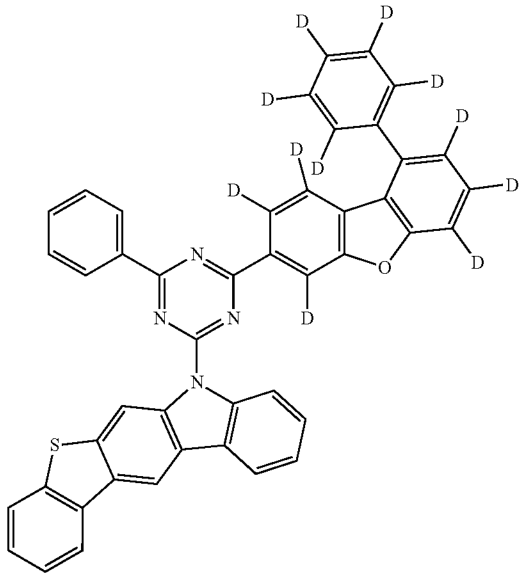
[A-85]
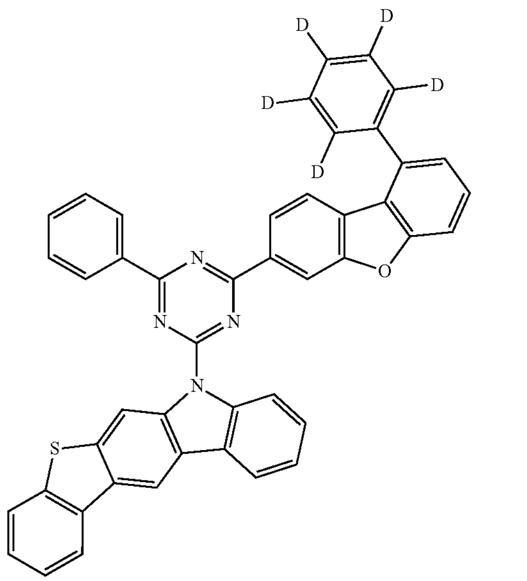
-continued
[A-86]
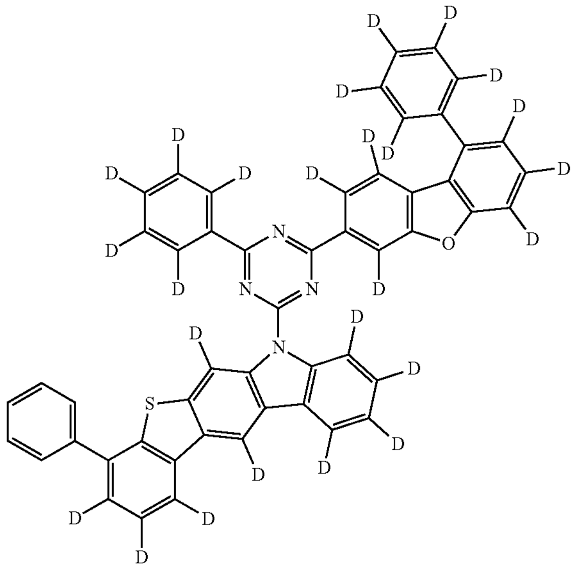
[A-87]
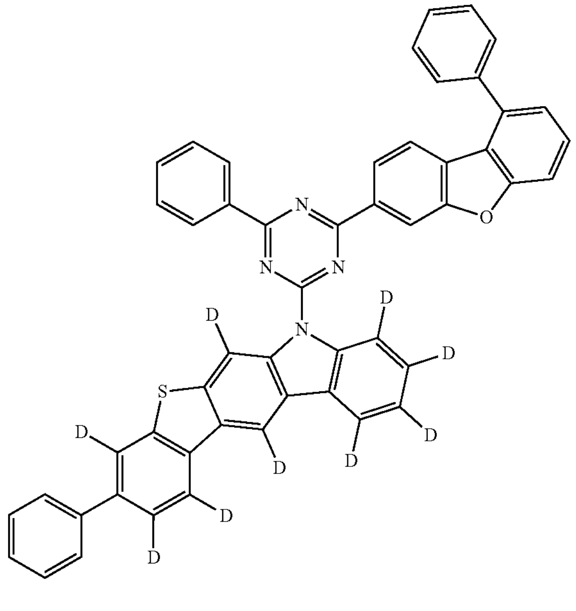

-continued
[A-88]
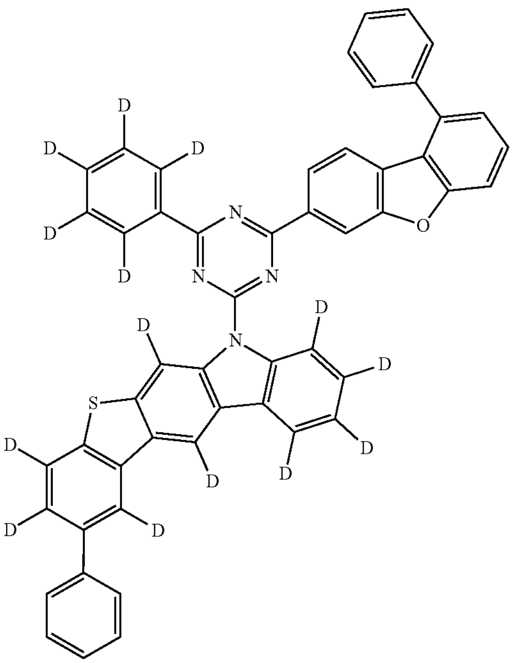
[A-89]
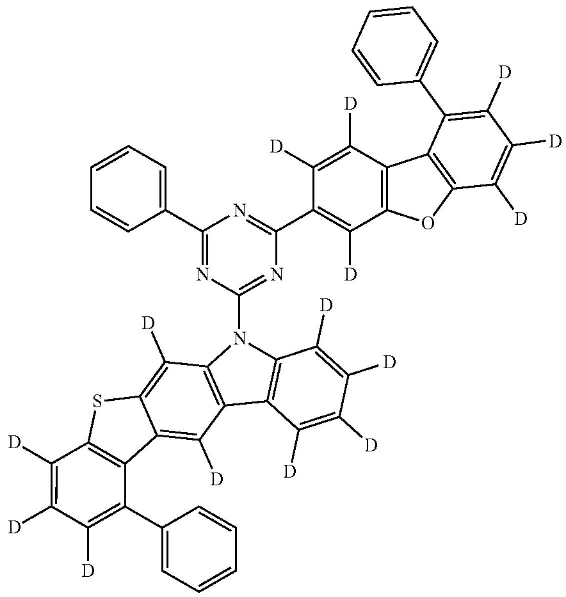
-continued
[A-90]
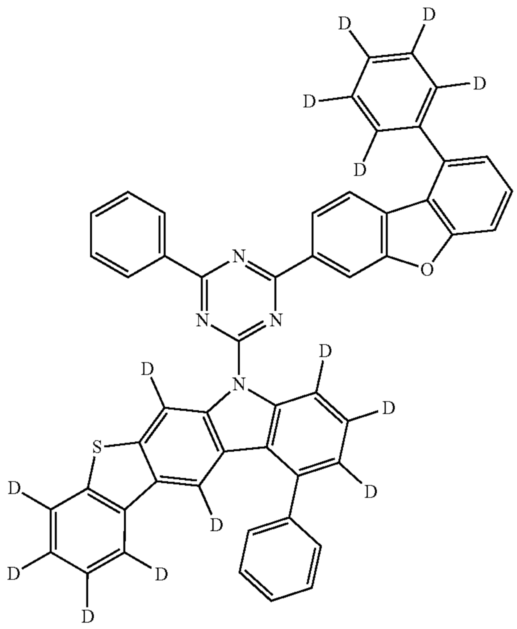
[A-91]
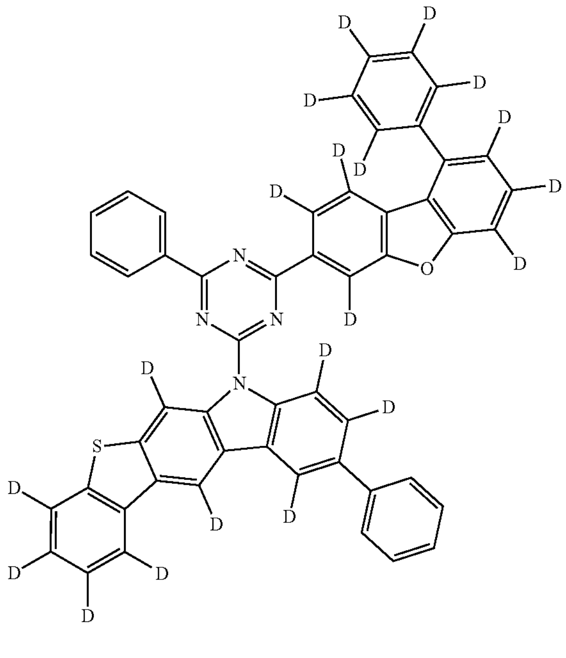

-continued
[A-92]
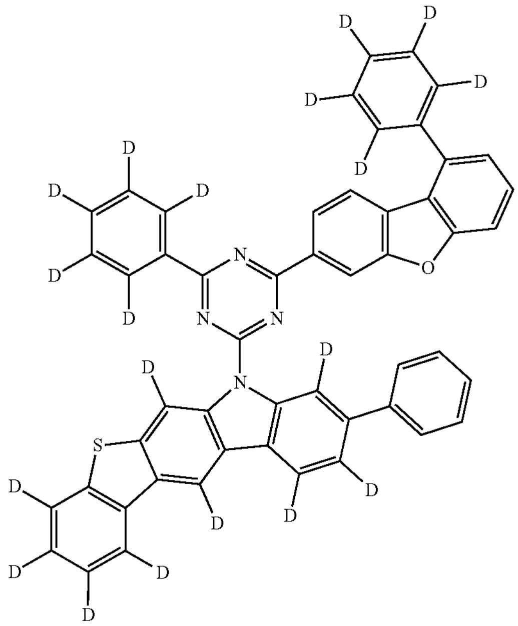
[A-93]
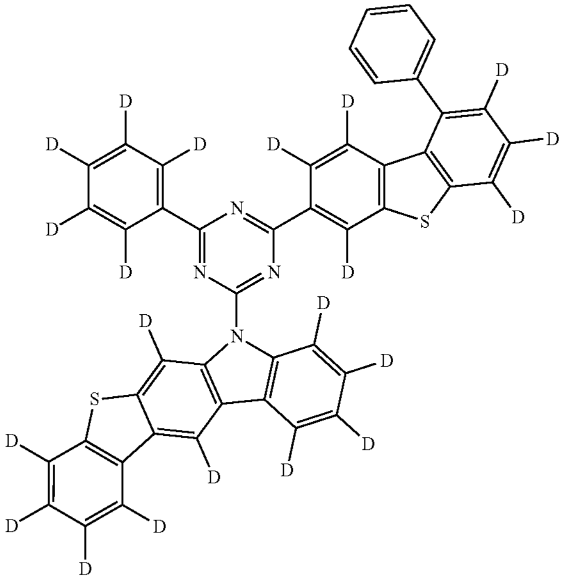
-continued
[A-94]
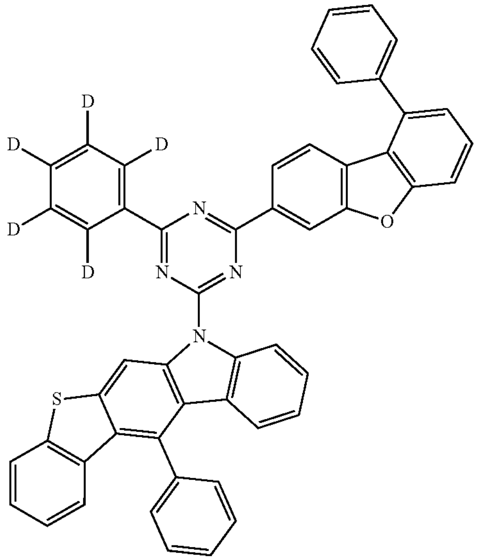
[A-95]
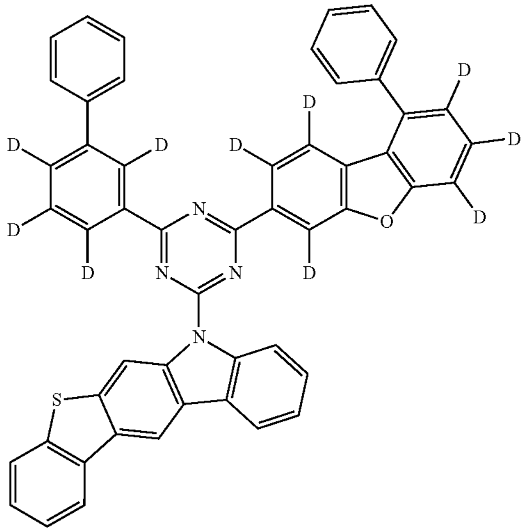

-continued
[A-96]
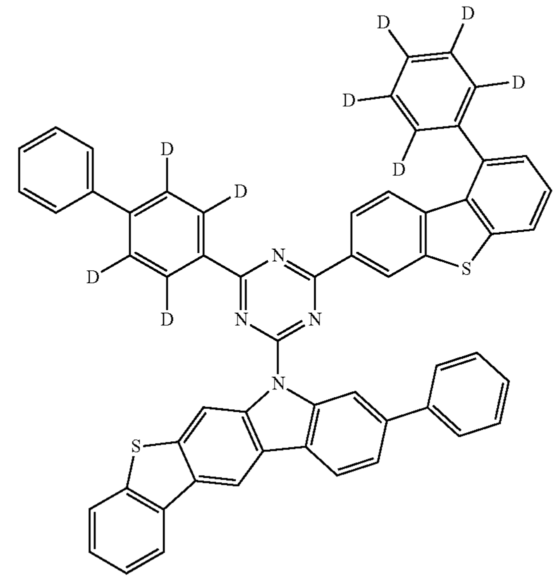
[A-97]
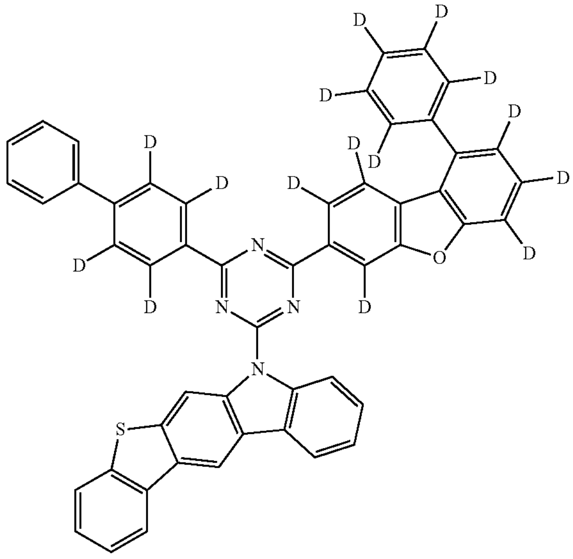
-continued
[A-98]
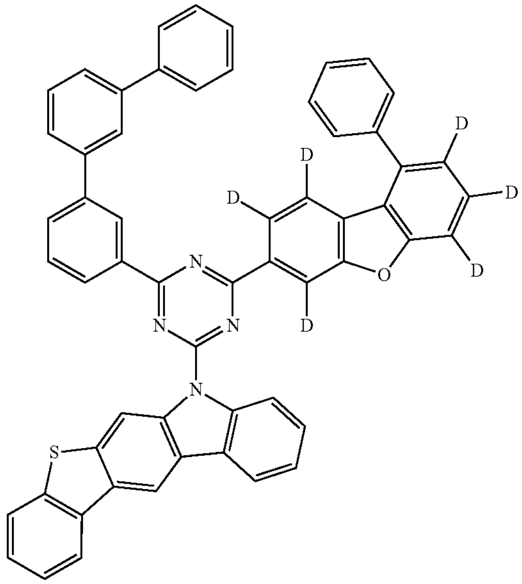
[A-99]
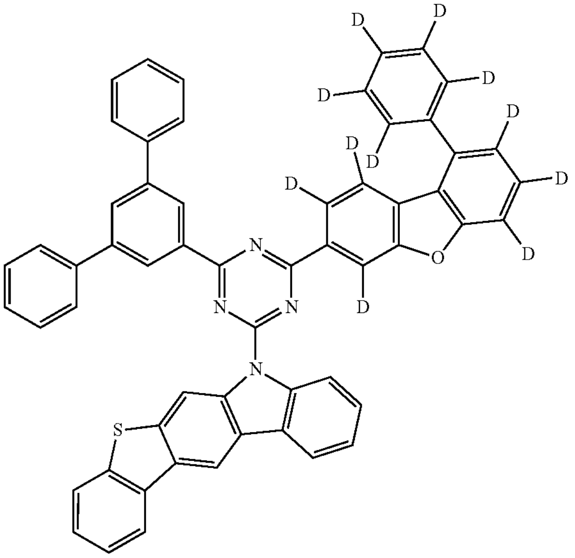

-continued
[A-100]
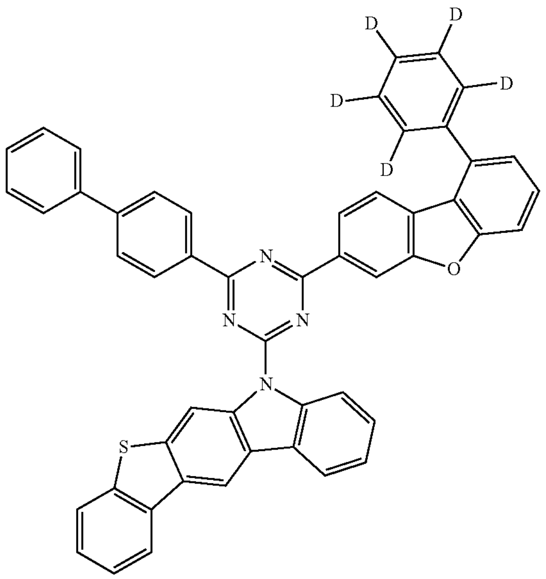
[B-1]
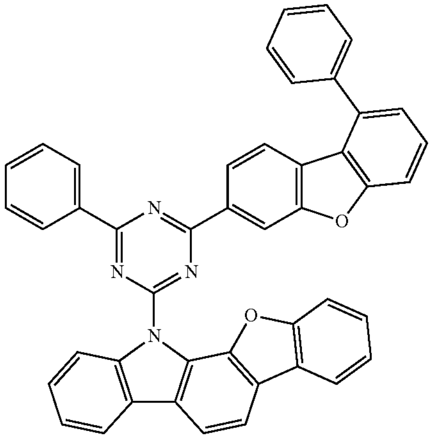
[B-2]
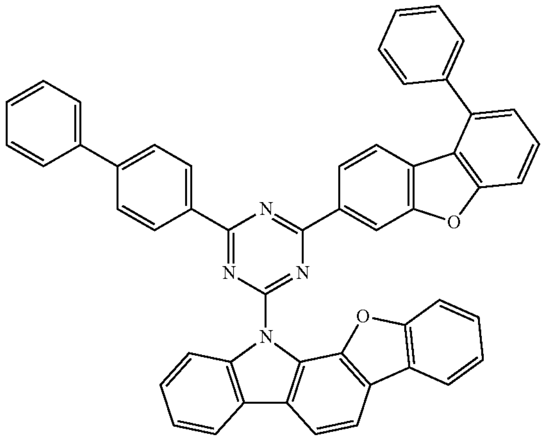
-continued
[B-3]
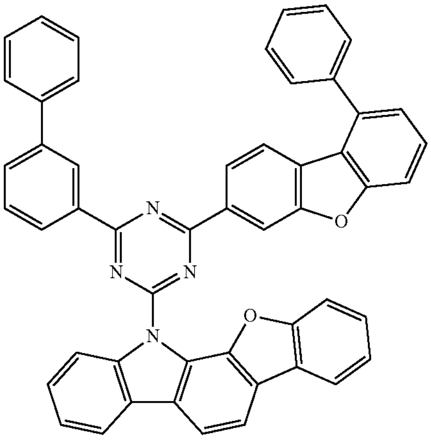
[B-4]
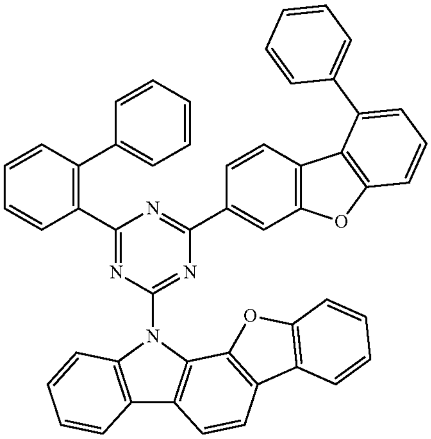
[B-5]
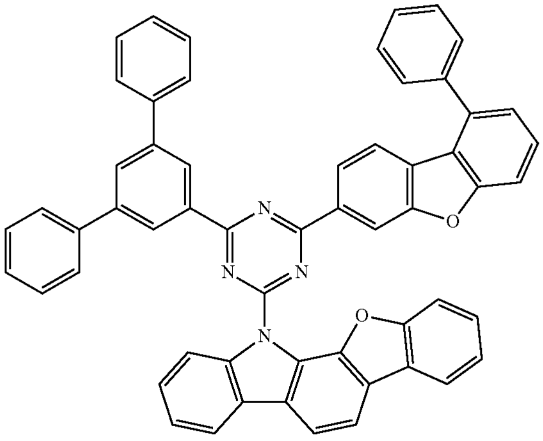

-continued
[B-6]
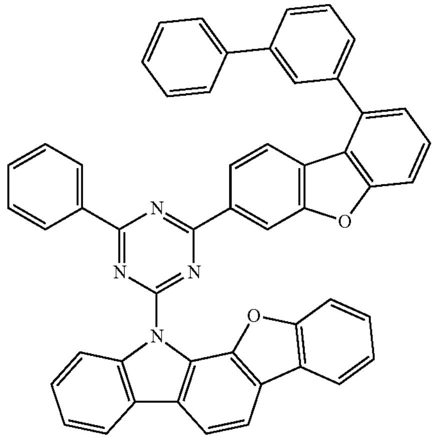
[B-7]
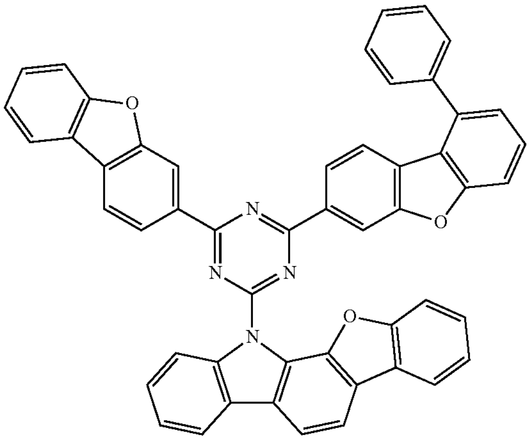
[B-8]
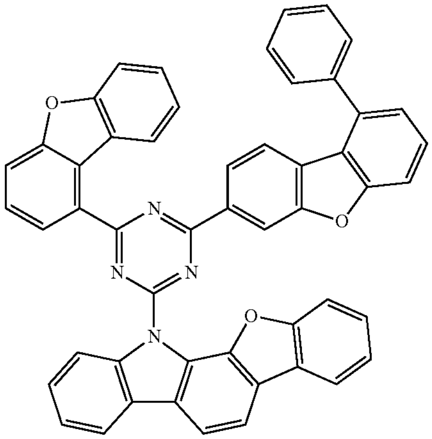
-continued
[B-9]
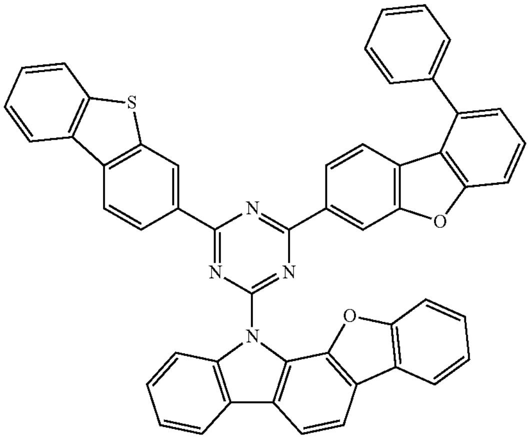
[B-10]
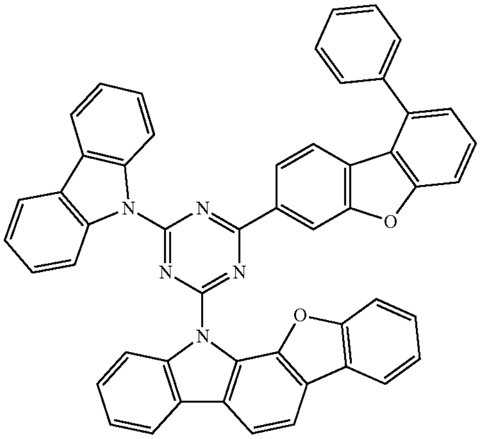
[B-11]
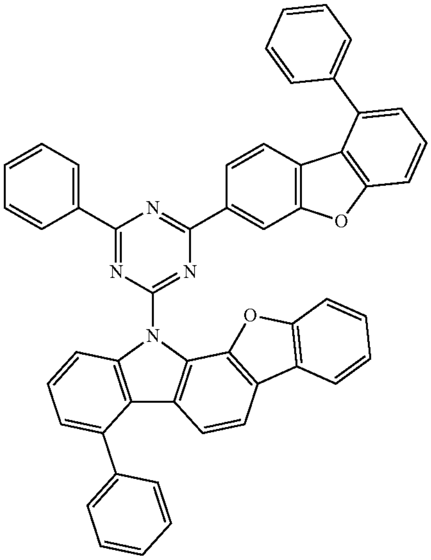

-continued
[B-12]
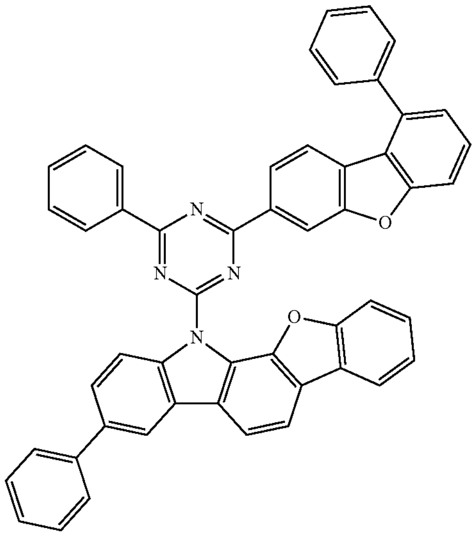
[B-13]
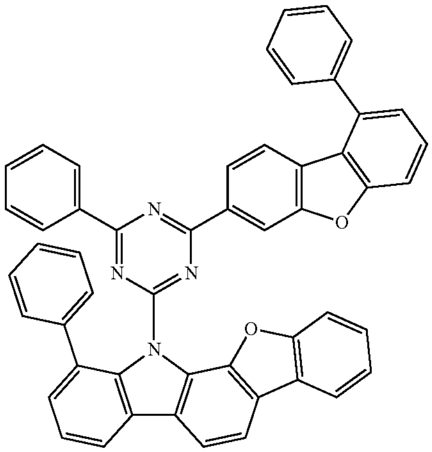
[B-14]
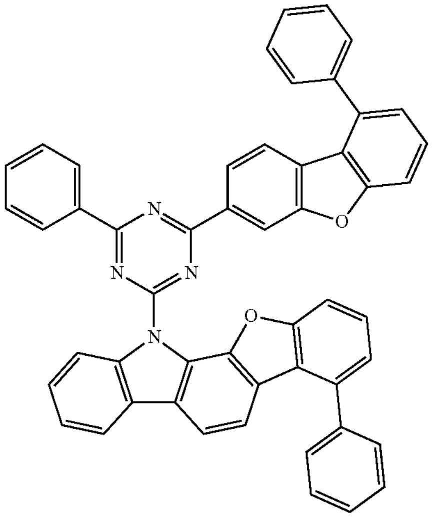
-continued
[B-15]
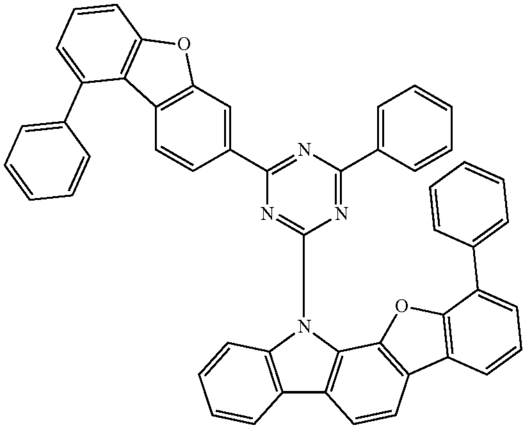
[B-16]
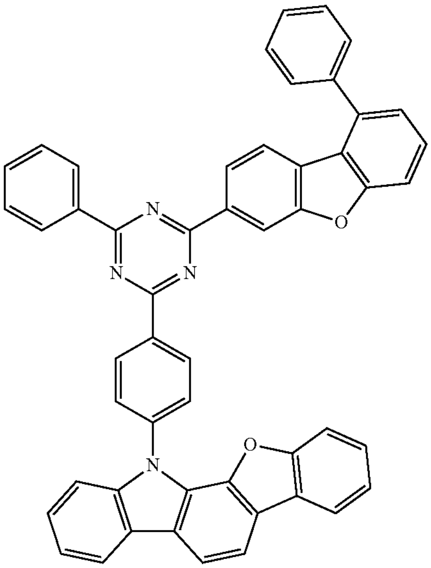
[B-17]
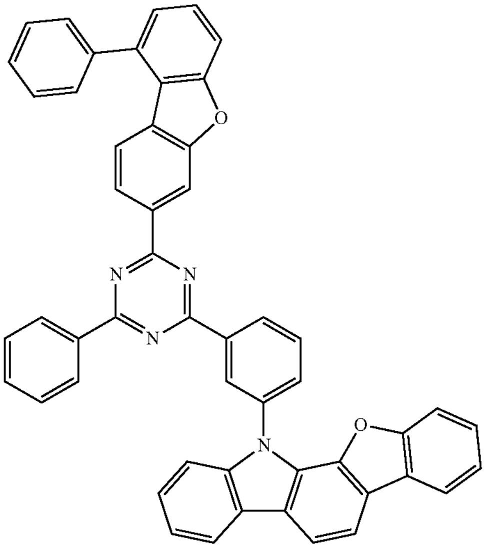

-continued
[B-18]
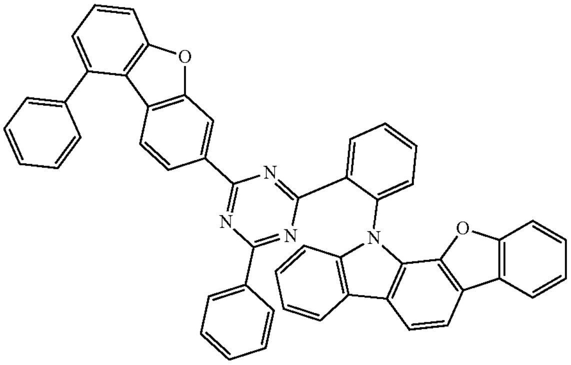
[B-19]
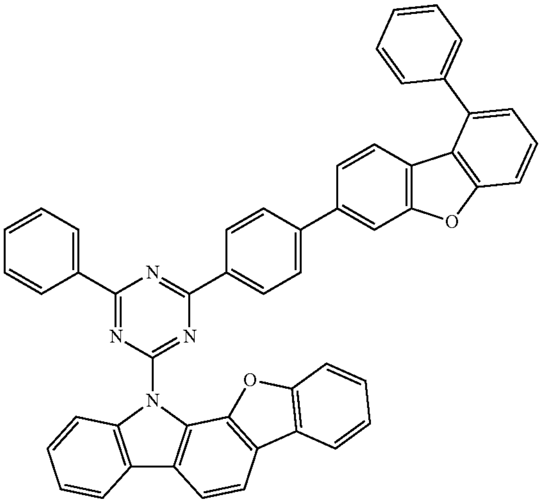
[B-20]
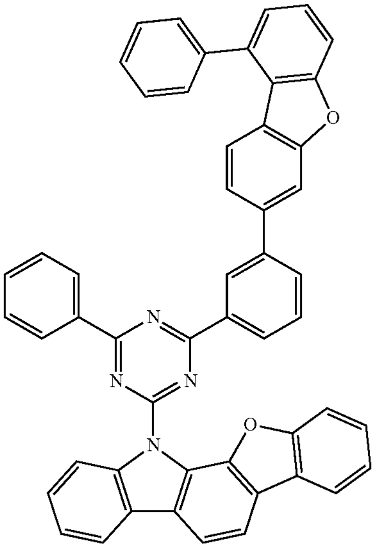
-continued
[B-21]
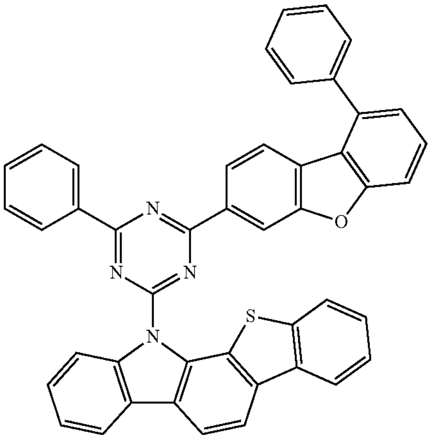
[B-22]
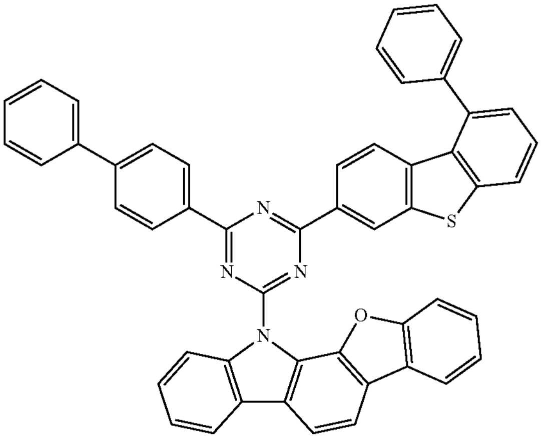
[B-23]
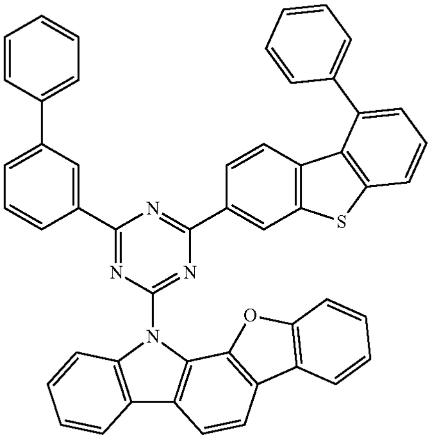

-continued
[B-24]
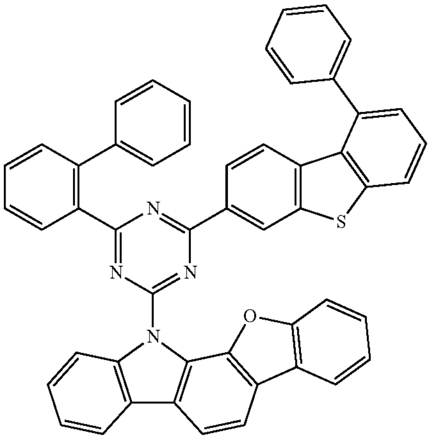
[B-25]
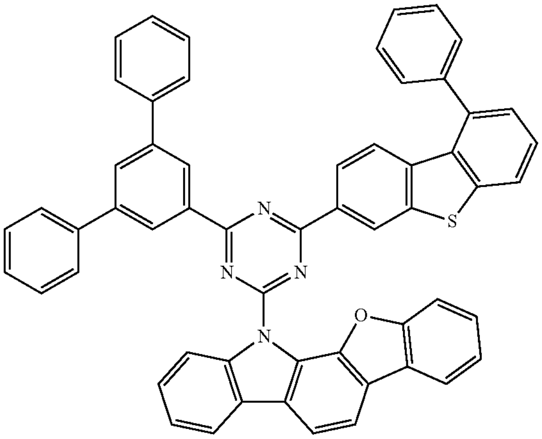
[B-26]
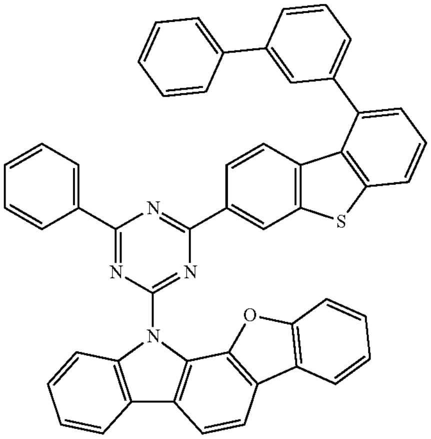
-continued
[B-27]
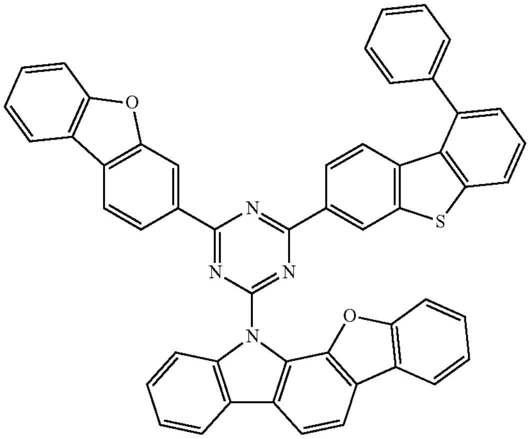
[B-28]
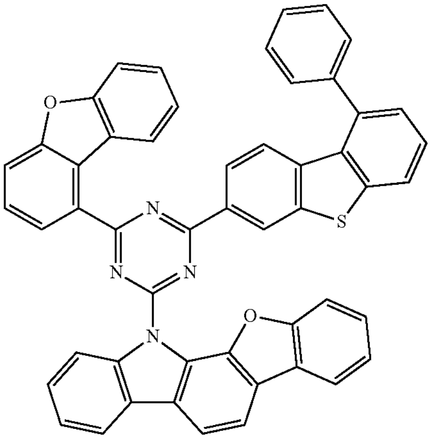
[B-29]
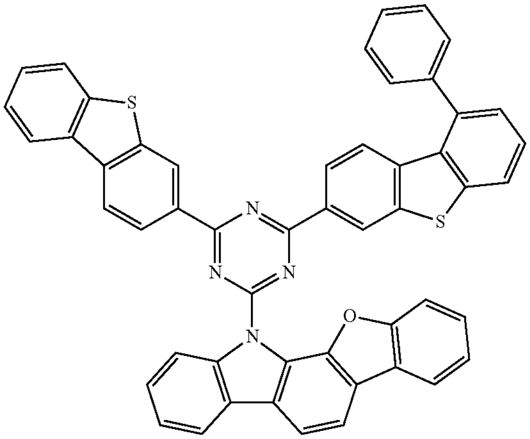

-continued
[B-30]
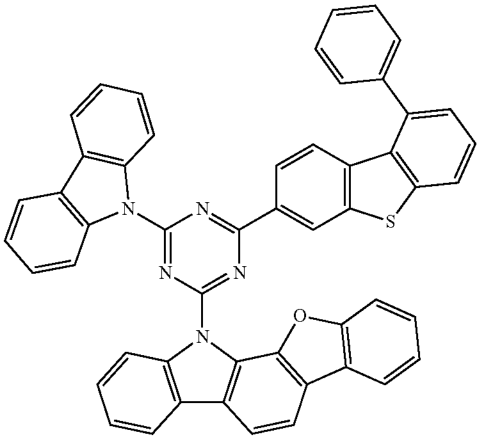
[B-31]
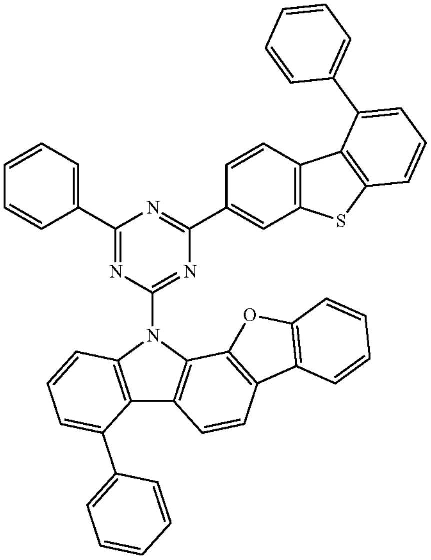
[B-32]
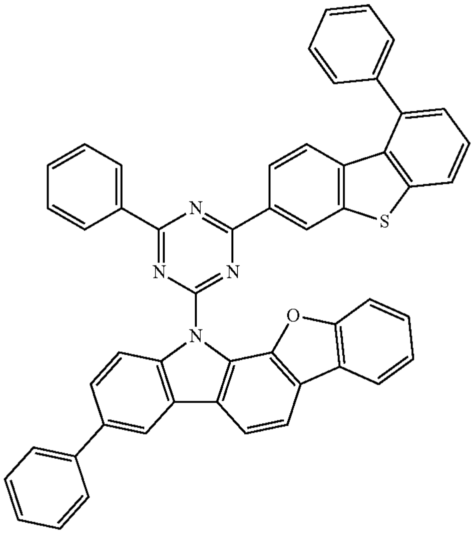
-continued
[B-33]
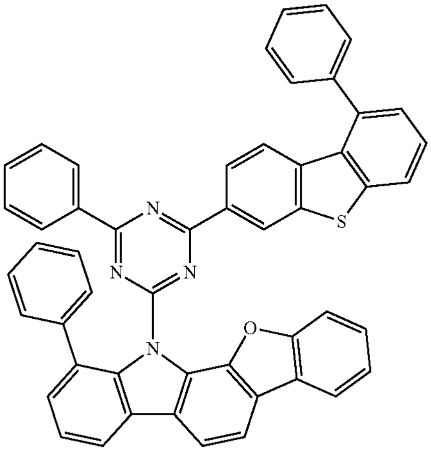
[B-34]
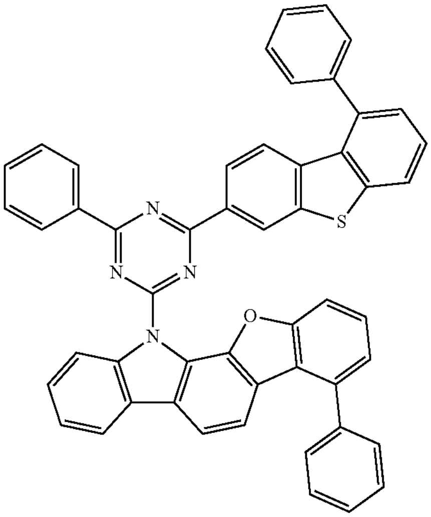
[B-35]
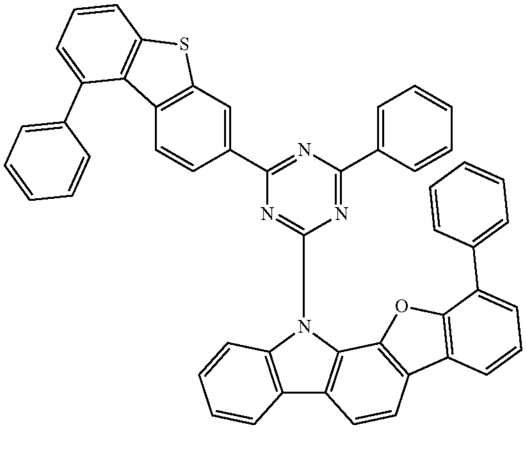

-continued
[B-36]
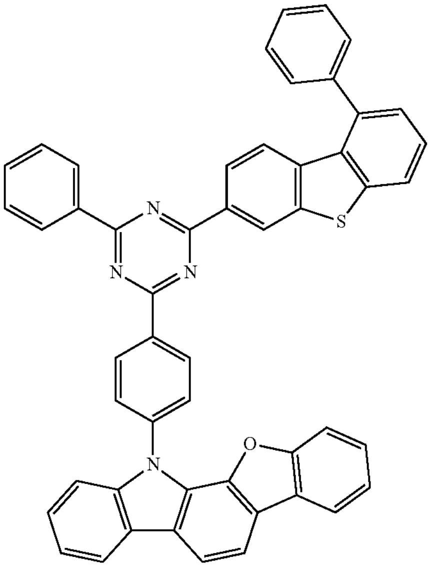
[B-37]
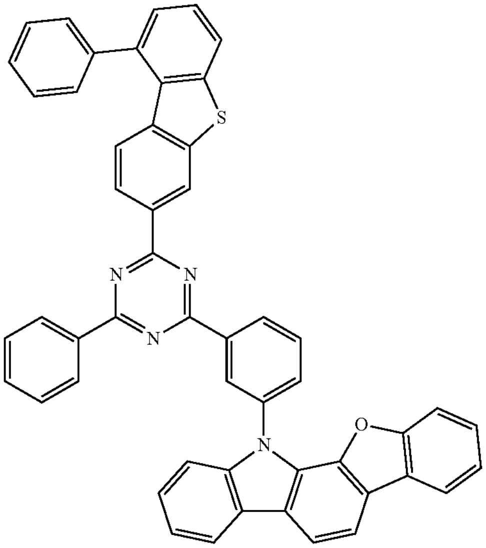
[B-38]
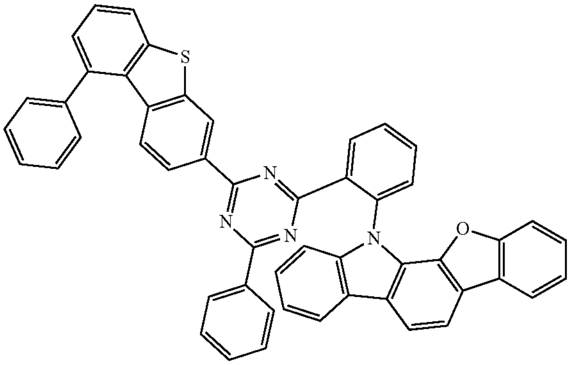
-continued
[B-39]
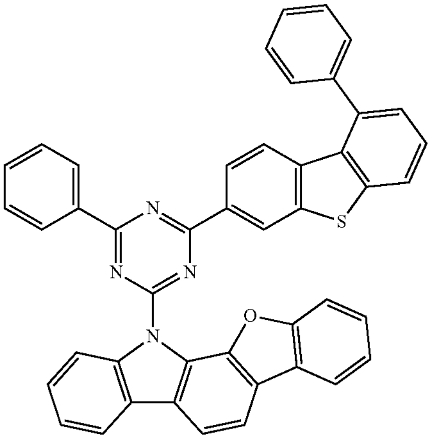
[B-40]
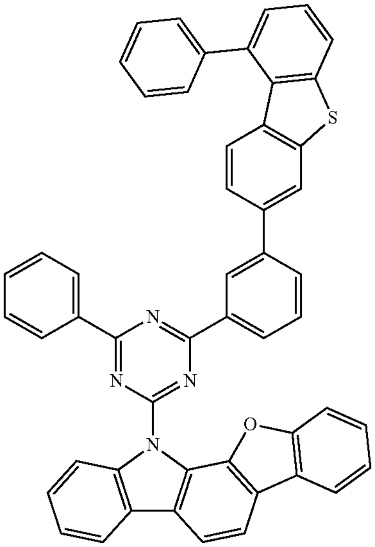
[B-41]
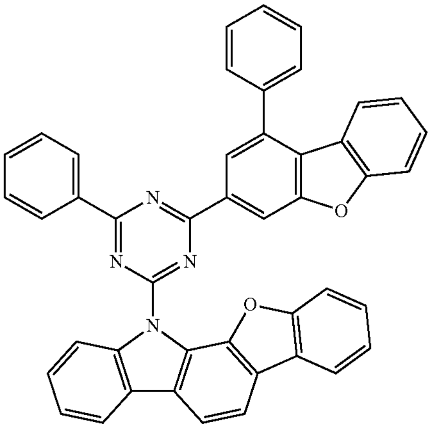

-continued
[B-42]
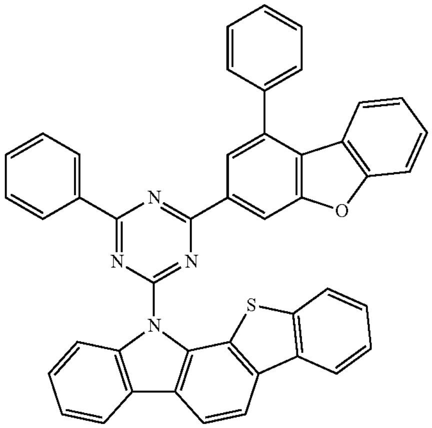
[B-43]
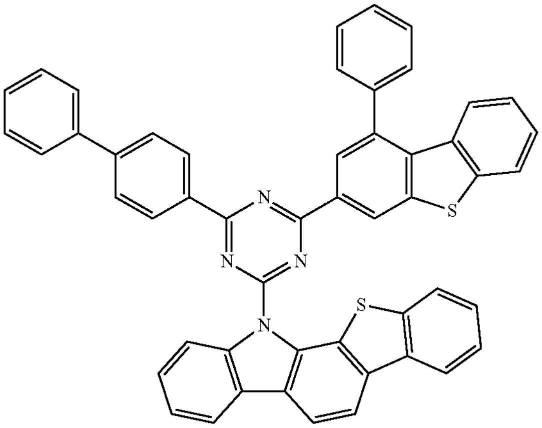
[B-44]
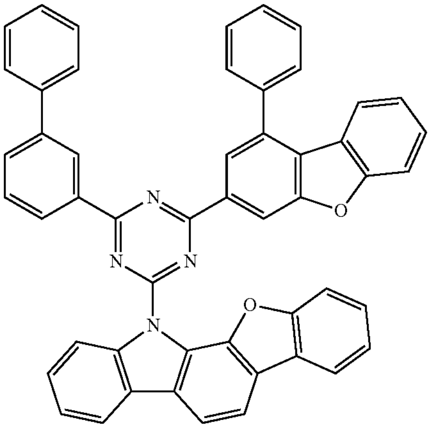
-continued
[B-45]
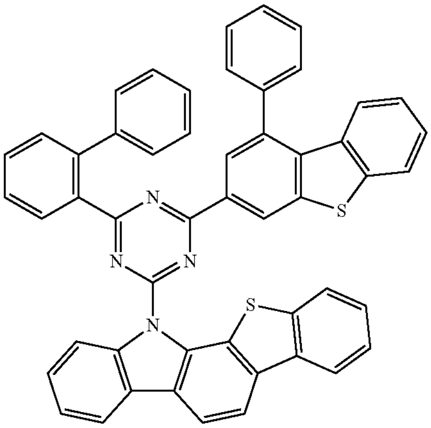
[B-46]
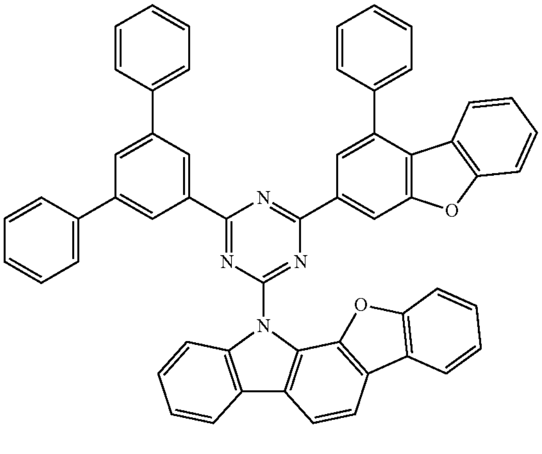
[B-47]
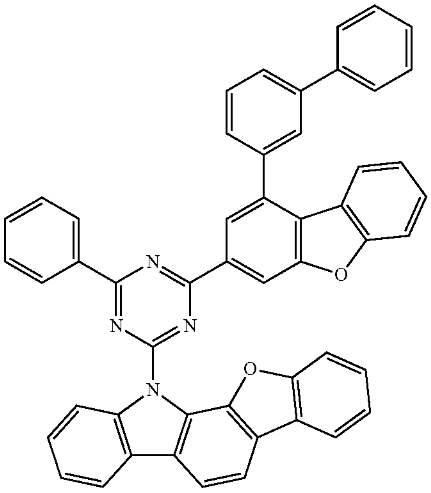

-continued
[B-48]
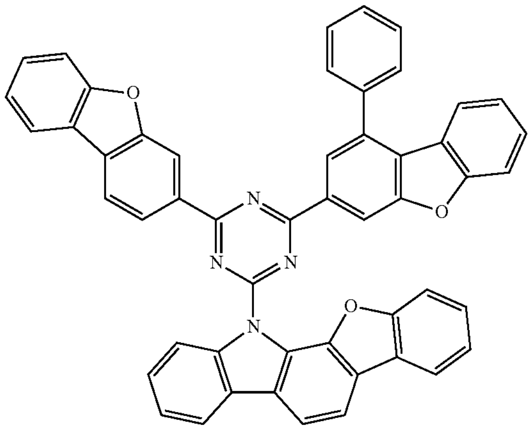
[B-49]
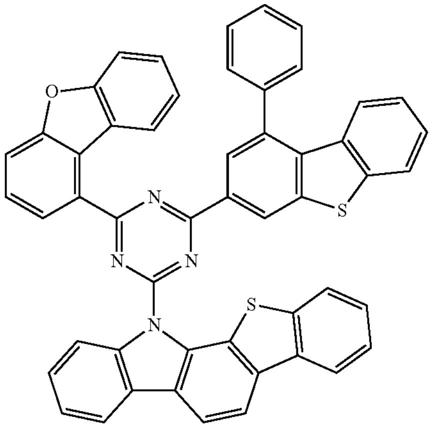
[B-50]
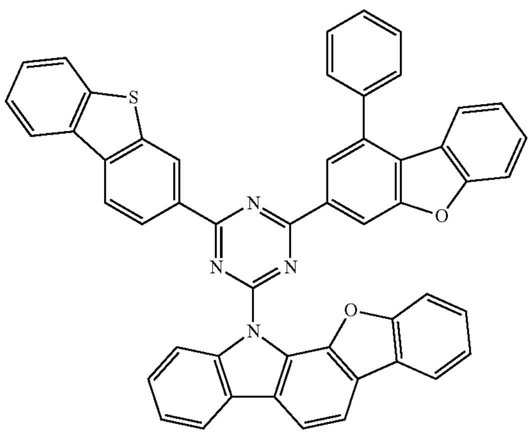
-continued
[B-51]
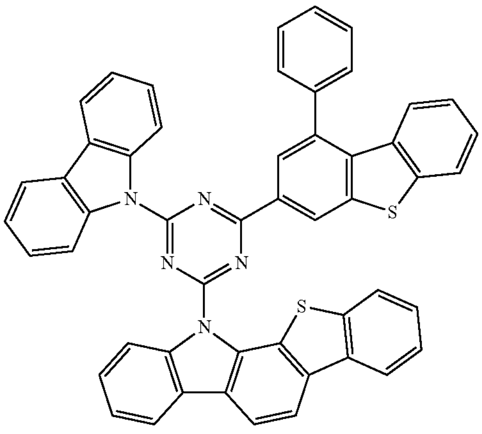
[B-52]
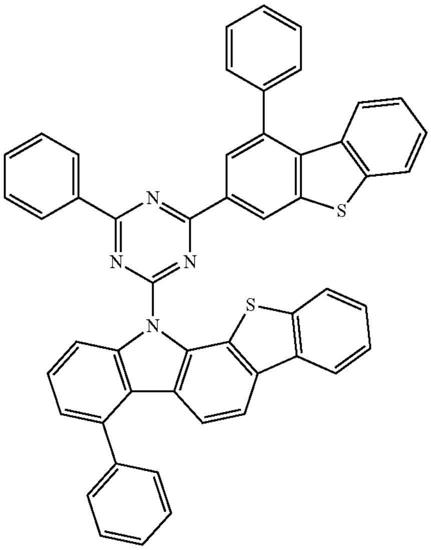
[B-53]
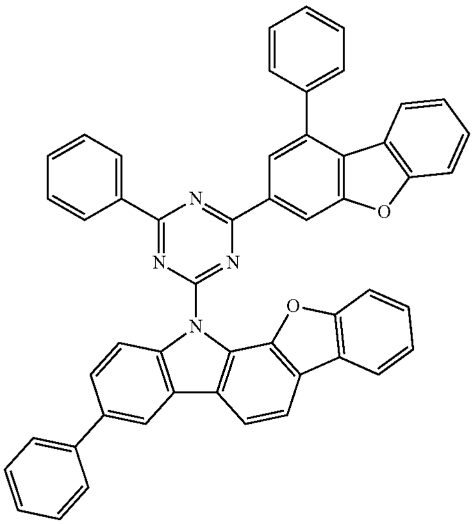

-continued
[B-54]
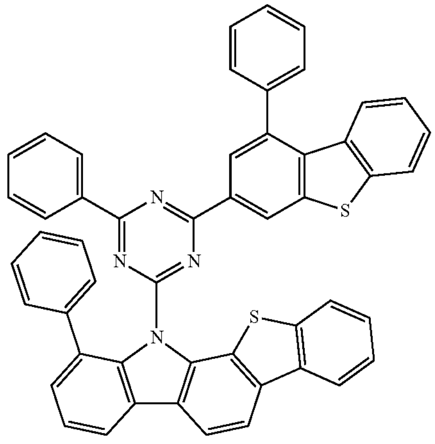
[B-55]
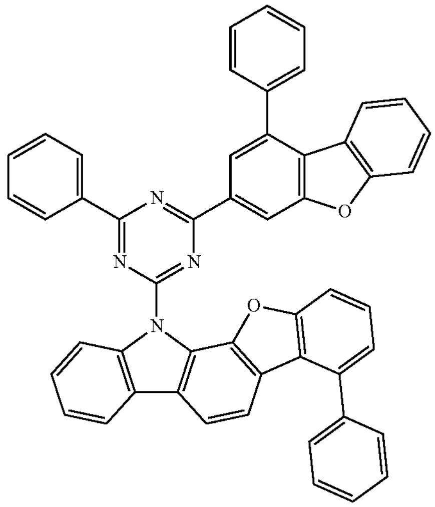
[B-56]
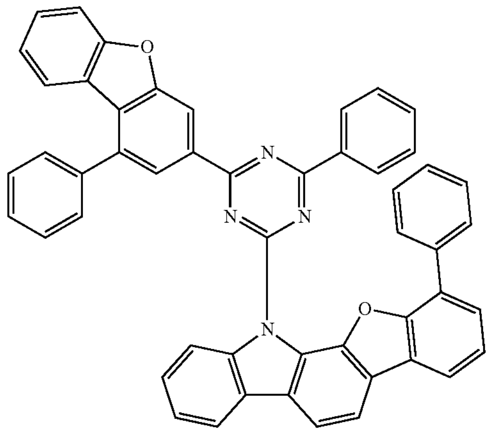
-continued
[B-57]
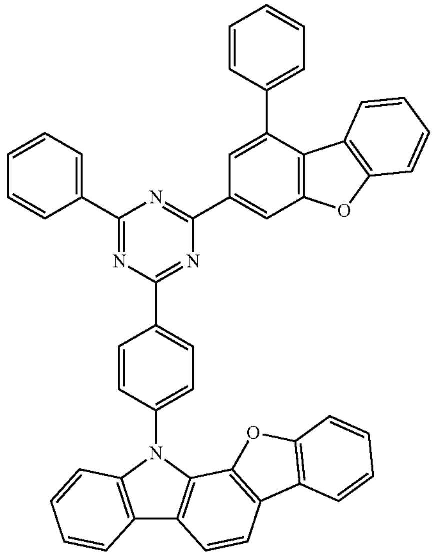
[B-58]
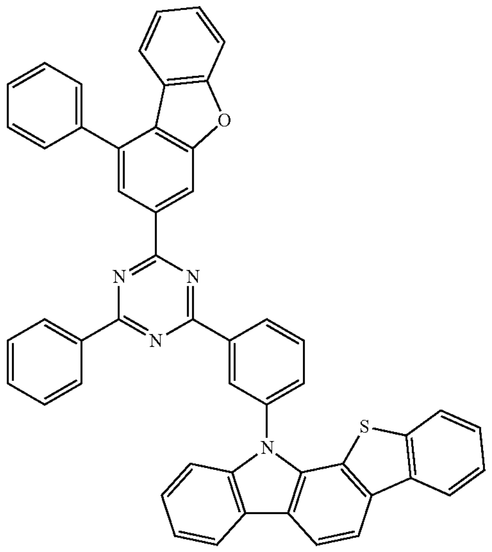
[B-59]
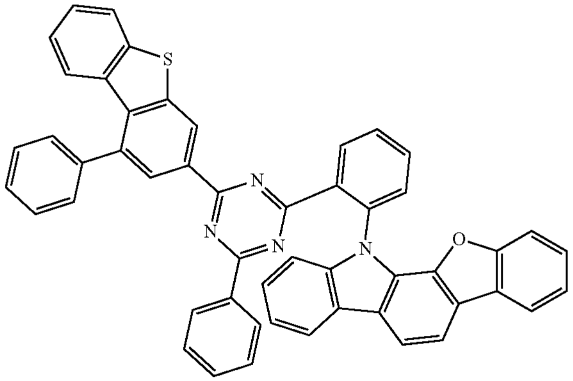

-continued
[B-60]
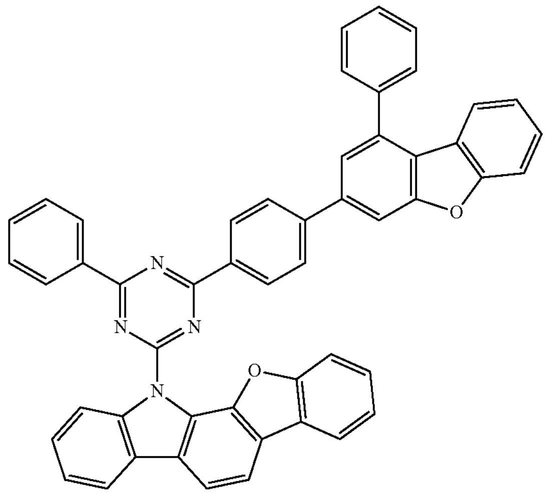
[B-61]
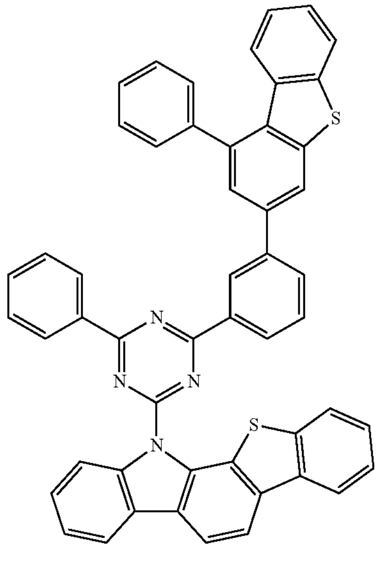
[B-62]
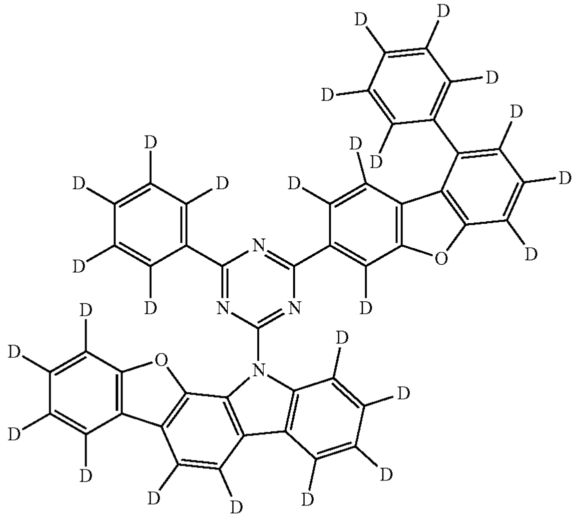
-continued
[B-63]
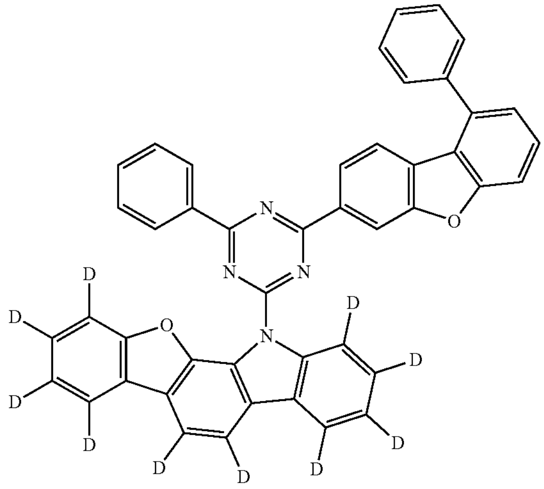
[B-64]
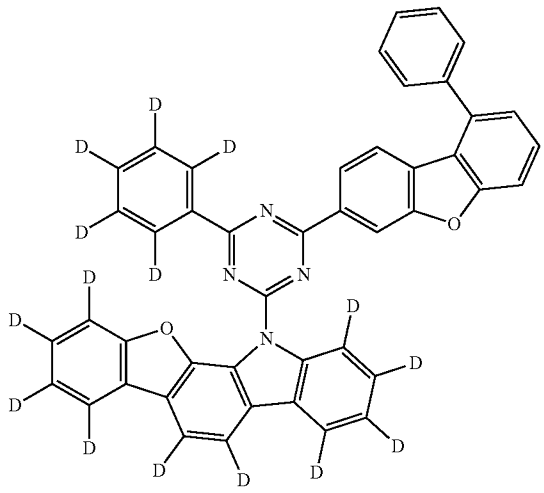
[B-65]
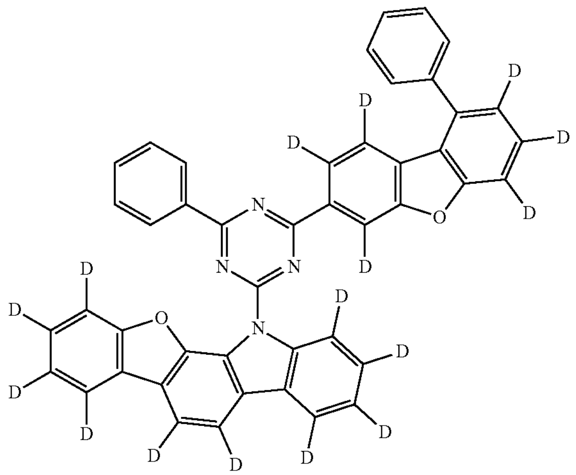

-continued
[B-66]
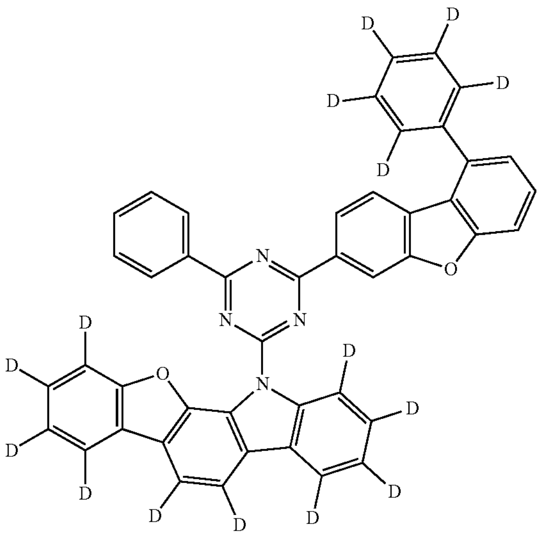
[B-67]
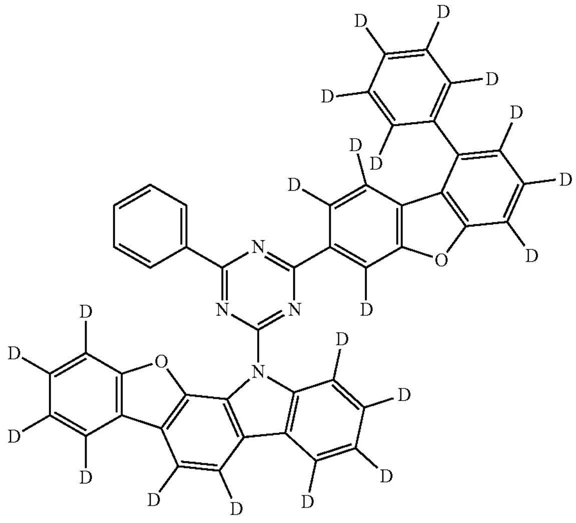
[B-68]
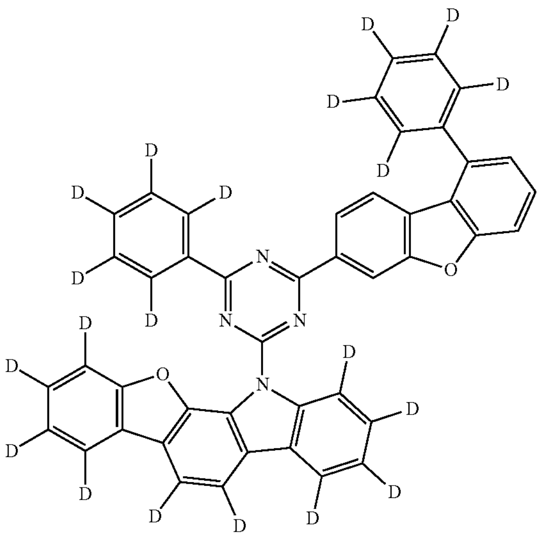
-continued
[B-69]
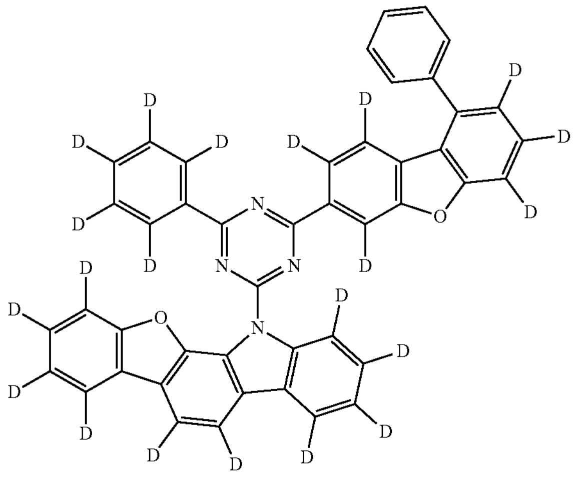
[B-70]
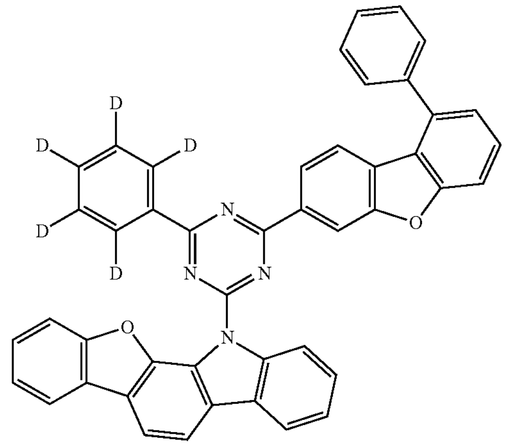
[B-71]
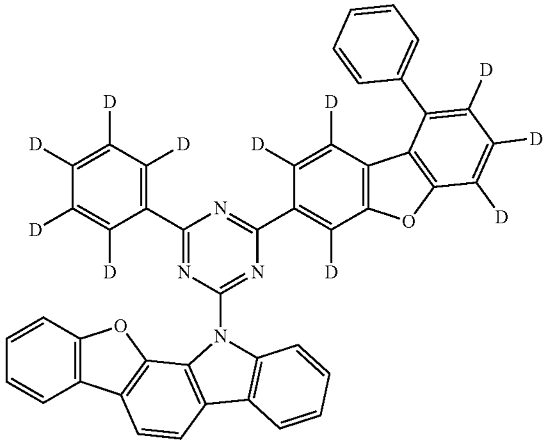

-continued
[B-72]
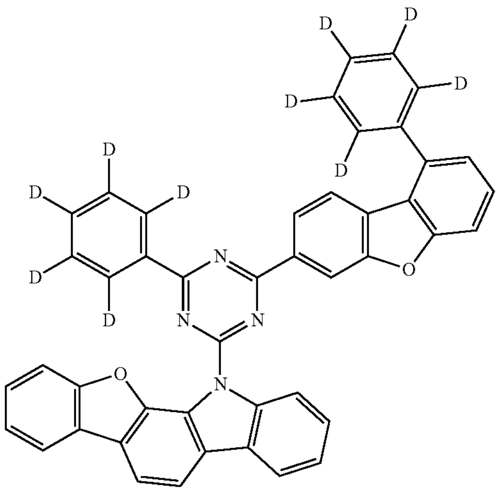
[B-73]
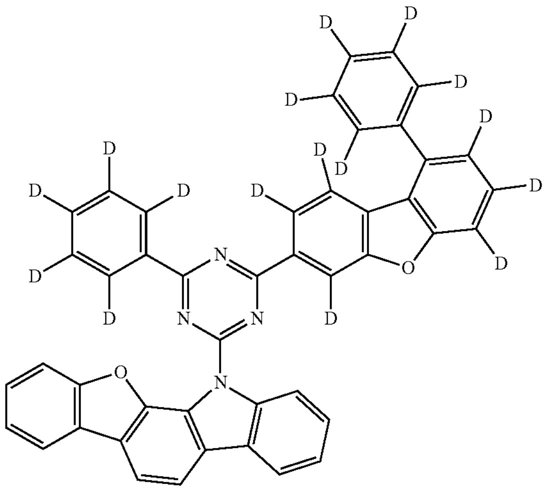
[B-74]
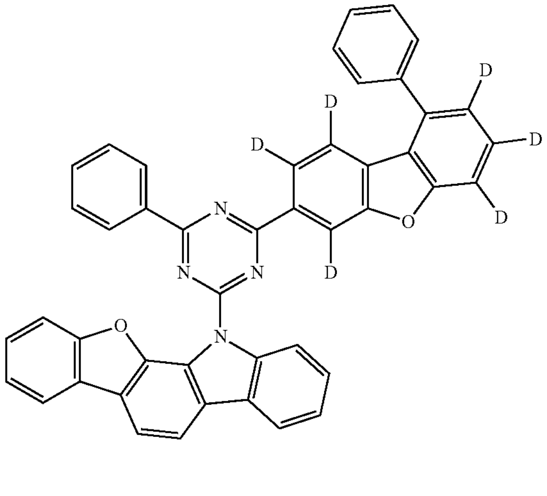
-continued
[B-75]
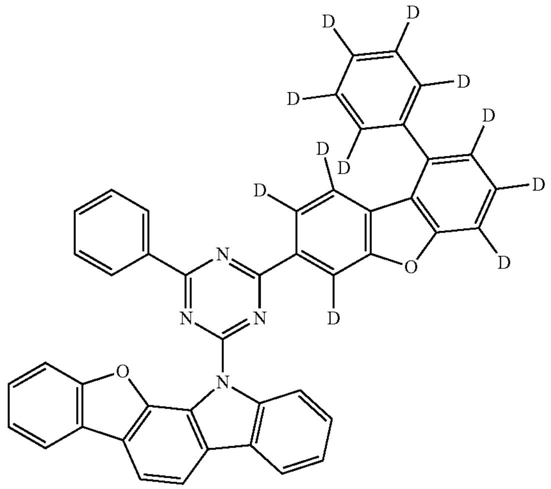
[B-76]
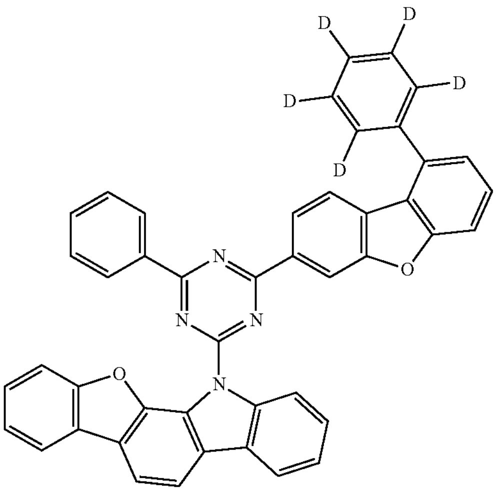
[B-77]
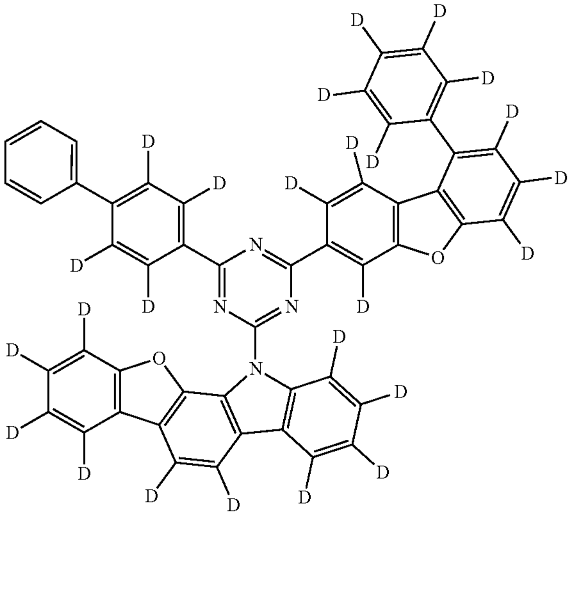

-continued
[B-78]
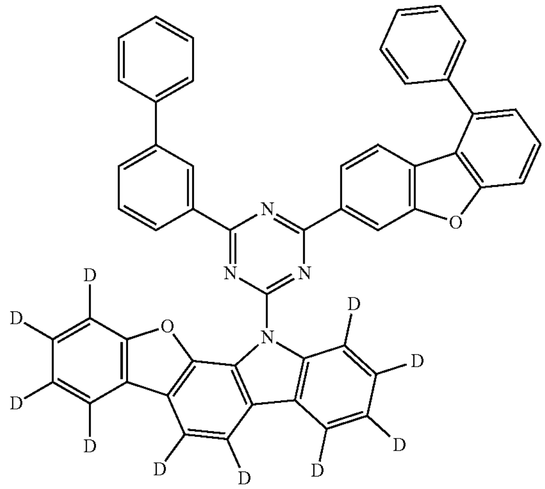
[B-79]
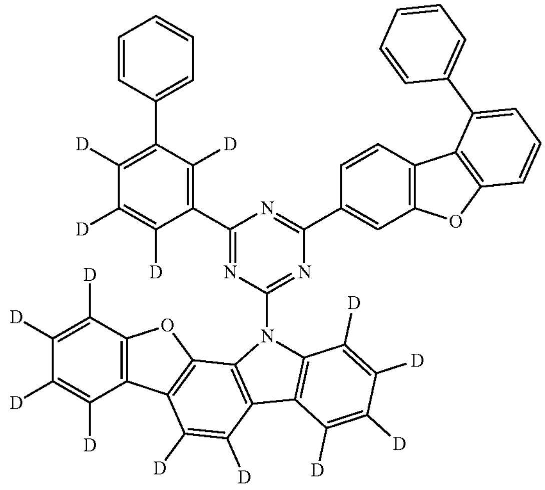
[B-80]
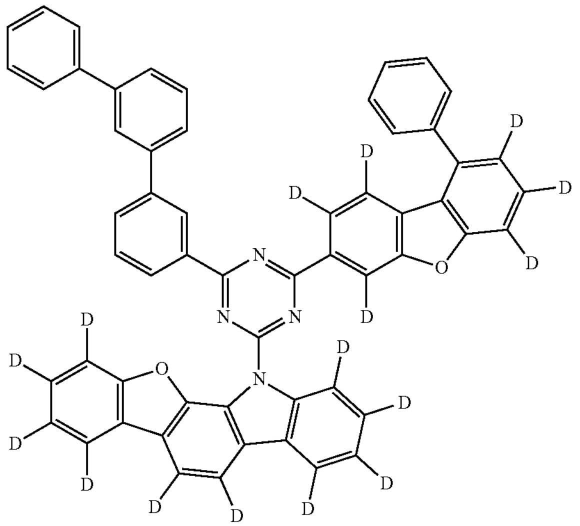
-continued
[B-81]
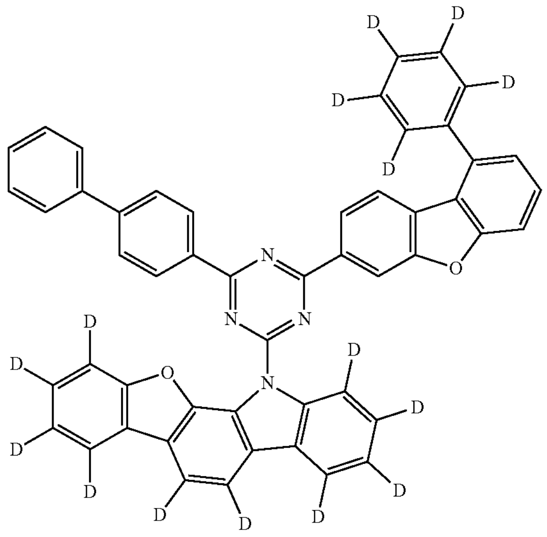
[B-82]
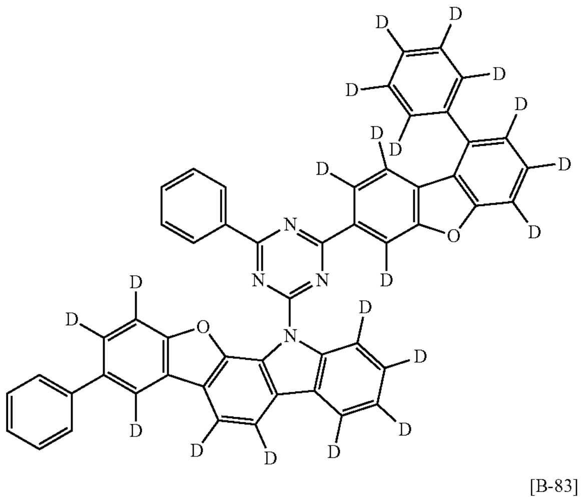
[B-83]
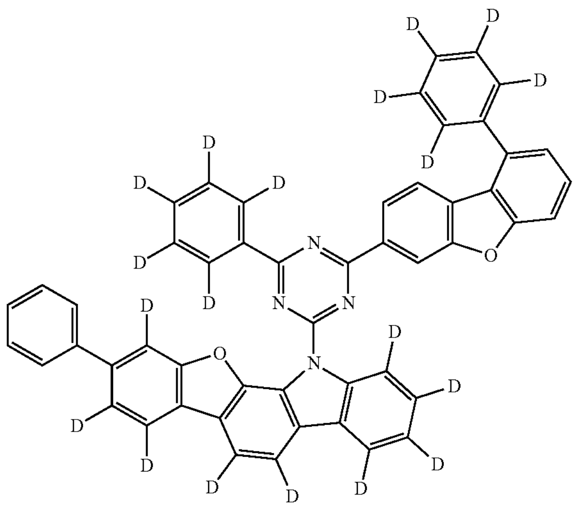

-continued
[B-84]
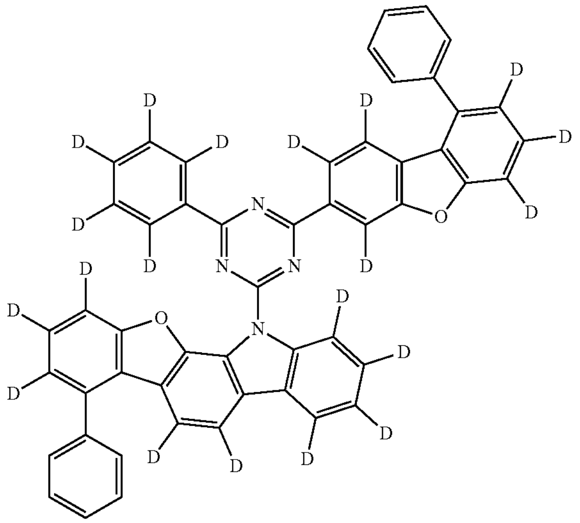
[B-85]
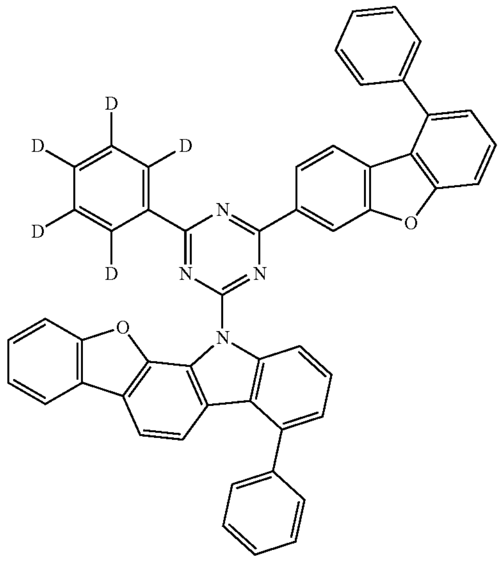
[B-86]
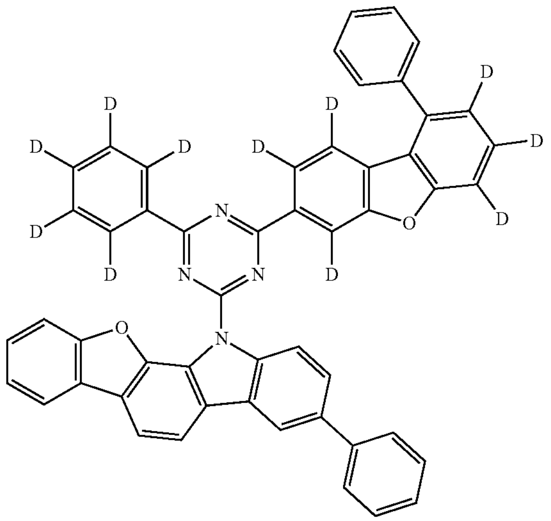
-continued
[B-87]
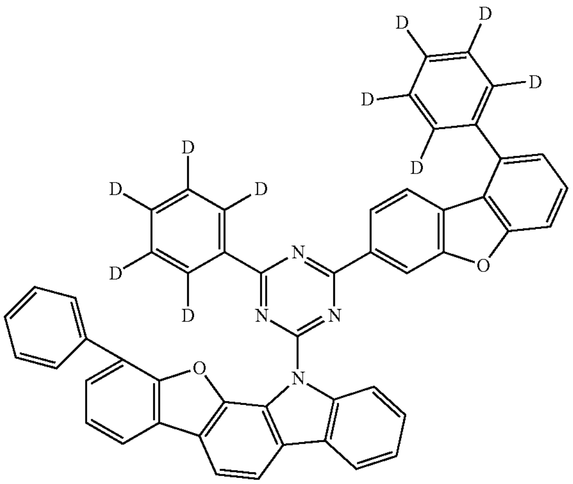
[B-88]
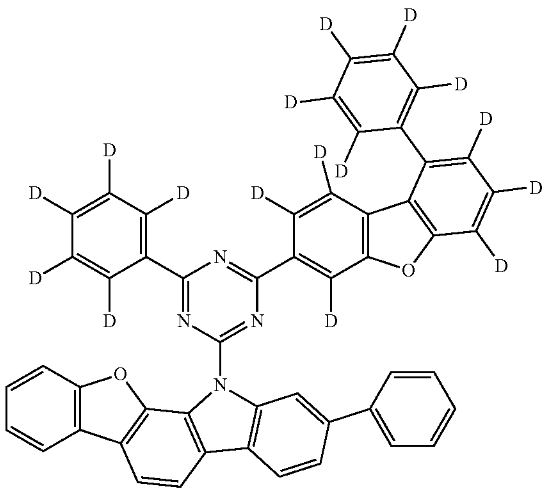
[B-89]
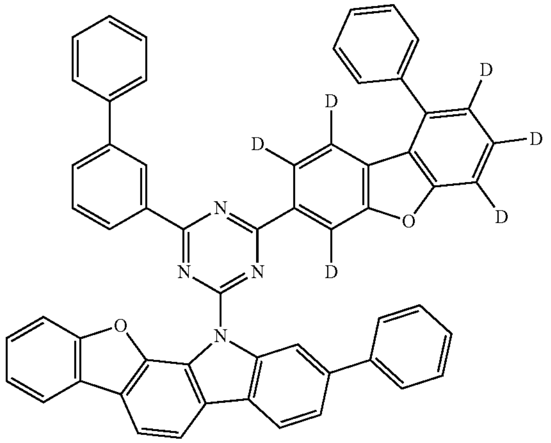

-continued
[B-90]
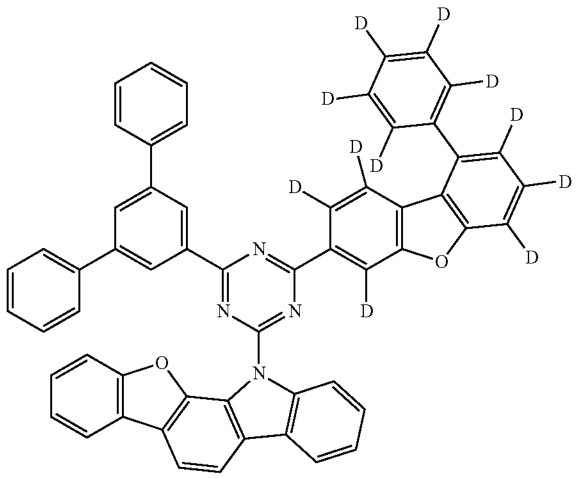
[B-91]
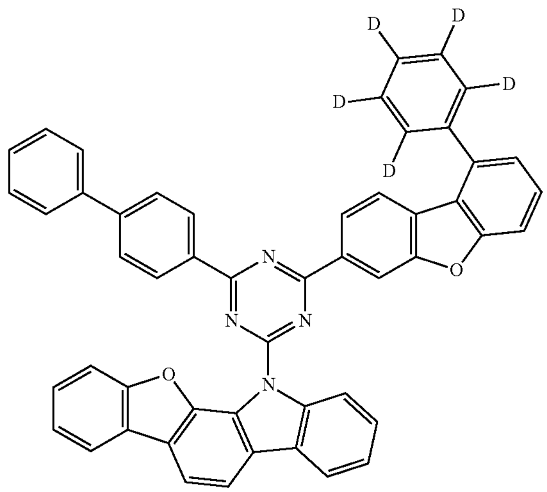
[B-92]
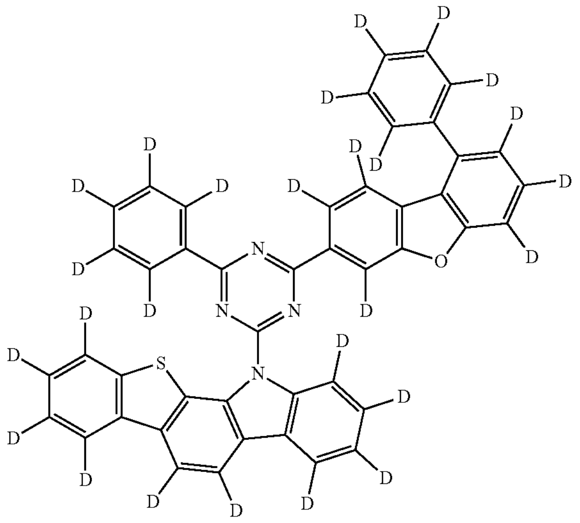
-continued
[B-93]
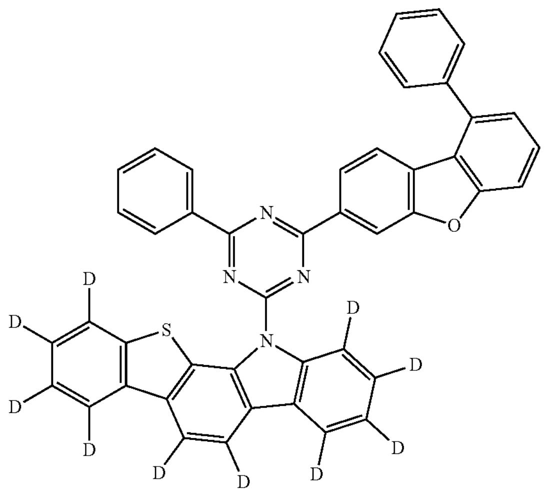
[B-94]
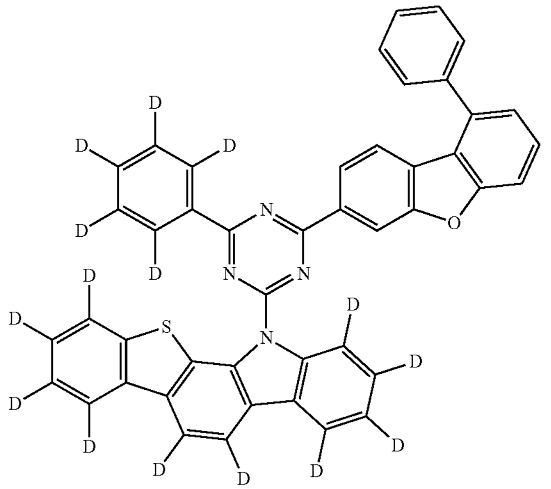
[B-95]
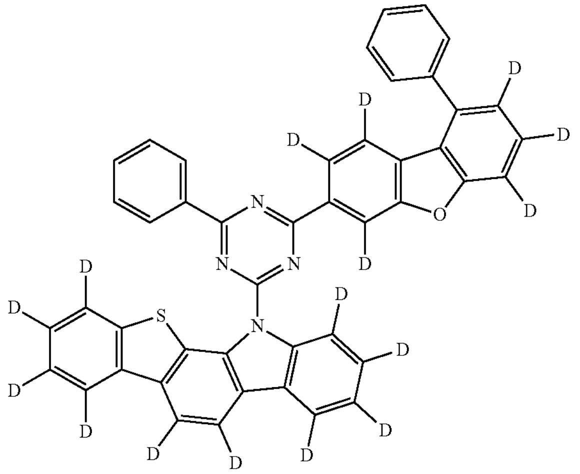

-continued
[B-96]
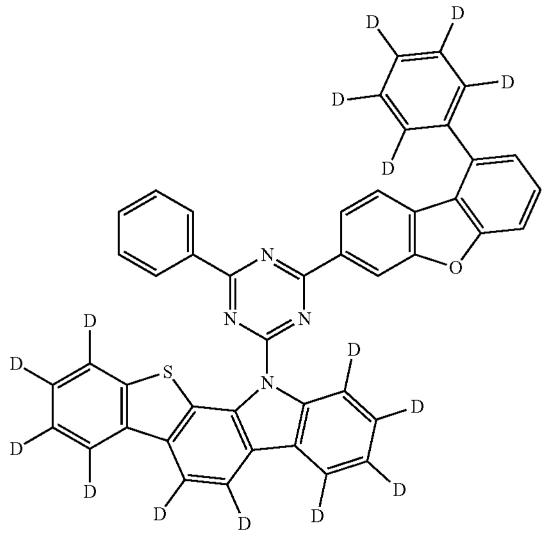
[B-97]
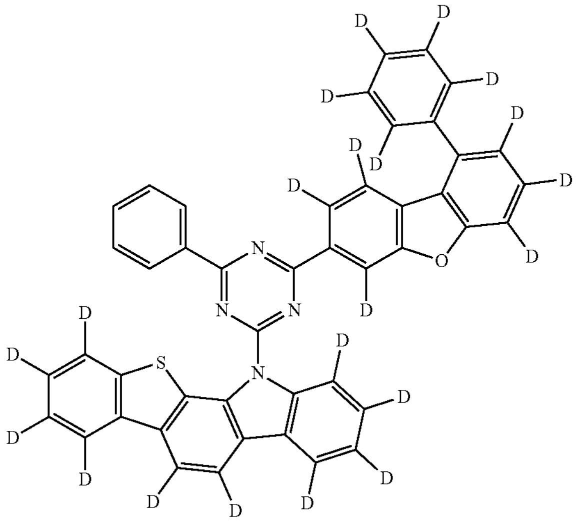
[B-98]
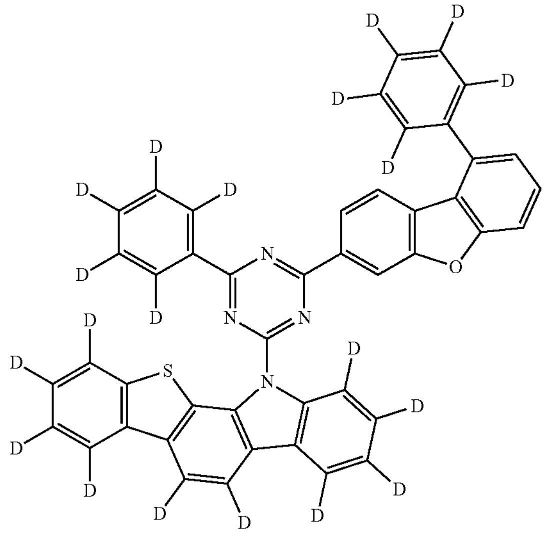
-continued
[B-99]
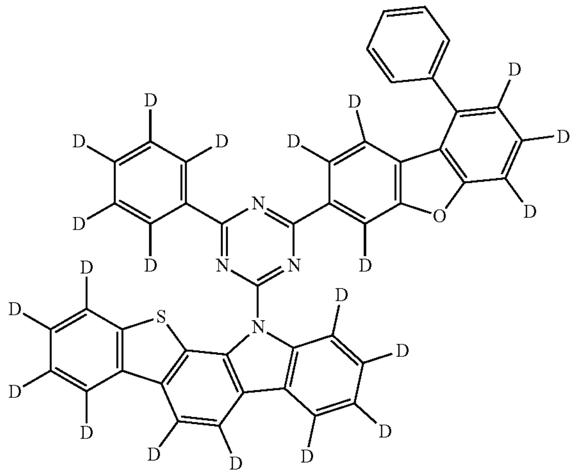
[B-100]
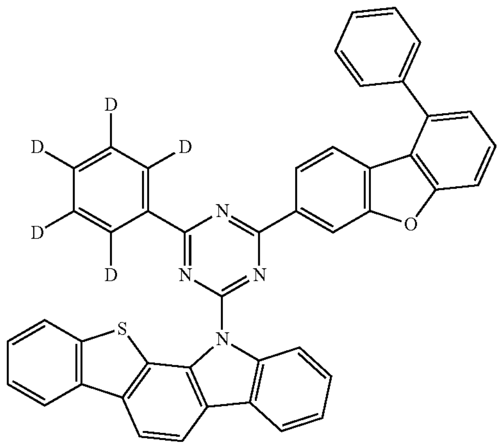
[B-101]
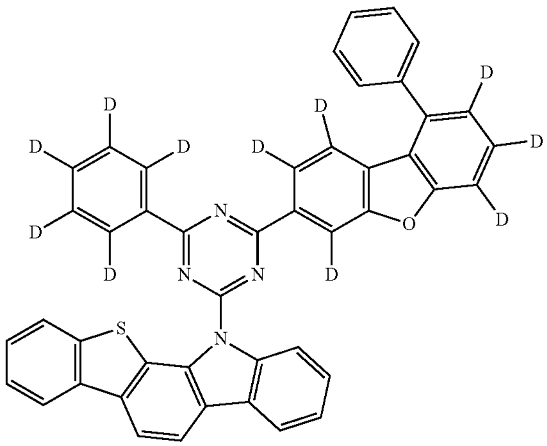

-continued
[B-102]
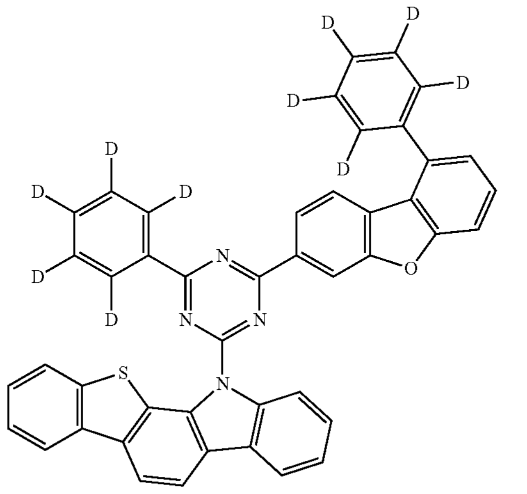
[B-103]
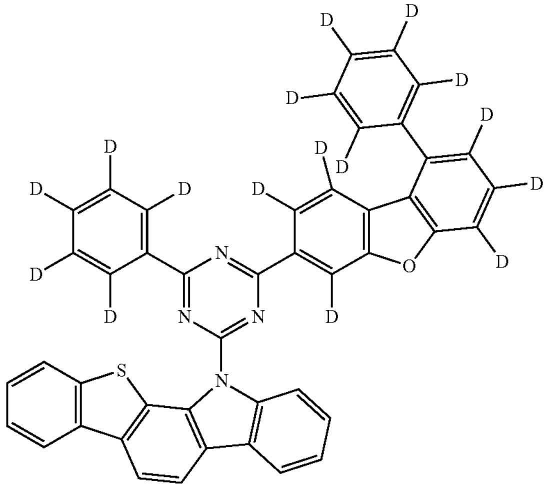
[B-104]
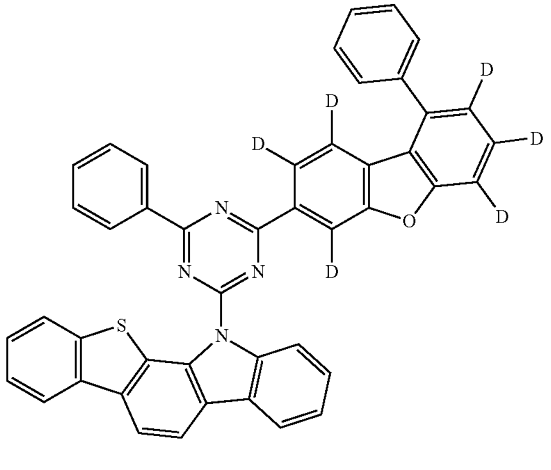
-continued
[B-105]
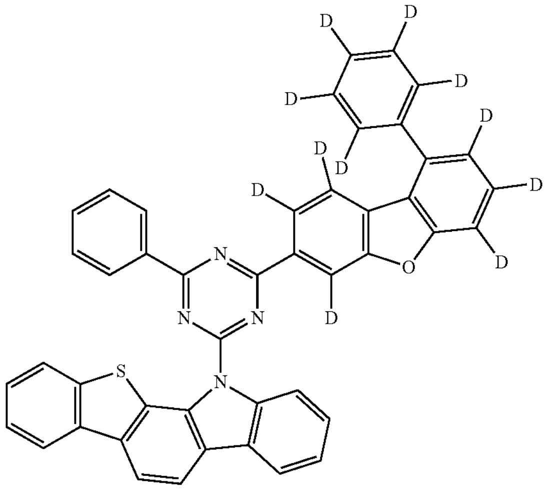
[B-106]
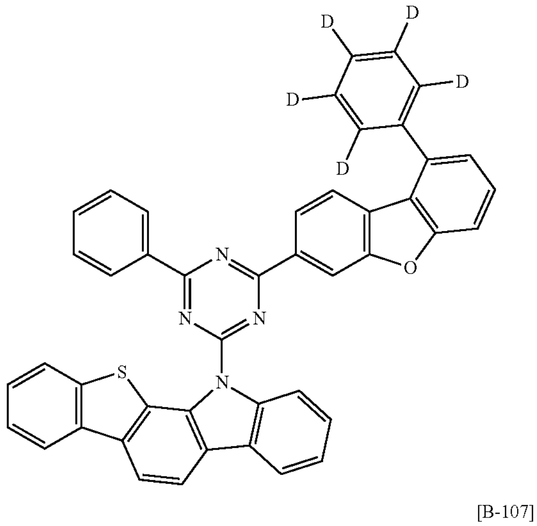
[B-107]
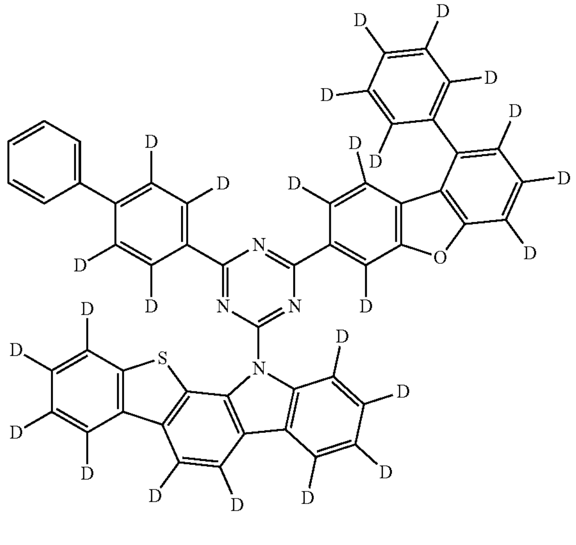

-continued
[B-108]
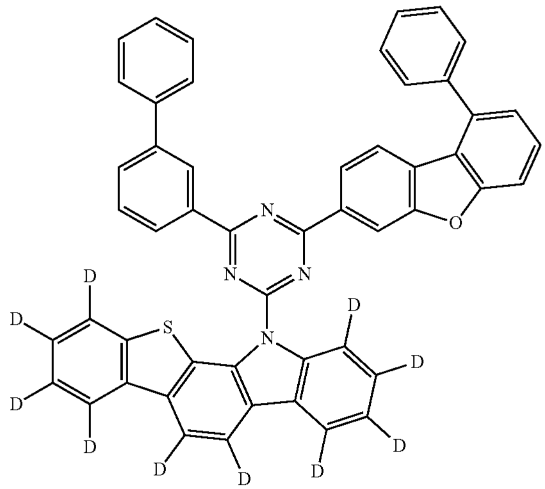
[B-109]
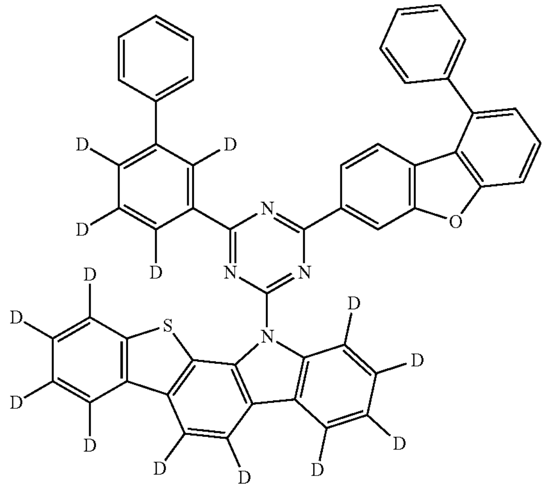
[B-110]
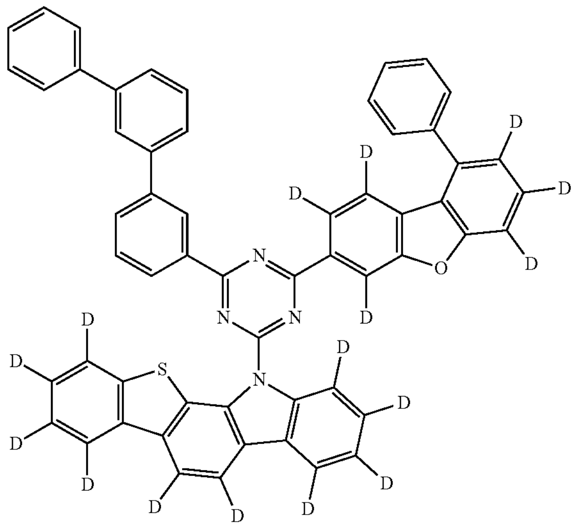
-continued
[B-111]
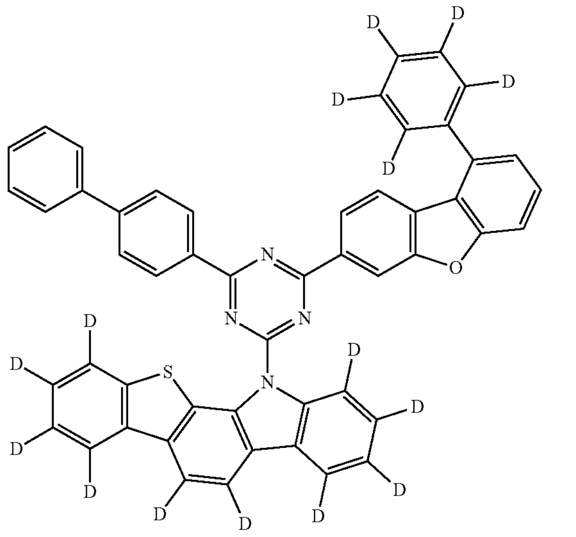
[B-112]
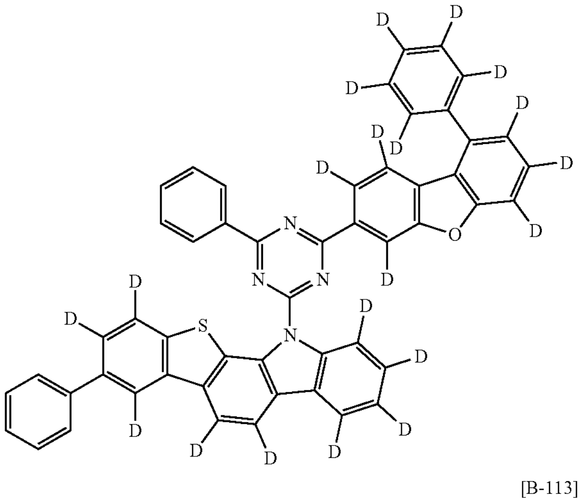
[B-113]
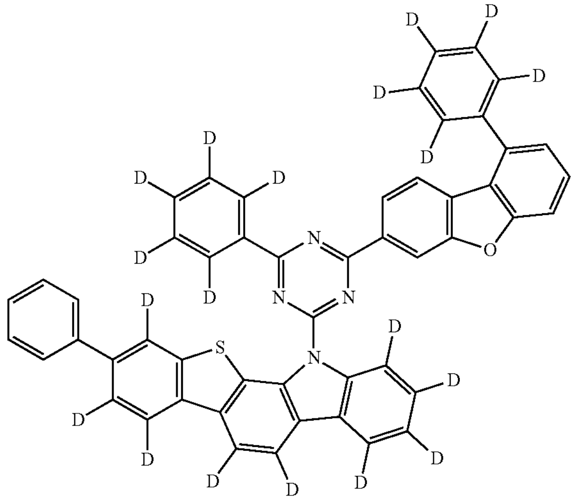

[B-114]
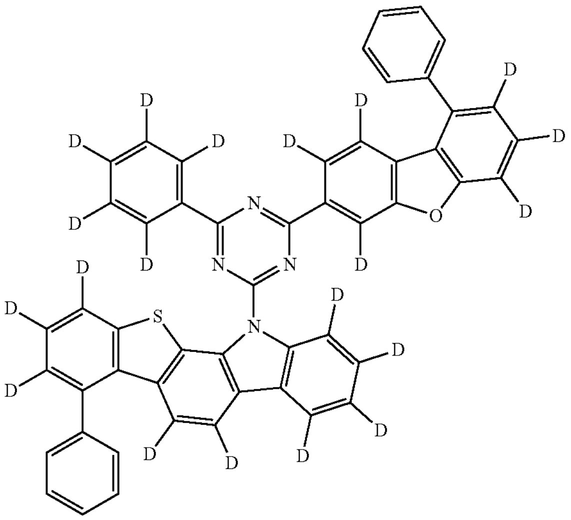
[B-115]
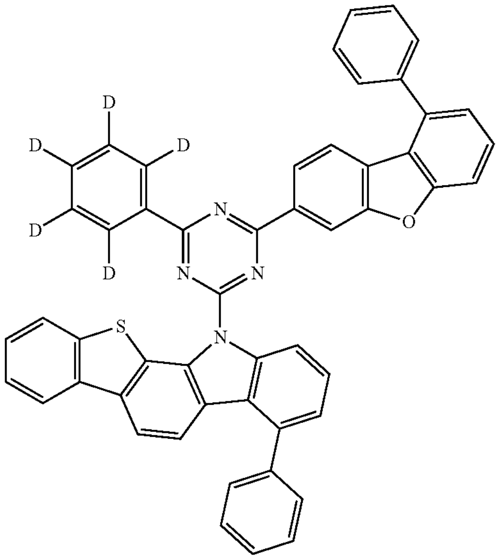
[B-116]
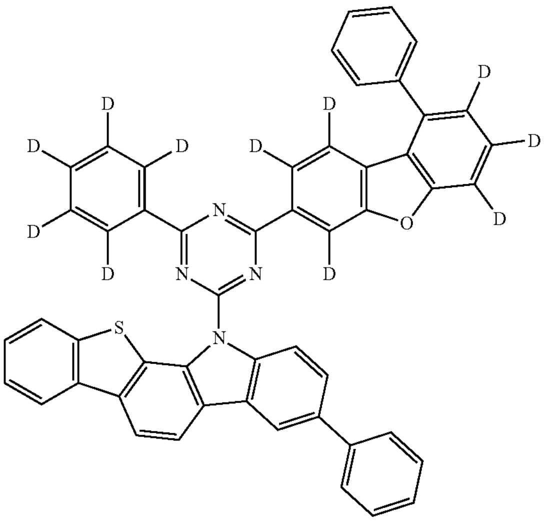
[B-117]
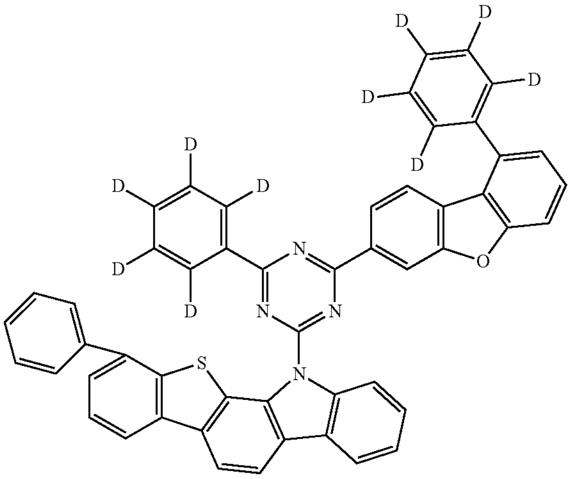
[B-118]
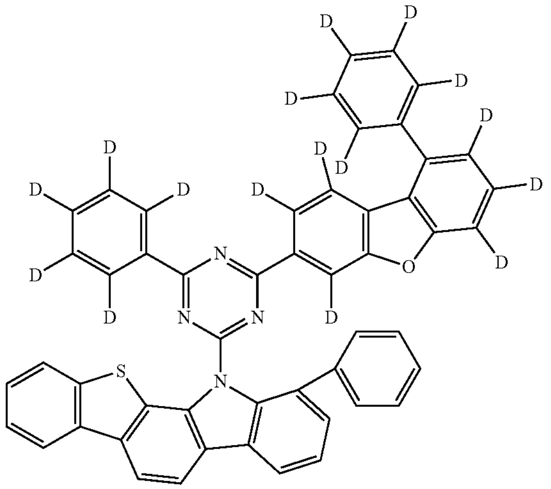
[B-119]
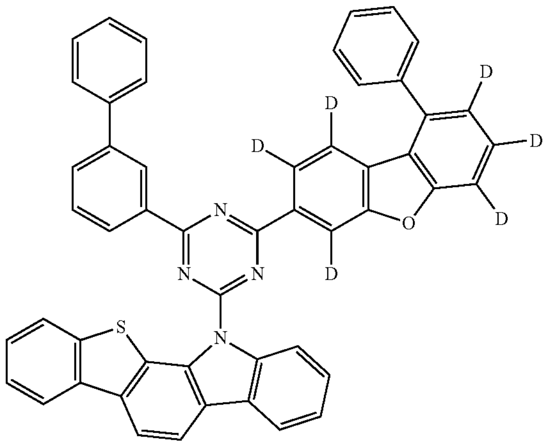

-continued
[B-120]
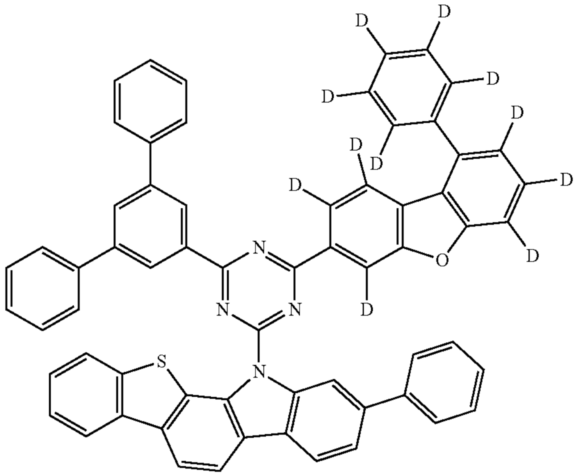
[B-121]
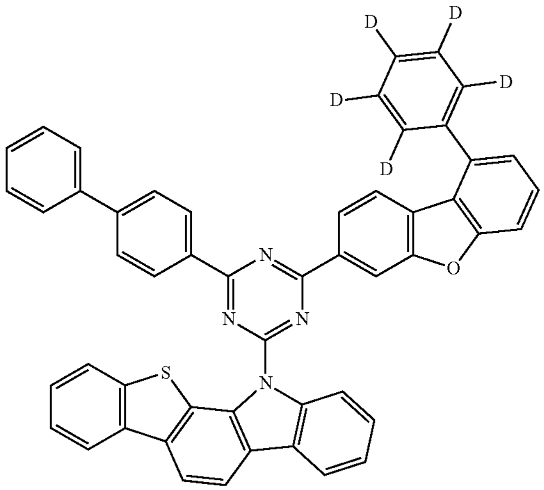
[C-1]
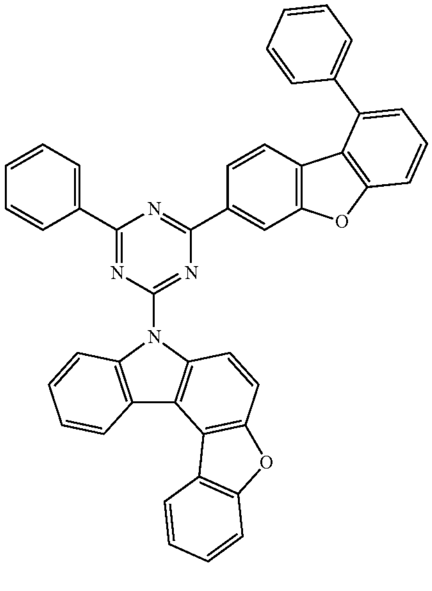
-continued
[C-2]
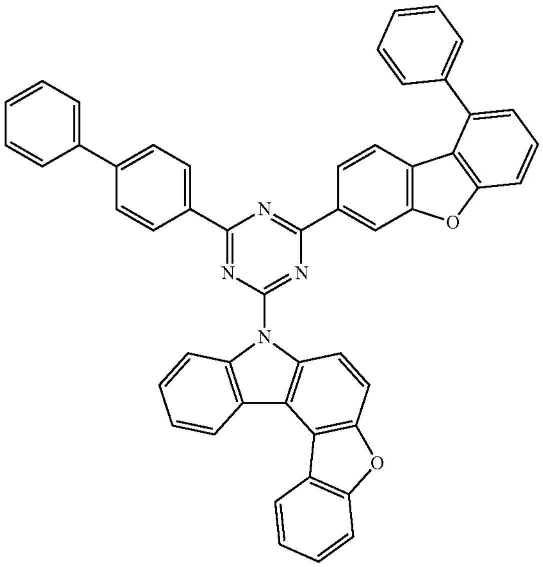
[C-3]
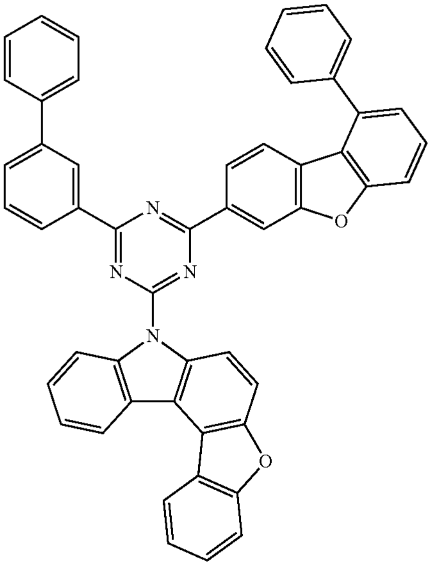

-continued
[C-4]
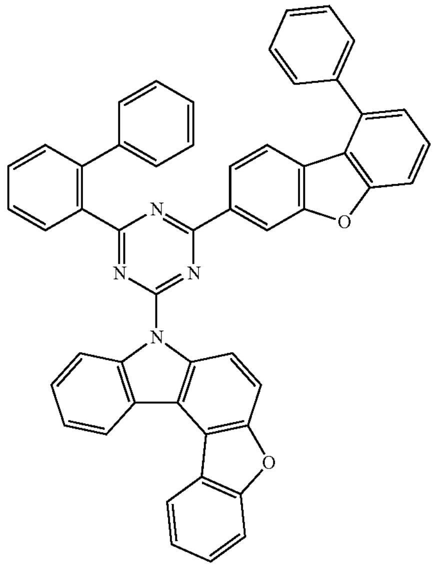
[C-5]
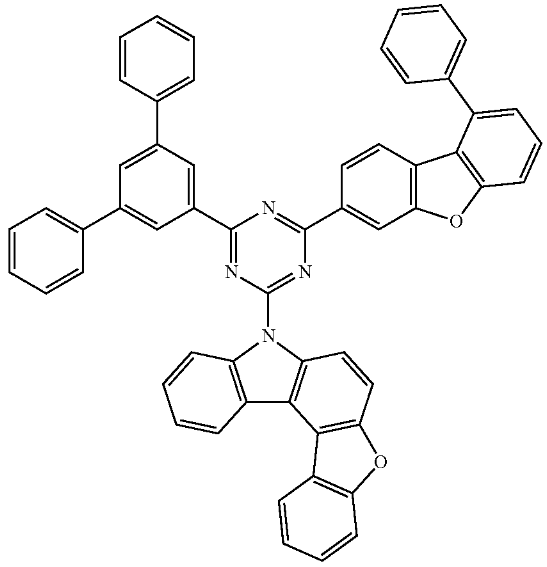
-continued
[C-6]
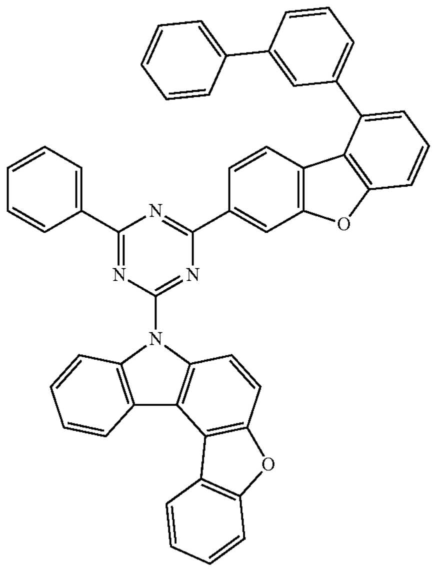
[C-7]
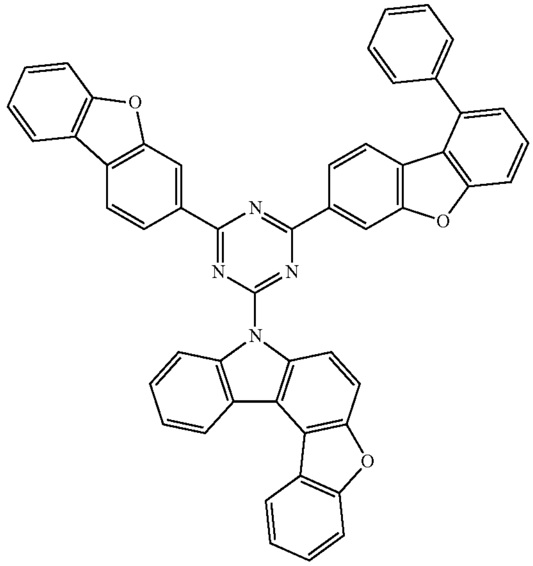

-continued
[C-8]
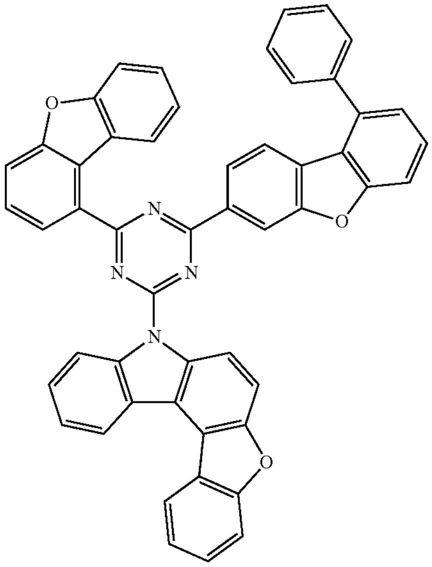
[C-9]
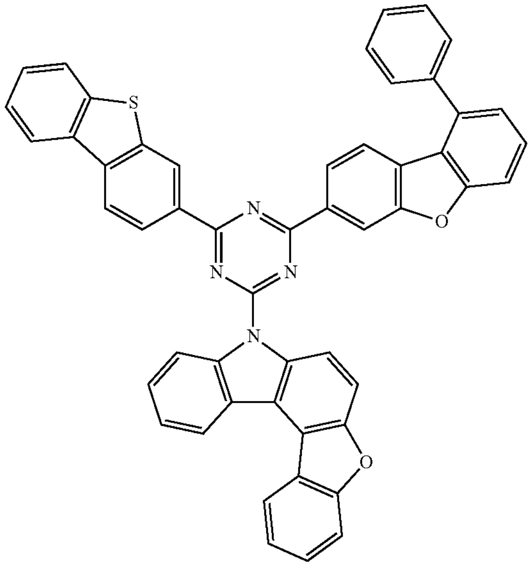
-continued
[C-10]
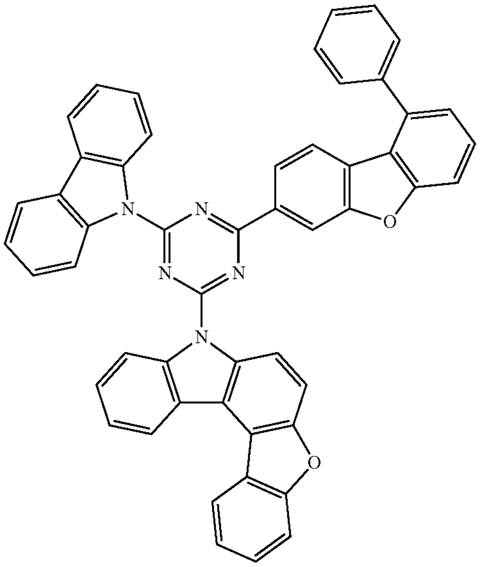
[C-11]
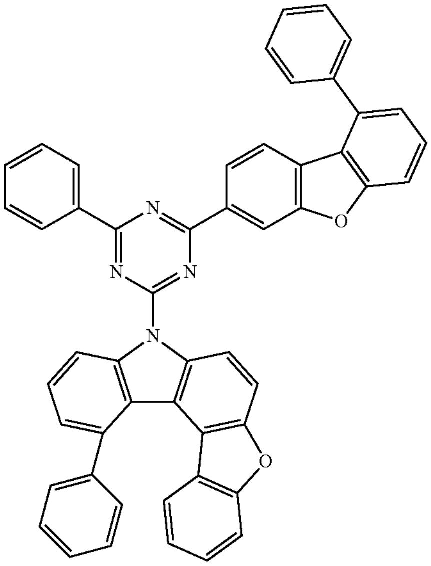

-continued
[C-12]
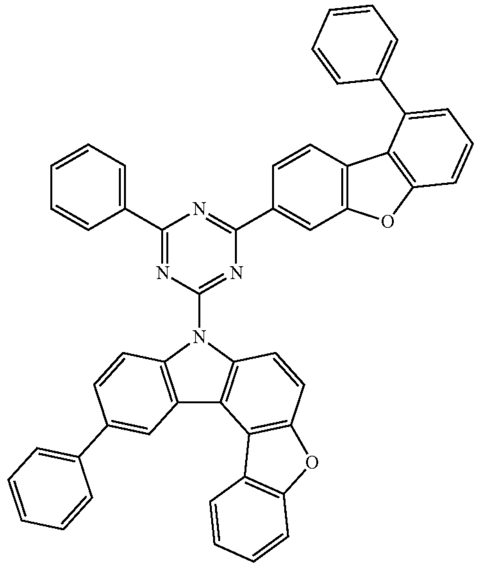
[C-13]
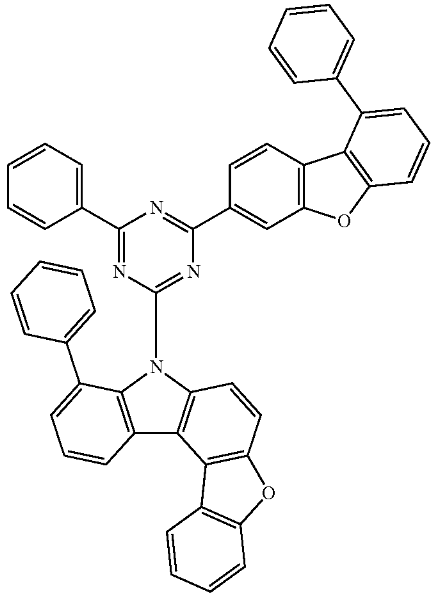
-continued
[C-14]
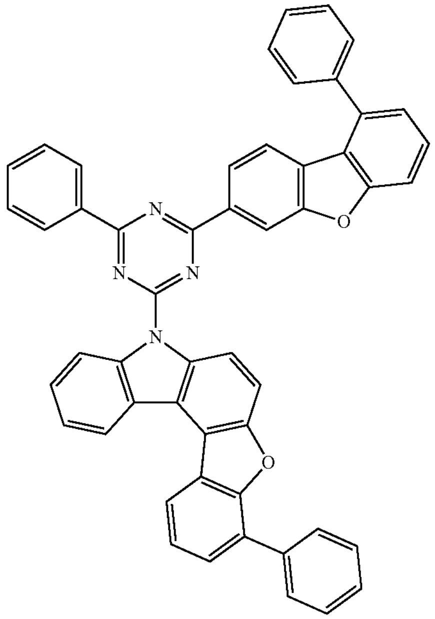
[C-15]
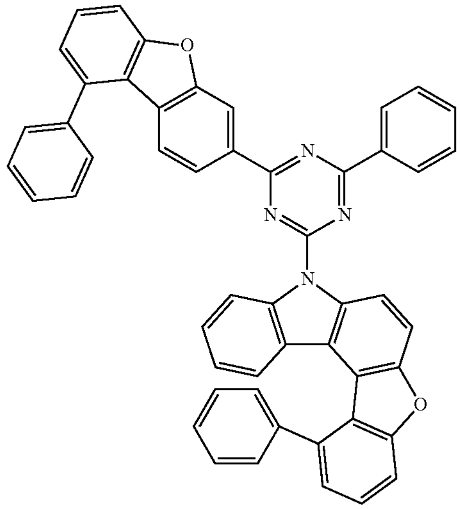

-continued
[C-16]
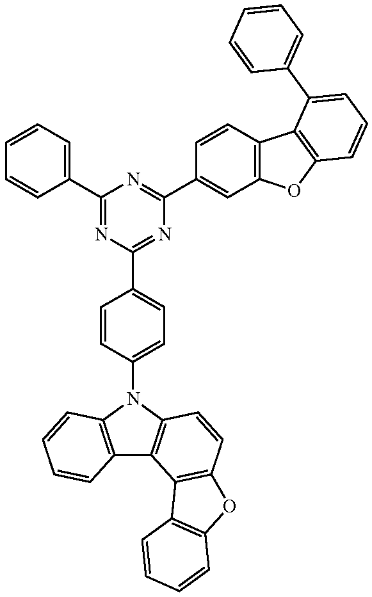
[C-17]
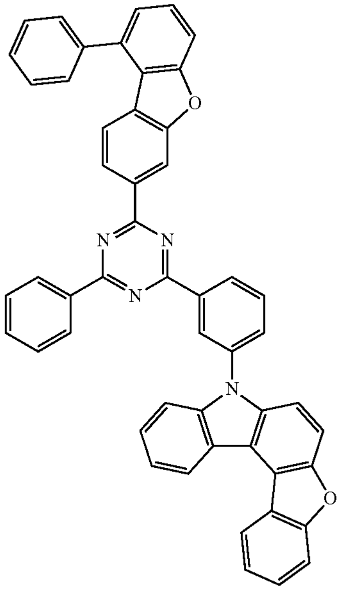
-continued
[C-18]
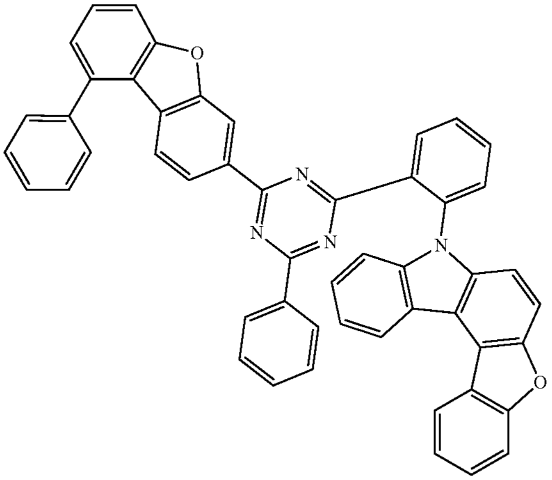
[C-19]
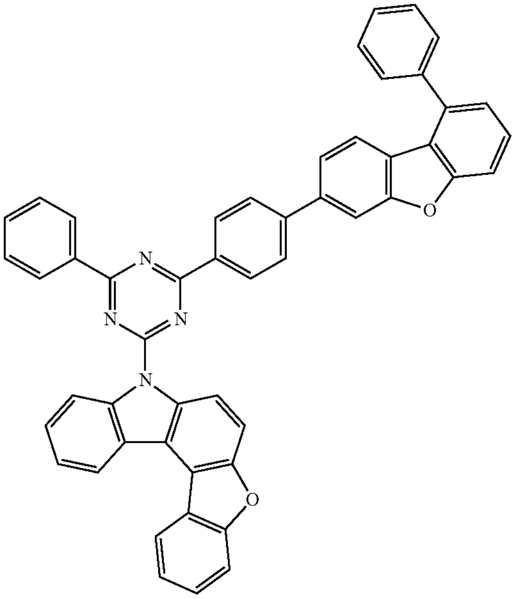

-continued
[C-20]
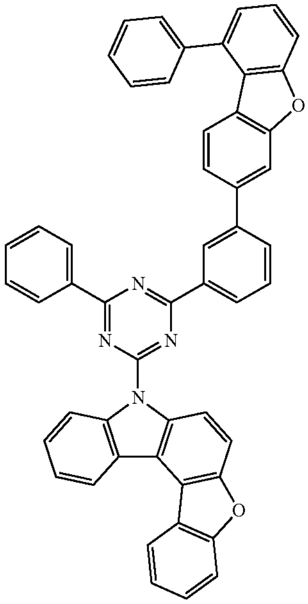
[C-21]
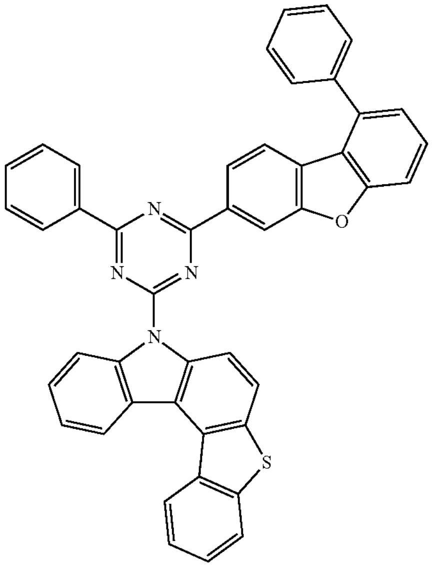
-continued
[C-22]
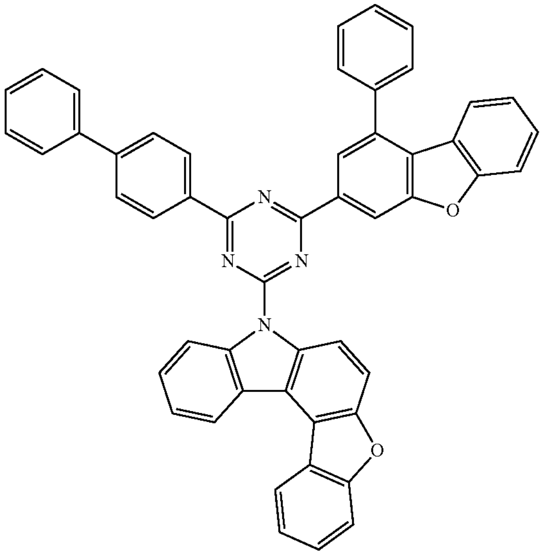
[C-23]
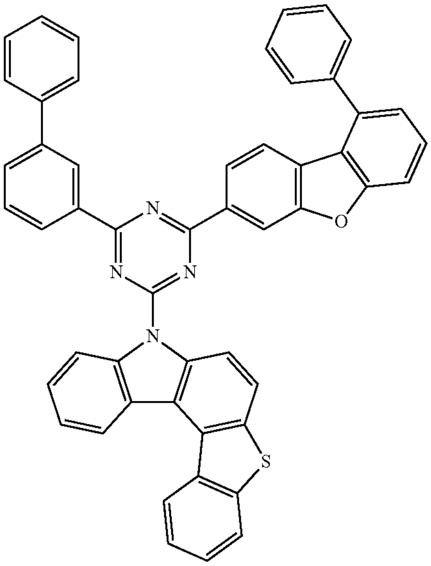

-continued
[C-24]
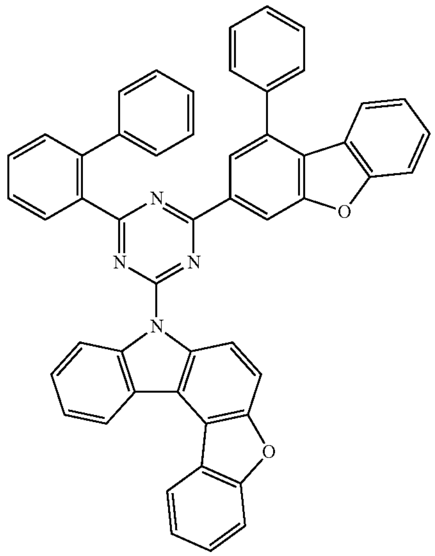
-continued
[C-26]
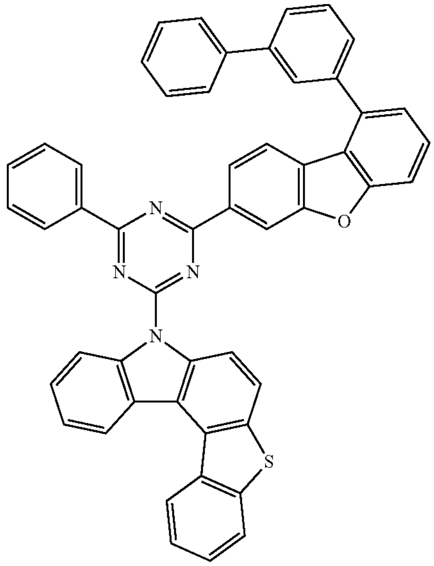
[C-25]
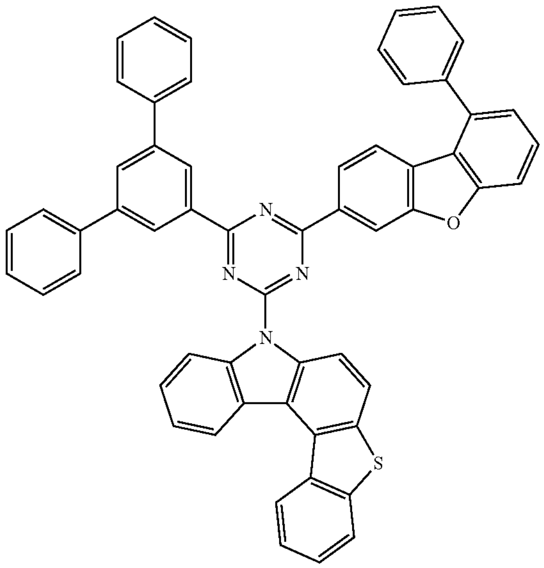
[C-27]
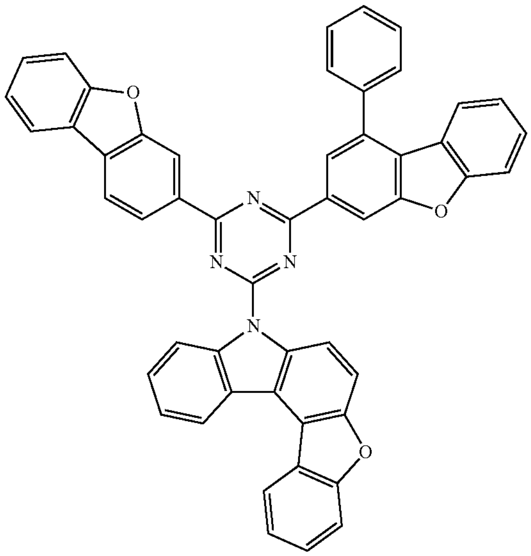

-continued
[C-28]
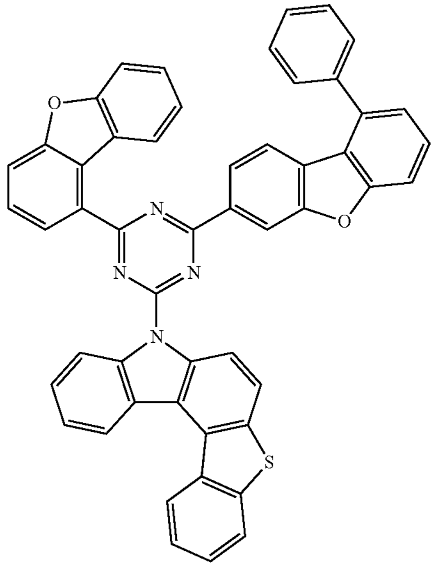
[C-29]
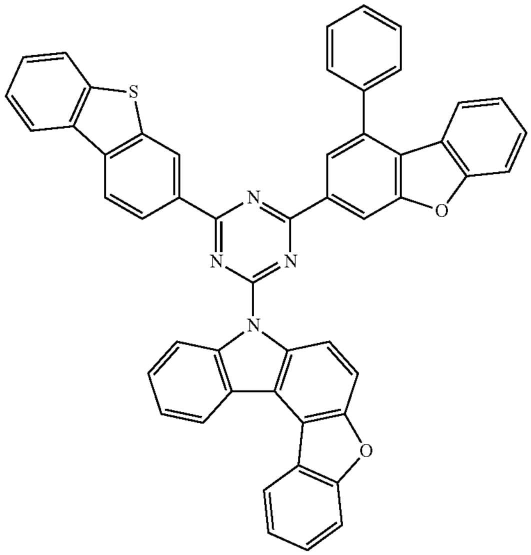
-continued
[C-30]
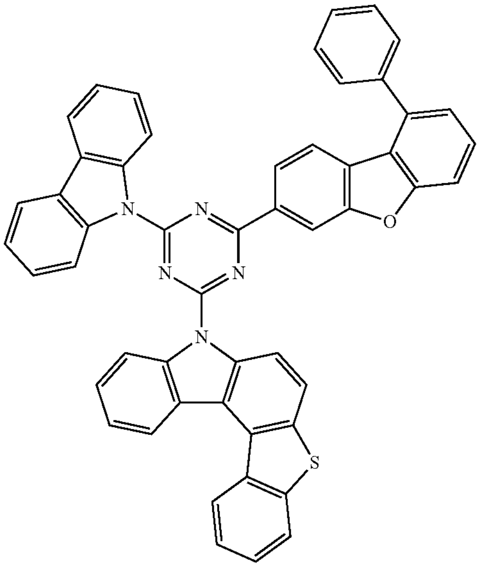
[C-31]
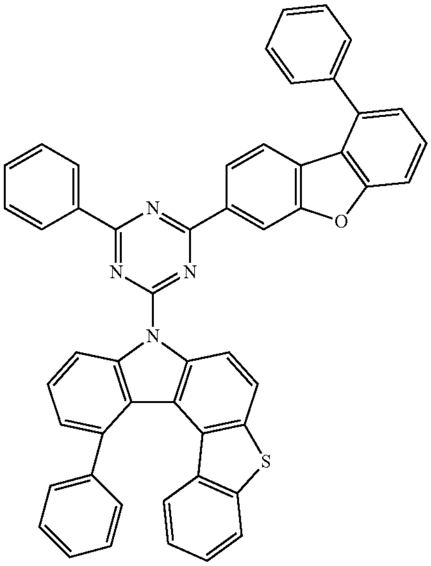

-continued
[C-32]
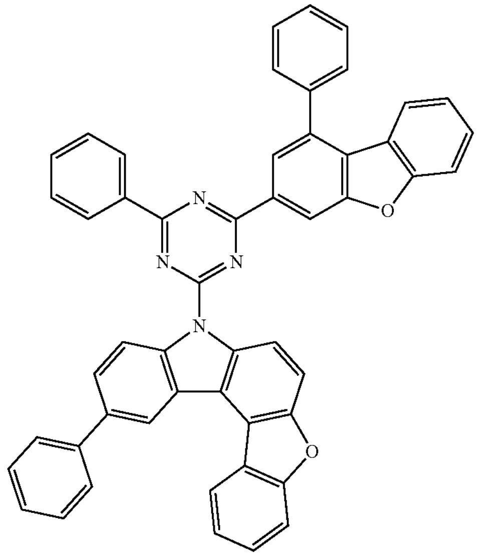
[C-33]
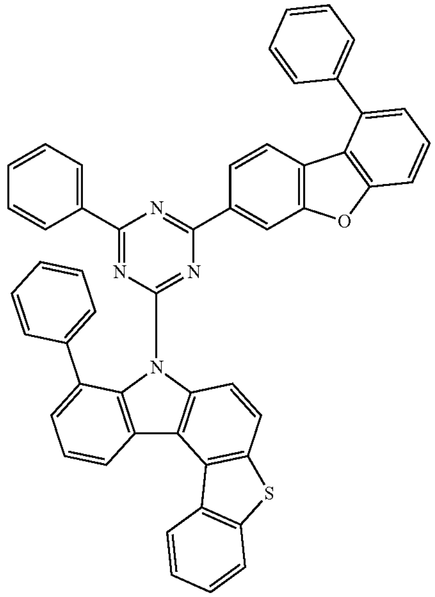
-continued
[C-34]
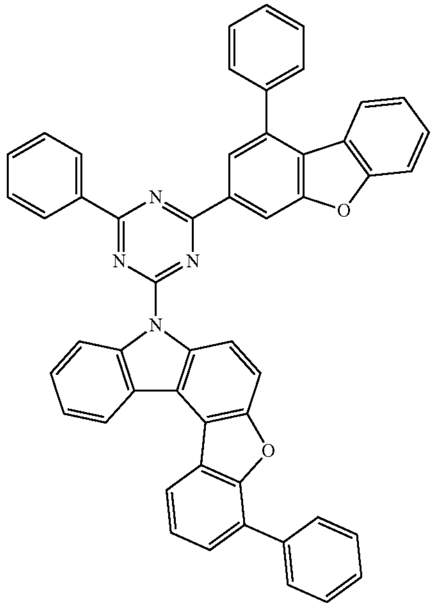
[C-35]
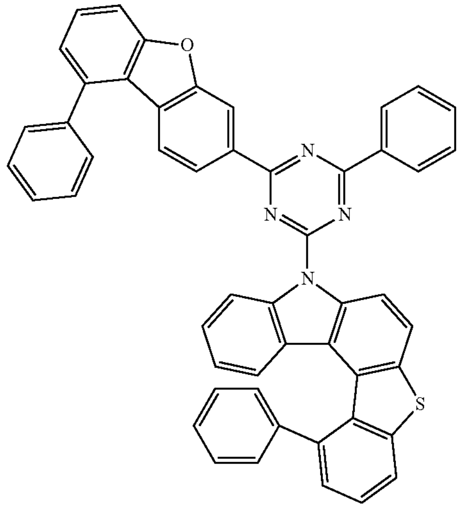

-continued
[C-36]
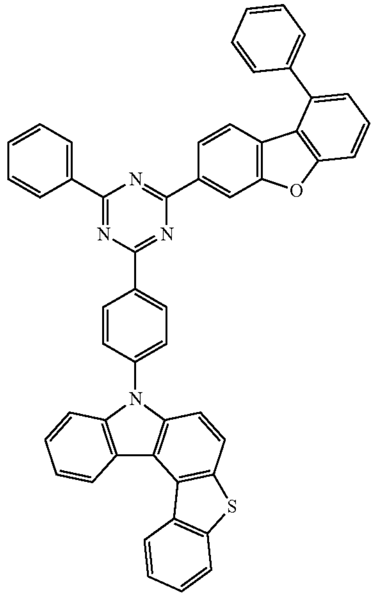
[C-37]
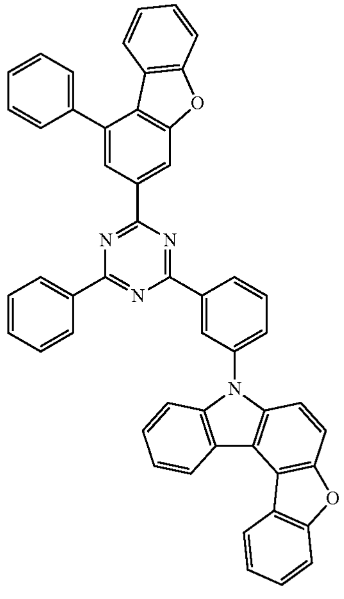
-continued
[C-38]
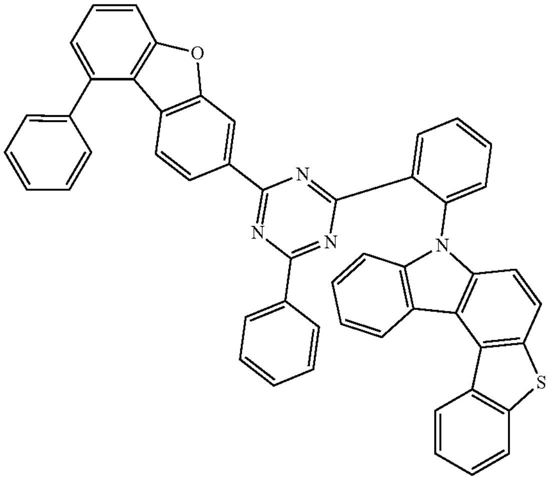
[C-39]
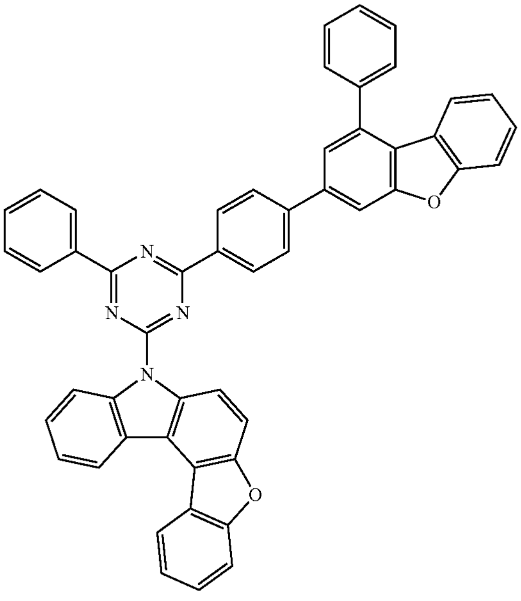

-continued
[C-40]
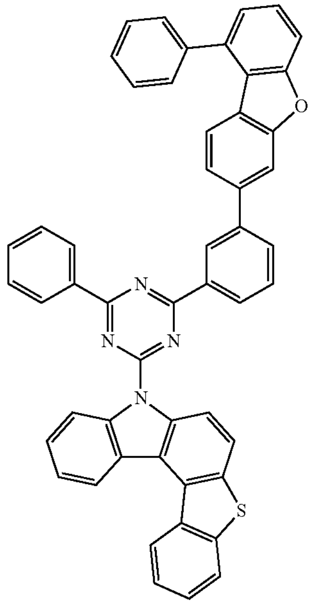
[C-41]
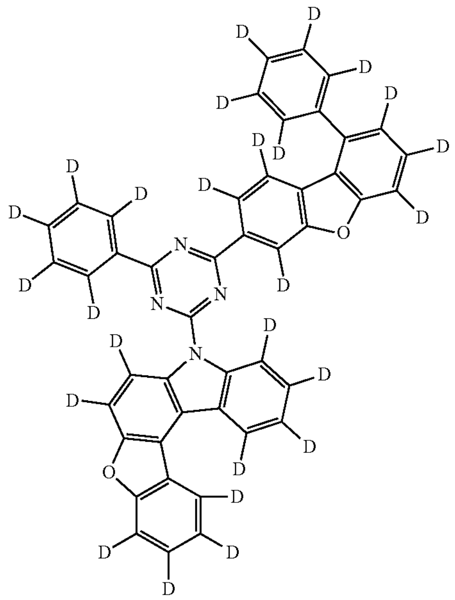
-continued
[C-42]
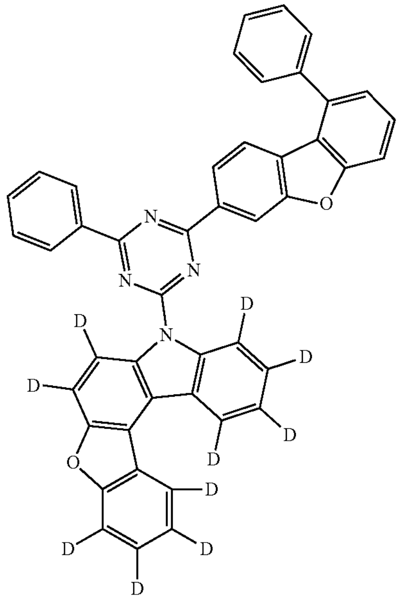
[C-43]
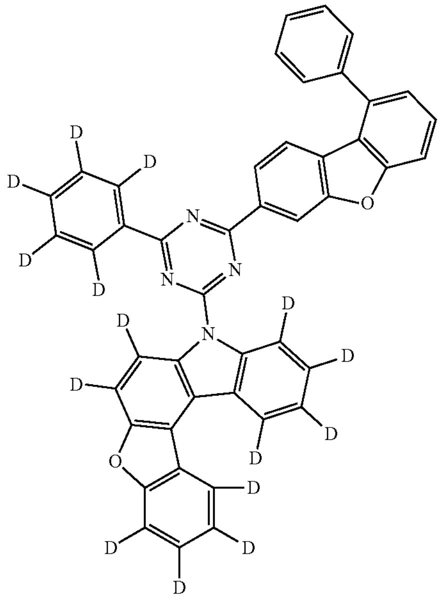

-continued
[C-44]
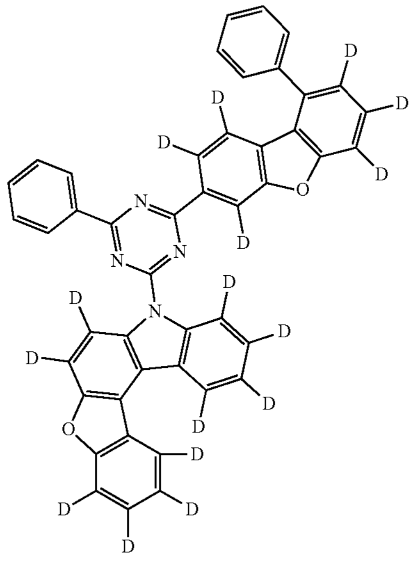
[C-45]
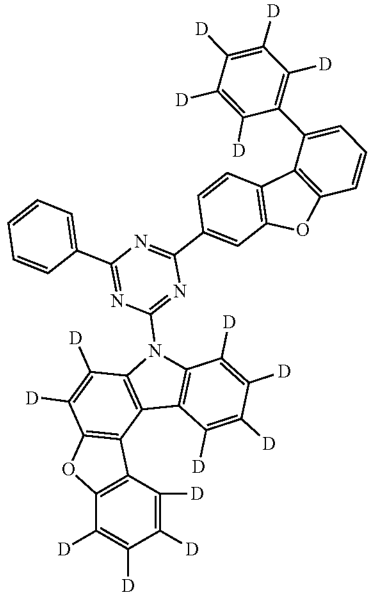
-continued
[C-46]
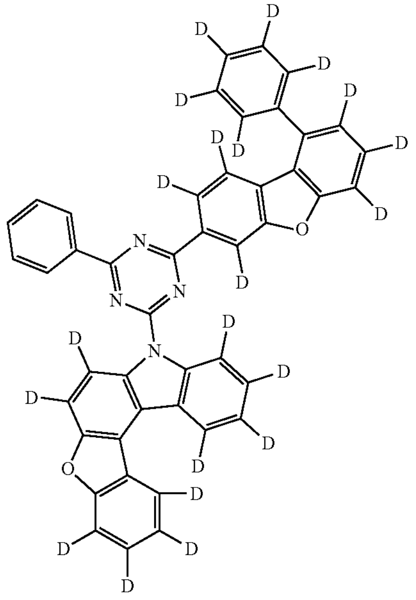
[C-47]
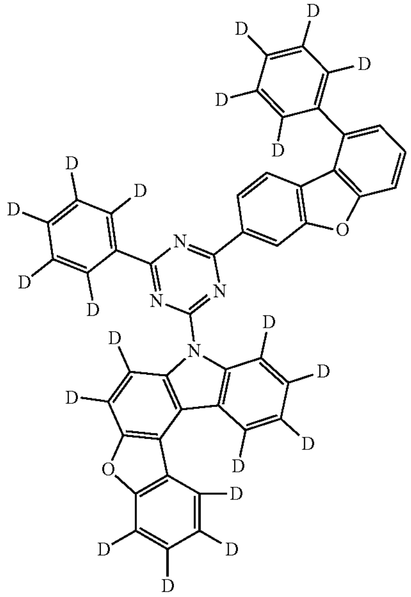

-continued
[C-48]
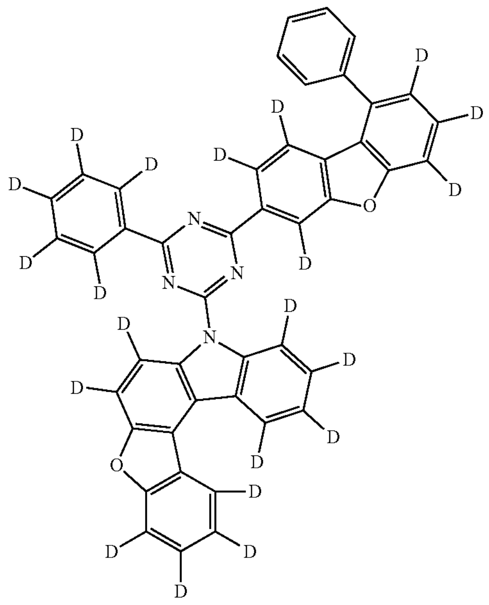
[C-49]
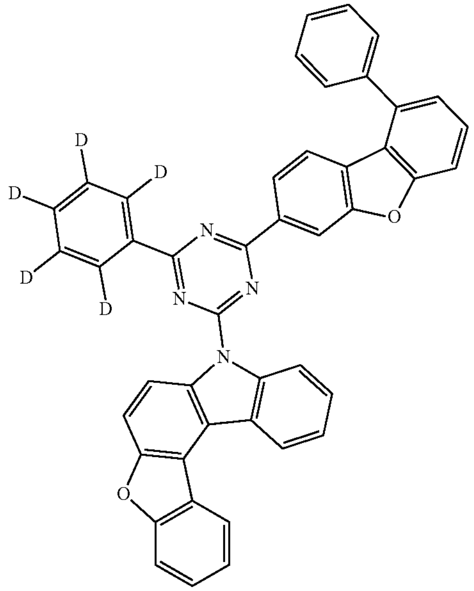
-continued
[C-50]
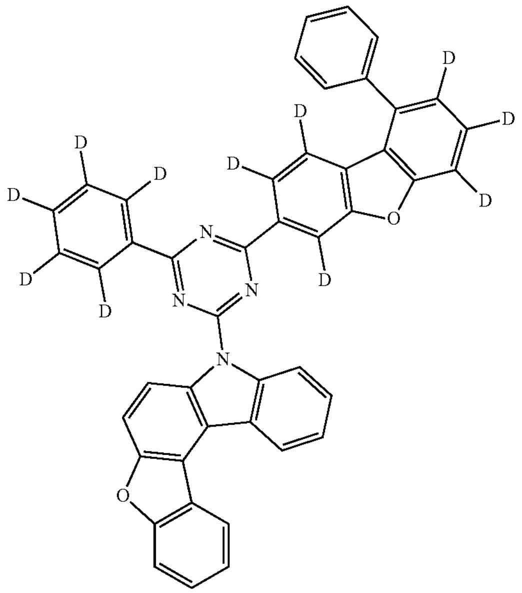
[C-51]
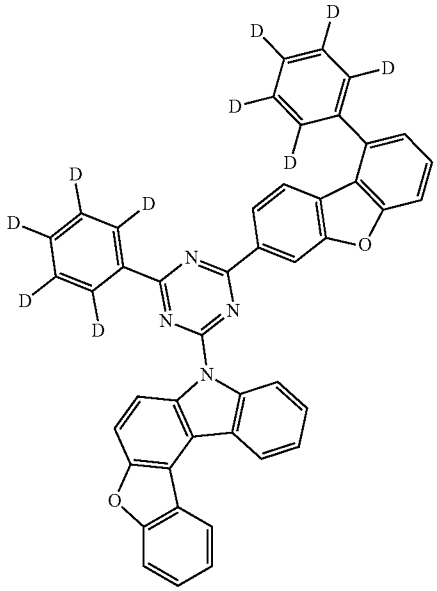

-continued
[C-52]
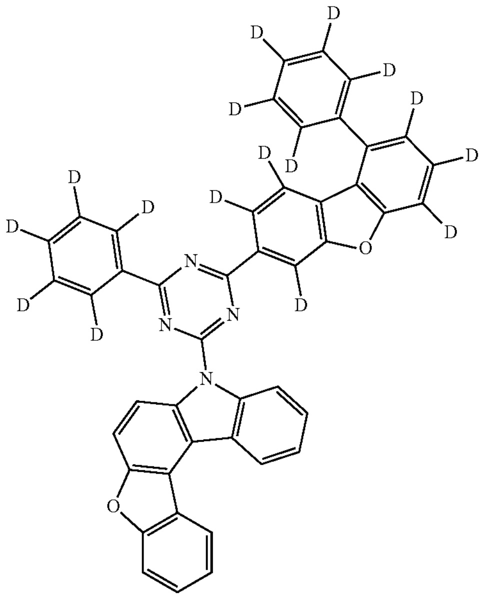
[C-53]
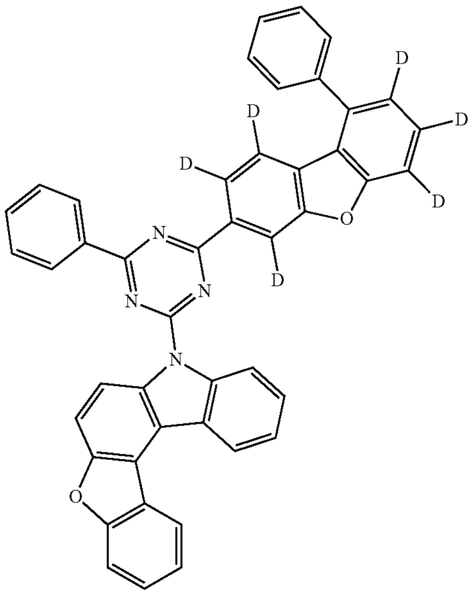
-continued
[C-54]
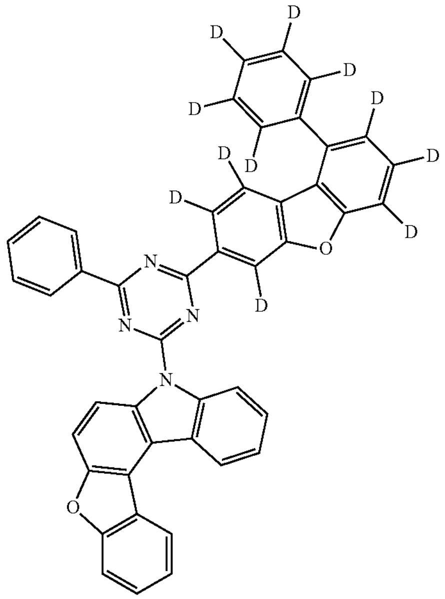
[C-55]
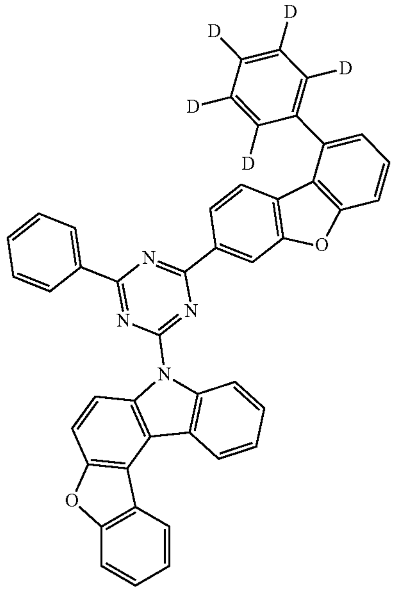

[C-56]
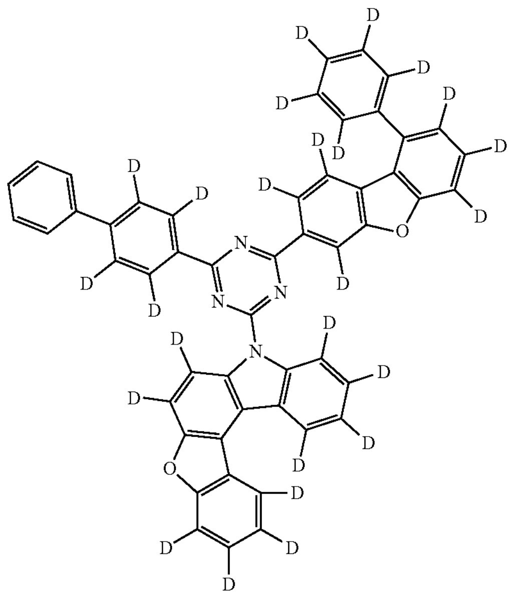
[C-57]
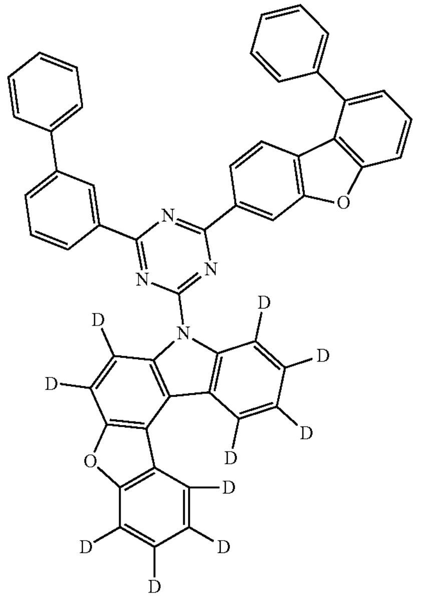
[C-58]
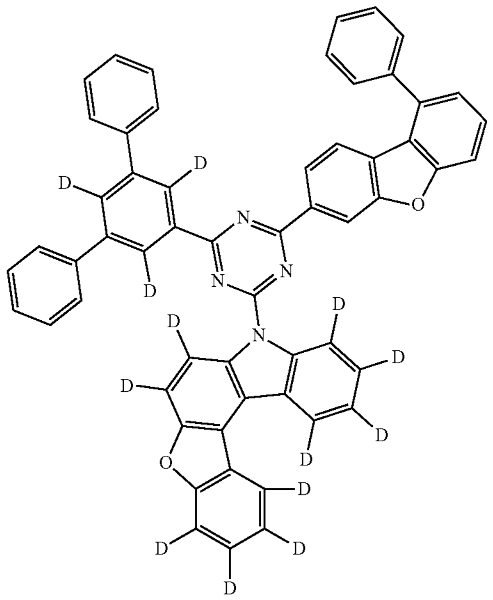
[C-59]
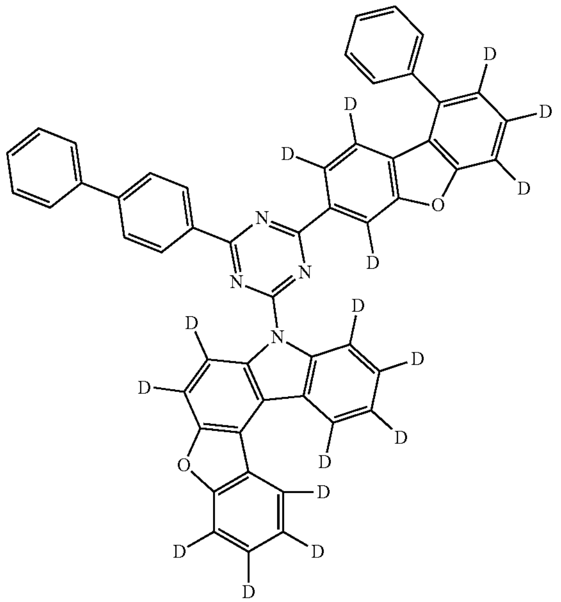

-continued
[C-60]
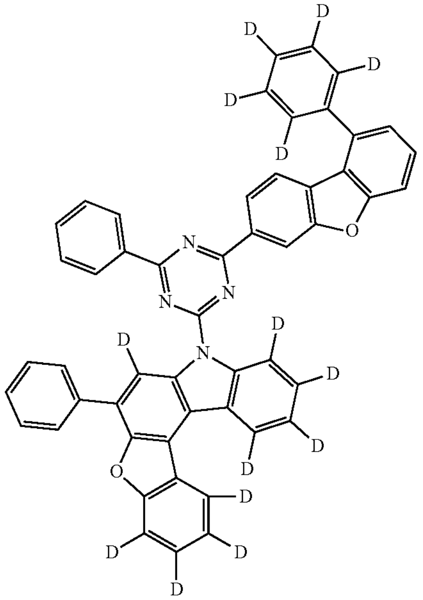
[C-61]
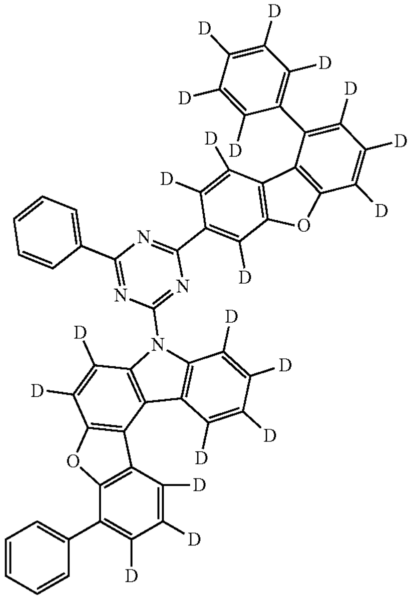
-continued
[C-62]
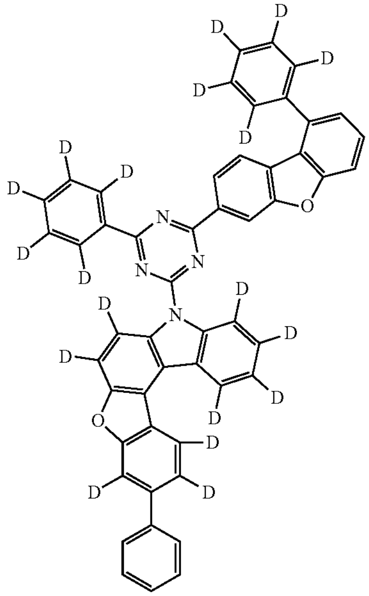
[C-63]
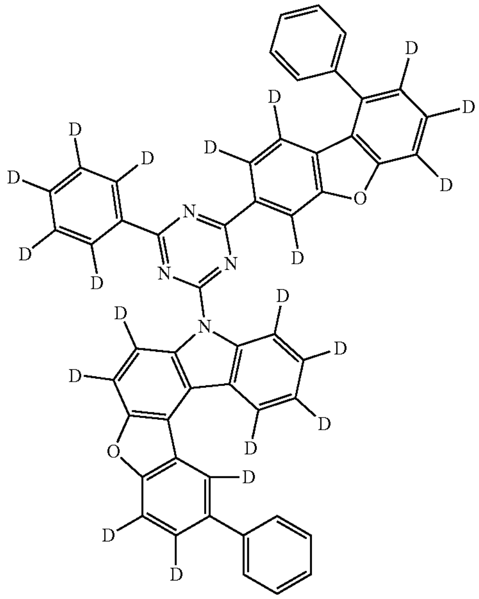

-continued
[C-64]
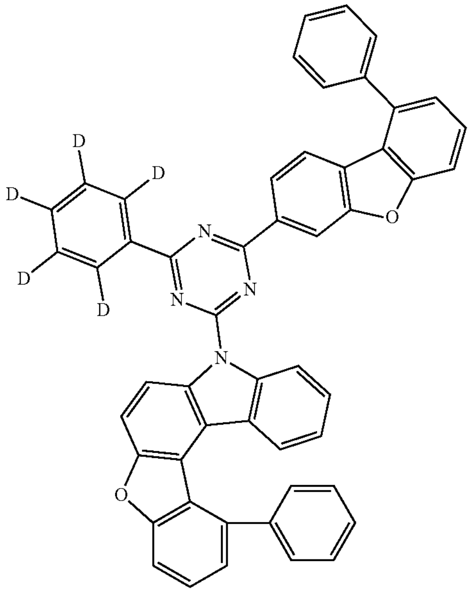
[C-65]
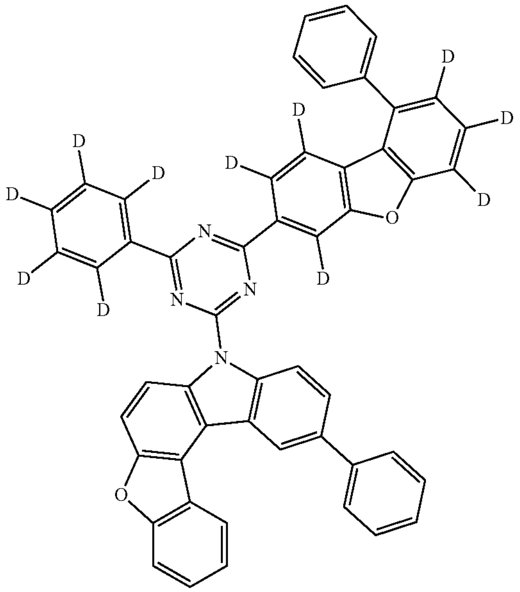
-continued
[C-66]
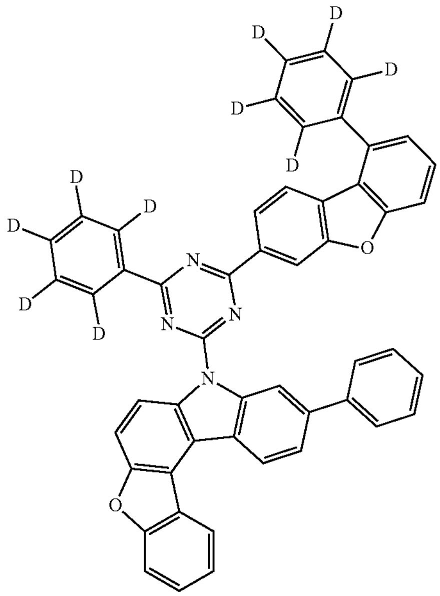
[C-67]
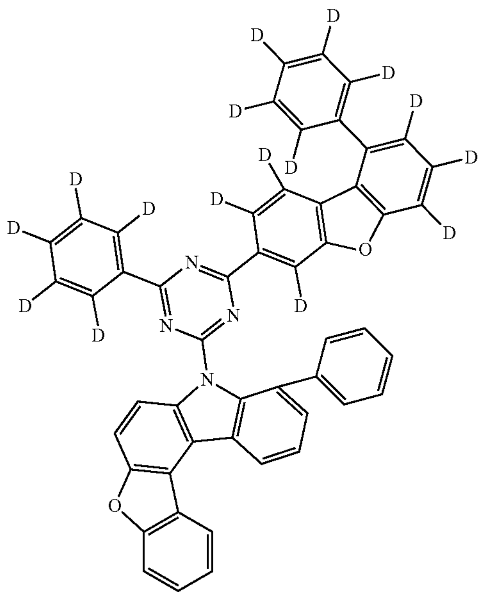

[C-68]
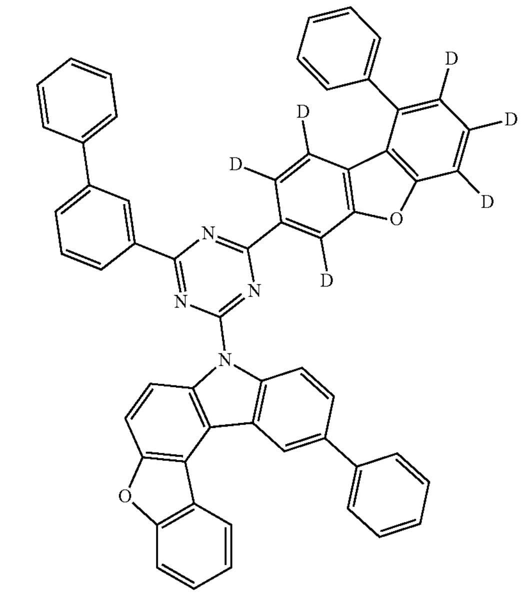
[C-70]
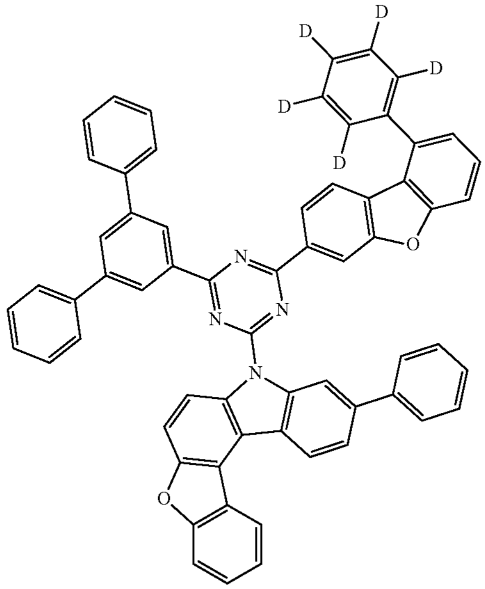
[C-69]
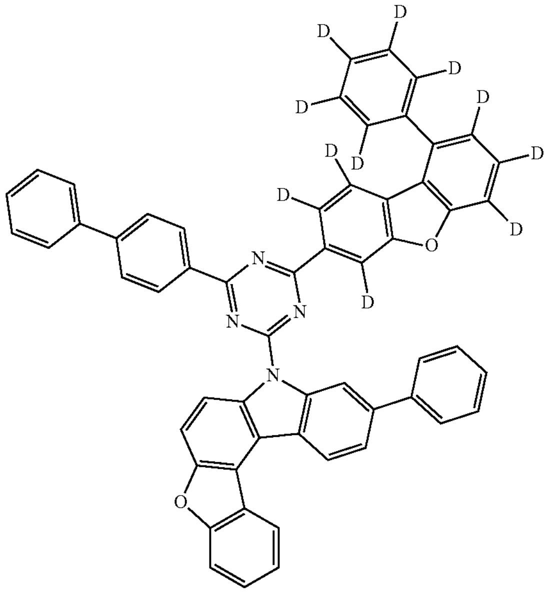
[C-71]
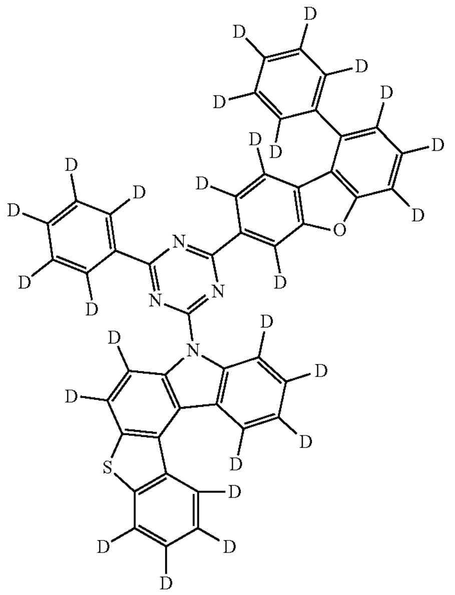

[C-72]
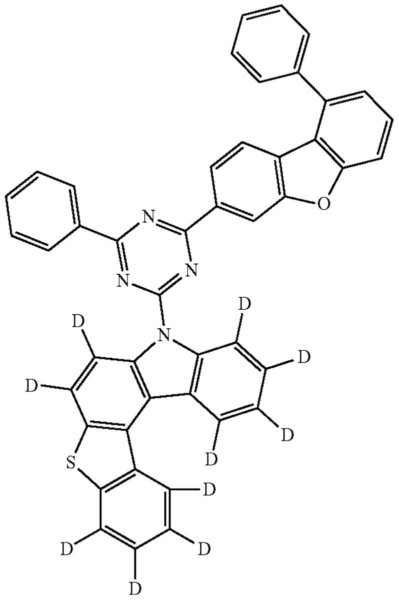
[C-73]
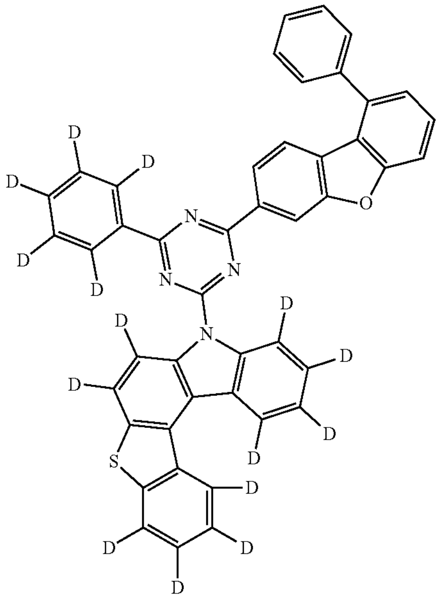
[C-74]
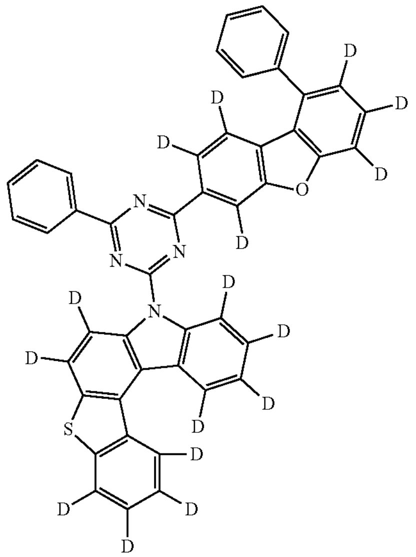
[C-75]
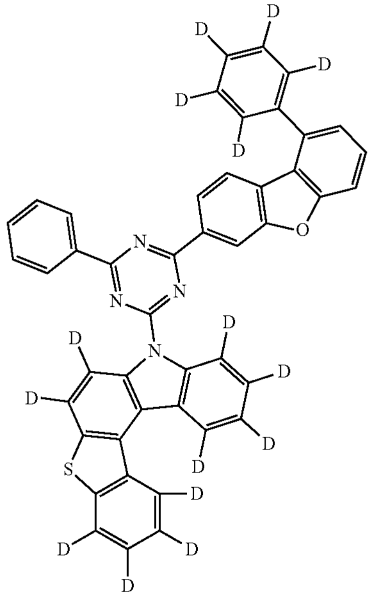

-continued
[C-76]
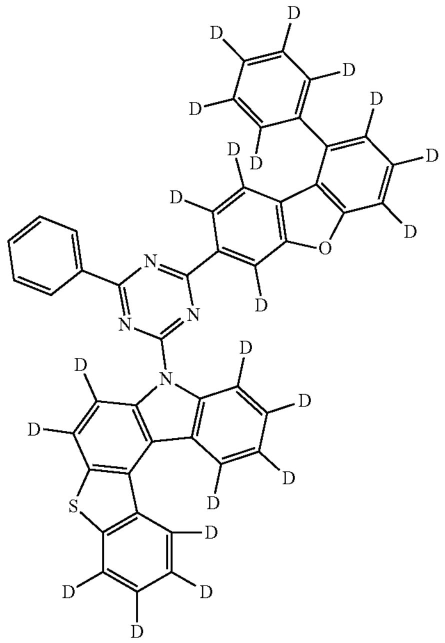
[C-77]
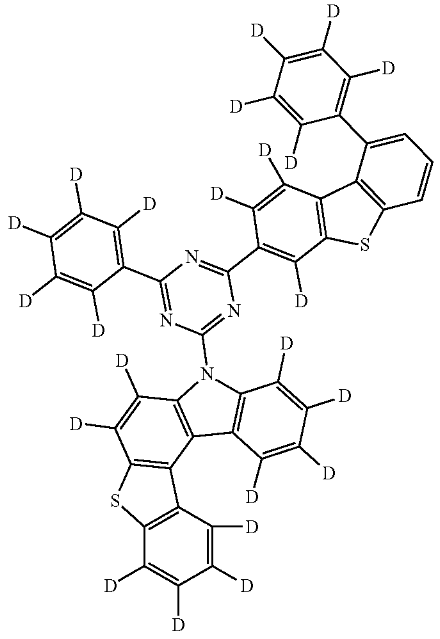
-continued
[C-78]
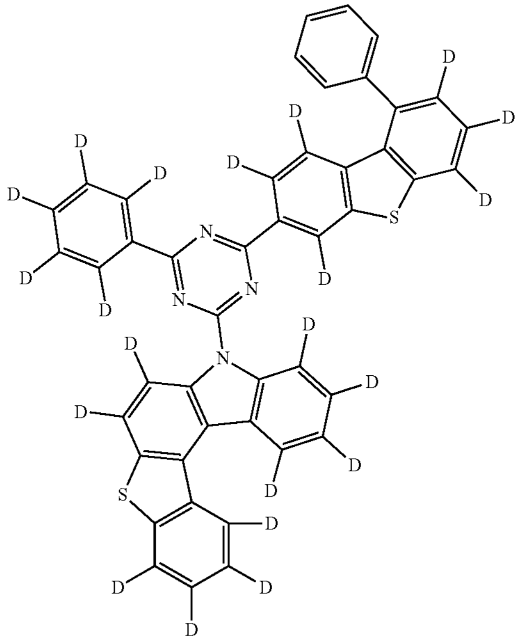
[C-79]
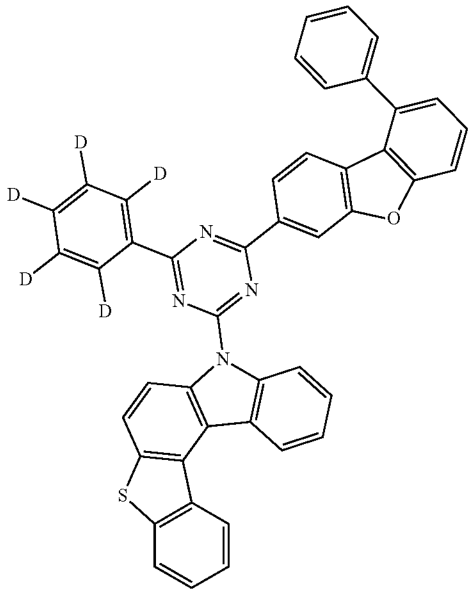

-continued
[C-80]
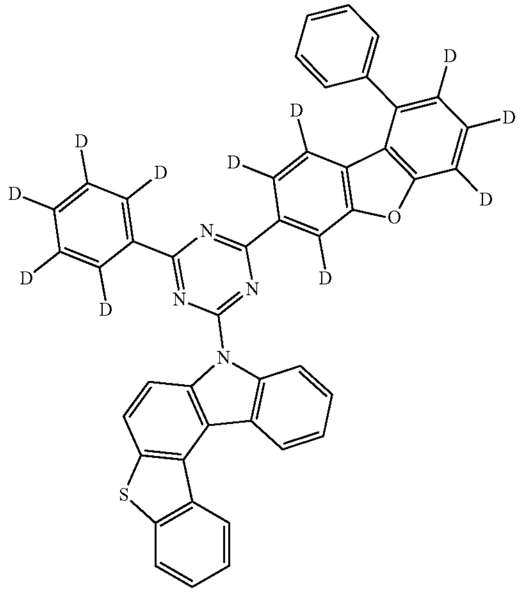
[C-81]
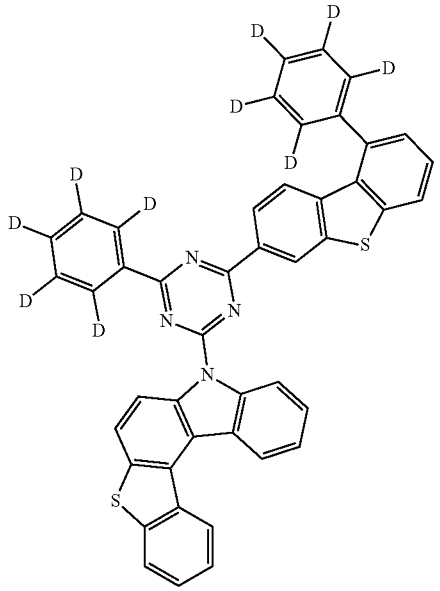
-continued
[C-82]
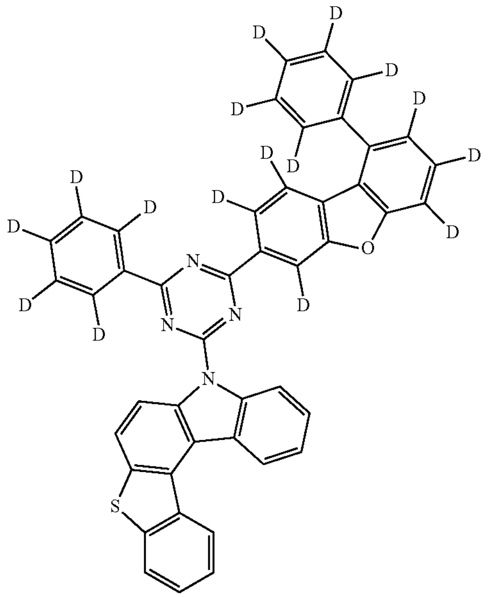
[C-83]
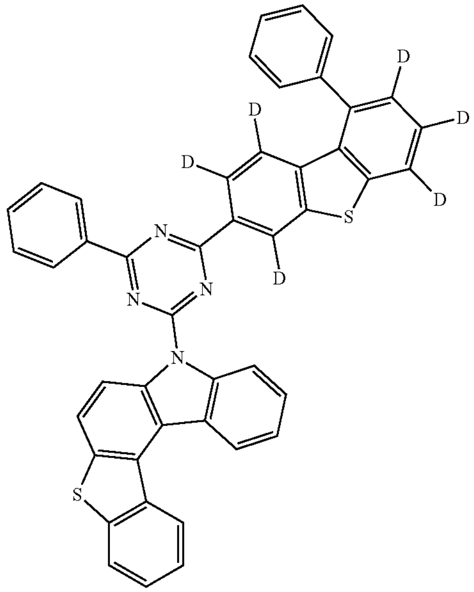

-continued
[C-84]
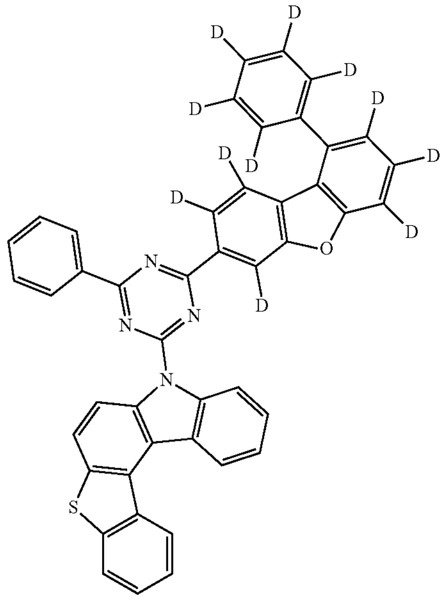
[C-85]
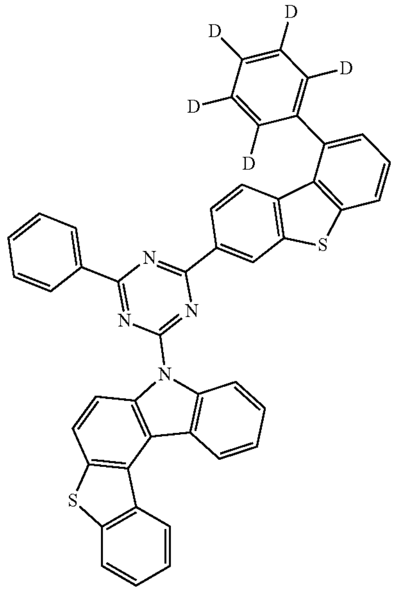
-continued
[C-86]
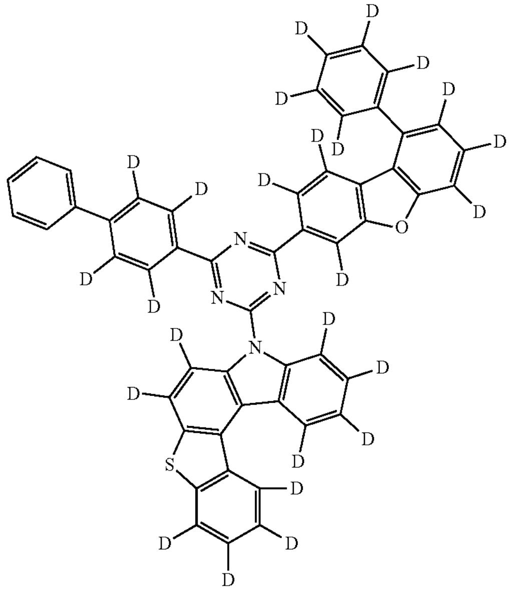
[C-87]
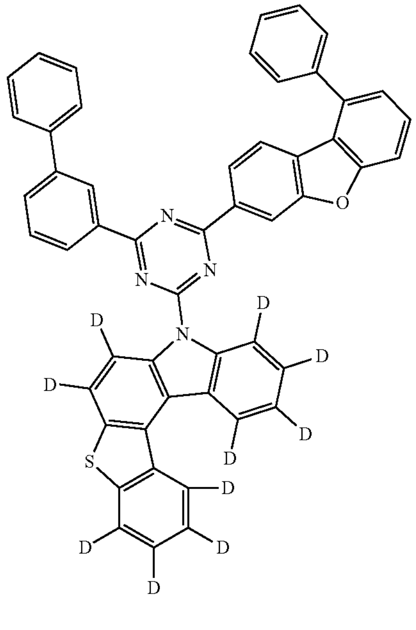

-continued
[C-88]
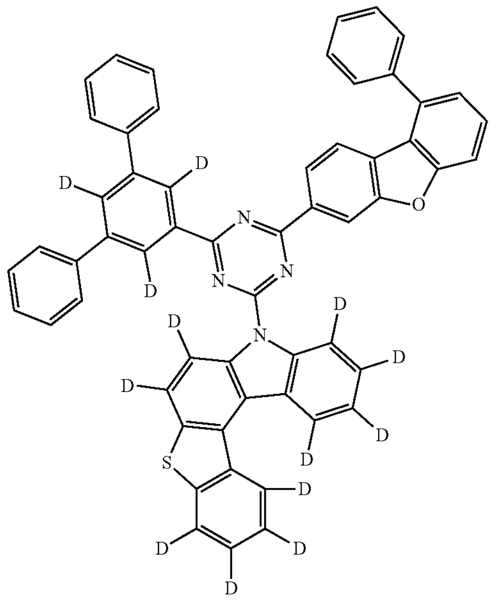
[C-89]
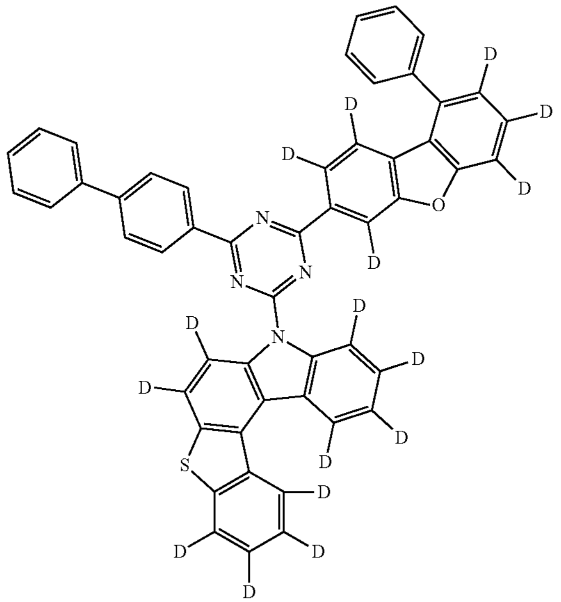
-continued
[C-90]
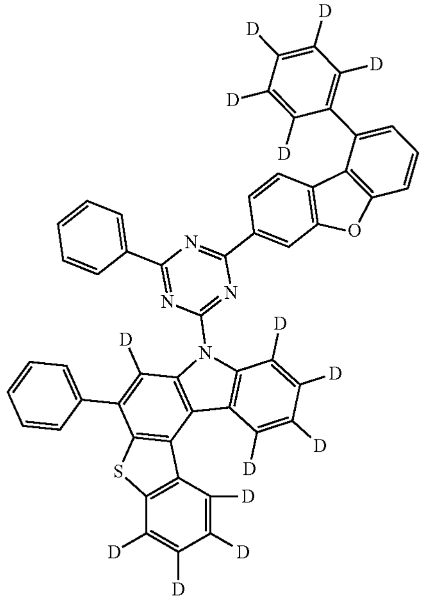
[C-91]
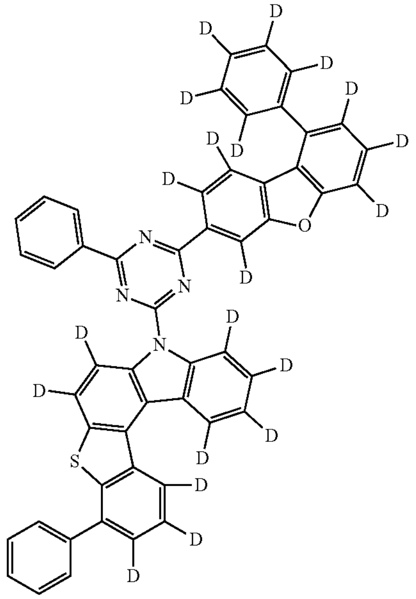

-continued
[C-92]
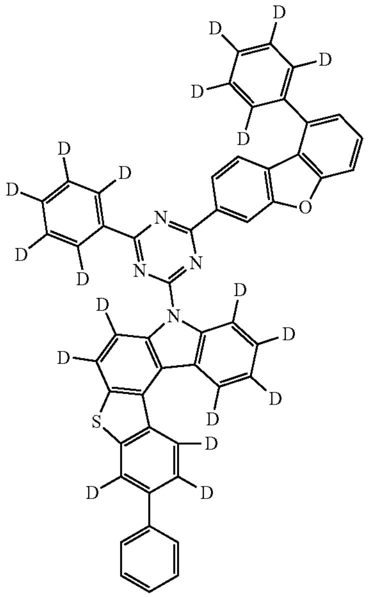
[C-93]
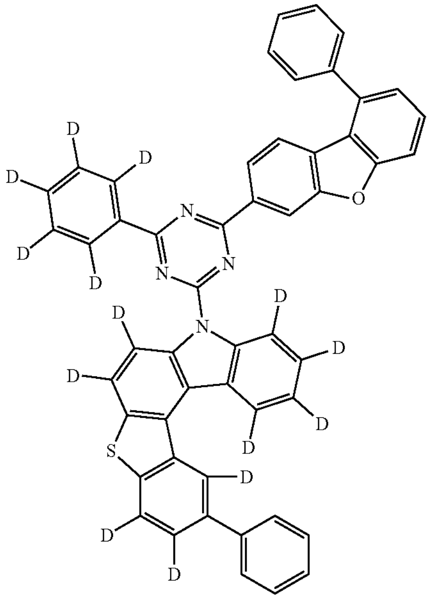
-continued
[C-94]
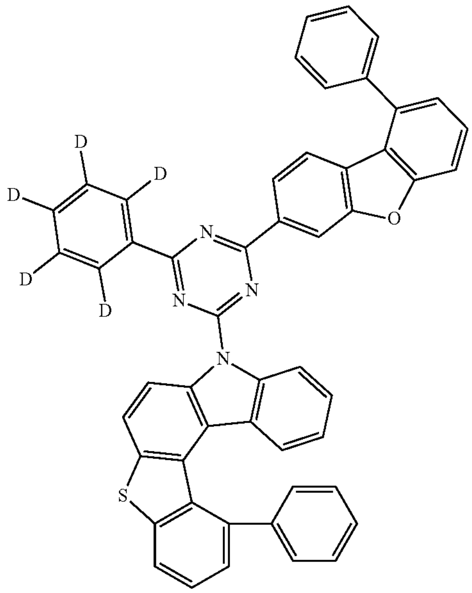
[C-95]
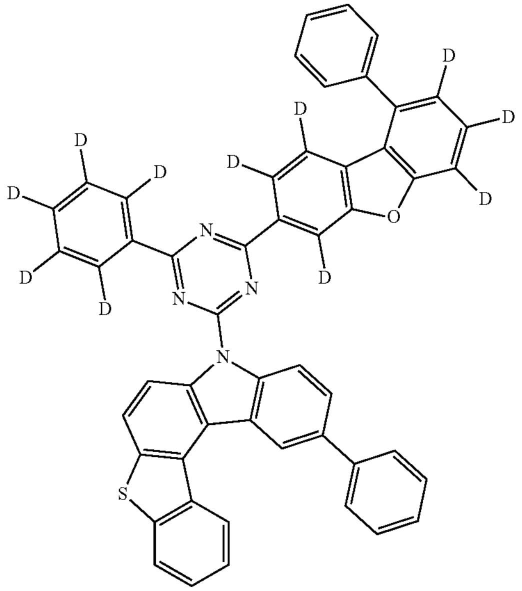

[C-96]
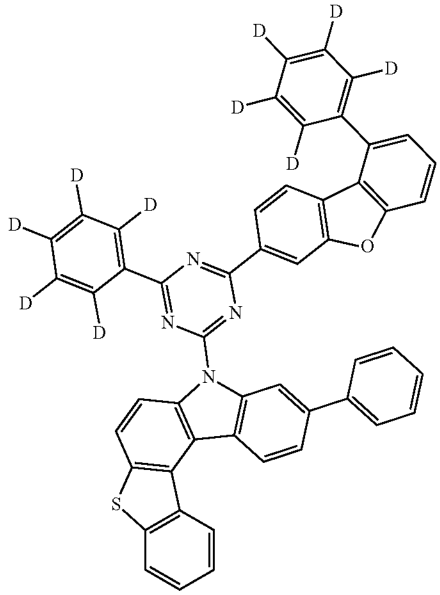
[C-97]
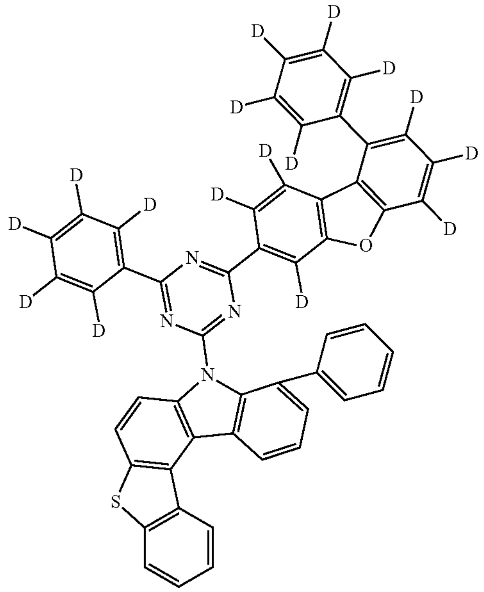
[C-98]
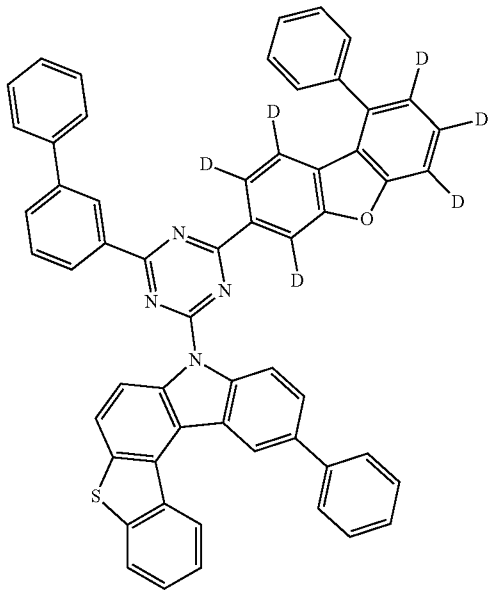
[C-99]
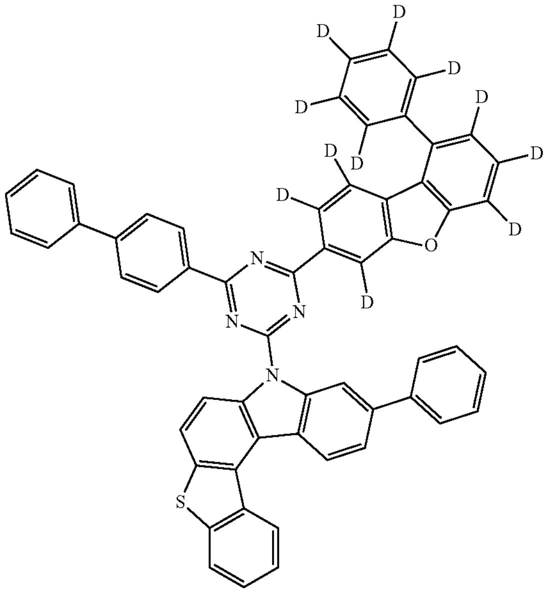

-continued
[C-100]
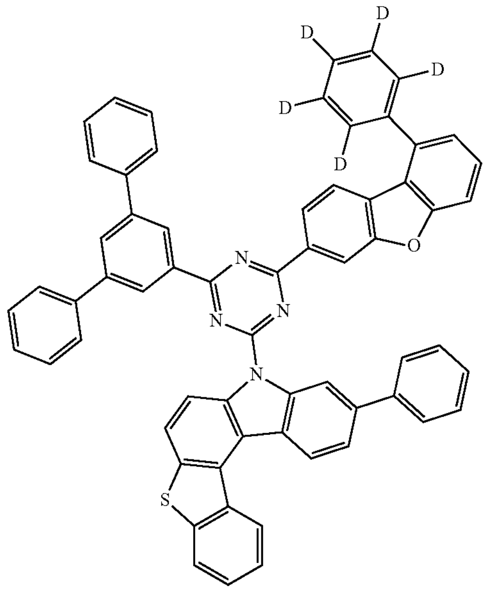
[D-1]
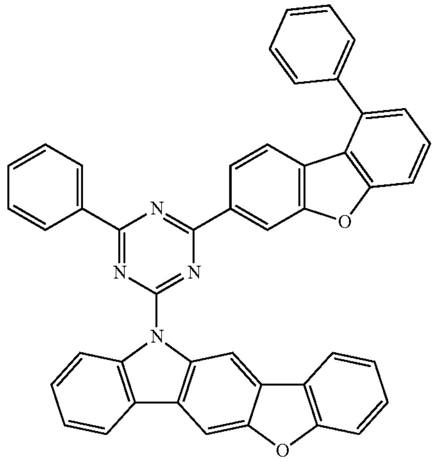
[D-2]
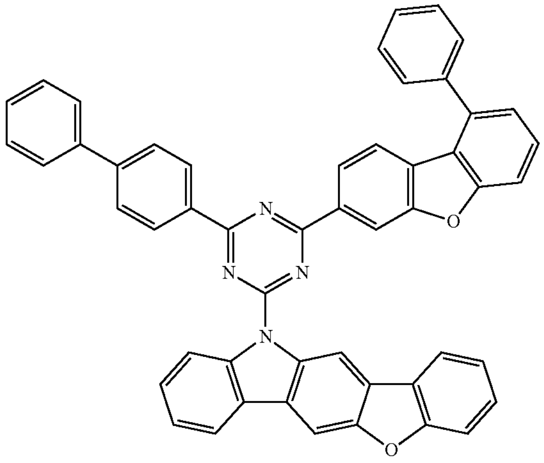
-continued
[D-3]
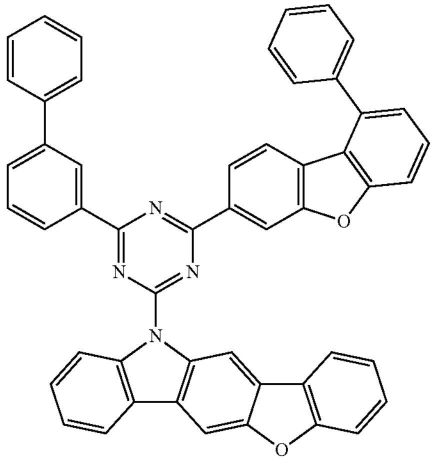
[D-4]
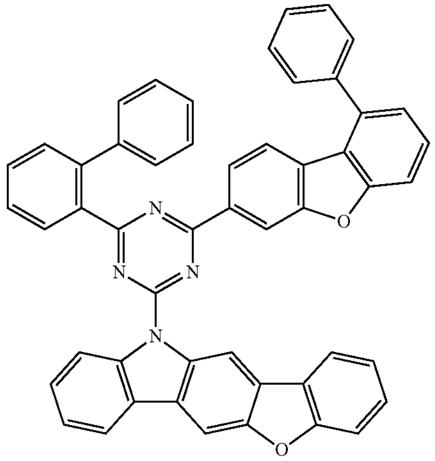
[D-5]
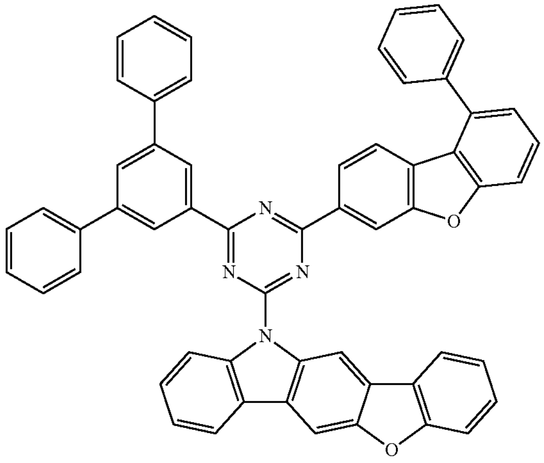

-continued
[D-6]
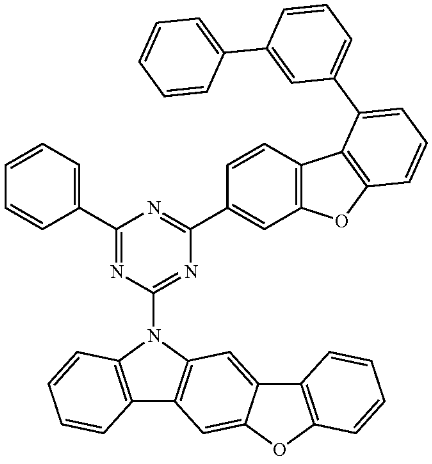
[D-7]
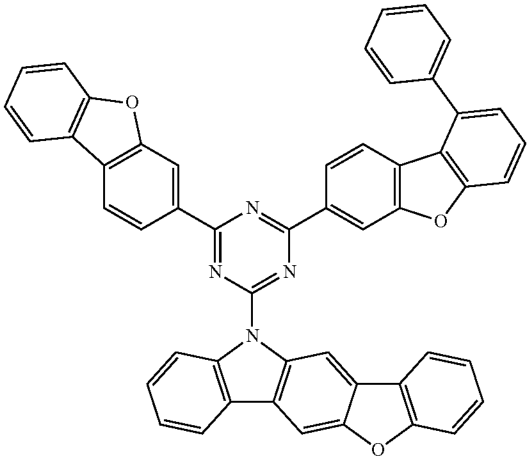
[D-8]
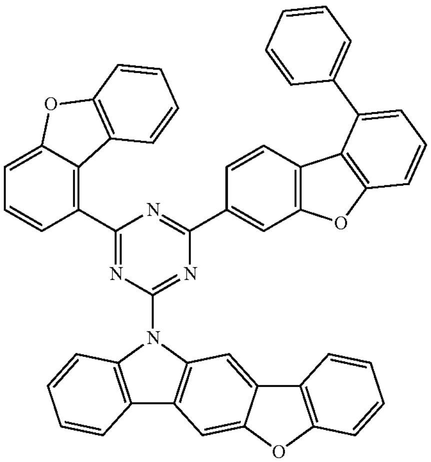
-continued
[D-9]
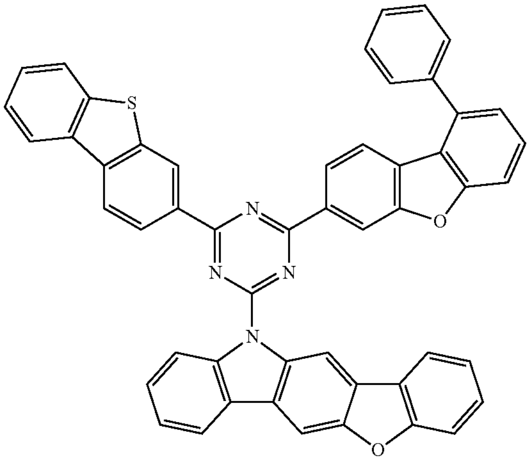
[D-10]
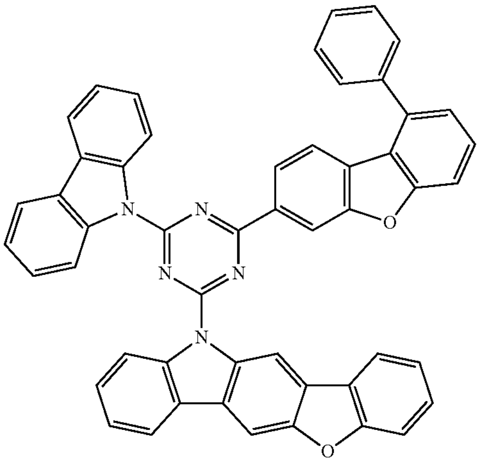
[D-11]
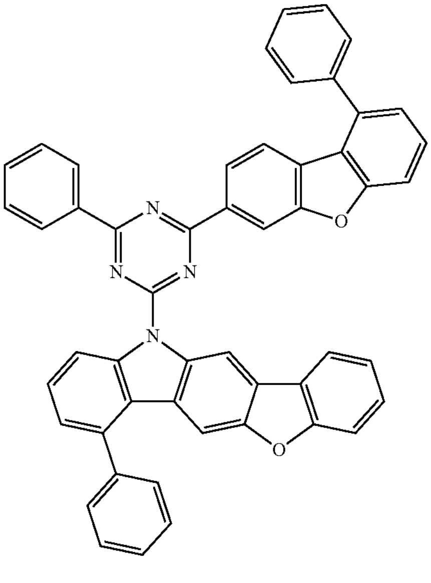

-continued
[D-12]
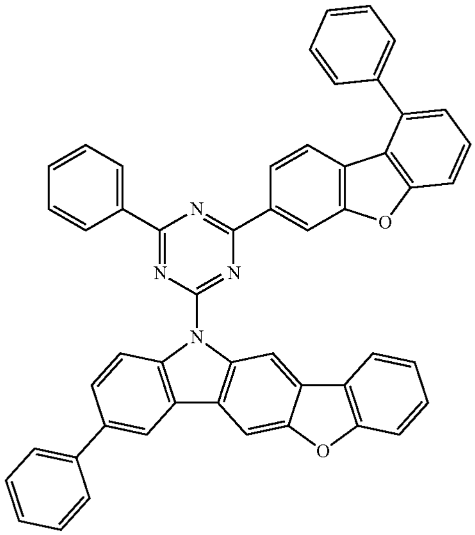
[D-13]
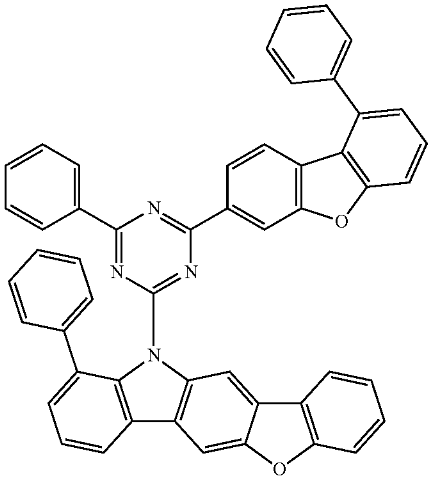
[D-14]
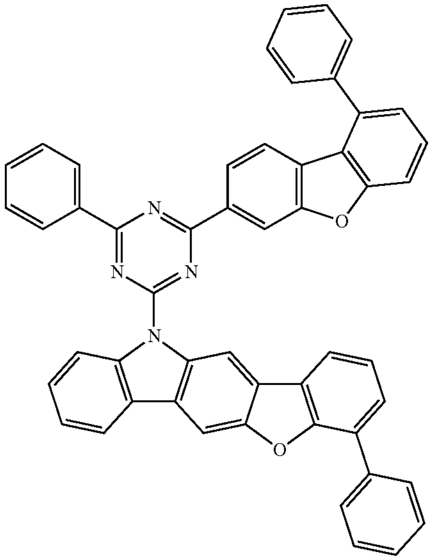
-continued
[D-15]
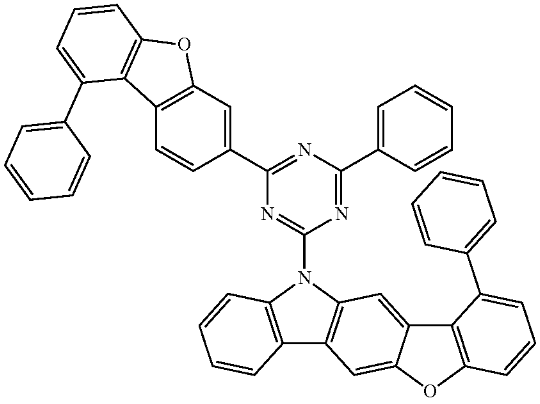
[D-16]
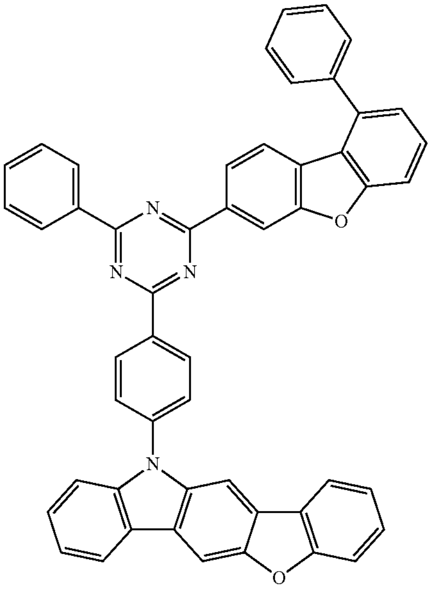
[D-17]
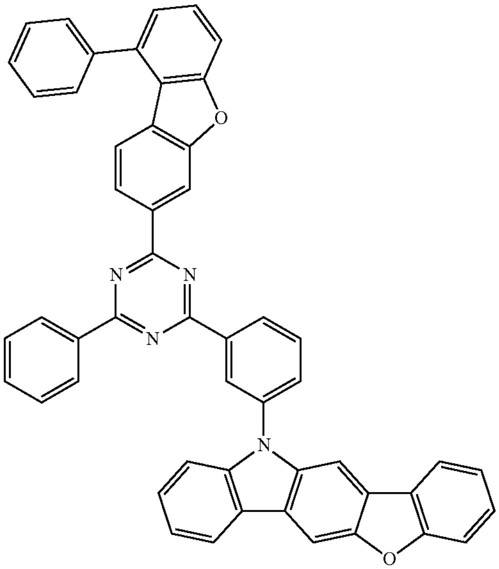

-continued
[D-18]
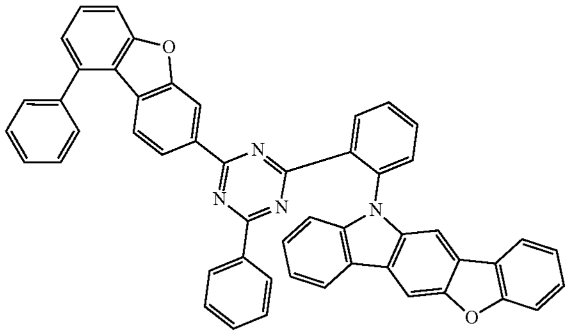
[D-19]
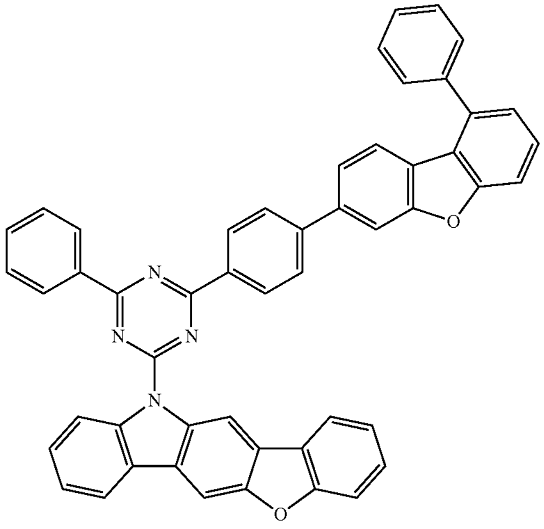
[D-20]
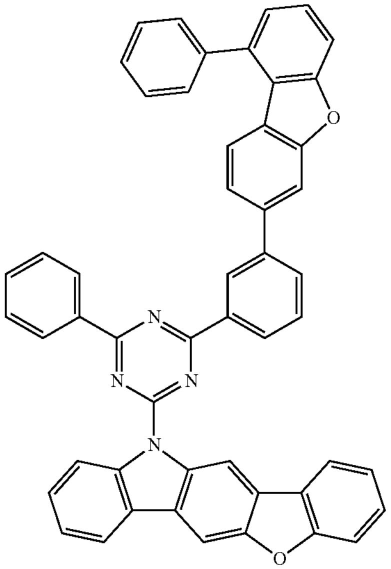
-continued
[D-21]
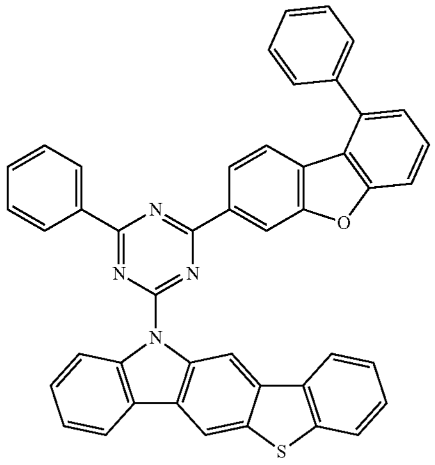
[D-22]
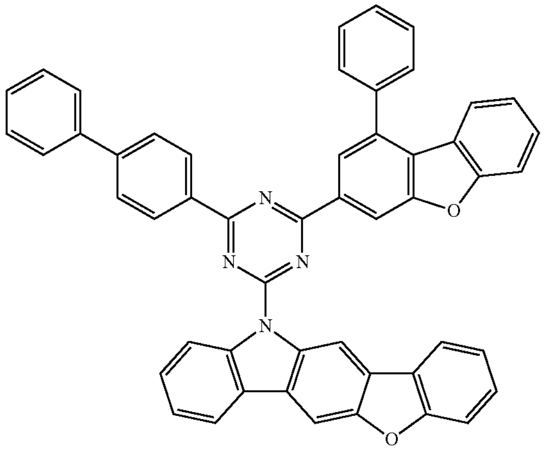
[D-23]
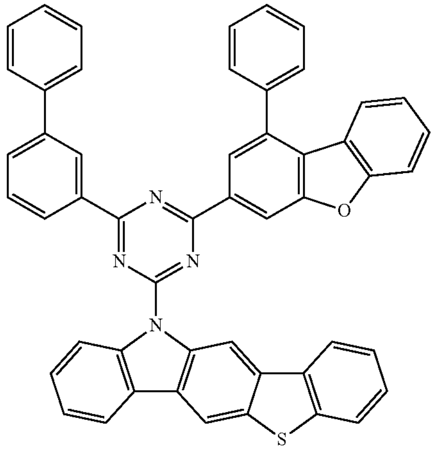

-continued
[D-24]
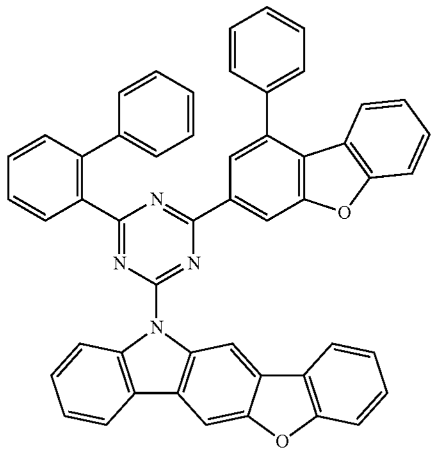
[D-25]
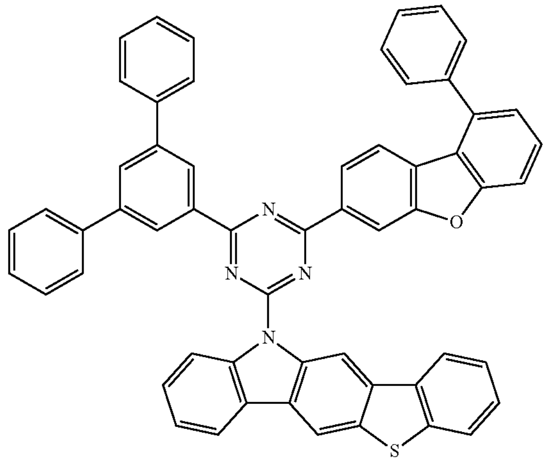
[D-26]
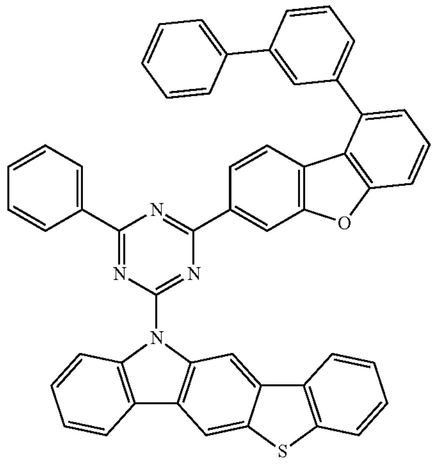
-continued
[D-27]
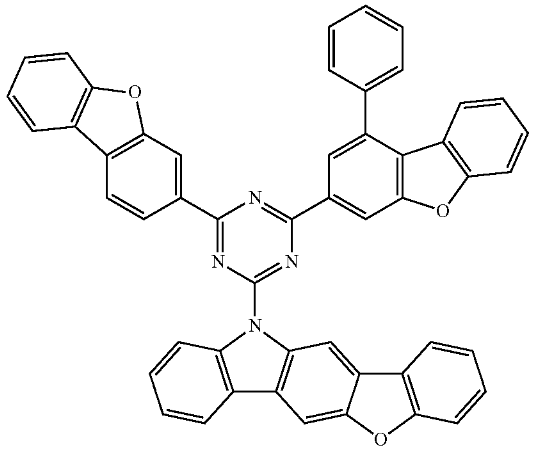
[D-28]
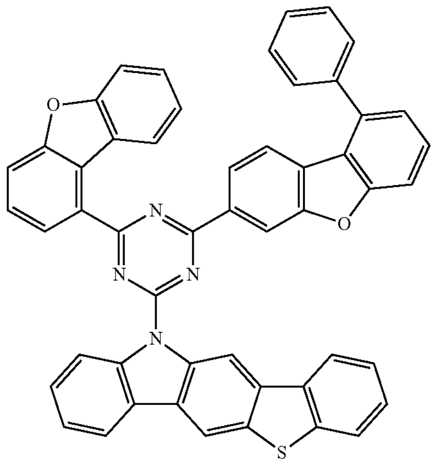
[D-29]
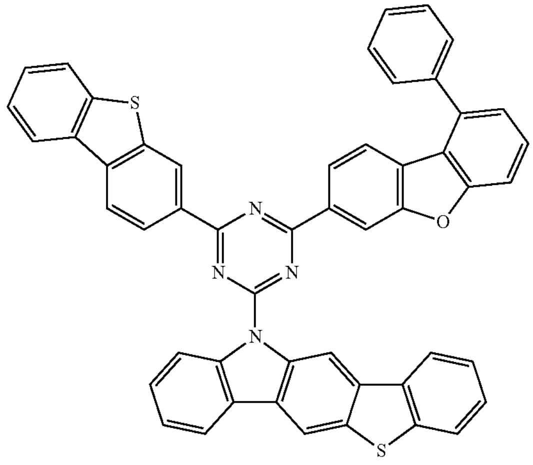

[D-30]
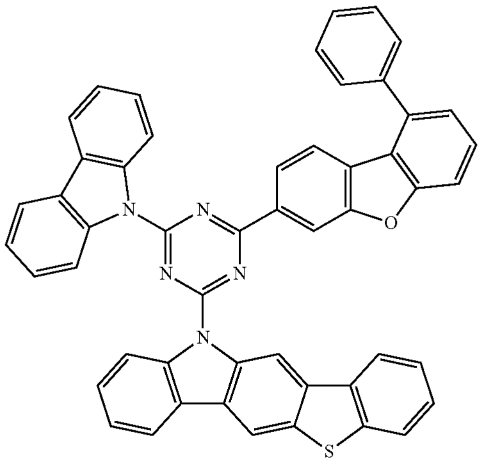
[D-31]
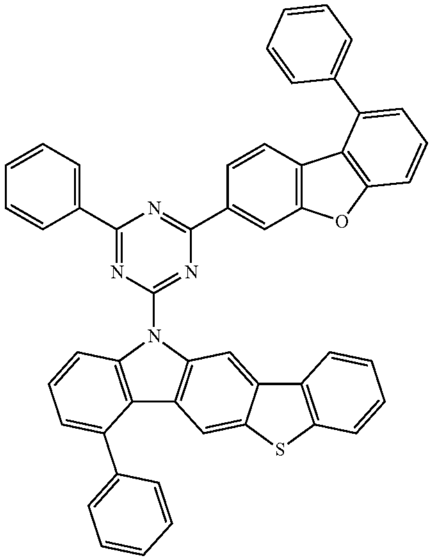
[D-32]
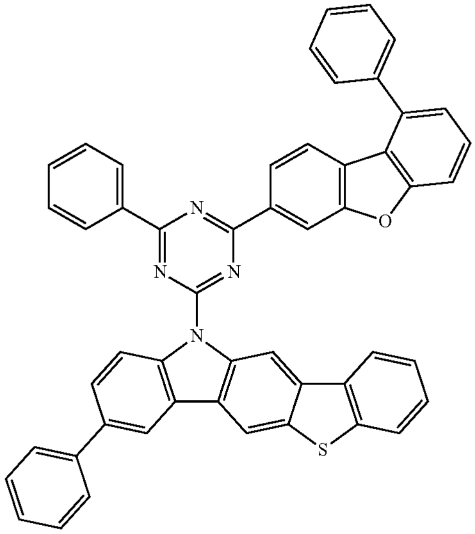
[D-33]
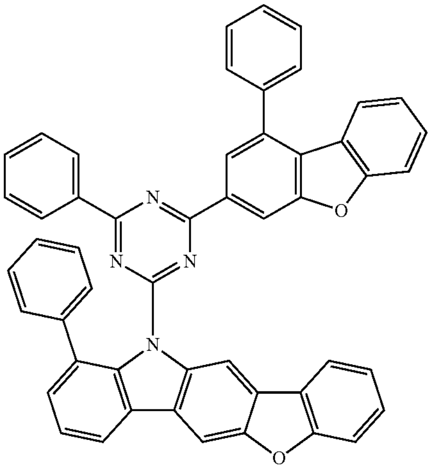
[D-34]
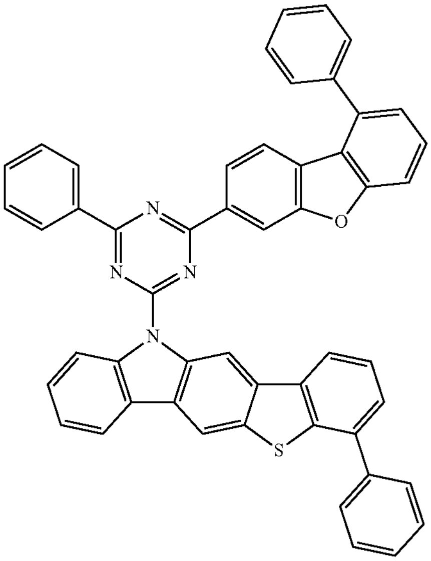
[D-35]
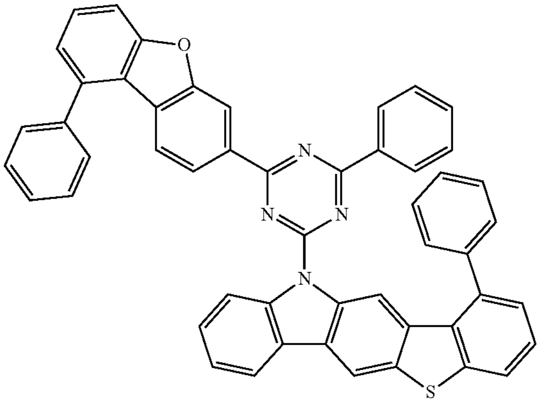

-continued
[D-36]
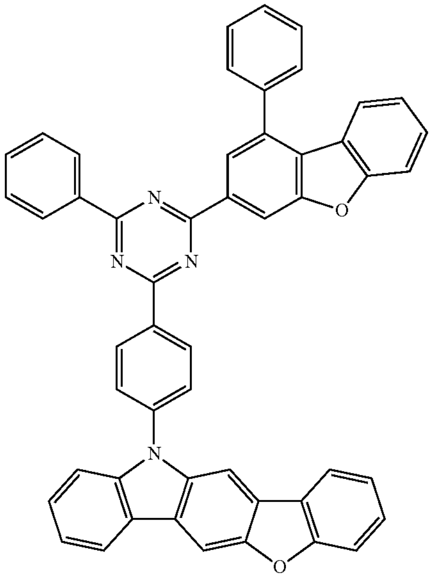
[D-37]
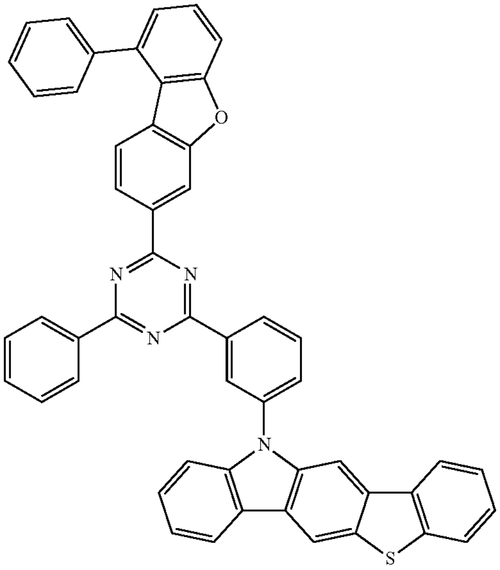
[D-38]
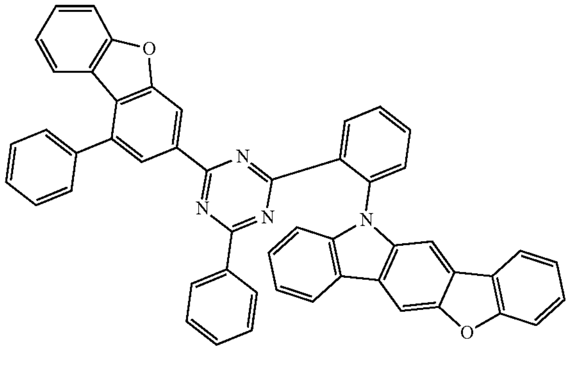
-continued
[D-39]
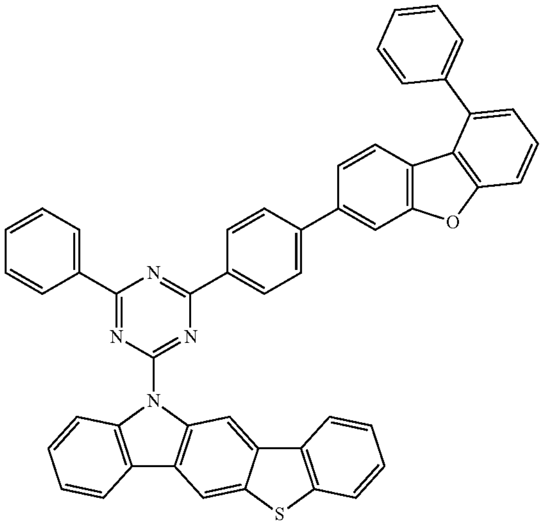
[D-40]
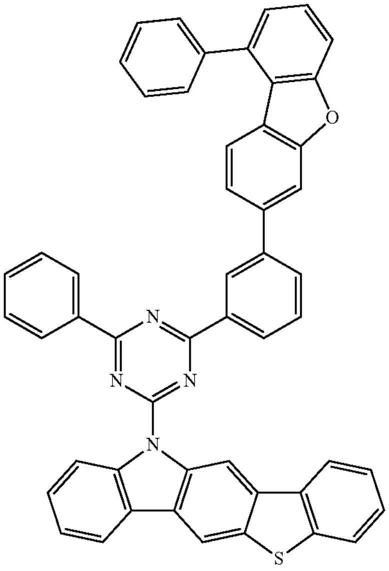

-continued
[D-41]
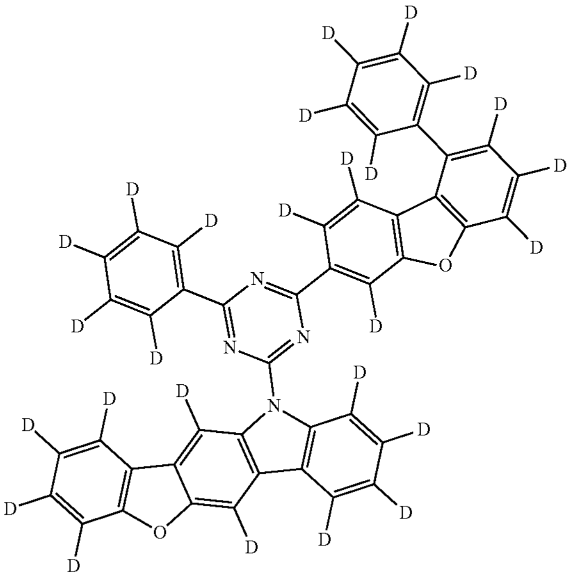
[D-42]
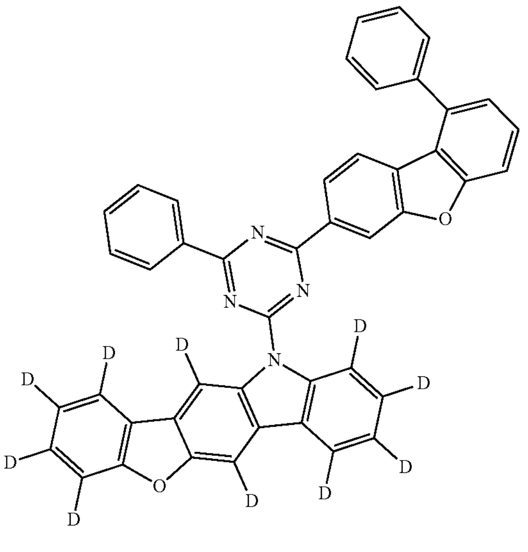
-continued
[D-43]
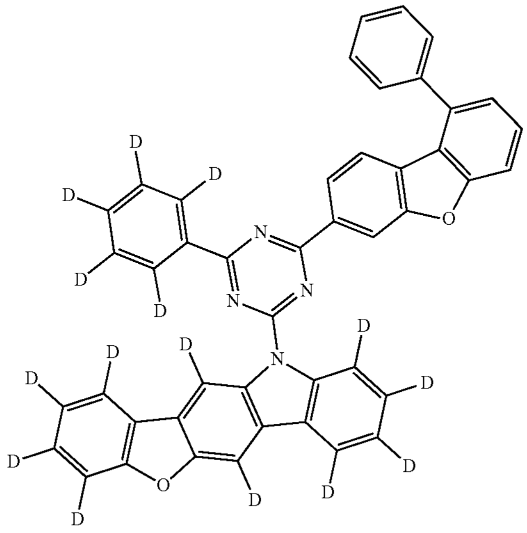
[D-44]
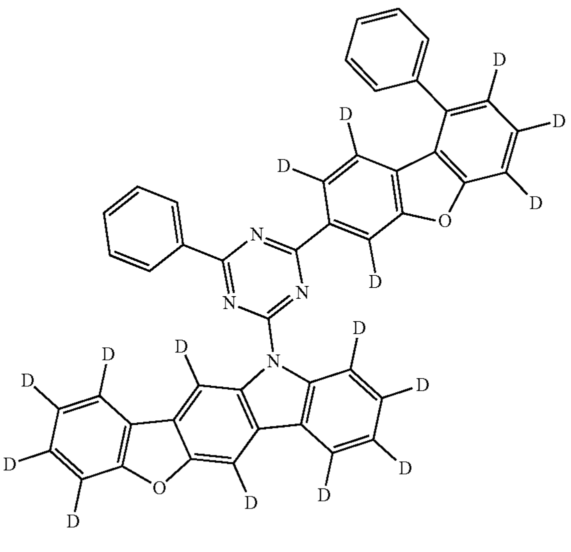

[D-45]
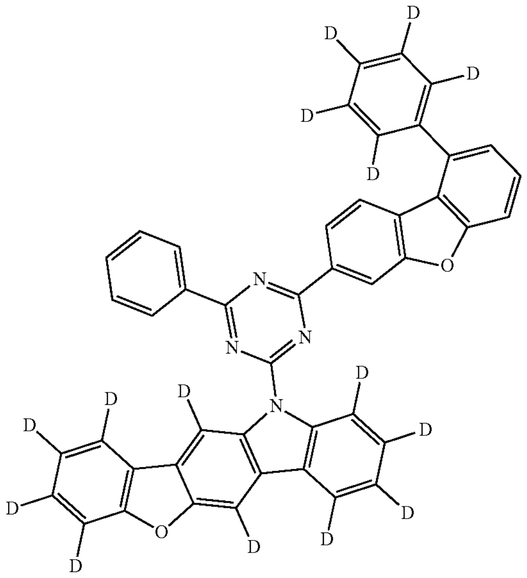
[D-46]
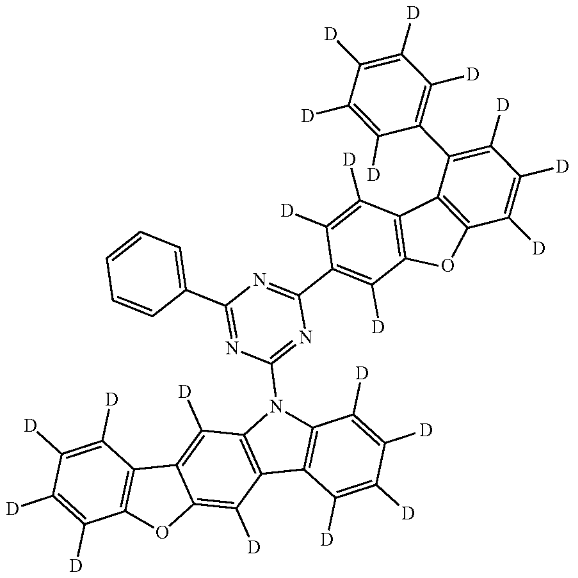
[D-47]
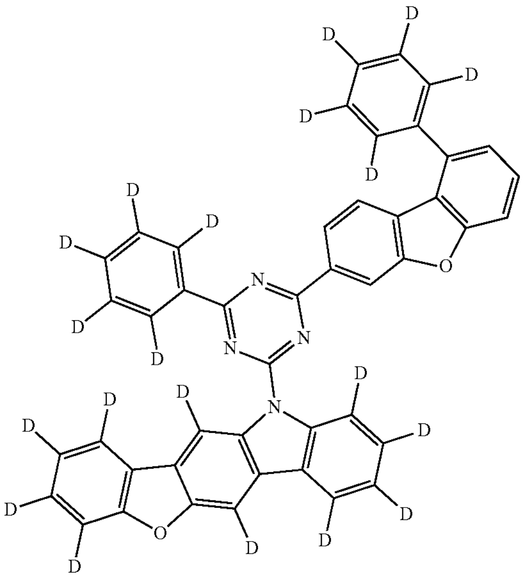
[D-48]
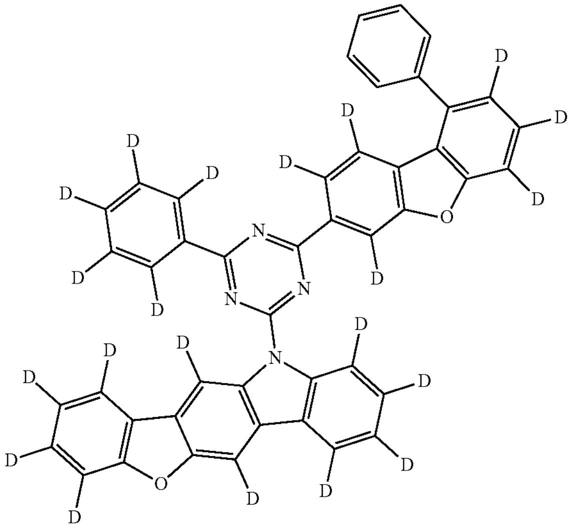
[D-49]
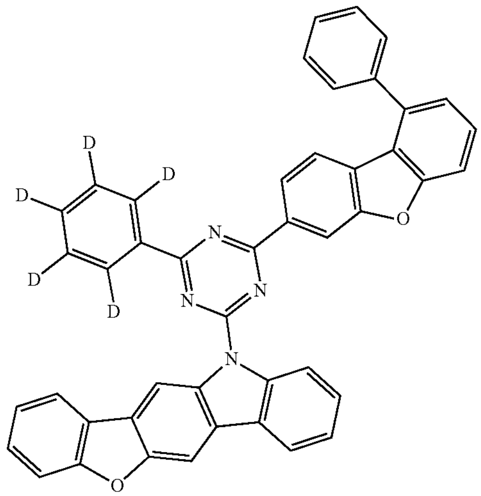

-continued
[D-50]
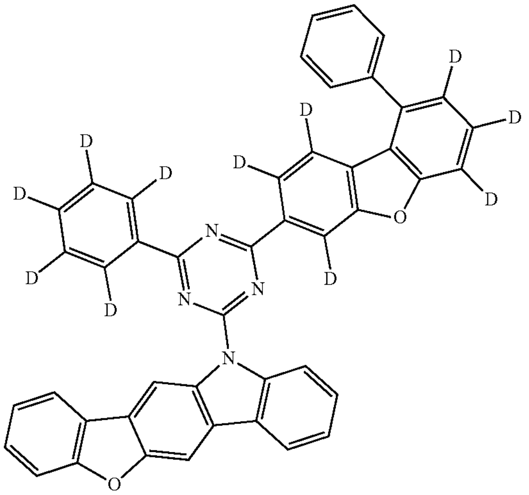
[D-51]
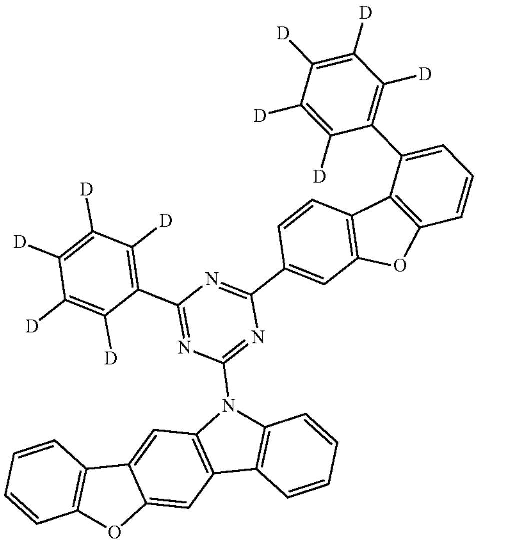
[D-52]
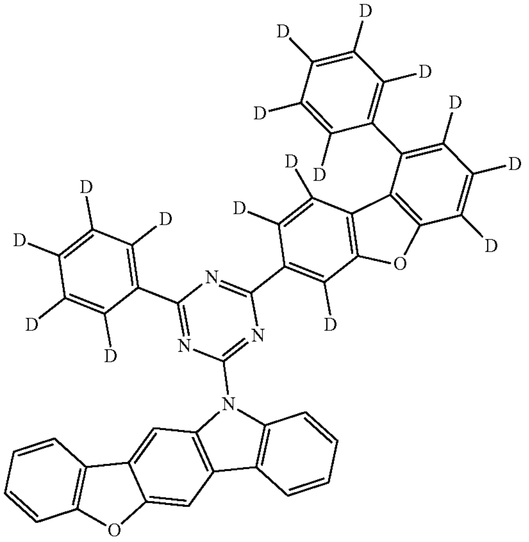
-continued
[D-53]
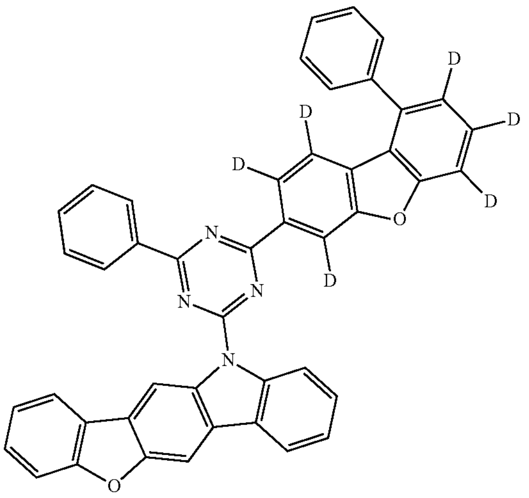
[D-54]
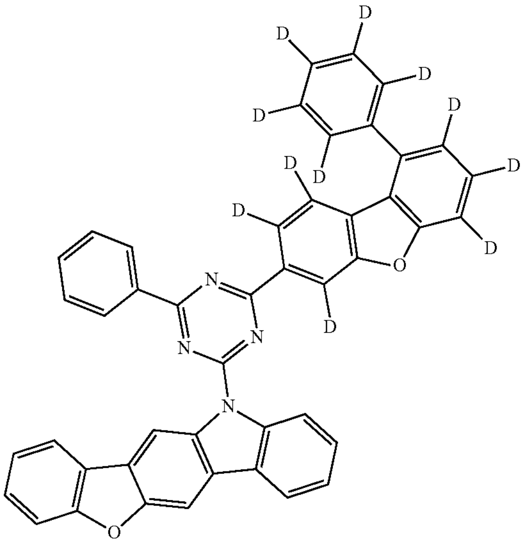
[D-55]
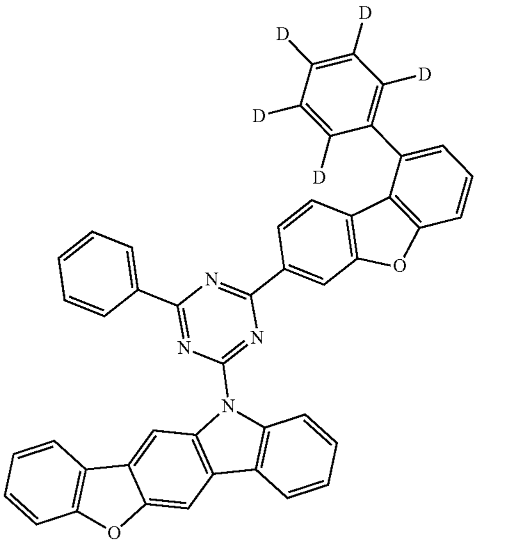

-continued
[D-56]
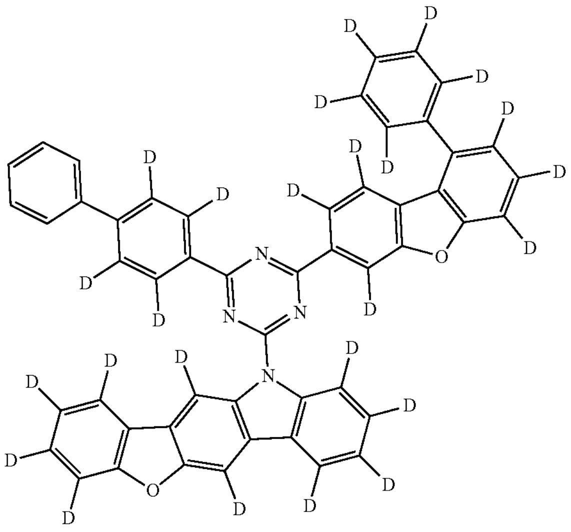
[D-57]
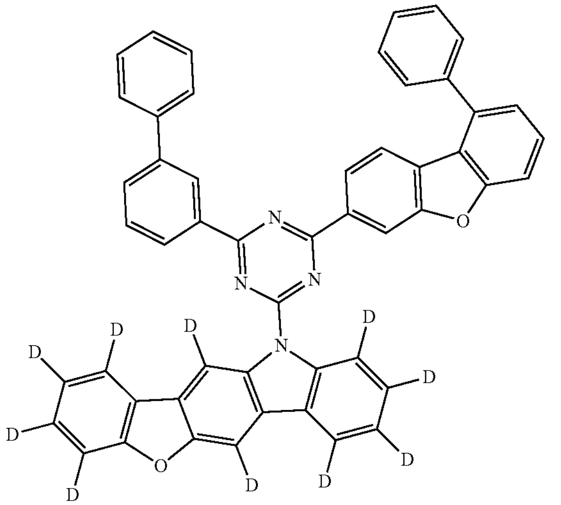
[D-58]
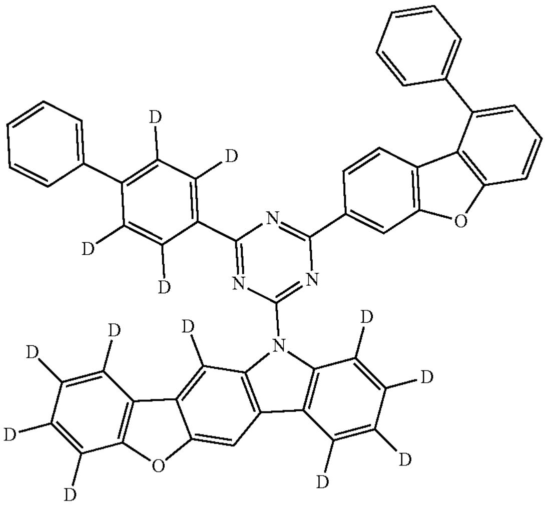
[D-59]
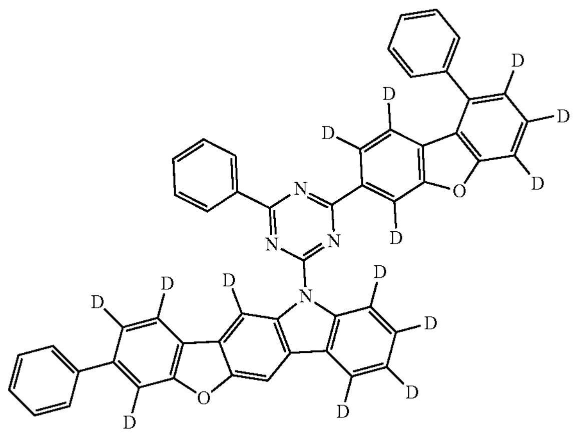
[D-60]
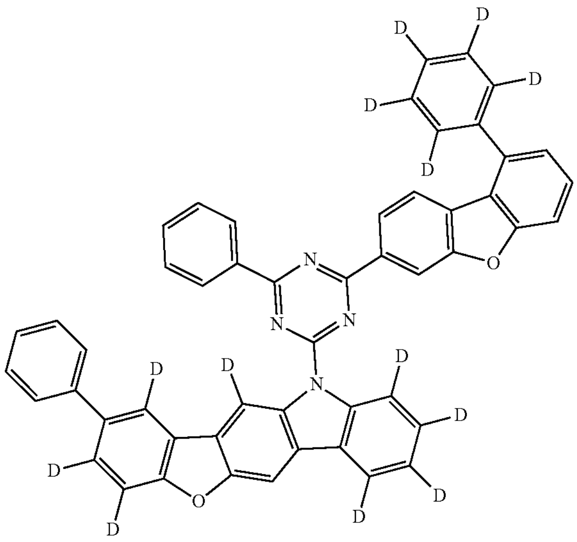
[D-61]
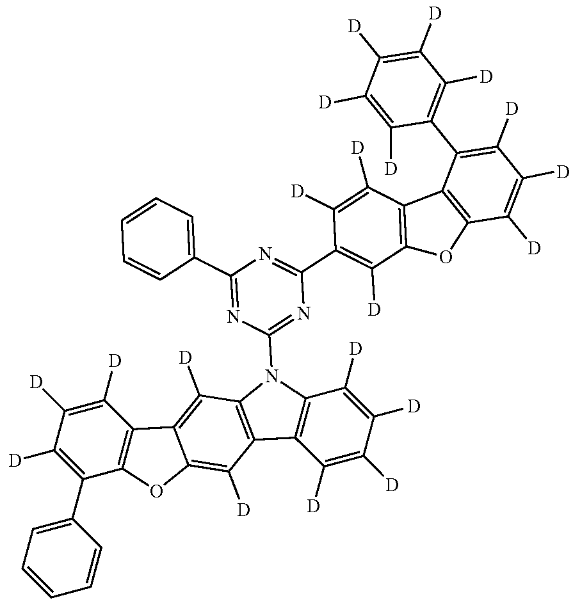

[D-62]
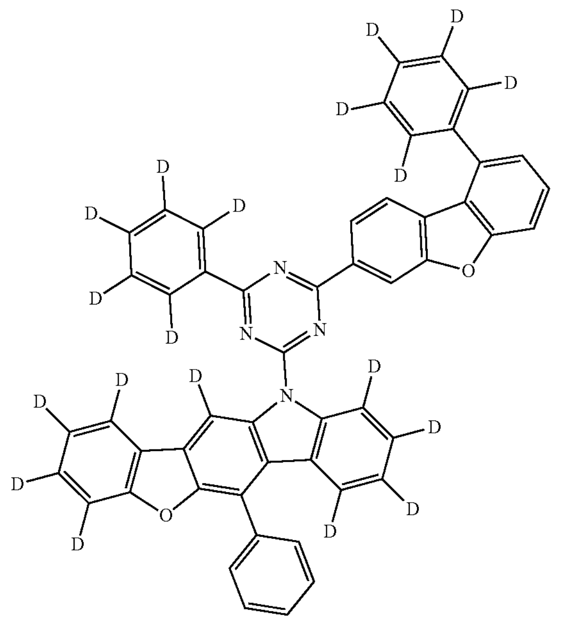
[D-63]
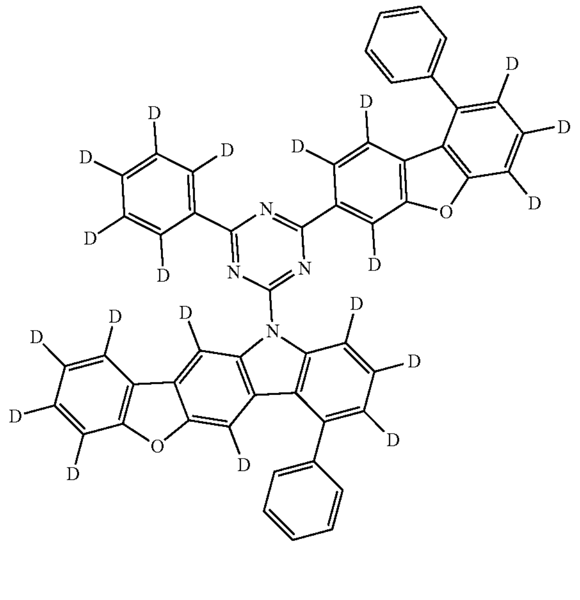
[D-64]
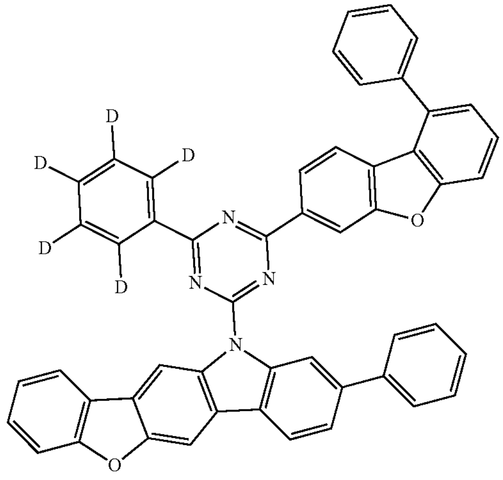
[D-65]
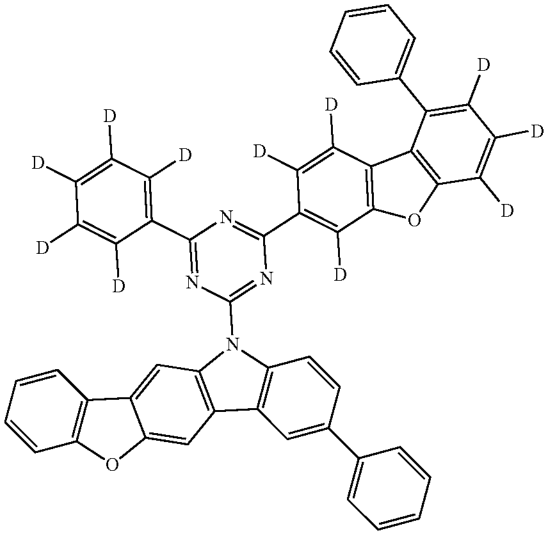
[D-66]
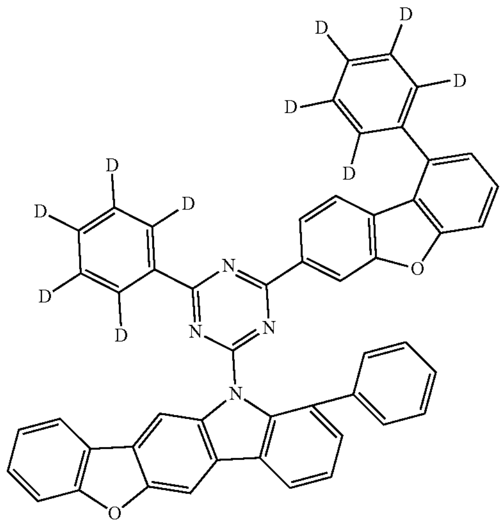

-continued
[D-67]
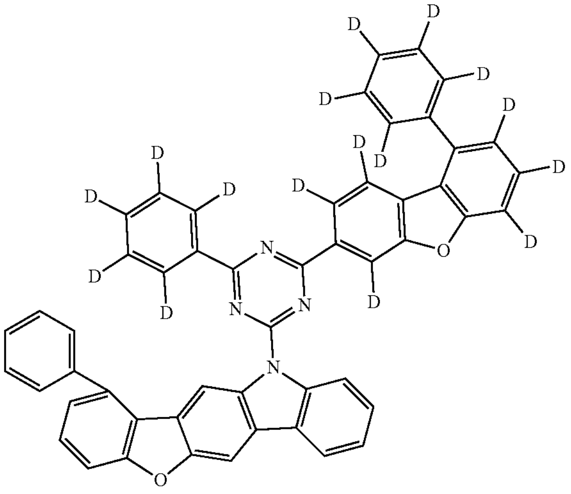
[D-68]
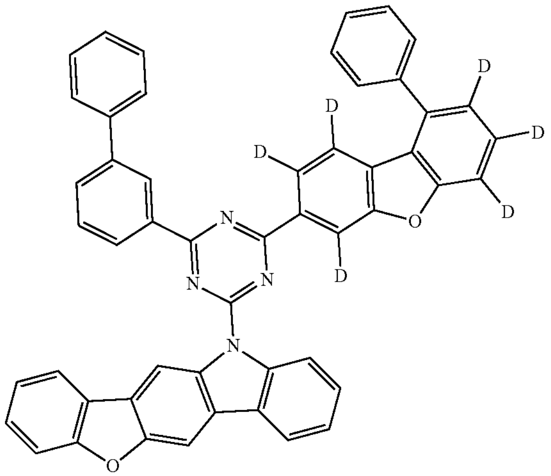
[D-69]
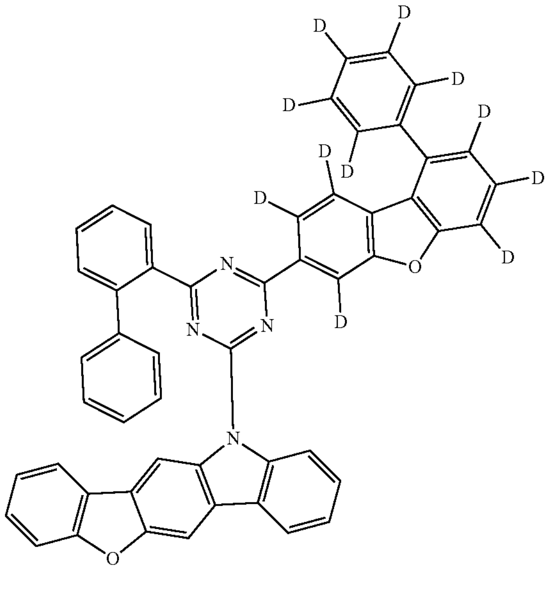
-continued
[D-70]
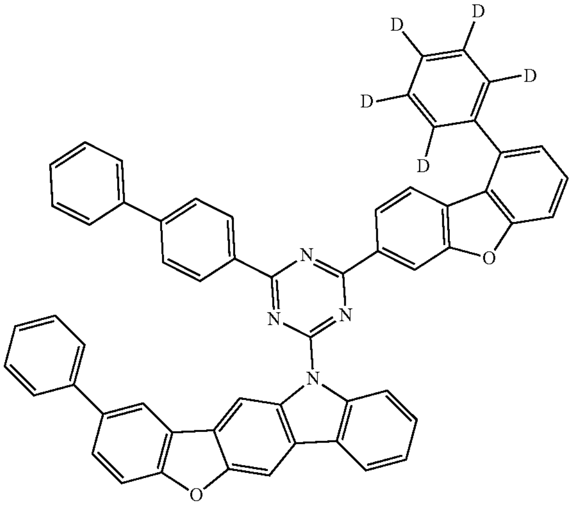
[D-71]
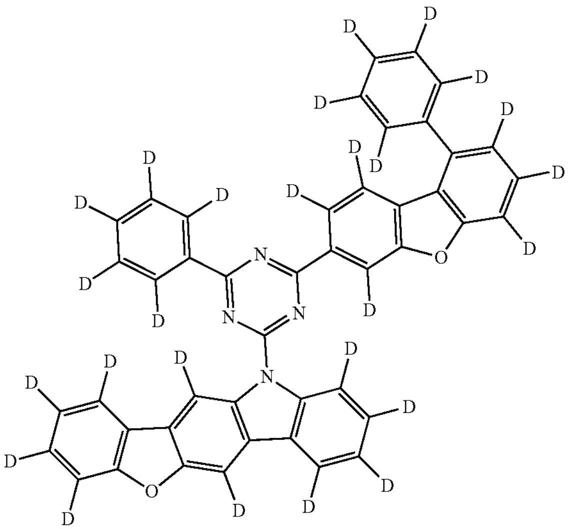
[D-72]
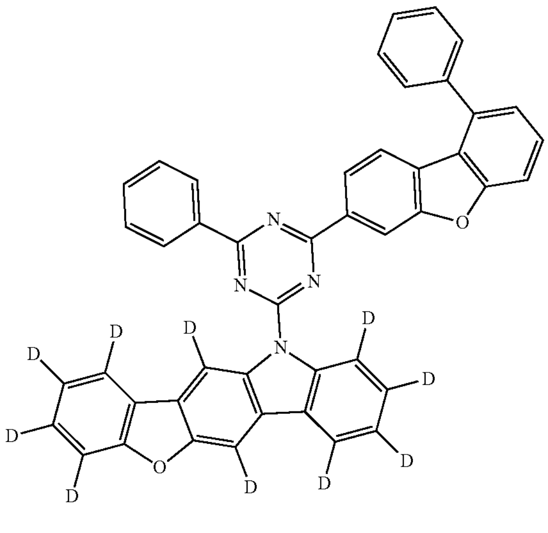

-continued
[D-73]
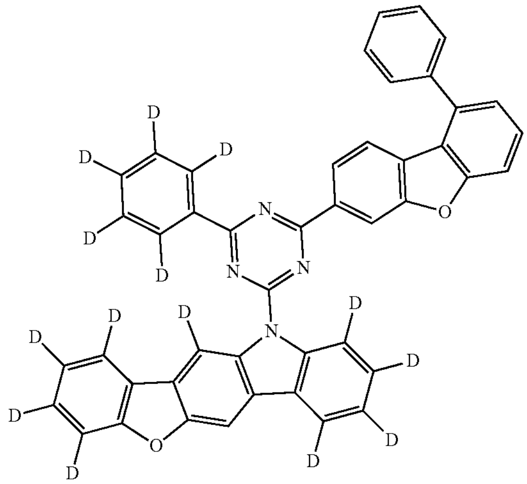
[D-74]
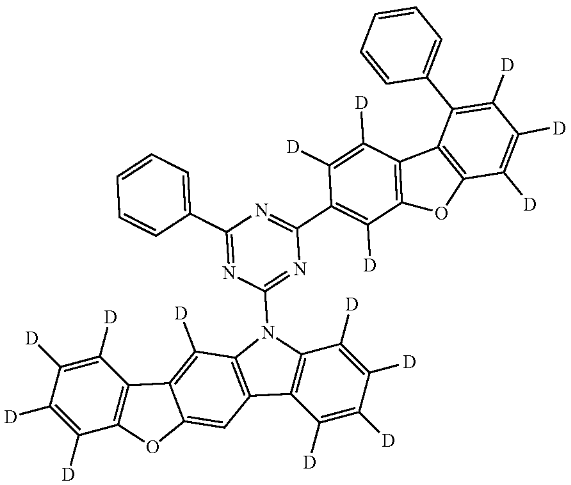
[D-75]
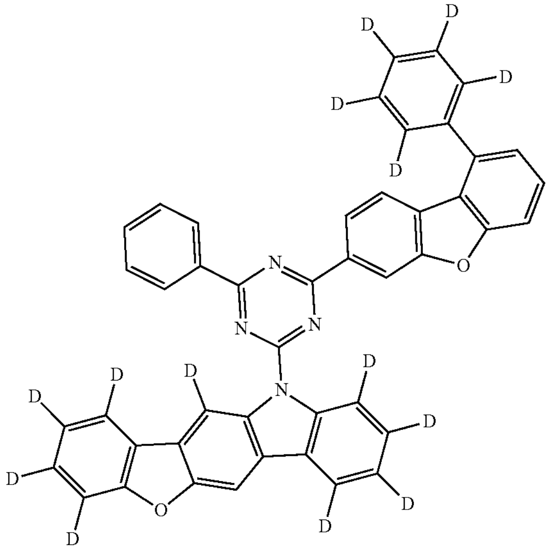
-continued
[D-76]
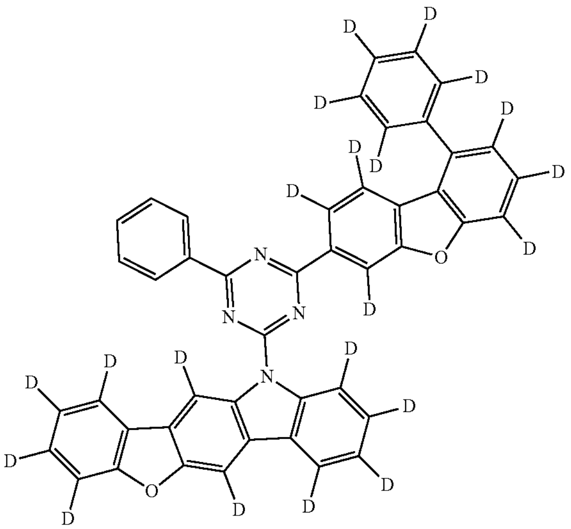
[D-77]
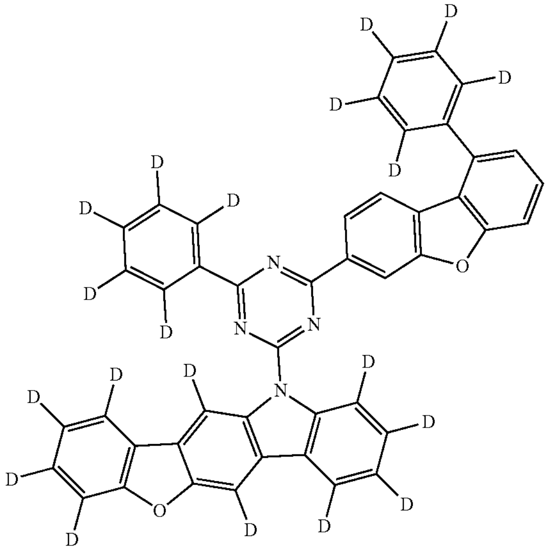
[D-78]
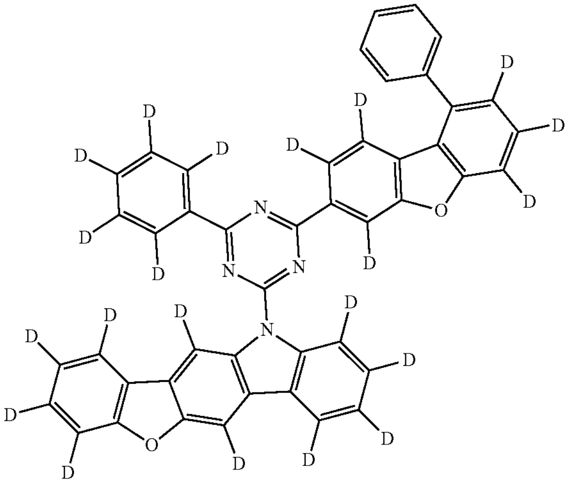

-continued
[D-79]
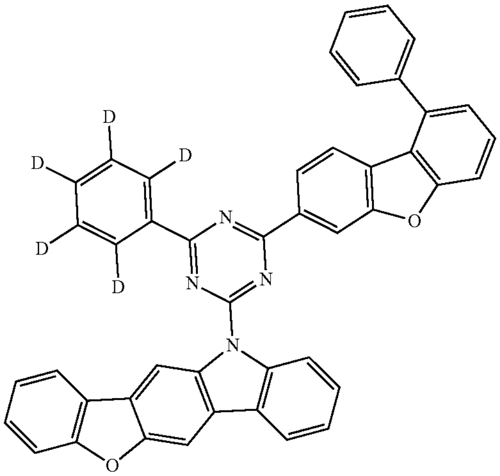
[D-80]
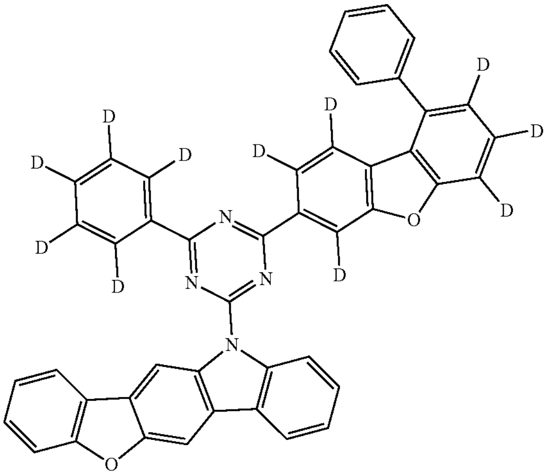
[D-81]
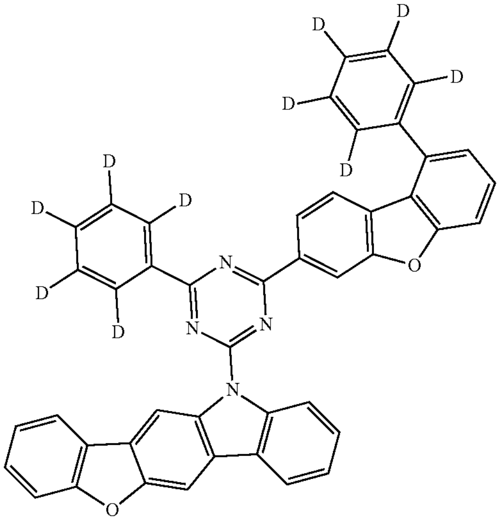
-continued
[D-82]
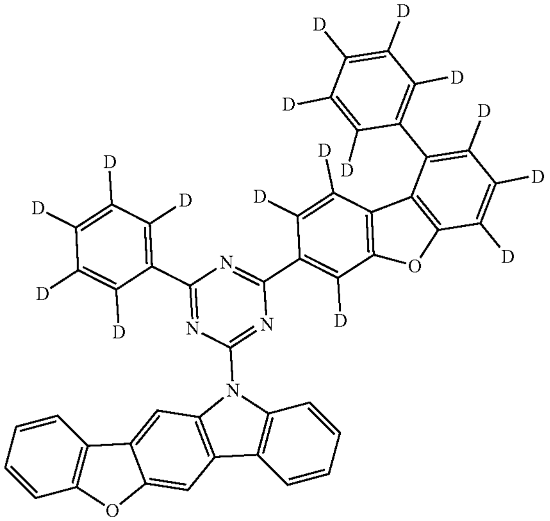
[D-83]
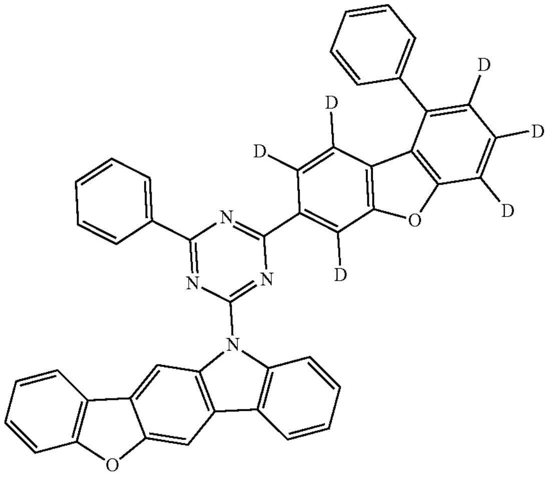
[D-84]
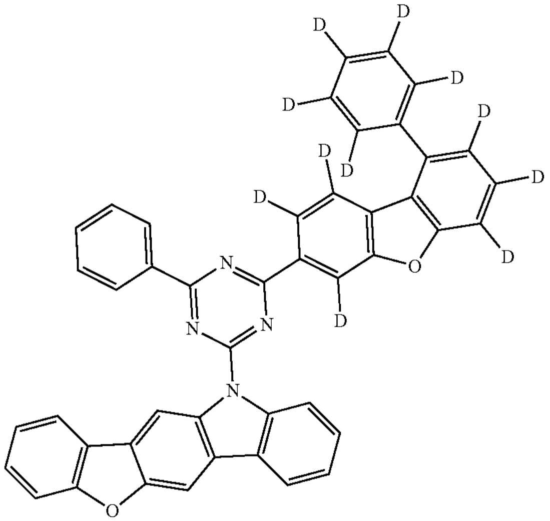

-continued
[D-85]
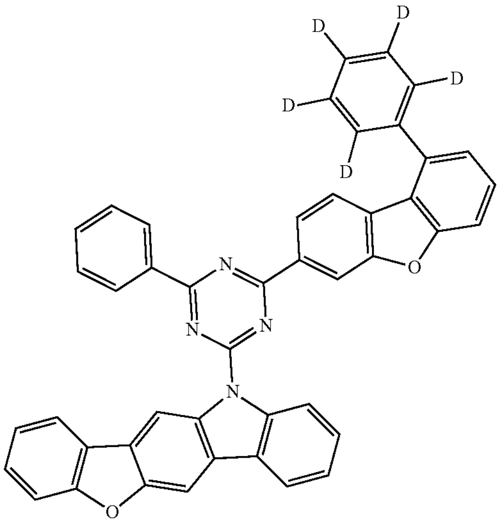
[D-86]
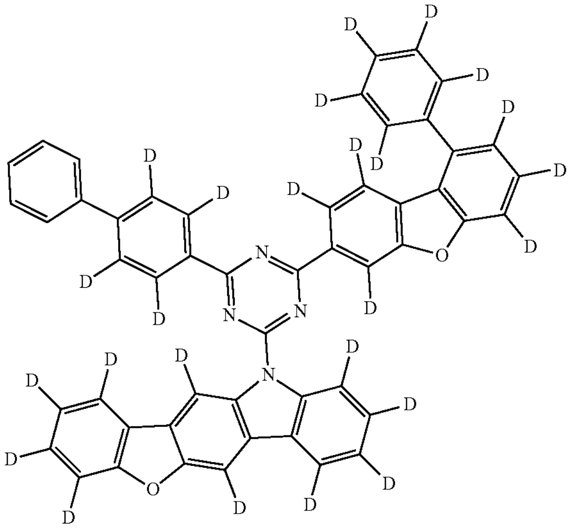
[D-87]
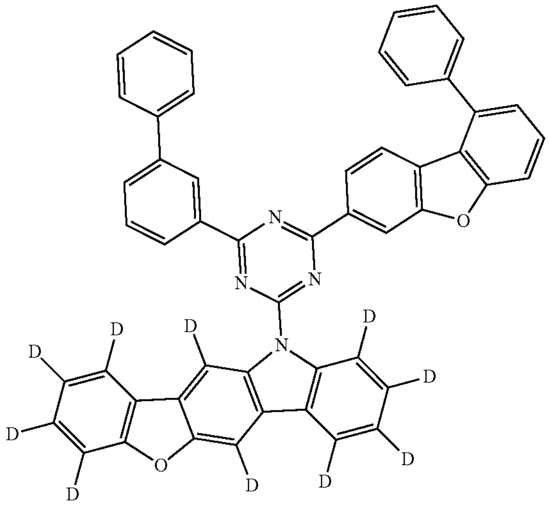
-continued
[D-88]
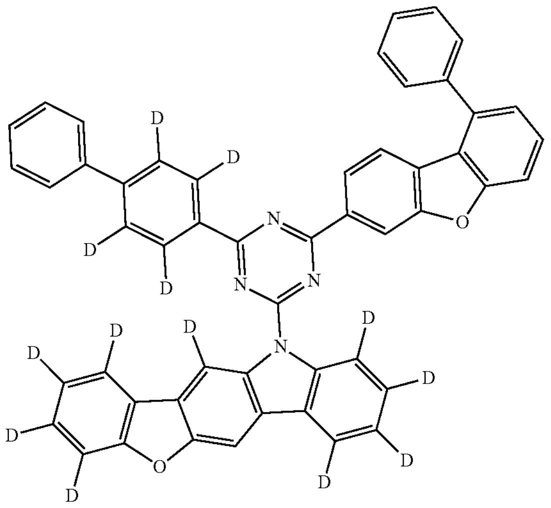
[D-89]
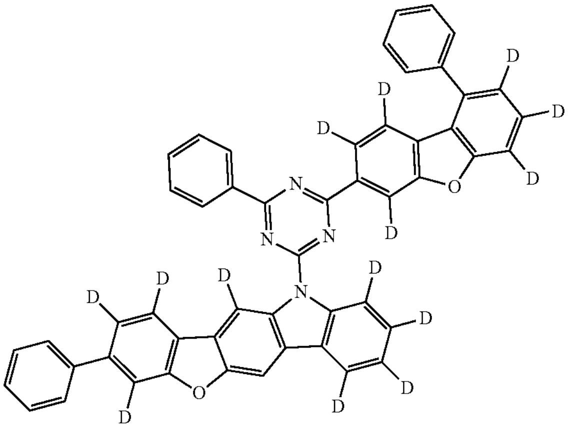
[D-90]
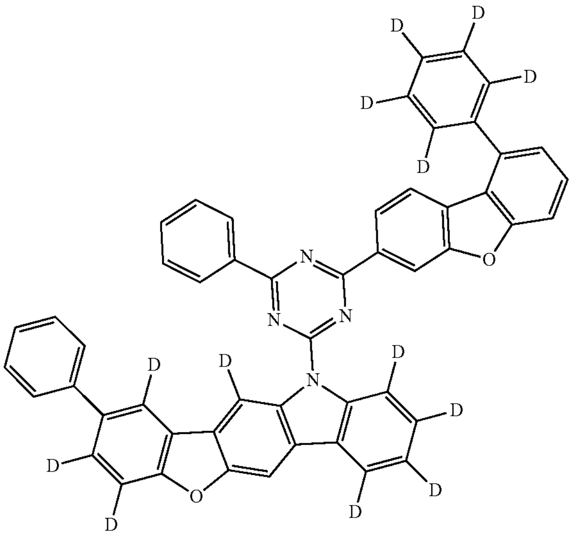

-continued
[D-91]
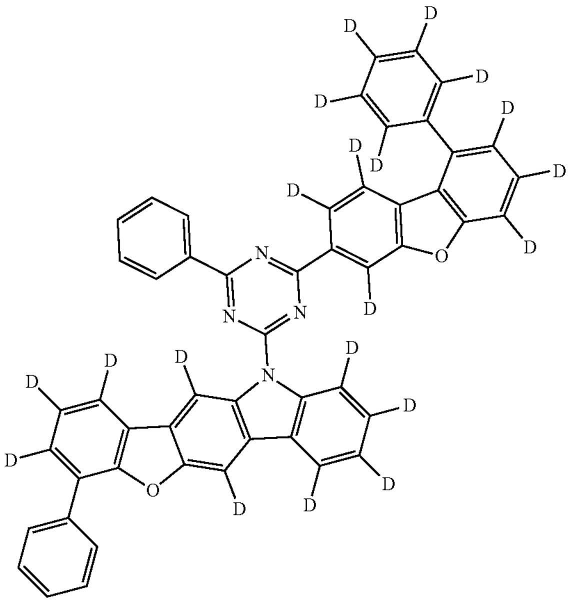
[D-92]
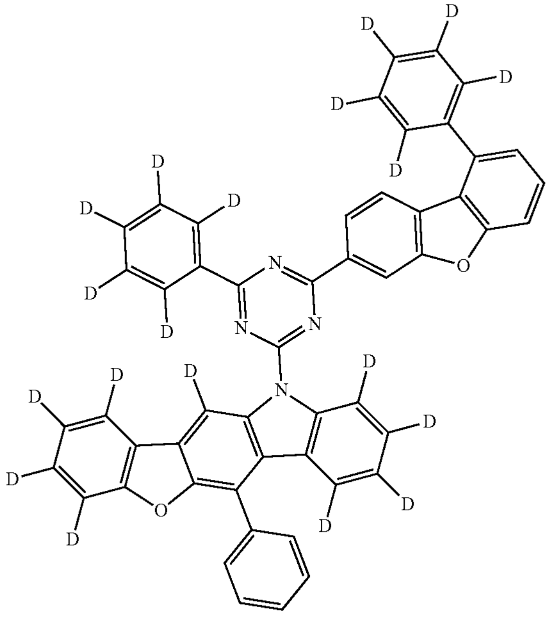
-continued
[D-93]
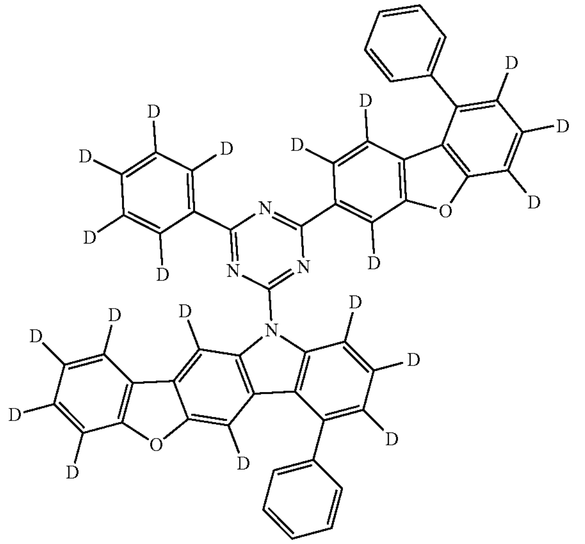
[D-94]
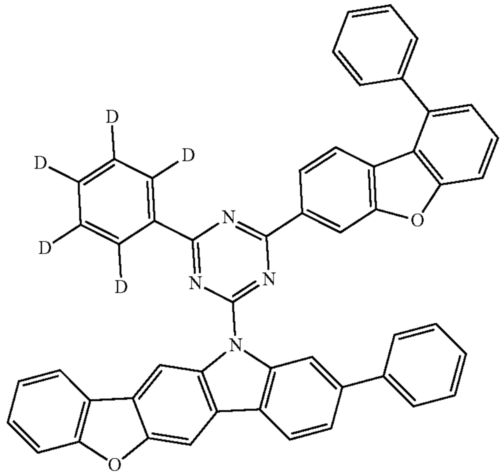
[D-95]
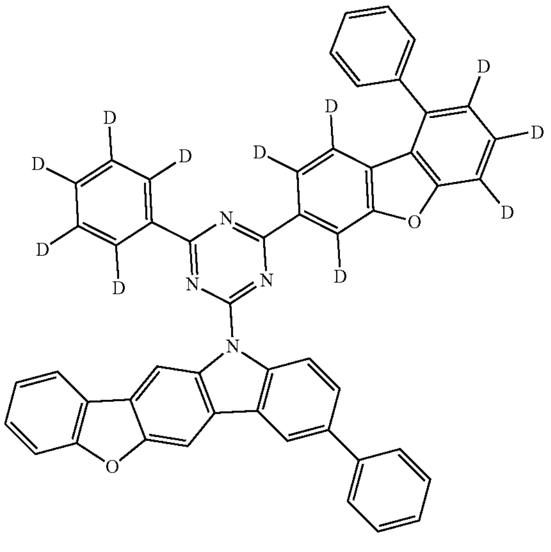

-continued
[D-96]
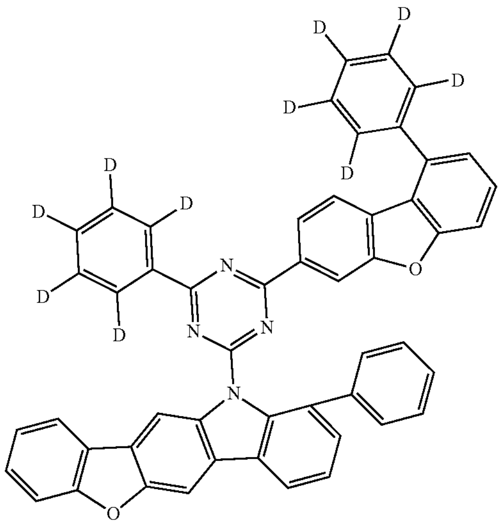
[D-97]
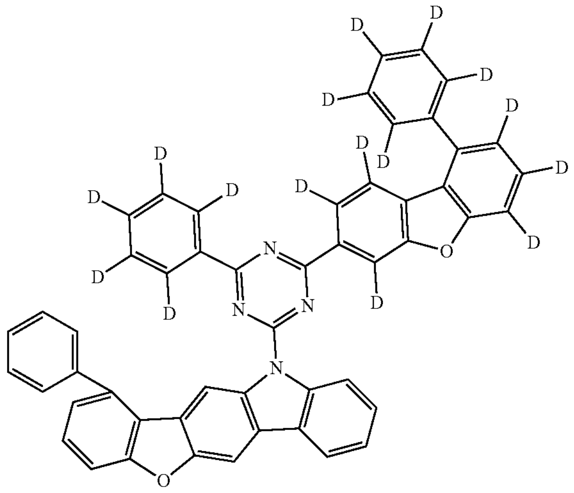
[D-98]
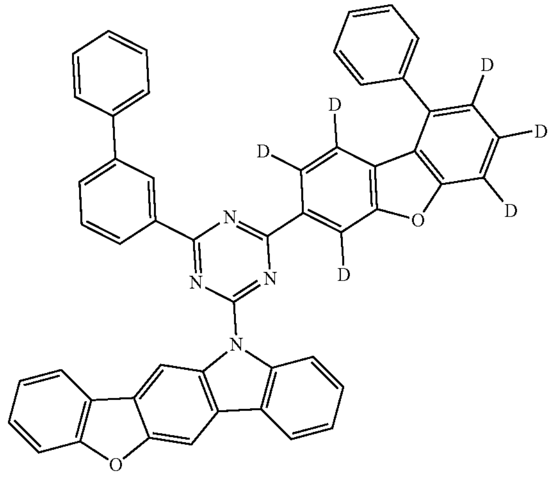
-continued
[D-99]
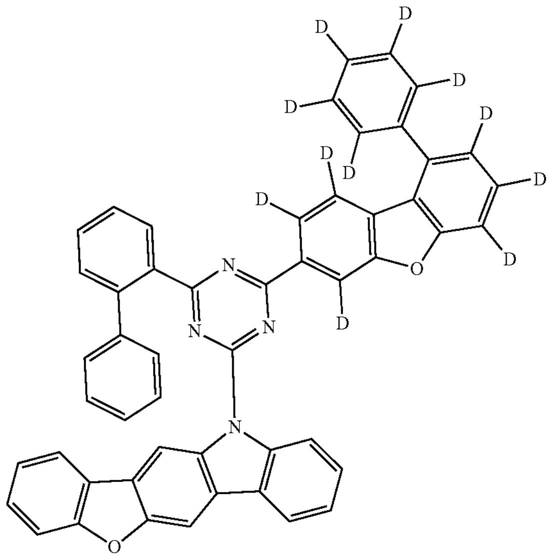
[D-100]
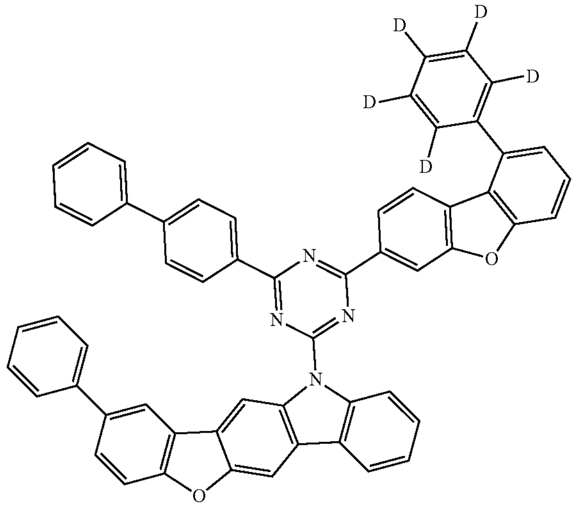
[E-1]
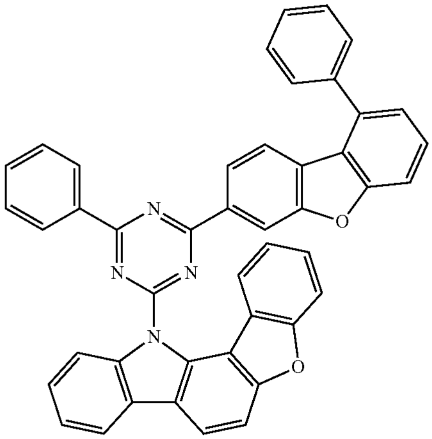

-continued
[E-2]
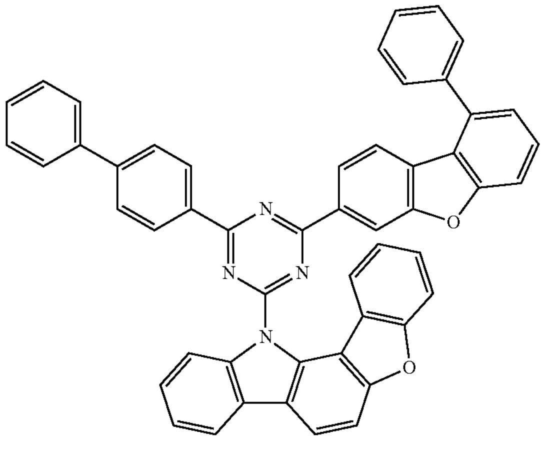
[E-3]
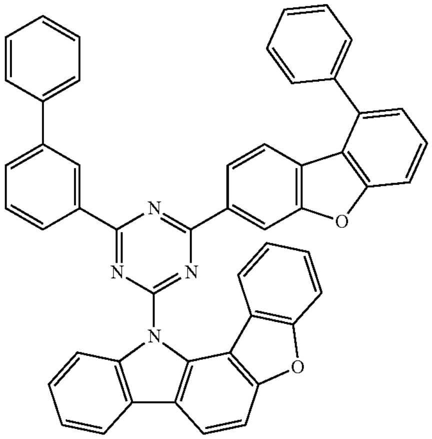
[E-4]
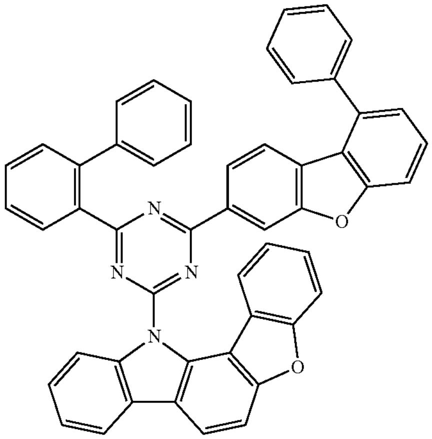
-continued
[E-5]
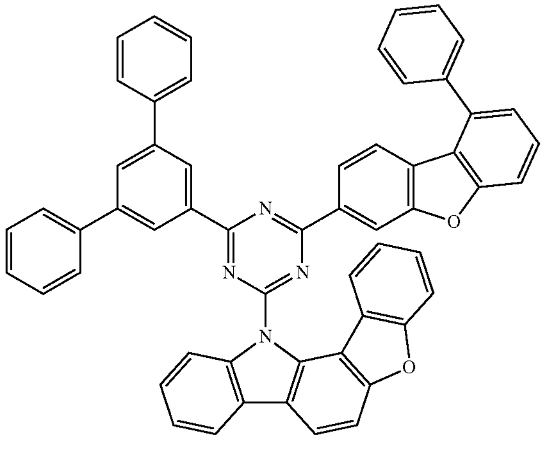
[E-6]
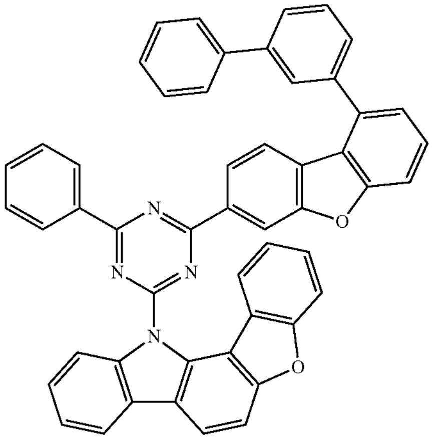
[E-7]
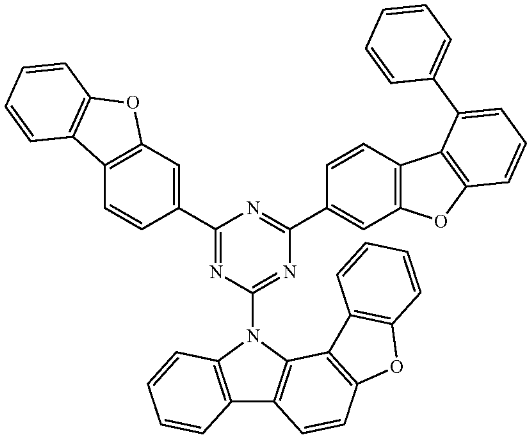

-continued
[E-8]
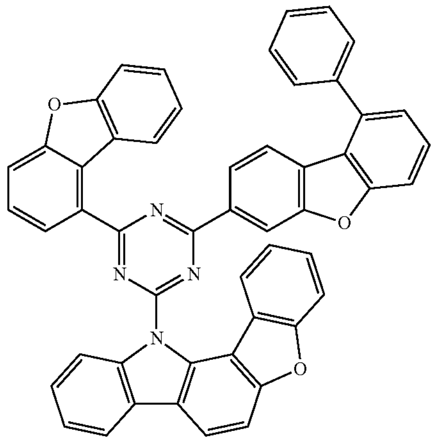
[E-9]
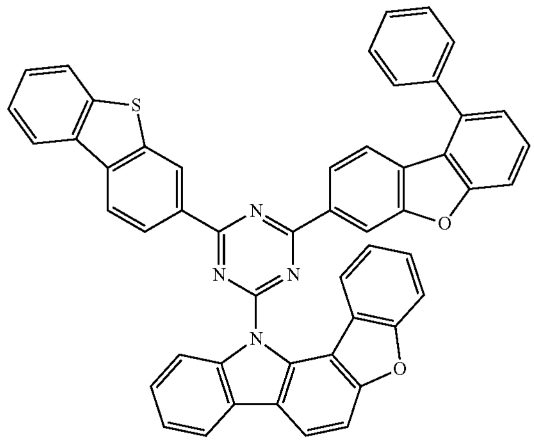
[E-10]
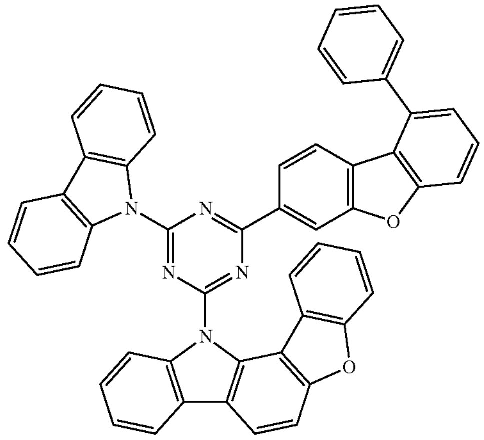
-continued
[E-11]
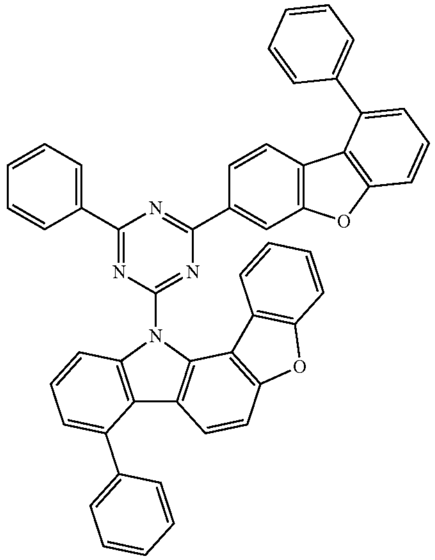
[E-12]
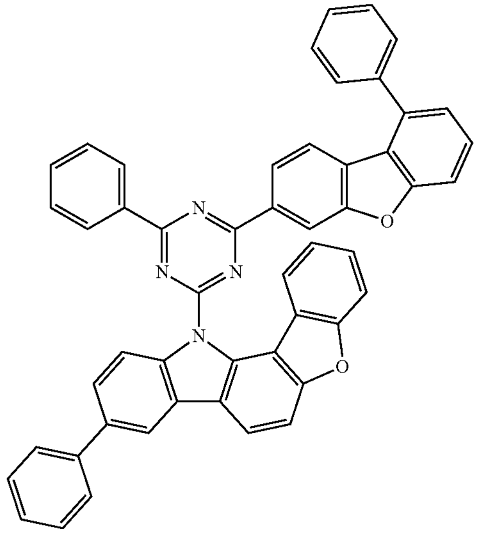
[E-13]
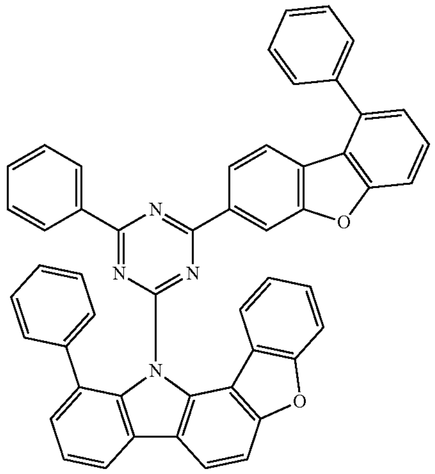

-continued
[E-14]
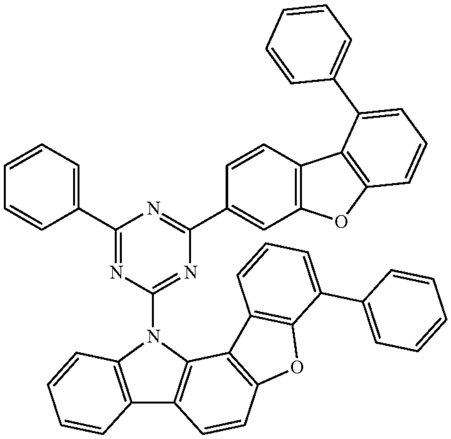
[E-15]
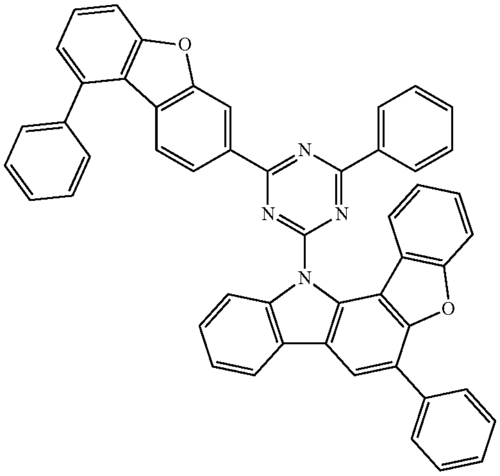
[E-16]
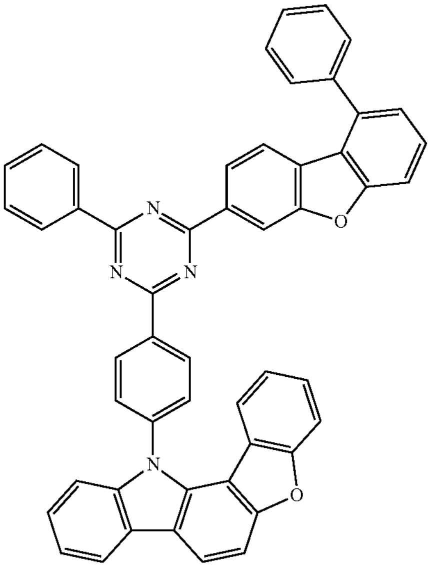
-continued
[E-17]
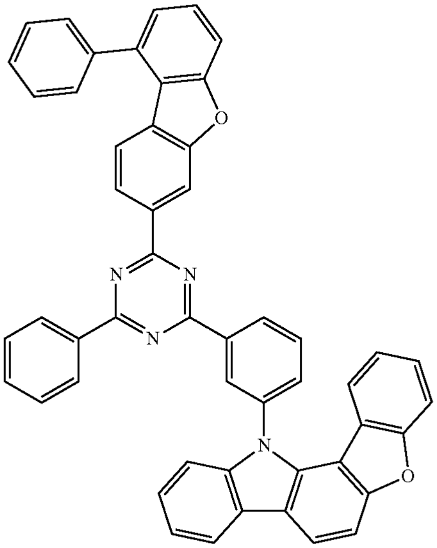
[E-18]
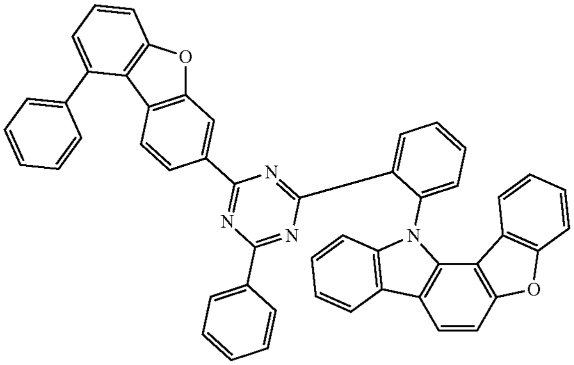
[E-19]
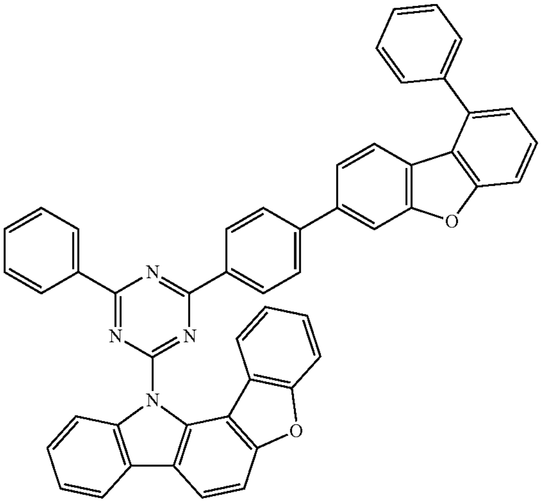

-continued
[E-20]
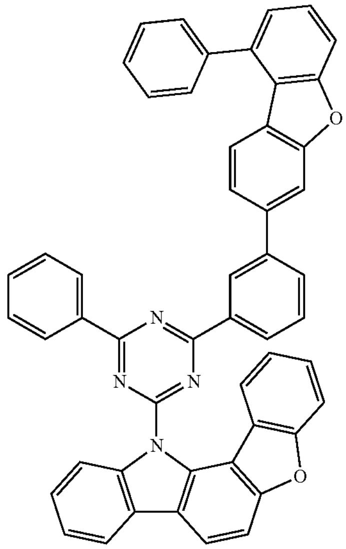
[E-21]
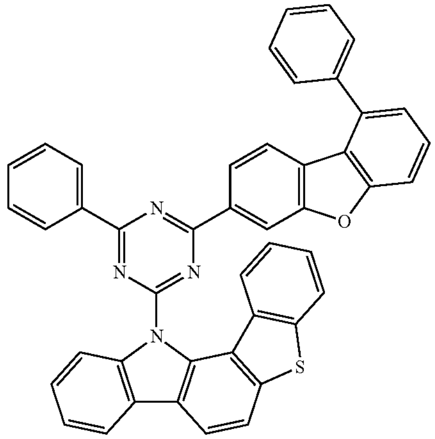
[E-22]
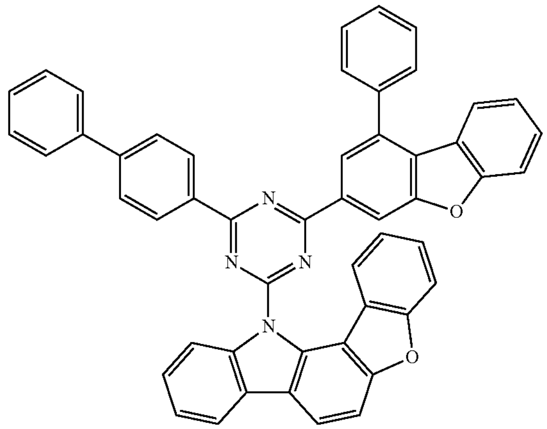
-continued
[E-23]
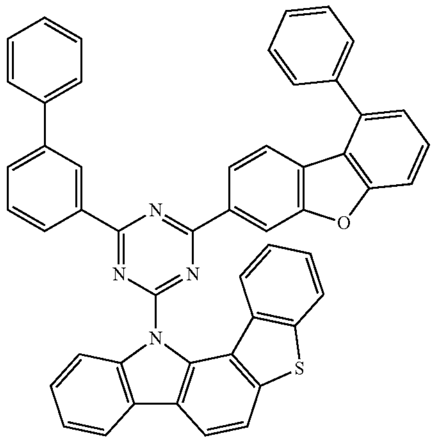
[E-24]
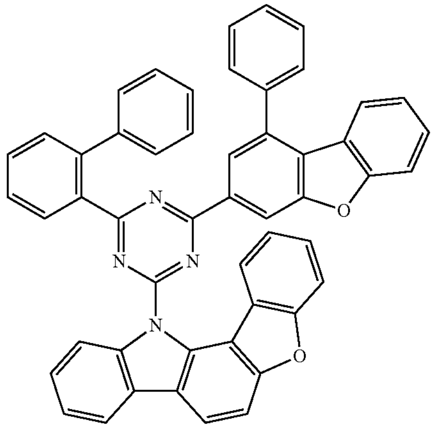
[E-25]
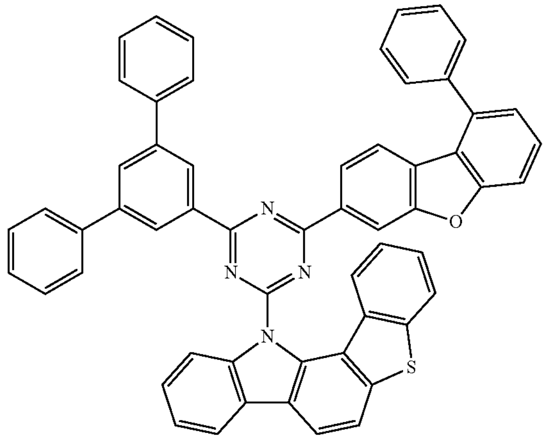

-continued
[E-26]
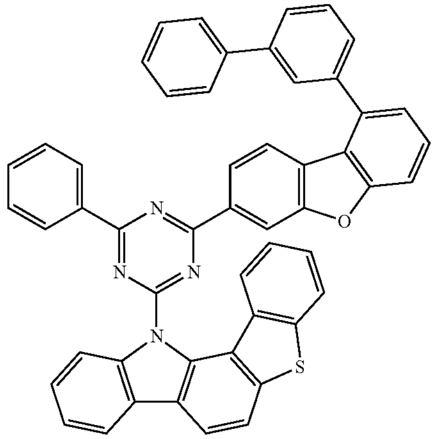
[E-27]
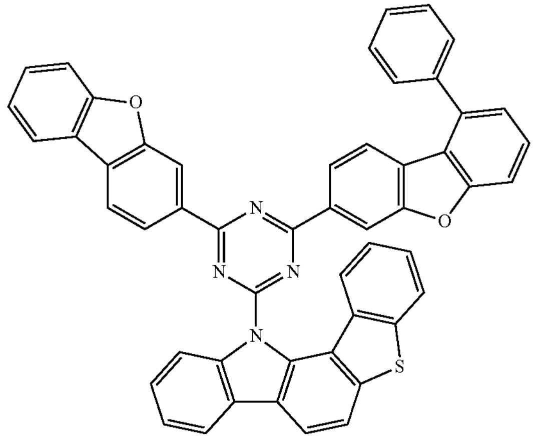
[E-28]
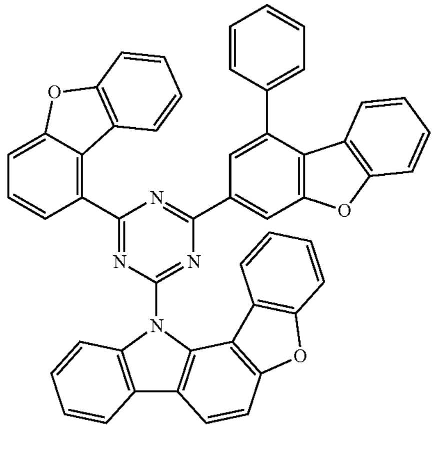
-continued
[E-29]
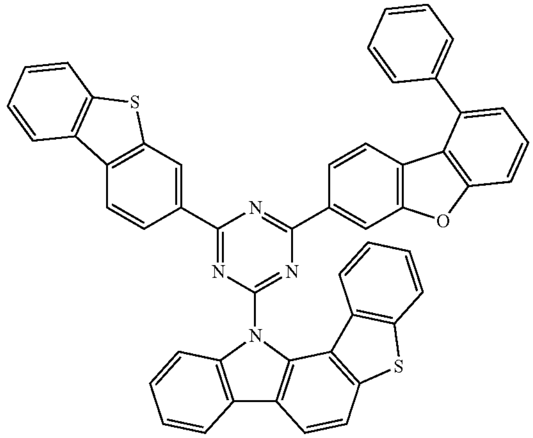
[E-30]
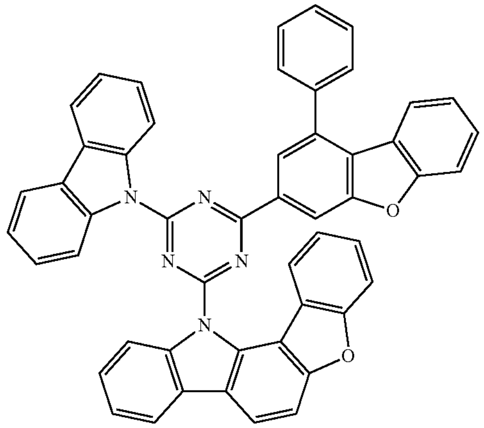
[E-31]
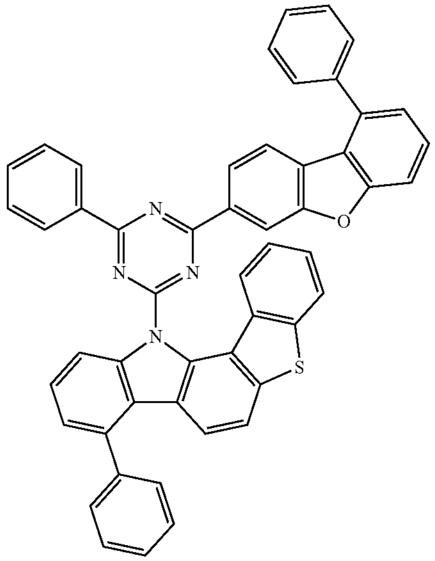

[E-32]
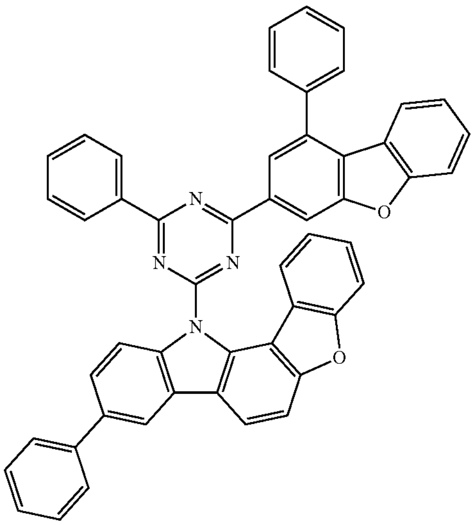
[E-33]
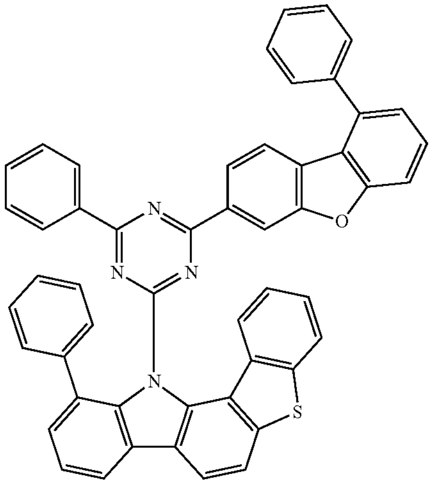
[E-34]
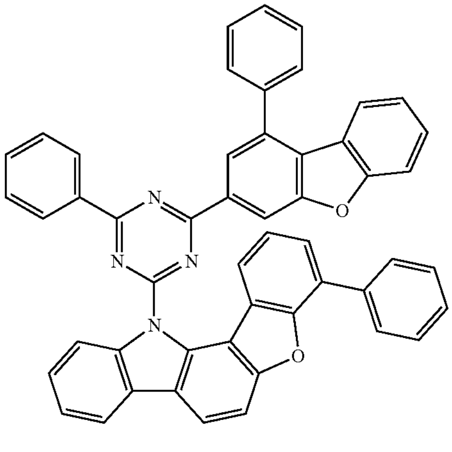
[E-35]
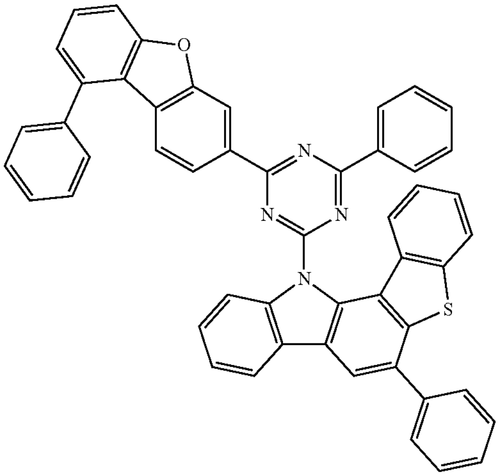
[E-36]
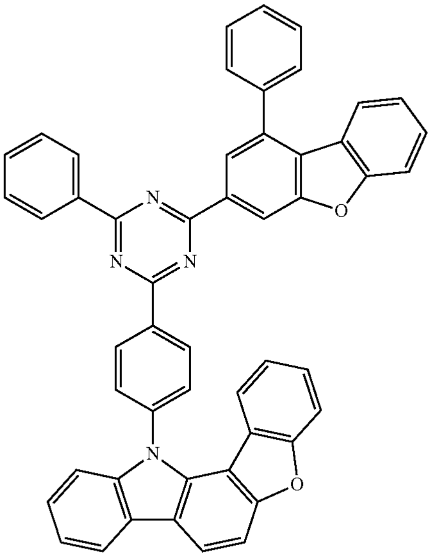
[E-37]
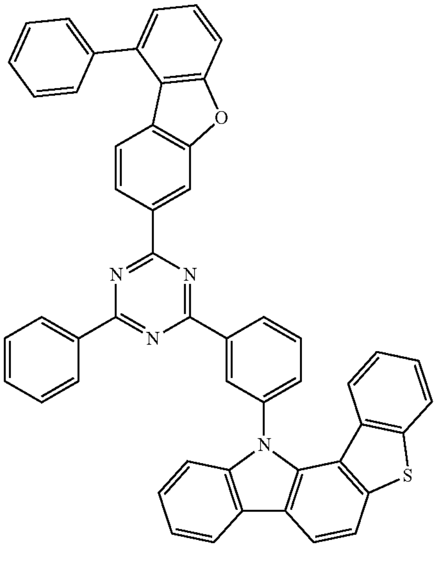

-continued
[E-38]
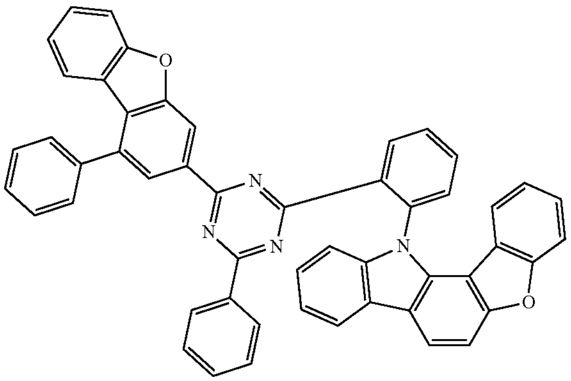
[E-39]
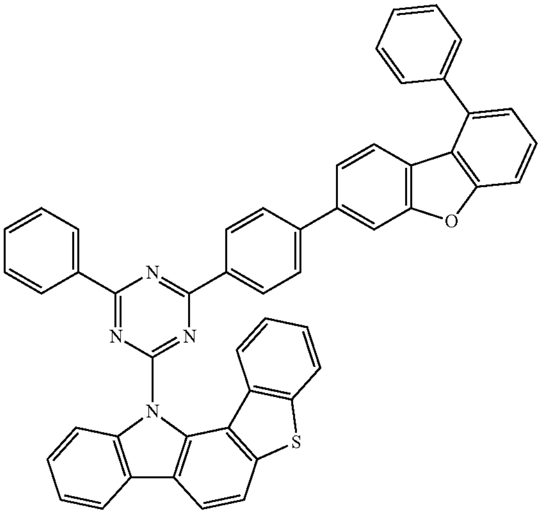
[E-40]
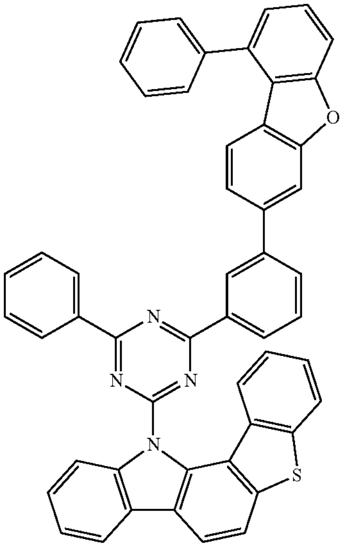
-continued
(E-41)
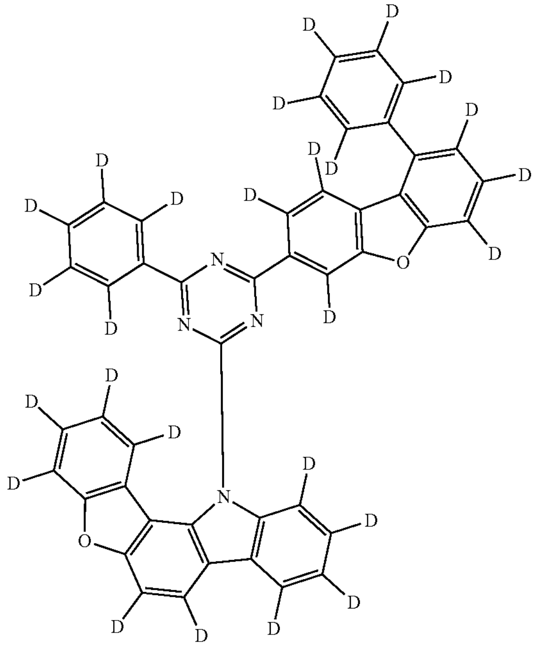
[E-42]
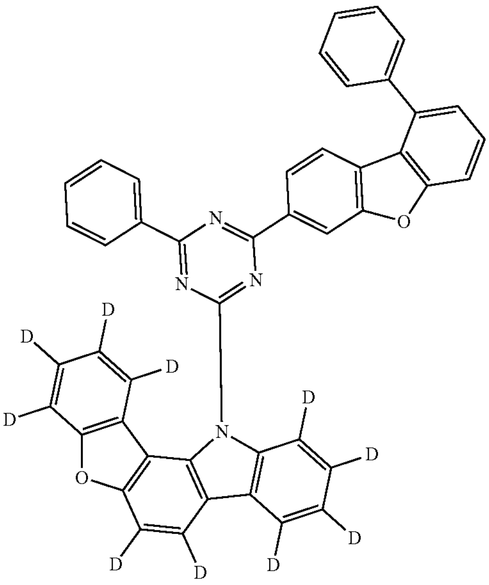

-continued
[E-43]
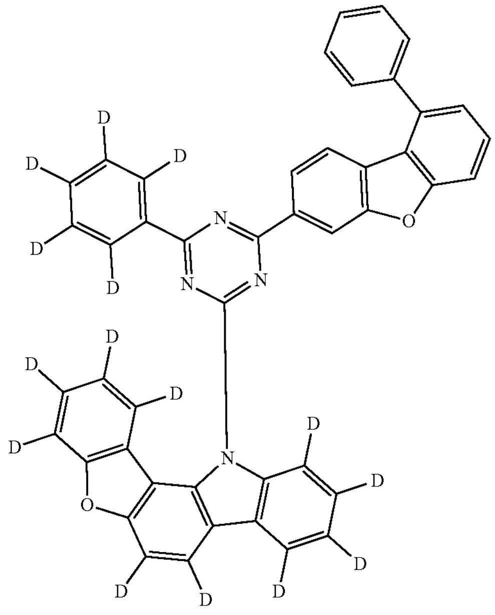
[E-44]
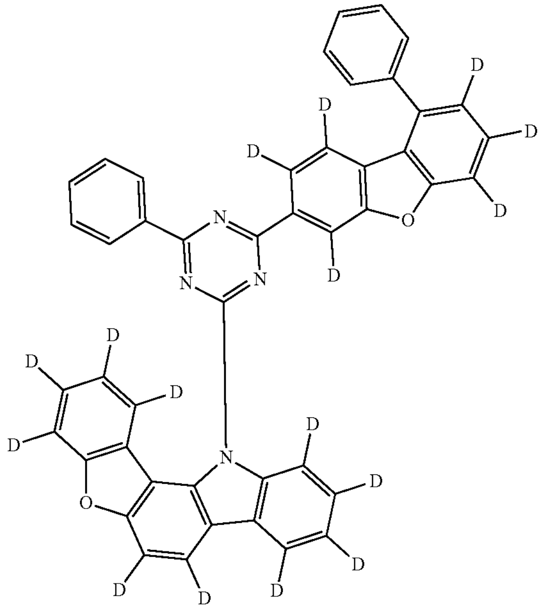
-continued
[E-45]
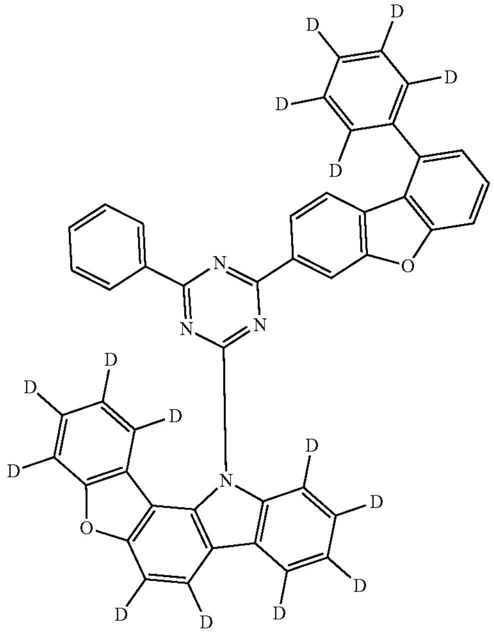
[E-46]
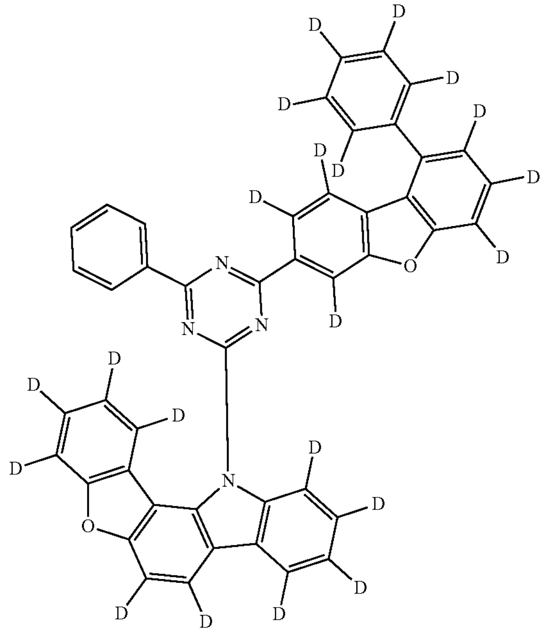

-continued
[E-47]
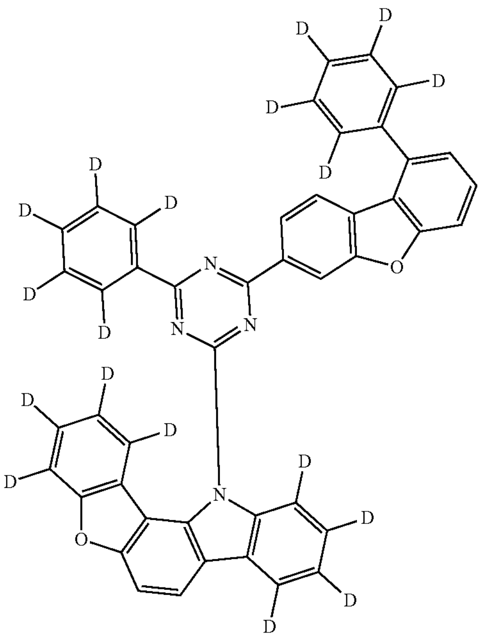
[E-48]
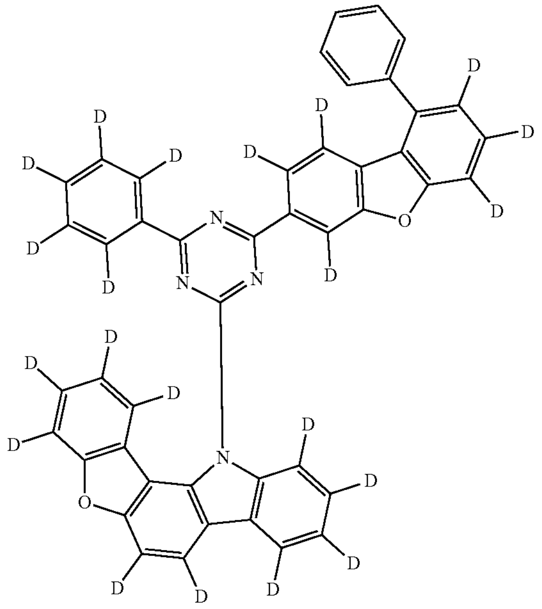
-continued
[E-49]
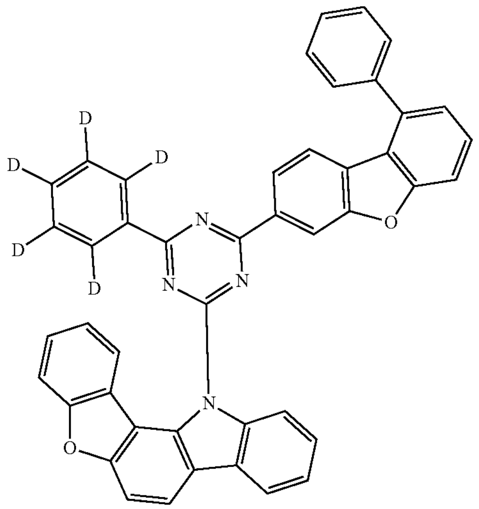
[E-50]
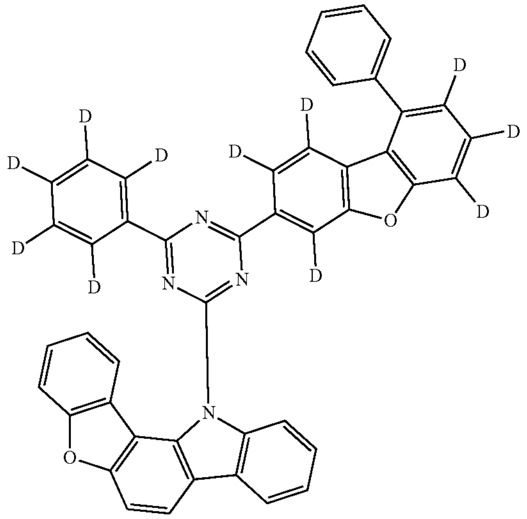
[E-51]
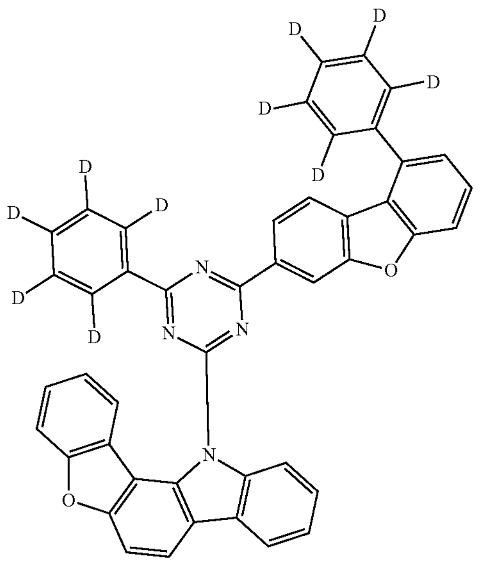

-continued
[E-52]
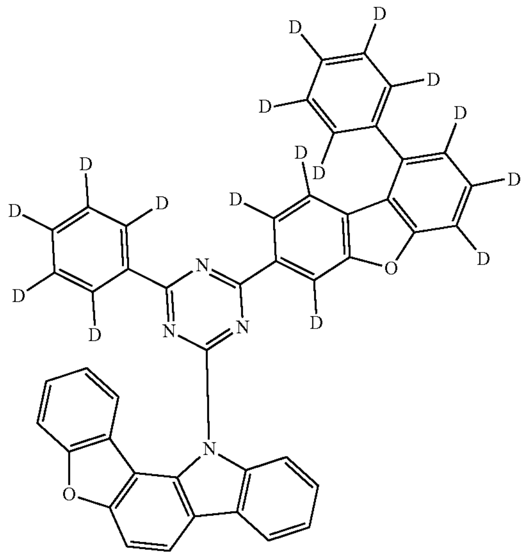
[E-53]
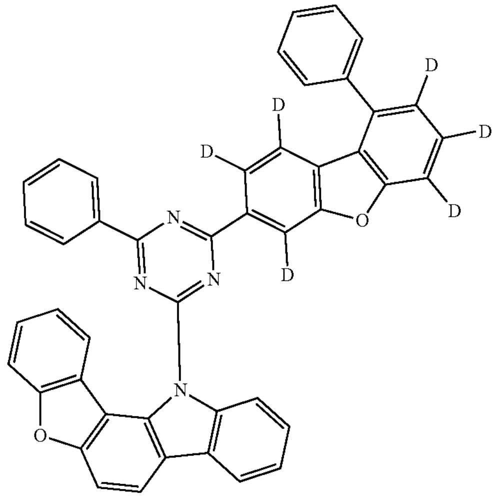
[E-54]
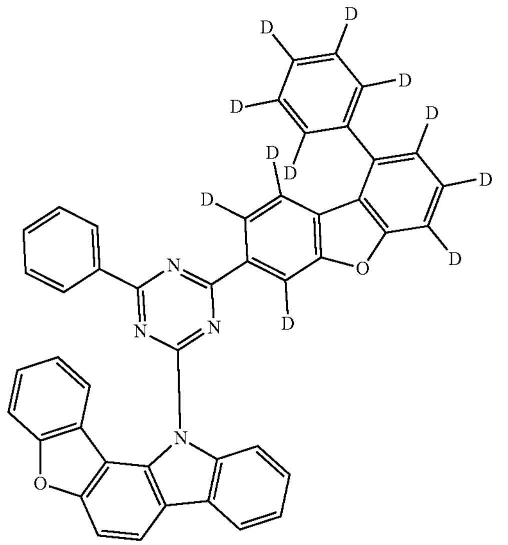
-continued
[E-55]
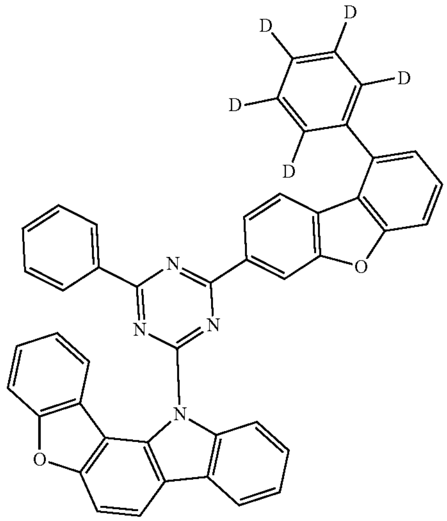
[E-56]
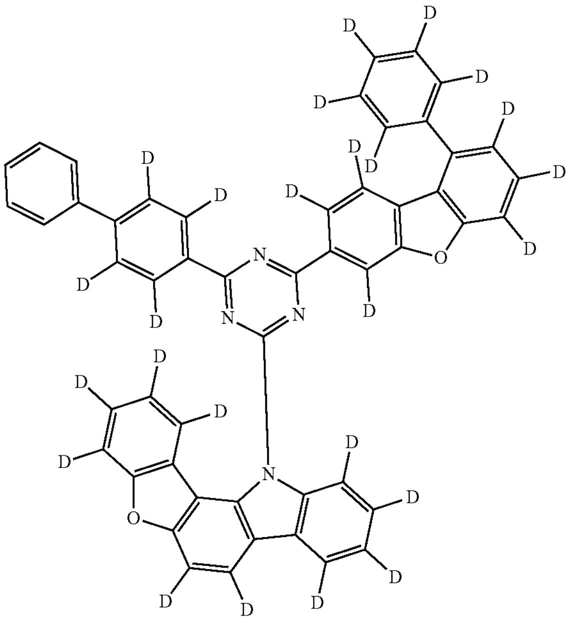

-continued
[E-57]
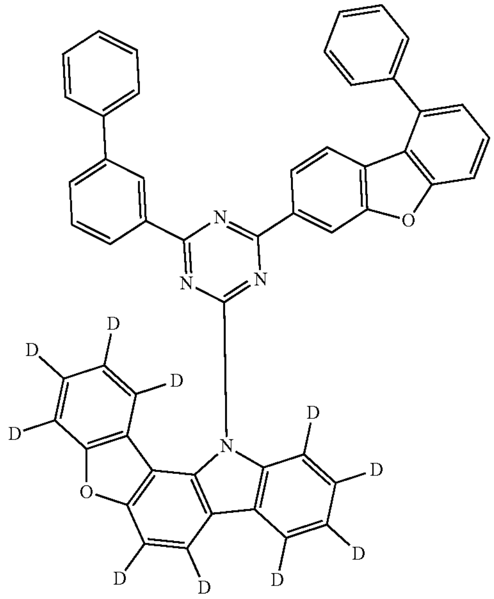
[E-58]
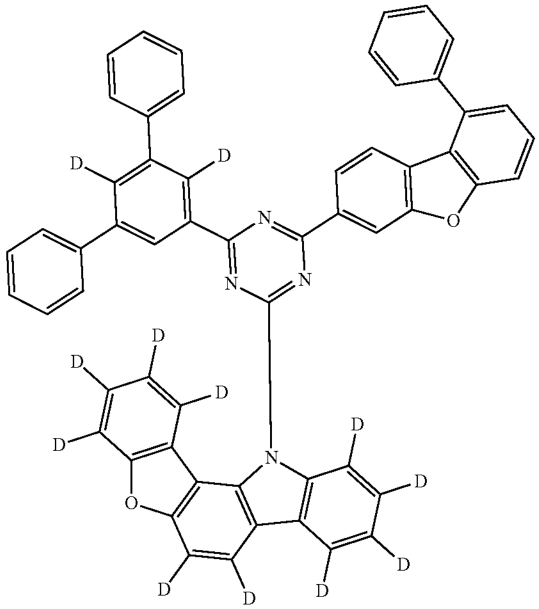
-continued
[E-59]
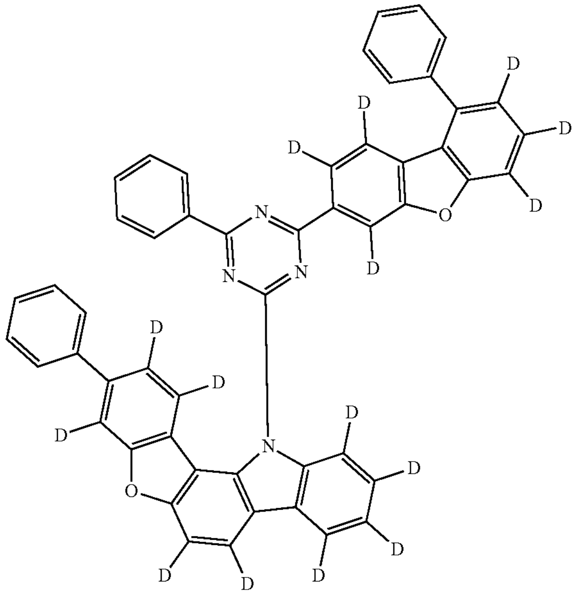
[E-60]
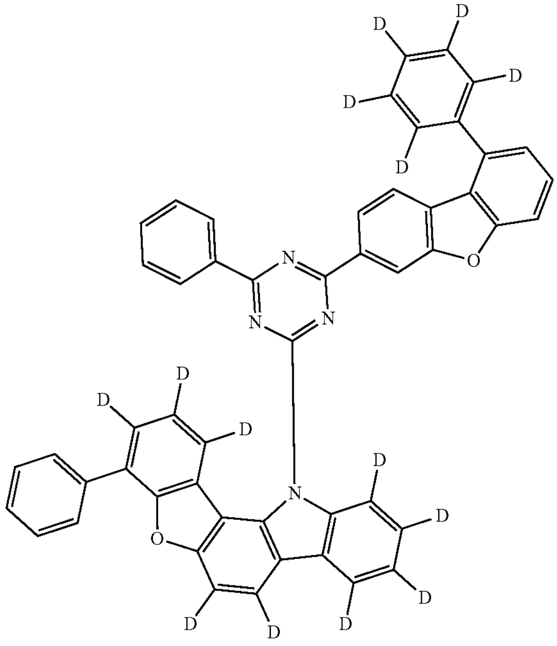

-continued
[E-61]
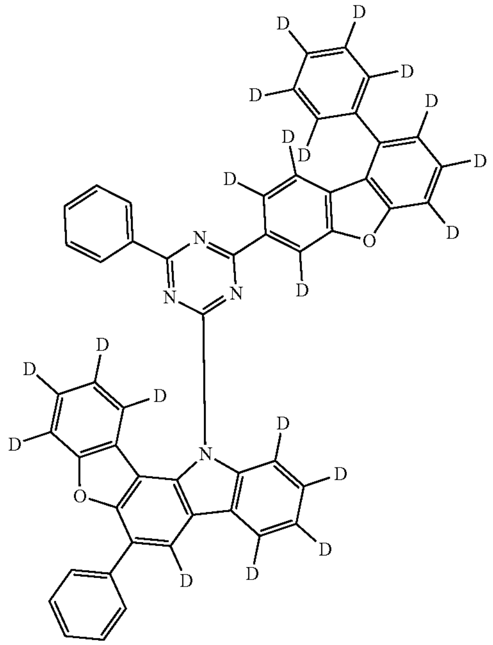
[E-62]
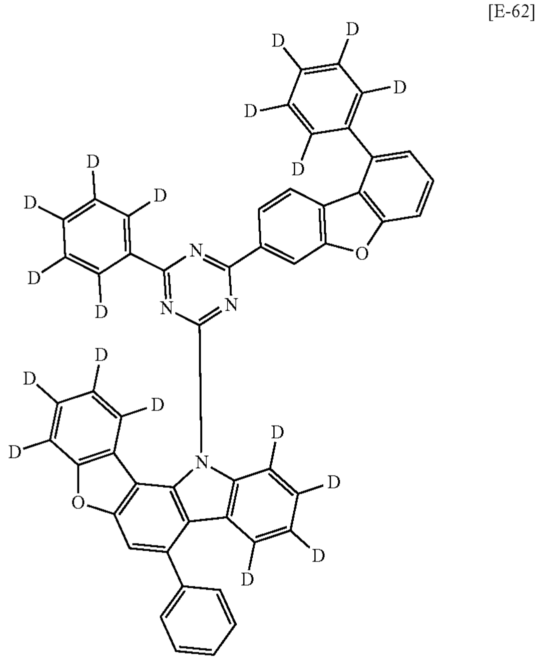
-continued
[E-63]
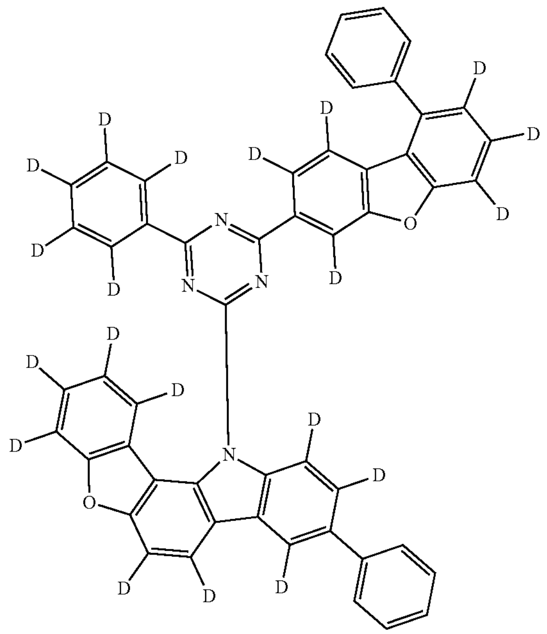
[E-64]
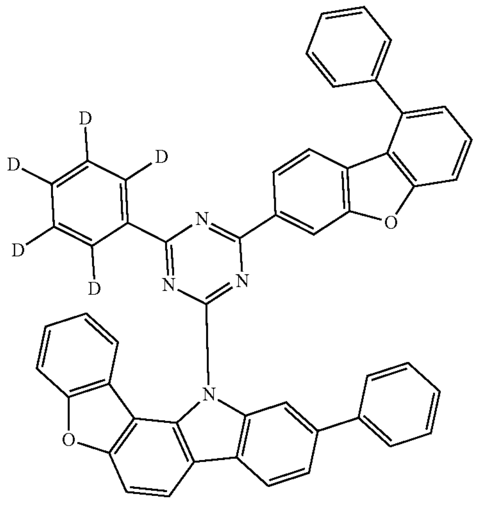

-continued
[E-65]
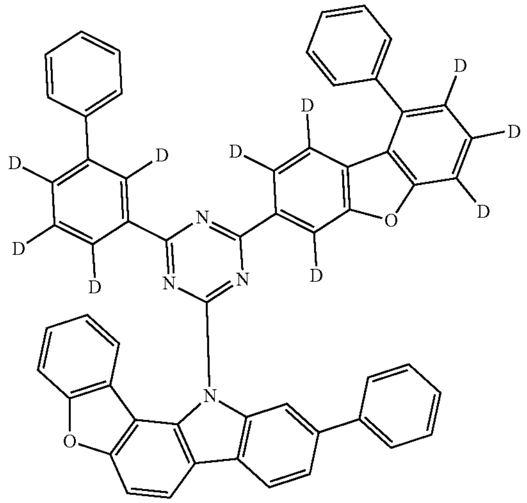
[E-66]
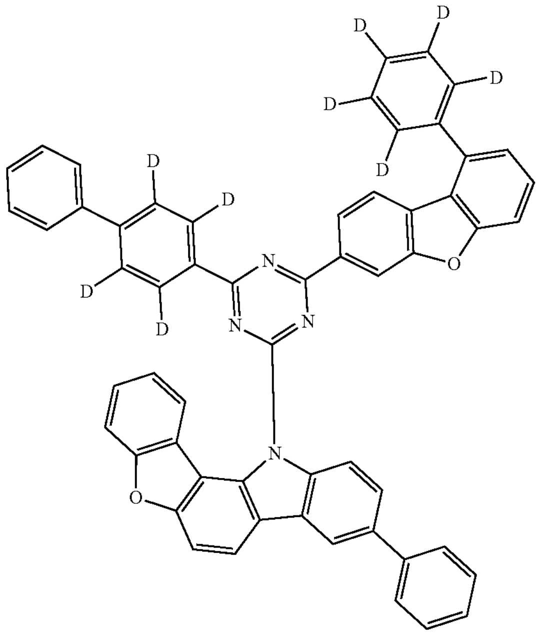
-continued
[E-67]
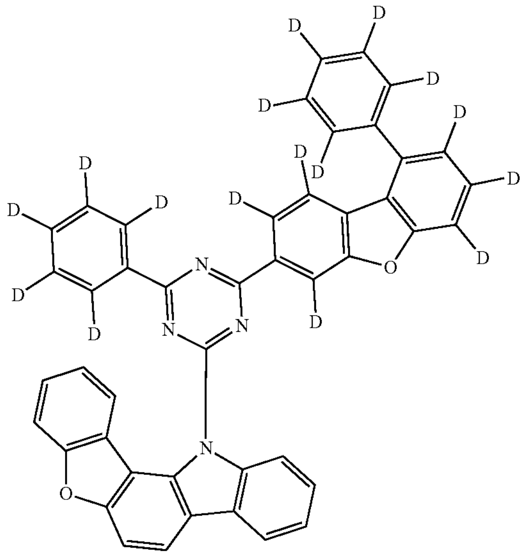
[E-68]
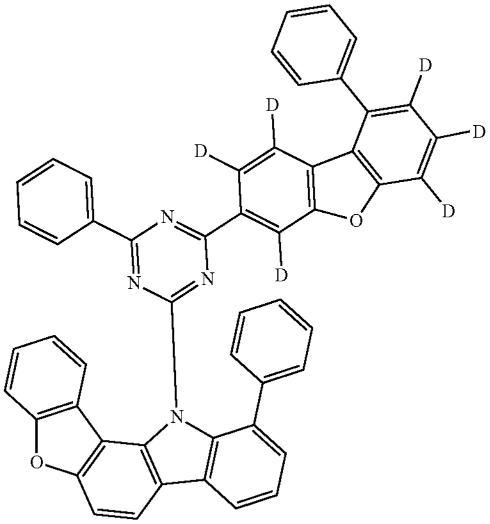

-continued
[E-69]
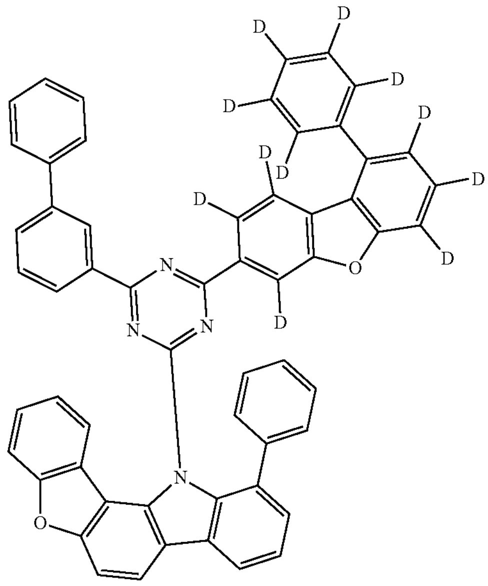
[E-70]
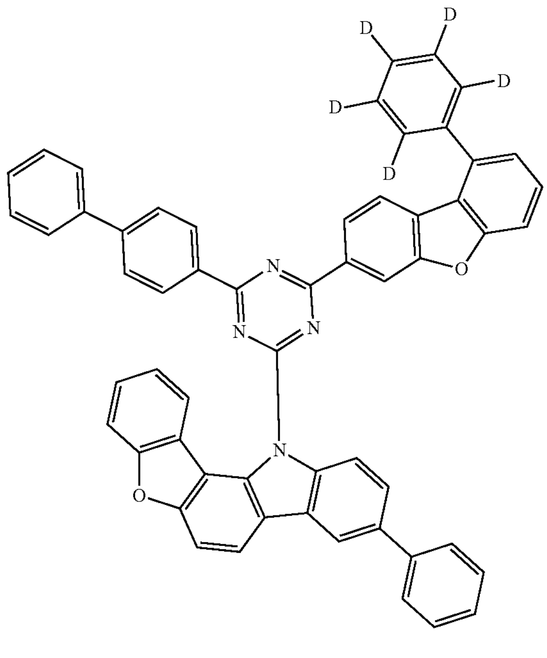
-continued
[E-71]
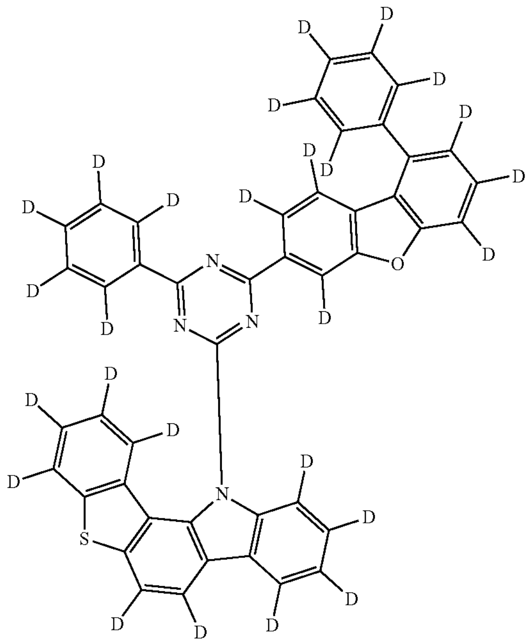
[E-72]
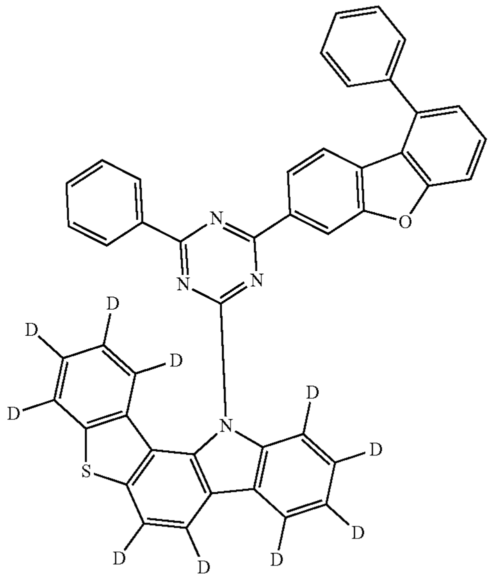

-continued
[E-73]
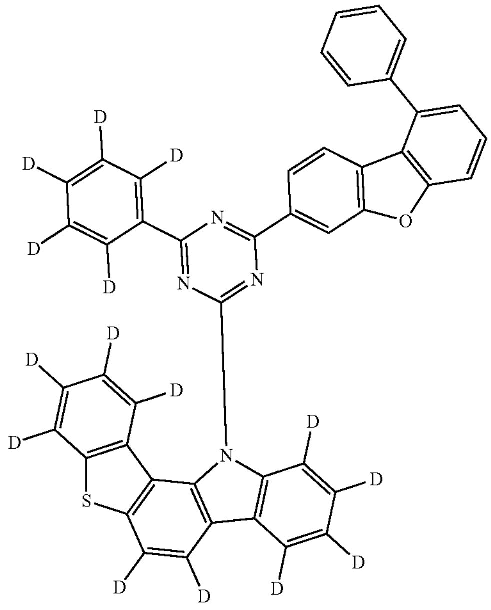
[E-74]
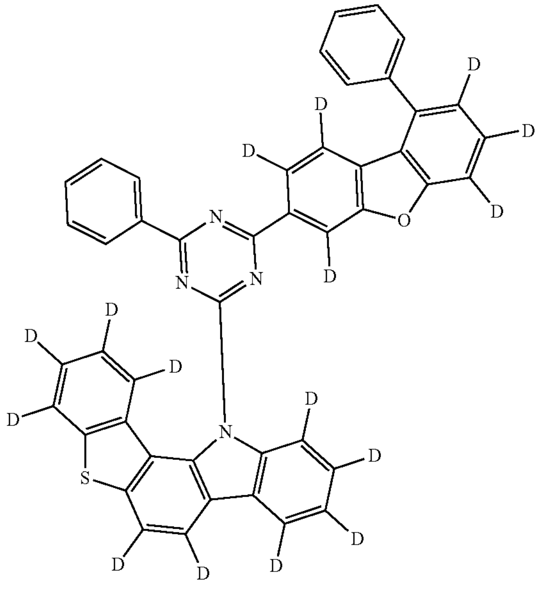
-continued
[E-75]
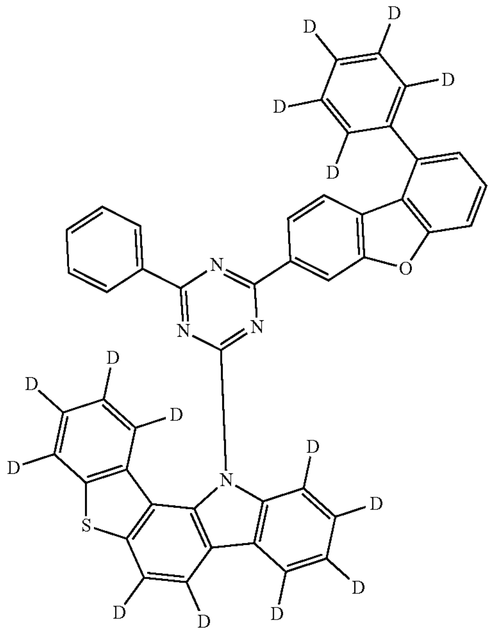
[E-76]
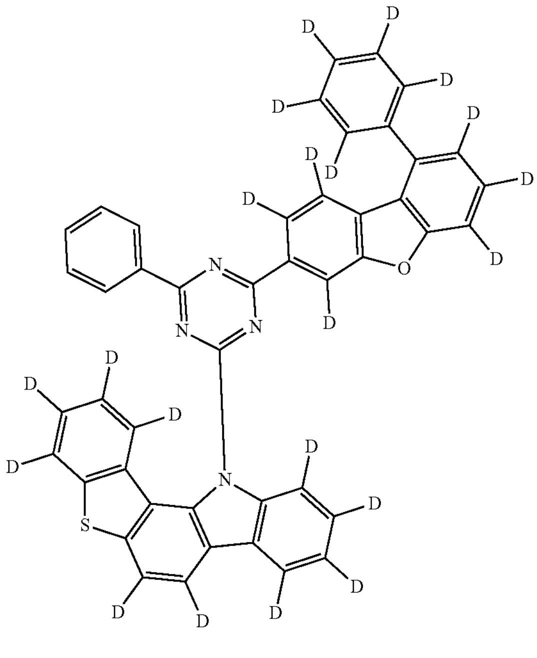

-continued
[E-77]
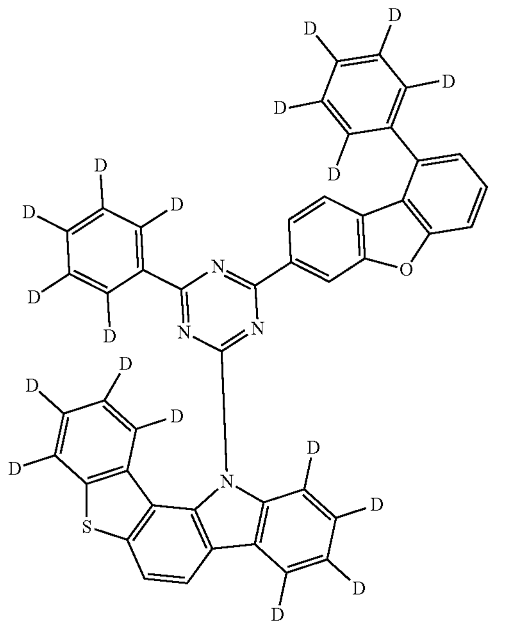
[E-78]
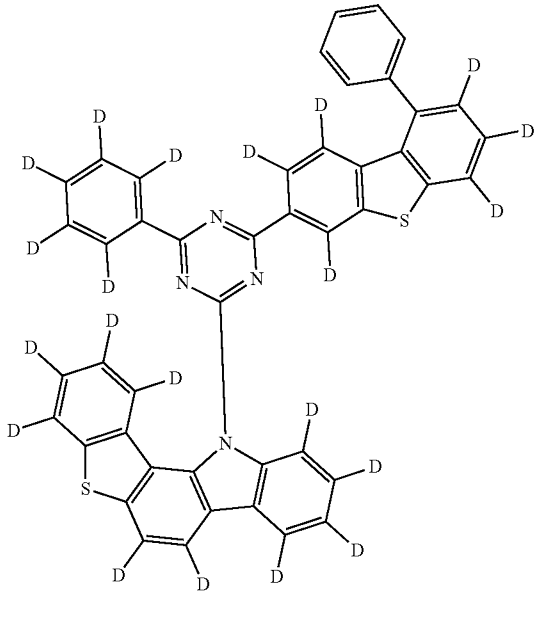
-continued
[E-79]
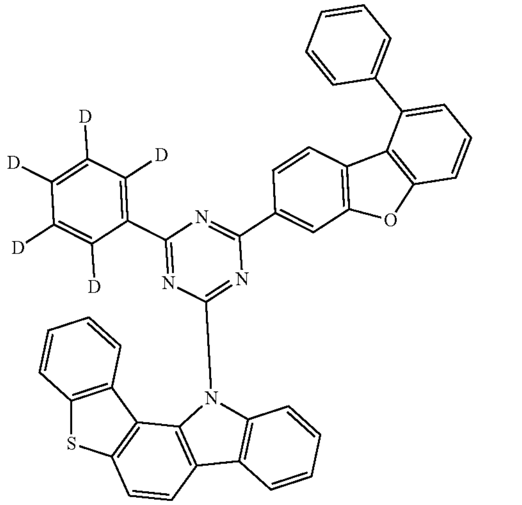
[E-80]
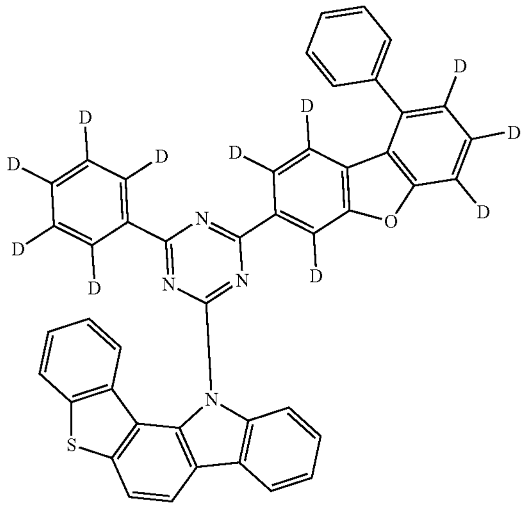
[E-81]
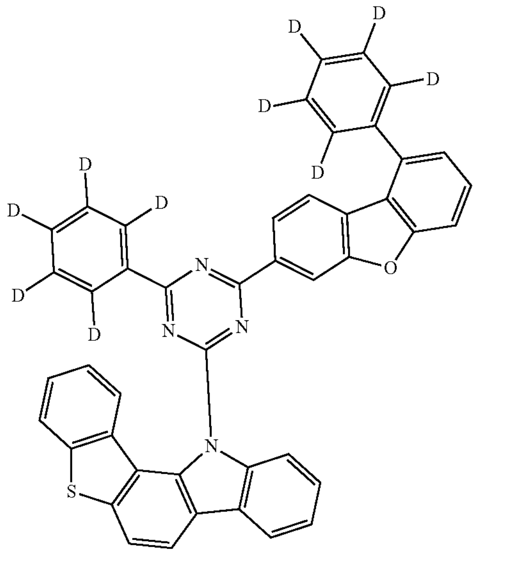

-continued
[E-82]
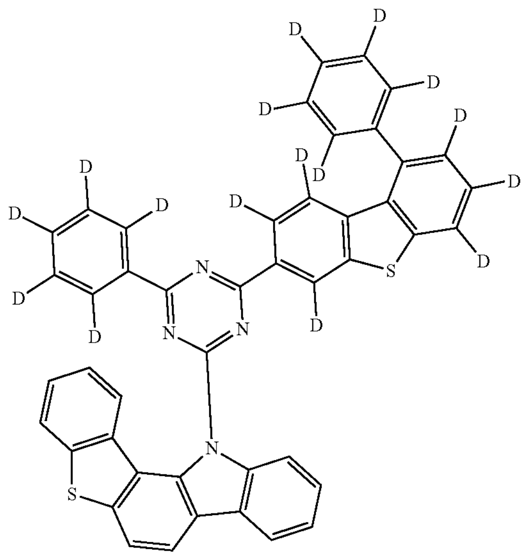
[E-83]
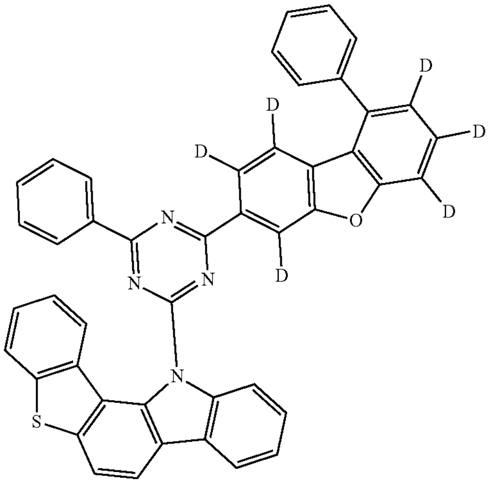
[E-84]
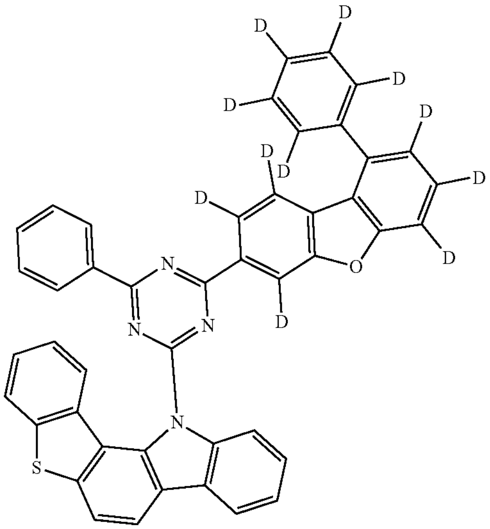
-continued
[E-85]
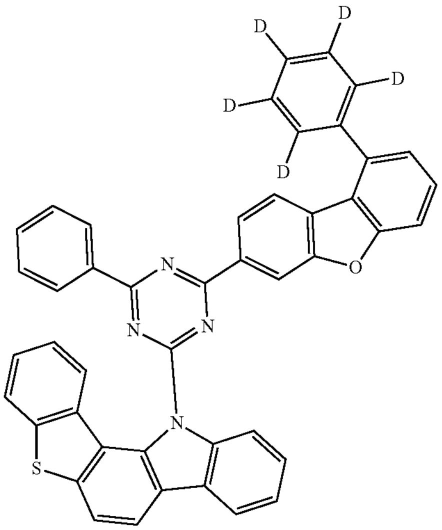
[E-86]
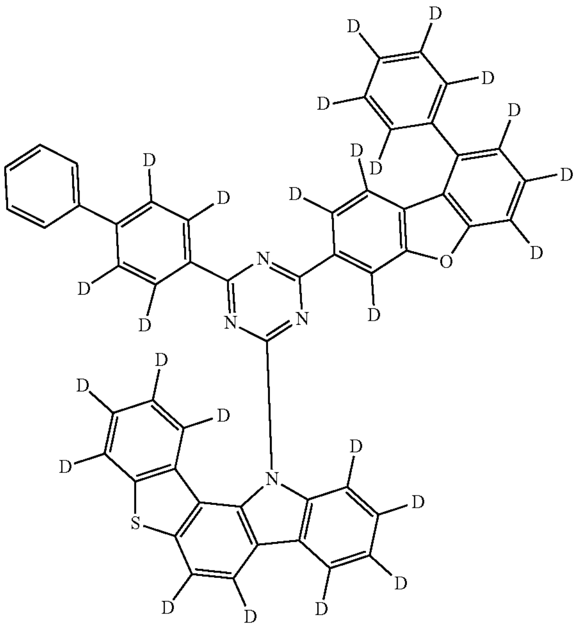

-continued
[E-87]
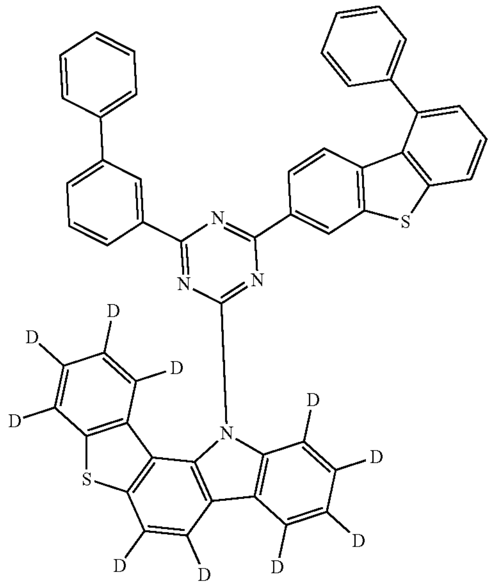
[E-88]
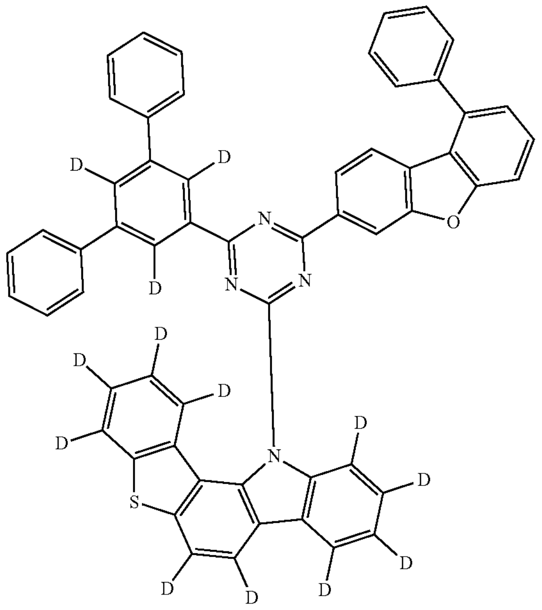
-continued
[E-89]
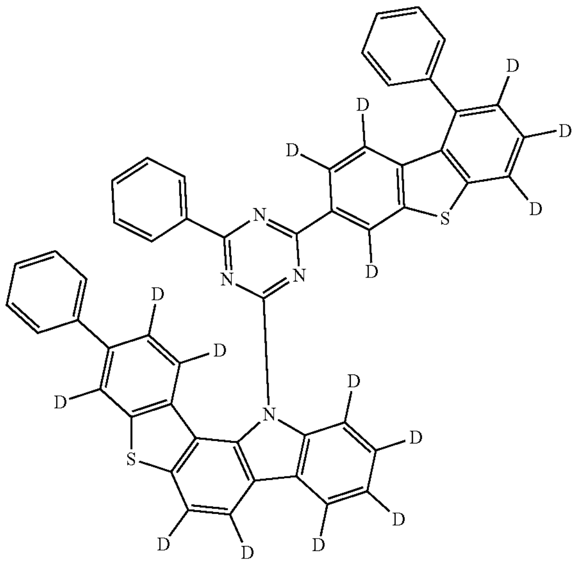
[E-90]
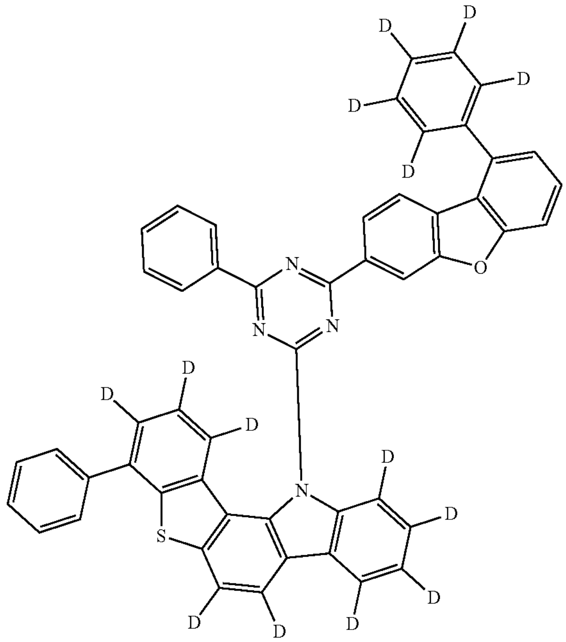

-continued
[E-91]
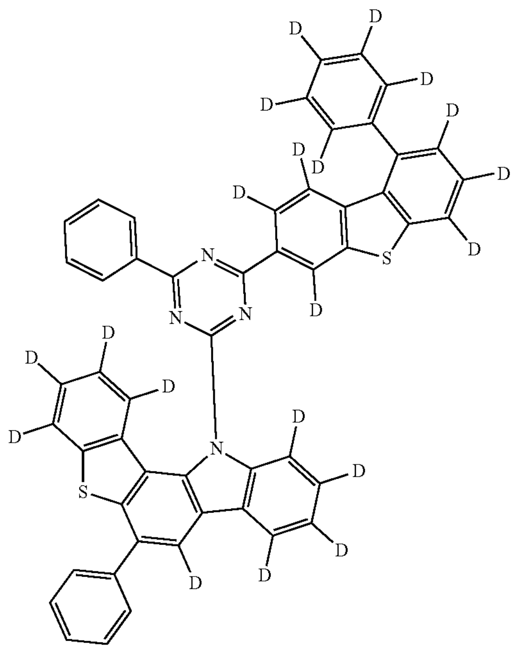
[E-92]
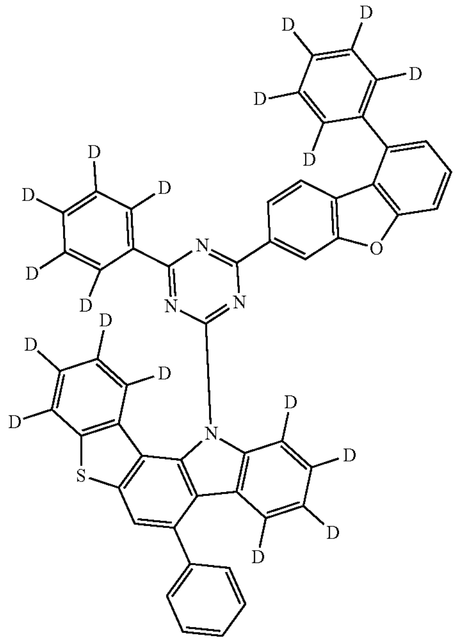
-continued
[E-93]
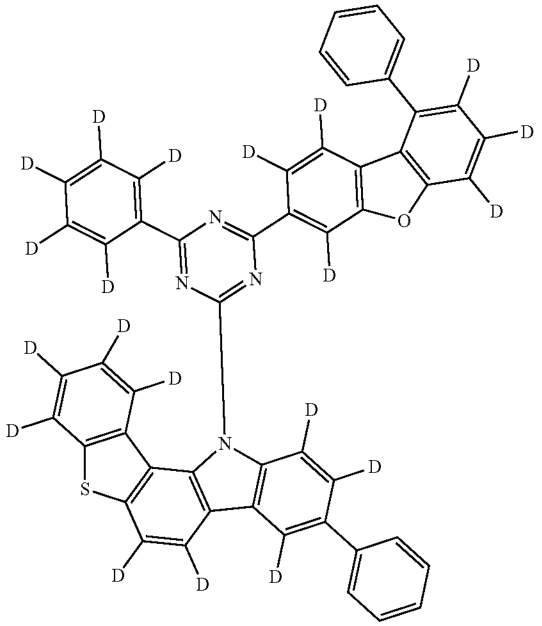
[E-94]
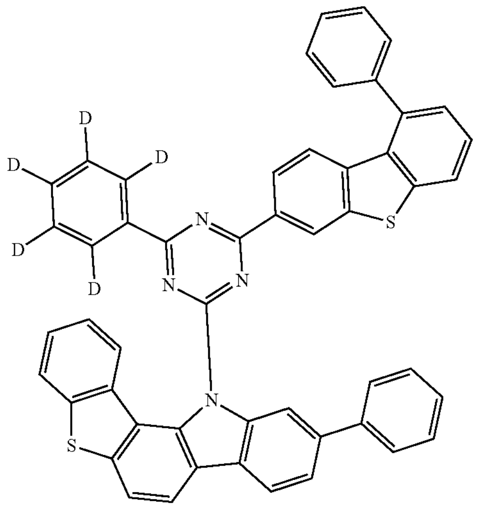

-continued
[E-95]
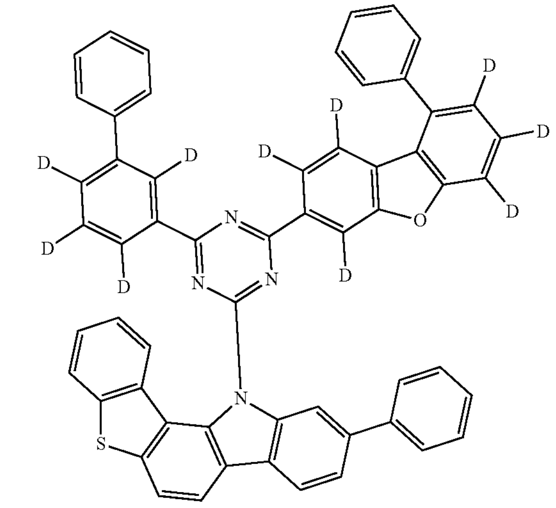
[E-96]
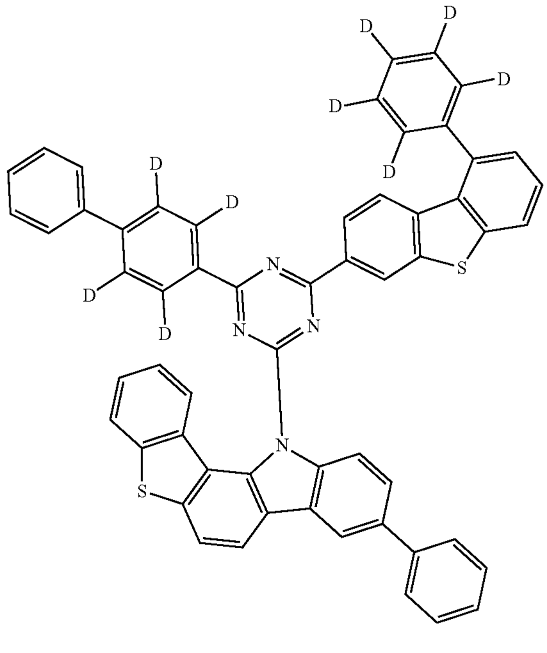
-continued
[E-97]
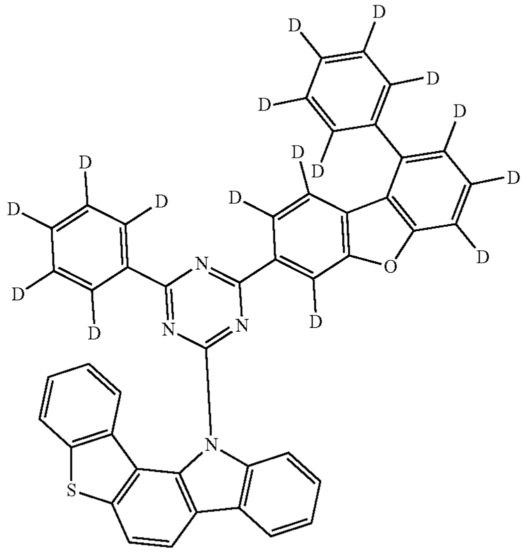
[E-98]
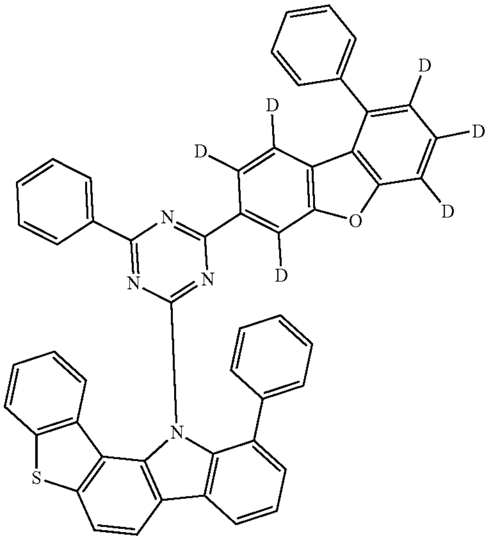

-continued
[E-99]
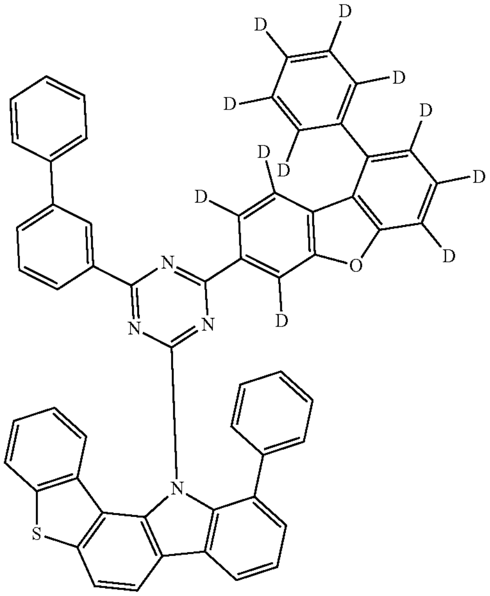
[E-100]
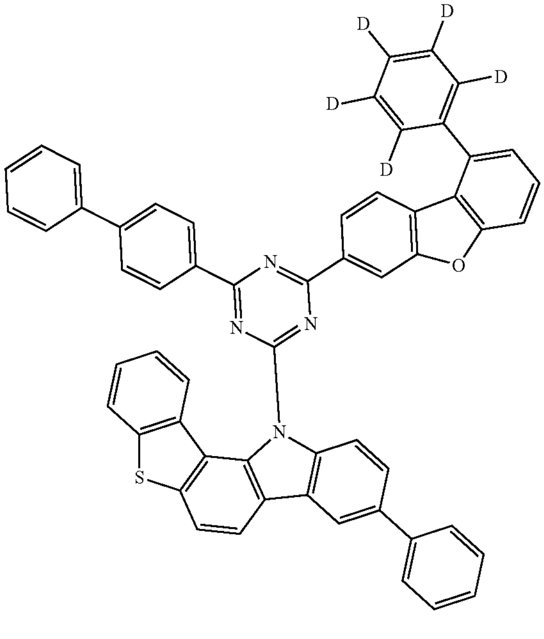
[F-1]
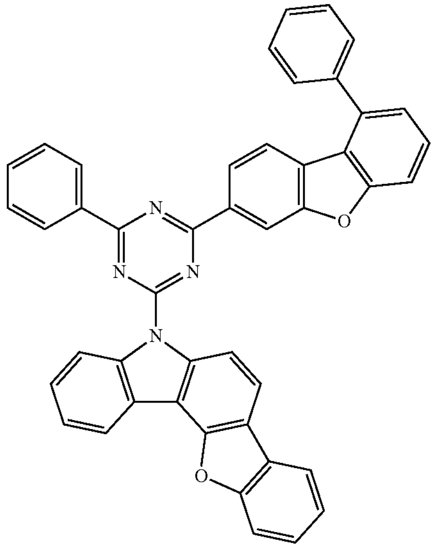
[F-2]
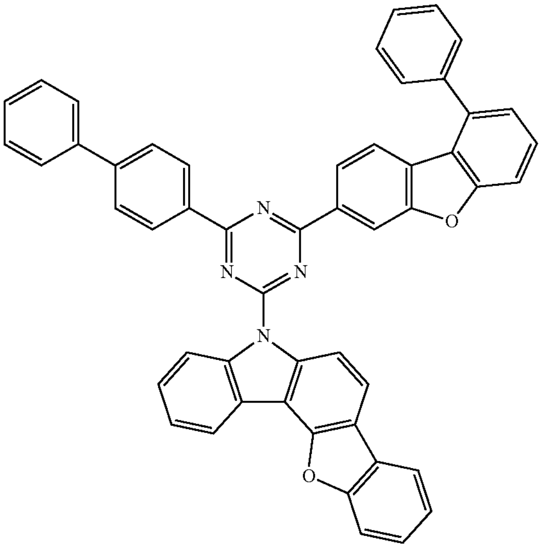
[F-3]
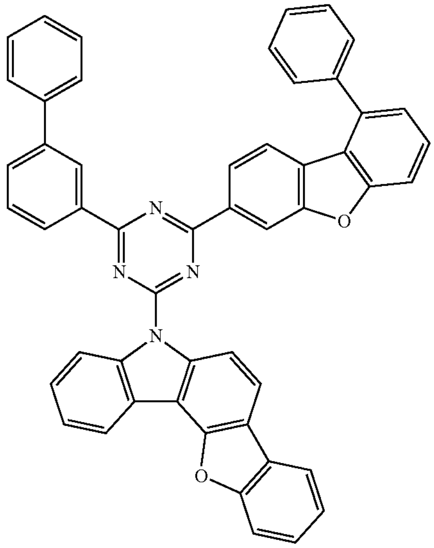

-continued
[F-4]
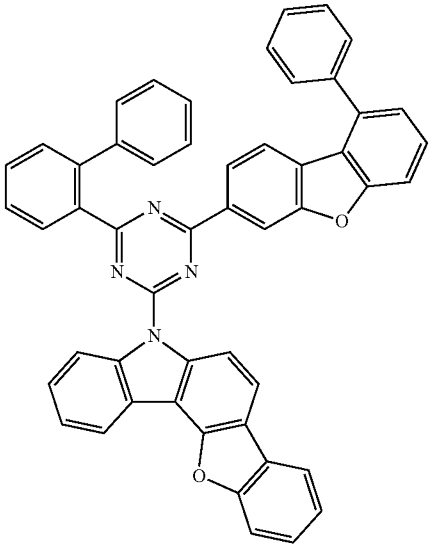
[F-5]
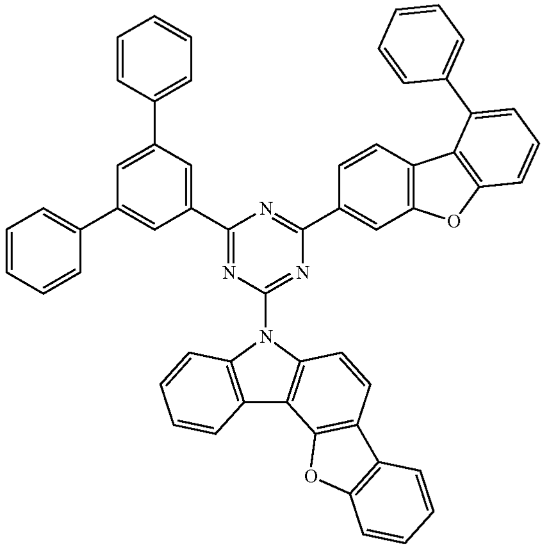
[F-6]
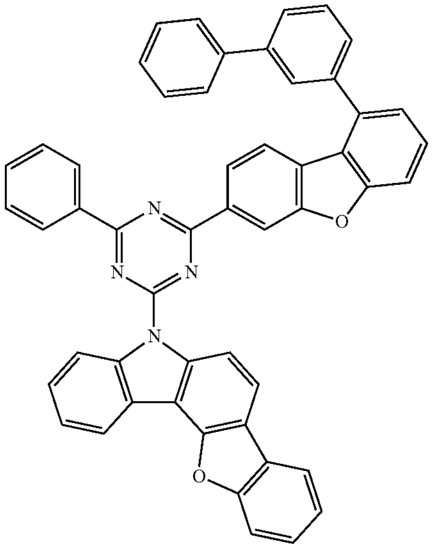
-continued
[F-7]
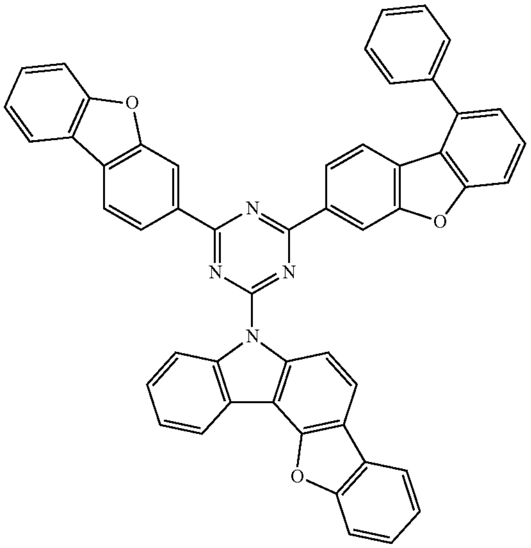
[F-8]
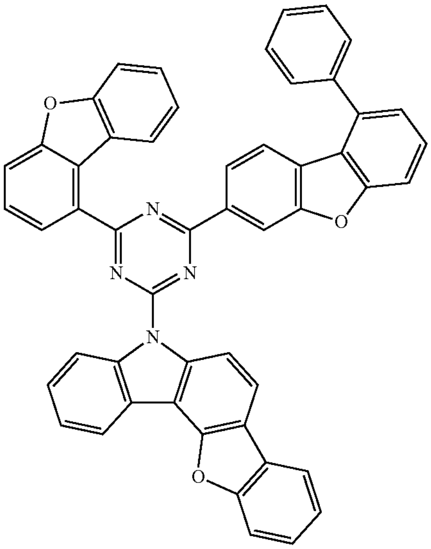

-continued
[F-9]
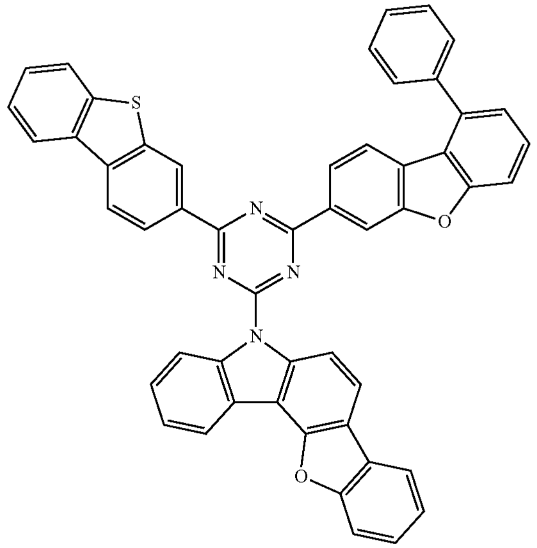
-continued
[F-11]
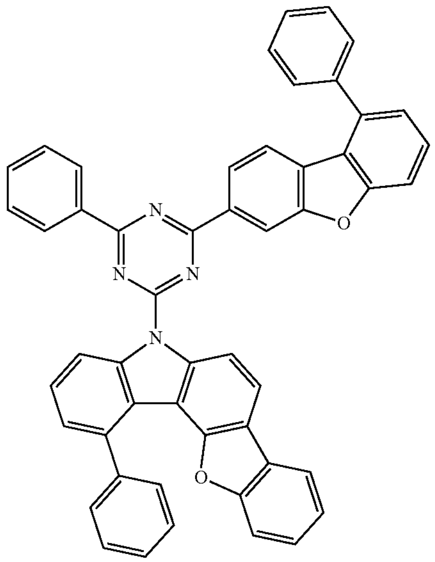
[F-10]
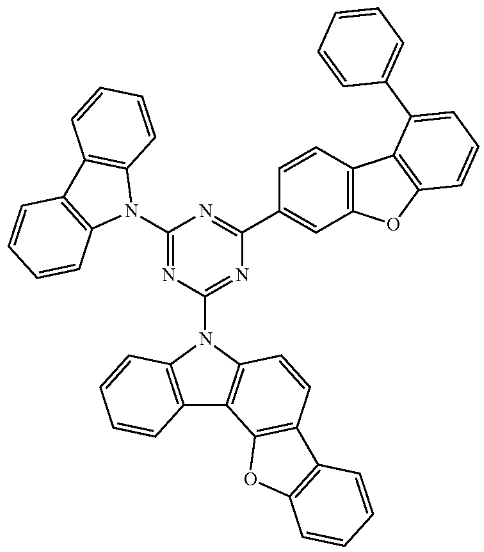
[F-12]
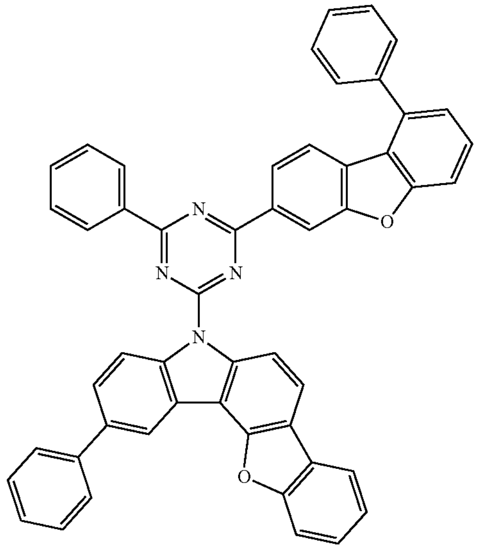

-continued
[F-13]
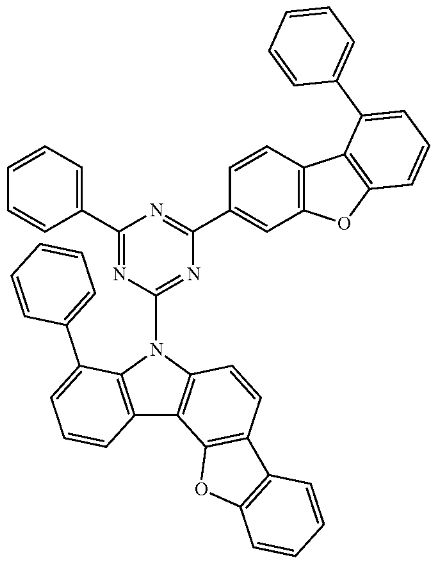
[F-14]
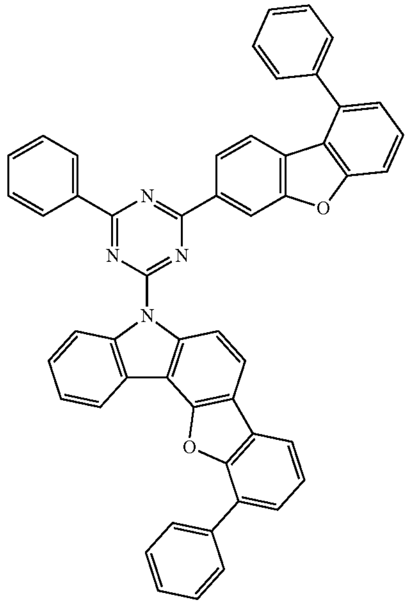
-continued
[F-15]
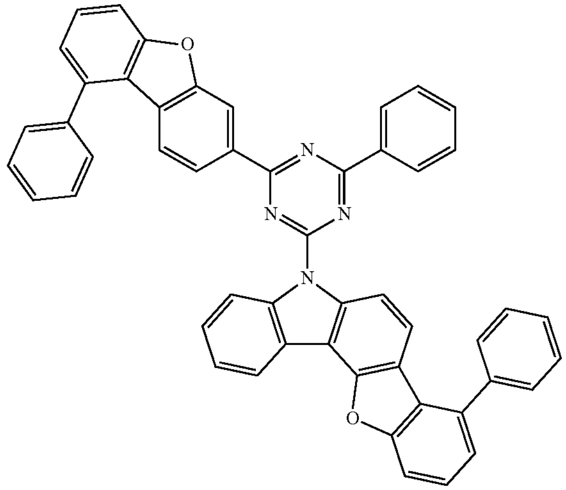
[F-16]
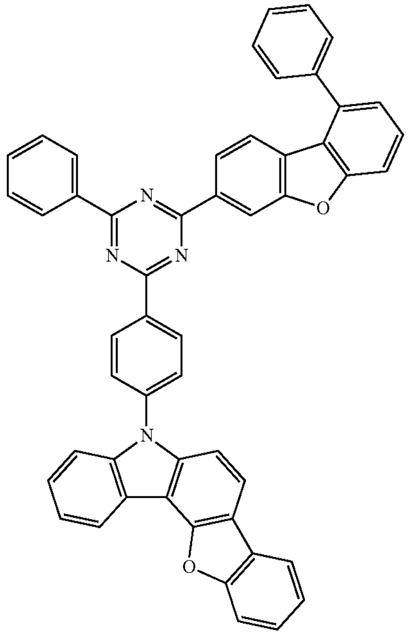

-continued
[F-17]
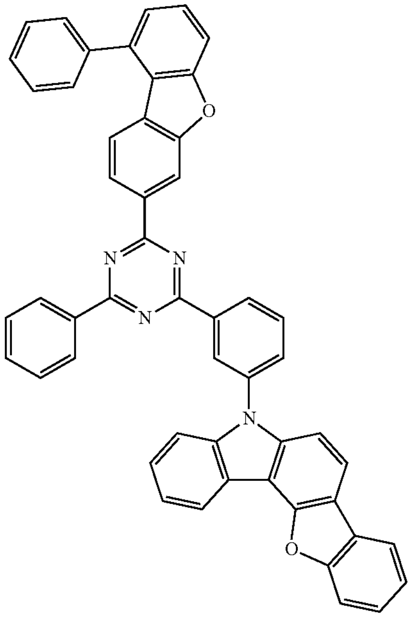
[F-18]
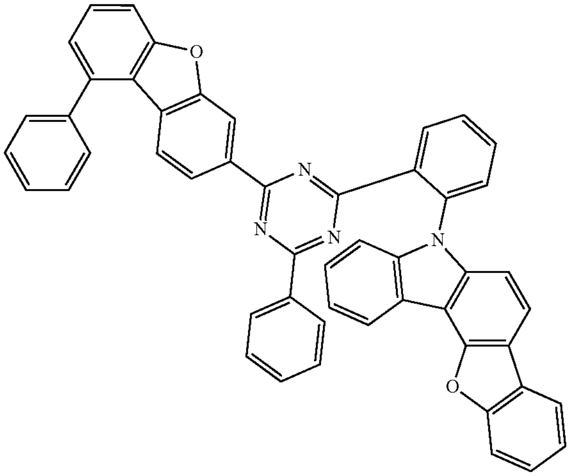
-continued
[F-19]
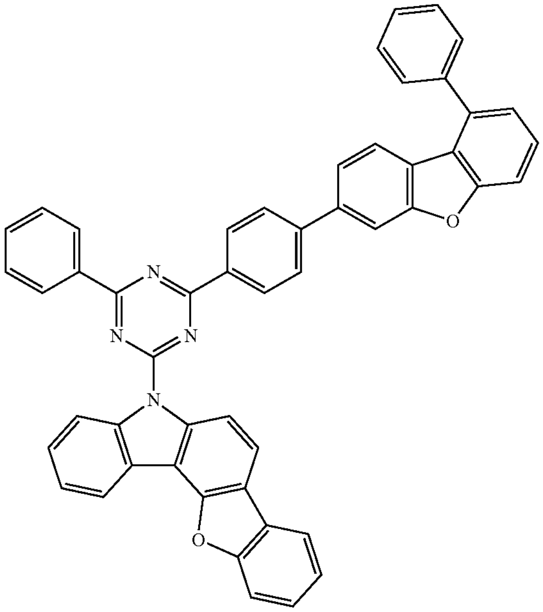
[F-20]
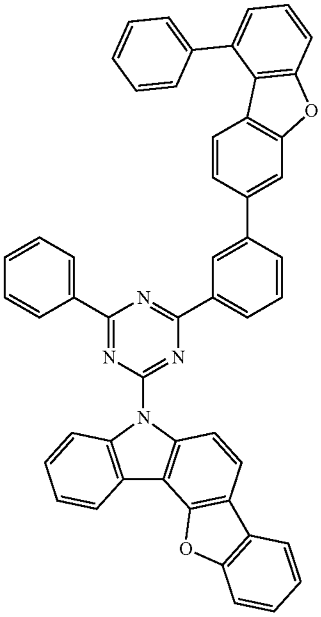

-continued
[F-21]
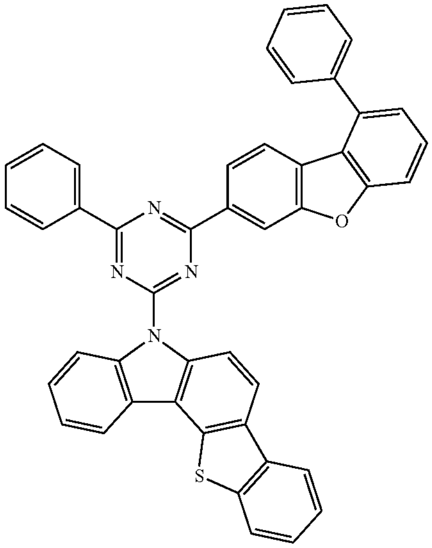
[F-22]
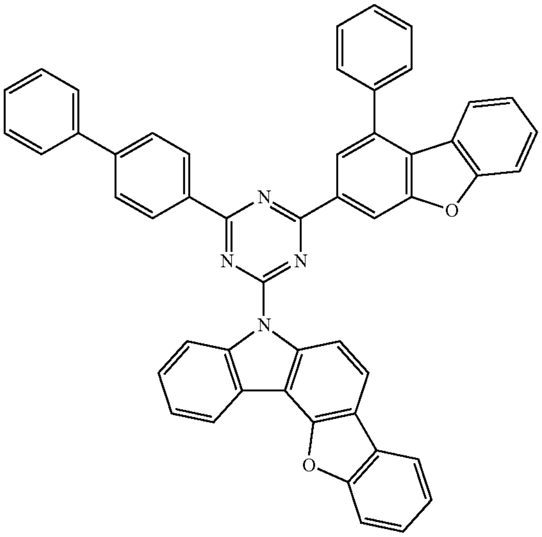
[F-23]
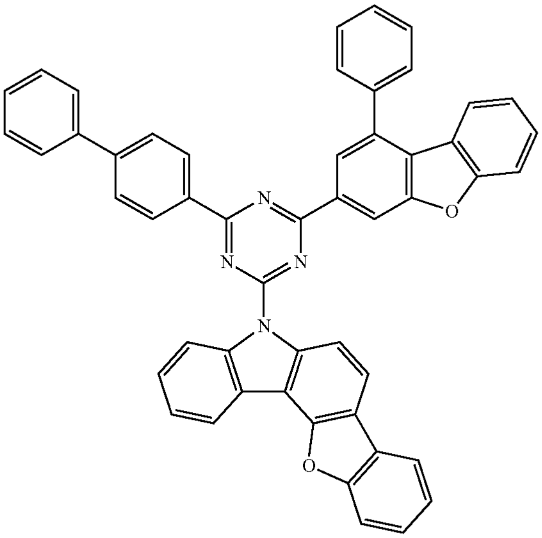
-continued
[F-24]
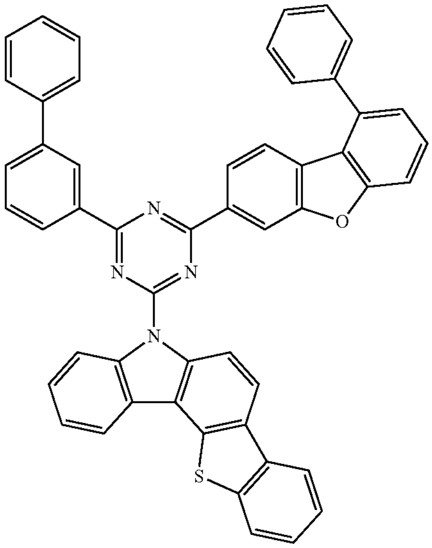
[F-25]
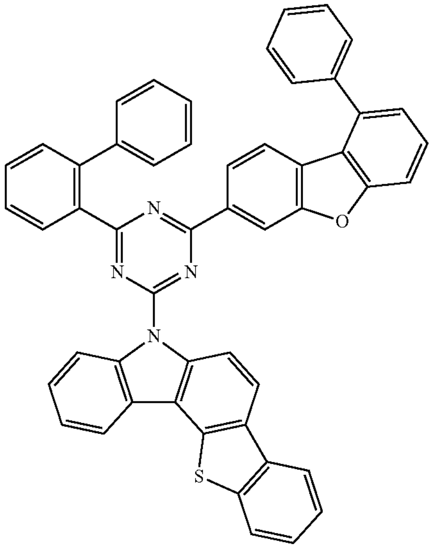
[F-26]
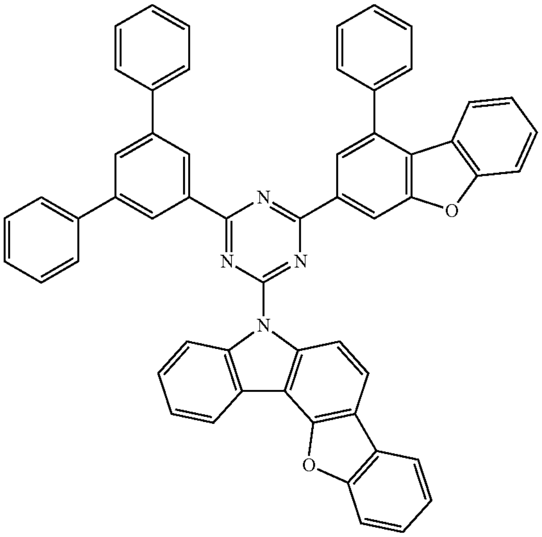

-continued
[F-27]
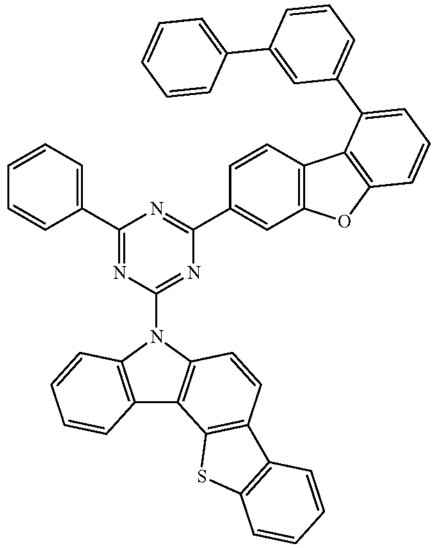
[F-28]
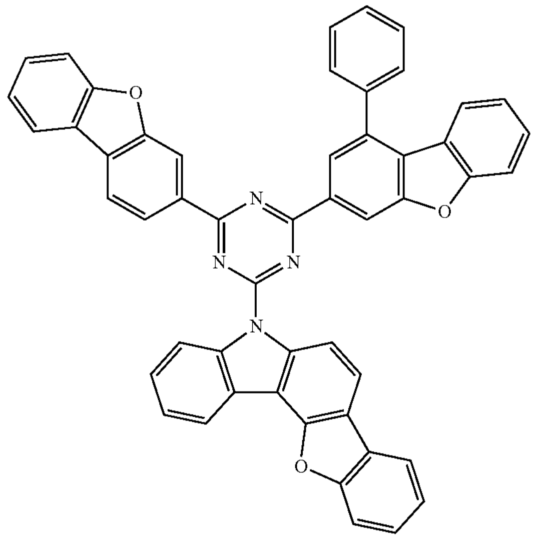
[F-29]
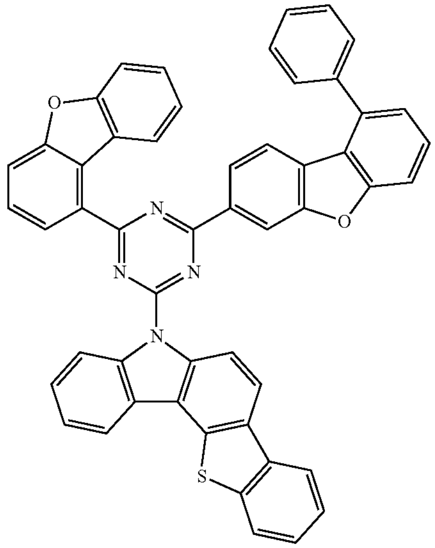
-continued
[F-30]
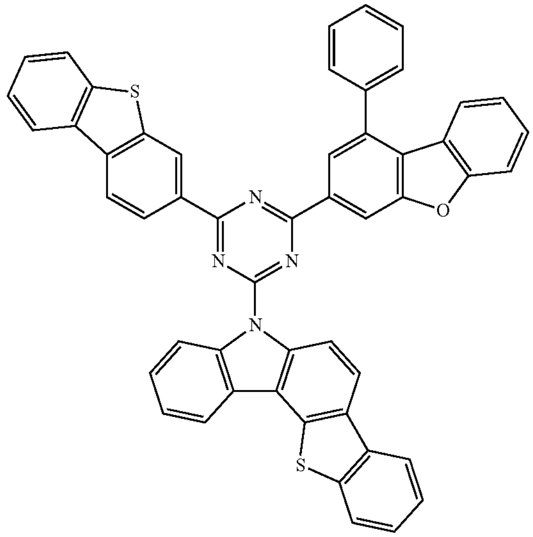
[F-31]
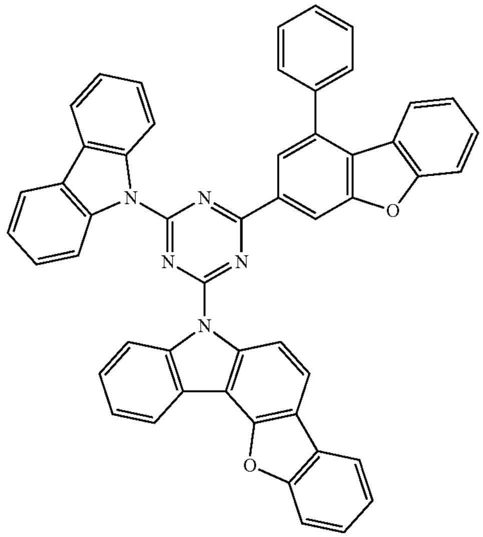

-continued
[F-32]
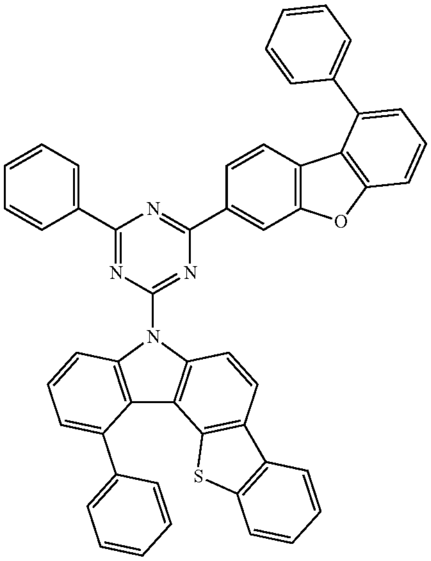
[F-33]
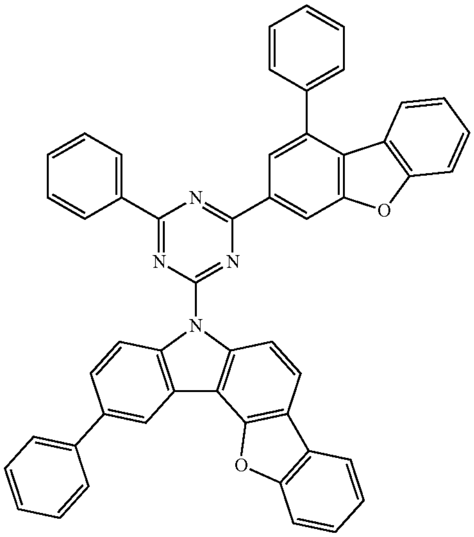
-continued
[F-34]
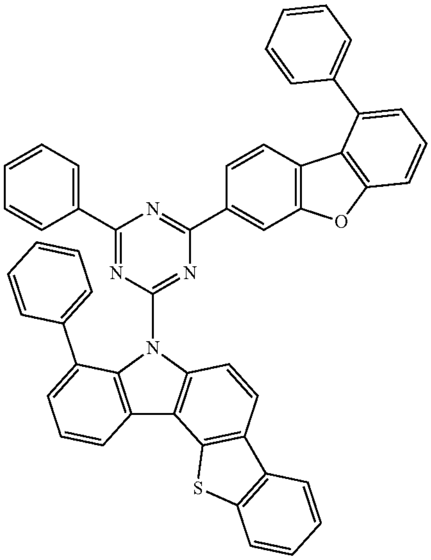
[F-35]
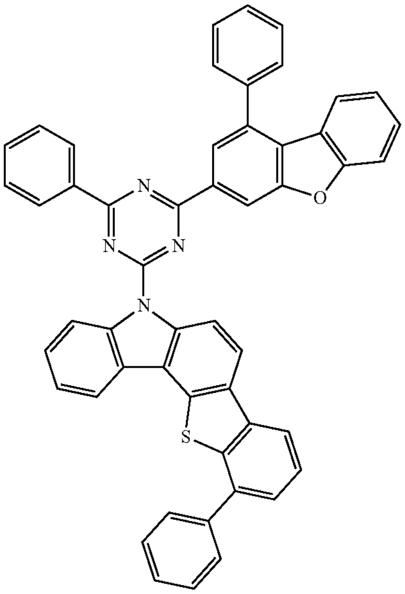
[F-36]
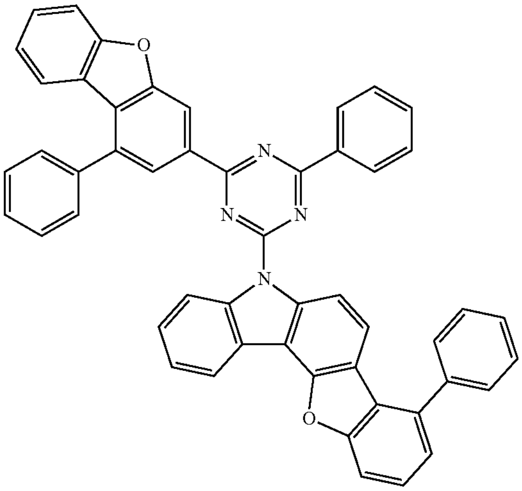

-continued
[F-37]
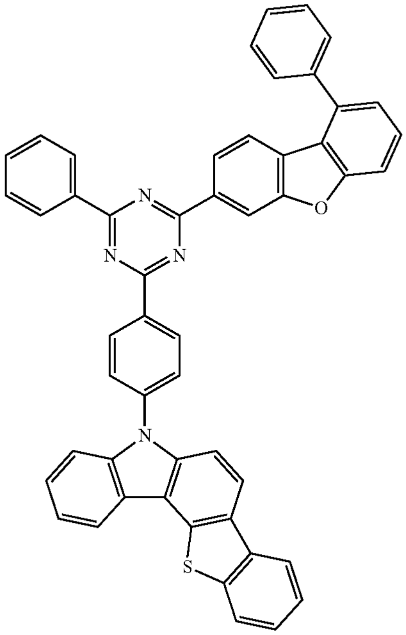
[F-38]
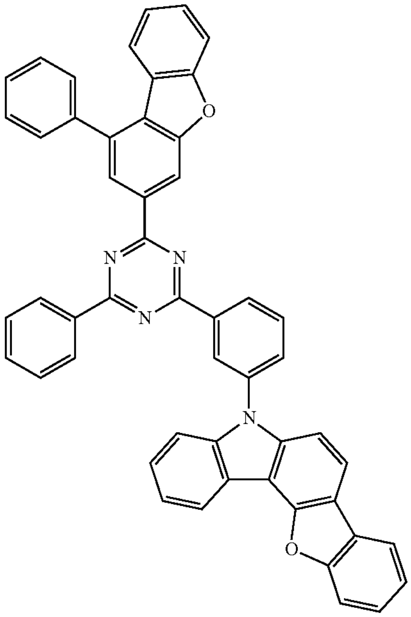
-continued
[F-39]
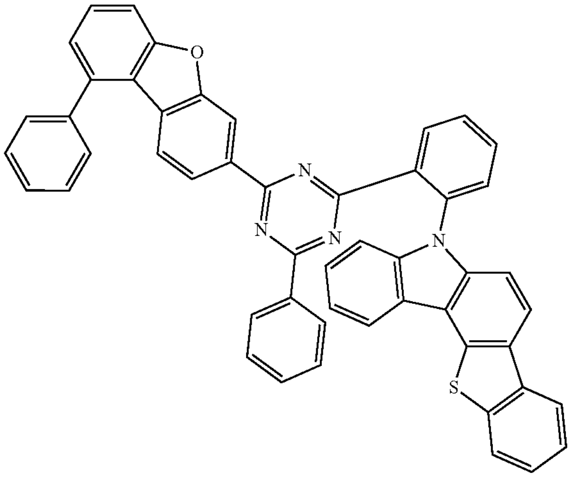
[F-40]
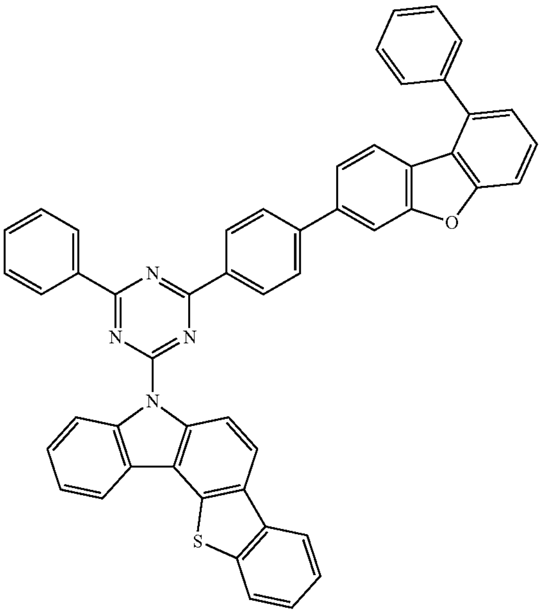

-continued
[F-41]
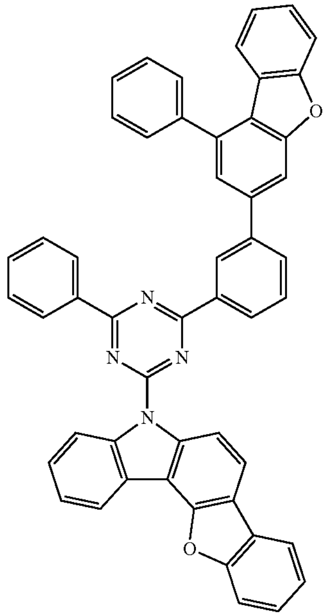
[F-42]
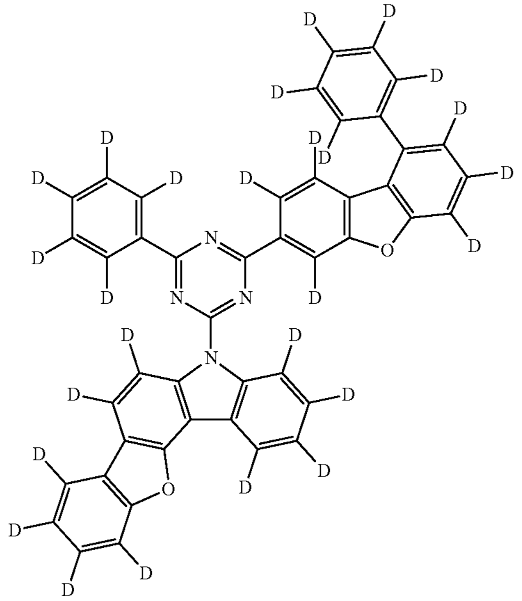
-continued
[F-43]
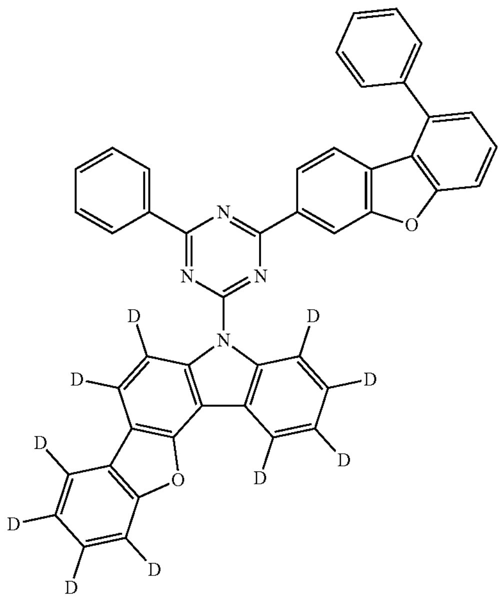
[F-44]
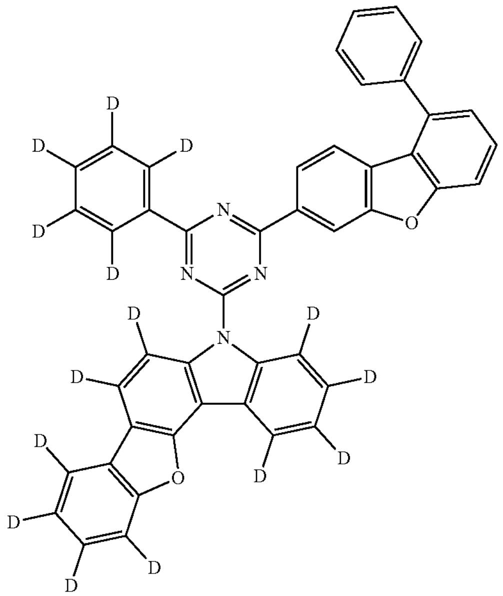

-continued
[F-45]
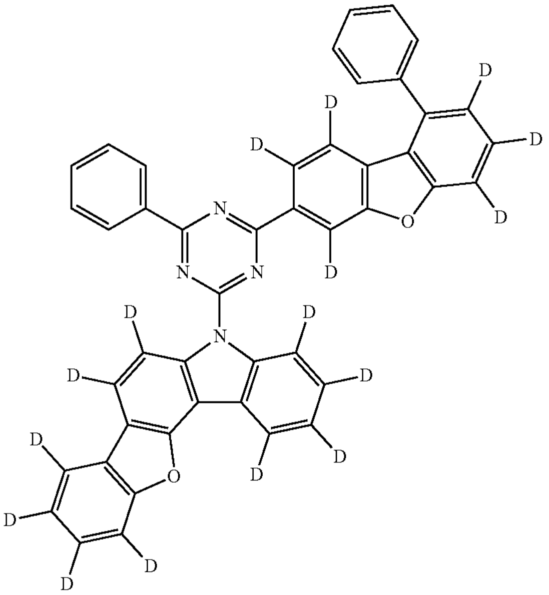
[F-46]
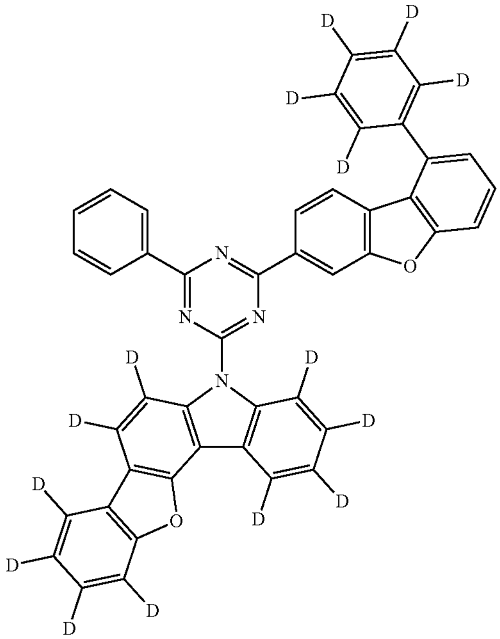
-continued
[F-47]
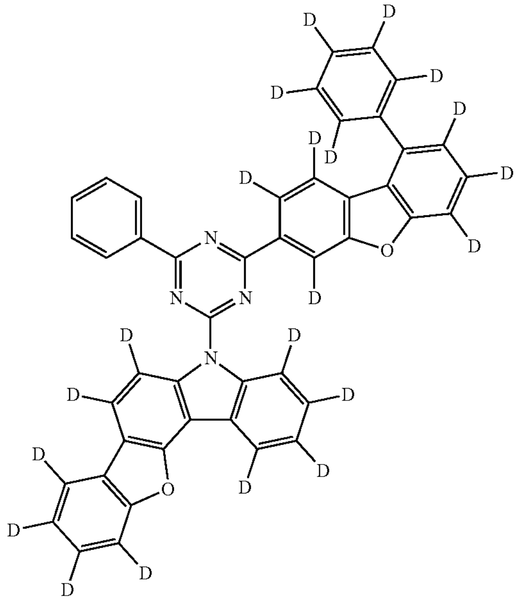
[F-48]
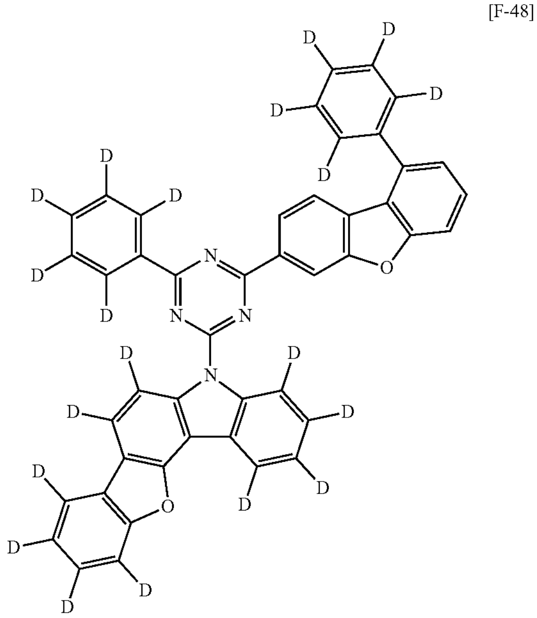

-continued
[F-49]
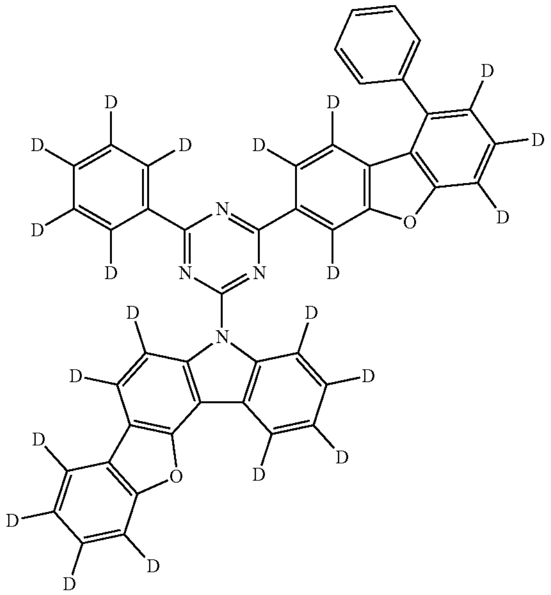
[F-50]
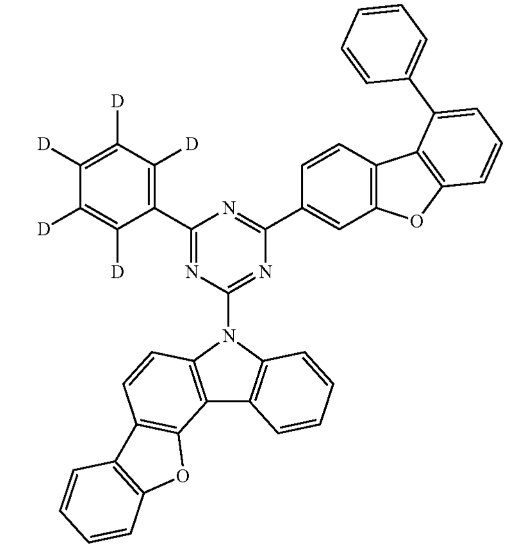
-continued
[F-51]
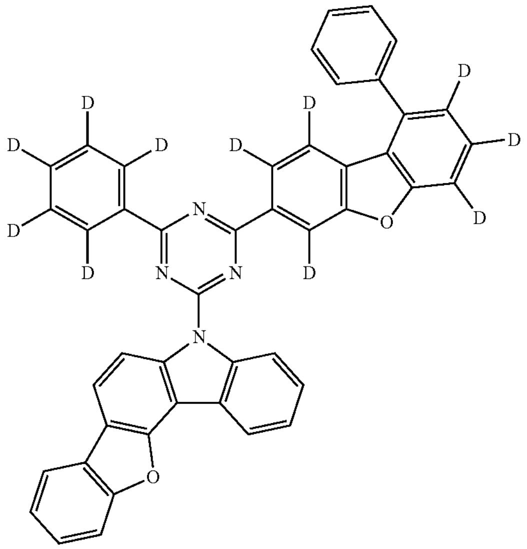
[F-52]
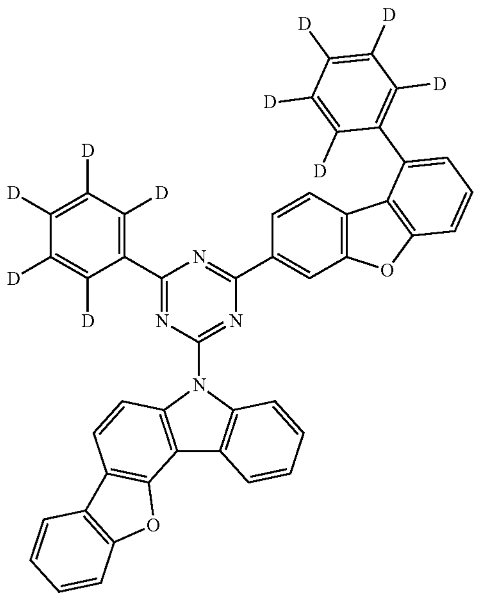

-continued
[F-53]
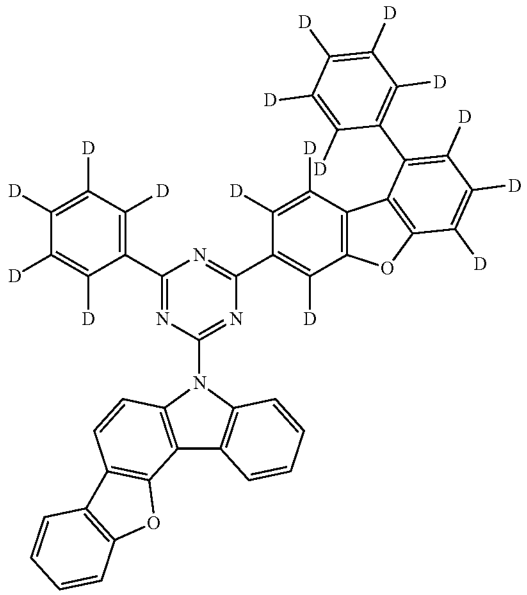
-continued
[F-55]
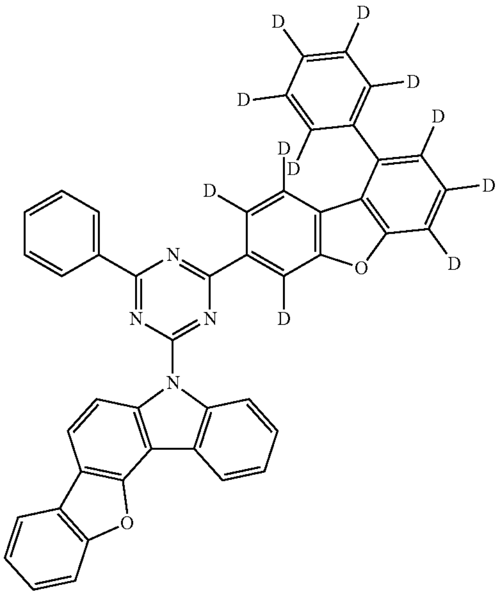
[F-54]
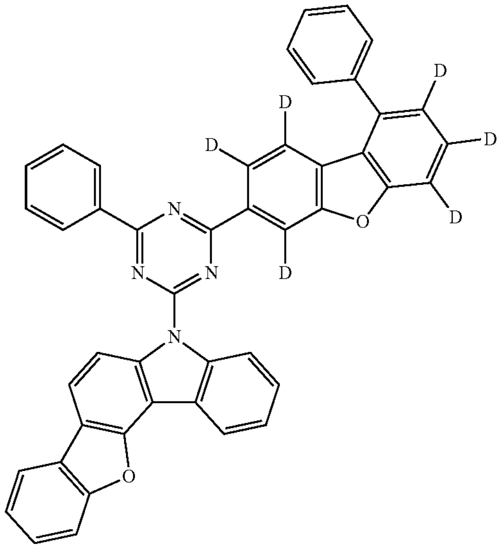
[F-56]
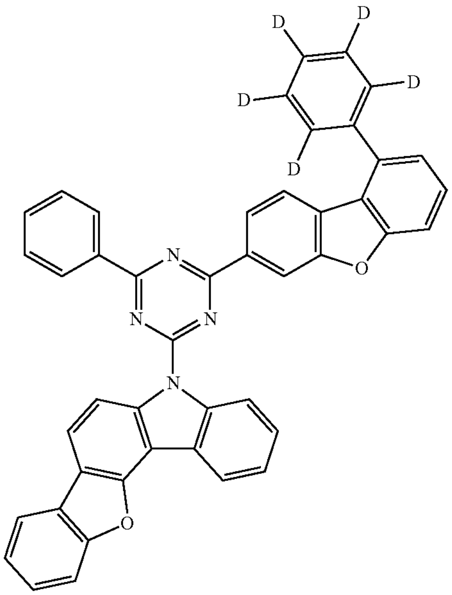

-continued
[F-57]
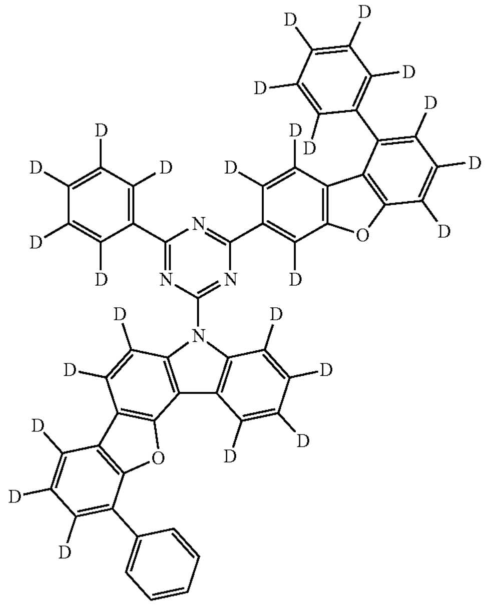
-continued
[F-59]
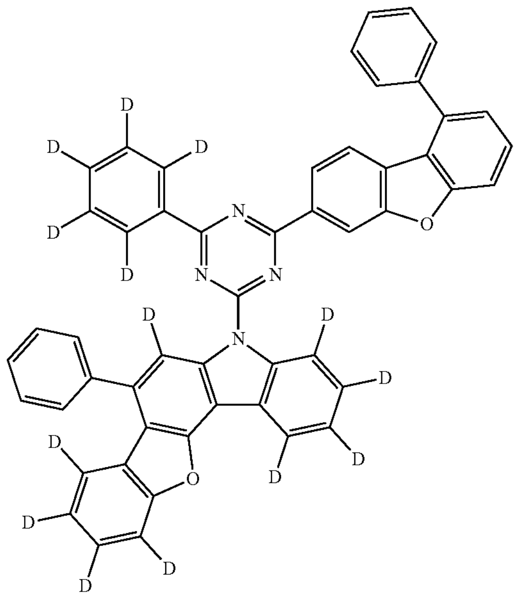
[F-58]
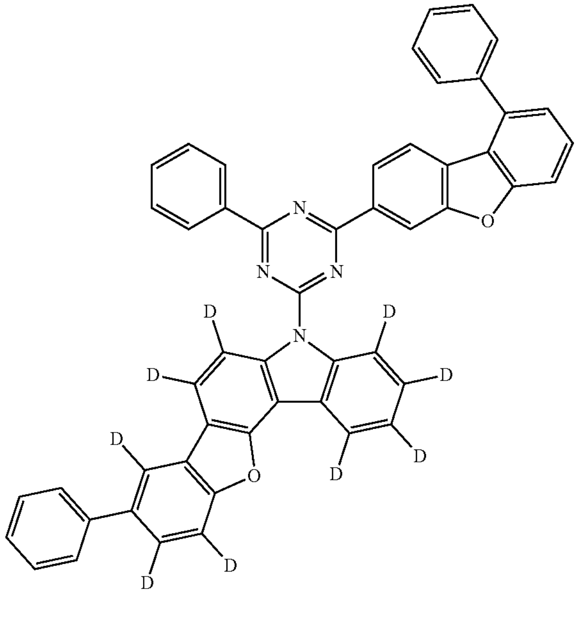
[F-60]
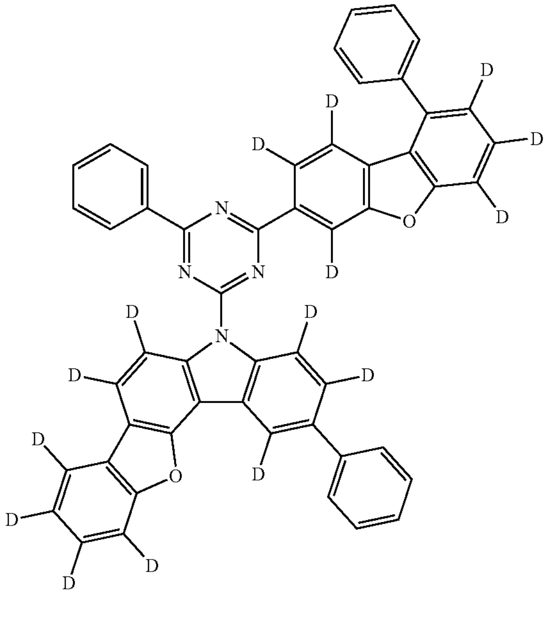

-continued
[F-61]
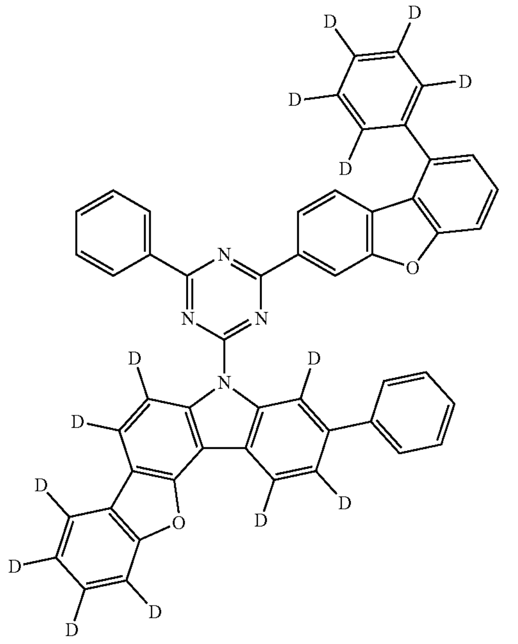
-continued
[F-63]
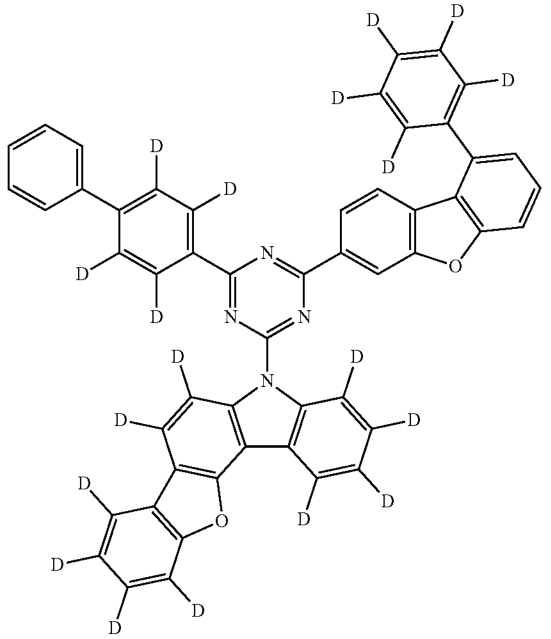
[F-62]
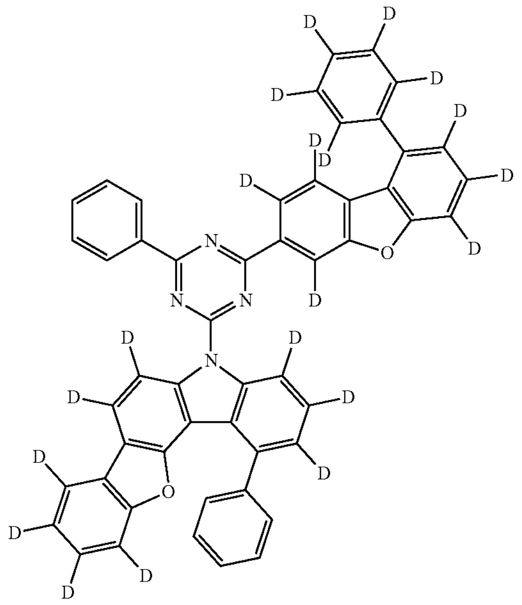
[F-64]
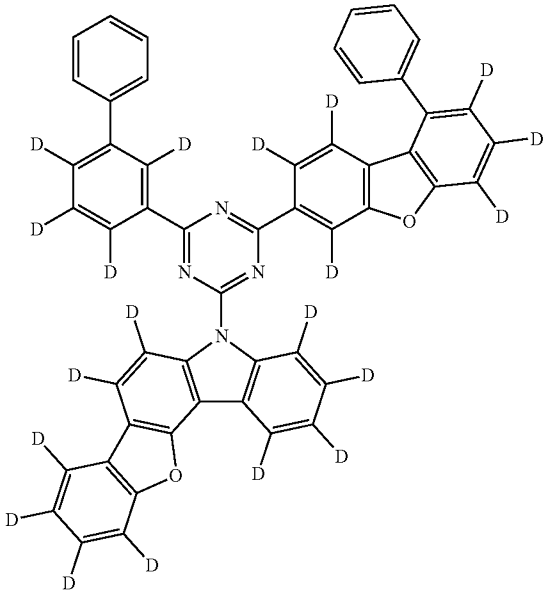

-continued
[F-65]
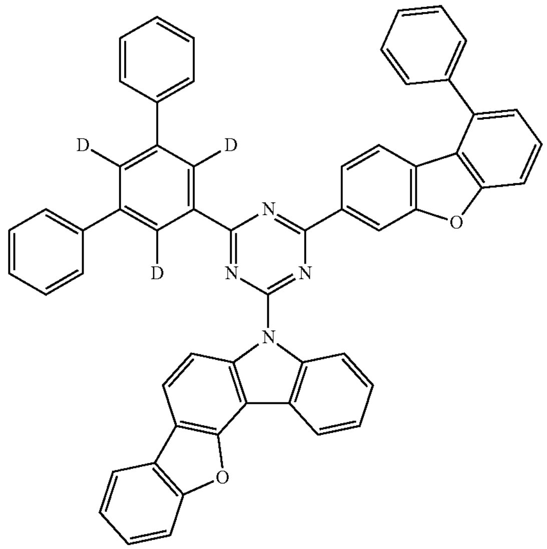
[F-66]
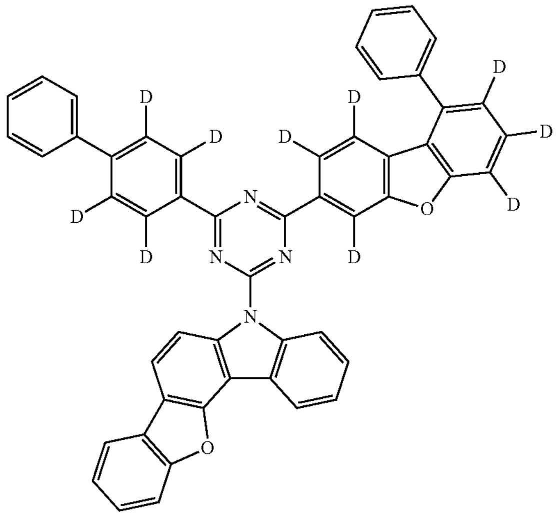
-continued
[F-67]
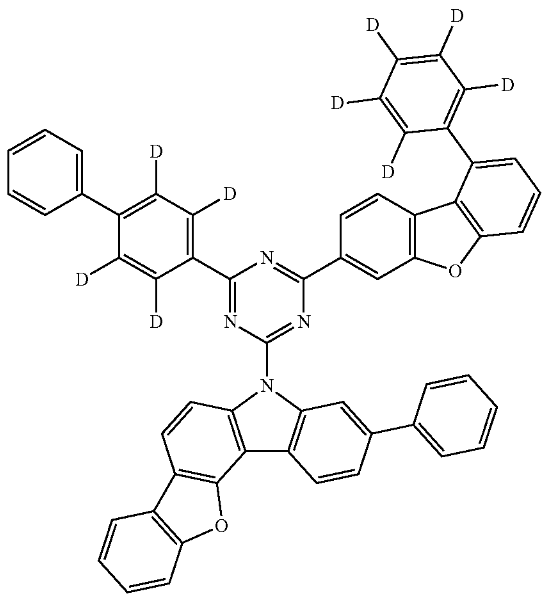
[F-68]
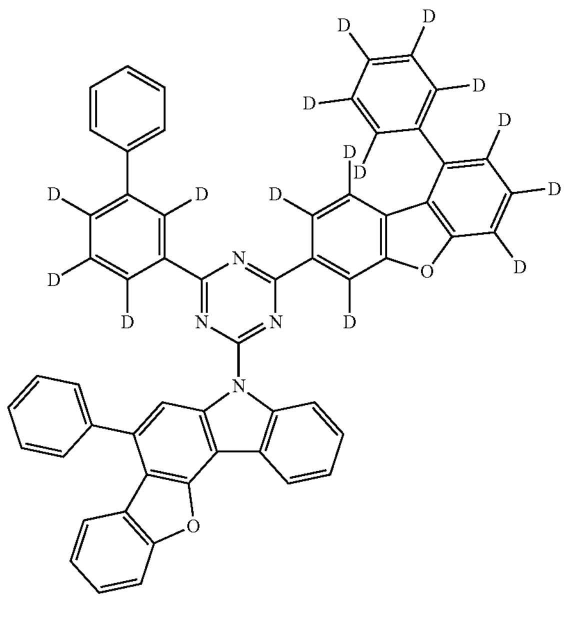

-continued
[F-69]
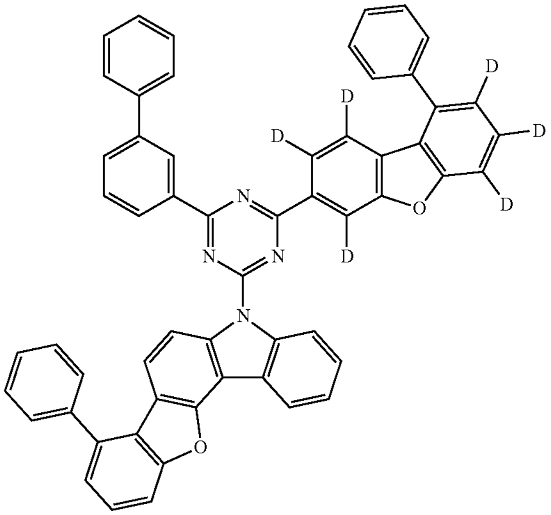
[F-70]
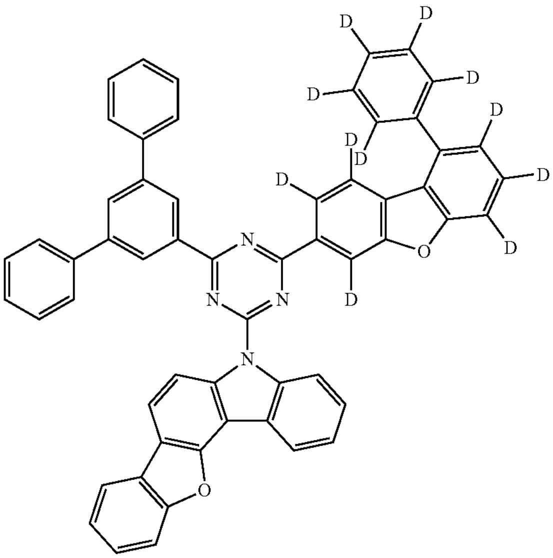
-continued
[F-71]
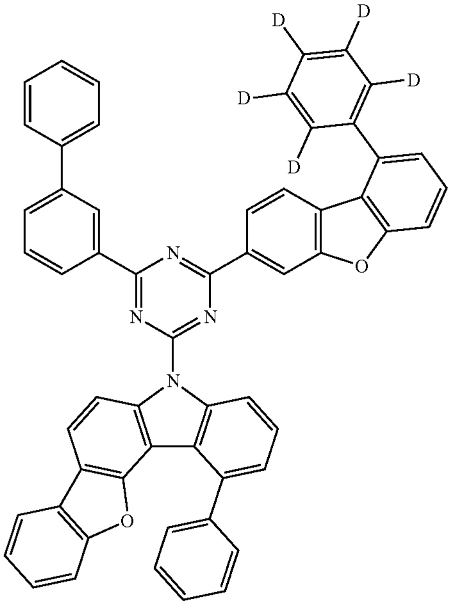
[F-72]
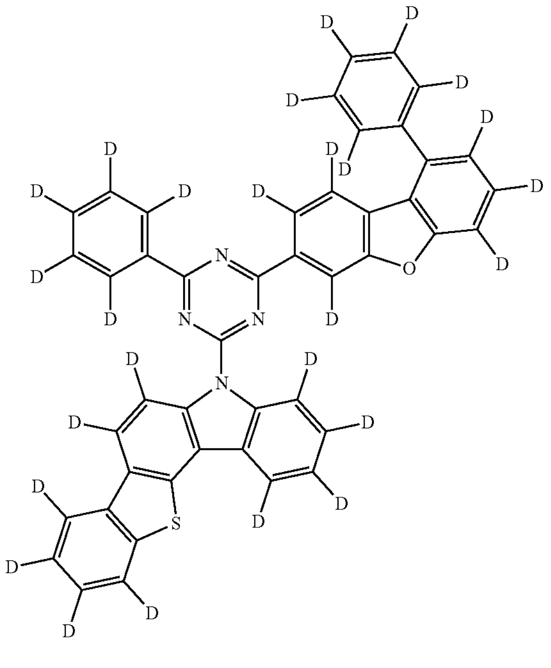

-continued
[F-73]
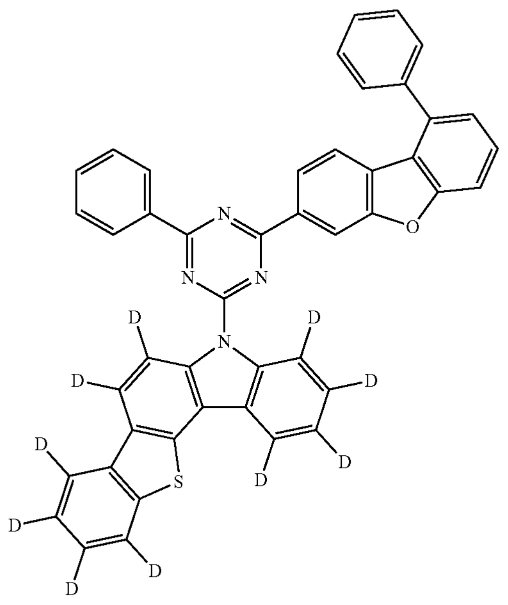
[F-74]
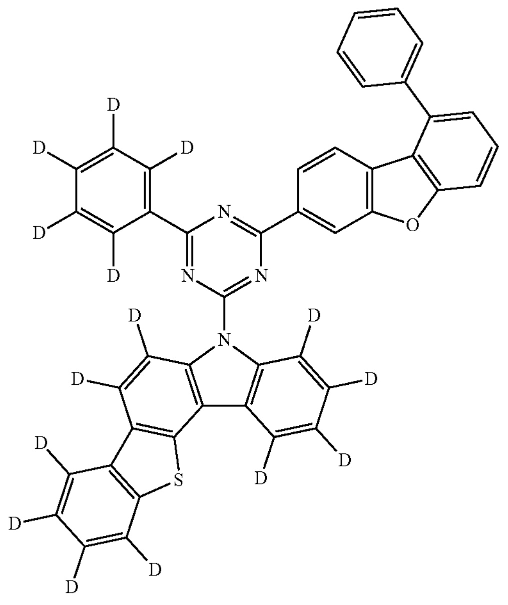
-continued
[F-75]
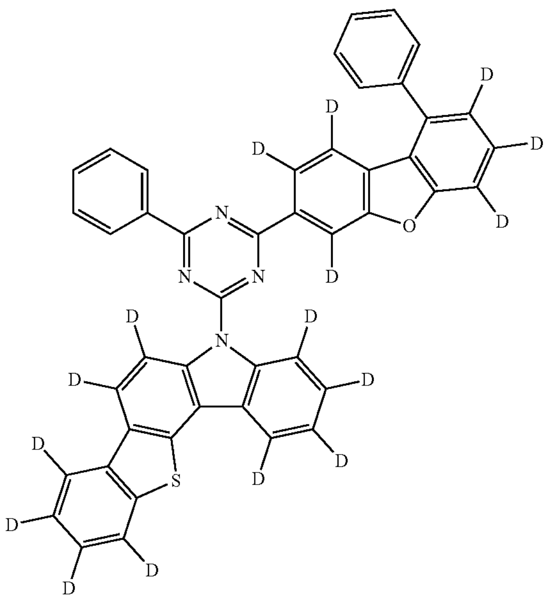
[F-76]
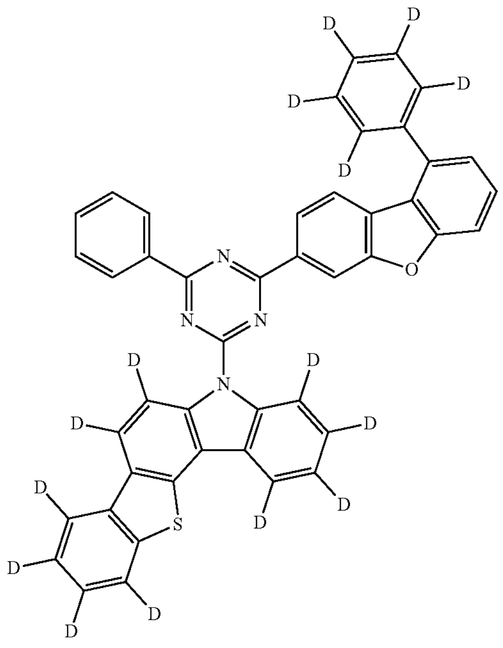

-continued
[F-77]
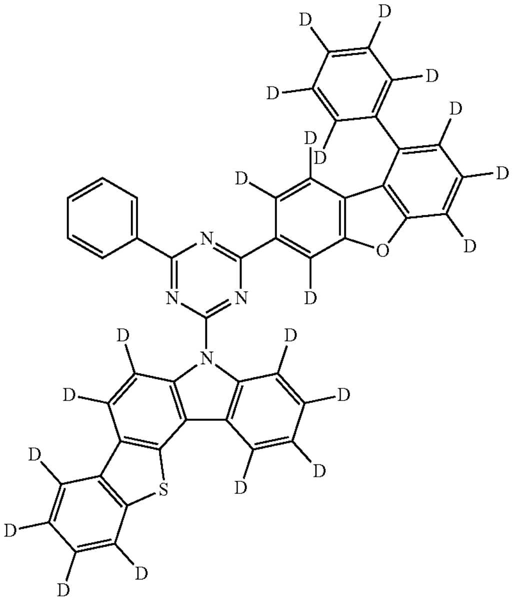
-continued
[F-79]
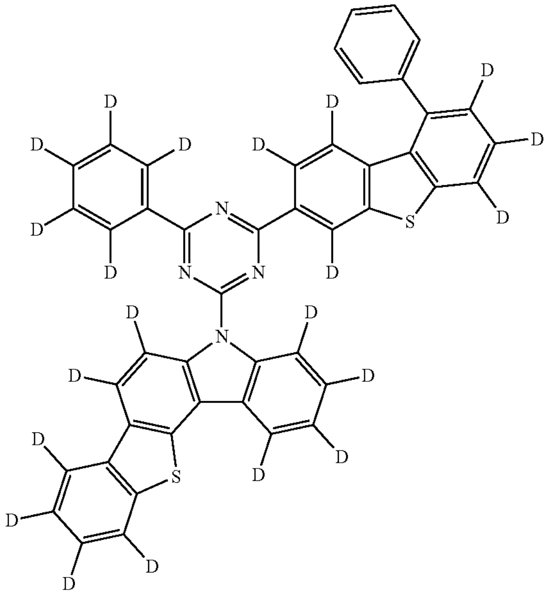
[F-78]
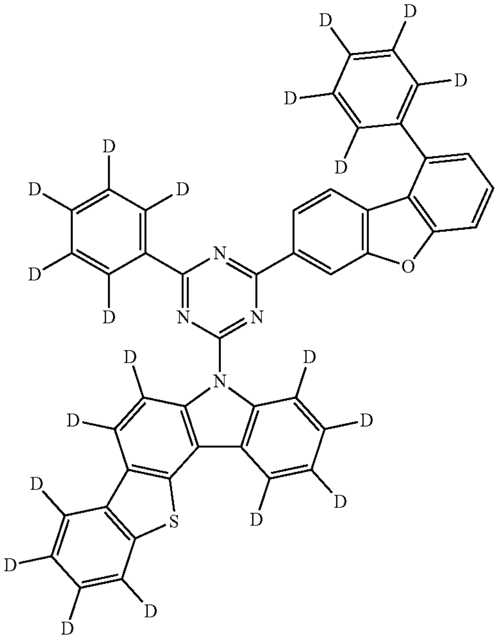
[F-80]
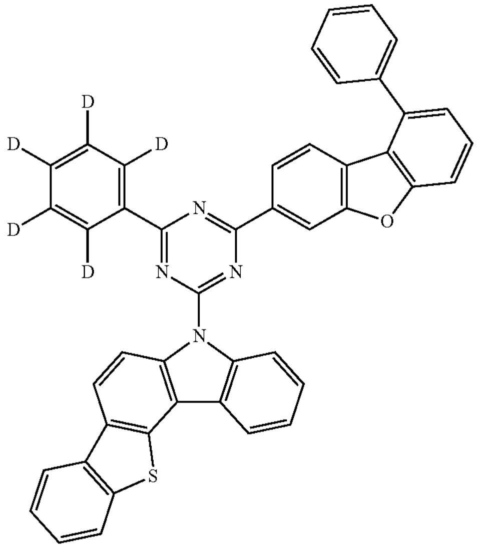

-continued
[F-81]
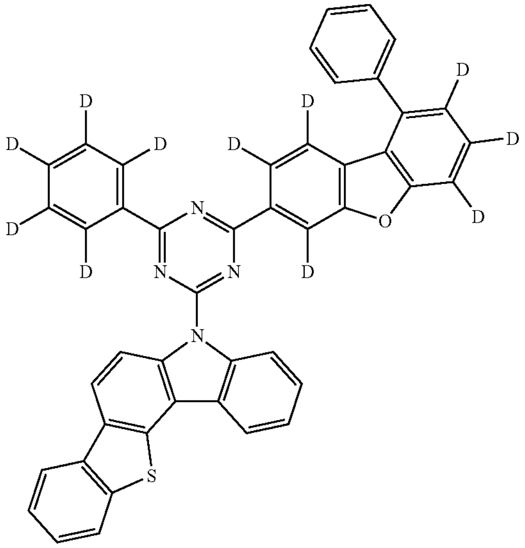
[F-82]
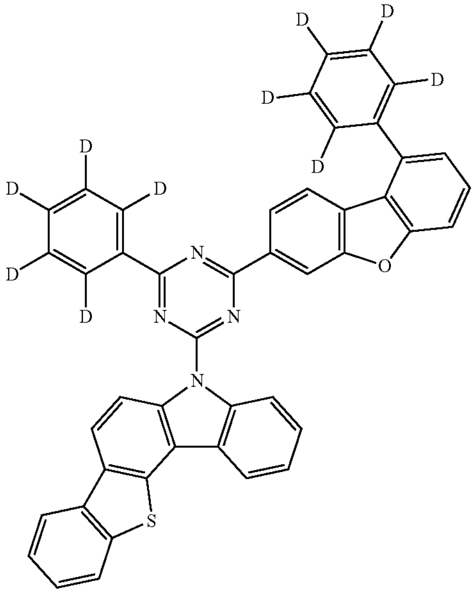
-continued
[F-83]
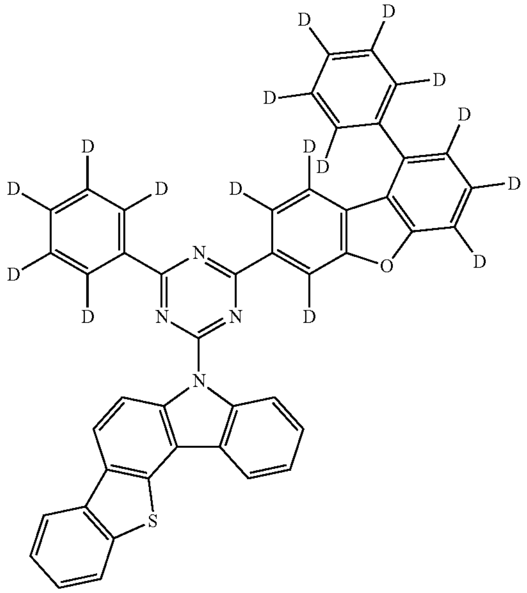
[F-84]
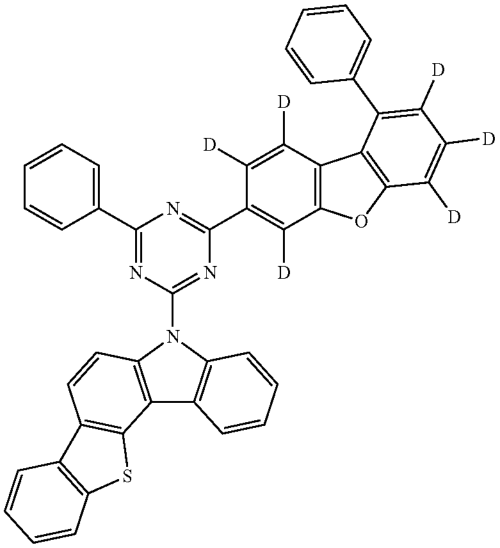

-continued
[F-85]
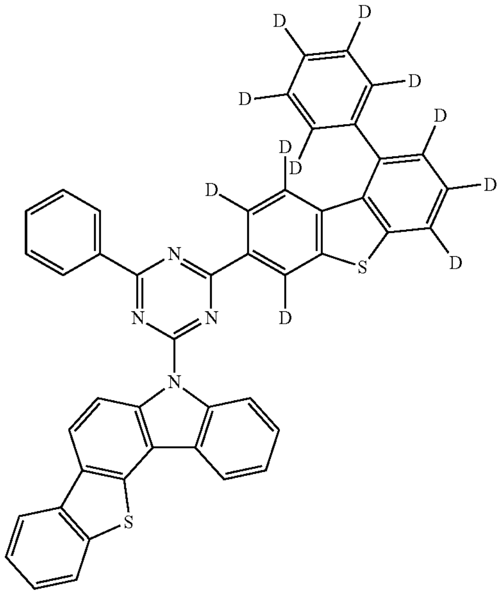
[F-86]
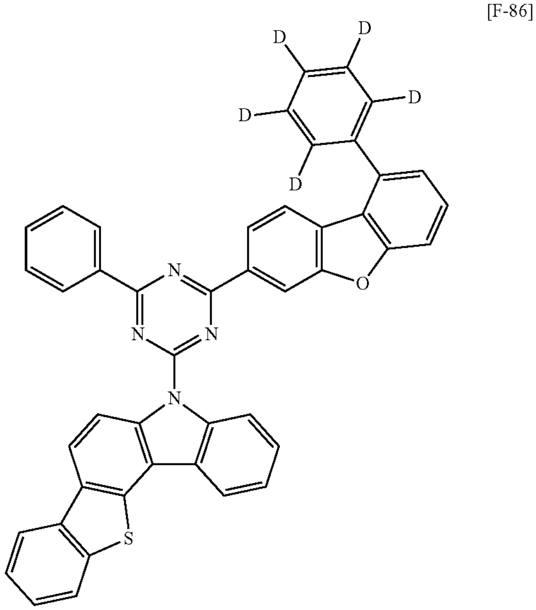
-continued
[F-87]
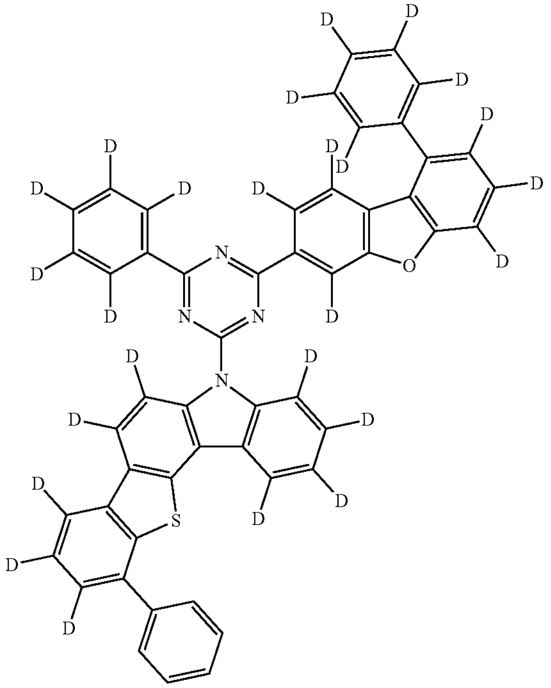
[F-88]
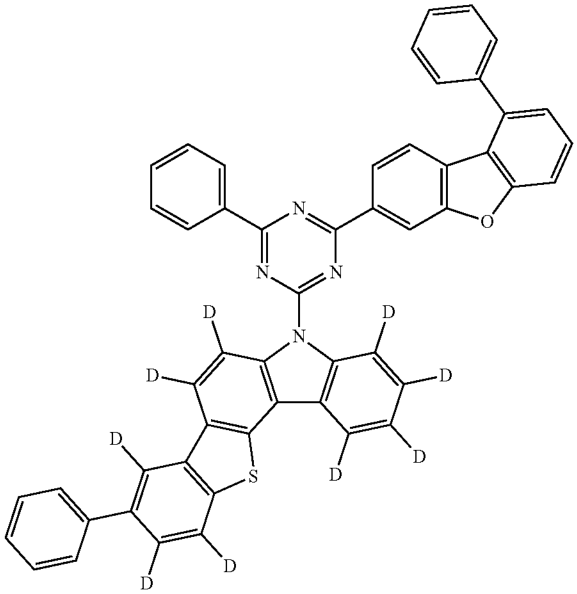

-continued
[F-89]
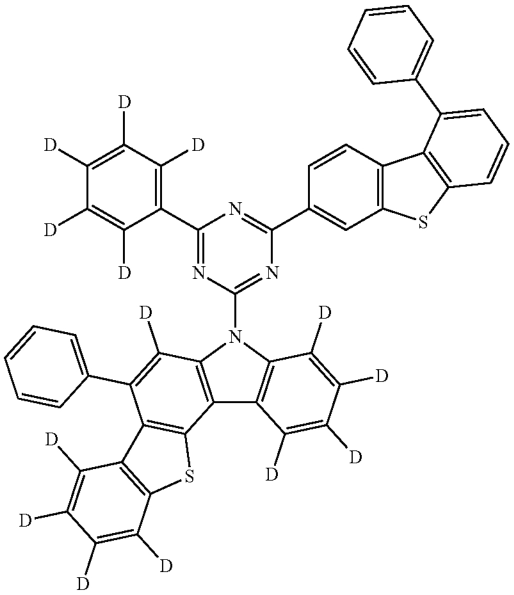
-continued
[F-91]
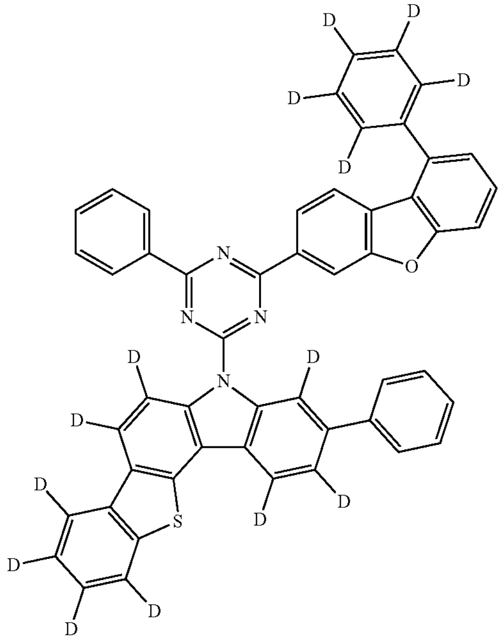
[F-90]
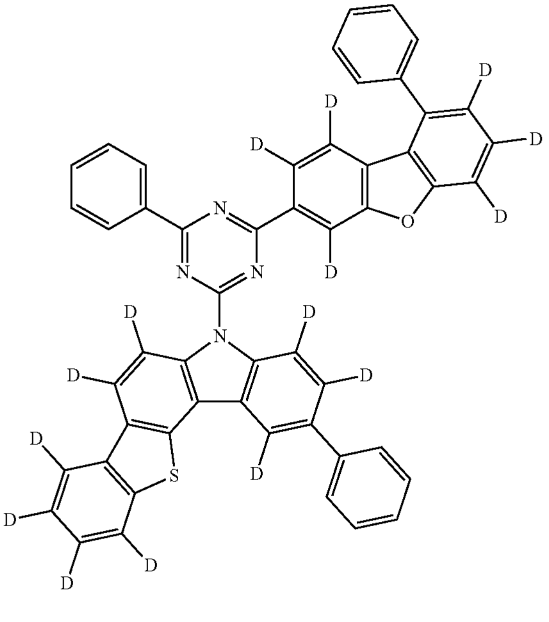
[F-92]
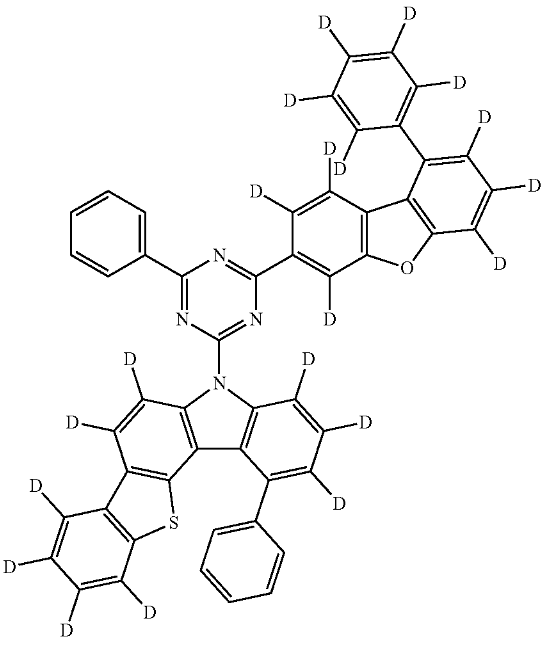

-continued
[F-93]
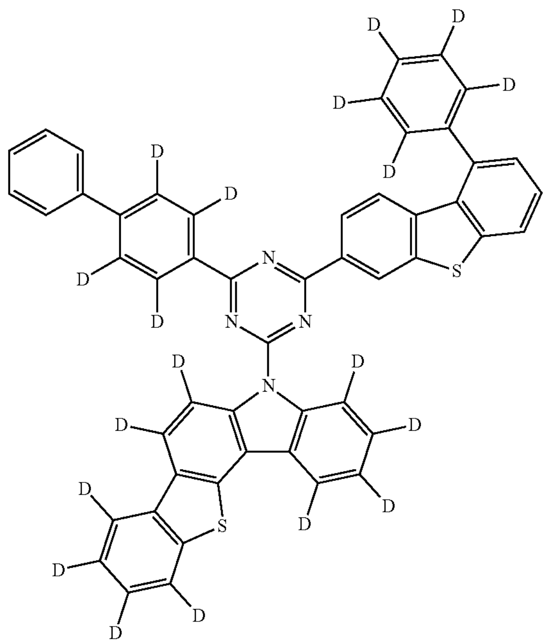
[F-94]
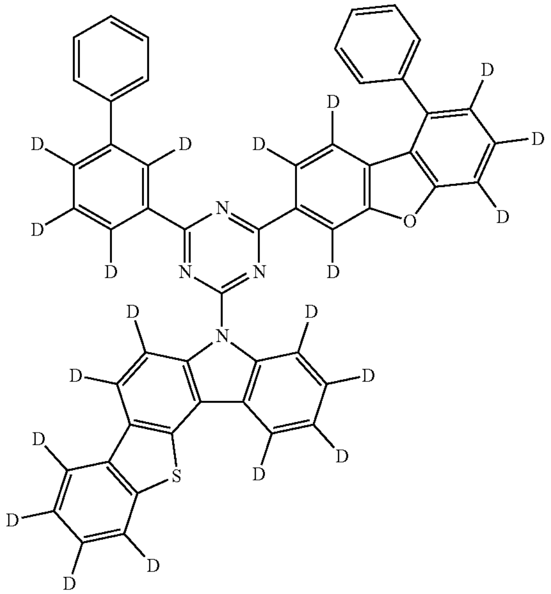
-continued
[F-95]
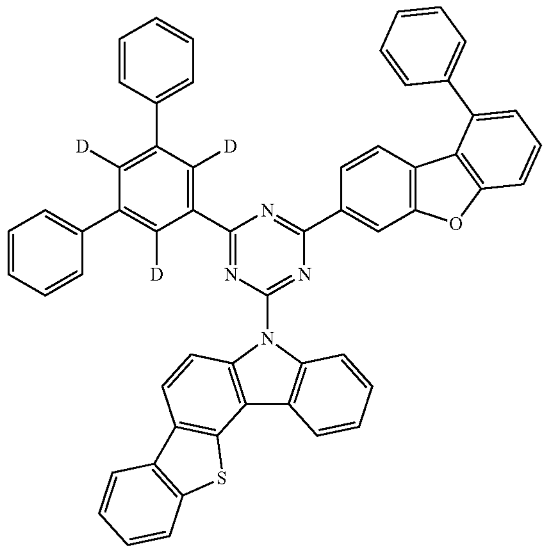
[F-96]
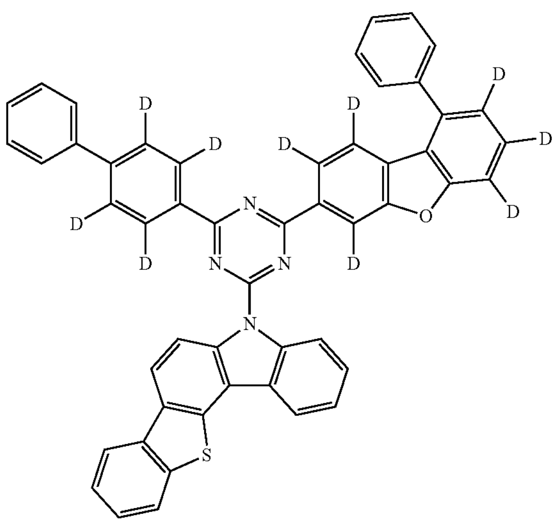

-continued
[F-97]
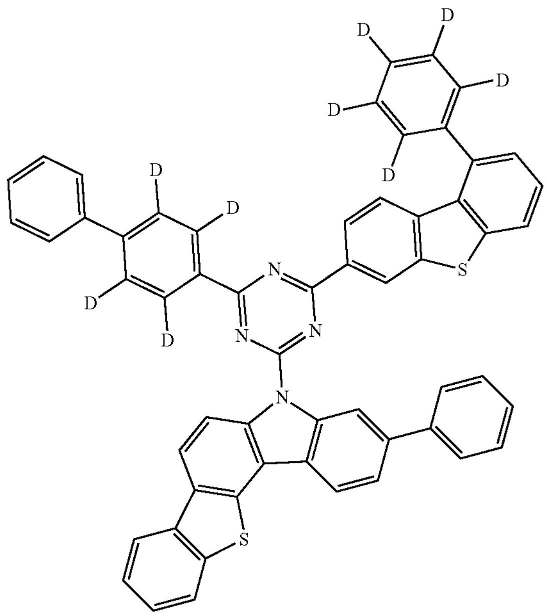
[F-99]
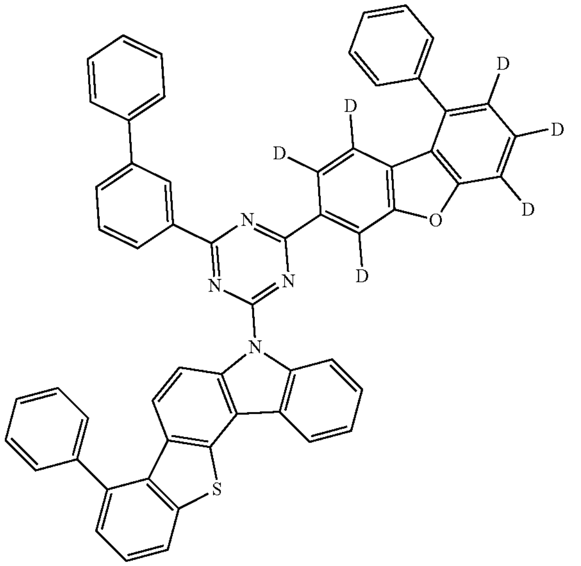
[F-98]
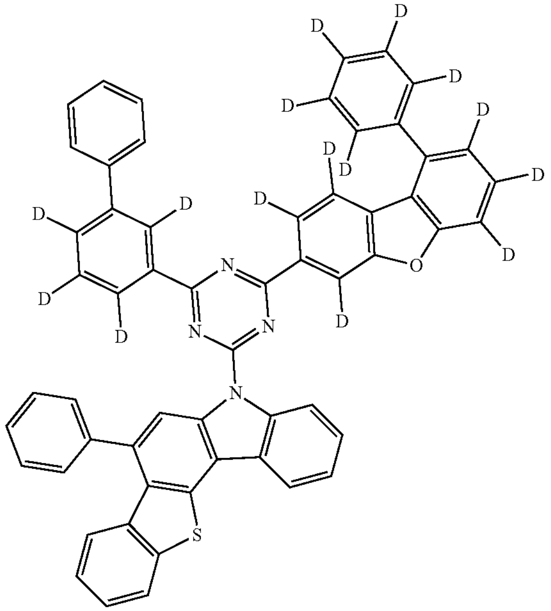
[F-100]
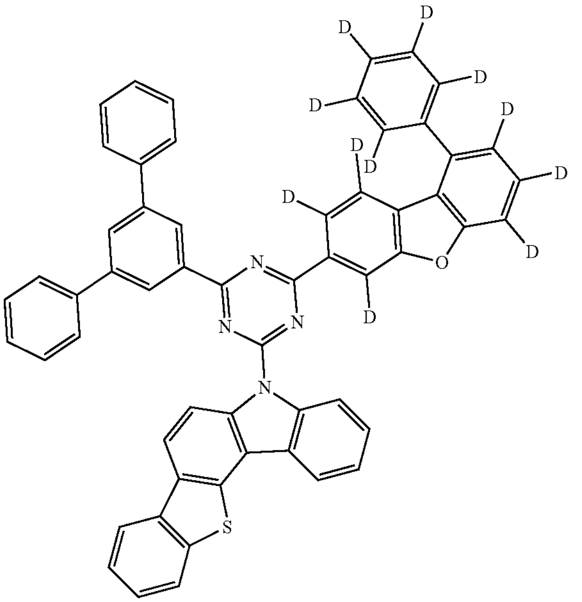

-continued

[F-101]

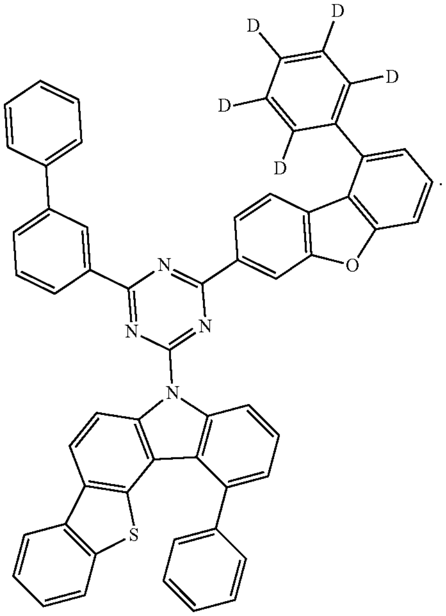

11. A composition for an organic optoelectronic element, comprising:

a first compound for an organic optoelectronic element, and a second compound for an organic optoelectronic element, wherein the first compound for the organic optoelectronic element includes the compound for the organic optoelectronic element of claim 1, and the second compound for the organic optoelectronic element includes a compound for an organic optoelectronic element represented by Chemical Formula 4:

[Chemical Formula 4]

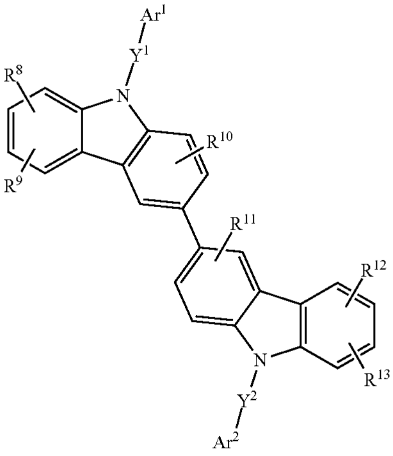

wherein, in Chemical Formula 4, $Y^1$ and $Y^2$ are each independently a single bond or a substituted or unsubstituted C6 to C20 arylene group, $Ar^1$ and $Ar^2$ are each independently a substituted or unsubstituted C6 to C20 aryl group or a substituted or unsubstituted C2 to C30 heterocyclic group, and $R^8$ to $R^{13}$ are each independently hydrogen, deuterium, a substituted or unsubstituted C1 to C10 alkyl group, a substituted or unsubstituted C6 to C20 aryl group, a substituted or unsubstituted C2 to C30 heterocyclic group, a cyano group, or a combination thereof.

12. The compound as claimed in claim 11, wherein:

moieties *—$Y^1$—$Ar^1$ and *—$Y^2$—$Ar^2$ of Chemical Formula 4 are one of substituents of each individually a moiety of Group II:

[Group II]

G-1

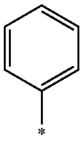

G-2

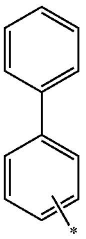

G-3

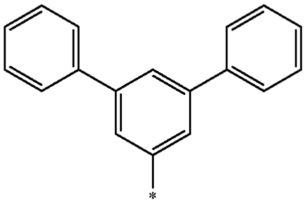

G-4

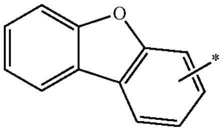

G-5

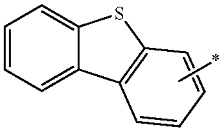

G-6

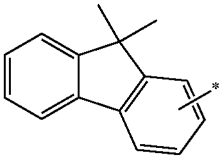

G-7

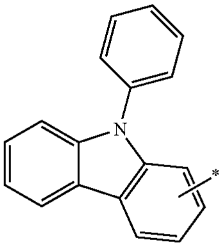

-continued
G-8
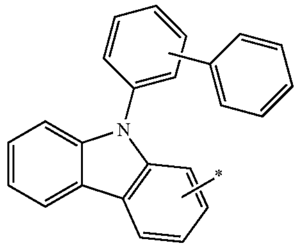
G-9
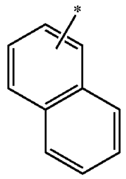
G-10
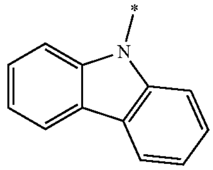
G-11
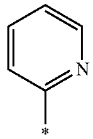
G-12
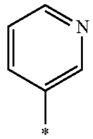
G-13
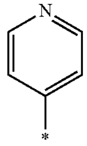
G-14
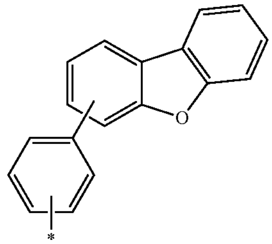
G-15
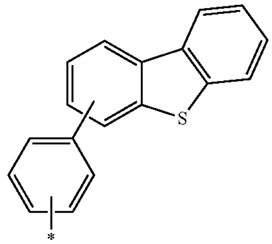
-continued
G-16
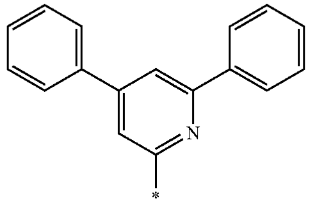
G-17
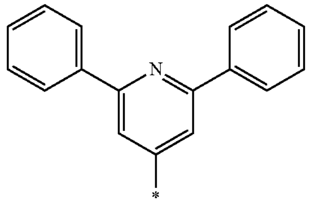
G-18
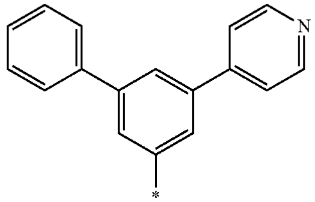
G-19
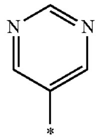
G-20
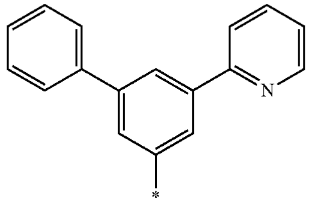
G-21
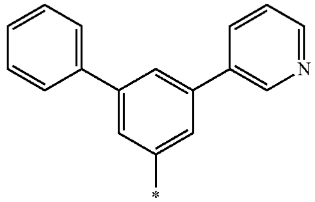
G-22
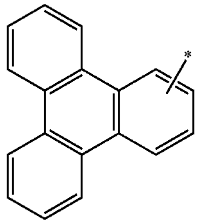

-continued

G-23

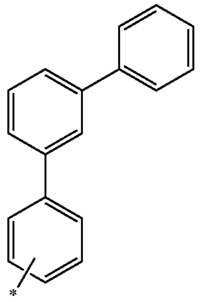

G-24

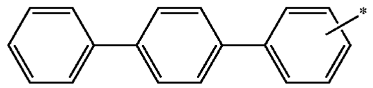

G-25

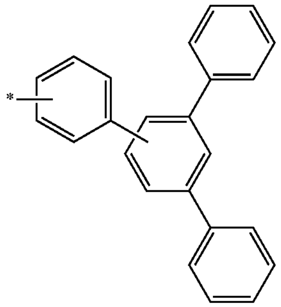

and in Group II, * is a linking point.

13. An organic optoelectronic element, comprising:

an anode and a cathode facing each other, and at least one organic layer between the anode and the cathode, wherein the organic layer includes the compound for the organic optoelectronic element of claim 1.

14. The organic optoelectronic element as claimed in claim 13, wherein:

the at least one organic layer includes a light emitting layer, and the light emitting layer includes the compound.

15. A display device comprising the organic optoelectronic element as claimed in claim 13.

16. An organic optoelectronic element, comprising:

an anode and a cathode facing each other, and at least one organic layer between the anode and the cathode, wherein the at least one organic layer includes the composition for the organic optoelectronic element as claimed in claim 11.

17. The organic optoelectronic element as claimed in claim 16, wherein;

the organic layer includes a light emitting layer, and the light emitting layer includes the composition.

18. A display device comprising the organic optoelectronic element as claimed in claim 16.

* * * * *